US009670549B2

(12) United States Patent
Mock et al.

(10) Patent No.: US 9,670,549 B2
(45) Date of Patent: Jun. 6, 2017

(54) GENE EXPRESSION SIGNATURES OF NEOPLASM RESPONSIVENESS TO THERAPY

(71) Applicant: The United States of America, as represented by the Secretary, Department of Health and Human Services, Washington, DC (US)

(72) Inventors: Beverly A. Mock, Bethesda, MD (US); John K. Simmons, Washington, DC (US); Aleksandra Michalowski, Middletown, MD (US); Jyoti Patel, Germantown, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 190 days.

(21) Appl. No.: 14/357,191

(22) PCT Filed: Nov. 12, 2012

(86) PCT No.: PCT/US2012/064693
§ 371 (c)(1),
(2) Date: May 8, 2014

(87) PCT Pub. No.: WO2013/071247
PCT Pub. Date: May 16, 2013

(65) Prior Publication Data
US 2014/0357660 A1 Dec. 4, 2014

Related U.S. Application Data

(60) Provisional application No. 61/558,402, filed on Nov. 10, 2011.

(51) Int. Cl.
| | | |
|---|---|---|
| *C12Q 1/68* | (2006.01) | |
| *G06F 19/20* | (2011.01) | |
| *G01N 33/574* | (2006.01) | |
| *A61K 31/4045* | (2006.01) | |
| *A61K 31/439* | (2006.01) | |

(52) U.S. Cl.
CPC ........ *C12Q 1/6886* (2013.01); *A61K 31/4045* (2013.01); *A61K 31/439* (2013.01); *G01N 33/57484* (2013.01); *G06F 19/20* (2013.01); *C12Q 2600/106* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | |
|---|---|---|
| 7,741,035 B2 | 6/2010 | Shaughnessy, Jr. et al. |
| 7,983,850 B2 | 7/2011 | Shaughnessy, Jr. et al. |
| 2008/0280779 A1 | 11/2008 | Shaughnessy, Jr. et al. |
| 2009/0149511 A1 | 6/2009 | Burk et al. |
| 2009/0215812 A1 | 8/2009 | Bedrosian et al. |
| 2010/0048414 A1 | 2/2010 | Weaver et al. |
| 2010/0093556 A1 | 4/2010 | Clarke et al. |
| 2010/0144673 A1 | 6/2010 | Shaughnessy, Jr. et al. |
| 2010/0247528 A1 | 9/2010 | Hunter et al. |
| 2010/0316629 A1 | 12/2010 | Shaughnessy, Jr. et al. |
| 2011/0086349 A1 | 4/2011 | Anjomshoaa et al. |

FOREIGN PATENT DOCUMENTS

| | | |
|---|---|---|
| EP | 2 385 370 | 11/2011 |
| WO | WO 2008/076447 | 6/2008 |
| WO | WO 2008/095050 | 8/2008 |
| WO | WO 2008/132176 | 11/2008 |
| WO | WO 2009/045443 | 4/2009 |
| WO | WO 2009/105154 | 8/2009 |
| WO | WO 2009/126310 | 10/2009 |

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Akcakanat, et al. "The Rapamycin-Regulated Gene Expression Signature Determines Prognosis for Breast Cancer," *Mol. Cancer*, 8, p. 75, 2009.
Attal, et al. "A Prospective Randomized Trial of Autologous Bone Marrow Transplantation and Chemotherapy in Multiple Myeloma," *N. Engl. J. Med.*, 335, pp. 91-97, 1996.
Barlogie, et al., "Superiority of Tandem Autologous Transplantation Over Standard Therapy for Previously Untreated Multiple Myeloma," *Blood*, 89, pp. 789-793, 1997.
Broyl, et al., "Gene Expression Profiling for Molecular Classification of Multiple Myeloma in Newly Diagnosed Patients," *Blood*, 116, pp. 2543-2553, 2010.

(Continued)

*Primary Examiner* — James Martinell
(74) *Attorney, Agent, or Firm* — Klarquist Sparkman, LLP

(57) ABSTRACT

Gene signatures for determining whether a neoplasm (such as a multiple myeloma neoplasm) is sensitive to mTORi/HDACi combination therapy and/or for determining the prognosis of a neoplasm in a subject are described. Some embodiments include determining whether a neoplasm is sensitive to mTORi/HDACi combination therapy by predicting whether mTORi/HDACi combination therapy will successfully treat the neoplasm, for example increasing survival of the subject with the neoplasm. In some embodiments, determining the prognosis includes predicting the outcome (such as chance of survival) of the subject with a neoplasm. Also disclosed are reagents, for example arrays, for use with the disclosed methods, as well as computer implementation of the disclosed methods.

10 Claims, 103 Drawing Sheets

(56) References Cited

OTHER PUBLICATIONS

Clinicaltrials.gov identifier No. NCT00918333; as available at http://clinicaltrials.gov/ ct2/show/NCT00918333 on Apr. 13, 2012 (5 pages).
Dai, et al. "A cell proliferation signature is a marker of extremely poor outcome in a subpopulation of breast cancer patients." *Cancer research* 65.10 (2005), pp. 4059-4066.
Dancey. "mTOR signaling and drug development in cancer." *Nature Reviews Clinical Oncology* 7.4 (2010), pp. 209-219.
Decaux, et al. "Prediction of survival in multiple myeloma based on gene expression profiles reveals cell cycle and chromosomal instability signatures in high risk patients and hyperdiploid signatures in low-risk patients: a study of the Intergroupe Francophone du Myélome." *Journal of Clinical Oncology*, Oct. 10, 2008, vol. 26, No. 29, pp. 4798-4805.
Ellis, et al. "Concurrent HDAC and mTORC1 inhibition attenuate androgen receptor and hypoxia signaling associated with alterations in microRNA expression." *PLoS ONE*, Nov. 7, 2011, vol. 6, issue 11, e27178.
Federico, et al. "Histone deacetylase inhibitors in the treatment of hematological malignancies and solid tumors." *BioMed Research International* 2011 (2010).
Hose, et al. "Proliferation is a central independent prognostic factor and target for personalized and risk-adapted treatment in multiple myeloma."*Haematologica* 96.1 (2011), pp. 87-95.
Jemal, et al., "Cancer Statistics, 2010," *CA Cancer J Clin.*, 60, pp. 277-300, 2010.
Kumar, et al. "Impact of gene expression profiling-based risk stratification in patients with myeloma receiving initial therapy with lenalidomide and dexamethasone." *Blood* 118.16 (2011), pp. 4359-4362.
Meissner et al. "Gene expression profiling in multiple myeloma—reporting of entities, risk, and targets in clinical routine." *Clinical Cancer Research* 17.23 (2011), pp. 7240-7247.
Mizuarai, et al. "Gene Expression-Based Pharmacodynamic Biomarkers: The Beginning of a New Era in Biomarker-Driven Anti-Tumor Drug Development," *Current Molecular Medicine*, 10, pp. 596-607, 2010.
Moreaux, et al. "A high-risk signature for patients with multiple myeloma established from the molecular classification of human myeloma cell lines." *Haematologica* 96.4 (2011), pp. 574-582.
Nishioka, et al. "Blockade of mTOR Signaling Potentiates the Ability of Histone Deacetylase Inhibitor to Induce Growth Arrest and Differentiation of Acute Myelogenous Leukemia Cells," *Leukemia*, 22, pp. 2159-2168, 2008 (Abstract Only).
Paik, et al. "A multigene assay to predict recurrence of tamoxifen-treated, node-negative breast cancer." *New England Journal of Medicine* 351.27 (2004), pp. 2817-2826.
Rosenwald, et al. "The proliferation gene expression signature is a quantitative integrator of oncogenic events that predicts survival in mantle cell lymphoma." *Cancer cell* 3.2 (2003), pp. 185-197.
Shaughnessy, et al. "A validated gene expression model of high-risk multiple myeloma is defined by deregulated expression of genes mapping to chromosome 1." *Blood* 109.6 (2007), pp. 2276-2284.
Shaughnessy, et al. "Pharmacogenomics of bortezomib test-dosing identifies hyperexpression of proteasome genes, especially PSMD4, as novel high-risk feature in myeloma treated with Total Therapy 3." *Blood* 118.13 (2011), pp. 3512-3524.
Stapnes et al. "Functional Characteristics and Gene Expression Profiles of Primary Acute Myeloid Leukaemia Cells Identify Patient Subgroups that Differ in Susceptibility to Histone Deacetylase Inhibitors," *Int. J. Oncol.*, 31, pp. 1529-1538, 2007.
Sullivan. "Characterizing the Individual and Combined Effect of Rapamycin and MS-275 on U266, a Multiple Myeloma Cell Line," *Laboratory of Cancer Biology, Center for Cancer Research*, Thesis, University Honors in Biology, 15 pages, Spring 2008.
Wedel, et al. "Molecular targeting of prostate cancer cells by a triple drug combination down—regulates integrin driven adhesion processes, delays cell cycle progression and interferes with the cdk-cyclin axis." *BMC Cancer*, Aug. 25, 2011, vol. 11, p. 375.
Wei, et al. "Gene expression-based chemical genomics identifies rapamycin as a modulator of MCL1 and glucocorticoid resistance." *Cancer Cell*, Oct. 2006, vol. 10, pp. 331-342.
Whitfield, et al. "Common markers of proliferation." *Nature Reviews Cancer* 6.2 (2006), pp. 99-106.
Zhan, et al. "The Molecular Classification of Multiple Myeloma," *Blood*, 108, pp. 2020-2028, 2006.

\* cited by examiner

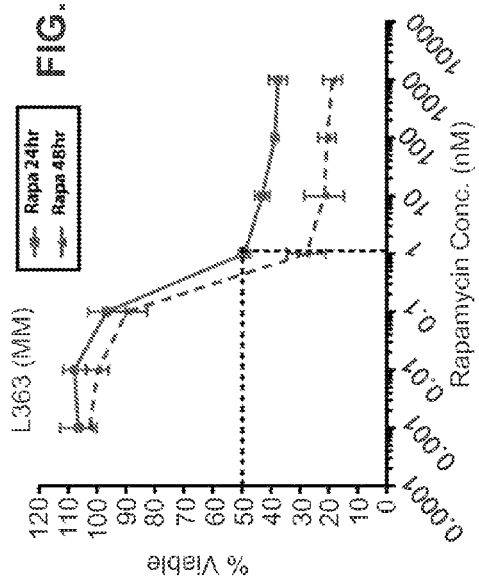
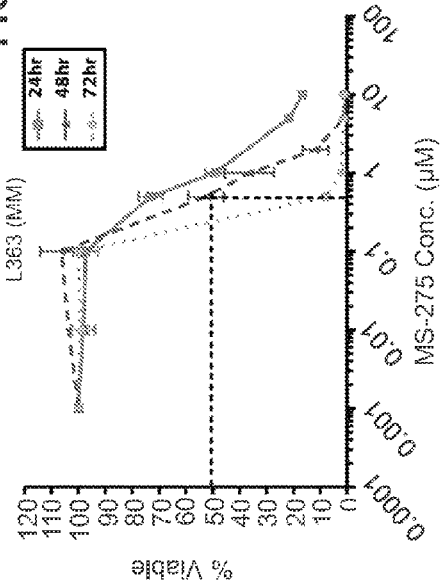
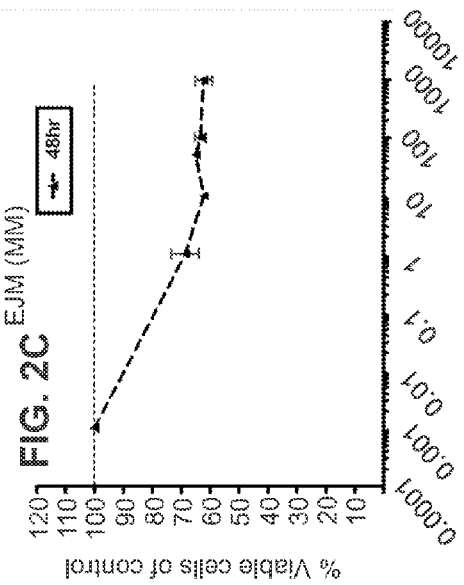
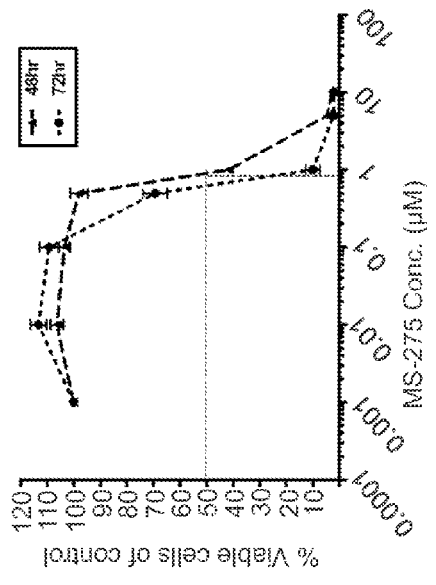

JeKo (MCL)

JeKo (MCL)

SP53 (MCL)

SP53 (MCL)

L363
Change in mouse body weight

U266
Change in mouse body weight

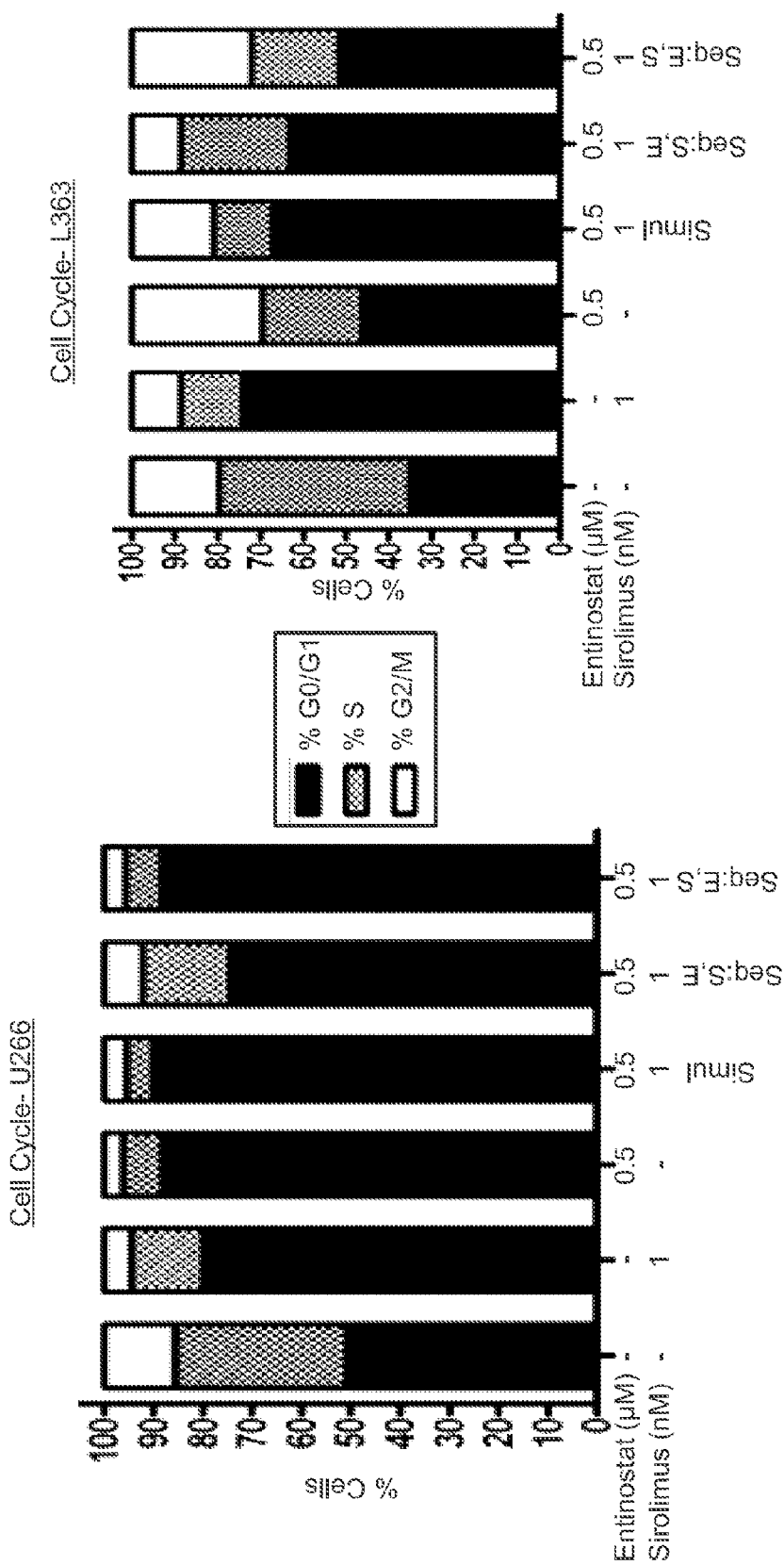

SP53 (MCL) cell cycle analysis

MS-275

Rapamycin

MS-275*Rapamycin
Q-value < 0.66

Combination
0.0011 < Q-value < 0.13

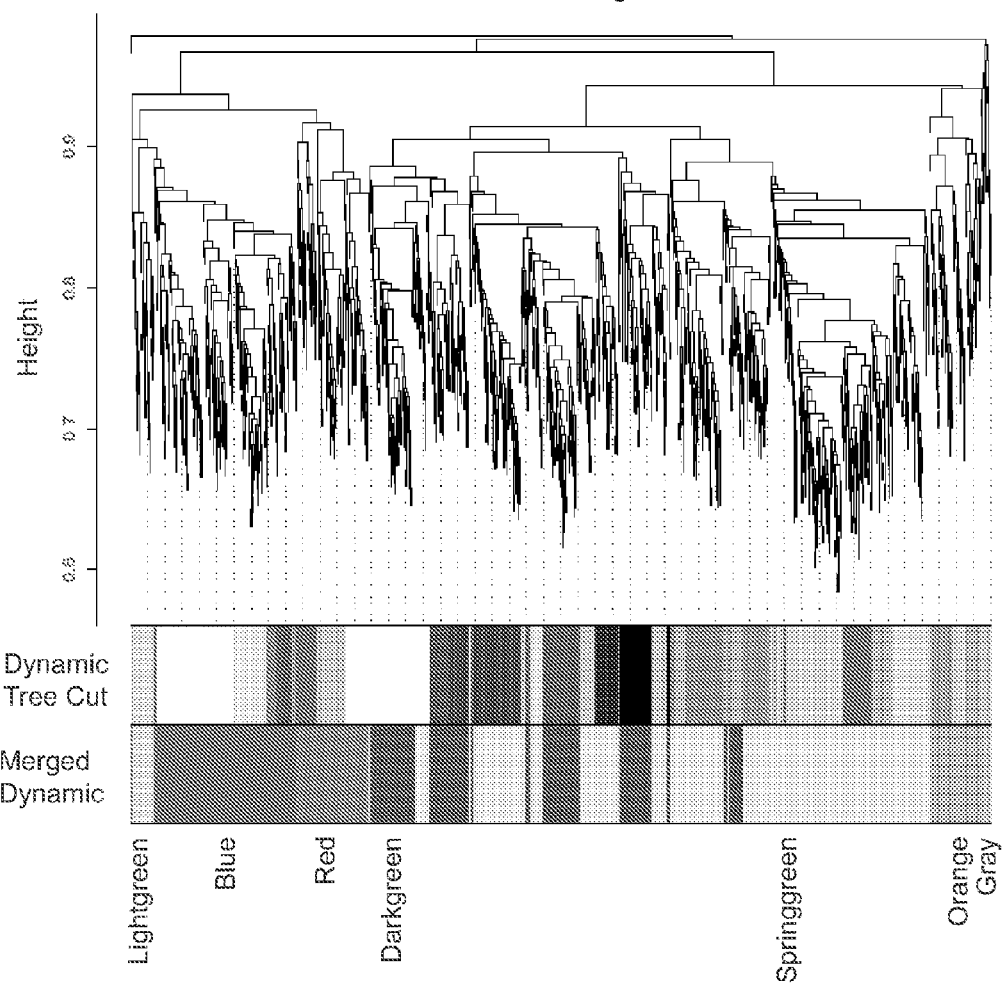

Scale-free topology fit of the connectivity distribution

Co-expression Network

Response Modules:

| Both HDACi/mTORi | mTORi Alone | HDACi Alone |
|---|---|---|
| Blue: 126 nodes | Red: 67 nodes | Springgreen: 418 nodes |
| Orange: 34 nodes | | Darkgreen: 256 nodes |

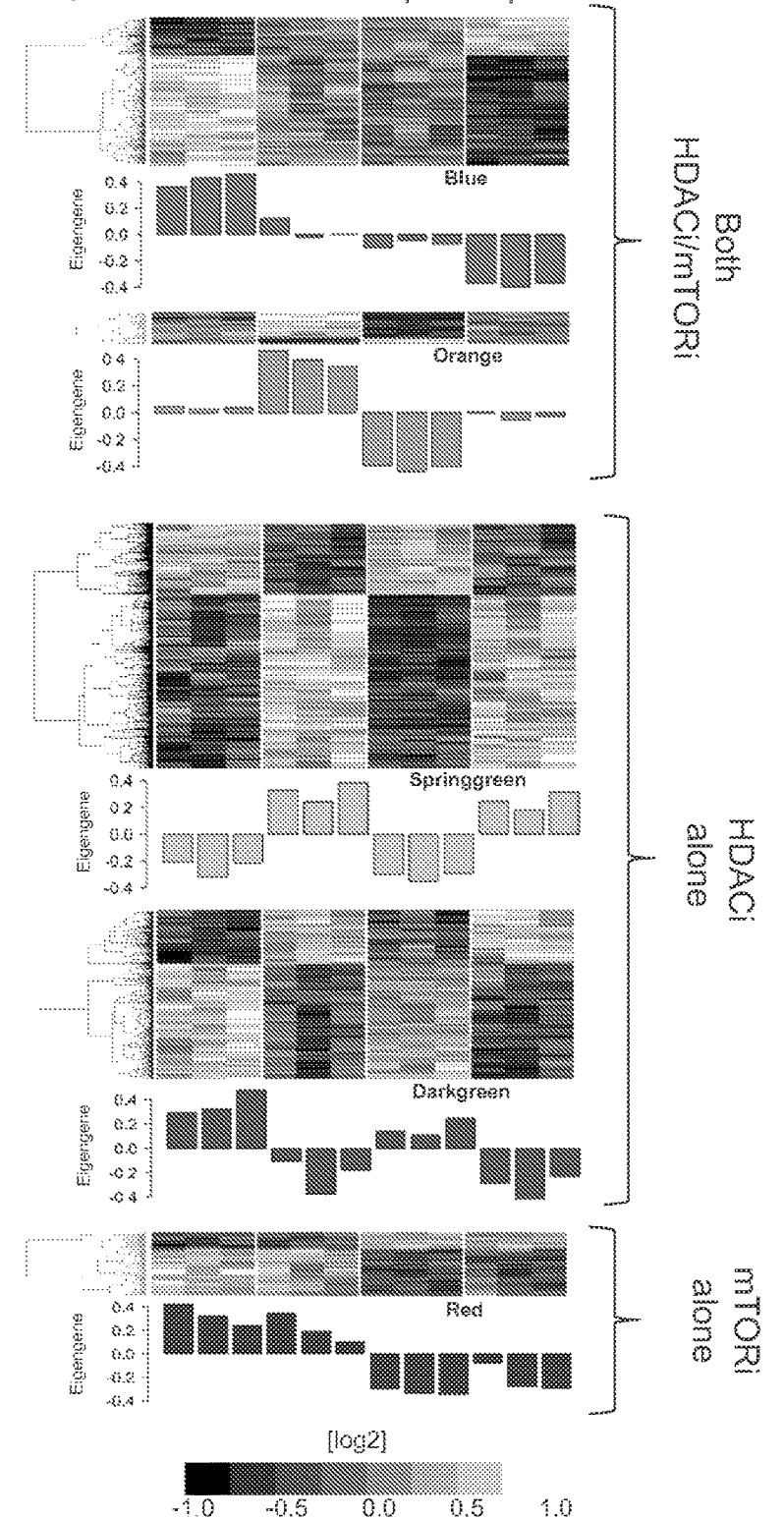

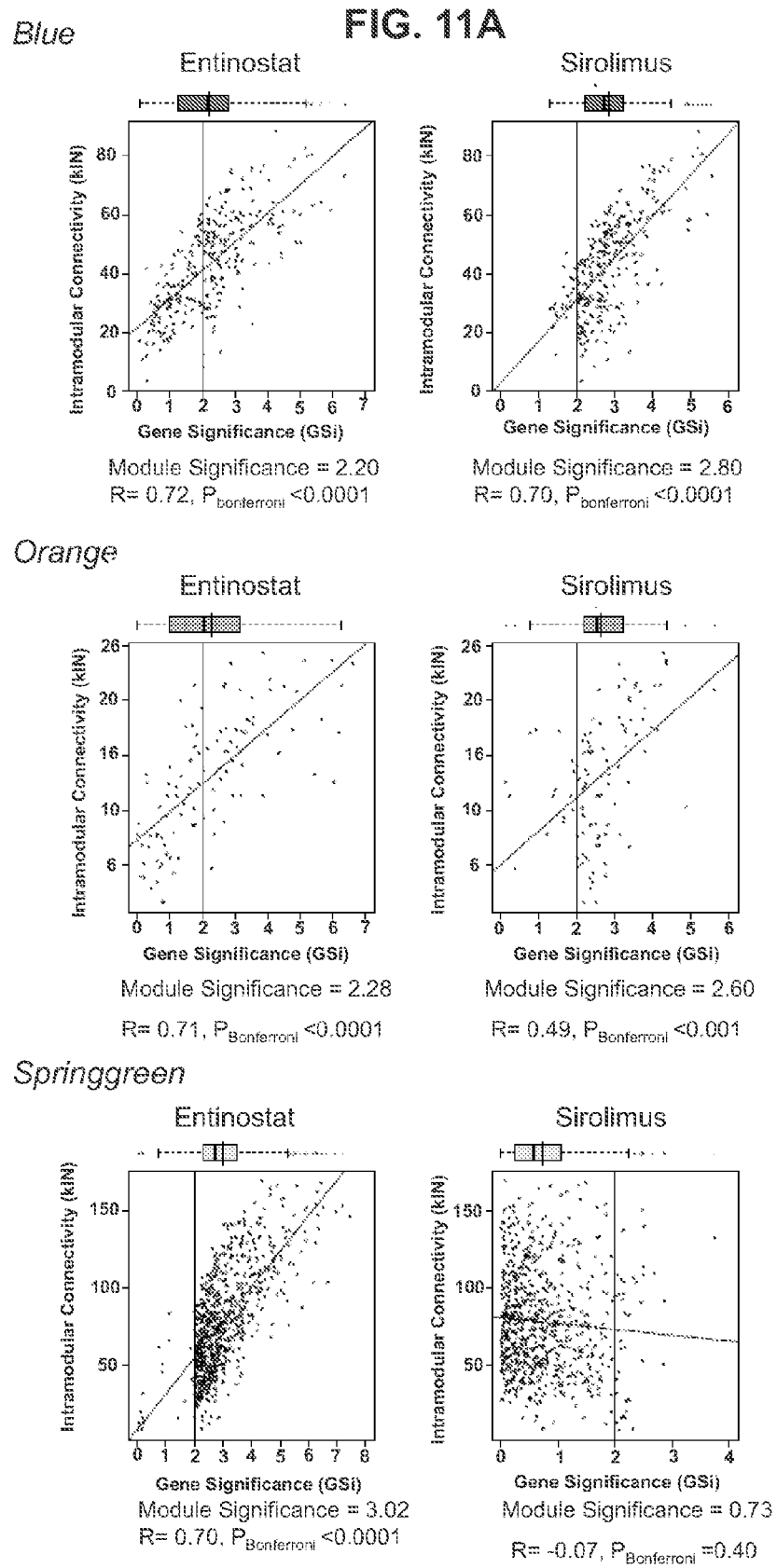

FIG. 11B
*Darkgreen*
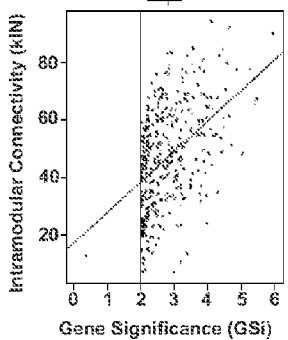
Entinostat
Module Significance = 2.82
R= 0.46, P< 0.0001
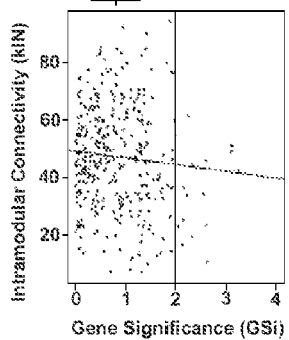
Sirolimus
Module Significance = 0.82
R= -0.08, P= 0.40
*Red*
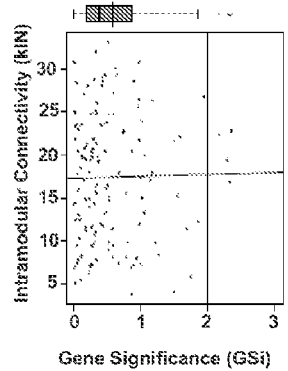
Entinostat
Module Significance = 0.60
R= 0.02, $P_{Bonferroni}$=1
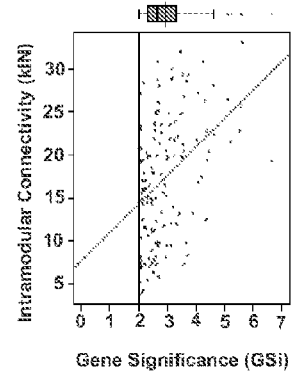
Sirolimus
Module Significance = 2.90
R= 0.40, $P_{bonferroni}$ < 0.0001
*Lightgreen*
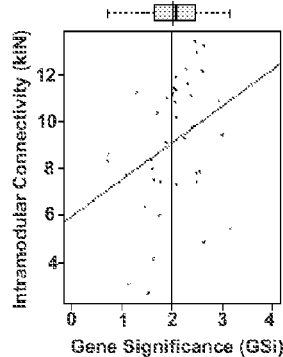
Entinostat
Module Significance = 2.0
R= 0.30, $P_{bonferroni}$ =0.24
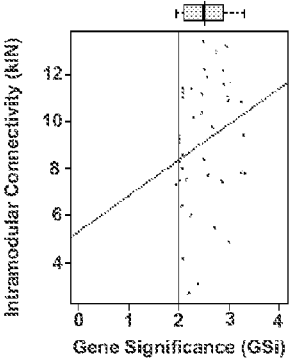
Sirolimus
Module Significance = 2.50
R= 0.23, $P_{bonferroni}$ = 0.88

FIG. 15A
Drug Response Signature
Combination vs. Control
Disease Signature
RELAPSED vs. Healthy
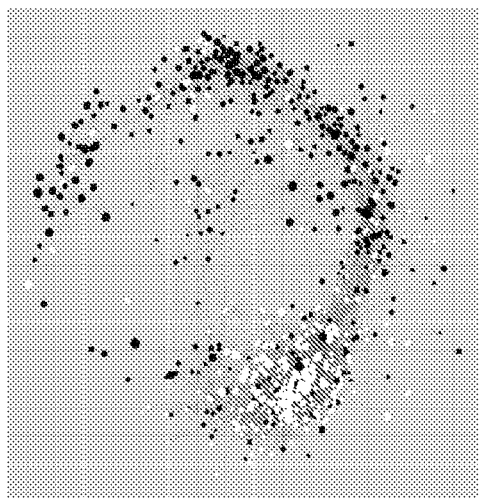
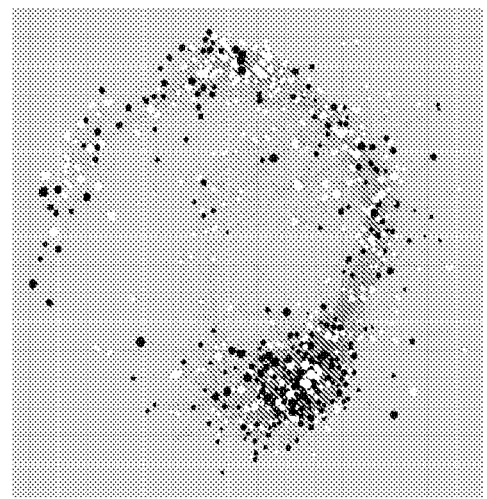

FIG.16A
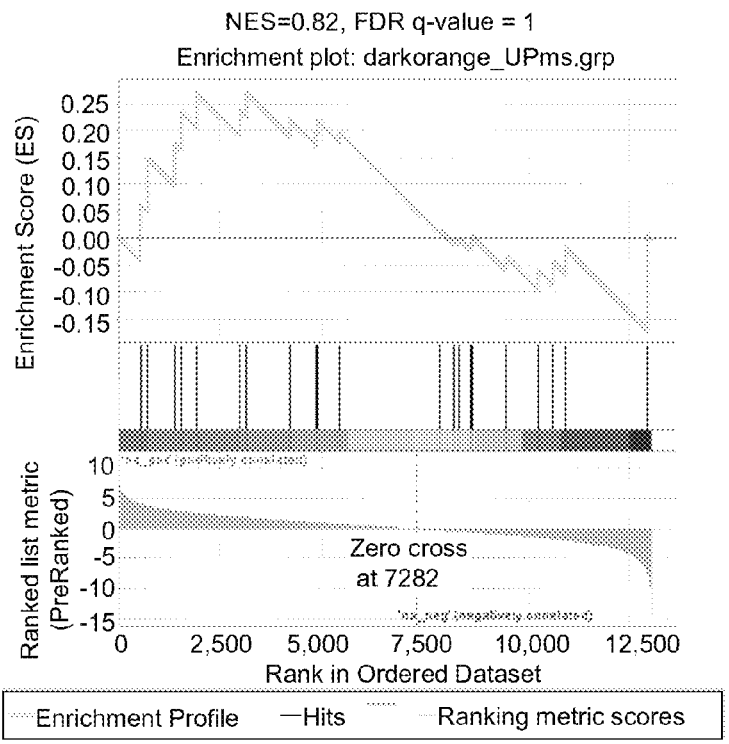
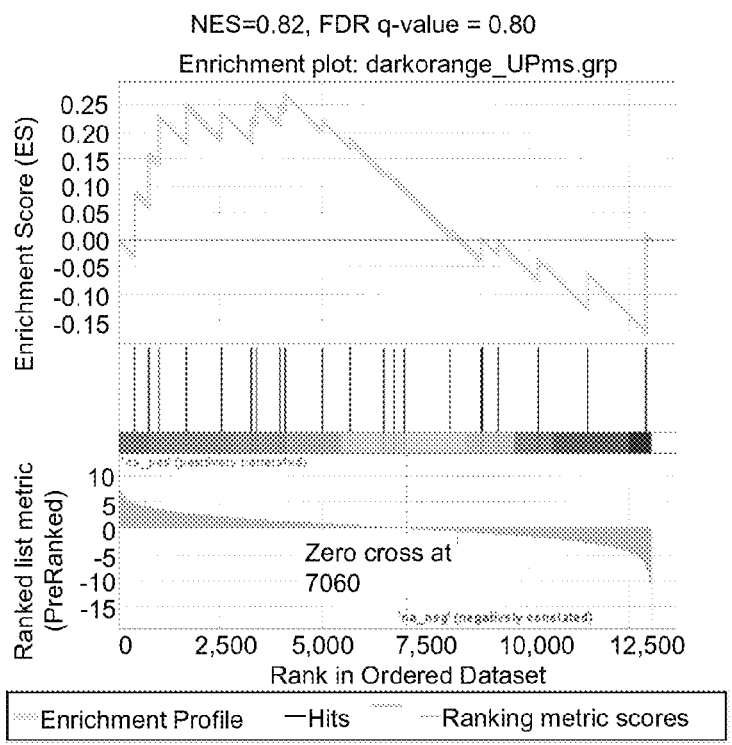

FIG.16B
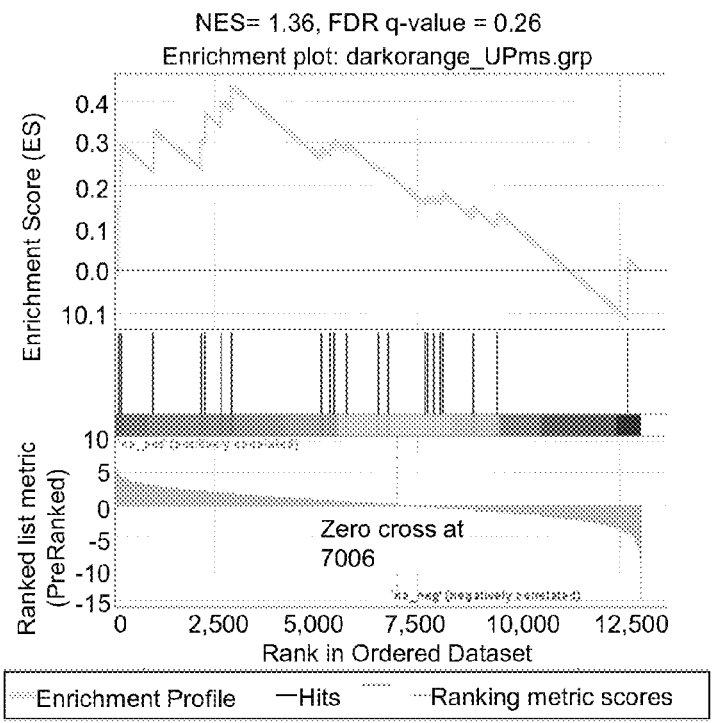
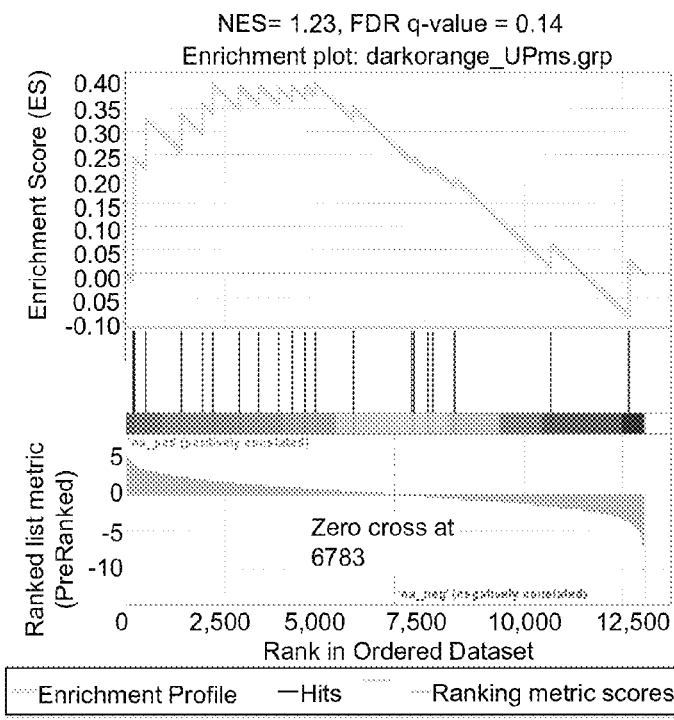

FIG.16C
Darkgreen_DOWN
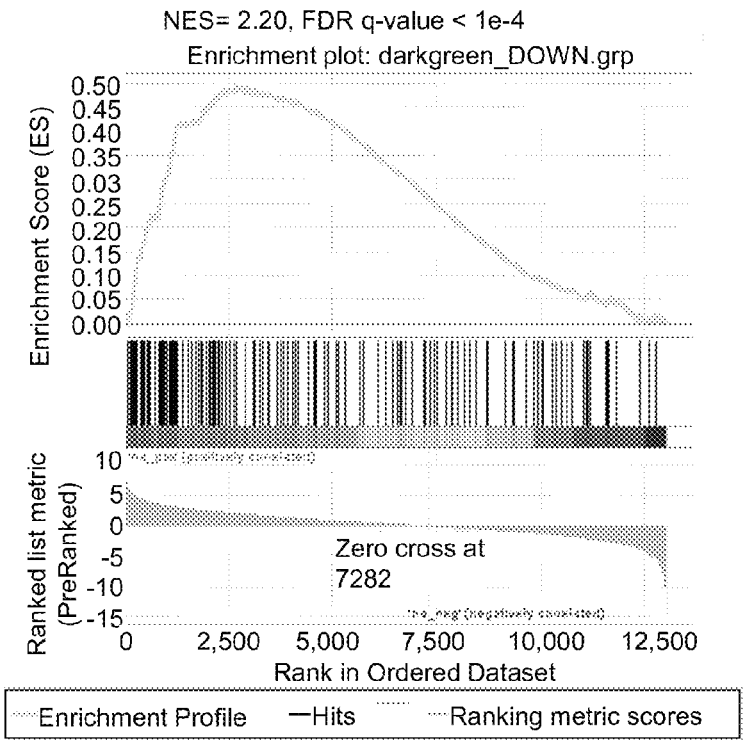
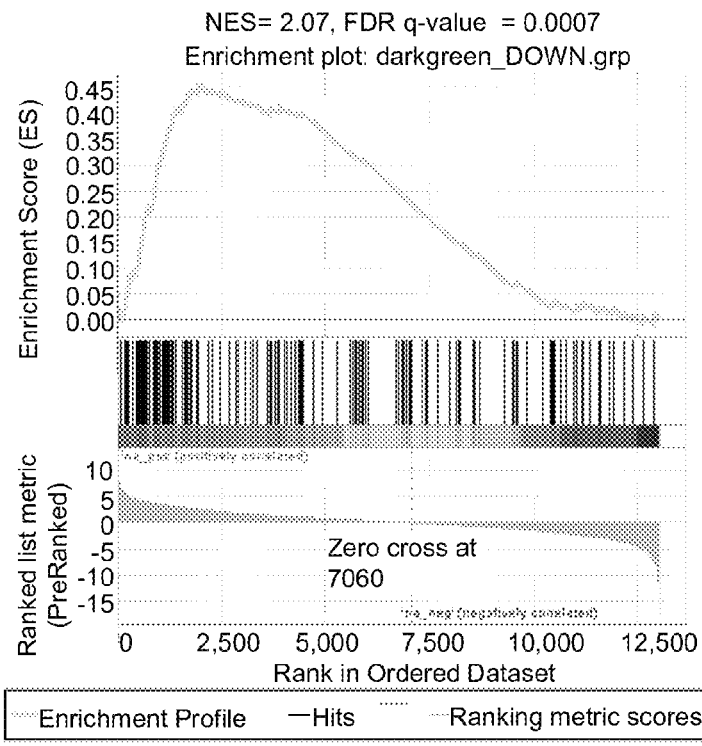

Darkgreen_DOWN      FIG.16D
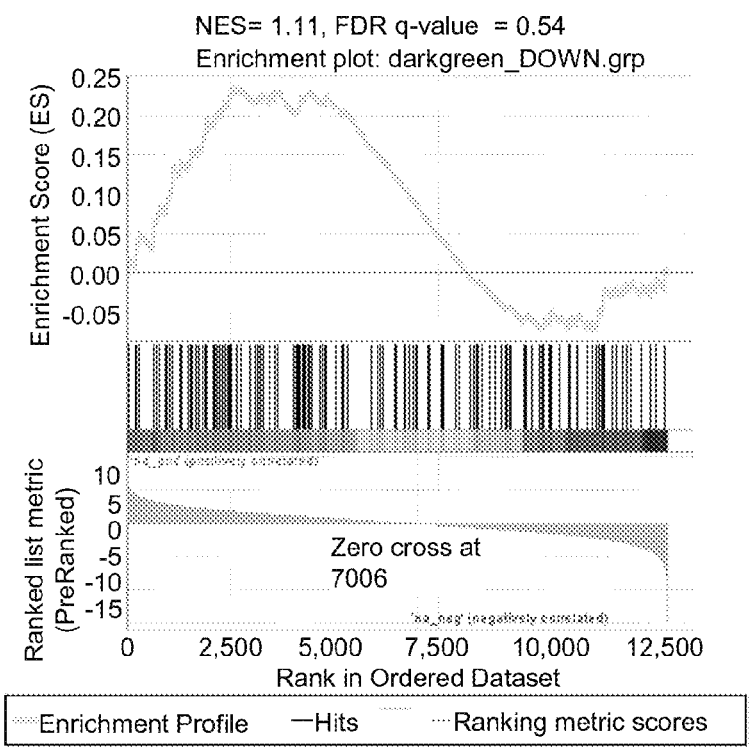
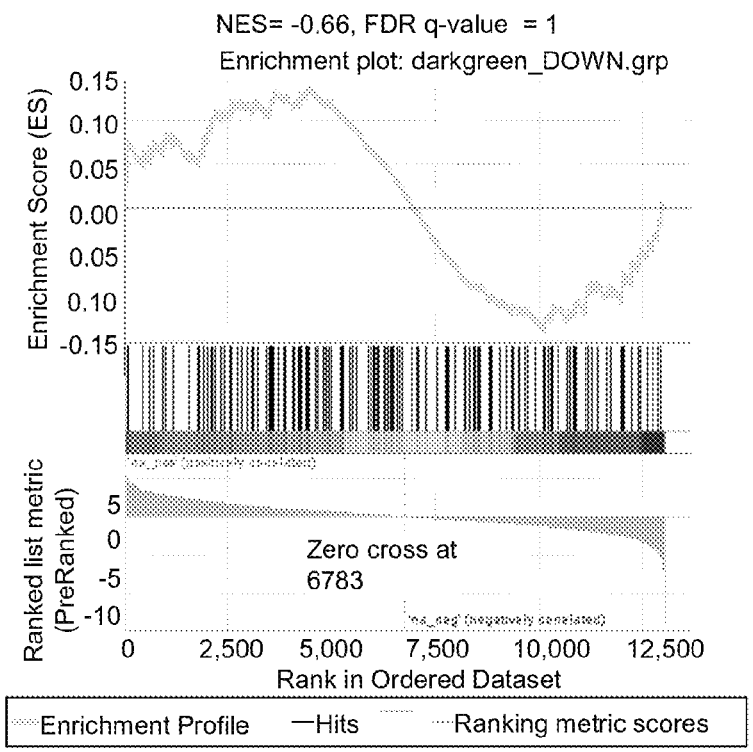

FIG.16E
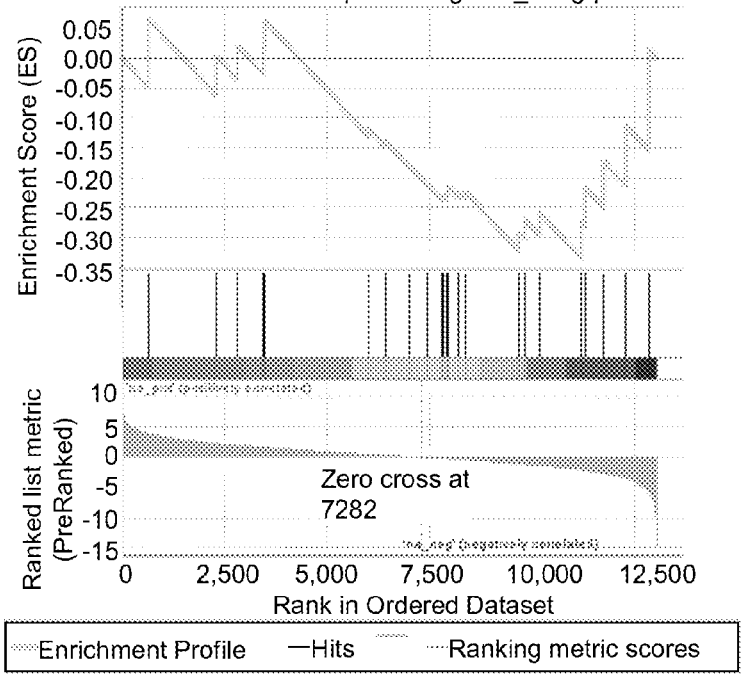
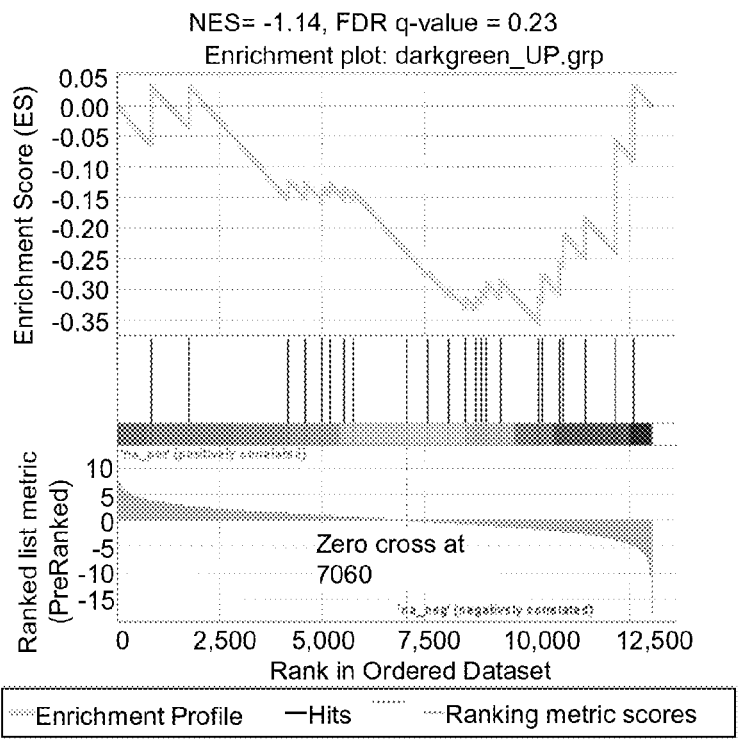

FIG.16F
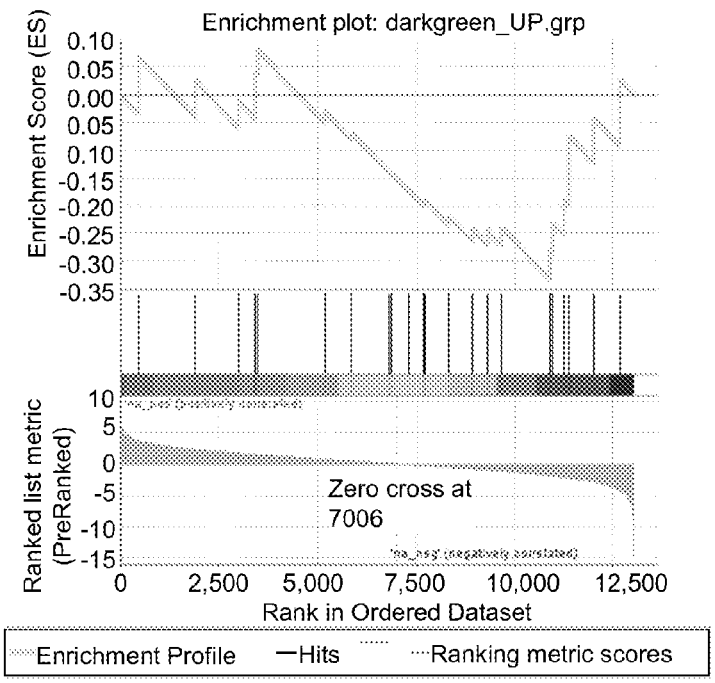
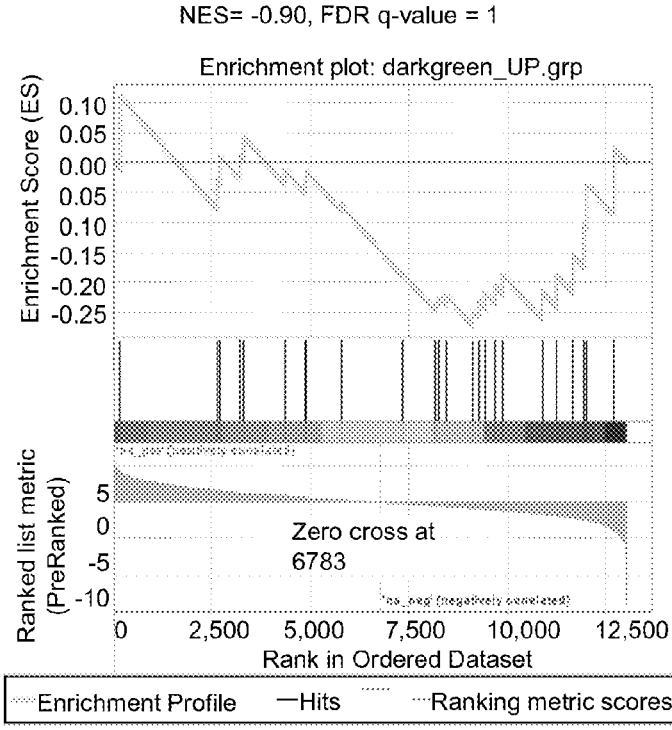

FIG.16G
Springgreen_DOWN
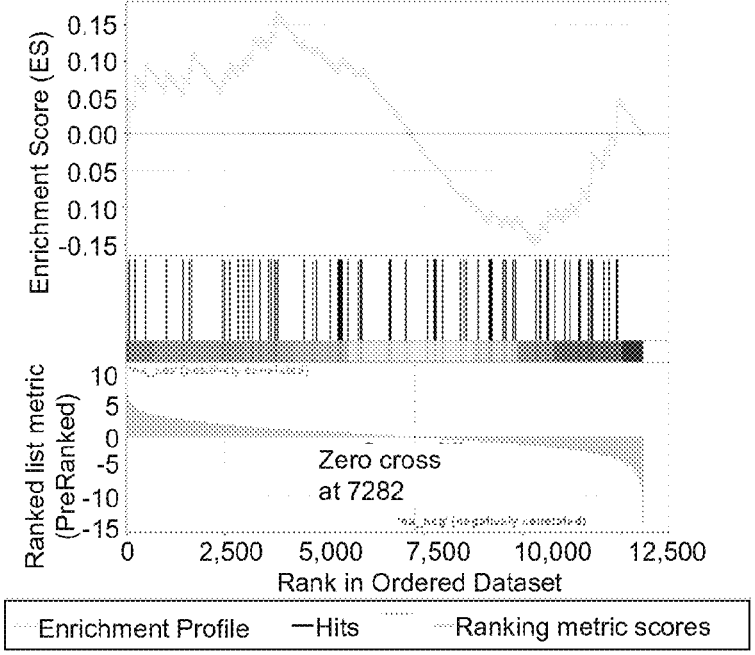
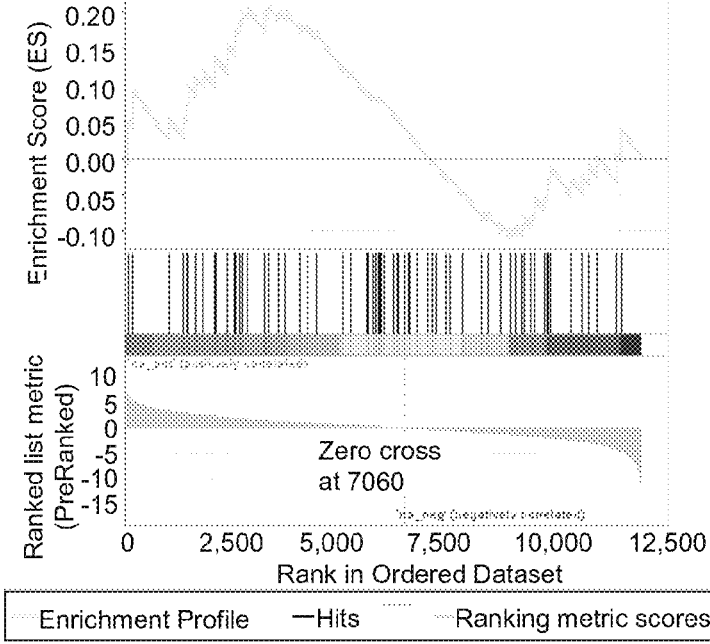

FIG.16H
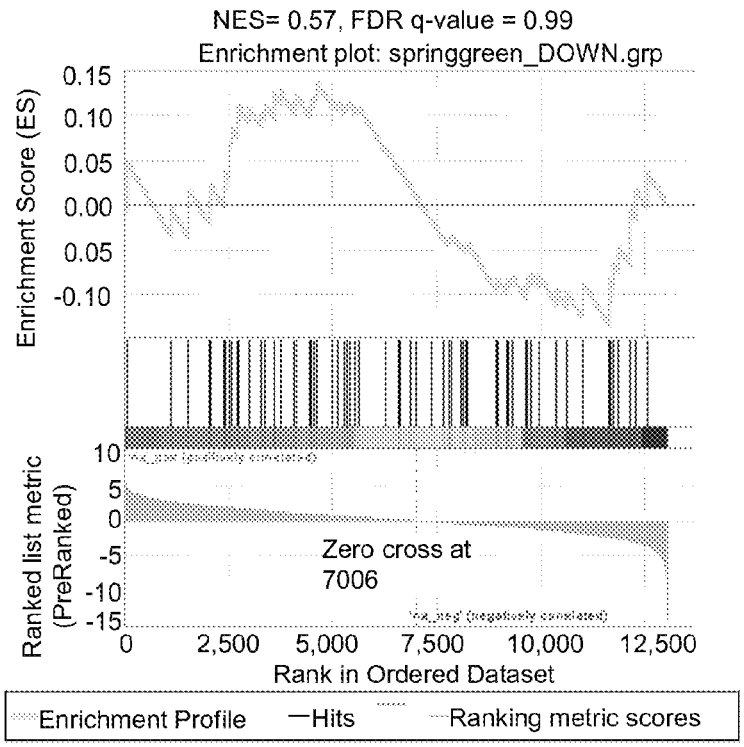
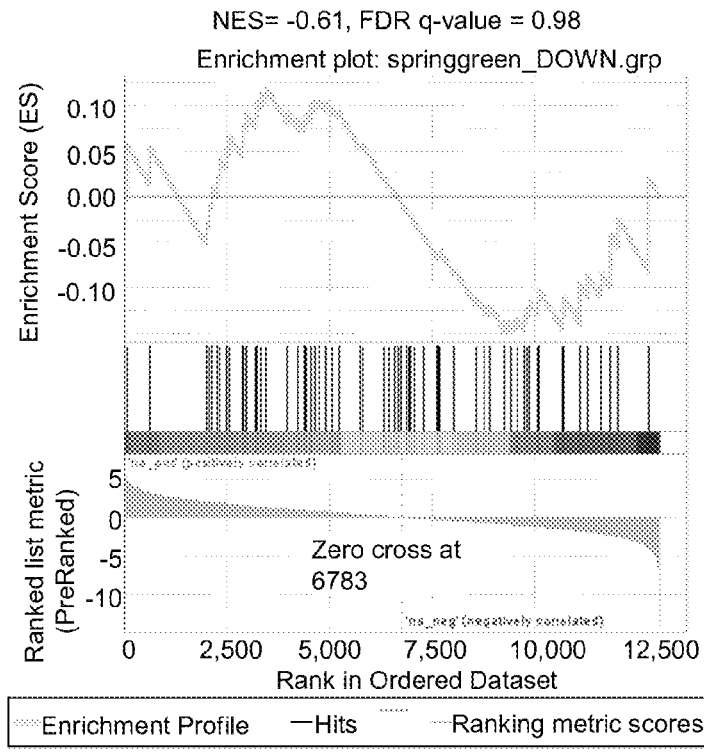

FIG.16I
Springgreen_UP
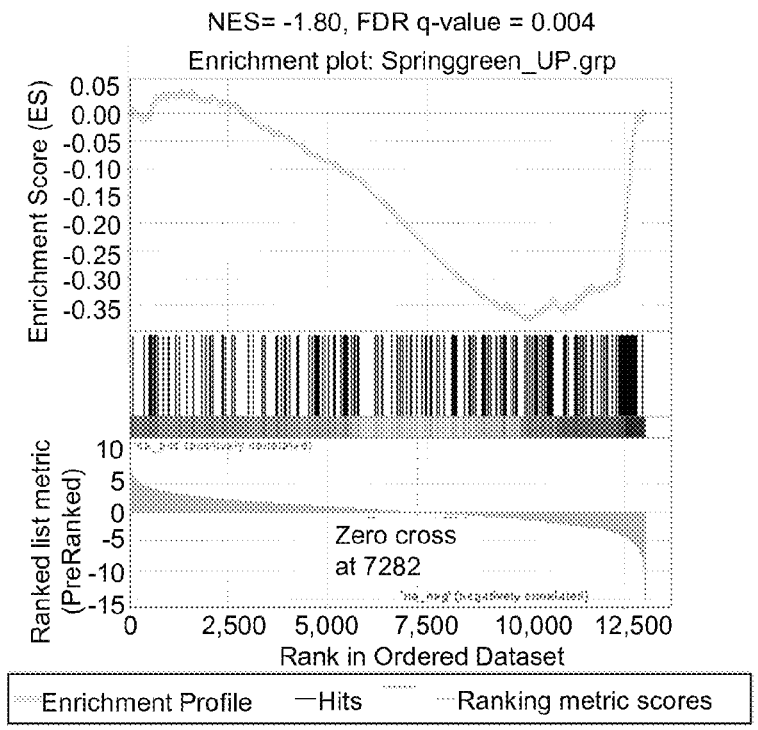
RELAPSED
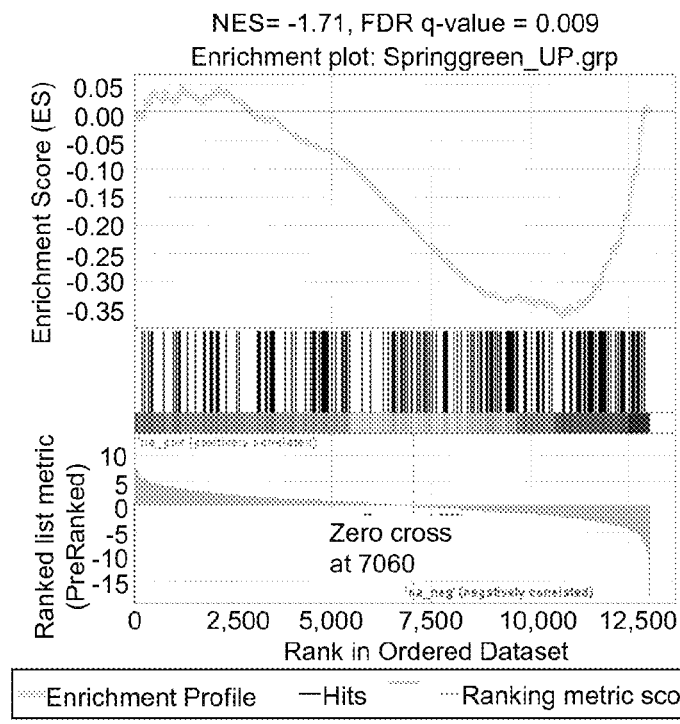
NEW

FIG.16J
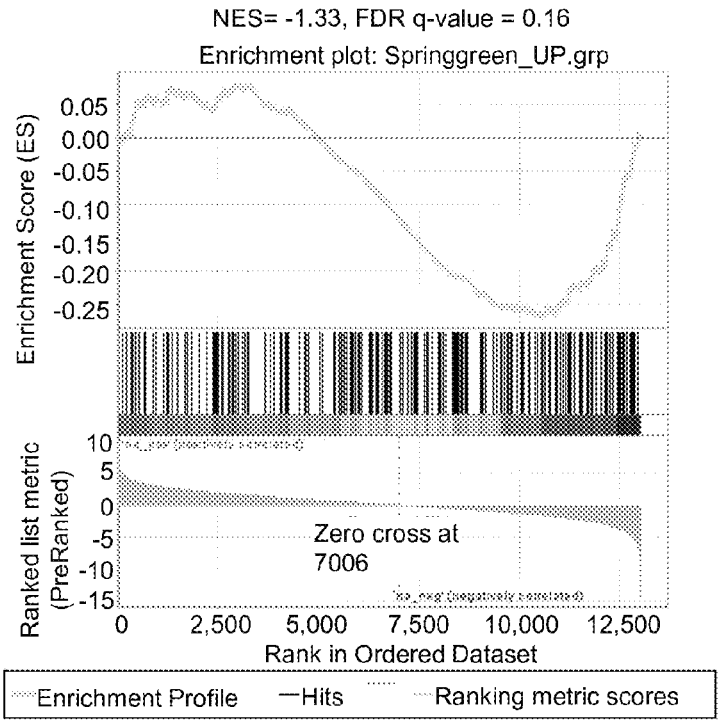
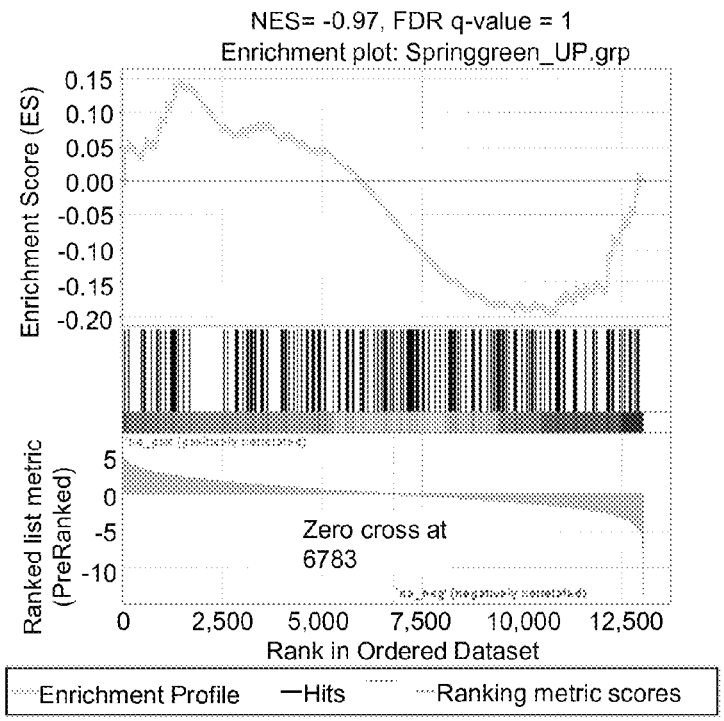

FIG.16K
Red_DOWN
RELAPSED
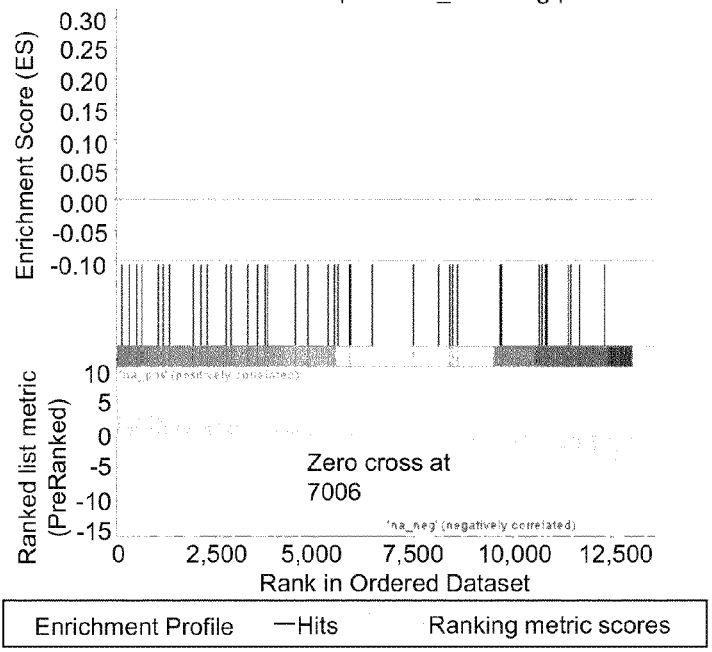
NEW
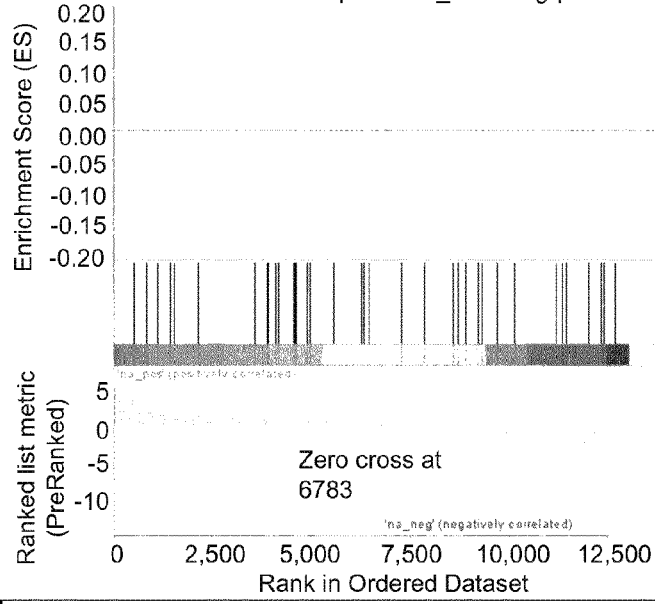

FIG.16L
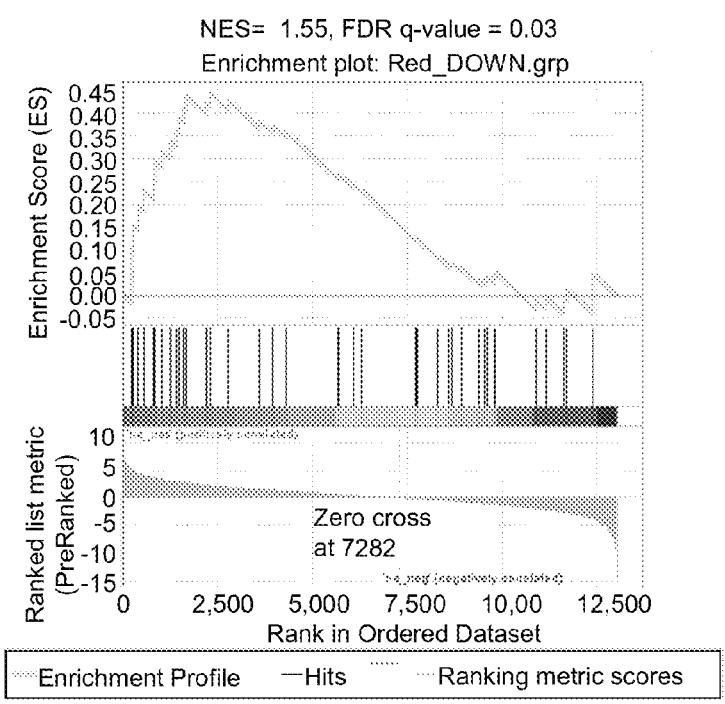
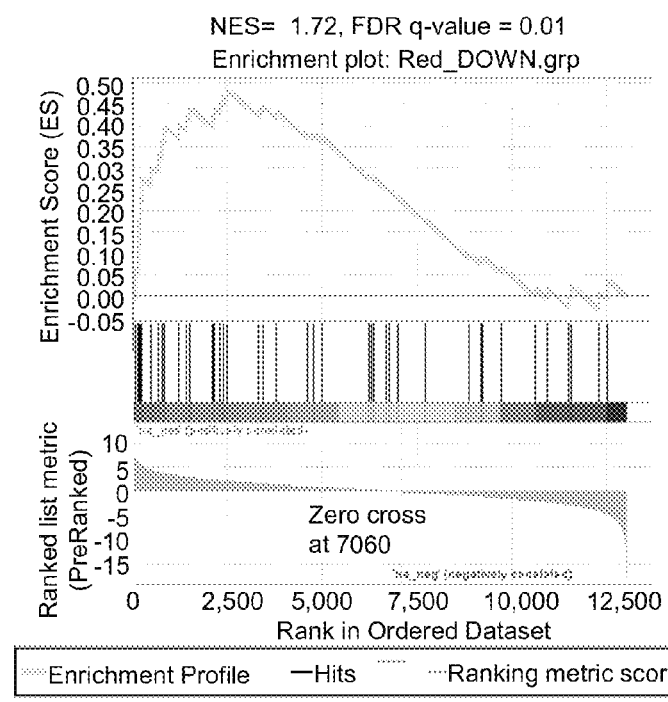

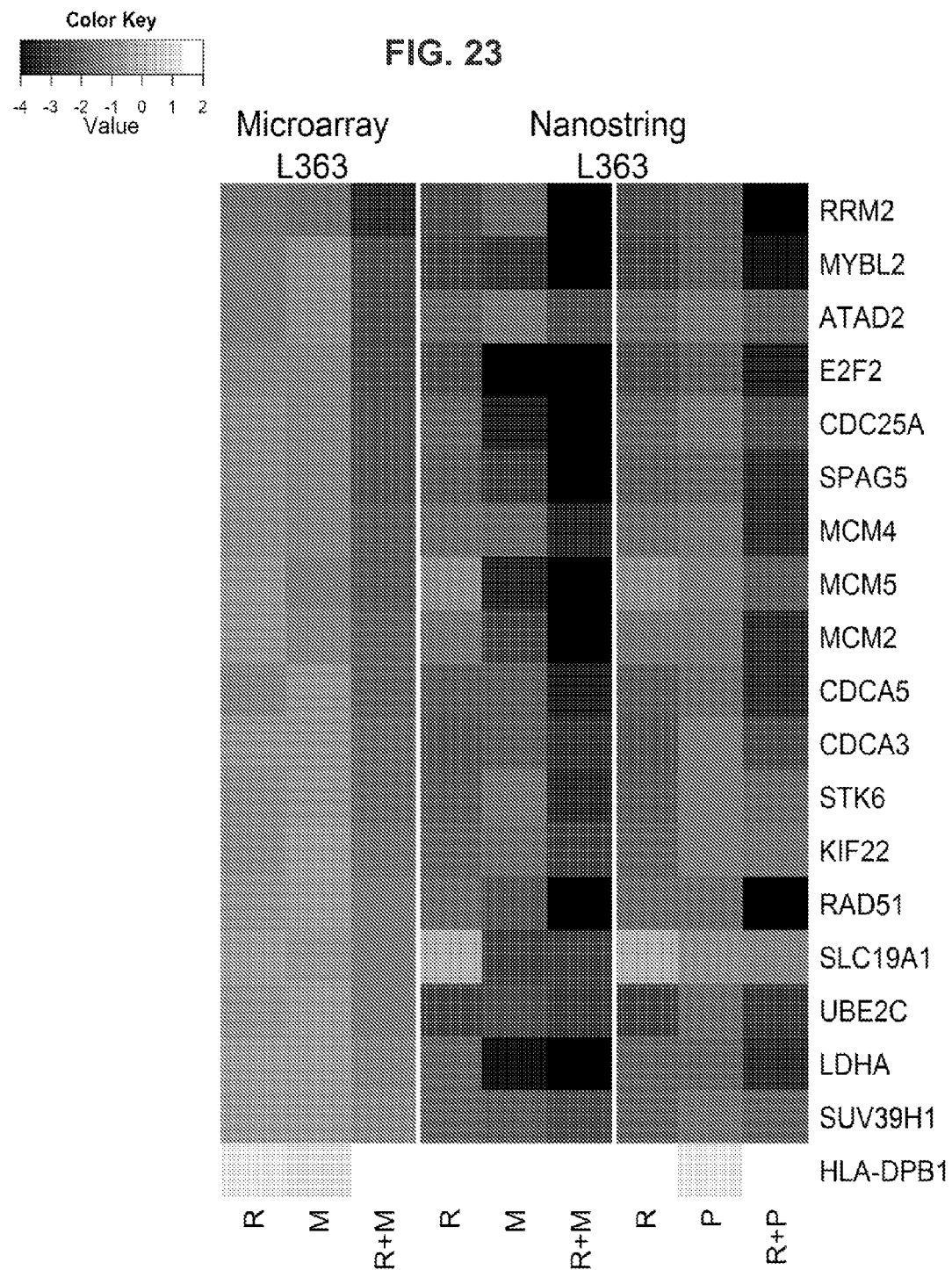

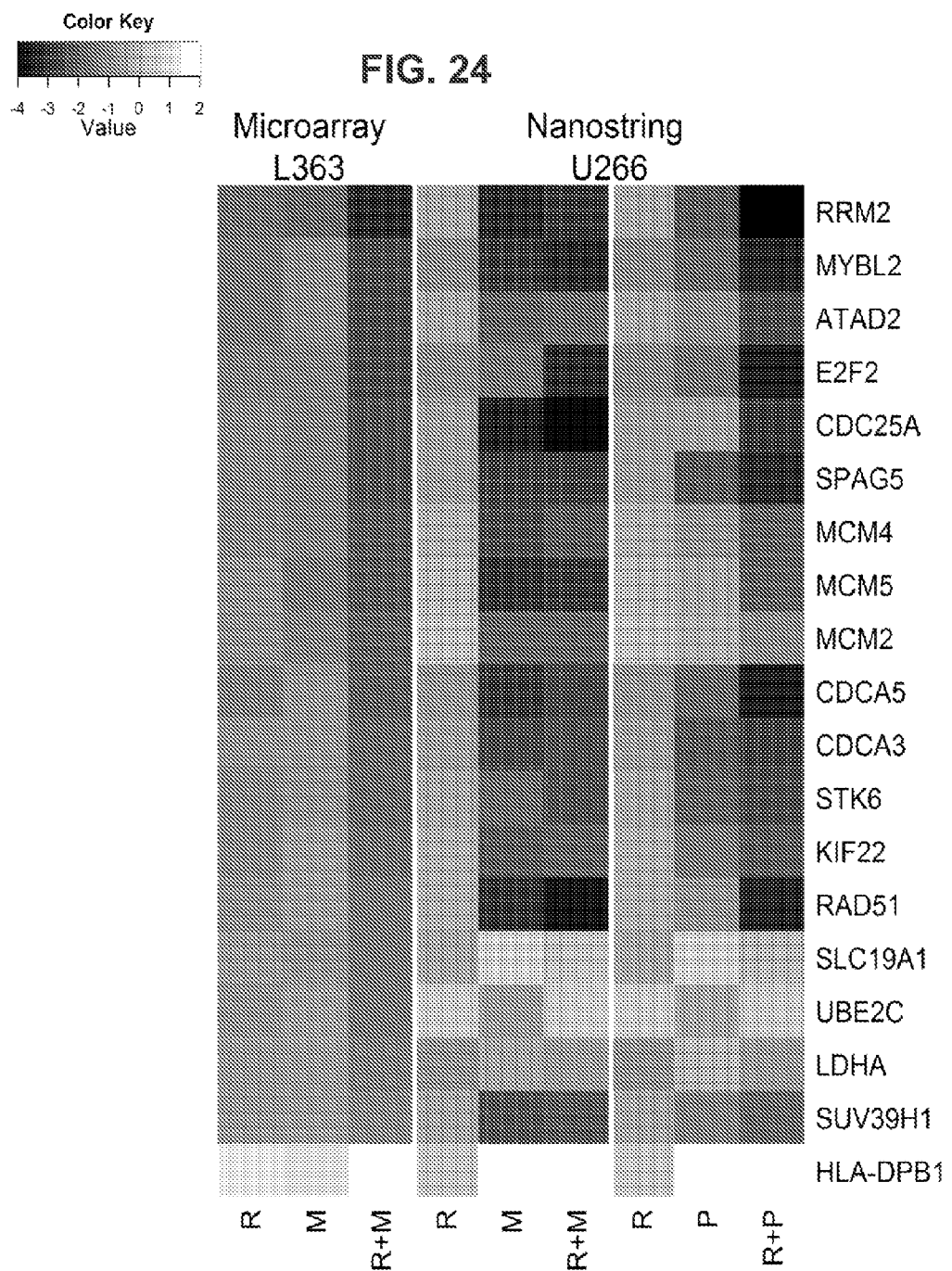

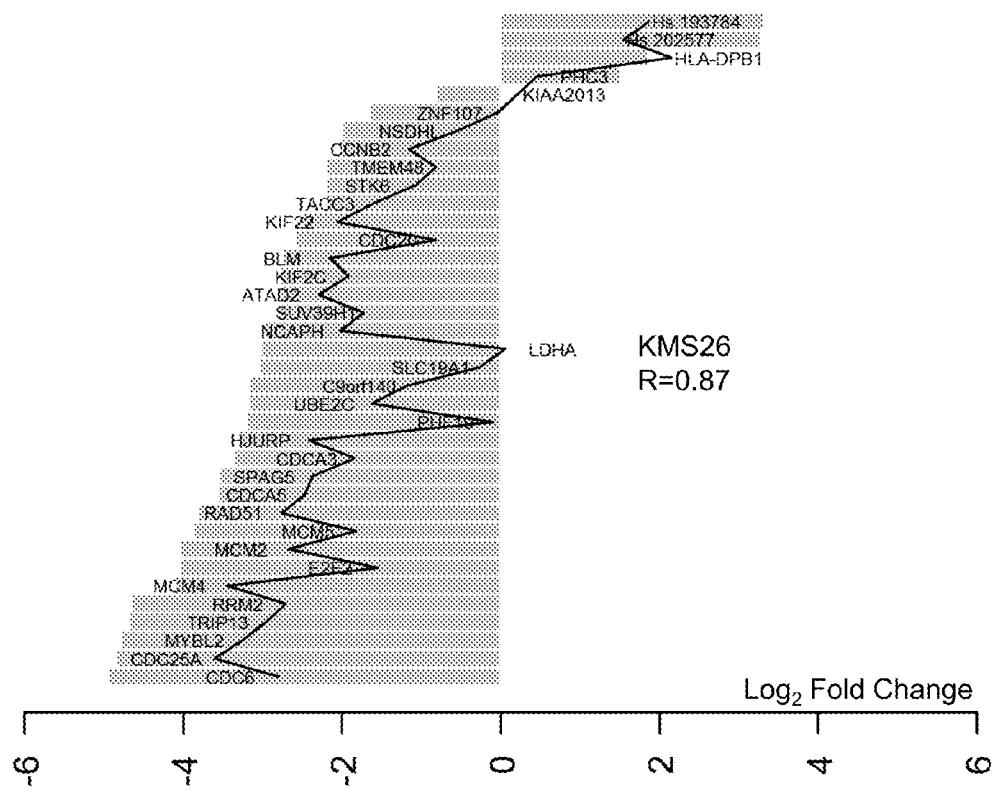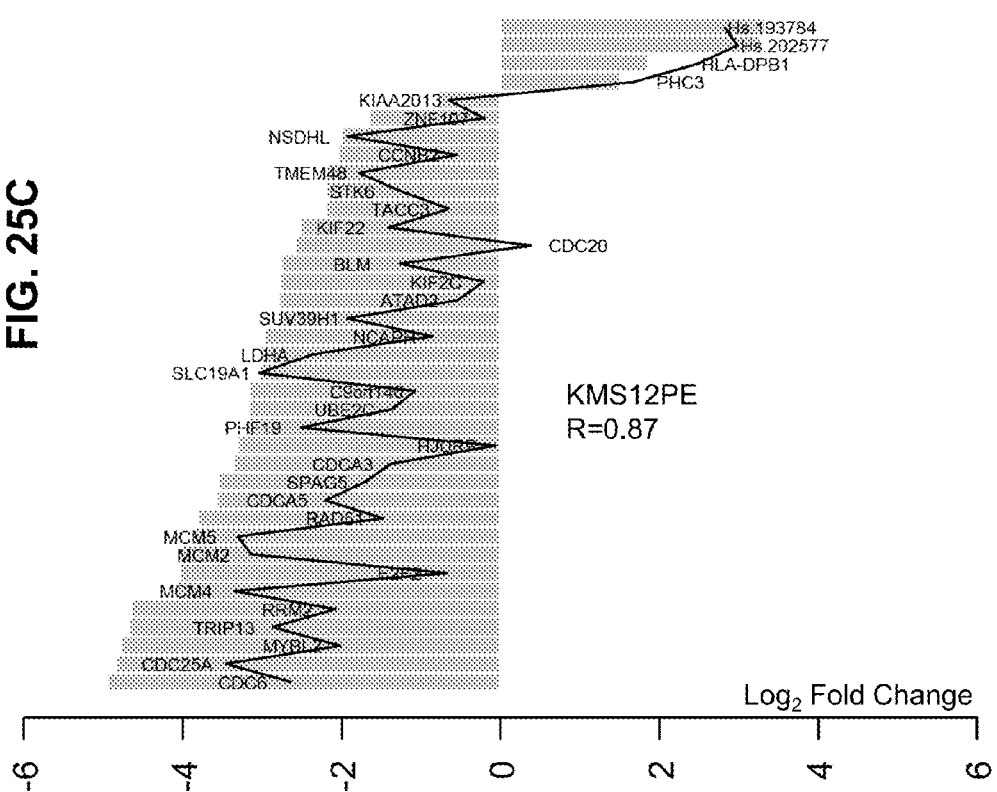
FIG. 25C

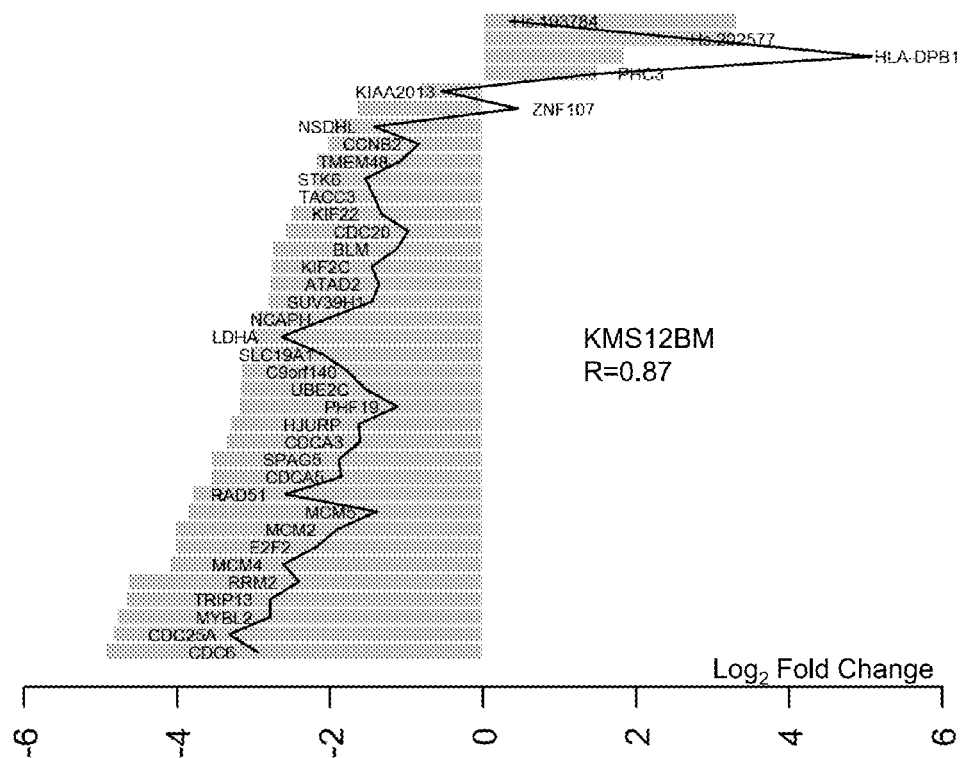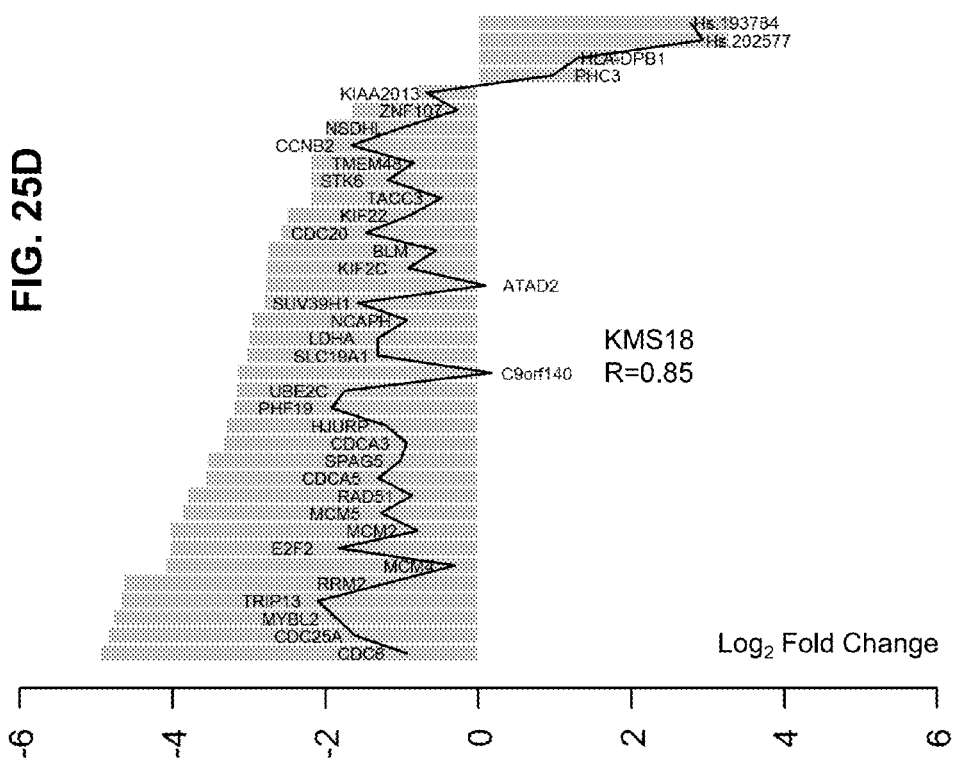
FIG. 25D

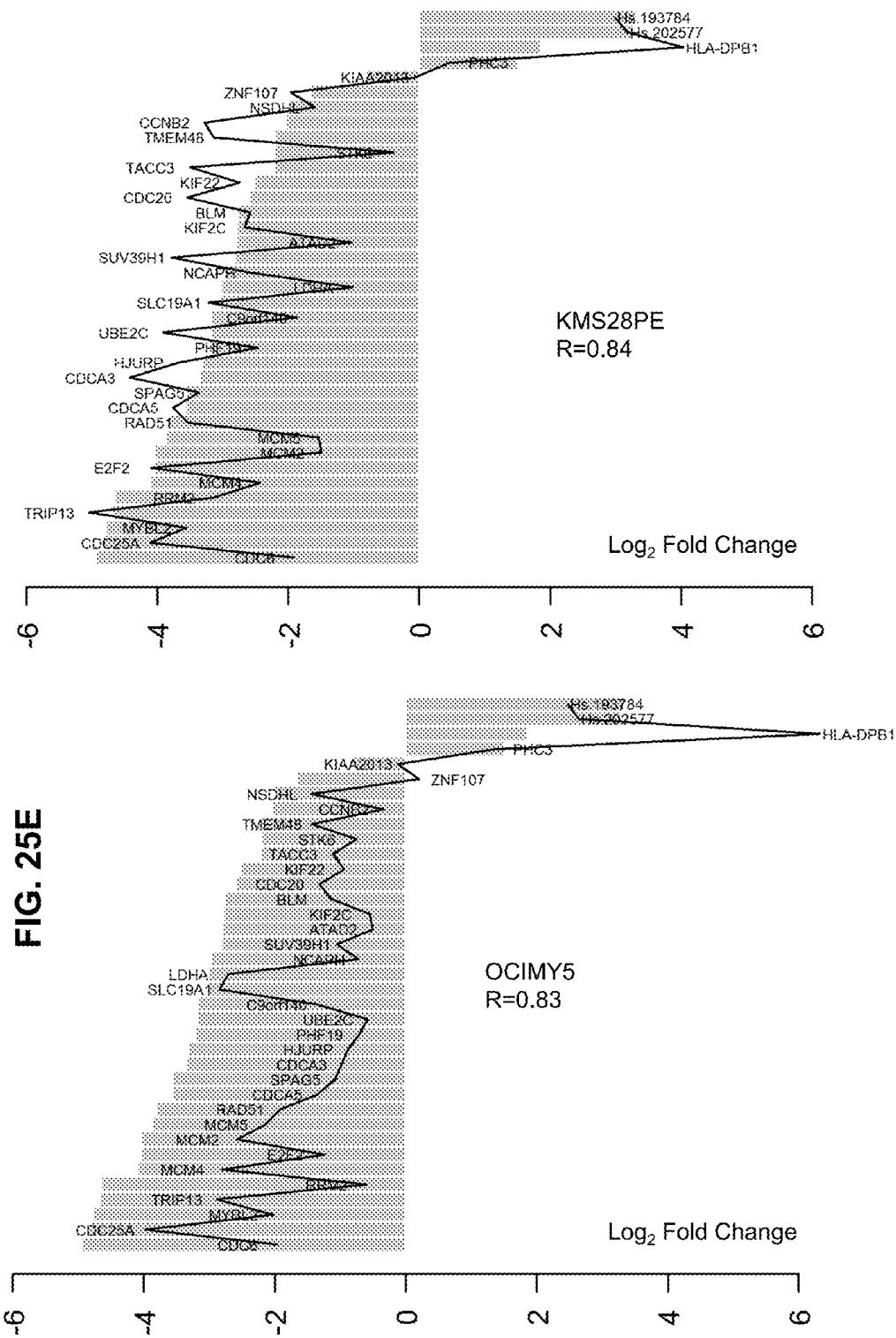

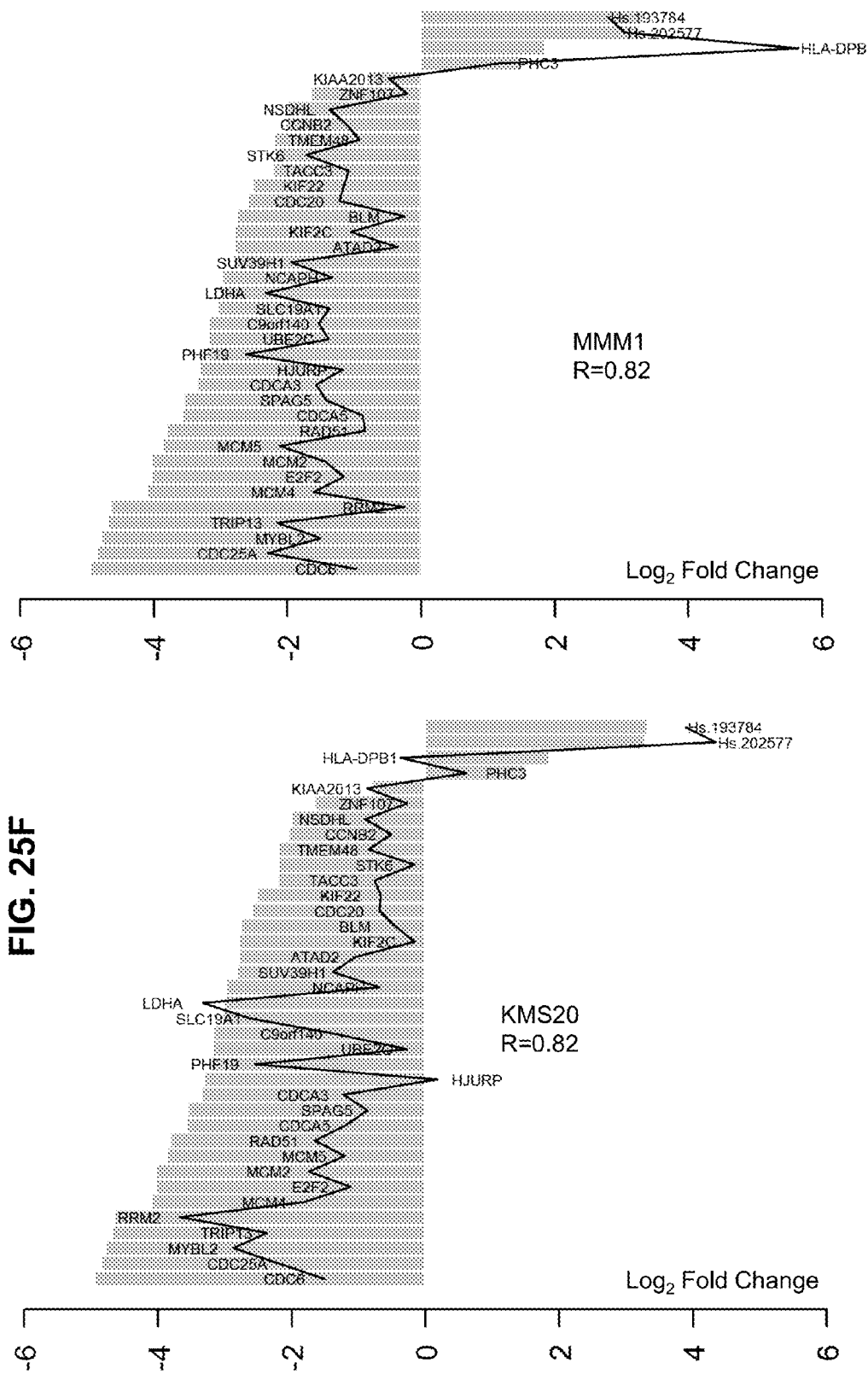

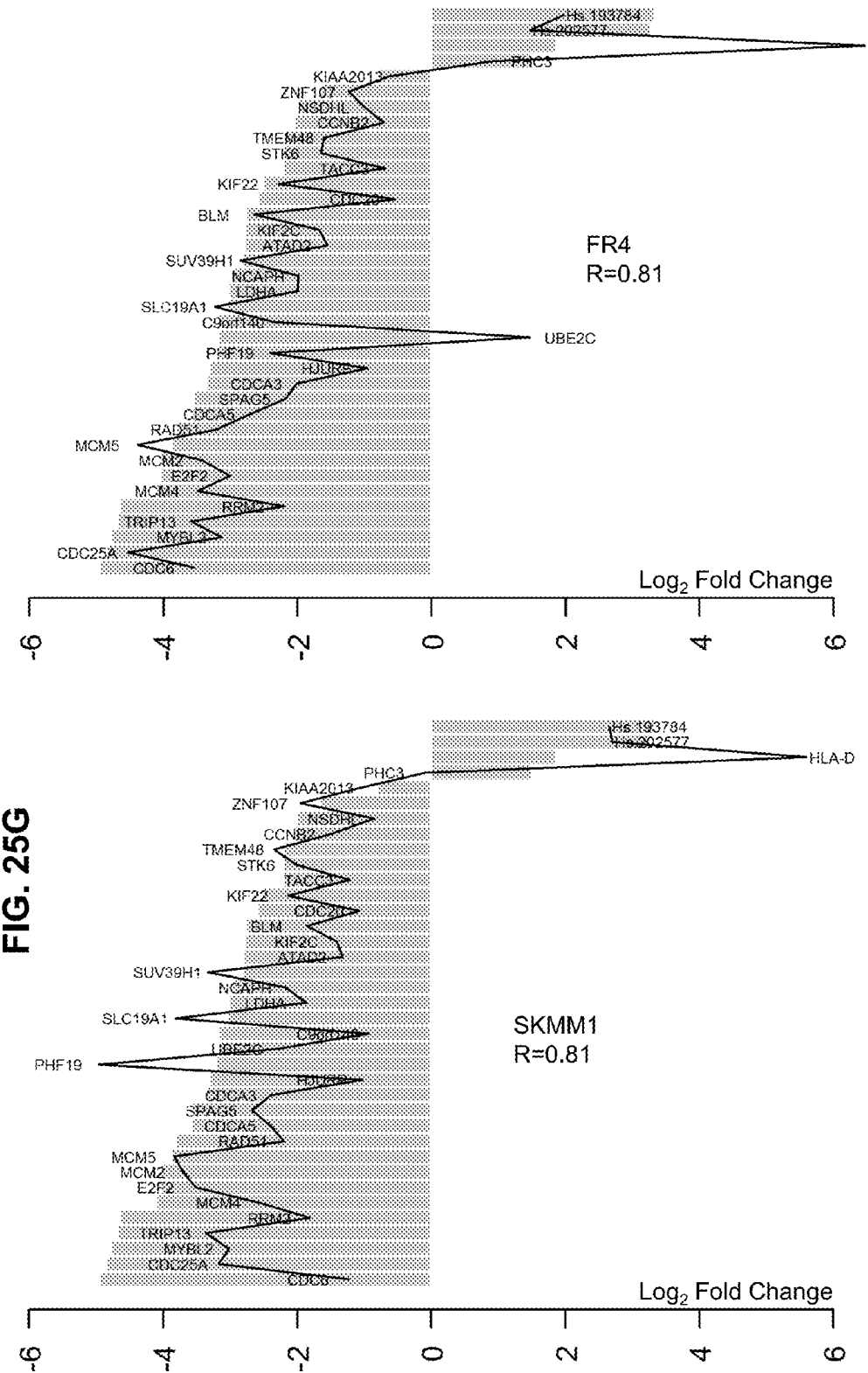

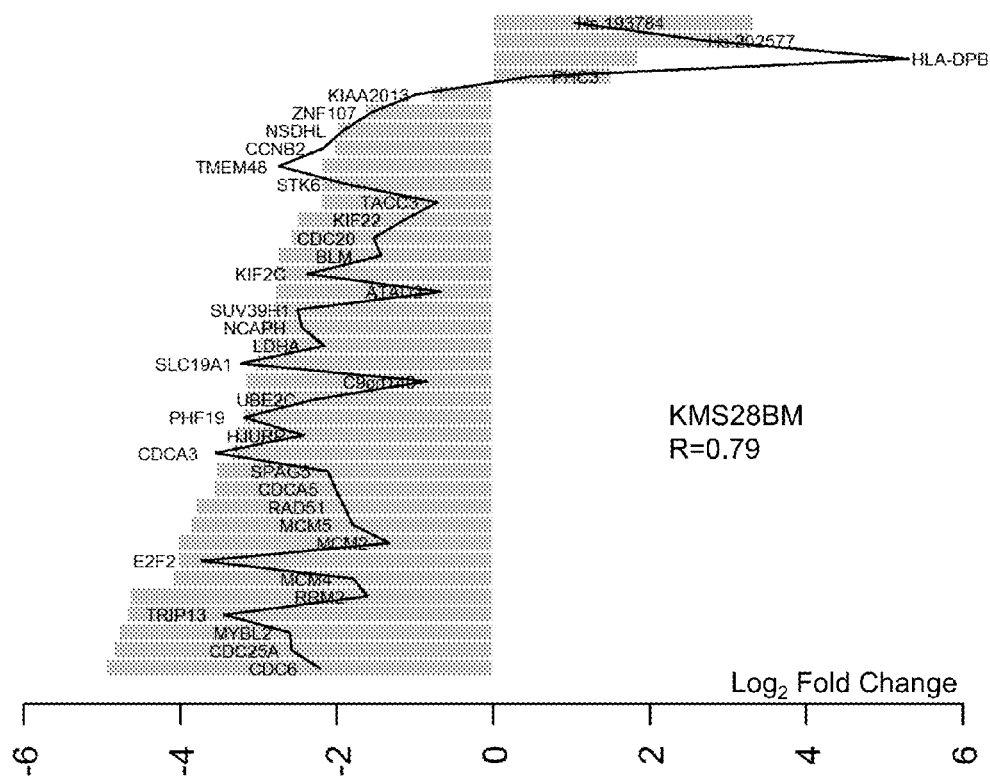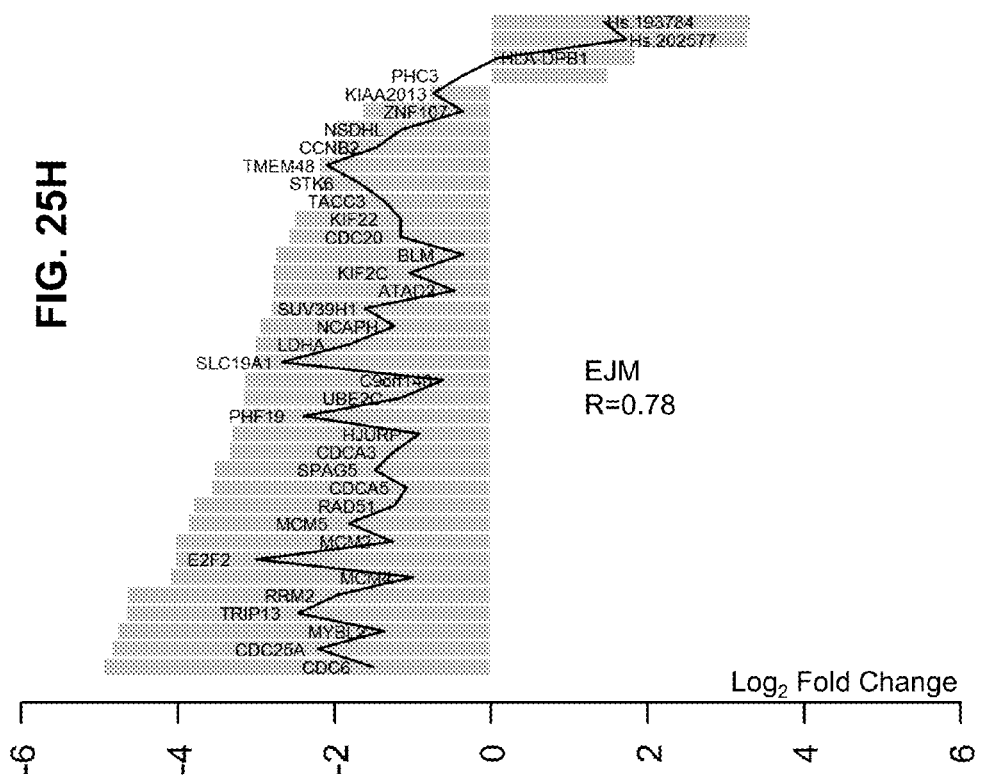
FIG. 25H

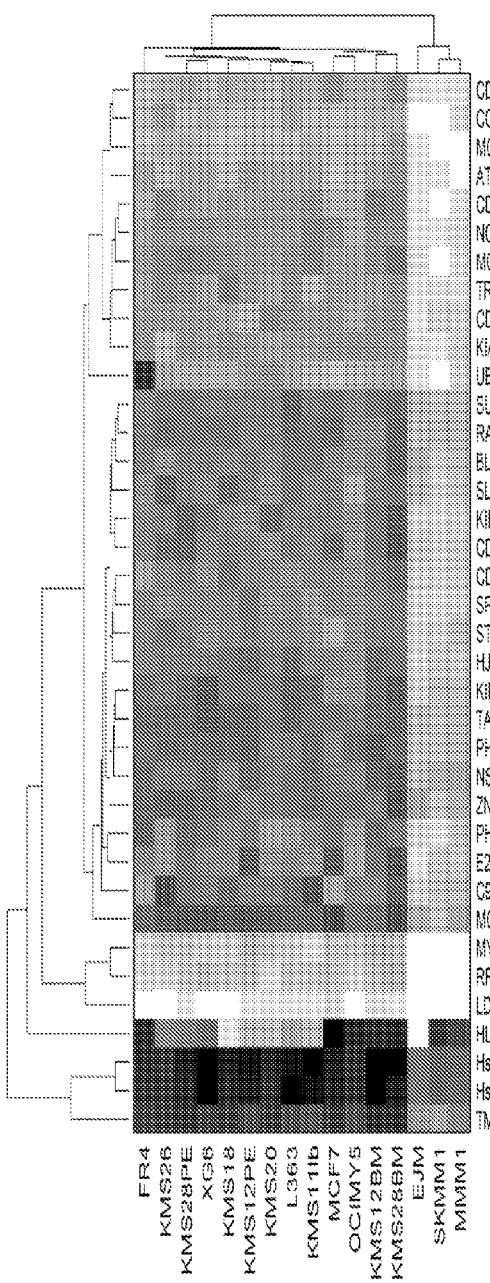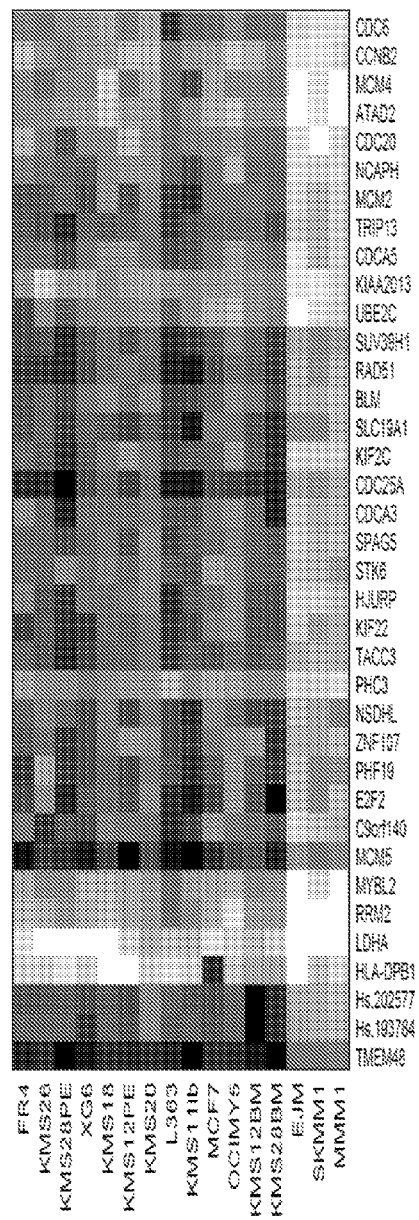
FIG. 27A UNT – log2 intensity, HC (euclidean, average link.)
FIG. 27B RM – log2 intensity, ordered by HC in UNT

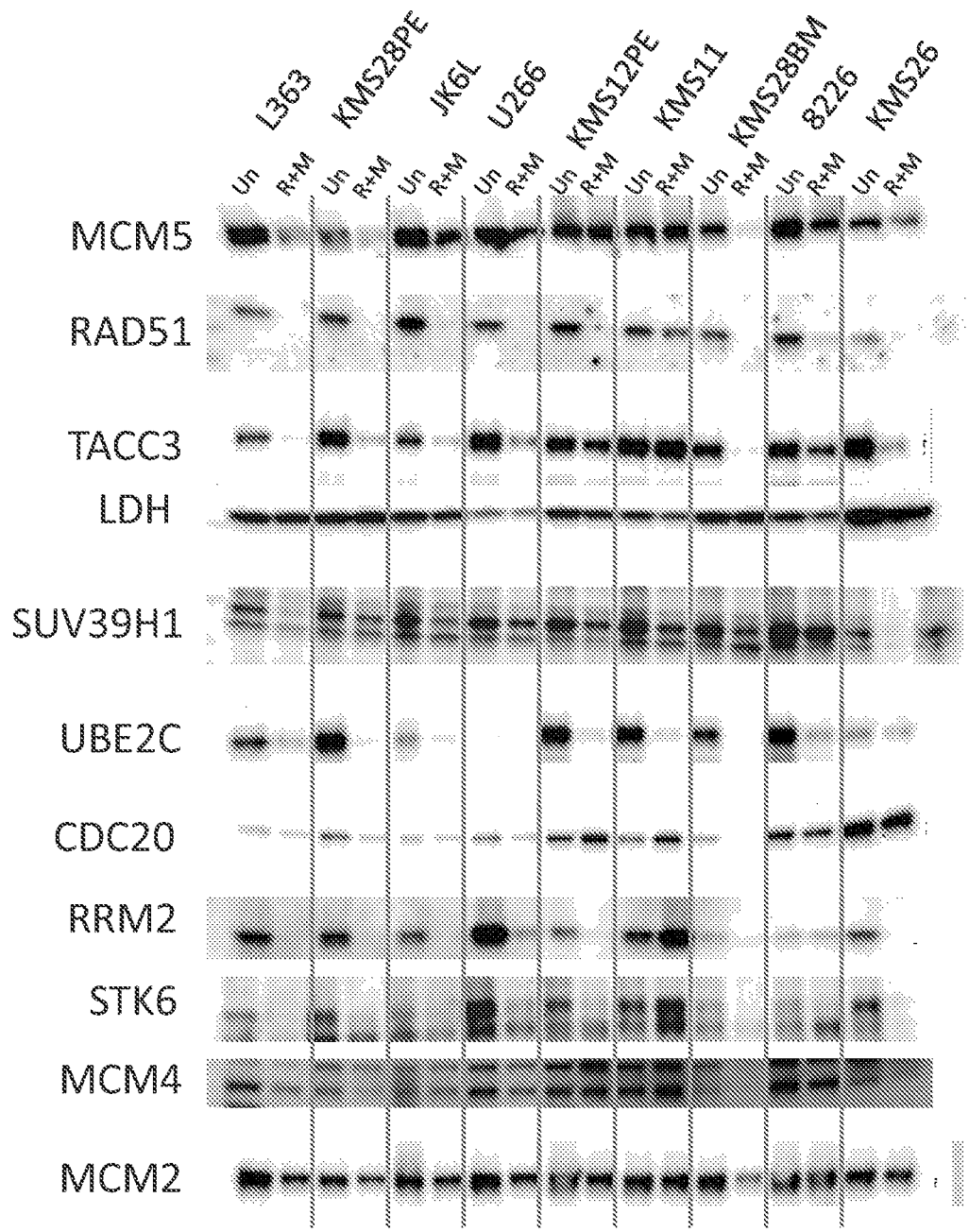

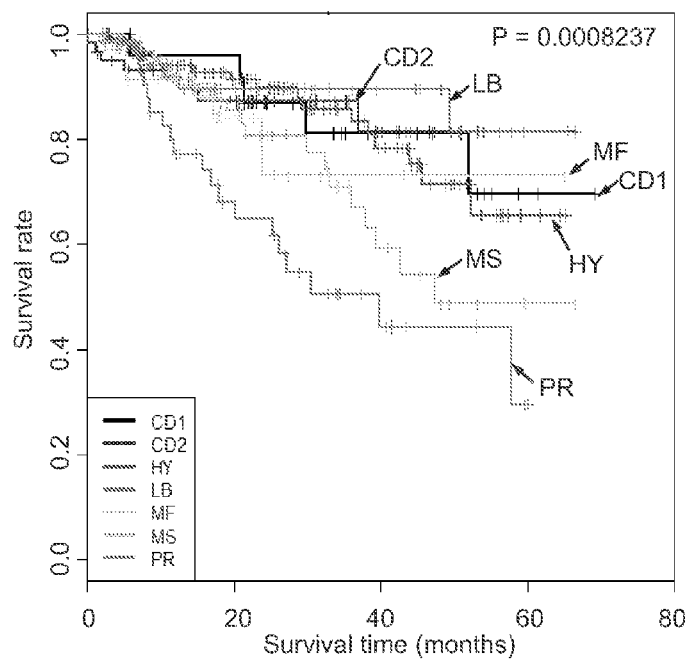
FIG. 29
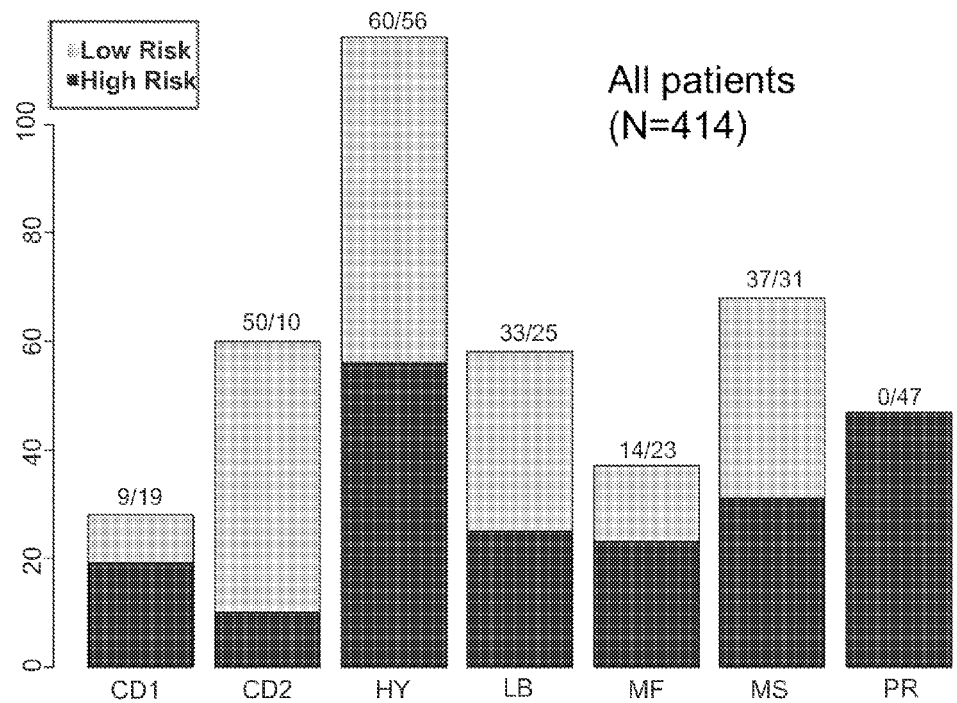

FIG. 30
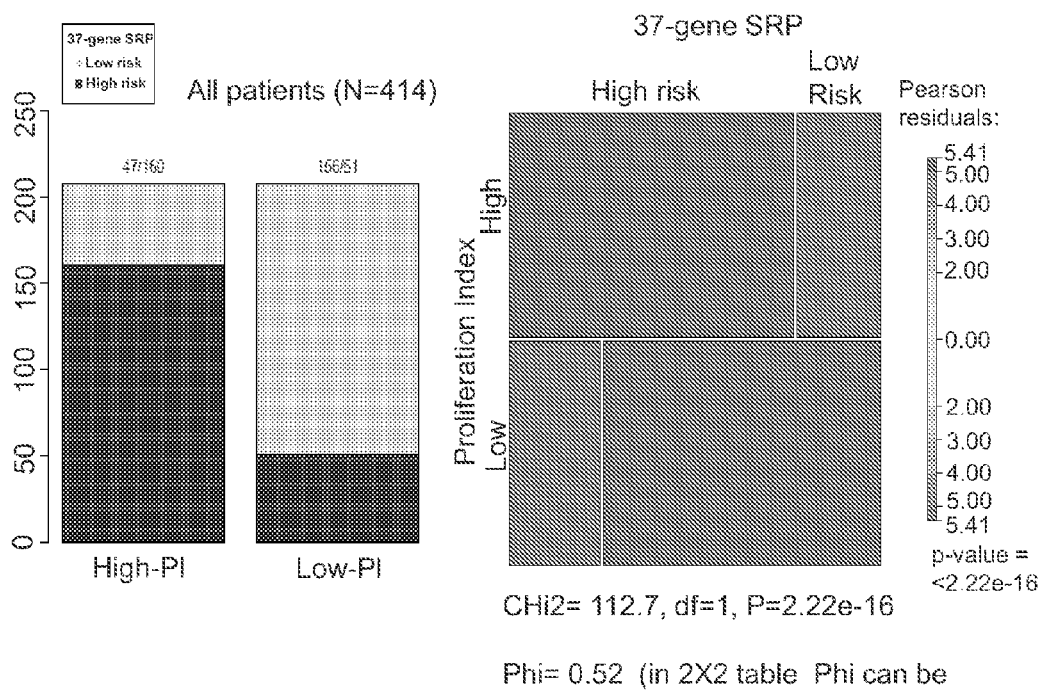
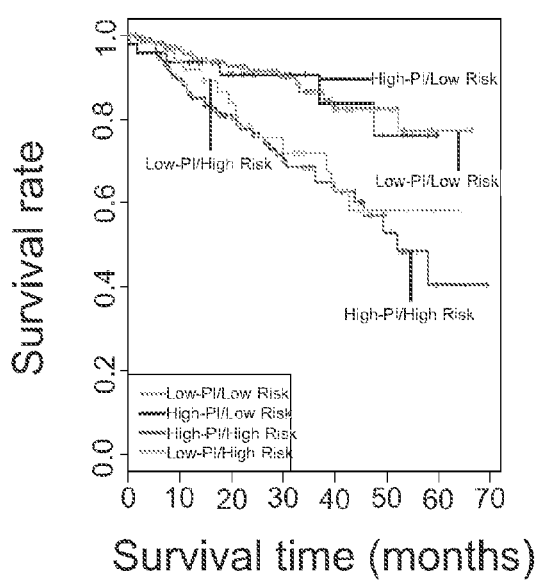
Proliferation index genes:
'TOP2A', 'BIRC5', 'CCNB2', 'NEK2', 'ANAPC7', 'STK6', 'BUB1', 'CDC2'('CDK1'), 'C10orf3'('CEP55'), 'ASPM', 'CDCA1'(NUF2')
In each patient: average expression of the genes
High PI: index greater than median PI in all patients
Low PI: index equal or less than median PI in all patients

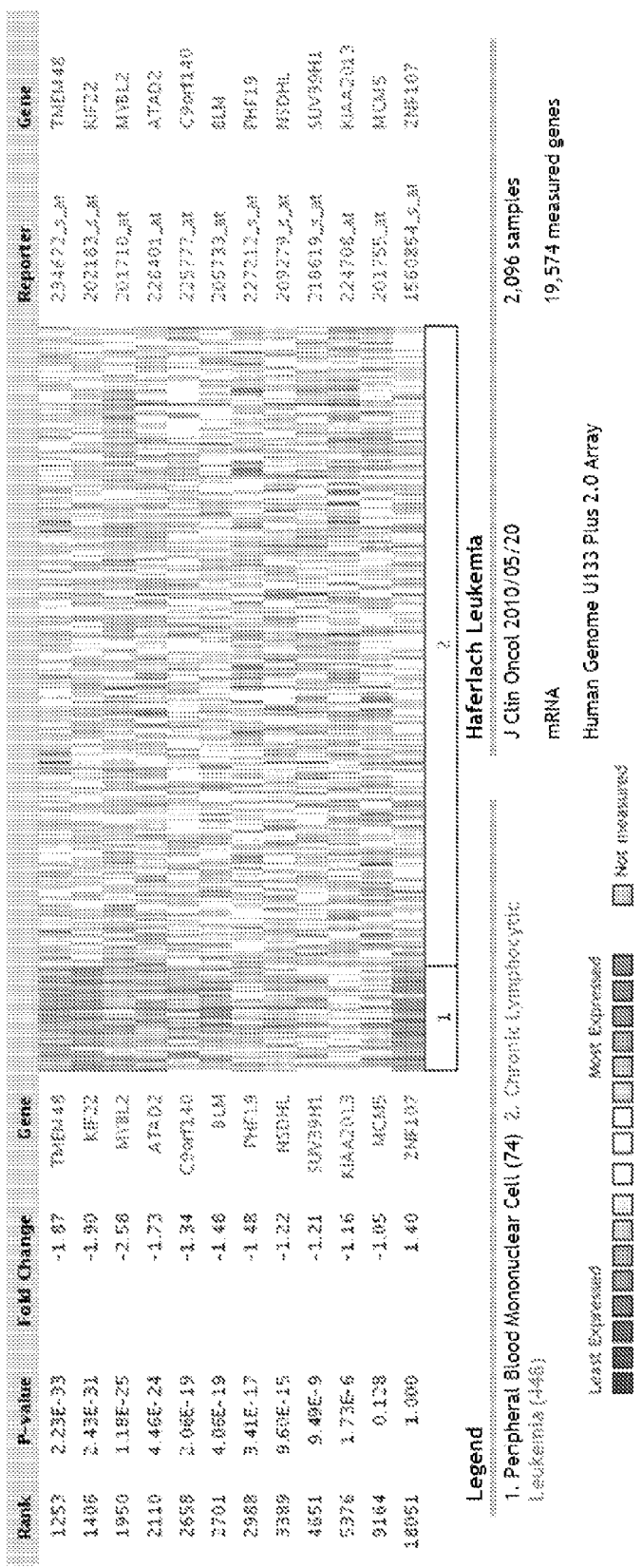

GENE EXPRESSION SIGNATURES OF NEOPLASM RESPONSIVENESS TO THERAPY

CROSS-REFERENCE TO RELATED APPLICATION

This application is the U.S. National Stage of International Application No. PCT/US2012/064693, filed Nov. 12, 2012, which was published in English under PCT Article 21(2), which in turn claims the benefit of U.S. Provisional Application No. 61/558,402, filed Nov. 10, 2011. The provisional application is incorporated by reference herein in its entirety.

PARTIES TO JOINT RESEARCH AGREEMENT

This invention was made under Public Health Service Cooperative Research and Development Agreement (PHS-CRADA) No. 00836 between the National Institutes of Health National Cancer Institute and Syndax Pharmaceuticals, Inc.

FIELD

This disclosure relates to cancer, and particularly to treatment of a neoplasm, methods of predicting treatment responsiveness of a neoplasm, and methods of determining prognosis of a subject with a neoplasm.

BACKGROUND

Histone deacetylase (HDAC) inhibitors (HDACi) and mechanistic target of Rapamycin (mTOR) inhibitors (mTORi) are known anti-cancer agents. The combined use of these agents is known to have anti-cancer efficacy against certain neoplasm subtypes; however, this combined treatment is not efficacious in all neoplasm subtypes, and is not efficacious against all neoplasms within a particular subtype.

SUMMARY

There is a need, for example, for methods of identifying neoplasms that are sensitive to mTORi/HDACi combination therapy, as well as for methods that enable determination of the likely outcome (e.g., prognosis) of a neoplasm or a subject having a neoplasm. Accordingly, disclosed herein are gene expression signatures indicative of neoplasms that are sensitive to mTORi/HDACi combination therapy. Detection of such a signature in a neoplasm sample from a subject can be used to identify a subject having a neoplasm sensitive to mTORi/HDACi combination therapy, as well as for identifying a therapeutically effective amount of such therapy for use in the subject.

Unexpectedly, these gene expression signatures are also useful for prognosis. Thus, in some embodiments, detection of one of the gene expression signatures in a neoplasm sample from a subject indicates a poor prognosis.

The foregoing and other objects, features, and advantages of the embodiments will become more apparent from the following detailed description, which proceeds with reference to the accompanying figures.

BRIEF DESCRIPTION OF THE DRAWINGS

FIGS. 5A-5E are a series of graphs and digital images illustrating cell cycle and apoptosis analysis of cells treated with Rapamycin, MS-275, or a combination thereof. Cell cycle analysis of (A) U266 and (B) L363 cells, control or treated with drugs for 48 hours. Cells were treated individually with entinostat, or sirolimus, or in combination with either simultaneous or sequential treatment. In sequential experiments, the first agent listed was added 24 hours prior to the addition of the second agent. Percentage of (C) U266 or (D) L363 cells in apoptosis was determined by Annexin V at 48 hours. Western blot of (E) U266 or L363 lysates after 48 hours of control, sirolimus, entinostat, or combination treatment probed for cleaved PARP.

FIGS. 9A-9B are a series of graphs illustrating modular network construction. (A) Average hierarchical clustering dendrogram of genes using the one minus topological overlap dissimilarity metric (Langfelder, *BMC Bioinformatics.*, 9:559, 2008). Branches of the dendrogram comprise densely interconnected, highly co-expressed genes (modules), assigned the original module colors (top bar) and the final merged module colors (bottom bar). The original modules were identified with the Dynamic Cut Tree algorithm and summarized by their first principal component of the expression values (module eigengene). Modules with highly correlated eigengenes (correlation coefficient >0.80) were merged into the final modules. The Gray module contains the unassigned genes. (B) Scale-free topology fit of the weighted gene co-expression network (soft threshold β=8). On the x-axis, log 10 of connectivity (k) is plotted, on the y-axis log 10 of the proportion of nodes having given connectivity (p(k)). The distribution of total connectivity (left) and intramodular connectivity (right) was examined. The straight line shows the power-law fit and the curved line shows the exponentially truncated power-law fit.

FIGS. 10A-10E are a series of graphs and charts illustrating network visualizations and module selection to identify the genes affected by both inhibitors. (A) Gene average linkage hierarchical clustering on topological overlap-based dissimilarity and drug-specific module partitioning. Five modules designated as blue, red, darkgreen, springgreen, and orange were identified. (B) The criteria for selection of the drug-related modules linked the ANOVA assessments of treatment effects of sirolimus and entinostat with the network module topology. On top are bar plots of the Pearson's correlation coefficients (r) of intramodular connectivity (kIN) and gene significance (GS) values in a module, and on the bottom are bar plots of the mean gene significance in a module (MS±SEM). An asterisk indicates that module relevance to a drug treatment was significant (p<0.01). (C) Network of the 901 most connected nodes (genes) from the drug-specific modules (Cytoscape edge-weighted, spring-embedded layout algorithm). At least 901 genes were affected by single and double agent treatment. Nodes are colored by module assignment, and sizes are proportional to within-module connectivity. (D) Venn diagram showing the number of genes with expression changes related to the individual or combination drug treatments. (E) Heatmaps of networks by module, corresponding to significant drug-specific effects (white, upregulated; black, downregulated): Cooperative Combination (blue), Neutral Combination (orange), entinostat (springgreen), entinostat (darkgreen), and sirolimus (red). Expression values are mean centered by rows. The eigengene values summarize the major vector (first principal component) of expression in a module. At least 126 genes contributing to the synergy of the drug combination were identified.

FIGS. 11A-11B are a series of scatter plots illustrating the relationship between drug treatment-based gene significance (negative log 10 P-value from two-way ANOVA models) and intramodular connectivity for each network module identified. The vertical line indicates the 0.01 threshold of gene significance. A regression line has been added to each plot. Box plots above the scatter plots depict the distribution of gene significance in a module; the additional vertical line crossing the inter-quartile box is the mean significance in a module. Pearson's correlation coefficient (R) and its significance (Bonferroni corrected P-values), as well as the module significance score (the mean GS) are reported below each plot. Genes in the blue and orange modules were affected by both drugs. Genes in the spring- and dark green modules were affected by MS-275 and genes in the red module were affected by rapamycin/sirolimus.

(FIG. 13A) Cooperative module genes co-expressed with the RRM2 hub gene (scaled kIN=0.67). Node size is proportional to intra-modular connectivity (scaled kIN from 0.37 to 1); the edge color darkens with an increase in pairwise adjacency (between 0.30-0.91, and corresponds to correlation coefficient 0.86-0.99); node label (starred/not starred) depicts the expression fold up-/down-regulation due to combination treatment). (FIG. 13B) Graph of RRM2 expression from microarray; the broken line indicates expected additive effect. (FIG. 13C) Comparison of RRM2 expression between healthy donor CD138+ cells and CD138+ cells from newly diagnosed and treatment relapsed patients in the GSE6477 patient dataset (Irizarry et al., *Biostatistics*, 4:249-264 2003). Western blot of lysates from the L363 cell line treated for 48 hours with sirolimus (10 nM), entinostat (0.5 µM), or Triapine (1 µM), or combinations thereof. (FIGS. 13D-E). L363 cell viability after 48 hour treatment with triapine and/or sirolimus. Significance between treatments was determined by repeated measures ANOVA with the Bonferroni correction.

FIGS. 15A-15C are a set of graphs illustrating enrichment of genes regulated by the drug combination in gene sets comparing patient and healthy plasma cells. (FIG. 15A) The expression pattern representing the disease signature, assessed by comparing relapsed MM patients with healthy controls (t-statistic, right) was the opposite of the drug response signature, assessed by treating L363 cells with the drug combination (fold change, left). Node color reflects the direction of gene expression: white genes overexpressed (patients) or up-regulated (drug treated cell line) and black is under-expressed (patients) or down-regulated (drug treated cell line). Note: Of the 901 top connected genes (FIG. 4C), 594 were available for gene expression analysis in dataset GSE6477. (FIG. 15B-C) Gene set enrichment analysis (GSEA) of the combination cooperative (blue) module up- and down-regulated genes. One-way ANOVA contrast t-statistics were used to rank the genes according to their correlation with either the Multiple Myeloma phenotype (red bar) or the healthy donor phenotype (blue bar). The graph on the bottom of each panel represents the ranked, ordered list of ~13,000 unique genes. Black vertical lines show the position of individual genes from a gene set module in the ordered list of genes. The green line is the profile of the running sum of the weighted enrichment score with the maximum deviation from zero encountered in the random walk (ES). The normalized enrichment score (NES) is the enrichment score adjusted for variation in the gene set size. GSEA was performed for the four groups of multiple myeloma patients reported in GSE6477 (Carrasco et al., *Cancer Cell,* 9:313-325, 2009; Chng et al., *Cancer Res.* 67:2982-2989, 2007).

FIGS. 16A-16L are a set of graphs illustrating GSEA enrichment score curves. Gene set enrichment analysis (GSEA) was performed with the network module gene sets, for which at least ten genes were available in the MM patient data (Red_UP and Orange_DOWN sets were excluded because of small number of genes). One-way ANOVA contrast t-statistics were used to rank the genes according to their correlation with either the Multiple Myeloma phenotype (red bar) or the healthy donor phenotype (blue bar). The graph on the bottom of each panel represents the ranked, ordered list of ~13,000 unique genes. Black vertical lines show the position of individual genes from a gene set module in the ordered list of genes. The green line is the profile of the running sum of the weighted enrichment score with the maximum deviation from zero encountered in the random walk (ES). The normalized enrichment score (NES) is the enrichment score adjusted for variation in the gene set size. GSEA were performed for the four groups of multiple myeloma patients in GSE6477 (Irizarry et al., *Biostatistics,* 4:249-264 2003). Some of the genesets enriched in new and relapsed patients were also enriched in SMM (smoldering myeloma) and monoclonal gammopathy of undetermined significance (MGUS) patients.

(FIG. 18A) (left) Cross-validated "training set" stratified into low risk (N=106) and high risk (N=101) groups (principal components classifier). Permutation P-value computed for the log-rank test. (right) Single split test set stratified into low risk (N=97) and high risk (N=110) groups. Asymptotic p-values were computed for the log-rank test. (FIG. 18B) Survival predictor gene expression (median centered) heatmap of 207 patients in test set. Samples are ordered by increasing risk score from the survival classifier and plotted above the heatmap. Black bars indicate death. (FIG. 18C-D) Cytoscape graph of 37 cooperative module genes in the survival prediction model. Top: node color (red/green) depicts the expression fold up-/down-regulation due to combination. Bottom: node color reflects value of univariate Cox regression coefficients: (white, increased risk of death associated with increasing gene expression; black, increased risk of death associated with decreasing gene expression). Node size reflects scaled intramodular connectivity, and hub genes are grouped on the left side of each sub-network. Increased adjacency (higher connection strength between nodes) is indicated by darker edge color. The drug combination effects are opposite to the gene expression associated with poor prognosis, except KIAA201 (triangular shape).

FIG. 23 is a heatmap showing log 2 expression fold change of 19 survival-associated, cooperatively affected genes in the MM cell line L363 as detected by microarray and Nanostring® platforms. Log 2 expression fold change is shown for single agent Rapamycin, MS-275, and panobinostat (a pan-HDAC inhibitor), as well as the combination of Rapamycin/MS-275, and Rapamycin/panobinostat.

FIG. 24 is a heatmap showing log 2 expression fold change of 19 survival-associated, cooperatively affected genes in the human MM cell line U266 as detected by the Nanostring® platform. Log 2 expression fold change is shown for single agent Rapamycin, MS-275, and panobinostat (a pan-HDAC inhibitor), as well as the combination of Rapamycin/MS-275, and Rapamycin/panobinostat.

FIGS. 25A-25H are a set of plots of log 2 fold change expression (untreated vs. Rapamycin+MS-275) of the survival-associated 37-gene cooperative drug response signature in 15 human MM cell lines and 1 human breast cancer cell line (MCF-7) for comparison. Shaded grey bars on each graph depict the log 2 expression fold change of R+M treated L363 (Combination responsive cell line) as a comparator. The r value for each line is the comparison of its response with L363. Of particular note, KMS-26, KMS-18, OCI-MY5, KMS-20, and EJM all have <EC50 response to this combination dose (10 nM Rapamycin+500 nM MS-275 for 48 hours).

FIGS. 27A-27C are a set of heatmaps illustrating the intensity of gene expression in a series of cell lines before and after mTORi/HDACi combination treatment. The log 2 gene expression intensity before (FIG. 27A) and after (FIG. 27B) Rapamycin/MS-275 combination treatment of the survival-associated 37-gene cooperative drug response signature in 15 human MM cell lines and one human breast cancer cell line (MCF-7; for comparison) is shown. Euclidean hierarchical clustering was used to cluster the genes and cell lines based on untreated expression. Of particular note, KMS-26, KMS-18, OCI-MY5, KMS-20, and EJM all have <EC50 response to this combination dose (10 nM Rapamycin+500 nM MS-275 for 48 hours). The pharmacodynamic nature of this gene expression classifier is further illustrated in FIG. 27C, where the log 2 fold change of gene expression is shown as measured at 8, 24, and 48 hour time points after in vitro combination treatment.

FIG. 28 is a series of digital images illustrating Western blots showing protein expression of 11 survival-associated cooperative drug response signature genes in untreated and R+M combination treated (48 hours) human MM cell lines.

FIG. 29 is a graph illustrating the distribution of patient groups classified by the 37-gene mTORi/HDACi signature in the seven molecular subtypes of MM (CD-1, CD-2 (CCND1/CCND3 subgroups 1 and 2), HY (hyperdiploid), LB (low bone disease), MF (MAF/MAFB), MS (MMSET), PR (proliferation subgroup)) as defined in GSE4581 (Zhan et al., *Blood,* 108:2020-2028, 2006). The graph shows survival rate on the Y-axis and survival time on the X-axis.

FIG. 30 illustrates the distribution of patient groups classified by the 37-gene mTORi/HDACi signature between patients having a HIGH or LOW Proliferation Index (PI) scores. The average expression of the 11 PI genes (Than et al., *Blood,* 108:2020-2028, 2006) was taken for each patient. HIGH PI defined as index higher than median PI of all 414 patients, and LOW PI defined as index lower than median. The 37 genes act in a fashion unlinked to proliferative index, despite the fact that most patients with a high proliferative index are likely to benefit from the drug combination.

DETAILED DESCRIPTION

I. Abbreviations

Figure 1A:
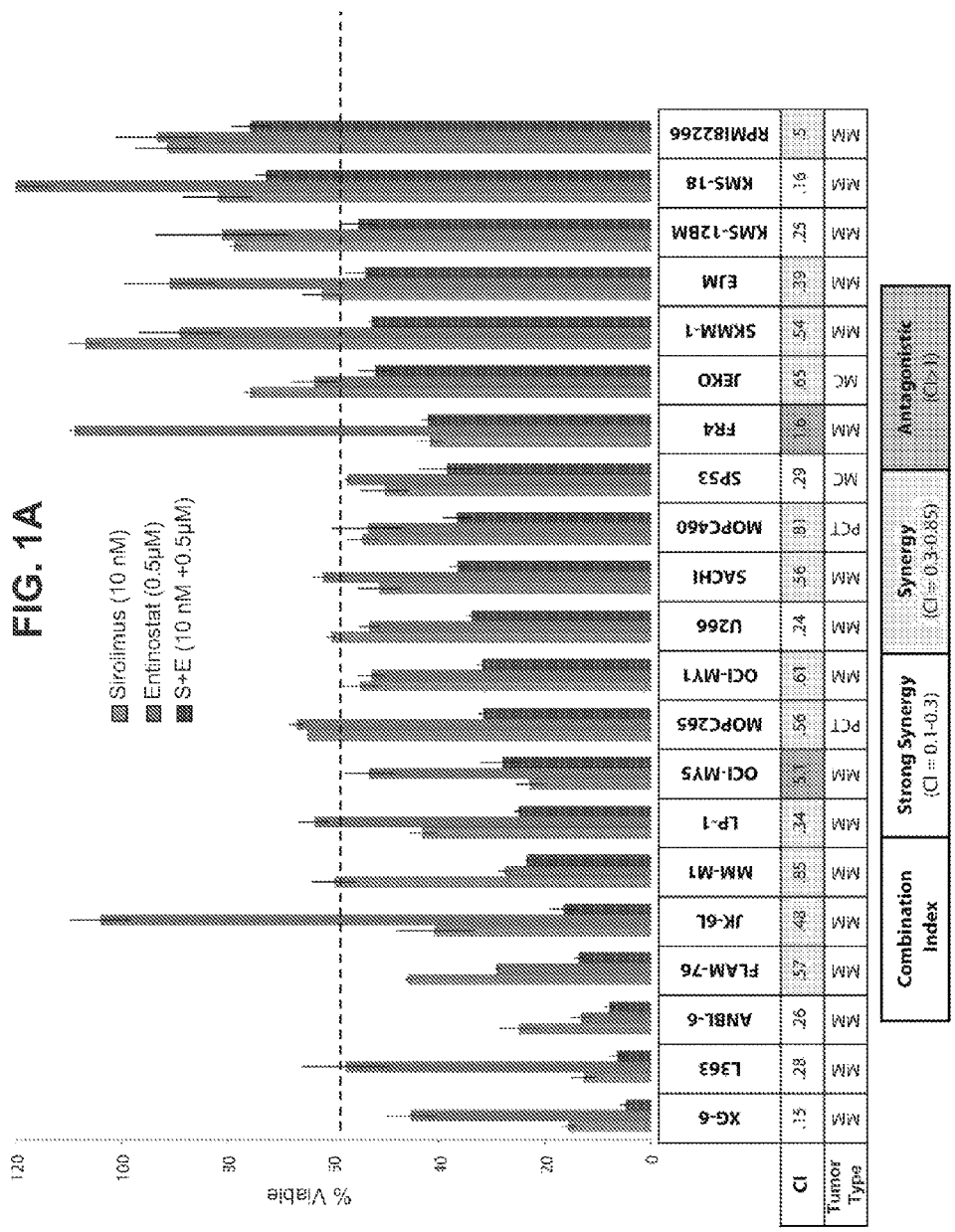
FIGS. 1A-1D are a series graphs illustrating in vitro and in vivo studies of growth inhibition. (A) Combination treatment with entinostat (also known as MS-275) and sirolimus (also known as Rapamycin) was synergistic in its effect on growth inhibition in 90% of multiple myeloma (MM), mouse plasmacytoma (PCT) and mantle cell lymphoma (MCL) cell lines tested. The bar graph shows, in order, sirolimus, Entinostat, and combination sirolimus and Entinostat, treatment for each cell line. (B) Time course photon flux imaging of L363 xenografts during treatment with vehicle (control) or entinostat (10 and 20 mg/kg), sirolimus (2.5 and 5 mg/kg), and the combination (2.5 mg/kg of sirolimus and 20 mg/kg entinostat). (C) Tumor weights of L363 xenografts at the conclusion of treatment. There were no palpable tumors in the mice receiving combination treatment. (D) Tumor weights of U266 xenografts after twelve weeks of treatment (except for untreated controls, which were collected at four weeks). In all panels, (*) represents p value <0.05 for the combination treatment relative to vehicle and single agent treatments (ANOVA, Bonferroni's multiple comparisons test).

ATAD2 ATPase family, AAA domain containing 2
BLM Bloom syndrome, RecQ helicase-like
C9orf140 Chromosome 9 open reading frame 140
CCNB2 Cyclin B2
CDC20 Cell division cycle 20 homolog (*S. cerevisiae*)
CDC25A Cell division cycle 25 homolog A (*S. pombe*)
CDC6 Cell division cycle 6 homolog (*S. cerevisiae*)
CDCA3 Cell division cycle associated 3
CDCA5 Cell division cycle associated 5
cDNA Complementary deoxyribonucleic acid
E2F2 E2F transcription factor 2
EST Expressed sequence tag
GSEA Gene Set Enrichment Analysis
HDAC Histone deacetylase
HDACi Histone deacetylase inhibitor
HJURP Holliday junction recognition protein
HLA-DPB1 Major histocompatibility complex, class II, DP beta 1
KIF22 Kinesin family member 22
KIF2C Kinesin family member 2C
LDHA Lactate dehydrogenase A
MCL Mantle cell lymphoma
MCM2 Minichromosome maintenance complex component 2
MCM4 Minichromosome maintenance complex component 4
MCM5 Minichromosome maintenance complex component 5
MGUS monoclonal gammopathy of undetermined significance
mTOR Mechanistic Target of Rapamycin
mTORi Mechanistic Target of Rapamycin inhibitor
MYBL2 V-myb myeloblastosis viral oncogene homolog (avian)-like 2
NCAPH Non-SMC condensin I complex, subunit H
NSDHL NAD(P) dependent steroid dehydrogenase-like
PCT Plasmacytoma
PHC3 Polyhomeotic homolog 3 (*Drosophila*)
PHF19 PHD finger protein 19
PBMC Peripheral blood mononuclear cell
RAD51 RAD51 homolog (RecA homolog, *E. coli*) (*S. cerevisiae*)
RRM2 Ribonucleotide reductase M2
SLC19A1 Solute carrier family 19 (folate transporter), member 1
SMM Smoldering myeloma
SPAG5 Sperm associated antigen 5
STK6 Aurora kinase A
SUV39H1 Suppressor of variegation 3-9 homolog 1 (*Drosophila*)
TACC3 Transforming, acidic coiled-coil containing protein 3
TMEM48 Transmembrane protein 48
TRIP13 Thyroid hormone receptor interactor 13
UBE2C Ubiquitin-conjugating enzyme E2C
ZNF107 Zinc finger protein 107

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which the embodiments belong. The word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present embodiments, suitable methods and materials are described below. All publications, patent applications, patents, and other references mentioned herein are incorporated by reference in their entirety. The nucleic acid and/or protein sequences corresponding to all GenBank Accession Nos. mentioned herein are incorporated by reference in their entirety as present in GenBank on Oct. 21, 2011. In case of conflict, the present specification, including explanations of terms, will control. In addition, the materials, methods, and examples are illustrative only and not intended to be limiting.

In order to facilitate review of the various embodiments, the following explanations of specific terms are provided:

Antibody: A polypeptide ligand comprising at least a light chain or heavy chain immunoglobulin variable region which specifically recognizes and binds an epitope of an antigen, such as one of the proteins disclosed herein or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, *Immunology*, 3rd Ed., W.H. Freeman & Co., New York, 1997.

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least one, to at least 3, at least 10, at least 20, at least 30, at least 50, at least 75, at least 100, at least 150, at least 200, at least 300, at least 500, least 550, at least 600, at least 800, at least 1000, at least 10,000, or more. In some examples, arrays include positive and/or negative controls, such as housekeeping markers. In particular examples, an array includes nucleic acid molecules, such as oligonucleotide sequences that are at least 15 nucleotides in length, such as about 15-40 nucleotides in length.

Breast cancer: A neoplasm of breast tissue that is or has potential to be malignant. The most common type of breast cancer is breast carcinoma, such as ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV). See, for example, Bonadonna et al., (eds), *Textbook of Breast Cancer: A clinical Guide the Therapy*, $3^{rd}$; London, Taylor & Francis, 2006.

Chemotherapeutic agent: Any chemical agent with therapeutic usefulness in the treatment of diseases characterized by abnormal cell growth. Such diseases include neoplasms (e.g., tumors) and cancer. For example, chemotherapeutic agents are useful for the treatment of cancer, including breast cancer and multiple myeloma. In one embodiment, a chemotherapeutic agent is an inhibitor of HDAC or mTOR activity, such as MS-275 or Rapamycin, respectively. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., Chemotherapy, Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Williams & Wilkins, 2005; Skeel, *Handbook of Cancer Chemotherapy* (6th ed.). Lippincott Williams & Wilkins, 2003). Combination chemotherapy is the administration of more than one agent to treat cancer (e.g., a combination of HDACi and mTORi for treatment of multiple myeloma).

Exemplary chemotherapeutic agents include microtubule binding agents, DNA intercalators or cross-linkers, DNA synthesis inhibitors, DNA and/or RNA transcription inhibitors, antibodies, kinase inhibitors, and gene regulators.

Control: A sample or standard used for comparison with an experimental sample. In some embodiments, the control is a sample obtained from a healthy patient or a non-neoplasm tissue sample obtained from a patient diagnosed with cancer. In other embodiments, the control is a neoplasm tissue sample obtained from a patient diagnosed with cancer. In some embodiments, the control is a neoplasm tissue sample obtained from a patient diagnosed with cancer, where the patient has not received mTORi/HDACi combination therapy for the neoplasm. In still other embodiments, the control is a historical control or standard reference value or range of values (such as a previously tested control sample, such as a group of cancer patients with known prognosis or outcome, or group of samples that represent baseline or normal values, such as the expression level of one or more genes listed in Table 6 or Table 7 in non-neoplasm tissue).

Contacting: Placement in direct physical association, for example solid, liquid or gaseous forms. Contacting includes, for example, direct physical association of fully- and partially-solvated molecules.

Decrease or Reduce: To reduce the quality, amount, or strength of something; for example a reduction in tumor burden. In one example, a therapy reduces a neoplasm (such as the size of a neoplasm, the number of neoplasms, the metastasis of a neoplasm, or combinations thereof), or one or more symptoms associated with a neoplasm, for example, as compared to the response in the absence of the therapy. In a particular example, a therapy decreases the size of a neoplasm, the number of neoplasms, the metastasis of a neoplasm, or combinations thereof, subsequent to the therapy, such as a decrease of at least 10%, at least 20%, at least 30%, at least 40%, at least 50%, at least 60%, at least 70%, at least 80%, or at least 90%. Such decreases can be measured using, e.g., the methods disclosed herein.

Detecting: To identify the existence, presence, or fact of something. General methods of detecting are known to the skilled artisan and may be supplemented with the protocols and reagents disclosed herein. For example, included herein are methods of detecting gene expression in a sample or a subject.

Determining or detecting the level of expression of a gene product: Detection of a level of expression in either a qualitative or quantitative manner, for example by detecting nucleic acid molecules or proteins, for instance using routine methods known in the art.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Differential expression: A difference, such as an increase or decrease, in the amount of messenger RNA, the conversion of mRNA to a protein, or both. In some examples, the difference is relative to a control or reference value, such as an amount of gene expression in tissue not affected by a disease, such as from sample isolated from a cell or tissue that is not neoplastic or from a different subject who does not have a neoplasm. Alternatively, the difference may be relative to another time point, to a treated (or untreated) sample, or any other variable selected. Detecting a differential level of expression can include measuring a difference in gene or protein expression, such as a difference in level of expression of one or more genes or proteins, such as the genes listed in Table 6 or Table 7 or proteins encoded thereby.

Gene expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Specific examples of ovarian endothelial cell tumor-associated molecules that are up-regulated in ovarian tumor endothelial cells are provided in Tables 2 and 4. Specific examples of ovarian endothelial cell tumor-associated molecules that are down-regulated in ovarian tumor endothelial cells are listed in Table 3. For example, EZH2, EGFL6, TNFAIP6, TWIST1, STC1, HOP, CSPG2, and PLXDC1 are upregulated or increased in expression in ovarian tumor endothelial cells, while TLOC1 and HS6ST2 are downregulated or decreased in expression in such cells.

Controls or standards for comparison to a sample, for the determination of differential expression, include samples believed to be normal (in that they are not altered for the desired characteristic, for example a sample from a subject who does not have cancer, such as ovarian cancer) as well as laboratory values, even though possibly arbitrarily set, keeping in mind that such values can vary from laboratory to laboratory.

Laboratory standards and values may be set based on a known or determined population value and can be supplied in the format of a graph or table that permits comparison of measured, experimentally determined values.

Gene expression signature: A gene expression signature includes a distinct or identifiable pattern of levels of gene expression, for instance a pattern of high and low levels of expression of a defined set of genes or gene-indicative nucleic acids such as ESTs or cDNAs or the protein encoded by a gene. In some examples, as few as three genes provides a signature, but more genes can be used in a signature, for example, at least five, at least six, at least ten, at least twelve, at least twenty, at least twenty-five, at least thirty, at least thirty-five, at least thirty-seven, or at least forty or more. A gene expression signature can be linked to a tissue or cell type (such as a neoplasm cell), to a particular stage of normal tissue growth or disease progression (such as advanced cancer), metastatic potential, responsiveness to a therapy, or to any other distinct or identifiable condition that influences gene expression in a predictable way. Gene expression signatures can include relative as well as absolute expression levels of specific genes, and can be viewed in the context of a test sample compared to a baseline or control gene expression profile (such as a sample from the same tissue type from a subject who does not have a neoplasm). In one example, a gene expression signature in a subject is read on an array (such as a nucleic acid or protein array).

Histone Deacetylase (HDAC): A zinc hydrolase that modulates gene expression through removal of the acetyl group on ε-N-acetyl lysine on the N-terminal tails of histones (e.g., H2A, H2B, H3 and H4), resulting in a closed nucleosomal structure. There are at least 18 HDACs in humans, which have been divided into four classes based on cellular localization and function (for review, see, e.g., Federico ad Bagella, *J. Biomed. Biotechnol.*, 2011:475641, 2011; Laneand and Chabner, *J. Clin. Oncol.*, 27:5459-5468, 2009). Class I includes HDACs 1, 2, 3, and 8 which are all nuclear and ubiquitously expressed. Class 11, being able to shuttle back and forth between the nucleus and the cytoplasm and believed to be tissue restricted, includes HDACs 4, 5, 6, 7, 9, and 10; within this class, HDACs 6 and 10 (class IIb) have two catalytic sites, are expressed only in the cytoplasm, and are involved in a variety of biological processes. Class III contains the structurally diverse NAD+-dependent sirtuin family, which does not act primarily on histones (Blander and Guarente, *Ann. Rev. Biochem.*, 73:417-435, 2004). Finally, the ubiquitously expressed HDAC11 represents Class IV. Nonhistone-molecules are also a target of HDACs (e.g., p53, E2F, GATA-1, YY1, ReIA, Mad-Max, c-Myc, NF-κB, HIF-1α, Ku70, α-tubulin, STAT3, Hsp90, TFIIE, TFIIF, and hormone receptors).

Histone Deacetylase Inhibitor (HDACi): An agent that reduces HDAC activity. The agent can be a competitive or noncompetitive HDAC inhibitor, and can interfere with deacetylase activity by affecting the enzymatic activity, disrupting the spatial conformation of the deacetylase, or interfering with transcription or translation pathways leading to production of the deacetylase. An HDACi can be any type of agent, including, but not limited to, chemical compounds, proteins, peptidomimetics, and antisense molecules or ribozymes. In several examples, the HDACi is MS-275, a HDAC inhibitor with high affinity for HDACs 1 and 3 that is in clinical testing for both solid tumors and lymphomas (Kummar et al., *Clin Cancer Res.*, 13:5411-5417, 2007; Gore et al., *Clin Cancer Res.*, 14:4517-4525, 2008; Gojo et al., *Blood*, 109:2781-2790, 2007; Hess-Stumpp, *Int J Biochem Cell Biol.*, 39:1388-1405, 2007)

Histone deacetylase inhibitor (HDACi) and mTOR inhibitor (mTORi) combination therapy: Treatment of a neoplasm (e.g., a multiple myeloma neoplasm) with a therapeutically effective amount of a combination of HDACi and mTORi. The HDACi and mTORi can be administered simultaneously, or sequentially.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11).

Isolated: A biological component (such as a nucleic acid, peptide, protein or protein complex, for example an antibody) that has been substantially separated, produced apart from, or purified away from other biological components in the cell of the organism in which the component naturally occurs, for instance, other chromosomal and extrachromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Label: An agent capable of detection, for example by ELISA, spectrophotometry, flow cytometry, or microscopy.

For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (*Molecular Cloning: A Laboratory Manual*, Cold Spring Harbor, N.Y., 1989) and Ausubel et al. (*In Current Protocols in Molecular Biology*, John Wiley & Sons, New York, 1998).

Mechanistic Target of Rapamycin (mTOR): A protein kinase of the PI3K/Akt signaling pathway that is ubiquitously expressed within cells and is a validated target in the treatment of certain cancer types (see, e.g., Dancey et al., *J. Nat. Rev. Clin. Oncol.*, 7:209-219, 2010). Activation of mTOR in response to growth, nutrient and energy signals leads to an increase in protein synthesis, which may contribute to neoplasm development. The mTOR signaling network plays a regulatory role in protein translation, cell growth and proliferation, metabolism, and autophagy, and is at the interface of both growth factor- and nutrient-sensing pathways (Zoncu et al., *Nat Rev Mol Cell Biol.*, 12:21-35, 2011; Laplante and Sabatini, *Curr Biol.*, 19:R1046-R1052, 2009; Meric-Bernstam and Gonzalez-Angulo, *J Clin Oncol.*, 27:2278-2287, 2009; Guertin and Sabatini, *Cancer Cell.*, 12:9-22, 2007). A representative GenBank Accession No. for mTOR nucleotide sequence is NM_004958 and a representative GenBank accession No. for mTOR protein sequence is NP_004949, both of which are incorporated by reference as provided in GenBank on Oct. 21, 2011.

mTOR inhibitor (mTORi): An agent that reduces mTOR activity. The agent can be a competitive or noncompetitive mTOR inhibitor, and can interfere with mTOR activity by affecting mTOR kinase activity, disrupting the spatial conformation of the mTOR kinase, or interfering with transcription or translation pathways leading to production of mTOR. The mTORi can be any agent, including, but not limited to, chemical compounds, proteins, peptidomimetics, and antisense molecules or ribozymes. Non-limiting examples of mTOR inhibitors include Rapamycin (sirolimus; Wyeth), Rapamycin derivatives (a.k.a., "rapalogs"; e.g., temsirolimus (CCI-779; Wyeth); everolimus (RAD001; Novartis); and ridaforolimus (deforolimus; AP23573; Ariad Pharmaceuticals)), and small-molecule mTOR kinase inhibitors (e.g., AZD8055 (AstraZeneca); PKI-179 (Wyeth); PKI-587 (Wyeth); XL765 (Exelixis); NvP-BEZ235 (Novartis)).

Multiple myeloma (MM): A malignancy of terminally differentiated antibody secreting B cells with ~20,000 new cases diagnosed yearly in the United States (Jemal et al., *CA Cancer J Clin.*, 60:277-300, 2010). MM is characterized by the accumulation of clonal plasma cells in the bone marrow (BM) and osteolytic bone lesions. The person of ordinary skill is familiar with tests used to determine the presence and severity of MM. For example, the Durie-Salmon staging system divides MM patients into three stages: Stages I, II, and III, corresponding to low, intermediate, and high cell mass, depending upon the severity of anemia, calcium level, kidney function, presence or absence of bone lesions, and the quantity of abnormal proteins. Approximately 25 percent of people with MM have high-risk disease. Treatment options include chemotherapy, treatment with immune modulating medications, and Autologous Stem Cell Transplant (ASCT) (Attal et al., *N. Engl. J. Med.*, 1996; 335:91-97; Barlogie et al., *Blood*, 1997; 89:789-793). However, patients invariably relapse, and MM remains a universal fatal disease. See, e.g., Rajkumar and Kyle, (eds), *Treatment of Multiple Myeloma and Related Disorders*, 1$^{st}$; Cambridge University Press, New York, 2006.

Neoplasm: An abnormal growth of tissue forming as a result of Neoplasia. Neoplasia is the abnormal proliferation of cells, whether malignant or benign, including abnormal growth of all pre-cancerous and cancerous cells and tissues. A tumor is a type of neoplasm; for example, non-limiting examples of neoplasms include solid and non-solid (e.g., hollow or liquid filled) tumors. A neoplasm also includes an abnormal growth of tissue associated with neoplasia of hematological cells (e.g., a hematological neoplasm, such as that occurring in lymphoma, leukemia, and myeloma).

The amount of a tumor or neoplasm in an individual is the "tumor burden," which can be measured as the total volume, number, metastasis, or combinations thereof of neoplasm or neoplasms (e.g., tumor or tumors) in a subject. A tumor or neoplasm that does not metastasize is referred to as "benign." A tumor or neoplasm that invades the surrounding tissue and/or can metastasize is referred to as "malignant."

Neoplasms and tumors of the same tissue type are primary neoplasms or tumors originating in a particular organ (such as breast). Neoplasms and tumors of the same tissue type may be divided into neoplasms or tumors of different sub-types. For examples, breast cancer tumors can be divided into ductal and lobular carcinomas, among others.

Oligonucleotide probes and primers: A probe includes an isolated nucleic acid (usually of 100 or fewer nucleotide residues) attached to a detectable label or reporter molecule, which is used to detect a complementary target nucleic acid molecule by hybridization and detection of the label or reporter. Primers are short nucleic acids, usually DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs (one "upstream" and one "downstream") can be used for amplification of a nucleic acid sequence, for example by polymerase chain reaction (PCR) or other in vitro nucleic-acid amplification methods. One of skill in the art will appreciate that the hybridization specificity of a particular probe or primer increases with its length. Thus, for example, a probe or primer comprising 20 consecutive nucleotides will anneal to a target with a higher specificity than a corresponding probe or primer of only 15 nucleotides. Thus, in order to obtain greater specificity, probes and primers can be selected that comprise about 20, 25, 30, 35, 40, 50 or more consecutive nucleotides.

Pharmaceutically acceptable carriers: The pharmaceutically acceptable carriers provided herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced.

Conservative substitutions replace one amino acid with another amino acid that is similar in size, hydrophobicity, etc. Variations in the cDNA sequence that result in amino acid differences, whether conservative or not, should be minimized in instances where it is desirable to preserve the functional and immunologic identity of the encoded protein. The immunologic identity of the protein may be assessed by determining if it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, 95%, 98% or 99% identical to the native amino acid sequence.

Prognosis: A prediction of the course of a disease, such as cancer (for example, breast cancer or multiple myeloma). The prediction can include determining the likelihood of a subject to develop aggressive, recurrent disease, to develop one or more metastases, to survive a particular amount of time (e.g., determining the likelihood that a subject will survive 1, 2, 3 or 5 years), to respond to a particular therapy (e.g., mTORi/HDACi combination therapy), to be resistant to a particular therapy (e.g., mTORi/HDACi combination therapy), to develop resistance to a particular therapy (e.g., mTORi/HDACi combination therapy) or combinations thereof. The prediction can also include determining whether a subject has, or is likely to have, a malignant or a benign neoplasm.

Rapalog: An mTOR inhibitor that is structurally and functionally related to Rapamycin.

Sample (or biological sample): A biological specimen, for example, a biological specimen containing lipid, carbohydrate, DNA, RNA (including mRNA), protein, or combinations thereof, obtained from a subject. In several examples, a sample is composed of macromolecular components, together or separated, obtained from biological material. Examples include, but are not limited to, peripheral blood, urine, saliva, tissue biopsy (e.g., bone marrow biopsy), needle aspirate (surgical specimen, and autopsy material. In some examples, a sample includes a neoplasm sample, such as a fresh, frozen, or fixed neoplasm sample.

Sensitive to treatment with: A condition (e.g., a neoplasm) that is responsive to an initial (and in some examples subsequent) therapy or treatment. For example, a condition (e.g., a neoplasm) that is statistically significantly responsive to an initial (and in some examples, subsequent) therapy or treatment. In an example, sensitivity refers to the responsiveness of a disease or symptom or progression thereof, such as the growth of a cancer, to an agent (such as a therapeutic agent, for example an HDACi or mTORi) or combination of agents (such a combination of one or more HDACi and mTORi). For example, an increased (relative) sensitivity refers to a state in which a neoplasm is more responsive to a given therapy or therapeutic agent or treatment, as compared to a neoplasm that is not sensitive to the treatment.

In certain examples, sensitivity or responsiveness of a cancer/neoplasm can be assessed using any endpoint indicating a benefit to the subject, including, without limitation: (1) inhibition, to some extent, of neoplasm growth, including slowing down and complete growth arrest; (2) reduction in the number of neoplasm cells; (3) reduction in neoplasm size or volume; (4) inhibition (such as reduction, slowing down or complete stopping) of neoplasm cell infiltration into adjacent peripheral organs and/or tissues; (5) inhibition (such as reduction, slowing down or complete stopping) of metastasis; (6) enhancement of anti-neoplasm immune response, which may, but does not have to, result in the regression or rejection of the neoplasm; (7) relief, to some extent, of one or more symptoms associated with the neoplasm; (8) increase in the length of survival following treatment; and/or (9) decreased mortality at a given point of time following treatment.

In some examples, sensitivity of a cancer/neoplasm to treatment can be assessed before treatment to determine if the cancer/neoplasm will respond to the treatment. In further examples, sensitivity of a cancer/neoplasm to treatment can be assessed after treatment of the cancer/neoplasm to determine if the cancer/neoplasm is responding to the treatment. In some embodiments, sensitivity of a cancer/neoplasm to treatment can be assessed after initiation of treatment (for example, no more than 8 hours, no more than 12 hours, no more than 1 day, no more than 2 days, no more than 3 days, no more than 4 days, no more than 5 days, no more than 6 days, no more than 1 week, no more than 2 weeks, no more than 3 weeks or no more than 1 month, such as 8 hours, 12 hours, 1 day, 2 days, 3 days, 4 days, 5 days, six days, 1 week, 2 weeks, 3 weeks or 1 month, following initiation of treatment), to determine if the neoplasm is responding to the treatment. In some such embodiments, the neoplasm has a response that includes changes in gene expression that can be detected before a physical response (such as reduction of tumor burden) is detectable.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J.*

*Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity with the proteins listed in Table 6 or Table 7.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity with the proteins listed in Table 6 or Table 7. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity with the genes listed in Table 6 or Table 7 as determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Subject: Any mammal, such as humans, non-human primates, pigs, sheep, cows, rodents and the like. In two non-limiting examples, a subject is a human subject or a murine subject. Thus, the term "subject" includes both human and veterinary subjects.

Therapeutically effective amount: The amount of an agent (such as a HDACi or mTORi) that alone or together with one or more additional agents (for example, a HDACi and mTORi combination), induces a desired response, such as, for example treatment of a neoplasm in a subject. Ideally, a therapeutically effective amount provides a therapeutic effect without causing a substantial cytotoxic effect in the subject.

In one example, a desired response is to decrease the size, volume, or number (such as metastases) of a neoplasm in a subject. For example, the agent or agents can decrease the size, volume, or number of neoplasms by a desired amount, for example by at least 5%, at least 10%, at least 15%, at least 20%, at least 25%, at least 30%, at least 50%, at least 75%, at least 90%, or at least 95% as compared to a response in the absence of the agent. In another example, a desired response is to increase the survival time or time of progression free survival by a desired amount, for example by at least 5%, at least 10%, at least 15%, at least 20%, at least 25%, at least 30%, at least 50%, at least 75%, at least 90%, or at least 95% or more, as compared to a response in the absence of the agent.

Several preparations disclosed herein are administered in therapeutically effective amounts. A therapeutically effective amount of a combination of HDACi and mTORi that is administered to a human or veterinary subject will vary depending upon a number of factors associated with that subject, for example the overall health of the subject. A therapeutically effective amount of a combination of HDACi and mTORi can be determined by varying the dosage and measuring the resulting therapeutic response, such as the regression of a neoplasm. Therapeutically effective amounts also can be determined through various in vitro, in vivo or in situ immunoassays. The disclosed agents can be administered in a single dose, or in several doses, as needed to obtain the desired response. However, the therapeutically effective amount of one or more agents can depend on the source applied, the subject being treated, the severity and type of the condition being treated, and the manner of administration.

Treating or Treatment: A therapeutic intervention (e.g., administration of a therapeutically effective amount of a combination of HDACi and mTORi) that reduces a sign or symptom of a disease or pathological condition related to a disease (such as a neoplasm). Treatment can also induce remission or cure of a condition, such as a neoplasm. In particular examples, treatment includes preventing a neoplasm, for example by inhibiting the full development of a neoplasm, such as preventing development of a metastasis or the development of a primary neoplasm. Prevention does not require a total absence of a neoplasm.

Reducing a sign or symptom associated with a neoplasm can be evidenced, for example, by a delayed onset of clinical symptoms of the disease in a susceptible subject (such as a subject having a neoplasm which has not yet metastasized), a reduction in severity of some or all clinical symptoms of the disease, a slower progression of the disease (for example by prolonging the life of a subject having neoplasm), a reduction in the number of relapses of the disease, an improvement in the overall health or well-being of the subject, or by other parameters well known in the art that are specific to the particular neoplasm.

Tumor burden: The total volume, number, metastasis, or combinations thereof of neoplasm or neoplasms (e.g., tumor or tumors) in a subject.

Under conditions sufficient for: A phrase that is used to describe any environment that permits a desired activity. In one example the desired activity is formation of an immune complex. In particular examples the desired activity is treatment of a neoplasm.

III. Genes Included in One or More of the Disclosed Gene Signatures

ATPase family, AAA domain containing 2 (ATAD2): Also known as Cancer-Associated AAA Nuclear Coregulator (e.g., GenBank Gene ID No: 29028). Nucleic acid and amino acid sequences for ATAD2 are publicly available. For example, GenBank Accession No. NM_014109 discloses an exemplary human ATAD2 nucleic acid sequence, and GenBank Accession No. NP_054828 discloses an exemplary human ATAD2 protein sequence, both of which are incorporated by reference as provided in GenBank on Oct. 21, 2011. One of skill in the art can identify additional ATAD2 sequences and variants thereof.

Aurora kinase A (STK6): Also known as Serine/Threonine Protein Kinase 15 (STK15), Homolog of Mouse STK6 (STK6), Aurora-Related Kinase 1 (ARK1), Aurora/Ipl1-Like Kinase (AIK), Aurora 2 and BTAK (e.g., GenBank Gene ID No: 6790). Nucleic acid and amino acid sequences for STK6 are publicly available. For example, GenBank Accession Nos. NM_198436, NM_198437, NM_003600, NM_198433, NM_198434 and NM_198435 disclose exemplary human STK6 nucleic acid sequences, and GenBank Accession No. NP_940838, NP_940839, NP_003591, NP_940835, NP_940836 and NP_940837 disclose exemplary human STK6 protein sequences, all of which are incorporated by reference as provided in GenBank on Oct. 21, 2011. One of skill in the art can identify additional STK6 sequences and variants thereof.

Bloom syndrome, RecQ helicase-like (BLM): Also known as DNA Helicase, RECP-Like, Type 2 (e.g., GenBank Gene ID No: 641). Nucleic acid and amino acid sequences for BLM are publicly available. For example, GenBank Accession No. NM_014109 discloses an exemplary human BLM nucleic acid sequence, and GenBank Accession No. NP_000048 discloses an exemplary human BLM protein sequence, both of which are incorporated by reference as provided in GenBank on Oct. 21, 2011. One of skill in the art can identify additional BLM sequences and variants thereof.

Cell division cycle 6 homolog (S. cerevisiae) (CDC6): Also known as Cell Division Cycle 18 (S. pombe), Homolog-Like (CDC18) and Cell Cycle Controller CDC6 (e.g., GenBank Gene ID No: 990). Nucleic acid and amino acid sequences for CDC6 are publicly available. For example, GenBank Accession No. NM_001254 discloses an exemplary human CDC6 nucleic acid sequence, and GenBank Accession No. NP_001245 discloses an exemplary human CDC6 protein sequence, both of which are incorporated by reference as provided in GenBank on Oct. 21, 2011. One of skill in the art can identify additional CDC6 sequences and variants thereof.

Cell division cycle 20 homolog (S. cerevisiae) (CDC20): Also known as Cell-Division Cycle Protein 20 (e.g., GenBank Gene ID No: 991). Nucleic acid and amino acid sequences for CDC20 are publicly available. For example, GenBank Accession No. NM_001255 discloses an exemplary human CDC20 nucleic acid sequence, and GenBank Accession No. NP_001246 discloses an exemplary human CDC20 protein sequence, both of which are incorporated by reference as provided in GenBank on Oct. 21, 2011. One of skill in the art can identify additional CDC20 sequences and variants thereof.

Cell division cycle 25 homolog A (S. pombe) (CDC25A): Known as CDC25A (e.g., GenBank Gene ID No: 993). Nucleic acid and amino acid sequences for CDC25A are publicly available. For example, GenBank Accession Nos. NM_001789 and NM_201567 disclose exemplary human CDC25A nucleic acid sequences, and GenBank Accession Nos. NP_001780 and NP_963861 disclose exemplary human CDC25A protein sequences, all of which are incorporated by reference as provided in GenBank on Oct. 21, 2011. One of skill in the art can identify additional CDC25A sequences and variants thereof.

Cell division cycle associated 3 (CDCA3): Also known as Trigger of Mitotic Entry 1 (TOME1) (e.g., GenBank Gene ID No: 83461). Nucleic acid and amino acid sequences for CDCA3 are publicly available. For example, GenBank Accession No. NM_031299 discloses an exemplary human CDCA3 nucleic acid sequence, and GenBank Accession No. NP_112589 discloses an exemplary human CDCA3 protein sequence, both of which are incorporated by reference as provided in GenBank on Oct. 21, 2011. One of skill in the art can identify additional CDCA3 sequences and variants thereof.

Cell division cycle associated 5 (CDCA5): Also known as Sororin (e.g., GenBank Gene ID No: 113130). Nucleic acid and amino acid sequences for CDCA5 are publicly available. For example, GenBank Accession No. NM_080668 discloses an exemplary human CDCA5 nucleic acid sequence, and GenBank Accession No. NP_542399 discloses an exemplary human CDCA5 protein sequence, both of which are incorporated by reference as provided in GenBank on Oct. 21, 2011. One of skill in the art can identify additional CDCA5 sequences and variants thereof.

Chromosome 9 open reading frame 140 (C9orf140): Also known as p42.3 (e.g., GenBank Gene ID No: 89958). Nucleic acid and amino acid sequences for C9orf140 are publicly available. For example, GenBank Accession No. NM_178448 discloses an exemplary human C9orf140 nucleic acid sequence, and GenBank Accession No. NP_848543.2 discloses an exemplary human C9orf140 protein sequence, both of which are incorporated by reference as provided in GenBank on Oct. 21, 2011. One of skill in the art can identify additional C9orf140 sequences and variants thereof.

Cyclin B2 (CCNB2): Also known as G2/Mitotic-Specific Cyclin-B2 (e.g., GenBank Gene ID No: 9133). Nucleic acid and amino acid sequences for CCNB2 are publicly available. For example, GenBank Accession No. NM_004701 discloses an exemplary human CCNB2 nucleic acid sequence, and GenBank Accession No. NP_004692 discloses an exemplary human CCNB2 protein sequence, both of which are incorporated by reference as provided in GenBank on Oct. 21, 2011. One of skill in the art can identify additional CCNB2 sequences and variants thereof.

E2F transcription factor 2 (E2F2): Known as E2F2 (e.g., GenBank Gene ID No: 1870). Nucleic acid and amino acid sequences for E2F2 are publicly available. For example, GenBank Accession No. NM_004091 discloses an exemplary human E2F2 nucleic acid sequence, and GenBank Accession No. NP_004082 discloses an exemplary human E2F2 protein sequence, both of which are incorporated by reference as provided in GenBank on Oct. 21, 2011. One of skill in the art can identify additional E2F2 sequences and variants thereof.

Holliday junction recognition protein (HJURP): Also known as FAKTS (e.g., GenBank Gene ID No: 55355). Nucleic acid and amino acid sequences for HJURP are publicly available. For example, GenBank Accession No. NM_018410 discloses an exemplary human HJURP nucleic acid sequence, and GenBank Accession No. NP_060880 discloses an exemplary human HJURP protein sequence, both of which are incorporated by reference as provided in GenBank on Oct. 21, 2011. One of skill in the art can identify additional HJURP sequences and variants thereof.

Hs.193784: Nucleic acid sequences for Hs.193784 are publicly available. For example, GenBank Accession No. BF476076 discloses an exemplary human Hs.193784 nucleic acid sequence which is incorporated by reference as provided in GenBank on Oct. 21, 2011. One of skill in the art can identify additional Hs.193784 sequences and variants thereof.

Hs.202577: Nucleic acid sequences for Hs.202577 are publicly available. For example, GenBank Accession No. AU144961 discloses an exemplary human Hs.202577 nucleic acid sequence, which is incorporated by reference as provided in GenBank on Oct. 21, 2011. One of skill in the art can identify additional Hs.202577 sequences and variants thereof.

KIAA2013: Also known as MGC33867 (e.g., GenBank Gene ID No: 90231). Nucleic acid and amino acid sequences for KIAA2013 are publicly available. For example, GenBank Accession No. NM_138346 discloses an exemplary human KIAA2013 nucleic acid sequence, and GenBank Accession No. NP_612355 discloses an exemplary human KIAA2013 protein sequence, both of which are incorporated by reference as provided in GenBank on Oct. 21, 2011. One of skill in the art can identify additional KIAA2013 sequences and variants thereof.

Kinesin family member 22 (KIF22): Also known as Kinesin-Like 4 (KNSL4), Kinesin-Like DNA-Binding Protein (KID); Origin Of Plasmid DNA Replication-Binding Protein (OBP) and Orip-Binding Protein (e.g., GenBank Gene ID No: 3835). Nucleic acid and amino acid sequences for KIF22 are publicly available. For example, GenBank Accession No. NM_007317 discloses an exemplary human KIF22 nucleic acid sequence, and GenBank Accession No. NP_015556 discloses an exemplary human KIF22 protein sequence, both of which are incorporated by reference as provided in GenBank on Oct. 21, 2011. One of skill in the art can identify additional KIF22 sequences and variants thereof.

Kinesin family member 2C (KIF2C): Also known as Kinesin-Like 6 (KNSL6) and Mitotic Centromere-Associated Kinesin (MCAK) (e.g., GenBank Gene ID No: 11004). Nucleic acid and amino acid sequences for KIF2C are publicly available. For example, GenBank Accession No. NM_006845 discloses an exemplary human KIF2C nucleic acid sequence, and GenBank Accession No. NP_006836 discloses an exemplary human KIF2C protein sequence, both of which are incorporated by reference as provided in GenBank on Oct. 21, 2011. One of skill in the art can identify additional KIF2C sequences and variants thereof.

Lactate dehydrogenase A (LDHA): Also known as LDH, Subunit M (e.g., GenBank Gene ID No: 3939). Nucleic acid and amino acid sequences for LDHA are publicly available. For example, GenBank Accession Nos. NM_001165416, NM_001165415, NM_001165414, NM_005566, NM_001135239 and NR_028500 disclose exemplary human LDHA nucleic acid sequences, and GenBank Accession Nos. NP_001158888, NP_001158887, NP_001158886, NP_005557 and NP_001128711 disclose exemplary human LDHA protein sequences, all of which are incorporated by reference as provided in GenBank on Oct. 21, 2011. One of skill in the art can identify additional LDHA sequences and variants thereof.

Major histocompatibility complex, class II, DP beta 1 (HLA-DPB1): Also known as HLA-DP Histocompatibility Type, Beta-1 Subunit (e.g., GenBank Gene ID No: 3115). Nucleic acid and amino acid sequences for HLA-DPB1 are publicly available. For example, GenBank Accession No. NM_002121 discloses an exemplary human HLA-DPB1 nucleic acid sequence, and GenBank Accession No. NP_002112 discloses an exemplary human HLA-DPB1 protein sequence, both of which are incorporated by reference as provided in GenBank on Oct. 21, 2011. One of skill in the art can identify additional HLA-DPB1 sequences and variants thereof.

Minichromosome maintenance complex component 2 (MCM2): Also known as Mitotin, Cell Division Cycle-Like 1 (CDCL1) and Nuclear Protein BM28 (BM28) (e.g., GenBank Gene ID No: 4171). Nucleic acid and amino acid sequences for MCM2 are publicly available. For example, GenBank Accession No. NM_004526 discloses an exemplary human MCM2 nucleic acid sequence, and GenBank Accession No. NP_004517 discloses an exemplary human MCM2 protein sequence, both of which are incorporated by reference as provided in GenBank on Oct. 21, 2011. One of skill in the art can identify additional MCM2 sequences and variants thereof.

Minichromosome maintenance complex component 4 (MCM4): Also known as homolog of cell division cycle 21 (*S. pombe*) (e.g., GenBank Gene ID No: 4173). Nucleic acid and amino acid sequences for MCM4 are publicly available. For example, GenBank Accession Nos. NM_005914 and NM_182746 disclose exemplary human MCM4 nucleic acid sequences, and GenBank Accession Nos. NP_005905 and NP_877423 disclose exemplary human MCM4 protein sequences, all of which are incorporated by reference as provided in GenBank on Oct. 21, 2011. One of skill in the art can identify additional MCM4 sequences and variants thereof.

Minichromosome maintenance complex component 5 (MCM5): Also known as cell division cycle 46 (CDC46) (e.g., GenBank Gene ID No: 4174). Nucleic acid and amino acid sequences for MCM5 are publicly available. For example, GenBank Accession No. NM_006739 discloses an exemplary human MCM5 nucleic acid sequence, and GenBank Accession No. NP_006730 discloses an exemplary human MCM5 protein sequence, both of which are incorporated by reference as provided in GenBank on Oct. 21, 2011. One of skill in the art can identify additional MCM5 sequences and variants thereof.

NAD(P) dependent steroid dehydrogenase-like (NSDHL): Also known as H105E3 (e.g., GenBank Gene ID No: 50814). Nucleic acid and amino acid sequences for NSDHL are publicly available. For example, GenBank Accession Nos. NM_015922 and NM_001129765 disclose exemplary human NSDHL nucleic acid sequences, and GenBank Accession Nos. NP_057006 and NP_001123237 disclose exemplary human NSDHL protein sequences, all of which are incorporated by reference as provided in GenBank on Oct. 21, 2011. One of skill in the art can identify additional NSDHL sequences and variants thereof.

Non-SMC condensin I complex, subunit H (NCAPH): Also known as condensin I complex, non-SMC subunit H, chromosome-associated protein H (CAPH) (e.g., GenBank Gene ID No: 23397). Nucleic acid and amino acid sequences for NCAPH are publicly available. For example, GenBank Accession No. NM_015341 discloses an exemplary human NCAPH nucleic acid sequence, and GenBank Accession No. NP_056156 discloses an exemplary human NCAPH protein sequence, both of which are incorporated by reference as provided in GenBank on Oct. 21, 2011. One of skill in the art can identify additional NCAPH sequences and variants thereof.

PHD finger protein 19 (PHF19): Also known as Growth Arrest- and DNA Damage-Inducible Gene GADD45, Beta (GADD45B) (e.g., GenBank Gene ID No: 4616). Nucleic acid and amino acid sequences for PHF19 are publicly available. For example, GenBank Accession No. NM_015675 discloses an exemplary human PHF19 nucleic acid sequence, and GenBank Accession No. NP_056490 discloses an exemplary human PHF19 protein sequence, both of which are incorporated by reference as provided in GenBank on Oct. 21, 2011. One of skill in the art can identify additional PHF19 sequences and variants thereof.

Polyhomeotic homolog 3 (*Drosophila*) (PHC3): Also known as Early development regulatory protein 3 (e.g., GenBank Gene ID No: 80012). Nucleic acid and amino acid sequences for PHC3 are publicly available. For example, GenBank Accession No. NM_024947 discloses an exemplary human PHC3 nucleic acid sequence, and GenBank Accession No. NP_079223 discloses an exemplary human PHC3 protein sequence, both of which are incorporated by reference as provided in GenBank on Oct. 21, 2011. One of skill in the art can identify additional PHC3 sequences and variants thereof.

RAD51 homolog (RecA homolog, *E. coli*) (*S. cerevisiae*) (RAD51): Also known as Homolog of RAD51A (*S. cerevisiae*) (RAD51A), Recombination Protein A (RECA) and Homolog of RECA, (*E. COLI*) (e.g., GenBank Gene ID No: 5888). Nucleic acid and amino acid sequences for RAD51 are publicly available. For example, GenBank Accession Nos. NM_002875, NM_001164269, NM_133487 and NM_001164270 disclose exemplary human RAD51 nucleic acid sequences, and GenBank Accession Nos. NP_002866, NP_001157741, NP_597994 and NP_001157742 disclose exemplary human RAD51 protein sequences, all of which are incorporated by reference as provided in GenBank on Oct. 21, 2011. One of skill in the art can identify additional RAD51 sequences and variants thereof.

Ribonucleotide reductase M2 (RRM2): Also known as Ribonucleotide Reductase, Small Subunit; Ribonucleotide Reductase, R2 Subunit (R2) (e.g., GenBank Gene ID No: 6241). Nucleic acid and amino acid sequences for RRM2 are publicly available. For example, GenBank Accession Nos. NM_001165931 and NM_001034 disclose exemplary human RRM2 nucleic acid sequences, and GenBank Accession Nos. NP_001159403 and NP_001025 disclose exemplary human RRM2 protein sequences, all of which are incorporated by reference as provided in GenBank on Oct. 21, 2011. One of skill in the art can identify additional RRM2 sequences and variants thereof.

Solute carrier family 19 (folate transporter), member 1 (SLC19A1): Also known as Folate Transporter (FOLT); Reduced Folate Carrier 1 (RFC1); Intestinal Folate Carrier 1 (IFC1) (e.g., GenBank Gene ID No: 6573). Nucleic acid and amino acid sequences for SLC19A1 are publicly available. For example, GenBank Accession Nos. NM_001205207, NM_194255 and NM_001205206 disclose exemplary human SLC19A1 nucleic acid sequences, and GenBank Accession Nos. NP_001192136, NP_919231 and NP_001192135 disclose exemplary human SLC19A1 protein sequences, all of which are incorporated by reference as provided in GenBank on Oct. 21, 2011. One of skill in the art can identify additional SLC19A1 sequences and variants thereof.

Sperm associated antigen 5 (SPAG5): Also known as Astrin (e.g., GenBank Gene ID No: 10615). Nucleic acid and amino acid sequences for SPAG5 are publicly available. For example, GenBank Accession No. NM_006461 discloses an exemplary human SPAG5 nucleic acid sequence, and GenBank Accession No. NP_006452 discloses an exemplary human SPAG5 protein sequence, both of which are incorporated by reference as provided in GenBank on Oct. 21, 2011. One of skill in the art can identify additional SPAG5 sequences and variants thereof.

Suppressor of variegation 3-9 homolog 1 (*Drosophila*) (SUV39H1): Also known as *Drosophila* SU(VAR)3-9, Homolog 1 (e.g., GenBank Gene ID No: 6839). Nucleic acid and amino acid sequences for SUV39H1 are publicly available. For example, GenBank Accession No. NM_003173 discloses an exemplary human SUV39H1 nucleic acid sequence, and GenBank Accession No. NP_003164 discloses an exemplary human SUV39H1 protein sequence, both of which are incorporated by reference as provided in GenBank on Oct. 21, 2011. One of skill in the art can identify additional SUV39H1 sequences and variants thereof.

Thyroid hormone receptor interactor 13 (TRIP13): Also known as Human Papillomavirus Type 16 E1 Protein-Binding Protein (16E1BP) (e.g., GenBank Gene ID No: 9319). Nucleic acid and amino acid sequences for TRIP13 are publicly available. For example, GenBank Accession Nos. NM_004237 and NM_001166260 disclose exemplary human TRIP13 nucleic acid sequences, and GenBank Accession Nos. NP_004228 and NP_001159732 disclose exemplary human TRIP13 protein sequences, all of which are incorporated by reference as provided in GenBank on Oct. 21, 2011. One of skill in the art can identify additional TRIP13 sequences and variants thereof.

Transforming, acidic coiled-coil containing protein 3 (TACC3): known as TACC3 (e.g., GenBank Gene ID No: 10460). Nucleic acid and amino acid sequences for TACC3 are publicly available. For example, GenBank Accession No. NM_006342 discloses an exemplary human TACC3 nucleic acid sequence, and GenBank Accession No. NP_006333 discloses an exemplary human TACC3 protein sequence, both of which are incorporated by reference as provided in GenBank on Oct. 21, 2011. One of skill in the art can identify additional TACC3 sequences and variants thereof.

Transmembrane protein 48 (TMEM48): Also known as Homolog of S. cerevisiae NDC1 (NDC1) (e.g., GenBank Gene ID No: 55706). Nucleic acid and amino acid sequences for TMEM48 are publicly available. For example, GenBank Accession Nos. NM_018087, NM_001168551 and NR_033142 disclose exemplary human TMEM48 nucleic acid sequences, and GenBank Accession Nos. NP_060557 and NP_001162023 disclose exemplary human TMEM48 protein sequences, all of which are incorporated by reference as provided in GenBank on Oct. 21, 2011. One of skill in the art can identify additional TMEM48 sequences and variants thereof.

Ubiquitin-conjugating enzyme E2C (UBE2C): Also known as Ubiquitin-Conjugating Enzyme UBCH10 (UBCH10) (e.g., GenBank Gene ID No: 11065). Nucleic acid and amino acid sequences for UBE2C are publicly available. For example, GenBank Accession Nos. NM_181800, NM_181799, NM_007019, NM_181801 and NM_181803 disclose exemplary human UBE2C nucleic acid sequences, and GenBank Accession Nos. NP_861516, NP_861515, NP_008950, NP_861517, NP_861518 and NP_861519 disclose exemplary human UBE2C protein sequences, all of which are incorporated by reference as provided in GenBank on Oct. 21, 2011. One of skill in the art can identify additional UBE2C sequences and variants thereof.

v-myb myeloblastosis viral oncogene homolog (avian)-like 2 (MYBL2): Also known as myb-related gene BMYB (e.g., GenBank Gene ID No: 4605). Nucleic acid and amino acid sequences for MYBL2 are publicly available. For example, GenBank Accession No. NM_002466 discloses an exemplary human MYBL2 nucleic acid sequence, and GenBank Accession No. NP_002457 discloses an exemplary human MYBL2 protein sequence, both of which are incorporated by reference as provided in GenBank on Oct. 21, 2011. One of skill in the art can identify additional MYBL2 sequences and variants thereof.

Zinc finger protein 107 (ZNF107): Also known as ZFD25 and Zinc Finger Protein 588 (ZNF588) (e.g., GenBank Gene ID No: 51427). Nucleic acid and amino acid sequences for ZNF107 are publicly available. For example, GenBank Accession Nos. NM_016220 and NM_001013746 disclose exemplary human ZNF107 nucleic acid sequences, and GenBank Accession Nos. NP_057304 and NP_001013768 disclose exemplary human ZNF107 protein sequences, all of which are incorporated by reference as provided in GenBank on Oct. 21, 2011. One of skill in the art can identify additional ZNF107 sequences and variants thereof.

III. Overview of Several Embodiments

Methods of determining if a neoplasm (e.g., a tumor) is sensitive to treatment with mTORi/HDACi combination therapy, methods of treating such neoplasms, and arrays useful for performing these methods are disclosed herein. Further disclosed are methods of prognosis, for example, methods of determining if a subject with a neoplasm has a decreased relative likelihood or time of survival. Additionally, methods of identifying a subject with a neoplasm not needing (or less likely to benefit from) adjuvant chemotherapy are disclosed.

In some embodiments, a method of determining if a neoplasm is sensitive to treatment with histone deacetylase inhibitor (HDACi) and mechanistic Target of Rapamycin (mTOR) inhibitor (mTORi) combination therapy is provided. This method includes comparing the level of expression in a neoplasm sample from a subject of three or more (such as at least six) genes listed in Table 6 to a control level of expression of the same three or more genes and identifying the neoplasm as sensitive to treatment with HDACi and mTORi combination therapy if there is a difference in the level of expression of the three or more genes in the neoplasm sample as compared to the control. In some embodiments, the methods further include detecting the level of expression in the neoplasm sample from the subject of the three or more (such as at least six) genes listed in Table 6. In some embodiments, comparing the level of expression in the neoplasm sample from the subject includes comparing the expression of at least three (such as at least six, or each of the) genes selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, ZNF107. In some embodiments, comparing the level of expression in the neoplasm sample from the subject includes comparing the expression of at least three genes selected from CDC25A, E2F2, RRM2, RAD51, SPAG5, and MCM4. In some embodiments, the difference in the level of expression includes an increase in the level of expression of one or more of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in the level of expression of one or more of Hs.193784, Hs.202577, HLA-DPB1, and PHC3. In some embodiments, the difference in the level of expression includes an increase in the level of expression of each of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in the level of expression of each of Hs.193784, Hs.202577, HLA-DPB1, and PHC3. In some embodiments, the difference in the level of expression includes an increase in expression of CDC25A, E2F2, RRM2, RAD51, SPAG5, and MCM4. In some such embodiments, the difference in the level of expression includes an increase in an aggregate gene expression value calculated from the level of expression of two or more of the genes selected from ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in an aggregate gene expression value calculated from the level of expression of two or more of the genes selected from Hs.193784, Hs.202577, HLA-DPB1, and PHC3.

In other embodiments, a method of determining prognosis of a subject with a neoplasm is provided. This method includes detecting the level of expression in a neoplasm sample from a subject of three or more (such as at least six) genes listed in Table 6, comparing the level of expression in a neoplasm sample from a subject of three or more genes listed in Table 6 to a control level of expression of the same three or more genes, and identifying the subject as having a poor prognosis if there is a difference in the level of expression of the three or more genes in the neoplasm sample as compared to the control. In some embodiments, the methods further include detecting the level of expression in the neoplasm sample from the subject of the three or more genes listed in Table 6. In some such embodiments, the three or more genes comprise at least three (or at least six or each of the) genes selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, ZNF107. In some embodiments, comparing the level of expression in the neoplasm sample from the subject includes comparing the expression of at least three (such as at least six) genes from CDC25A, E2F2, RRM2, RAD51, SPAG5, and MCM4. In some embodiments, the difference in the level of expression includes an increase in expression of one or more of ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in the level of expression of one or more of Hs.193784, Hs.202577, KIAA2013, HLA-DPB1, and PHC3. In some embodiments, the difference in the level of expression includes an increase in expression of CDC25A, E2F2, RRM2, RAD51, SPAG5, and MCM4. In some such embodiments, the difference in the level of expression includes an increase in an aggregate gene expression value calculated from the level of expression of two or more genes selected from ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in an aggregate gene expression value calculated from the level of expression of two or more genes selected from Hs.193784, Hs.202577, KIAA2013, HLA-DPB1, and PHC3. In some embodiments, the poor prognosis includes decreased overall survival, decreased relapse-free survival, decreased metastasis-free survival, or a combination of two or more thereof.

In several embodiments, comparing the level of expression of a gene to a control level of expression include detecting the level of expression of the gene.

Some embodiments include a method of treating a subject with a neoplasm. Such embodiments include selecting a subject with a neoplasm determined to be sensitive to treatment with histone deacetylase inhibitor (HDACi) and mechanistic Target of Rapamycin (mTOR) inhibitor (mTORi) combination therapy according to the methods provided herein and administering a therapeutically effective amount of HDACi and mTORi combination therapy to the subject, wherein the HDACi and mTORi combination therapy treats the neoplasm in the subject. In some such embodiments, The HDACi comprises MS-275, Panobinostat, Vorinostat, or a combination of two or more thereof. In other embodiments, the mTORi comprises rapamycin, temsirolimus, ridaforolimus, everolimus or a combination of two or more thereof. In some embodiments, wherein the neoplasm is determined not to be sensitive to mTORi/HDACi combination therapy, the neoplasm is treated with an alternate therapy.

Still other embodiments include a method of identifying a subject with a neoplasm not needing adjuvant chemotherapy. For example, such methods include comparing detecting the level of expression in a sample from the neoplasm of three or more (such as at least six) genes listed in Table 6 to a control level of expression of the same three or more genes, wherein the neoplasm is an estrogen receptor-positive breast neoplasm, wherein the subject is not in need of adjuvant chemotherapy if there is not a difference between the level of expression of the three or more genes in the sample from the neoplasm as compared to the control. In some such examples, the method further includes detecting the level of expression in the sample from the neoplasm of the three or more genes listed in Table 6.

In several embodiments of the provided methods, detecting the level of expression of three or more (such as at least six) genes includes detecting the level of expression of at least one nucleic acid molecule. For example, several of the provided methods include microarray analysis, nuclease protection assay, real-time quantitative polymerase chain reaction, or Nanostring® assay. In other embodiments of the provided methods, detecting the level of expression of the three or more genes comprises detecting the level of expression of three or more proteins encoded by genes listed in Table 6. Such methods can include, for example, detecting the level of expression of the three or more proteins comprises protein microarray analysis. In several embodiments of the methods described herein, the control level of expression of the three or more genes comprises the level of expression of the three or more genes in a control sample. In several of the methods described herein, the neoplasm is one of the following: multiple myeloma, mantle cell lymphoma, Burkitt's lymphoma, breast, melanoma, sarcoma, prostate, lung, leukemia, renal, colon or brain neoplasm. Additional embodiments include a solid support having arrayed thereon at least one nucleic acid probe or antibody specific for each of three or more (such as at least six) genes selected from the group consisting of genes listed in Table 6 or protein encoded therefrom and at least one probe or antibody specific for a control. In some such embodiments, the three or more genes include at least three (or at least six or each of the) genes selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, ZNF107.

IV. Methods of Determining Neoplasm Sensitivity or Prognosis

Described herein is the identification of gene signatures that indicate whether a neoplasm (such as a multiple myeloma neoplasm) is sensitive to mTORi/HDACi combination therapy and/or that correlate with the prognosis of a subject with a neoplasm. In some embodiments, using a gene signature to determine whether a neoplasm is sensitive to mTORi/HDACi combination therapy includes predicting whether mTORi/HDACi combination therapy will successfully treat the neoplasm, for example by increasing survival of the subject with the neoplasm. In other examples, using a gene signature to determine the prognosis includes predicting the outcome (such as chance of survival) of the subject with a neoplasm. In still other embodiments, using a gene signature to determine if a neoplasm is sensitive to mTORi/HDACi combination therapy includes predicting the response of the neoplasm to mTORi/HDACi therapy following initiation of mTORi/HDACi therapy. The disclosed methods optionally include detecting the expression level of three or more (such as at least six) genes listed in Table 6 or Table 7 in a neoplasm sample obtained from a subject with the neoplasm. For example, some embodiments include detecting and/or comparing the expression level of three or more genes (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, or at least 37 genes, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 genes) in a neoplasm sample obtained from a subject with the neoplasm, wherein the genes are selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. In some embodiments, the methods include detecting and/or comparing the expression level of CDC25A, E2F2, RRM2, RAD51, SPAG5, and MCM4. In some embodiments, the methods include detecting and/or comparing the expression level of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 in a neoplasm sample obtained from a subject with the neoplasm. In further embodiments, the method includes detecting the expression level of three or more (such as 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122, 123 or 124) of the genes disclosed in Table 6. In some embodiments, the methods also include comparing the expression level of the three or more (such as at least six) genes in the neoplasm sample to their expression level in a control and identifying the neoplasm as sensitive to treatment with mTORi/HDACi combination therapy if there is a difference in expression level (such as an increase or a decrease in expression) of the three or more genes in the neoplasm sample as compared to the control.

Several embodiments include identification of a gene expression signature including gene expression upregulation or downregulation, or both, compared to a control, as listed for three or more more genes (such as six; for example, the 37 genes of the blue module) listed in one of columns (1)-(4) of Table 6 or Table 7. For example, some embodiments include identifying a gene expression signature as shown in Table 6 or Table 7 for three or more genes (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, or at least 37 genes, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 genes) in a neoplasm sample obtained from a subject with the neoplasm, wherein the genes are selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. In some embodiments, the methods include identifying the gene expression signature as shown in Table 6 or Table 7 for ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 in a neoplasm sample obtained from a subject with the neoplasm. In further embodiments, the method includes identifying a gene expression signature as shown for three or more (such as 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122, 123 or 124) of the genes disclosed in Table 6. In some embodiments, the methods include comparing the gene expression signature of the three or more (such as at least six) genes in the neoplasm sample to the gene expression signature of the corresponding genes in a control. In additional embodiments, the methods include detecting the level of gene expression in the sample to identify the disclosed gene expression signature.

In some embodiments, a gene expression signature including gene expression upregulation or downregulation, or both, compared to a control, as listed for three or more more genes (such as six; for example, the 37 genes of the blue module) listed in column (1) of Table 6 is used to identify a subject with a neoplasm (such as multiple myeloma) having poor prognosis. In one embodiment, a gene expression signature including gene expression upregulation or downregulation, or both, compared to a control, as listed for three or more more genes (such as six; for example, the 37 genes of the blue module) listed in column (3) of Table 6 is used to identify a neoplasm (such as multiple myeloma) as sensitive to mTORi/HDACi combination treatment before initiation of mTORi/HDACi combination treatment. In another embodiment, a gene expression signature including gene expression upregulation or downregulation, or both, compared to a control, as listed for three or more genes (such as six; for example, the 37 genes of the blue module) listed in column (4) of Table 6 is used to identify a neoplasm (such as multiple myeloma) as sensitive to HDACi/mTORi therapy following initiation of mTORi/HDACi combination treatment (for example, 8 hours, 12 hours, 1 day, 2 days, 3 days, 4 days, 5 days, six days, 1 week, 2 weeks, 3 weeks or 4 weeks following initiation of therapy).

Expression levels of the disclosed genes can be detected using any suitable means known in the art. For example, detection of gene expression can be accomplished by detecting nucleic acid molecules (such as RNA) using nucleic acid amplification methods (such as RT-PCR), array analysis (such as microarray analysis), ribonuclease protection assay, bead-based assays, or Nanostring®. Detection of gene expression can also be accomplished using assays that detect the proteins encoded by the genes, including immunoassays (such as ELISA, Western blot, RIA assay, or protein arrays). Additional methods of detecting gene expression are well known in the art, and representative examples are described in greater detail below.

Several embodiments include comparing the expression level of one or more genes with a control. The control can be any suitable control against which to compare expression level of a gene (such as three or more of the genes disclosed in Table 6 or Table 7) in a neoplasm sample. In some embodiments, the control is the expression level of a gene or genes in a non-neoplasm tissue. In some examples, the non-neoplasm tissue is obtained from the same subject, such as non-neoplasm tissue that is adjacent to the neoplasm. In other examples, the non-neoplasm tissue is obtained from a healthy control subject. In other embodiments, the control is a reference value or ranges of values. For example, the reference value can be derived from the average expression values obtained from a group of healthy control subjects or non-neoplasm tissue from a group of cancer patients. In some examples, the control includes a level of expression of a gene signature (such as normalized expression or aggregate values described below) from a control or reference dataset (such as microarray data from one or more neoplasms or non-neoplasm tissue, such as publicly available datasets). In other examples, the control includes expression level of one or more housekeeping genes (which can include, but are not limited to beta-actin, hypoxanthine phosphoribosyltransferase (HPRT), glyceraldehyde-3-phosphate dehydrogenase (GAPDH), glucuronidase (GUS), transferrin receptor (TFRC), and/or peptidylprolyl isomerase A (PPIA)) in the neoplasm sample.

In some embodiments, the expression level of the disclosed genes (such as three or more of the genes listed in Table 6 or Table 7) is normalized relative to the expression level of one or more housekeeping genes in the same neoplasm sample. In some examples, an aggregate value is obtained by calculating the level of expression of each of the genes (e.g., each of the genes in a gene expression signature) and using a positive or negative weighting for each gene depending on whether it is positively or negatively regulated by a condition (e.g., mTORi/HDACi combination therapy or survival risk score). In some examples, normalized expression of the gene (or normalized expression of the gene signature) or an aggregate value is determined to be increased or decreased as compared to median normalized expression of the gene (or gene signature) or an aggregate value for a set of neoplasms. In some examples, the median normalized expression or aggregate value is obtained from publicly available microarray datasets, such as breast cancer or multiple myeloma microarray datasets. In one example, a median normalized expression or aggregate value for the gene signature is determined using the microarray datasets utilized in Example 1, below.

In some embodiments, a score is calculated from the normalized expression level measurements. The score can be utilized to provide cut off points to identify a neoplasm as sensitive or less likely to be sensitive to mTORi/HDACi therapy, subjects at risk (such as low, medium, or high risk) for neoplasm recurrence or progression and/or low, medium, or high sensitivity to a therapy (such as mTORi/HDACi combination therapy). In some examples, the cut-off points are determined using training and validation datasets. In one example, a supervised approach is utilized to establish the cut-off that distinguishes responders from non-responders (such as mTORi/HDACi combination therapy responders/non-responders), for example by comparing gene signature expression in responders and non-responders. In other examples, an unsupervised approach is utilized to empirically determine a cut-off level (for example, top 50% vs. bottom 50% or top tercile vs. bottom tercile) that is predictive of outcome. The cut-off determined in the training set is tested in one or more independent validation sets. In one example, the GSE4581 dataset is utilized as a training dataset and/or validation dataset.

In some examples, the results of the gene expression analysis are provided to a user (such as a clinician or other health care worker, laboratory personnel, or patient) in a perceivable output that provides information about the results of the analysis. In some examples, the output can be a paper output (for example, a written or printed output), a display on a screen, a graphical output (for example, a graph, chart, or other diagram), or an audible output.

In some examples, the output is a numerical value (such as an expression level of one or more of the genes listed in Table 6 or Table 7, or a gene expression signature listed for three or more of the genes listed in Table 6 or Table 7) in the sample or a relative amount of one or more of the disclosed genes in the sample as compared to a control. In additional examples, the output is a graphical representation, for example, a graph that indicates the value (such as amount or relative amount) of one or more of the disclosed genes in the sample from the subject on a standard curve. In a particular example, the output (such as a graphical output) shows or provides a cut-off value or level that indicates that the neoplasm is sensitive to mTORi/HDACi combination therapy and/or the subject has a poor prognosis if the value or level is above the cutoff and indicates that the neoplasm is less likely to be sensitive to mTORi/HDACi combination therapy and/or the subject has a good prognosis if the value or level is below the cut-off. In some examples, the output is communicated to the user, for example by providing an output via physical, audible, or electronic means (for example by mail, telephone, facsimile transmission, email, or communication to an electronic medical record).

The output can provide quantitative information (for example, an amount of one or more of the disclosed genes in a sample or an amount of one or more of the disclosed genes relative to a control sample or control value) or can provide qualitative information (for example, a determination of mTORi/HDACi combination therapy sensitivity and/or a prognosis). In additional examples, the output can provide qualitative information regarding the relative amount of one or more of the disclosed genes in the sample, such as identifying presence of an increase in one or more of the disclosed genes relative to a control, a decrease in one or more of the disclosed genes relative to a control, or no difference in one or more of the disclosed genes relative to a control.

In some examples, the gene expression analysis may include determination of other clinical information (such as determining the amount of one or more additional cancer biomarkers in the sample). In some examples, the gene expression analysis includes an array, such as an oligonucleotide or antibody array and the output of the test includes quantitative or qualitative information about one or more of the disclosed genes, as well as quantitative or qualitative information about one or more additional genes.

A. Identification of a Neoplasm Sensitive to mTORi/HDACi Therapy

Neoplasms that Will Respond to Therapy (Prognostic Identification of Neoplasms)

In some embodiments of the disclosed methods, detecting a difference in the level of expression of three or more (such as at least six) genes listed in Table 6 or Table 7 in the neoplasm sample relative to the control can be used to determine whether a neoplasm is sensitive to mTORi/HDACi combination therapy, for example, before mTORi/HDACi therapy is initiated. For example, some embodiments include detecting a difference in the expression level of three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) genes in a neoplasm sample obtained from a subject with the neoplasm compared to a control, wherein at least three of the genes are selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. Detecting a difference in the expression level of these genes compared to the control indicates that the neoplasm is sensitive to mTORi/HDACi combination therapy. In some examples, an increase in expression level of one or more of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in expression of one or more of Hs.193784, Hs.202577, HLA-DPB1, and PHC3 in the neoplasm sample relative to the control indicates that the neoplasm is sensitive to mTORi/HDACi combination therapy. In other examples, an increase in expression level of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and a decrease in expression of Hs.193784, Hs.202577, HLA-DPB1, and PHC3 in the neoplasm sample relative to the control indicates that the neoplasm is sensitive to mTORi/HDACi combination therapy. In some embodiments, a statistically significant increase or decrease in the expression level of the three or more genes (such as an increase or decrease of at least about 1-fold (100%), for example, at least about 1.5-fold, about 2-fold, about 2.5-fold, about 3-fold, about 4-fold, about 5-fold, about 7-fold or about 10-fold) indicates that the neoplasm is sensitive to mTORi/HDACi combination therapy.

In other examples, detection of a gene expression signature as shown for three of more of the genes listed in Table 6 or Table 7 as determined by normalized expression or an aggregate value as compared to a control indicates that the neoplasm is sensitive to mTORi/HDACi combination therapy. In some embodiments, detection of a gene expression signature as shown in Table 6 or Table 7 for three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) of the ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 genes as determined by normalized expression or an aggregate value or a Sensitivity Index (SI) score as compared to a control indicates that the neoplasm is sensitive to mTORi/HDACi combination therapy.

Neoplasms Responding to Therapy (Pharmacodynamic Identification of Neoplasms)

In some embodiments of the disclosed methods, detecting a difference in the level of expression of three or more (such as at least six) genes listed in Table 6 or Table 7 in the neoplasm sample relative to the control can be used to determine the pharmacodynamic effect of mTORi/HDACi therapy on the neoplasm. In several such embodiments, detecting a difference in the level of expression of three or more (such as at least six) genes listed in Table 6 or Table 7 is used to determine whether a neoplasm is responding (e.g., on a molecular level) to mTORi/HDACi combination therapy after mTORi/HDACi therapy is initiated (for example, 8 hours, 12 hours, 1 day, 2 days, 3 days, 4 days, 5 days, six days, 1 week, 2 weeks, 3 weeks or 4 weeks following initiation of therapy). One non-limiting example of the advantage of this approach to determine whether a neoplasm (or a subject with a neoplasm) has a favorable molecular response to the mTORi/HDACi treatment before a physical response (such as reduction of tumor burden) can be detected. For example, some embodiments include detecting a difference in the expression level of three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) genes in a neoplasm sample obtained from a subject with the neoplasm compared to a control (such as a control neoplasm sample obtained from the subject before therapy was initiated), wherein at least three of the genes are selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. Detecting a difference in the expression level of these genes compared to the control indicates that the neoplasm is sensitive to mTORi/HDACi combination therapy. In some examples, a decrease in expression level of one or more of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or an increase in expression of one or more of Hs.193784, Hs.202577, HLA-DPB1, and PHC3 in the neoplasm sample relative to the control indicates that the neoplasm is responding to mTORi/HDACi combination therapy. In other examples, an decrease in expression level of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and an increase in expression of Hs.193784, Hs.202577, HLA-DPB1, and PHC3 in the neoplasm sample relative to the control indicates that the neoplasm is responding to mTORi/HDACi combination therapy. In some embodiments, a statistically significant increase or decrease in the expression level of the three or more genes (such as an increase or decrease of at least about 1-fold (100%), for example, at least about 1.5-fold, about 2-fold, about 2.5-fold, about 3-fold, about 4-fold, about 5-fold, about 7-fold or about 10-fold) indicates that the neoplasm is responding to mTORi/HDACi combination therapy.

In some embodiments, identification of a gene expression signature including gene expression upregulation or downregulation, or both, compared to a control, as listed for three or more more genes (such as at least six; for example, the 37 genes of the blue module) in column (4) of Table 6 is used to identify a neoplasm responding to mTORi/HDACi combination therapy. In several embodiments, the gene expression signature can be determined by normalized expression or an aggregate value or SI score.

In some embodiments, a SI score is used to identify a neoplasm as sensitive to mTORi/HDACi therapy. For example, the SI score can be calculated as the mean of the absolute value change in normalized gene expression for each of the genes detected, wherein the change in gene expression is a change in gene expression compared to a control. For example, the control can be a set value of gene expression, a detected gene expression from a control sample, such as healthy tissue sample, or a neoplasm sample that has not been treated. In some non-limiting embodiments, a control neoplasm sample can be obtained from a subject before initiation of mTORi/HDACi therapy, and one or more samples can be taken following initiation of mTORi/HDACi therapy. In one embodiment, the SI score can be calculated according to the following formula:

$$SI = \frac{1}{n}\sum_{i=1}^{n} |\log_2 X_{RM_i} - \log_2 X_{UNT_i}|$$

wherein SI is the Sensitivity Index Score, n is the number of genes analyzed, $X_{RM_i}$ is the normalized gene expression measured after treatment with mTORi/HDACi therapy, and $X_{UNT_i}$ is the normalized gene expression measured before treatment with mTORi/HDACi therapy. For example, in some embodiments, a control neoplasm sample can be obtained from a subject before initiation of mTORi/HDACi therapy, and one or more samples can be taken following initiation of mTORi/HDACi therapy. In one embodiment, the SI score can be calculated according to the following formula:

$$SI = \frac{1}{37}\sum_{i=1}^{37} |\log_2 X_{RM_i} - \log_2 X_{UNT_i}|$$

wherein SI is the Sensitivity Index Score, $X_{RM_i}$ is the normalized gene expression measured after treatment with mTORi/HDACi therapy, and $X_{UNT_i}$ is the normalized gene expression measured before treatment with mTORi/HDACi therapy. In one example (as shown in the above formula), the expression level of all 37 genes of the blue module listed in Table 6 (ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107) can be measured in the control sample and the sample obtained from the subject following initiation of mTORi/HDACi therapy. The SI score can then be used to identify a neoplasm as a sensitive (or not) to the mTORi/HDACi therapy. One non-limiting example of the advantages of this approach is that the SI score can be used to define whether a neoplasm (or a subject with a neoplasm) has a favorable molecular response to the mTORi/HDACi treatment. In this example, upon determination of a non-sensitive SI score of a neoplasm after initial mTORi/HDACi treatment, a clinician may choose to discontinue mTORi/HDACi therapy, as the patient would not be predicted to receive clinical benefit. The person of ordinary skill in the art will appreciate that the SI score indicative of a neoplasm sensitive to mTORi/HDACi treatment will vary, for example, based on the dosage of the treatment and particular mTORi and HDACi used.

B. Identification of an Optimal Dosage of mTORi for Use with mTORi/HDACi Combination Therapy Some examples include identification of an optimal dosage of mTORi for use in mTORi/HDACi combination treatment of a subject. For example, in some embodiments the gene expression level in the neoplasm sample of three or more (such as at least six) genes listed in Table 6 or Table 7 is correlated with a control to determine the optimal dosage of mTORi for use with mTORi/HDACi combination therapy for the subject. For example, some embodiments include correlation of the expression level of three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) genes in a neoplasm sample obtained from a subject with the neoplasm with a control, wherein at least three of the genes are selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. In some examples, the level of gene expression can be determined before, during and/or after mTORi/HDACi combination therapy to determine the optimal dosage of HDACi during a course of therapy (for example, to determine if the optimal dosage of HDACi has increased or decreased during the course of therapy).

In other examples, a gene expression signature in the neoplasm sample as shown for three of more of the genes listed in Table 6 or Table 7 as determined by normalized expression or an aggregate value is correlated with a control to identify an optimal dosage of mTORi for use in mTORi/HDACi combination treatment of the subject. Several embodiments include correlation of a gene expression signature as shown in Table 6 or Table 7 for three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) of the ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 genes as determined by normalized expression or an aggregate value with a control to identify an optimal dosage of mTORi for use in mTORi/HDACi combination treatment of the subject. In some examples, the gene expression signature can be determined before, during and/or after mTORi/HDACi combination therapy to determine the optimal dosage of mTORi during a course of therapy (for example, to determine if the optimal dosage of mTORi has increased or decreased during the course of therapy).

In several examples, the control includes response expression profiles of the three or more (such as at least six) genes from a neoplasm treated with mTORi/HDACi combination therapy. In other examples, the control includes expression profiles of the three or more (such as at least six) genes from an in vitro analysis of mTORi/HDACi combination therapy, for example from treatment of neoplasm cells (such as a multiple myeloma cell line) with mTORi/HDACi combination therapy. In several examples, the gene expression profile from the in vitro analysis is correlated with the gene expression profile from a neoplasm sample to identify the optimal mTORi dosage for use for mTORi/HDACi combination therapy for the neoplasm. Such correlation methods are known to the skilled artisan (see, e.g., examples of such methods provided in Tanaka et al., *J. Clin. Oncol.*, 26:1596-1602, 2008, which is incorporated by reference herein). Thus, in some examples, the gene expression level of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 in the neoplasm is correlated with the gene expression level of these genes from an in vitro analysis of mTORi/HDACi combination therapy to determine the optimal mTORi dosage for mTORi/HDACi combination therapy for the neoplasm. In some examples, the gene expression level (or gene signature) (y) can be used to determine an optimal dosage correlation value (x) that correlates the optimal mTORi dose (z) for combination mTORi/HDACi therapy for the neoplasm in the following manner: y=−0.563046+1.025323x, wherein the optimal dosage (z) is correlated with the optimal dosage correlation value according to known methods (e.g., methods provided in Tanaka et al., *J. Clin. Oncol.*, 26:1596-1602, 2008, which is incorporated by reference herein)

In several examples, the HDACi includes MS-275 and the mTORi includes Rapamycin.

C. Determining Prognosis of a Subject with a Neoplasm

In some embodiments of the disclosed methods, detecting a difference in the level of expression of three or more (such as at least six) genes listed in Table 6 or Table 7 in a neoplasm sample relative to a control (e.g., expression of the three or more genes in a control sample) is used to determine a prognosis for the neoplasm in a subject (such as, for example, squamous cell lung carcinoma, cutaneous melanoma, pleomorphic liposarcoma, colon adenoma, multiple myeloma, papillary renal cell carcinoma, melanoma, glioblastoma, chronic lymphocytic leukemia, invasive breast carcinoma stroma, ovarian serous cystadenocarcinoma, invasive breast carcinoma, glioblastoma, mantle cell lymphoma, or a breast neoplasm or multiple myeloma neoplasm in a subject). For example, some embodiments include detecting a difference in the expression level of three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) genes in a neoplasm sample obtained from a subject with the neoplasm compared to a control, wherein at least three of the genes are selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. Detecting a difference in the expression level of these genes compared to the control indicates that the neoplasm has a poor prognosis. For some examples, an increase in expression level of three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) of ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in expression level of one or more of Hs.193784, Hs.202577, KIAA2013, HLA-DPB1, and PHC3 in the neoplasm sample relative to a control genes indicates that the neoplasm has a poor prognosis. In other examples, an increase in expression level of ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and a decrease in expression of Hs.193784, Hs.202577, KIAA2013, HLA-DPB1, and PHC3 in the neoplasm sample relative to the control indicates that the neoplasm has a poor prognosis. In some embodiments, a statistically significant increase or decrease in the expression level of the three or more genes (such as an increase or decrease of at least about 1-fold (100%), for example, at least about 1.5-fold, about 2-fold, about 2.5-fold, about 3-fold, about 4-fold, about 5-fold, about 7-fold or about 10-fold) indicates that the neoplasm has a poor prognosis.

In other examples, detection of a gene expression signature as shown for three or more of the genes listed in Table 6 or Table 7 as determined by normalized expression or an aggregate value as compared to a control indicates that the neoplasm has a poor prognosis. In some embodiments, detection of a gene expression signature as shown in Table 6 or Table 7 for three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) of the ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 genes as determined by normalized expression or an aggregate value as compared to a control indicates that the neoplasm has a poor prognosis.

In several embodiments, detection of a difference in gene expression or a gene expression signature that indicates that a neoplasm has a poor prognosis, further indicates that the subject with the neoplasm has a poor prognosis.

Poor prognosis can refer to any negative clinical outcome, such as, but not limited to, a decrease in likelihood of survival (such as overall survival, relapse-free survival, or metastasis-free survival), a decrease in the time of survival (e.g., less than 5 years, or less than one year), presence of a malignant neoplasm, an increase in the severity of disease, resistance to therapy (e.g., resistance to mTORi/HDACi combination therapy), a decrease in response to therapy (e.g., development of resistance to mTORi/HDACi combination therapy), an increase in neoplasm recurrence, an increase in metastasis, or the like. In particular examples, a poor prognosis is a decreased chance of survival (for example, a survival time of equal to or less than 60 months, such as 50 months, 40 months, 30 months, 20 months, 12 months, 6 months, or 3 months, or less, from time of diagnosis or first treatment). The relative "poorness" of a prognosis, in various examples, may be in comparison to historical measure of other subjects with the same or similar neoplasm or cancer, or similar presentation of symptoms of neoplasm or cancer, for example.

In other embodiments of the disclosed methods, detecting no significant difference in expression level (such as no statistically significant difference) of three or more (such as at least six) genes listed in Table 6 or Table 7 in the neoplasm sample (such as a breast neoplasm or multiple myeloma neoplasm sample) relative to the control indicates that the subject has a good prognosis. In still other examples, detecting no statistically significant increase or decrease in expression of the gene expression signature as determined by normalized expression or an aggregate value as compared to a control indicates that the subject has a good prognosis.

In several embodiments, detection of a difference in gene expression or a gene expression signature that indicates that a neoplasm has a good prognosis, further indicates that the subject with the neoplasm has a good prognosis.

Good prognosis can refer to any positive clinical outcome, such as, but not limited to, an increase in likelihood of survival (such as overall survival, relapse-free survival, or metastasis-free survival), an increase in the time of survival (e.g., more than 5 years, more than one year, or more than two months), absence or reduction of a malignant neoplasm or tumor burden, a decrease in the severity of disease, likelihood of benefit of the subject to therapy (e.g., mTORi/HDACi combination therapy), an increase in response to therapy (e.g., mTORi/HDACi combination therapy), an decrease in neoplasm recurrence, or the like. In some examples, a good prognosis includes an increased chance of survival (for example increased overall survival, relapse-free survival, or metastasis-free survival). In an example, an increased chance of survival includes a survival time of at least 24 months from time of diagnosis, such as 24 months, 36 months, 48 months, 60 months, 72 months, 84 months, 96 months, 120 months, 150 months, or more from time of diagnosis or first treatment. The relative "goodness" of a prognosis, in various examples, may be in comparison to historical measure of other subjects with the same or similar neoplasm or cancer, or similar presentation of symptoms of neoplasm or cancer, for example.

In some embodiments, detection of a neoplasm with a good prognosis prior to treatment with mTORi/HDACi therapy can be used to identify a subject as likely to benefit from mTORi/HDACi therapy. In some embodiments, a prognostic index (PI) score is used to stratify subjects likely versus unlikely to benefit from combined mTORi/HDACi therapy. In some embodiments, the gene expression level in a neoplasm sample from a subject for three or more (such as at least six or each) of the 37 genes listed in Table 7 is determined and a corresponding PI score is calculated according to the following formula:

$$PI = \Sigma_i w_i x_i - 4.552161$$

wherein $w_i$ and $x_i$ are the weight (as defined in Table 7), and logged gene expression of the $i$th gene as detected in the neoplasm sample prior to treatment. In some embodiments, calculation of a PI score of $\geq -0.061194$ using the above formula for a neoplasm sample from a subject indicates that the subject is likely to benefit from mTORi/HDACi therapy.

D. Identifying the Need of Adjuvant Chemotherapy in a Subject with an Estrogen Receptor-Positive Breast Cancer Neoplasm In some embodiments, determining the prognosis of a subject with a neoplasm includes identifying a subject with an estrogen receptor-positive breast cancer neoplasm not needing adjuvant chemotherapy. Methods and reagents for identifying an estrogen receptor-positive breast neoplasm are well known to the person of ordinary skill (see, e.g., van't Veer et al., *Nature*, 415:530-536, 2002; van de Vijver et al., *N. Engl. J. Med.*, 347:1999-2009, 2002). For example, in some embodiments of the disclosed methods, detecting a difference in the level of expression of three or more genes listed in Table 6 or Table 7 in an estrogen receptor-positive breast cancer neoplasm sample from the subject relative to a control can be used to determine if the subject is in need of adjuvant chemotherapy. For example, some embodiments include detecting a difference in the expression level of three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) genes in the neoplasm sample obtained from the subject compared to a control, wherein at least three of the genes are selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. Detecting a difference in the expression level of these genes compared to the control indicates that the subject is in need of adjuvant chemotherapy for treatment of the estrogen receptor-positive breast cancer neoplasm. In some embodiments, an increase in expression level of three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) of ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in expression level of one or more of Hs.193784, Hs.202577, KIAA2013, HLA-DPB1, and PHC3 in the neoplasm sample relative to a control indicates that the subject is in need of adjuvant chemotherapy. In other examples, detecting an increase in expression level of ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and a decrease in the expression level of Hs.193784, Hs.202577, KIAA2013, HLA-DPB1, and PHC3 in the neoplasm sample relative to the control indicates that the subject is in need of adjuvant chemotherapy. In some embodiments, a statistically significant increase or decrease in the expression level of the three or more genes (such as an increase or decrease of at least about 1-fold, for example, at least about 1.5-fold, about 2-fold, about 2.5-fold, about 3-fold, about 4-fold, about 5-fold, about 7-fold or about 10-fold) indicates that the neoplasm has a poor prognosis.

In other examples, detection of a gene expression signature as shown for three of more of the genes listed in Table 6 or Table 7 as determined by normalized expression or an aggregate value as compared to a control indicates that subject is in need of adjuvant chemotherapy for the estrogen receptor-positive breast neoplasm. In some embodiments, detection of a gene expression signature as shown in Table 6 or Table 7 for three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) of the ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 genes as determined by normalized expression or an aggregate value as compared to a control indicates that the subject is in need of adjuvant chemotherapy for the estrogen receptor-positive breast neoplasm.

In other embodiments of the disclosed methods, detecting no significant difference in expression level (such as no statistically significant difference) of three or more genes listed in Table 6 or Table 7 in the estrogen receptor-positive breast neoplasm sample relative to the control indicates that the subject is not in need of adjuvant chemotherapy for the estrogen receptor-positive breast neoplasm. For example, some embodiments include detecting no significant difference in the expression level of three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) genes in the neoplasm sample obtained from the subject compared to a control, wherein at least three of the genes are selected from the group consisting of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. If no significant difference in expression level (such as no statistically significant difference) of the three or more genes in the neoplasm sample relative to the control is detected, then adjuvant chemotherapy is not needed to treat the neoplasm. In some such embodiments no significant difference in the expression level of each of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 compared to a control indicates that the estrogen receptor-positive neoplasm is not in need of adjuvant chemotherapy.

In still other examples, detecting no statistically significant increase or decrease in expression of the gene expression signature as determined by normalized expression or an aggregate value as compared to a control indicates that the subject has a good prognosis.

In other examples, detection of no significant (such as no statistically significant) expression of a gene expression signature as shown for three of more of the genes listed in Table 6 or Table 7 as determined by normalized expression or an aggregate value as compared to a control indicates that the subject is in not need of adjuvant chemotherapy for the estrogen receptor-positive breast neoplasm. In some embodiments, detection of no significant (such as no statistically significant) expression of a gene expression signature as shown in Table 6 or Table 7 for three or more (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or at least 37) of the ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 genes as determined by normalized expression or an aggregate value as compared to a control indicates that the subject is in not need of adjuvant chemotherapy for the estrogen receptor-positive breast neoplasm.

E. Computer-Based Implementation of Certain Embodiments

As used herein, "a computer-based system" refers to the hardware means, software means, and data storage means used to analyze information of the present embodiments. In some embodiments, the computer-based systems include a central processing unit (CPU), input means, output means, and data storage means. A skilled artisan can readily appreciate that any one of the currently available computer-based systems are suitable for use in the present embodiments. The data storage means may comprise any manufacture comprising a recording of the present information as described above, or a memory access means that can access such a manufacture.

The analytic methods described herein can be implemented by use of computer systems. For example, any of the comparison steps described above may be performed by means of software components loaded into a computer or other information appliance or digital device. When so enabled, the computer, appliance or device may then perform the above-described steps to assist the analysis of values associated with a one or more genes (for example a value that correlates with the expression of a particular gene in the manner described above, or for comparing such associated values. The above features embodied in one or more computer programs may be performed by one or more computers running such programs.

In some embodiments, a computer system suitable for implementation of the disclosed analytic methods includes internal components and is linked to external components. The internal components of this computer system include a processor element interconnected with main memory. The external components include mass storage. This mass storage can be one or more hard disks (which are typically packaged together with the processor and memory). Such hard disks are preferably of 1 GB or greater storage capacity. Other external components include user interface devices, which can be a monitor, together with inputting device, which can be a "mouse", or other graphic input devices, and/or a keyboard. A printing device can also be attached to the computer. Typically, computer system is also linked to network link, which can be part of an Ethernet link to other local computer systems, remote computer systems, or wide area communication networks, such as the Internet. This network link allows the computer system to share data and processing tasks with other computer systems.

Loaded into memory during operation of this system are several software components, which are both standard in the art and special to the instant disclosure. These software components collectively cause the computer system to function according to the disclosed methods. In some embodiments, the software components are stored on mass storage. In some embodiments, the software components include an operating system, which is responsible for managing the computer system and its network interconnections. This operating system can be, for example, of the Microsoft Windows' family, such as Windows 7, or earlier or later versions. The software components also include common languages and functions conveniently present on this system to assist programs implementing the disclosed methods. Many high or low level computer languages can be used to program the analytic methods. Instructions can be interpreted during run-time or compiled. Preferred languages include C/C++, FORTRAN, R and JAVA®. Most preferably, the methods are programmed in mathematical software packages that allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), and S-Plus from Math Soft (Cambridge, Mass.). In an exemplary implementation, to practice the methods, a user first loads microarray experiment data into the computer system. These data can be directly entered by the user or from other computer systems linked by the network connection, or on removable storage media such as a CD-ROM, floppy disk, tape drive, ZIP® drive or through the network. Next the user causes execution of expression profile analysis software, which performs the disclosed methods.

In another exemplary implementation, a user first loads microarray experiment data into the computer system. This data is loaded into the memory from the storage media or from a remote computer, for example, from a dynamic geneset database system, through the network. Next the user causes execution of software that performs the comparison of gene expression data from a neoplasm sample with a control (as described herein) to detect a difference of gene expression between the neoplasm sample and the control.

Alternative computer systems and software for implementing the analytic methods of this will be apparent to one of skill in the art.

Thus, any of the disclosed methods can be implemented as computer-executable instructions stored on one or more computer-readable storage media (e.g., non-transitory computer-readable media, such as one or more optical media discs, volatile memory components (such as DRAM or SRAM), or nonvolatile memory components (such as hard drives)) and executed on a computer (e.g., any commercially available computer, including smart phones or other mobile devices that include computing hardware). Any of the computer-executable instructions for implementing the disclosed techniques as well as any data created and used during implementation of the disclosed embodiments can be stored on one or more computer-readable media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers. For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, R, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

Any of the computer-readable media herein can be non-transitory (e.g., memory, magnetic storage, optical storage, or the like). Any of the storing actions described herein can be implemented by storing in one or more computer-readable media (e.g., computer-readable storage media or other tangible media). Any of the things described as stored can be stored in one or more computer-readable media (e.g., computer-readable storage media or other tangible media).

Any of the methods described herein can be implemented by computer-executable instructions in (e.g., encoded on) one or more computer-readable media (e.g., computer-readable storage media or other tangible media). Such instructions can cause a computer to perform the method. The technologies described herein can be implemented in a variety of programming languages. Any of the methods described herein can be implemented by computer-executable instructions stored in one or more computer-readable storage devices (e.g., memory, magnetic storage, optical storage, or the like). Such instructions can cause a computer to perform the method.

Some embodiments include a method performed by a computer system, the computer system including a screen, software that displays gene expression levels on the screen, a keyboard or mouse for interfacing with the software, and a memory that stores a list or lists of the expression levels of genes in a neoplasm sample. The method includes, for example, analyzing the list or lists of the level of expression in a neoplasm sample of three or more genes listed in Table 6 to a control level of expression data set of the same three or more genes; and identifying the neoplasm as sensitive to treatment with HDACi and mTORi combination therapy when an increase or decrease in the level of expression of the three or more genes in the neoplasm sample relative to the control exceeds a predefined limit.

Additional embodiments include a method implemented at least in part by a computer, the method comprising receiving a gene expression dataset (e.g., a list of gene expression levels) comprising a gene expression level for each of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107. The gene expression level of genes in the dataset is compared to a control gene expression level of the same genes and a difference in the gene expression level of the genes in the dataset as compared to the control gene expression level of the same genes is calculated (for example, as described herein). In several embodiments, the calculated difference in the gene expression level of the genes in the dataset as compared to the control gene expression level of the same genes is displayed in a user interface. In additional embodiments, the method further includes identifying the neoplasm as sensitive to treatment with HDACi and mTORi combination therapy if there is a difference in the gene expression level of the genes in the dataset as compared to the control gene expression level of the same genes.

In other embodiments, one or more computer-readable storage devices comprising computer-executable instructions for performing any one or more of the methods described herein are provided.

V. Detecting Gene Expression Level

As described below, the level of expression of genes listed in Table 6 or Table 7 in a sample can be detected using any one of a number of methods well known in the art. Although exemplary methods are provided, the disclosure is not limited to such methods. Detection of expression level of either mRNA or protein is contemplated herein.

The disclosure includes isolated nucleic acid molecules that include specified lengths of nucleotide sequences, such as the nucleotide sequences of the genes listed in Table 6 or Table 7. Such molecules can include at least 10, at least 15, at least 20, at least 25, at least 30, at least 35, at least 40, at least 45, at least 50, or more consecutive nucleotides of these sequences or more, and can be obtained from any region of the disclosed genes. In some examples, particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100, or even at least 200 nucleotides long, or from about 6 to about 50 nucleotides, for example about 10-25 nucleotides, such as 12, 15, or 20 nucleotides. In one example, an oligonucleotide is a short sequence of nucleotides of at least one of the genes disclosed in Table 6 or Table 7, for example at least one of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107.

A. Methods for Detecting Nucleic Acids

Gene expression level can be determined by detecting mRNA encoding the gene of interest. Thus, the disclosed methods can include determining mRNA encoding three or more of the genes disclosed in Table 6 or Table 7 and described herein. In particular examples, mRNA encoding three or more of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 is detected. In some examples, the mRNA is quantitated.

In some examples, the disclosed genes are detected utilizing an oligonucleotide probe. Such probes include short sequence of nucleotides, such as at least 8, at least 10, at least 15, at least 20, at least 21, at least 25, or at least 30 nucleotides in length, used to detect the presence of a complementary sequence by molecular hybridization.

RNA can be isolated from a sample of a neoplasm (for example, a breast neoplasm or multiple myeloma neoplasm) from a subject, a sample of adjacent non-neoplasm tissue from the subject, a sample of neoplasm-free tissue from a normal (healthy) subject, or combinations thereof, using methods well known to one skilled in the art, including commercially available kits. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, *Biotechniques* 6:56-60 (1988), and De Andres et al., *Biotechniques* 18:42-44 (1995). In one example, RNA isolation can be performed using a purification kit, buffer set and protease from commercial manufacturers, such as QIAGEN (Valencia, Calif.), according to the manufacturer's instructions. For example, total RNA from cells (such as those obtained from a subject) can be isolated using QIAGEN RNeasy® mini-columns. Other commercially available RNA isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from neoplasm or other biological sample can also be isolated, for example, by cesium chloride density gradient centrifugation.

Methods of gene expression level profiling include methods based on hybridization analysis of polynucleotides, methods based on sequencing of polynucleotides, and proteomics-based methods. In some examples, mRNA expression level in a sample is quantified using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992) or quantitative real-time PCR. Alternatively, antibodies can be employed that can recognize specific duplexes, including DNA duplexes, RNA duplexes, and DNA-RNA hybrid duplexes or DNA-protein duplexes. Bead-based multiplex assays (such as Luminex xMAP® assay) can also be utilized. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, for example in normal and neoplasm tissues, with or without drug treatment, to characterize patterns of gene expression levels, to discriminate between closely related mRNAs, and to analyze RNA structure.

Methods for quantitating mRNA are well known in the art. In some examples, the method utilizes RT-PCR. For example, extracted RNA can be reverse-transcribed using a GeneAmp® RNA PCR kit (Perkin Elmer, Calif., USA), following the manufacturer's instructions. In some embodiments, gene expression levels can be determined using a gene expression analysis technology that measure mRNA in solution. Examples of such gene expression analysis technologies include, but not limited to, RNAscope™, RT-PCR, Nanostring®, QuantiGene®, gNPA®, microarray, and sequencing. For example, methods of Nanostring use labeled reporter molecules, referred to as labeled "nanoreporters," that are capable of binding individual target molecules. Through the nanoreporters' label codes, the binding of the nanoreporters to target molecules results in the identification of the target molecules. Methods of Nanostring are described in U.S. Pat. No. 7,473,767 (see also, Geiss, *Nature Biotechnology*, 26, 317-325, 2008).

For example, TaqMan® RT-PCR can be performed using commercially available equipment. The system can include a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available from PE Applied Biosystems (Foster City, Calif.).

The steps of a representative protocol for quantitating gene expression level using fixed, paraffin-embedded tissues as the RNA source, including mRNA isolation, purification, primer extension and amplification are given in various published journal articles (see Godfrey et al., *J. Mol. Diag.* 2:84-91, 2000; Specht et al., *Am. J. Pathol.* 158:419-29, 2001). Briefly, a representative process starts with cutting about 10 µm thick sections of paraffin-embedded neoplasm tissue samples or adjacent non-cancerous tissue. The RNA is then extracted, and protein and DNA are removed. Alternatively, RNA is isolated directly from a neoplasm sample or other tissue sample. After analysis of the RNA concentration, RNA repair and/or amplification steps can be included, if necessary, and RNA is reverse transcribed using gene specific promoters followed by RT-PCR.

In some embodiments, the primers used for the amplification are selected so as to amplify a unique segment of the gene of interest (such as mRNA encoding one of the genes listed in Table 6 or Table 7, such as ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107). In some embodiments, expression levels of other genes are also detected (for example one or more control or housekeeping genes). Primers that can be used to amplify one or more of the genes listed in Table 6 or Table 7 (such as ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107) are commercially available or can be designed and synthesized according to well known methods.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some examples, gene expression level is identified or confirmed using microarray techniques. Thus, the gene expression signatures can be measured in either fresh or paraffin-embedded neoplasm tissue, using microarray technology. In this method, the nucleic acid sequences of interest (including cDNAs and oligonucleotides) are plated, or arrayed, on a microchip substrate. The arrayed sequences are then hybridized with isolated nucleic acids (such as cDNA or mRNA) from cells or tissues of interest. Just as in the RT-PCR method, the source of mRNA typically is total RNA isolated from neoplasms, and optionally from corresponding noncancerous tissue and normal tissues or cell lines.

In a specific embodiment of the microarray technique, PCR amplified inserts of cDNA clones are applied to a substrate in a dense array. In some examples, the array includes at least one probe specific to each of at least three of the disclosed genes (such as those in Table 6 or Table 7). In some examples, oligonucleotide probes specific for the nucleotide sequences of each of three or more genes listed in Table 6 or Table 7 (such as ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107) are arrayed on the substrate. The arrayed sequences can include, consist essentially of, or consist of these sequences. The microarrayed nucleic acids are suitable for hybridization under stringent conditions. Labeled cDNA probes may be generated, for example through incorporation of fluorescent nucleotides by reverse transcription of RNA extracted from tissues of interest. Labeled cDNA probes applied to the array hybridize with specificity to each spot of DNA on the array. After stringent washing to remove non-specifically bound probes, the array is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression level and expression level patterns in the neoplasm sample of the genes listed in Table 6 or Table 7 (for example, ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107). Microarray analysis can be performed by commercially available equipment, following the manufacturer's protocols, such as are supplied with Affymetrix® GeneChip® technology (Affymetrix, Santa Clara, Calif.), or Agilent's microarray technology (Agilent Technologies, Santa Clara, Calif.).

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

In situ hybridization (ISH) is another method for detecting and comparing expression levels of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression level of the disclosed genes.

Sample cells or tissues are treated to increase their permeability to allow a probe, such as a gene-specific probe, to enter the cells. The probe is added to the treated cells, allowed to hybridize at pertinent temperature, and excess probe is washed away. A complementary probe is labeled so that the probe's location and quantity in the tissue can be determined, for example, using autoradiography, fluorescence microscopy or immunoassay. The sample may be any sample as herein described, such as a non-neoplasm sample or a neoplasm sample. Since the sequences of the genes of interest are known, probes can be designed accordingly such that the probes specifically bind the gene of interest.

In situ PCR is the PCR-based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, $^3$H-CTP or biotin-16-dUTP), which have been incorporated into the PCR products during thermal cycling.

In some embodiments of the detection methods, the expression level of one or more "housekeeping" genes or "internal controls" can also be evaluated. These terms include any constitutively or globally expressed gene (or protein, as discussed below) whose presence enables an assessment of gene (or protein) levels of the disclosed gene expression signature. Such an assessment includes a determination of the overall constitutive level of gene transcription and a control for variations in RNA (or protein) recovery.

For example, in some non-limiting embodiments, a high throughput method by which to gain information about gene expression is the nucleic acid microarray (e.g., a gridded nucleic acid microarray), in which a transparent support, such as a microscope slide, containing dozens to hundreds to thousands or more of immobilized nucleic acid samples is hybridized in a manner very similar to the northern and Southern blot. An ideal support allows effective immobilization of nucleic acid sequences (i.e., probes) onto its surface, and robust hybridization of target nucleic acid sequences with the probe. Following hybridization with dye-tagged nucleic acids, the array is "read" using a laser scanner to stimulate (to fluorescence) the dye attached to nucleic acid targets hybridized to the probes on the support. The motorized stage executes a programmed comb scan pattern that sequentially traverses the array in the X direction, and then steps a pixel width in the Y direction, producing a bi-directional raster pattern. Part of the dye fluorescence is captured by the scanner objective, filtered into red and green signals that are routed to each respective photomultiplier tube (PMT) where they are converted to electrical signals that are amplified, filtered and sampled by an analog-to-digital (A/D) converter. The scanner software converts the A/D converter output into a high-resolution image. The pixel intensity of each spot on the image is proportional to the number of dye molecules and hence the number of probe nucleic acids on the array that are hybridized with the target nucleic acids.

B. Methods for Detecting Proteins

In some examples, the expression level in a sample of three or more proteins encoded by the genes disclosed in Table 6 or Table 7 is analyzed. In particular examples, the expression level in a sample of three or more (e.g., ten or more, 30 or more 37 or more, or all of the) proteins encoded by ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 is analyzed. Suitable samples include biological samples containing protein obtained from a neoplasm (such as a breast neoplasm or multiple myeloma neoplasm) of a subject, from non-neoplasm tissue of the subject, and/or protein obtained from one or more samples of cancer-free subjects. Detecting a difference in the level of the three or more proteins encoded by the genes in Table 6 or Table 7 (such as ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107) in a neoplasm sample from the subject relative to a control, such as an increase or decrease in protein expression level, indicates the prognosis or diagnosis of the subject, as described above.

Antibodies specific for the proteins encoded by the genes listed in Table 6 or Table 7 (such as ATAD2, BLM, C9orf140, CCNB2, CDC20, CDC25A, CDC6, CDCA3, CDCA5, E2F2, HJURP, HLA-DPB 1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 can be used for detection and quantitation of proteins by one of a number of immunoassay methods that are well known in the art, such as those presented in Harlow and Lane (*Antibodies, A Laboratory Manual*, CSHL, New York, 1988). Antibodies specific for the proteins encoded by the genes listed in Table 6 or Table 7 are commercially available or can be generated using standard methods known to the person of ordinary skill.

Any standard immunoassay format (such as ELISA, Western blot, or RIA assay) can be used to measure protein levels. Thus, in one example, the levels of three or more the proteins encoded by the genes listed in Table 6 or Table 7 (such as ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 in a sample (for example, a multiple myeloma or breast neoplasm sample) can readily be evaluated using these methods. Immunohistochemical techniques can also be utilized for gene detection and quantification, for example using formalin-fixed, paraffin embedded (FFPE) slides coupled with an automated slide stainer (for example, available from Ventana Medical Systems, Inc., Tucson, Ariz.). General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating the disclosed proteins, a sample that includes cellular proteins (for example a breast neoplasm sample or multiple myeloma neoplasm sample) can be used. Quantitation of proteins can be achieved by immunoassay. The level of proteins can be assessed in the neoplasm sample and optionally in adjacent non-neoplasm tissue sample or in a tissue sample from a cancer-free subject. The level of the disclosed proteins in the neoplasm sample can be compared to level of the proteins from a sample from a cancer-free subject or other control (such as a standard value or reference value). A significant increase or decrease in the amount can be evaluated using statistical methods known in the art.

Quantitative spectroscopic methods, such as SELDI, can be used to analyze protein expression in a sample (such as neoplasm tissue, non-cancerous tissue, and tissue from a cancer-free subject). In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586). SELDI is a solid phase method for desorption in which the analyte is presented to the energy stream on a surface that enhances analyte capture or desorption.

In another example, antibodies are immobilized onto the surface using a bacterial Fc binding support. The chromatographic surface is incubated with a sample, such as a sample of a neoplasm. The antibodies on the chromatographic surface can recognize the antigens present in the sample. The unbound proteins and mass spectrometric interfering compounds are washed away and the proteins that are retained on the chromatographic surface are analyzed and detected by SELDI-TOF. The Mass Spectrometry profile from the sample can be then compared using differential protein expression mapping, whereby relative expression levels of proteins at specific molecular weights are compared by a variety of statistical techniques and bioinformatic software systems.

C. Arrays for Profiling Gene Expression Levels

In particular embodiments provided herein, arrays can be used to evaluate a disclosed gene expression signature, for example to determine a prognosis of a patient with cancer (for example, multiple myeloma or breast cancer) and/or determine whether a neoplasm is sensitive to HDACi and mTORi combination therapy. When describing an array that consists of probes or primers specific for three or more of the genes listed in Table 6 or Table 7 or the proteins encoded by these genes, such an array includes oligonucleotide probes or primers specific for these genes or antibodies specific for these proteins, and can further include control probes or antibodies (for example to confirm the incubation conditions are sufficient). In some embodiments, the array consists of probes, primers, or antibodies specific for 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 of the genes listed in Table 7, and can further include one or more control probes, primers, or antibodies. In some embodiments, the array consists of probes, primers, or antibodies specific for 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122, 123 or 124 of the genes listed in Table 6, and can further include one or more control probes, primers, or antibodies.

In one embodiment, the array includes, consists essentially of, or consists of oligonucleotide probes or primers or antibodies specific for each of three or more genes listed in Table 6 or Table 7 (such as three ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107) or the proteins encoded by these genes. In some embodiments, the array further includes one or more control probes, primers, or antibodies. Exemplary control probes include GAPDH, β-actin, and 18S RNA or antibodies that recognize proteins encoded by these genes. In one example, an array is a multi-well plate (e.g., 96 or 384 well plate). The oligonucleotide probes or primers or antibodies can include one or more detectable labels, to permit detection of binding between the probe and target (such as one of the genes listed in Table 6 or Table 7, or a protein encoded by one of these genes.

In some embodiments, the array may further include probes, primers, or antibodies specific for additional genes, such as about 5, 10, 20, 30, 40, 50, 60, 70, 80, 90 or 100 additional genes, or the proteins encoded by these genes.

1. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluoride, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide or antibody thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In another example, a surface activated organic polymer is used as the solid support surface. One example of a surface activated organic polymer is a polypropylene material aminated via radio frequency plasma discharge. Other reactive groups can also be used, such as carboxylated, hydroxylated, thiolated, or active ester groups.

2. Array Formats

A wide variety of array formats can be employed in accordance with the present disclosure. One example includes a linear array of oligonucleotide or antibody bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and reaction solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217:306-10, 1994. In one example, oligonucleotides are synthesized onto the support using conventional chemical techniques for preparing oligonucleotides on solid supports (such as PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, oligonucleotide probes or antibodies on the array include one or more labels that permit detection of oligonucleotide probe:target sequence hybridization complexes or antibody:protein complexes.

VI. Methods of Treatment

Several embodiments described herein include identification of a neoplasm in a subject sensitive to mTORi/HDACi combination therapy. In several embodiments, the methods include selecting an mTORi/HDACi combination therapy for the subject. In further examples, the selected mTORi/HDACi combination therapy is administered to the subject. Subjects that can benefit from the disclosed methods include human and veterinary subjects.

mTORi/HDACi combination therapy includes administration to a subject one or more agents that inhibit the activity of one or more HDAC molecules and one or more mTOR molecules. The combination therapy can be achieved with the use of a single agent (that inhibits both mTOR and HDAC) or a combination of one or more agents that inhibit mTOR and one or more agents that inhibit HDAC. The HDACi and mTORi can be administered simultaneously or sequentially.

In several embodiments, about 0.001 to about 5000 mg of the HDACi and/or mTORi is administered to the subject per day. For example, about 0.01, 0.05, 0.1, 0.5, 1, 2, 3, 4, 5, 6, 7, 8, 9, 10, 15, 20, 30, 40, 50, 60, 70, 80, 90 or 100 mg/day of the agent can be administered to the subject, such as from about 0.01 to 0.1, 0.1 to 1, 1 to 10 or 10 to 100 mg/day of the agent can be administered to the subject. In particular examples, the subject is administered one or more agents on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months. For example, the subjects can be orally administered 1, 5, 10, 20, 30, 40, 50, 60, 70, 80, 90 or 100 mg/day LBH589 (Panobinostat), or more, in combination with 0.5, mg/day RAD001 (everolimus). In some examples, the subject is administered the HDACi on days 1, 3, 5, 15, 17 and 19 of a 28 day cycle and the mTORi every day of the 28 day cycle.

The person of ordinary skill is familiar with HDAC inhibitors, as well as protocols for their administration to a subject. For example, HDAC inhibitors include (1) small molecular weight carboxylates (e.g., 4-phenylbutyrate and valproic acid); (2) hydroxamic acids (e.g., Suberoylanilide Hydroxamic Acid (SAHA; Vorinostat; Zolinza; Octanedioic acid hydroxyamide phenylamide), PXD101 (Belinostat), LAQ824, LBH-589 (Panobinostat), Pyroxamide, trichostatin A (TSA), oxamflatin and CHAPs, such as, CHAP1 and CHAP 31); (3) benzamides (e.g., MS-275 (Entinostat; SNDX-275; MS-275; MS-27-275), CI-994 (Tacedinaline; PD-123654; GOE-5549; Acetyldinaline), mecetinostat (MGCD0103)); and (4) cyclic peptides (Trapoxin A, trapoxin B, despeptides and Apicidin (Drummond et al., *Ann. Rev. Pharmacol. Toxicol.*, 45:495-528, 2005; Marks et al., *J. Natl. Cancer Inst.*, vol. 92, no. 15, pp. 1210-1216, 2000; Prince et al., *Clin. Cancer Res.*, 15:3958-3969, 2009). Additional HDAC inhibitors include ML-210; M344 (D237); Tubastatin A; Scriptaid; NSC 3852; NCH 51 (PTACH); HNHA (Heptanomide); BML-281; CBHA; Salermide; Pimelic Diphenylamide; ITF2357 (Givinostat); PCI-24781 (CRA-02478); APHA Compound 8; Droxinostat; SB939, Resminostat (4SC-201), CUDC-101, AR-42, CHR-2845, CHR-3996, 4SC-202, sulphoraphane.

Pan-HDACs inhibitors include, e.g., SAHA, LBH-589 (Panobinostat), PXD101 (Belinostat); and isotype/class-specific HDACs inhibitors include, e.g., romidepsin, mecetinostat (MGCD0103) and MS-275 (Prince et al., *Clin. Cancer Res.*, 15:3958-3969, 2009). SAHA and romidepsin (Istodax; FK228) are HDACs inhibitors approved by the U.S. Food and Drug Adminitration (FDA) for the treatment of refractory cutaneous T-cell lymphoma (CTCL; Marks and Breslow. *Nat, Biotechnol.*, 25:84-90, 2007; Piekarz et al., *J. Clin. Oncol.*, 27:5410-5417, 2009). Additionally, examples of HDAC inhibitors can be found in U.S. Pat. Nos. 5,369,108, 5,700,811, 5,773,474, 5,055,608, 5,175,191, as well as, Yoshida et al., *Bioassays*, 17:423-430, 1995; Saito et al., *Proc. Natl. Acad. Sci. U.S.A.*, 96:4592-4597, 1999; Furamai et al., *Proc. Natl. Acad. Sci. U.S.A.*, 98: 87-92, 2001; Komatsu et al., *Cancer Res.*, 61:4459-4466, 2001; Su et al., *Cancer Res.*, 60:3137-3142, 2000; Lee et al., *Cancer Res.*, 61:931-934, 2001; Suzuki et al., *J. Med. Chem.*, 42:3001-3003, 1999.

The person of ordinary skill is also familiar with mTOR inhibitors, as well as protocols for their administration to a subject. For example, such inhibitors include Rapamycin (sirolimus; Wyeth) and Rapamycin derivatives (e.g., temsirolimus (CCI-779; Wyeth); everolimus (RAD001; Novartis); and ridaforolimus (deforolimus; AP23573; Ariad Pharmaceuticals)), and small-molecule mTOR kinase inhibitors (e.g., AZD8055 (AstraZeneca); PKI-179 (Wyeth); PKI-587 (Wyeth); XL765 (Exelixis); NvP-BEZ235 (Novartis)). The person of ordinary skill is also familiar with protocols for administration of mTOR inhibitors; (See, e.g., the following references (which are incorporated by reference herein in their entirety as they relate to mTOR inhibitors and administration thereof): Dancey, *Nat. Rev. Clin. Oncol.*, 7:209-219, 200; Chan et al., *J. Clin. Oncol.*, 23:5314-5322, 2005; Witzig, et al., *J. Clin. Oncol.*, 23:5347-5356, 2005; Ansell et al., *J. Clin. Oncol.*, 24:a2732, 2006; Oza, et al., *J. Clin. Oncol.*, 24:a3003, 2006; Oza et al., *J. Clin. Oncol.*, 26:a5516, 2008; Pandya et al., *J. Thorac. Oncol.*, 2:1036-1041, 2007; Margolin et al., *Cancer*, 104:1045-1048, 2005; Chang et al., *Invest. New Drugs*, 23:357-361, 2005; Galanis et al., *J. Clin. Oncol.*, 23:5294-5304, 2005; Duran et al., Br. J. *Cancer*, 95:1148-1154, 2006; Farag et al., *J. Clin. Oncol.*, 24: a7616, 2006; Yee et al., *Blood (ASHAnnual Meeting Abstracts)*, 104:a4523, 2004; Okuno et al., *J. Clin. Oncol.*, 24:a9504, 2006; Soria et al., *Ann. Oncol.*, 20:1674-1681, 2009; Wolpin et al., *J. Clin. Oncol.*, 27:193-198, 2009; Yee et al., *Clin. Cancer. Res.*, 12:5165-5173, 2006; Yao et al., *J. Clin. Oncol.*, 26:4311-4318, 2008; Rao et al., *J. Clin. Oncol.*, 25:a8530, 2007; Chawla et al., *J. Clin. Oncol.*, 24:a9505, 2006; Rizzieri et al., *Clin. Cancer Res.*, 14:2756-2762, 2008; Colombo et al., *J. Clin. Oncol.*, 25:a5516, 2007; Bissler et al., *N. Engl. J. Med.*, 358:140-151, 2008; Garrido-Laguna et al., *J. Clin. Oncol.*, 27:a4612, 2009). In some examples, the mTORi includes an agent that inhibits activation of mTOR, for example a PI3K inhibitor such as GDC-0941, BKM 120, GS-1101, PX-886, or an AKT inhibitor such as perifosine, MK-2206, GSK2110183. In some examples, an agent is used that inhibits both HDAC and mTOR (or an upstream activator of mTOR, such as PI3K), for example, CURD-906 or CURD-907 (Curis, Inc., which inhibit both PI3K and HDAC).

In some examples, the method further includes selecting a therapy other than mTORi/HDACi combination therapy for such a subject. In further examples, the selected therapy is administered to the subject. In some examples, the selected therapy includes radiation therapy and/or one or more chemotherapeutic agents. Chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antineoplasm antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin. Chemotherapeutic agents can be administered individually, or in combination. Selection and therapeutic dosages of such agents are known to those skilled in the art, and can be determined by a skilled clinician.

VII. Neoplasm Samples

The disclosed methods can be used to determine the responsiveness of a neoplasm to a therapy (such as mTORi/HDACi combination therapy) or to determine the prognosis of a subject with a neoplasm. In some examples, the neoplasm is a solid neoplasm, such as a sarcoma or carcinoma, including fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In other examples, the neoplasm includes an abnormal cell growth occurring in a hematological cancer, including leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms; including Burkitt's lymphoma and mantle cell lymphoma), multiple myeloma, plasmacytoma, Waldenstrom's macroglobulinemia, heavy chain disease, myelodysplastic syndrome, and myelodysplasia.

Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, etc.), tissue biopsies (e.g., neoplasm biopsies), fine-needle aspirates, and/or tissue sections (e.g., cryostat tissue sections and/or paraffin-embedded tissue sections). In other examples, the sample includes circulating neoplasm cells. In particular examples, neoplasm samples are used directly (e.g., fresh or frozen), or can be manipulated prior to use, for example, by fixation (e.g., using formalin) and/or embedding in wax (such as formalin-fixed paraffin-embedded tissue samples).

EXAMPLES

The following examples are provided to illustrate particular features of certain embodiments, but the scope of the claims should not be limited to those features exemplified.

Example 1

Identification of Synergistic Effects of HDAC/mTOR Inhibition

This example describes the efficacy of combined HDAC and mTOR inhibition for the treatment of neoplasms. The utility of combining sirolimus and entinostat to control proliferation and growth of malignant B cell tumors was assessed.

Two central pathways frequently dysregulated in cancer are the PI3K/Akt/mTOR/p53(mTOR) and Cyclin/CDK/CDKI/Rb(CDK) pathways. mTOR and CDK pathway dysregulation is common in B cell neoplasias, including mantle cell lymphoma (MCL; Dal Col et al., *Blood,* 111:5142-5151, 2008 and Rizzatti et al., *Br J Haematol.* 2005; 130:516-526), multiple myeloma (MM; Dilworth et al. *Blood.* 2000; 95:1869-1871, and Peterson et al. *Cell.* 2009; 137:873-886), Burkitt's lymphoma (Klangby et al. *Blood.* 1998; 91:1680-1687 and Sanchez-Beato et al. *Am J Pathol.* 2001; 159:205-213). and mouse plasmacytoma (PCT; Bliskovsky et al., *Proc Natl Acad Sci USA.* 2003; 100:14982-14987; Zhang et al., *Proc Natl Acad Sci USA.* 1998; 95:2429-2434; Zhang et al *Mol Cell Biol.* 2001; 21:310-318; Mock et al. *Blood.* 1997; 90:4092-4098; Mock et al. *Proc Natl Acad Sci USA.* 1993; 90:9499-9503; Potter et al. *Cancer Res.* 1994; 54:969-975; and Potter et al. *Curr Top Microbiol Immunol.* 1988; 137:289-294), where genetic predisposition is determined in part by alleles of Mtor and Cdkn2a.

mTOR pathway dysregulation mechanistically involves mutations, activation by growth factor receptor pathways, PTEN loss, and amplification of AKT and DEPTOR. mTOR, a serine-threonine kinase forming two complexes, mTORC1 (mTOR, RAPTOR, PRAS40, mLST8, DEPTOR) and mTORC2 (mTOR, RICTOR, PROTOR, mLST8, SIN1, DEPTOR), phosphorylates a number of downstream targets (most notably pS6, 4EBP1, AKT) that regulate transcription/translation, cell proliferation/survival, immune responses, metabolism, and autophagy. Rapamycin (sirolimus), a relatively specific inhibitor of mTORC1, can also affect mTORC2 following prolonged exposure. Clinical investigations using Rapamycin or its analogs as single agents have shown modest long-term benefit despite initial antitumor activity.

Similarly, dysregulation of the cyclin dependent kinase (CDK) pathway often involves Cyclin/CDK amplification or reduced activity of a tumor suppressor gene in the pathway (Rb and cyclin-dependent kinase inhibitors (CDKI), including p16 and p21), via genetic or epigenetic mechanisms. HDAC inhibition in MM cell lines negatively regulates the Rb pathway (decreased phospho-Rb, decreased cyclin D1 and E2f1 expression), and positively regulates the p53 pathway (enhanced p53 activity, increased p21 and p27 expression). The benzamide, entinostat (MS-275), is a selective Class I HDAC inhibitor capable of reactivating tumor suppressor gene pathways, which can in turn reduce CDK activity. In contrast to pan-HDAC inhibitors, entinostat has strong activity against HDAC1, weak activity for HDACs2 and 3, some activity for HDAC9, and no activity against HDAC8 (Witt et al. *Cancer Lett.* 2009; 277:8-21 and Bantscheff et al., *Nat Biotechnol.* 2011; 29:255-265). Combining HDAC inhibitors with other therapies has shown efficacy in clinical trials for MM (Badros et al., *Clin Cancer Res.* 2009; 15:5250-5257) and breast cancer (Huang et al., *Cancer Lett.* 2011; 307:72-79), despite the relatively modest benefit of these inhibitors as single agents (Federico et al., *J Biomed Biotechnol.* 2011; 2011:475641; Gojo et al., *Blood.* 2007; 109:2781-2790; Gore et al., *Clin Cancer Res.* 2008; 14:4517-4525; Hess-Stumpp et al., *Int J Biochem Cell Biol.* 2007; 39:1388-1405; and Kummar et al., *Clin Cancer Res.* 2007; 13:5411-5417).

Methods

Cell Lines.

Human MM cell lines L363, U266, EJM, KMS12, KMS18, 8226, FR-4, JK-6L, ANBL-6, FLAM-76, XG-6, OCI-MY1, OCI-MY5, LP-1, MM-M1, SKMM-1, and SACHI were derived and authenticated as previously described (Gabrea et al., Genes Chromosomes Cancer, 47:573-590, 2008). XRPC24 (X24:interleukin (IL)-6 independent, p16 positive), MOPC265 (IL-6 dependent, p16 positive), and MOPC460 (IL-6 dependent, p16 negative, p53 partial deletion) cells were derived from pristane-induced PCTs from BALB/c mice. 107403 cells (p16 deleted) were cloned from a myc-ras retroviral-induced PCT from DBA/2 mice. MM cell lines were cultured in RPMI-1640 (2 mM L-glutamine, 10% fetal bovine serum (FBS), 100 U/ml penicillin, 100 µg/ml streptomycin). Mouse cell lines were cultured in RPMI-1640 with 50 µM β-mercaptoethanol and 10 ng/ml IL-6, except X24 which is IL-6 independent.

Drugs.

For in vitro studies: MS-275 (Sigma-Aldrich), sirolimus (Developmental Therapeutics Program (DTP), NCI) and triapine (Nanotherapeutics) were dissolved in DMSO at 10 mM (stored at −20° C.). For in vivo studies: A 50 mg/ml stock of Rapamycin (DTP, NCI) was prepared in ethanol (stored at −20° C.), and diluted at the time of injection to final concentration in 5% Tween-80, 5% polyethylene glycol-400 (Sigma, St Louis, Mo.). Entinostat (MS-275) (Syndax) was used in suspension made with 20% hydroxypropyl β-cylodextrin (Sigma). For in vivo studies, entinostat was generously provided by Syndax Pharmaceuticals Inc. Triapine and sirolims were generously provided by Nanotherapeutics Inc. and DTP, NCI, respectively.

Cell Proliferation Assay.

50,000 cells were seeded in 96-well (200 µl/well) plates and incubated with sirolimus and/or entinostat for 24-72 hours. WST-1 reagent (Roche) was used per manufacturer's protocol.

In Vivo Studies.

Athymic, NCr-nu/nu mice (Frederick, Md.) were used under institutionally approved (ACUC, NCI) protocols. For visualization, MM cells were infected with pSicoLV-luciferase-green fluorescent protein fusion gene. Growth of luc/GFP positive cells was measured weekly by bioluminescence using a XenogenIVIS®100 system. Sirolimus and entinostat (200 µl of each) were administered daily five days a week for four (L363) or twelve (U266) weeks by i.p. injection and oral gavage, respectively.

Combination Index Calculations.

CompuSyn (ComboSyn, Inc.) was used to assess synergy/additivity/antagonism of the drug combination by the Chou-Talalay method (Chou, *Cancer Res.* 70:440-446. 2010).

Flow Cytometry.

Cell cycle (stained with propidium iodide/RNAse buffer) and apoptosis assays (stained with Annexin-V-PE/7AAD) were done by FACScan flow cytometry and quantified using ModfitLT3.1 (Verity Software House) and BD CellQuest-Pro.

Westerns.

Antibodies were obtained from Cell Signaling and used at 1:1000 dilutions.

Figure 4A:
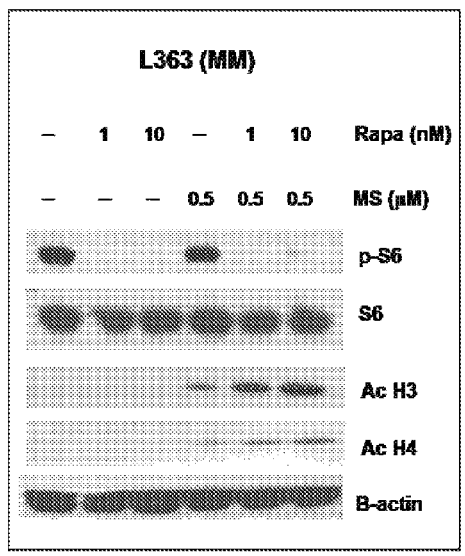
FIGS. 4A-4C are a set of digital images illustrating Western showing analysis of (A) L363, (B) U266, (C) SP53, and cell lysates from either untreated cells or cells treated with the indicated single agent or combination of agents. S6 phosphorylation and H3/H4 acetylation (AcH3/H4) are targets of mTOR and HDAC inhibition, respectively.
Figure 4B:
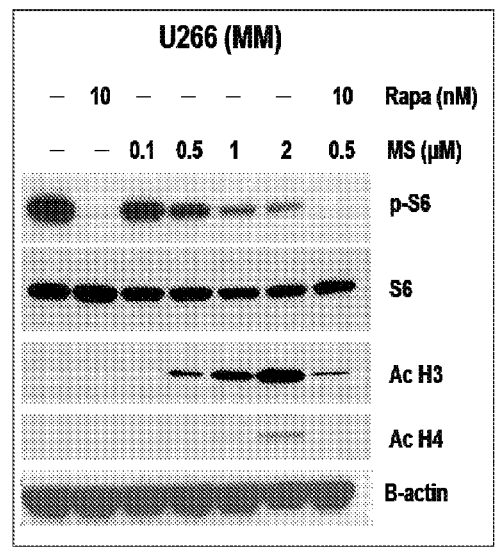
Figure 4C:
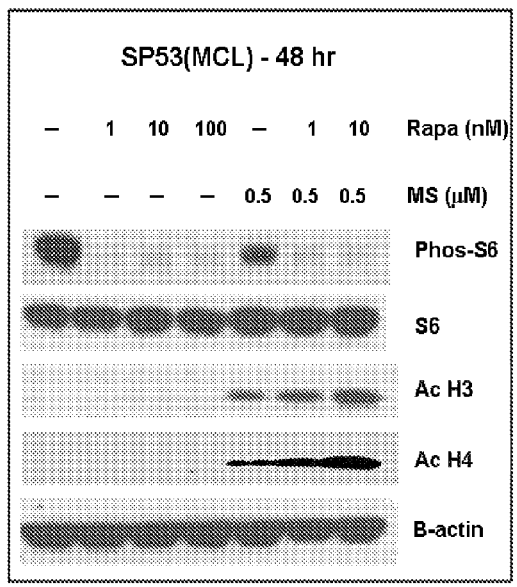
Figure 6A:
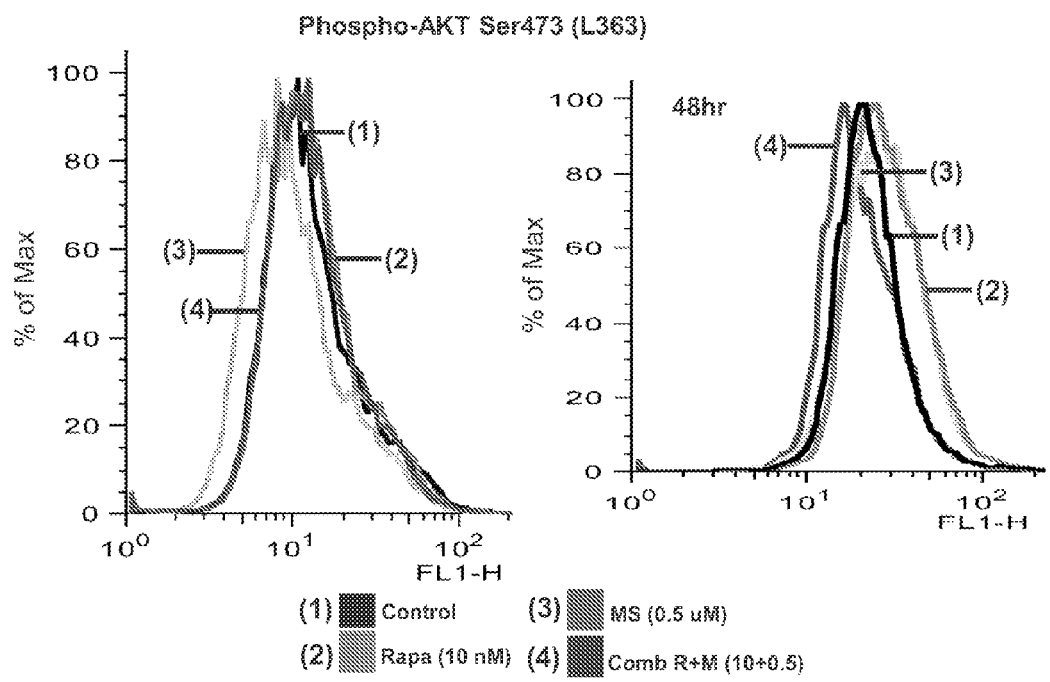
FIGS. 6A-6E are a series of graphs and digital images illustrating flow cytometry analysis studies. Flow cytometry analysis of L363 for phospho-proteins: (A) 4 hour and 48 hour untreated cells and cells treated with single agents or the combination stained with p-AKT$^{Ser\ 473}$ antibody; (B) 4 hour untreated, single agent or combination treated cells stained with p-ERK1/2$^{Thr202/Tyr204}$ antibody. p-AKT$^{Ser473}$ levels were increased slightly by sirolimus compared to other treatments and untreated cells. Combination treated cells had lower p-AKT$^{Ser473}$ levels and considerably lower p-ERK1/2$^{Thr202/Tyr204}$ levels compared to levels in cells individual drug treatment. Cell cycle analysis of (C) SP53 (MCL) cell line treated with single drugs and combination at 48 hours. R1+M2 indicates that sirolimus was given 24 hours prior to entinostat treatment; M1+R2 indicates that entinostat treatment preceded sirolimus by 24 hours. Western blot of control, single agent, and combination treated (D) L363 or (E) U266 cells at 48 hours.
Figure 6B:
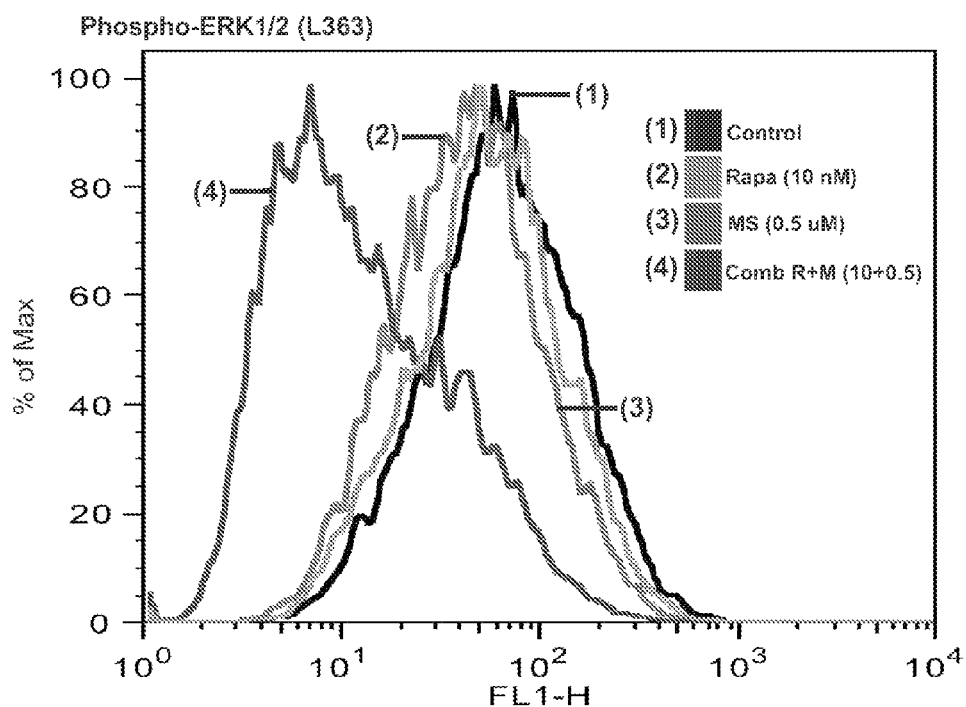
Figure 6C:
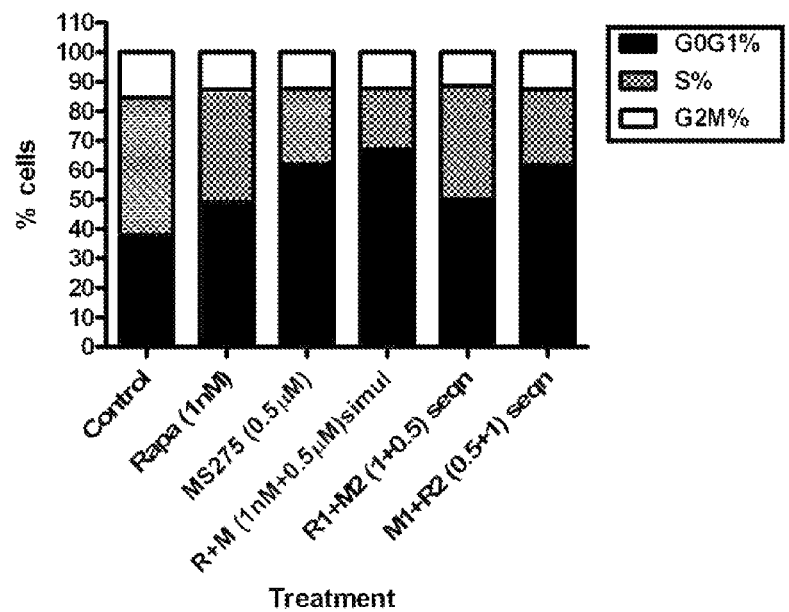

Results mTORi/HDACi combination inhibits tumor growth. The effects of sirolimus or entinostat alone on MM, MCL, and PCT cell line viability were concentration and time dependent (FIG. 2A-L). Low doses of sirolimus (10 nM) and entinostat (0.5 µM) were tested in a panel of seventeen human MM cell lines, two MCL cell lines, and two mouse PCT cell lines (FIG. 1A; Table 1). This dose combination decreased p-S6 and increased acetylation of histones H3/H4 (FIG. 4), indicating effective target inhibition for sirolimus and entinostat, respectively. Consistent with previous reports of same-class drugs, the addition of entinostat to sirolimus prevents AKT activation often seen with rapalog treatment (Zhang et al., *Blood,* 117:1228-1238, 2011) (FIG. 6A). Engagement of the pro-survival MAPK pathway is frequently observed in MM (Annunziata et al., *Blood,* 117: 2396-2404, 2011 and Giuliani et al., *Leukemia,* 18:628-635, 2004); MAPK activation was reduced by the combination as evidenced by decreased pERK1/2 (FIG. 6B).

Figure 2E:
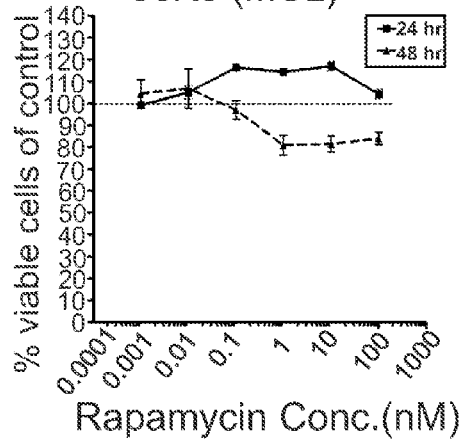
FIGS. 2A-2P are a series of graphs illustrating dose response curves in a panel of cell lines. Single agent dose response curves for (A,B) L363 (MM), (C,D) EJM (MM), (E,F) JeKo (MCL), (G,H) SP53 (MCL), (I,J) MOPC265 (PCT), (K,L) MOPC460 (PCT) cell lines. For fine-tuning the combination dose in L363 (MM) cells, CompuSyn analyses of the dose-responses for L363 cells was performed and is shown in the (M) dose-effect curve, (N) the combination index plot and (O) the normalized isobologram. (P) Single agent and combination treatment had little effect on viability of PBMCs from healthy volunteers (n=2) at 24 or 48 hours.
Figure 2F:
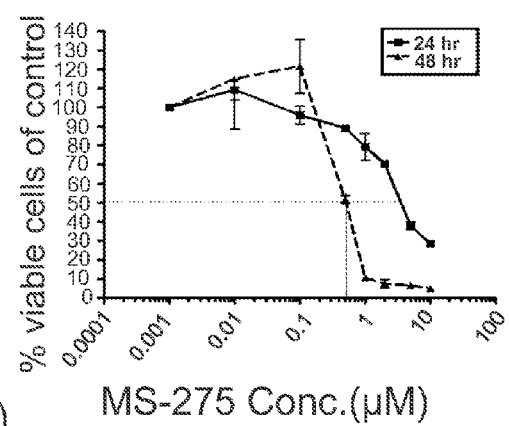
Figure 2G:
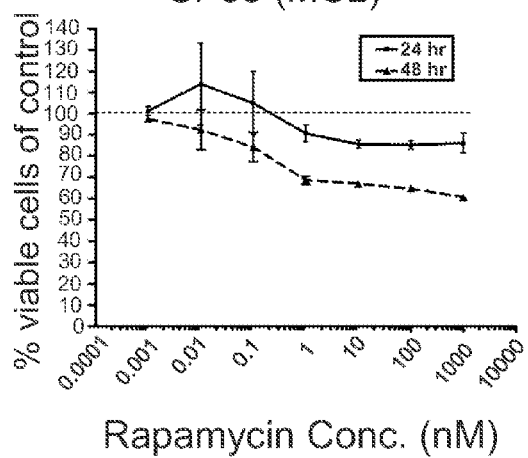
Figure 2H:
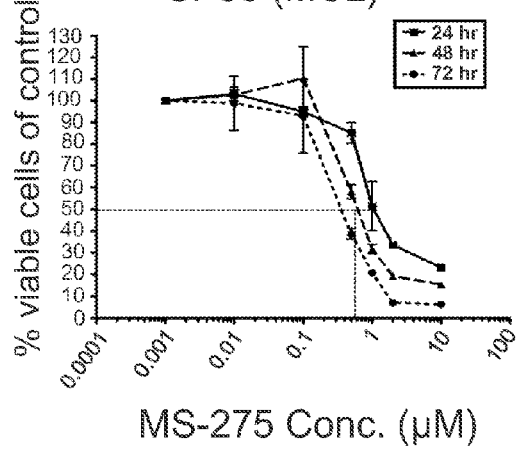
Figure 2I:
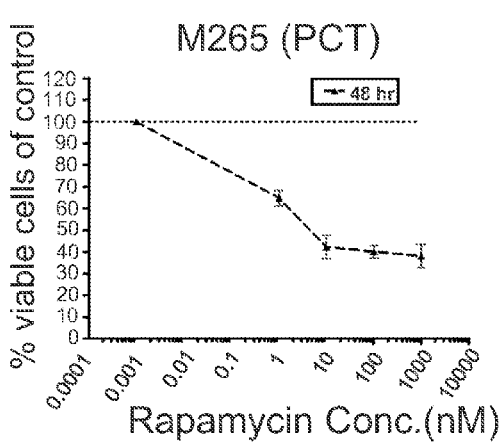
Figure 2J:
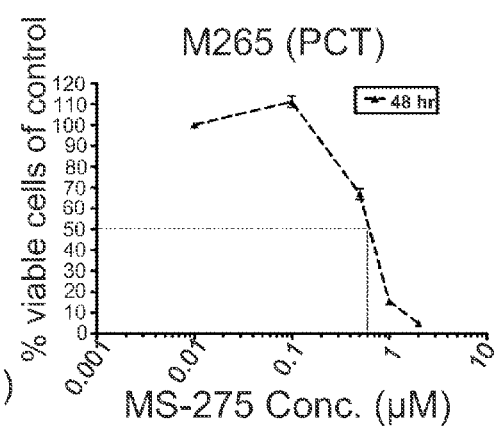
Figure 2K:
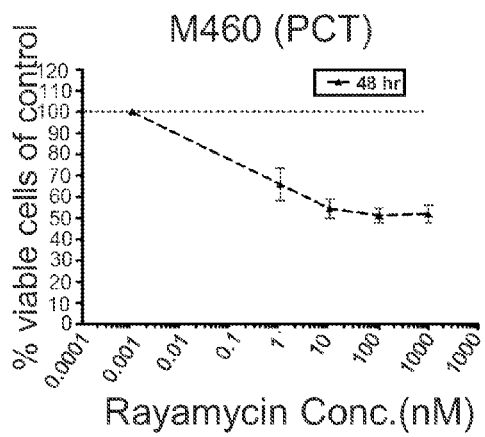
Figure 2L:
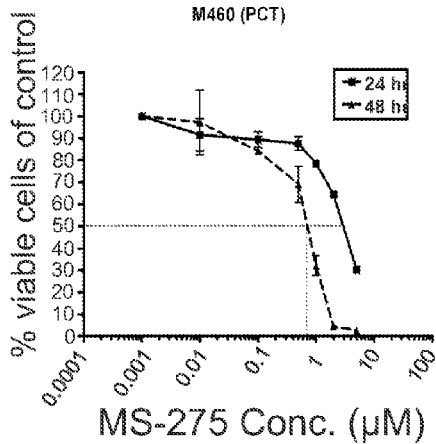
Figure 2M:
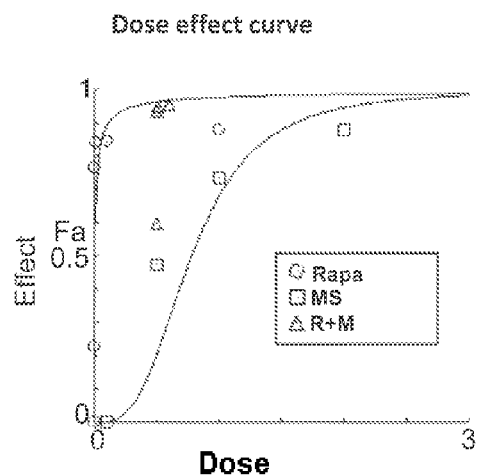
Figure 2N:
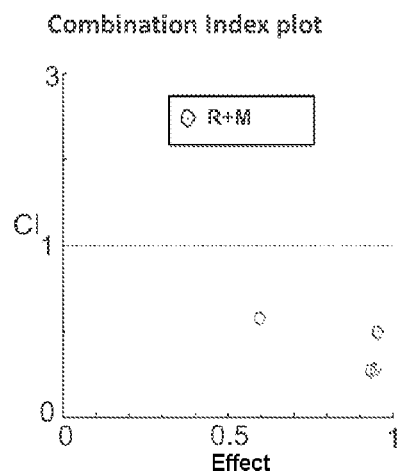
Figure 2O:
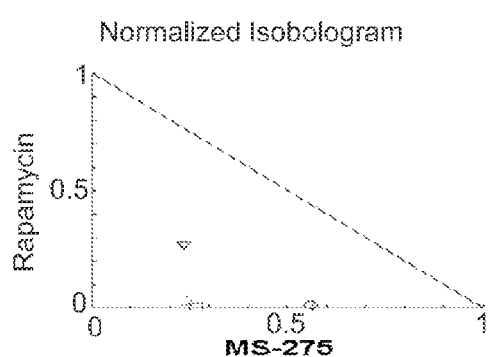
Figure 2P:
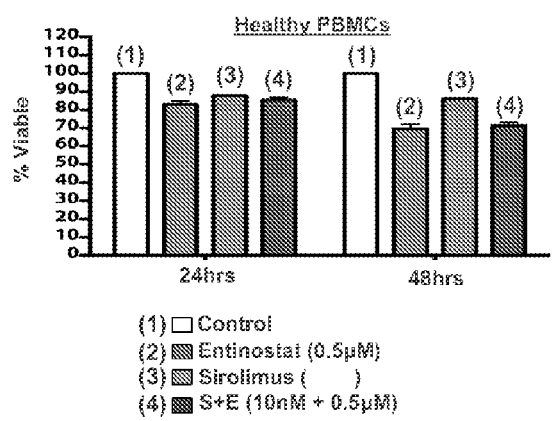

Compared with single drug treatment, the combination inhibited cell growth (p<0.01) in most cell lines. This dose combination was active (c.>EC50) in 19/21 lines; KMS18 and RPMI8226 were not as sensitive at these doses. Drug synergy, as defined by the Chou-Talalay method (Combination Index <1) (Chou, *Cancer Res.* 70:440-446. 2010), was also observed in 19/21 lines (FIGS. 1A, 2M-O; Table 1); sirolimus alone was as effective as the drug combination for the two MM cell lines OCI-MY5 and FR4. The combination treatment was relatively nontoxic to human PBMCs from healthy donors (FIG. 2P).

Figure 1B:
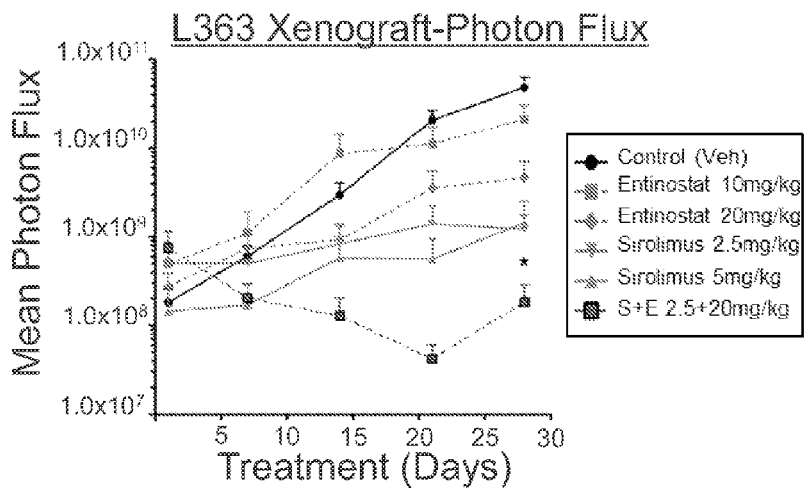
Figure 1C:
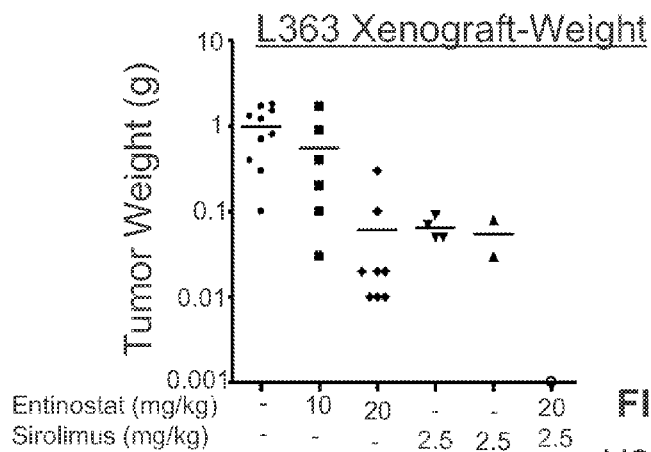
Figure 1D:
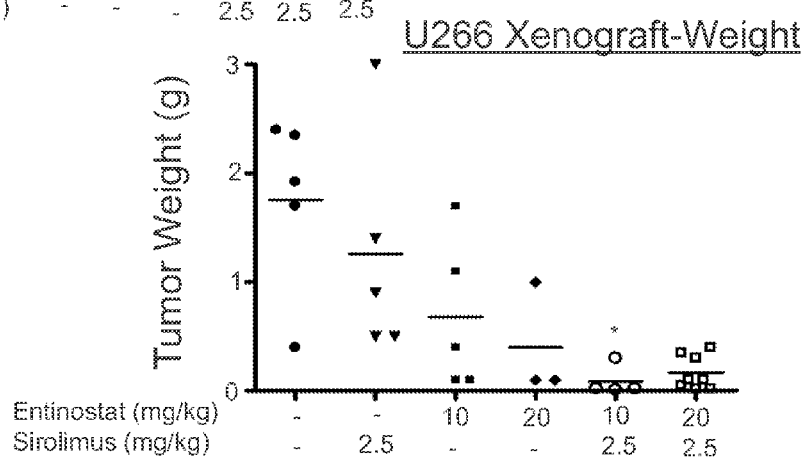
Figure 3A:
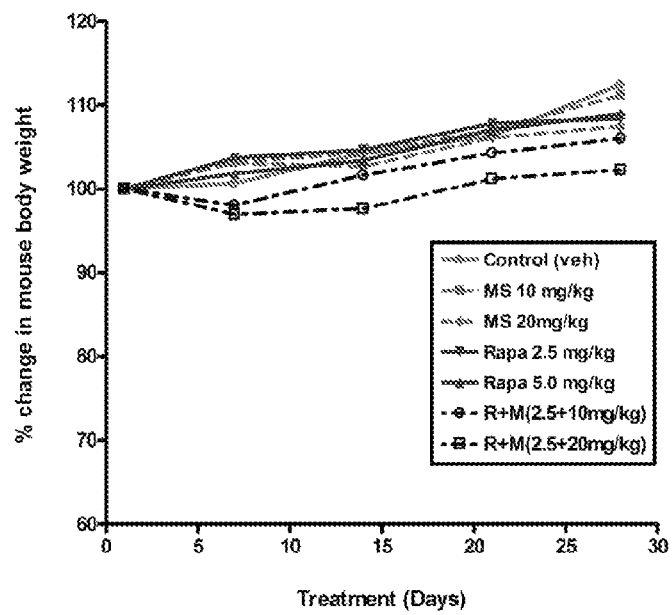
FIGS. 3A-3B are a set of graphs illustrating body weight of control and drug-treated tumor bearing nude mice over time. (A) L363 or (B) U266 xenografts with vehicle (control) or treatment with MS-275 (10 and 20 mg/kg), Rapamycin (2.5), and the combination (2.5 mg/kg of Rapamycin and either 10 or 20 mg/kg MS-275). Animals in the control arm of the U266 study were euthanized at 4 weeks due to tumor burden.
Figure 3B:
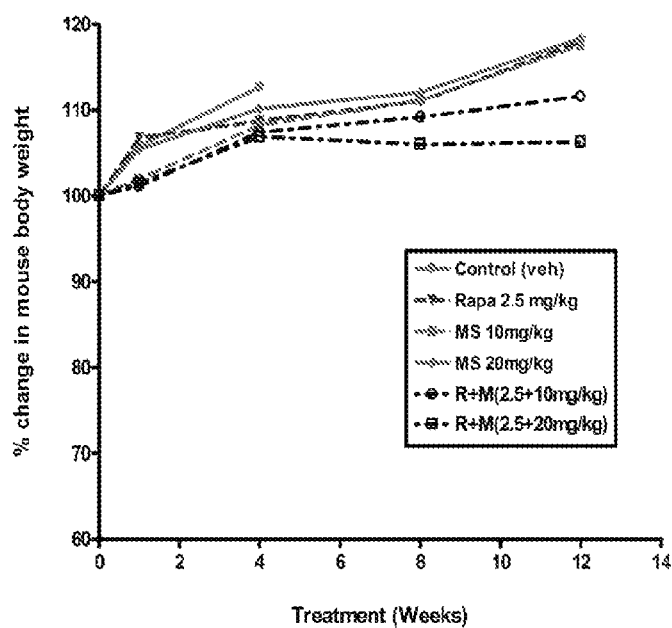

In vivo combination activity was tested in xenograft experiments. L363 MM cells were xenografted on flanks of nude mice and grown for eleven days before randomization to treatment groups (control, combination, and two dose points for each single agent). Tumors were imaged weekly in vivo for 28 days of treatment (FIG. 1B), after which mice were euthanized and tumors weighed. The control and single agent arms had palpable tumors, while no dissectible tumors were found in the combination group (FIG. 1C). Subsequently, a less sensitive line, U266, was grown for three weeks to a tumor volume of 50 mm³ prior to treatment group randomization. Tumor burden in the control arm necessitated euthanasia by treatment week 4. In the single agent groups, tumor progression was delayed, but outgrowth eventually occurred. By contrast, the combination treatment prevented tumor growth for three months, with no or small tumors present at necropsy (FIG. 1D). No treatment-related illnesses or significant weight were observed (FIG. 3).

Combining Entinostat with Sirolimus Enhances Cell Cycle Arrest and Apoptosis.

Figure 5C:
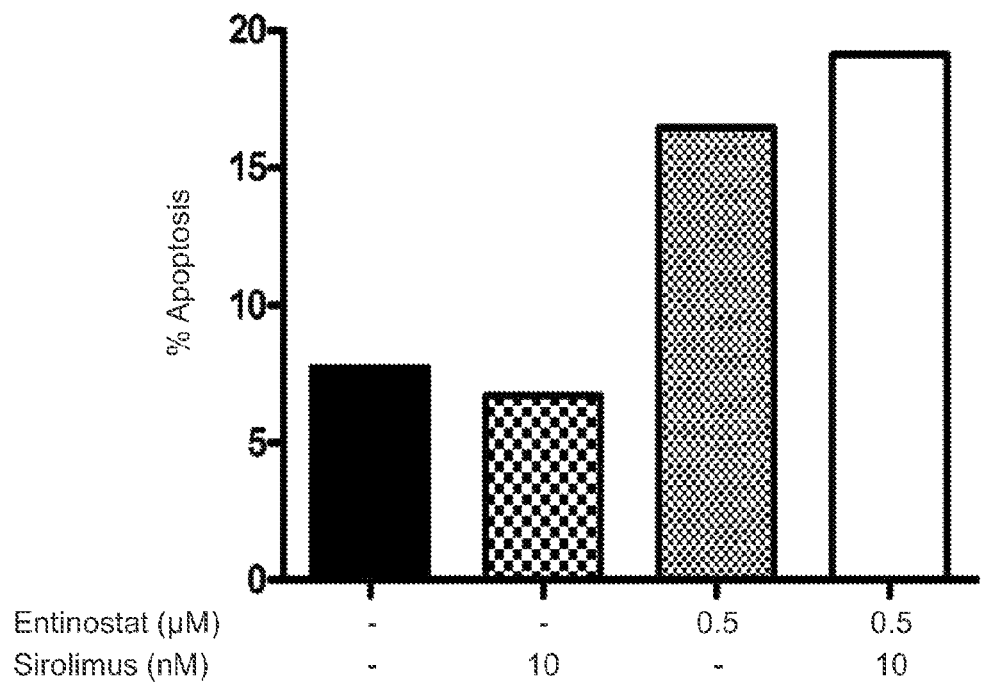
Figure 5D:
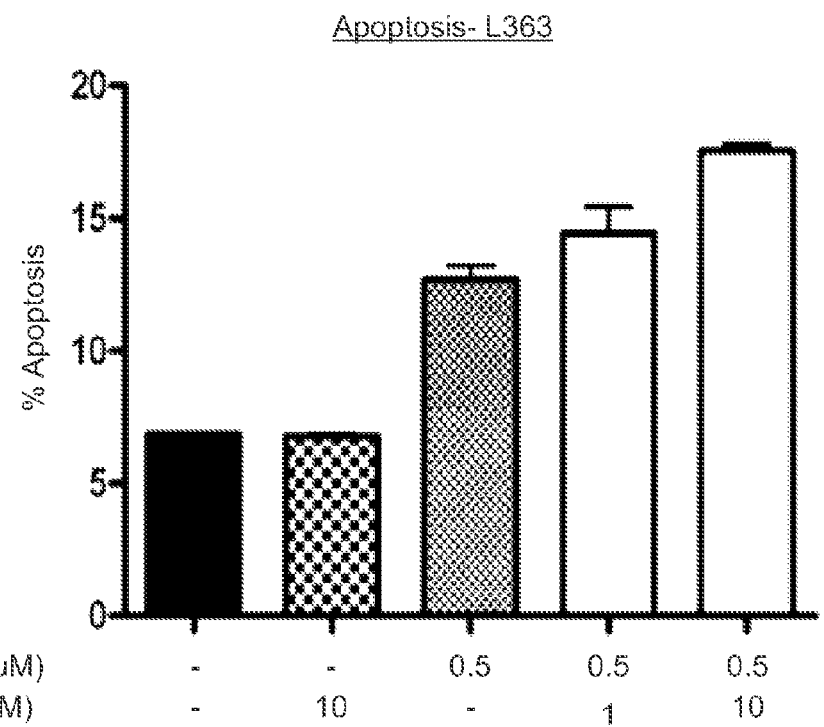
Figure 5E:
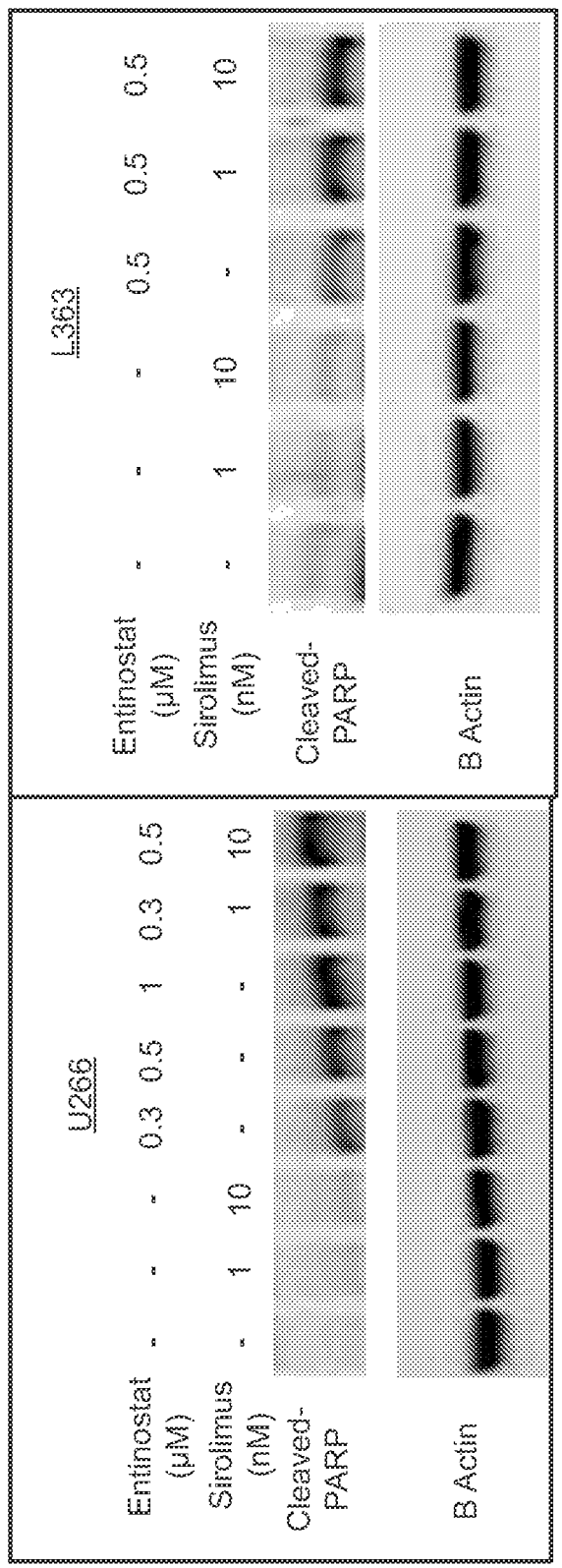
Figure 6D:
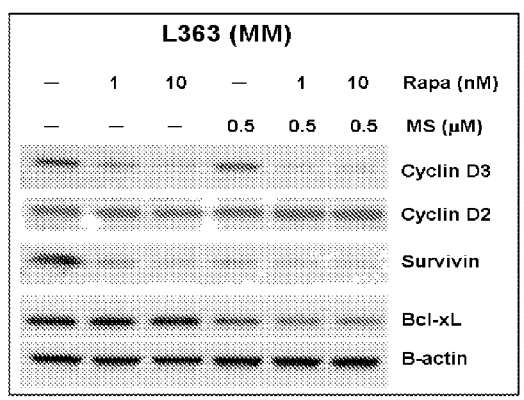
Figure 6E:
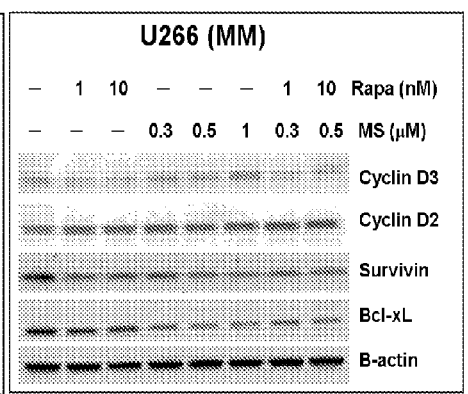

Sirolimus caused arrest/slowing of many tumor cells in G1 phase (FIGS. 5A,B; 6C). Cells in S phase were greatly reduced (FIGS. 5A,B; 6C), and G1 arrest was enhanced by the sirolimus/entinostat combination treatment in most cell lines, except L363, which underwent G2/M arrest. Annexin V-7AAD staining showed increased apoptosis in combination compared to single agent treatments (FIG. 5C,D). Consistent with enhanced apoptosis, PARP cleavage was observed in cells treated with entinostat or the combination, but not with sirolimus (FIG. 5E); the combination reduced expression of anti-apoptotic proteins BCL-xL and Survivin (FIG. 6D,E).

Example 2

Identification of Molecular Synergy of Combination by Transcriptional Co-Expression Analysis This example describes gene expression signatures that can be used to predict whether a neoplasm is sensitive to combined HDAC and mTOR inhibition and/or to predict prognosis of a subject with a neoplasm. Systems-level weighted gene co-expression network analyses were used to determine the transcriptional underpinnings of the mTORi/HDACi drug combination. This approach revealed a gene signature highly enriched with genes cooperatively affected by the drugs and significantly dysregulated in MM patients (GEO database), and identified a set of markers with clinical potential to predict which patients, based on their gene expression patterns, may benefit most from this combination treatment.

Methods

Microarray and Bioinformatics.

L363 cells were treated with either 1 nM or 10 nM sirolimus, 0.5 µM entinostat or the combination for 48 hours. Total RNA was extracted with TRIzol (Invitrogen) from three separate experiments. Labeled aRNA prepared from 1 µg RNA (MessageAmp™ II aRNA Amplification kit; Ambion) was hybridized to Affymetrix (Santa Clara, Calif., USA) HG-U133 Plus 2 array chips, processed on Workstation 450, and analyzed with Gene Chip Operating Software (Affymetrix).

Microarray Data Pre-Processing.

Figure 7:
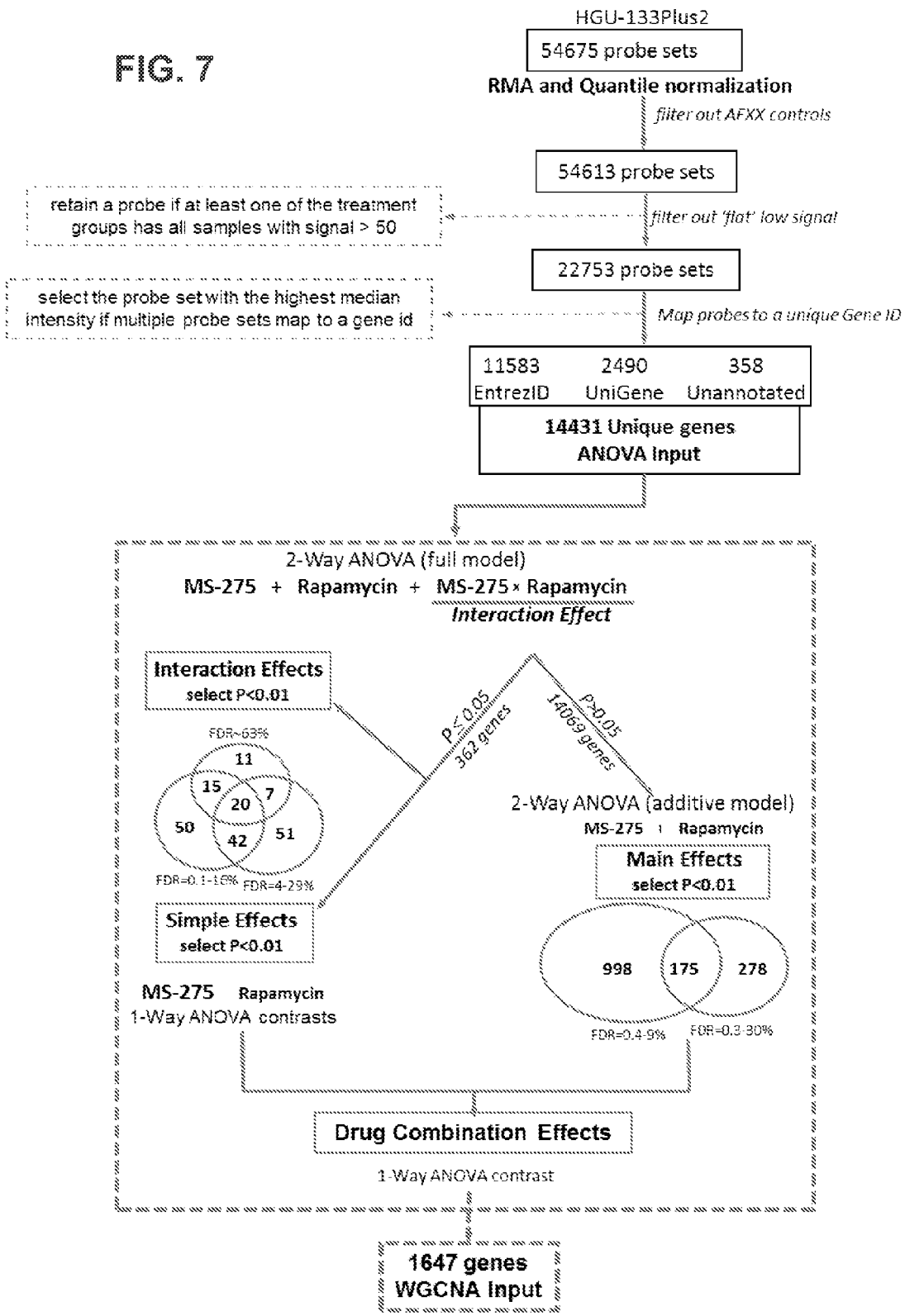
FIG. 7 is a diagram illustrating analytic workflow for microarray data pre-processing and analyses of variance (ANOVA). The 1647 genes selected with the ANOVA models were used to generate a network of highly co-expressed genes by weighted gene co-expression network analysis WGCNA.
Figure 8A:
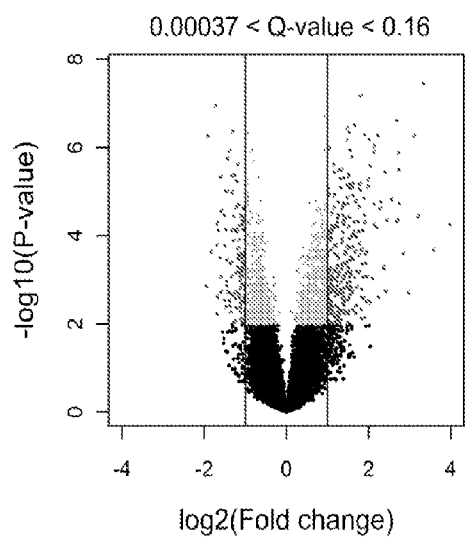
FIGS. 8A-8D are a series of volcano plots of statistical significance against expression change in the set of genes analyzed with the ANOVA models. On the y-axis, negative log 10 of p-values from an ANOVA test are plotted and the log 2 fold changes in expression on the x-axis. Genes with statistically significant treatment at the 0.01 significance level are shaded medium grey. Genes with expression change greater than two-fold lie outside the vertical lines and are colored with a darker shadow. The Q-values (Storey and Tibshirani, *Proc. Natl. Acad. Sci. U.S.A.*, 100:9440-9445, 2003) indicate the range of false discovery rates for the gene selections at the 0.01 significance level. (A) Additive two-way ANOVA main effect for the MS-275 treatment. (B) Additive two-way ANOVA main effect for the Rapamycin treatment. (C) Full two-way ANOVA interaction effect for the MS-275 and Rapamycin treatments. (D) One-way ANOVA contrast for the combined treatment effect.
Figure 8B:
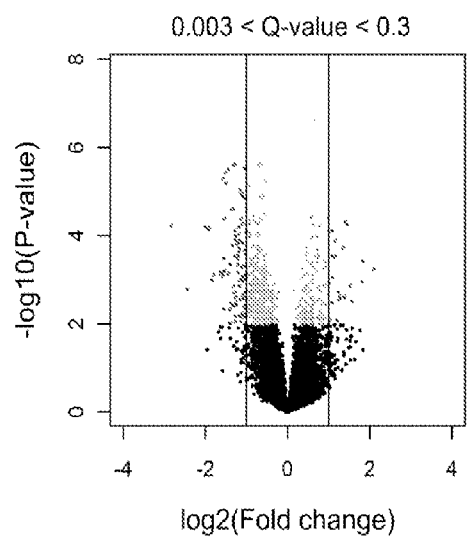
Figure 8C:
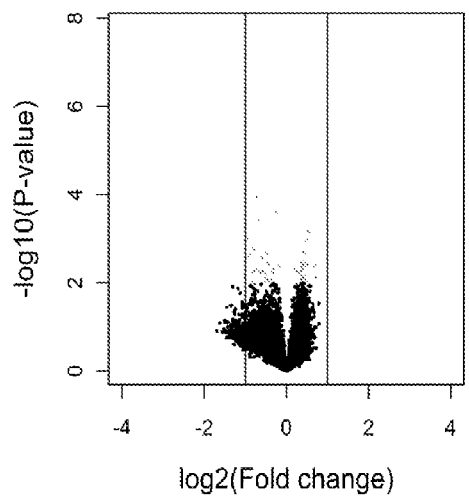
Figure 8D:
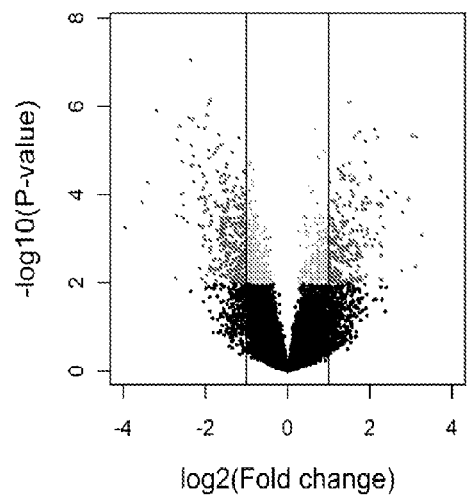

Affymetrix (Santa Clara, Calif., USA) HG-U133 Plus 2 CEL files were imported to the R Bioconductor affy package and processed with the RMA algorithm (Irizarry et al., *Biostatistics*, 4:249-264, 2003). A schematic of the workflow for pre-processing is provided online (FIG. 7). Probe sets with low signal across all arrays were removed. Multiple probe sets corresponding to the same gene were replaced by the one with the maximal median intensity. Around 14K genes were available for the statistical analyses.

Analysis of Variance.

Univariate two-way ANOVA models were applied to examine the combined expression effects of entinostat and sirolimus (Slinker, *J. Mol. Cell. Cardiol.*, 30:723-731, 1998) (see workflow: FIG. 7, 8). Specifically, a significant interaction term in the two-by-two factorial ANOVA was used as an indication of transcriptional synergy for the drug combination (P<0.05). Otherwise, when the interaction was not significant, the additive two-way ANOVA model was fitted and the main effects for each individual drug treatment tested. When the interaction was significant, the individual simple effects for the entinostat and sirolimus treatments were estimated with one-way ANOVA contrasts. The simple effect for the drug combination treatment was also estimated for each gene. Using the method of Storey and Tibshirani (Storey et al., *Proc Natl Acad Sci USA*, 100:9440-9445, 2003) the P-values were converted to the false discovery rate Q-values. The analyses were done using R programming language (R: A Language and Environment for Statistical Computing. R: A Language and Environment for Statistical Computing. 2011) and the gregmisc and qvalue libraries.

WGCNA.

Network modeling was performed using Weighted Gene Co-expression Analysis as proposed by Langfelder and Horvath (Zhang et al., *Stat Appl Genet Mol Biol.*, 4:e17, 2005) and implemented in the R WGCNA library (Langfelder, *BMC Bioinformatics*, 9:559, 2008). In the network, nodes represented gene expression profiles across the experiments and the undirected edges represented the correlation-based strength of connection among genes. In the first step, the unsigned Pearson's correlation coefficients were determined for all pair-wise comparisons of gene-expression profiles, which were then transformed into the adjacency matrix using a power function: $a_{ij}=|cor(x_i, x_j)|^\beta$. The power adjacency function converted the co-expression similarity measure into a continuous strength of connection (weight), while allowing retention of all co-expression relationships among genes and scale-free network properties by emphasizing large correlations at the expense of small ones. Furthermore, the connectivity, $k_i$, of the i-th node was defined as the sum of its adjacencies with all other nodes in the network ($k_i=\Sigma a_{ij}$). The power coefficient $\beta=8$ was applied when building the network, which resulted in the connectivity distribution satisfying the exponentially truncated power-law. In such networks the degree of connectivity of the most connected nodes (hubs) is smaller than expected in a pure scale-free network, due to the scale-free properties preserved within a narrower range of the node connectivities (Langfelder et al., *Bioinformatics*, 24:719-720, 2008).

In forming network modules (sets of genes whose expression profiles were highly correlated across experiments), the adjacency was further transformed using the topological overlap measure (interconnectedness). The topological overlap matrix ($TOM_{ij}$) defined commonality of network neighbors for each pair of nodes and its symmetrical distance matrix ($d_{ij}=1-TOM_{ij}$) was used to identify highly interconnected groups of nodes with a clustering algorithm. The network modules were detected using the agglomerative average linkage hierarchical clustering and automated dynamic cut tree algorithm (Langfelder et al., *Bioinformatics*, 24:719-720, 2008), with a minimum module size of 20 genes. Each module represented a group of genes with similar expression pattern summarized by the module eigengene ($ME_i$), computed as the first principal component of a module's expression matrix. Module eigengenes were utilized to define a measure of module membership ($MM_i$) for a node as the signed correlation of a node profile with the corresponding module eigengene.

Assessing which modules captured genes relevant to particular drug treatments, the two-way ANOVA gene significance ($GS_i=-\log 10$ P-value$_i$) was integrated with the network concepts of module significance ($MS_i$) and intramodular connectivity ($kIN_i$). The module significance measure was calculated as the average gene significance for all nodes in a particular module. Intramodular connectivity for the i-th node quantified its co-expression with all the other nodes in a given module by the sum of a node's adjacencies within the module. The relation between the intramodular connectivity and gene significance was estimated with Pearson's correlation coefficient and Fisher's asymptotic test implemented in the WGCNA package. A combination of module significance equal or greater than 2.0 (negative log 10 of 0.01) with a significant correlation of gene significance and intramodular connectivity (Bonferroni corrected P-value<0.05) was used to associate a network module with a drug response.

In the final step a top connectivity network was selected. Spurious or isolated connections with the topological overlap less than 0.25 were removed. In addition, the nodes were selected based upon the measure of module membership (absolute value of MM>0.8) and the gene significance of the module-specific drug effects (GS>2). Extremely highly connected nodes (hub genes) were defined within each module, setting the cutoff threshold for scaled intramodular connectivity ($kIN_{sc}=kIN/kIN_{maximum}$) to 0.6 and pairwise adjacency to 0.66 (corresponding to the pairwise Pearson's correlation coefficient of 0.95).

Functional Over-Representation.

The NIH Database for Annotation, Visualization, and Integrated Discovery (DAVID) Bioinformatics Resource was used to determine over-representation of Gene Ontology (GO) (Huang et al., Nat Protoc. 4:44-57, 2009 and Huang et al, Curr Protoc Bioinformatics, Chapter 13: Unit 13-11, 2009) terms. DAVID's GO FAT functional categories (GO subsets with broadest terms filtered out) were tested. The significance of the functional enrichment was identified with a modified Fisher's exact test (EASE score) followed by the Benjamini correction for multiple comparisons and using 0.05 as a p-value cutoff. Lists of enriched GO terms were summarized with semantically non-redundant terms using the REVIGO algorithm (Supek et al., PLoS One, 6:e21800, 2011) with SimRel and medium similarity options.

Results

Gene Co-Expression Network Analysis Identifies an mTORi/HDACi Cooperative

Drug Response.

Figure 9B:
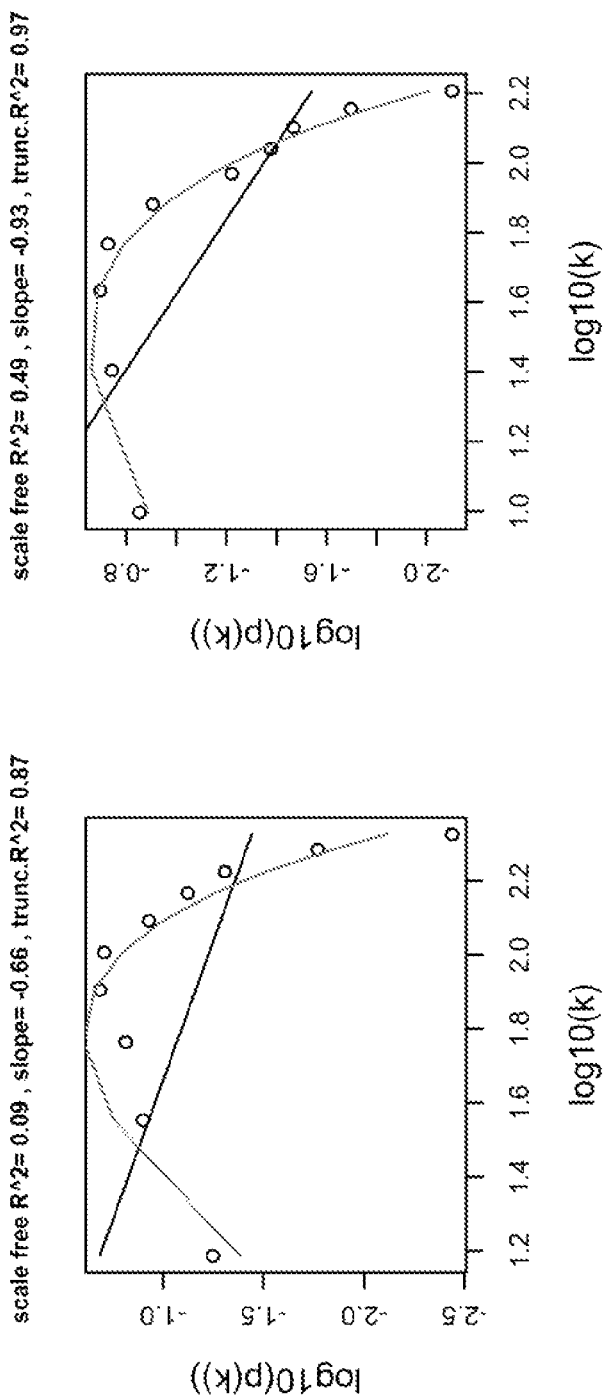
Figure 10A:
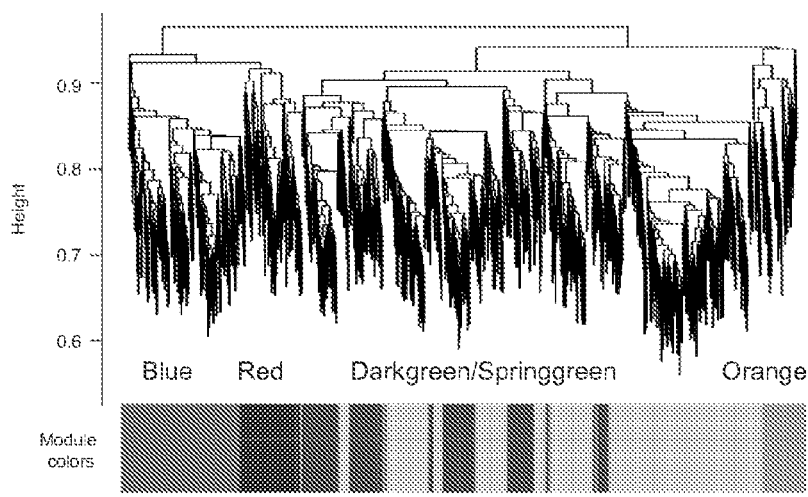
Figure 10B:
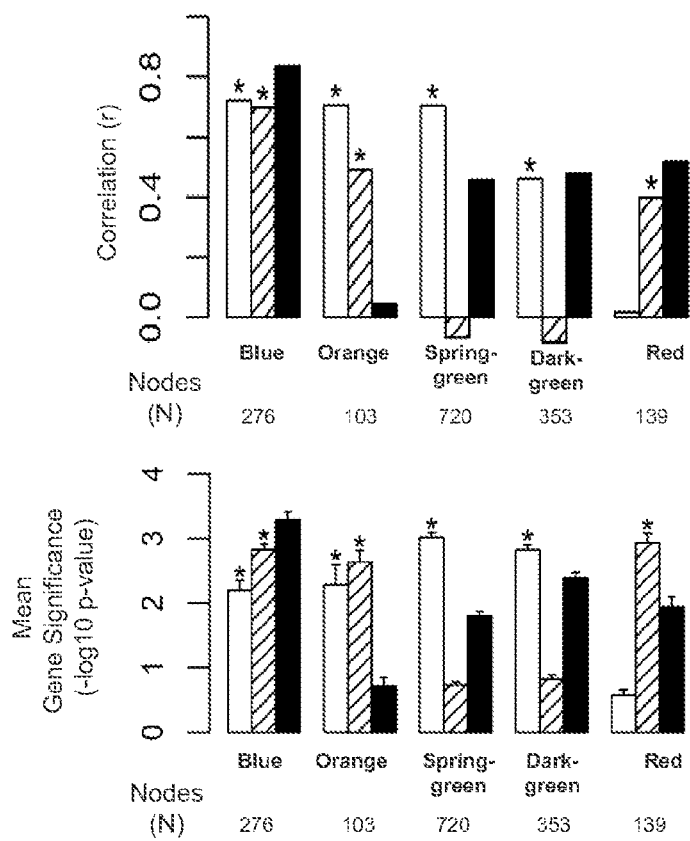

To define, at a systems-level, the cellular responses underlying the synergistic effects of mTOR and HDAC inhibition, whole genome expression profiles of MM cells treated with each inhibitor individually, and in combination, were generated. Weighted gene co-expression network analysis (WGCNA) was used to identify sets of highly correlated genes (gene modules), by constructing a network based on pairwise Pearson's correlations between expression profiles, followed by unsupervised hierarchical clustering on topological dissimilarity (Zhang et al., Stat Appl Genet Mol Biol., 4:17, 2005; FIG. 9: WGCNA cluster dendrogram/scale free topology). Using this approach, five modules, color-coded blue, orange, red, darkgreen, and springgreen, of co-expressed genes (FIGS. 9-11), were analyzed. As the gene expression effects within a module were likely to arise from a common perturbation (Horvath et al., Proc Natl Acad Sci USA., 103:17402-17407, 2006) (i.e. a single drug or drug combination), gene expression effects were assigned in the modules to drug treatments (Pearson's correlation measures of intramodular connectivity and mean significance of genes; FIGS. 10B, 11). From these comparisons, both drugs affected expression of the genes in the blue and orange modules, sirolimus those in the red module, and entinostat, the genes in both green modules (FIG. 10).

Using network and intramodular connectivity values (FIG. 11), a drug response network of 901 highly connected genes (FIG. 10C-E: color-coded by module and sized by degree of connectivity) was defined from the set of 1647 genes whose expression levels were altered by the drug treatments (FIG. 7). The eigengene graphs and heatmaps (FIG. 10E), demonstrate the relationship of each drug's effects to the overall expression pattern of up- and down-regulated genes. The HDAC inhibitor alone induces upregulation of some genes (springgreen module), and down-regulation of others, mostly in the darkgreen module. In general, Rapamycin alone (red) down-regulates gene expression. Two gene modules were affected by both drugs. In one (orange), each drug induces an opposing transcriptional response, leading to no net expression change (i.e., neutral) when combined. Notably, in the other (blue), genes are altered cooperatively by both drugs so that the expression change of the combination is greater than that of either individual treatment.

Figure 12:
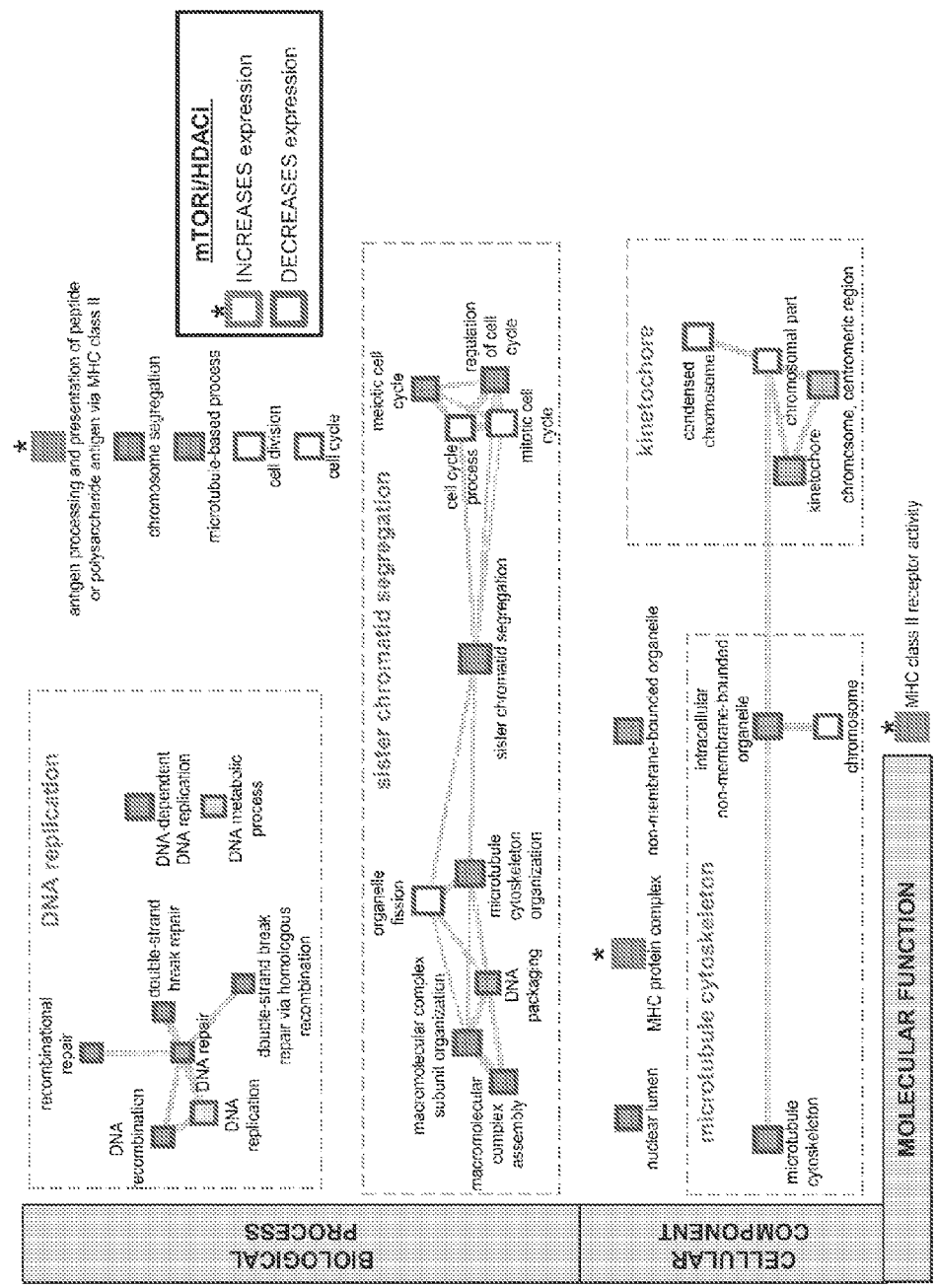
FIG. 12 is a diagram illustrating the functional enrichment of genes cooperatively regulated by mTORi/HDACi and REVIGO visualization of functionally-related GO terms for the Cooperative Combination (blue) module.

Functional relationships of genes affected in each drug response module (FIG. 10C) were assessed for over-representation of gene ontology (GO) terms (DAVID database (Huang et al., Nat Protoc., 4:44-57, 2009); FIG. 12, Table 2). Down-regulated genes from the cooperative module showed significant functional enrichment (p<0.001) for genes involved in cell cycle (especially mitotic functions), as well as DNA replication/repair (FIG. 12). The up-regulated genes included a number of HLA genes, and were enriched for involvement in the MHC complex and class II receptor activity (p<0.0001).

RRM2 Inhibition Enhances DNA Damage Response and Decreases MM Cell Viability

Figure 13A:
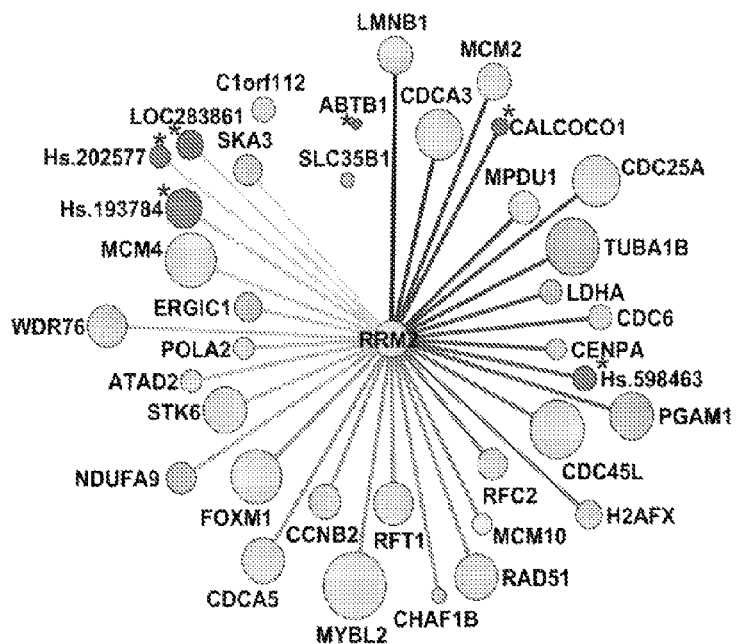
FIGS. 13A-13E are a series of graphs and digital images illustrating hub gene RRM2 validation. RRM2 is involved in DNA replication.
Figure 13B:
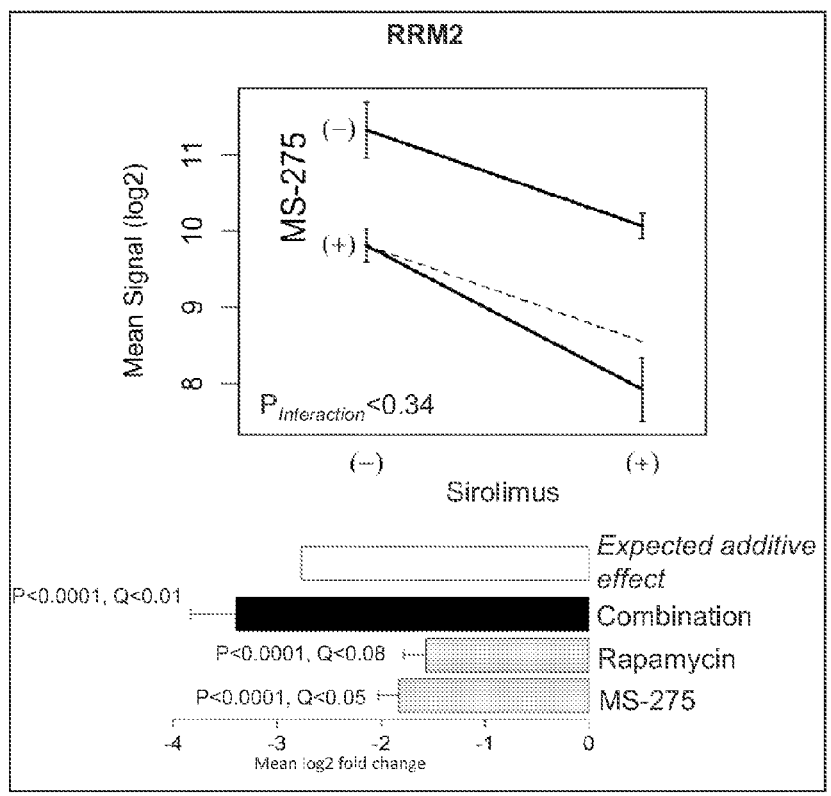
Figure 13C:
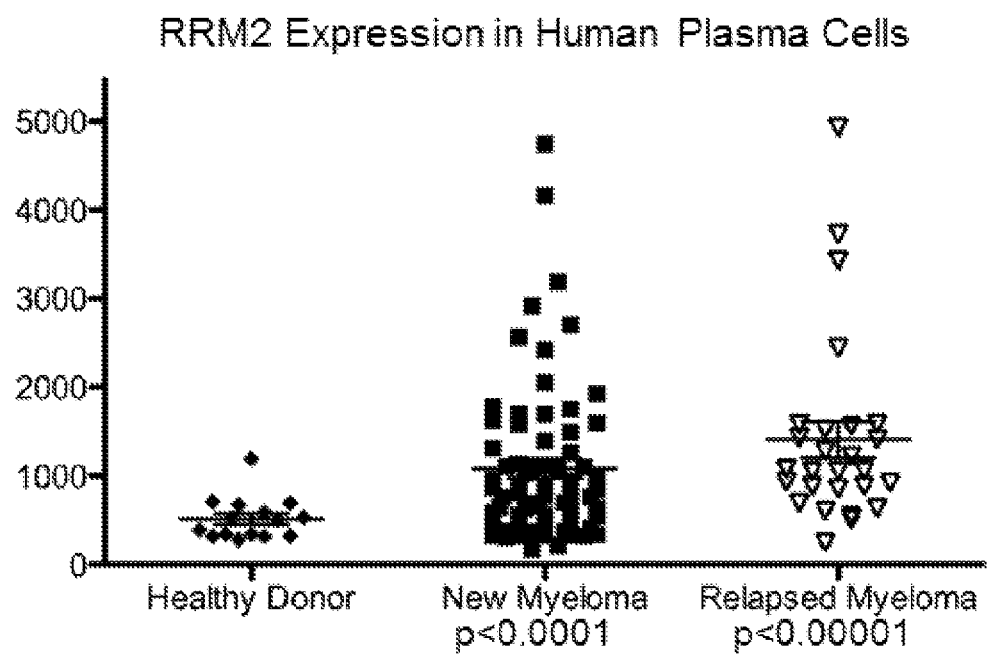
Figure 13D:
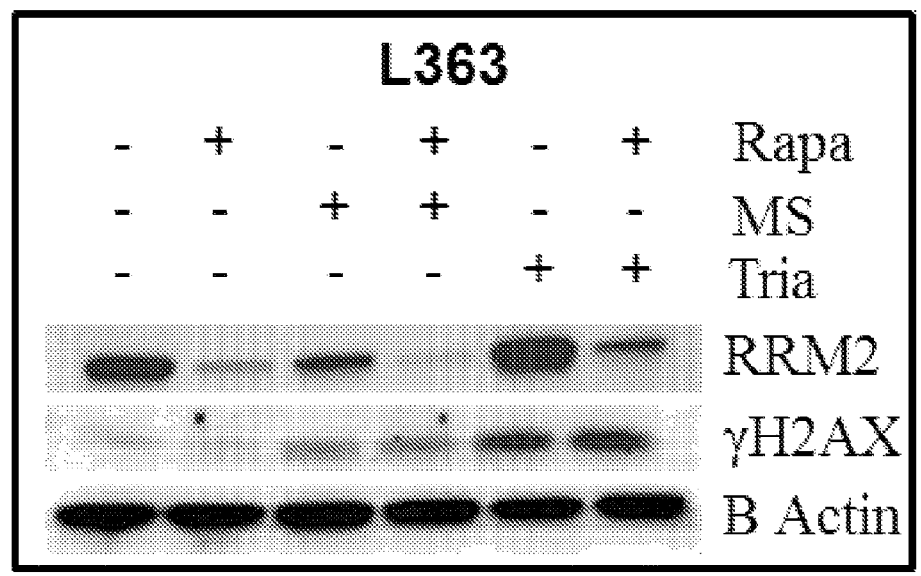
Figure 13E:
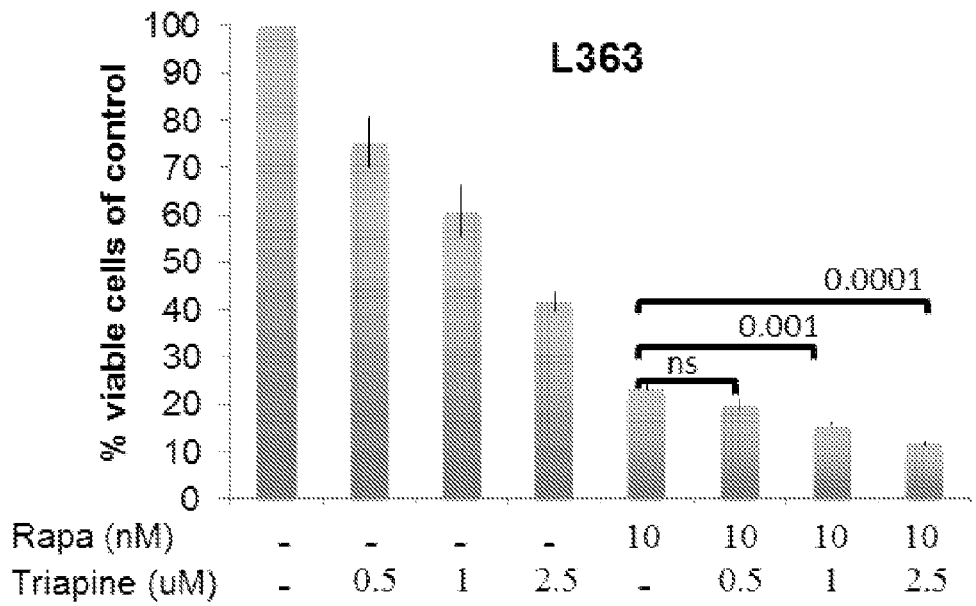

WGCNA analysis identifies the genes/hubs most connected to all other genes within an expression module. As the cooperative module was enriched with genes functionally involved in DNA replication/repair, the hub gene, ribonucleotide reductase M2 (RRM2), was focused on for additional follow up and validation. Many of the genes highly connected (by WGCNA) to the RRM2 hub are involved in DNA replication and DNA metabolic processes (DAVID GO terms); five are hub genes in the cooperative module (FIGS. 13A, 10E). RRM2 had one of the largest expression decreases with the drug combination (FIG. 13B), was a leading edge gene enriched in both new and refractory patient datasets (FIG. 13C, Table 5), and was one of the 37 genes in the prognostic classifier (FIG. 18). Western blot analysis of L363 cells treated with single drugs and the combination confirmed the decrease in RRM2 protein expression predicted by GEP (FIG. 13D). RRM2 is essential for DNA synthesis/repair, and its inhibition by RNAi increases the DNA damage marker γH2AX (Zhang et al. J Biol Chem., 284:18085-18095, 2009). The mTORi/HDACi combination treatment also increased γH2AX in L363 cells (FIG. 13D). Treatment of L363 cells with triapine, an inhibitor that specifically blocks RRM2 enzymatic activity, also increased yH2AX (FIG. 13D). Previously reported effective concentrations of triapine for other tumor cell lines (Barker et al., Clin Cancer Res., 12:2912-2918, 2006) also inhibited MM cell viability, and combining it with sirolimus led to greater inhibition than with individual drugs (FIG. 13E). Thus, RRM2 is a validated target contributing to the combination drug effect.

Example 3

Identification of Clinically-Linked Markers of Combination Activity and Synergy

Figure 14:
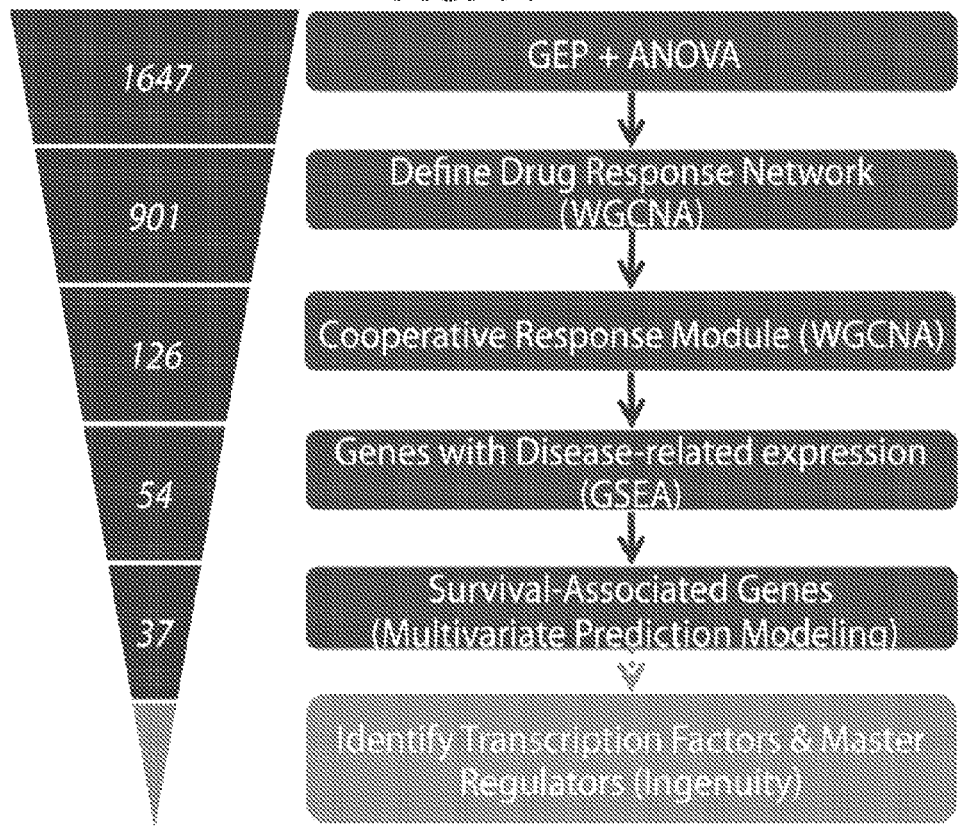
FIG. 14 shows a workflow schematic detailing filtering steps to define genes cooperatively affected by mTORi/HDACi combination treatment and associated with survival in MM patients.

Methods:

A schematic of the bioinformatic workflow used to identify the 37-gene classifier based on differential expression between normal and neoplastic cells and expression correlation with prognosis is shown in FIG. 14.

Publicly Available Microarray Data Sets.

Raw data (Affymetrix HG-U133_2 CEL files) from primary bone marrow samples of multiple myeloma patients and healthy donors were obtained from the GEO database (GSE6477) (Carrasco et al., Cancer Cell, 9:313-325, 2009; Chng et al., Cancer Res. 67:2982-2989, 2007) and processed with the RMA algorithm (Irizarry et al., Biostatistics, 4:249-264, 2003). One-way ANOVA contrasts were used to estimate the differences in gene expression between the healthy donors (N=15) and the different classes of multiple myeloma, i.e., newly diagnosed (N=75), relapsed (N=28), SMM (N=23, smoldering multiple myeloma), and MGUS (N=21, monoclonal gammopathy of uncertain significance). The ANOVA t-statistic was used as the ranking metric in the Gene Set Enrichment Analysis (GSEA). MASS normalized data (Affymetrix HG-U133 Plus2) from 414 newly diagnosed multiple myeloma patients (CD-138+-selected plasma cells from bone marrow samples) were downloaded from GEO (GSE 4581 (Zhan et al., Blood, 108:2020-2028, 2006)) and utilized in the survival risk prediction analysis.

GSEA.

Gene Set Enrichment Analysis (GSEA) was applied as described previously (Subramanian et al., Proc Natl Acad Sci USA, 102:15545-15550, 2005) to test the enrichment of the WGCNA network modules in the human microarray data with respect to multiple myeloma patients and healthy donors (Carrasco et al., Cancer Cell, 9:313-325, 2009; Chng et al., Cancer Res. 67:2982-2989, 2007). The pre-ranked GSEA version (Subramanian et al., Proc Natl Acad Sci USA, 102:15545-15550, 2005) was performed with 5000 permutations of the module gene sets. The data were ranked based on the t-statistic from one-way ANOVA planned comparisons. A FDR q-value less than 0.1 was considered significant.

Survival Analysis.

Whether the cooperative gene signature of entinostat and sirolimus was predictive of overall survival in patients with MM disease (Than et al., Blood, 108:2020-2028, 2006) was tested. A multivariate survival risk predictor was built using the principal components method of Bair and Tibshirani (Bair et al., PLoS Biol., 2:E108, 2004) as implemented in the BRB-Array Tools developed by Dr. Richard Simon and BRB-Array Tools Development Team (linus.nci.nih.gov/BRB-ArrayTools.html). The applied model is based on 'supergenes' that were defined here with the first three principal component linear combinations from genes whose expression was univariately correlated with survival (Cox regression p-value <0.05). The 'supergene' expression is related to survival time using Cox proportional hazards modeling to derive a regression coefficient (weight) for each 'supergene', which is then used for computing the risk score as the weighted combination of the 'supergenes'. This multivariate model was tested in two complementary validation schemes (10-fold cross-validation and single training/test split) to assign risk-group membership for clinical samples. Kaplan-Meier survival curves were plotted for the low- and high-risk groups (a risk score lower or higher than the 50th percentile in the training set). To assess the significance of prediction in the cross-validated model a permutation log-rank test was used. The survival data was randomly permuted among the patients, repeating the whole risk prediction procedure 5000 times. The p-value was calculated as the proportion of permuted test statistics that were as large as or larger than the observed value. The survival difference between the two risk groups in the single split validation procedure was assessed by the asymptotic log-rank test. A p-value of 0.05 was chosen as the significance threshold for both the log-rank tests.

In Vitro Drug Testing

MM, breast, melanoma and prostate cancer cell lines were treated with 10 nM rapamycin, 500 nM MS-275, 2.5 nM panobinostat, individually or in combination for 48 hours unless otherwise indicated in the text.

Quantification of Signature Gene Expression.

Total RNA was isolated from cells using Qiagen RNeasy Mini Kit. 100 ng of total RNA was used for gene expression analysis using a Nanostring custom Gene Expression probe set. The Nanostring procedure was performed per manufactures instructions, and raw data was analyzed using nSolver Analysis Software (Geiss, Nature Biotechnology 2008, PMID 18278033).

Genes Targeted by the Drug Combination are Frequently Dysregulated in MM

Disease-Related Differential Expression.

Figure 10C:
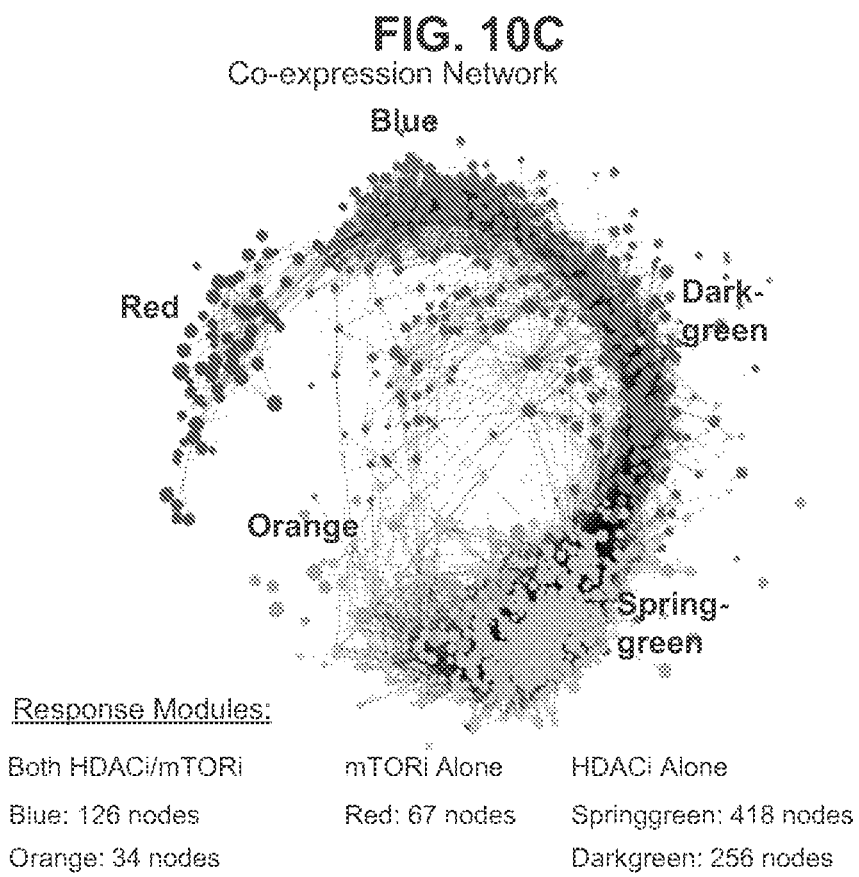
Figure 10D:
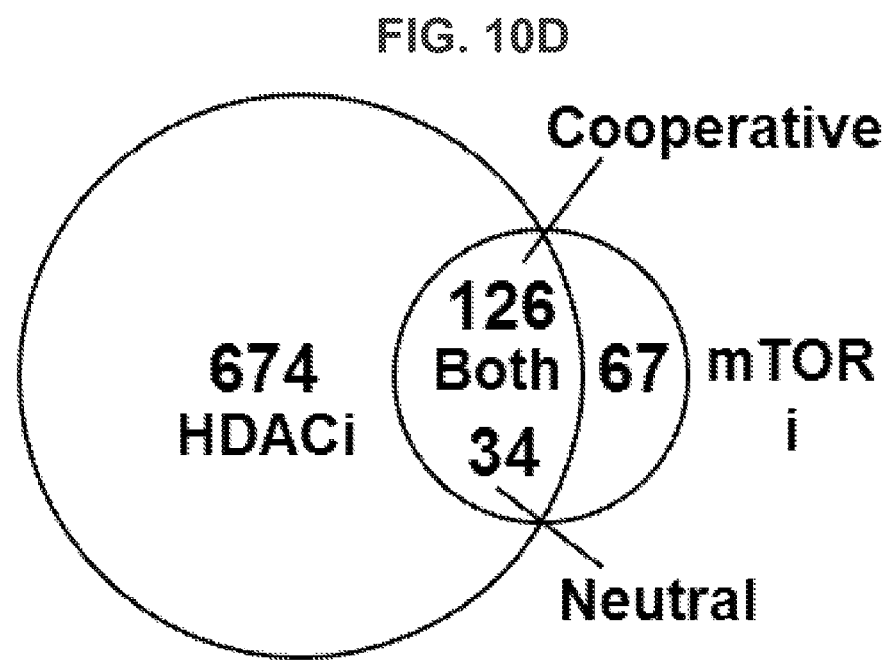

To determine if genes altered by mTORi/HDACi were dysregulated in MM cells or precursor lesions, gene set enrichment analysis (GSEA) was used to test whether the gene set defined by the drug responsive co-expression network (FIG. 10C; Table 4) was over-represented/enriched in MM (newly diagnosed or treatment refractory), SMM (smoldering myeloma), or MGUS (monoclonal gammopathy of undetermined significance) patients relative to CD138+ cells from healthy donors (GSE6477; Carrasco et al., Cancer Cell, 9:313-325, 2006). The up- and down-regulated genes of each drug responsive module were tested separately and a high proportion of these were significantly enriched in the four disease gene sets (FIGS. 15B-15C; Tables 4,5).

Figure 15B:
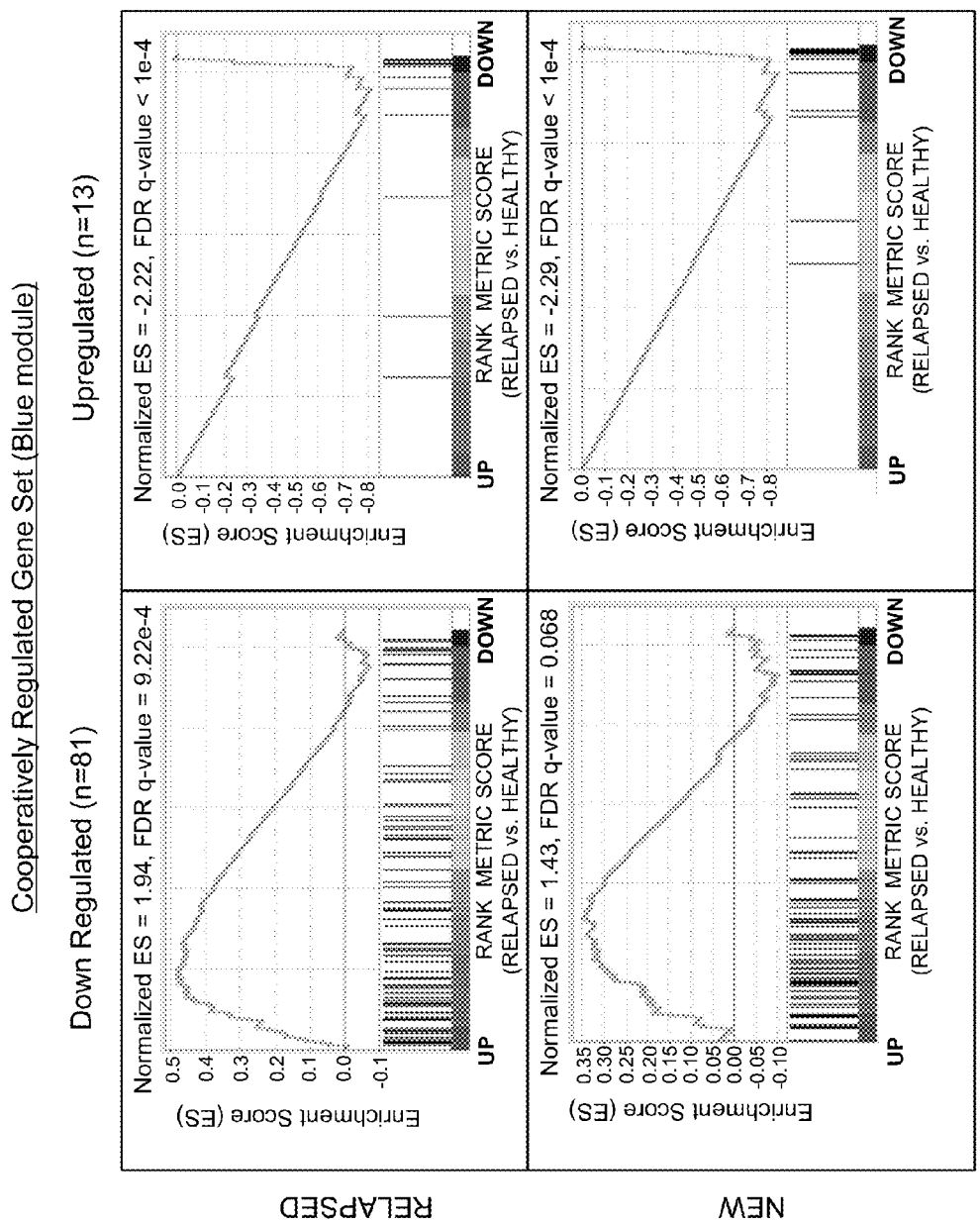
Figure 15C:
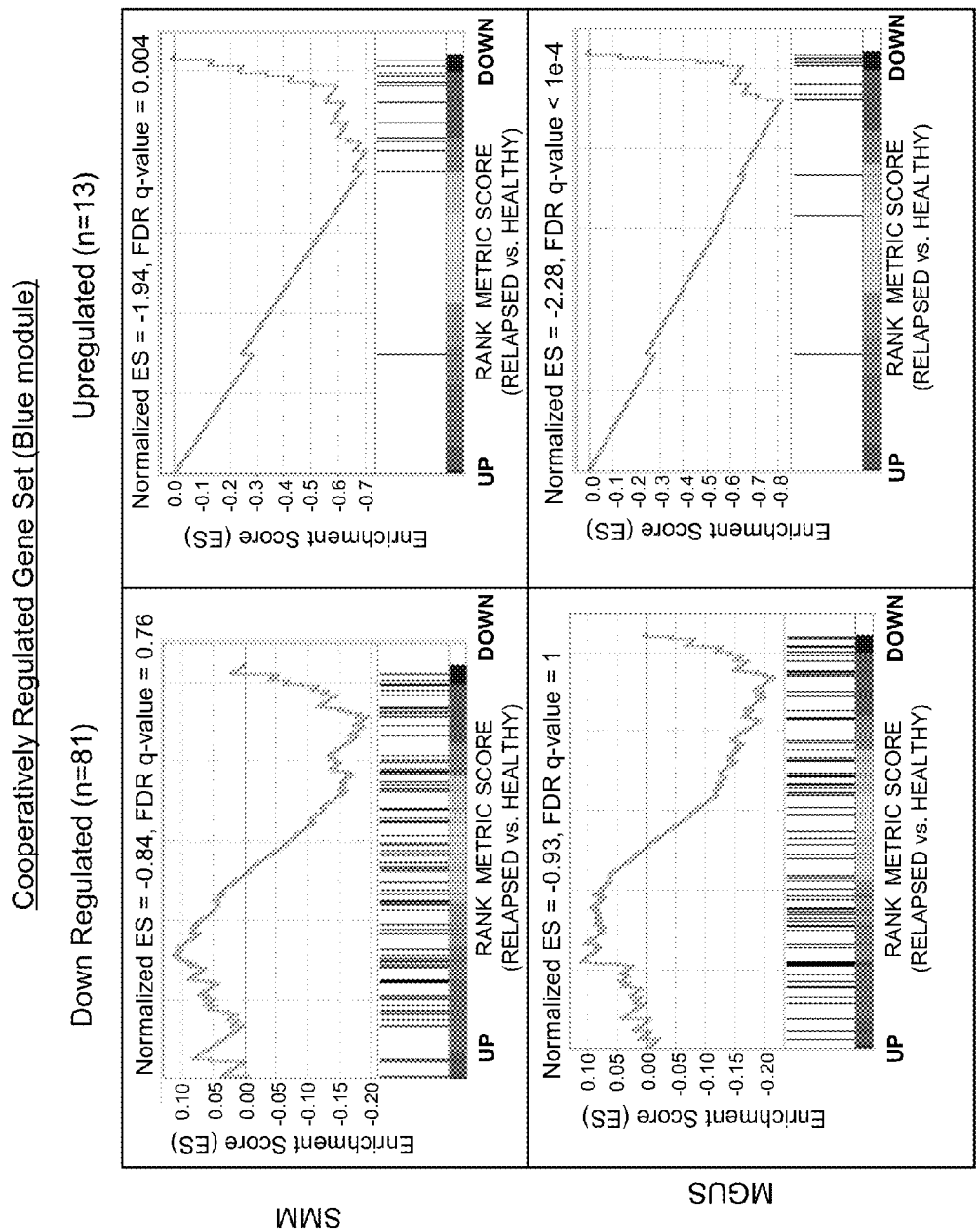

The MM patient-specific GEP of the 901 genes in the drug-response network was largely the inverse of the in vitro drug combination-specific GEP (FIG. 15A). This trend was most significant among genes in the cooperative (blue) module, where 94 genes responded this way. In this module, genes down-regulated by the drug combination were found to be over-expressed in new and relapsed MM patients versus healthy donors, while the genes up-regulated were typically under-expressed in both MM patients and premalignant patient groups (SMM and MGUS) (FIGS. 15B-15C). Enrichment scores for all genes within modules are shown in Table 5.

Expression of Genes Affected by mTORi/HDACi Treatment In Vitro is Correlated with Better Patient Survival.

Figure 17:
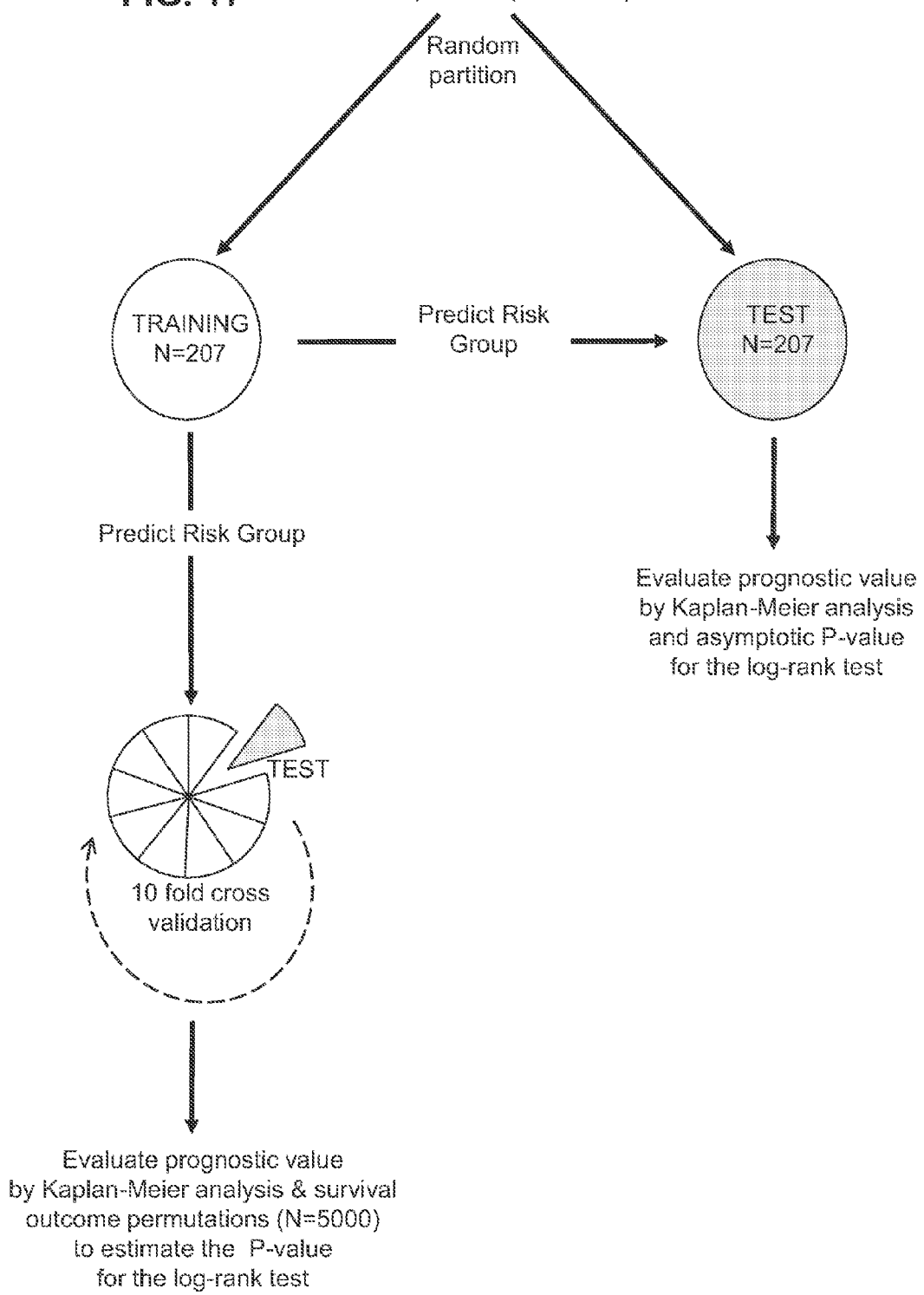
FIG. 17 depicts a schematic diagram of the ten-fold cross-validation and single split validation scheme for the training and testing of the multivariate survival risk predictor (37 genes) using the principal component method of Bair and Tibshirani (*J Biol Chem.;* 284:18085-18095, 2009) and BRB-ArrayTools software. The patient dataset published by Than et al. (GSE4581; *Blood,* 108:2020-2028, 2006) was used to build the predictor.

The expression of genes comprising the 37 gene combination (blue module) response signature was tested to determine if they would correlate with patient survival in order for the drug combination to have potential clinical utility. As a proxy test for the potential clinical value of the drug response, a gene expression prognostic classifier was developed from the cooperative drug response signature using supervised principal components analysis (Bair et al., PLoS Biol., 2:E108, 2004) employing two validation schemes (FIG. 17). A classifier for the cooperative drug signature was built from the 37 genes most strongly associated with overall survival in MM patients (GSE4581:training set univariate Cox regression p-value <0.05) (Table 7). The validated Kaplan-Meier survival curves for the predicted low- and high-risk groups (FIG. 18A) show statistically significant separation of the groups (log-rank test permutation p=0.009 and asymptotic p=0.017 in the training and test sets, respectively).

Figure 18A:
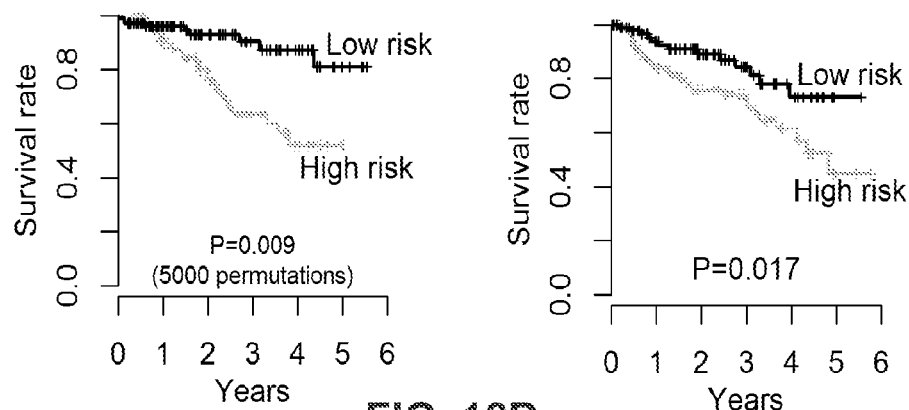
FIGS. 18A-18D are a series of graphs illustrating that the expression of cooperative (blue) module genes correlates with survival in multiple myeloma patients. Kaplan-Meier survival curves showing overall survival in patients.
Figure 18B:
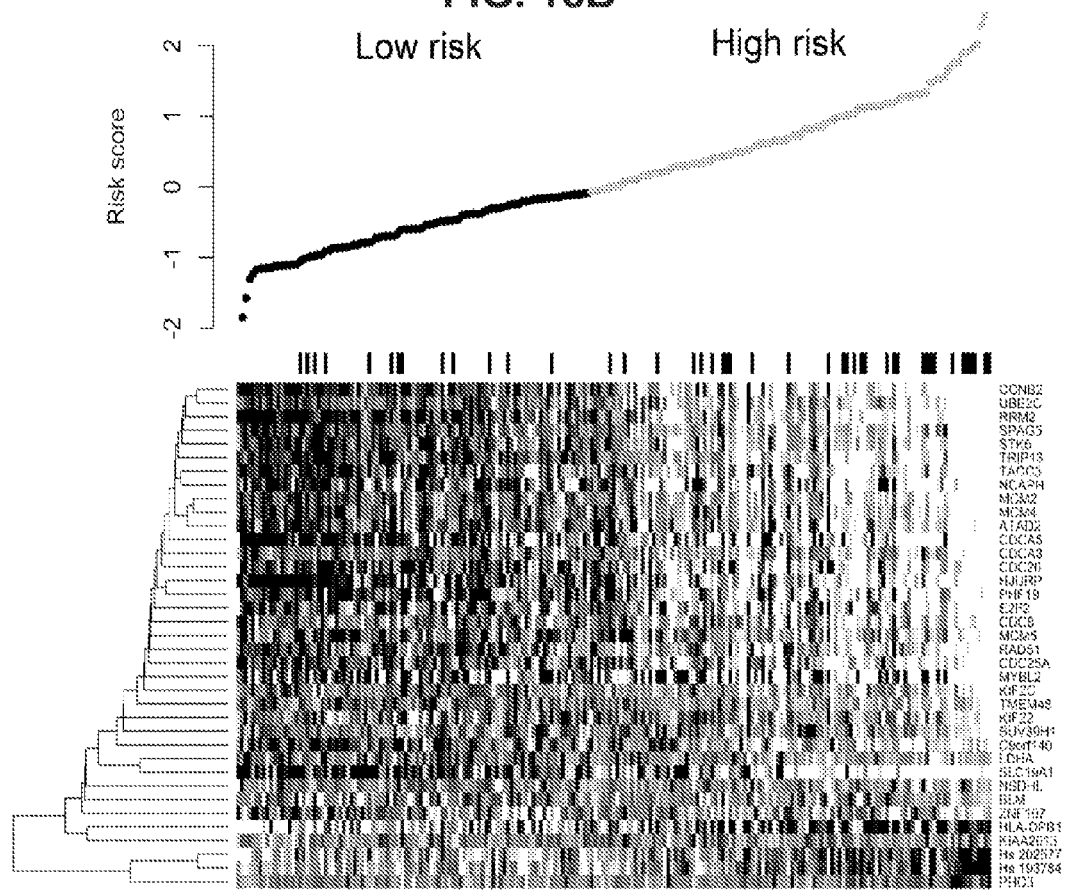
Figure 18C:
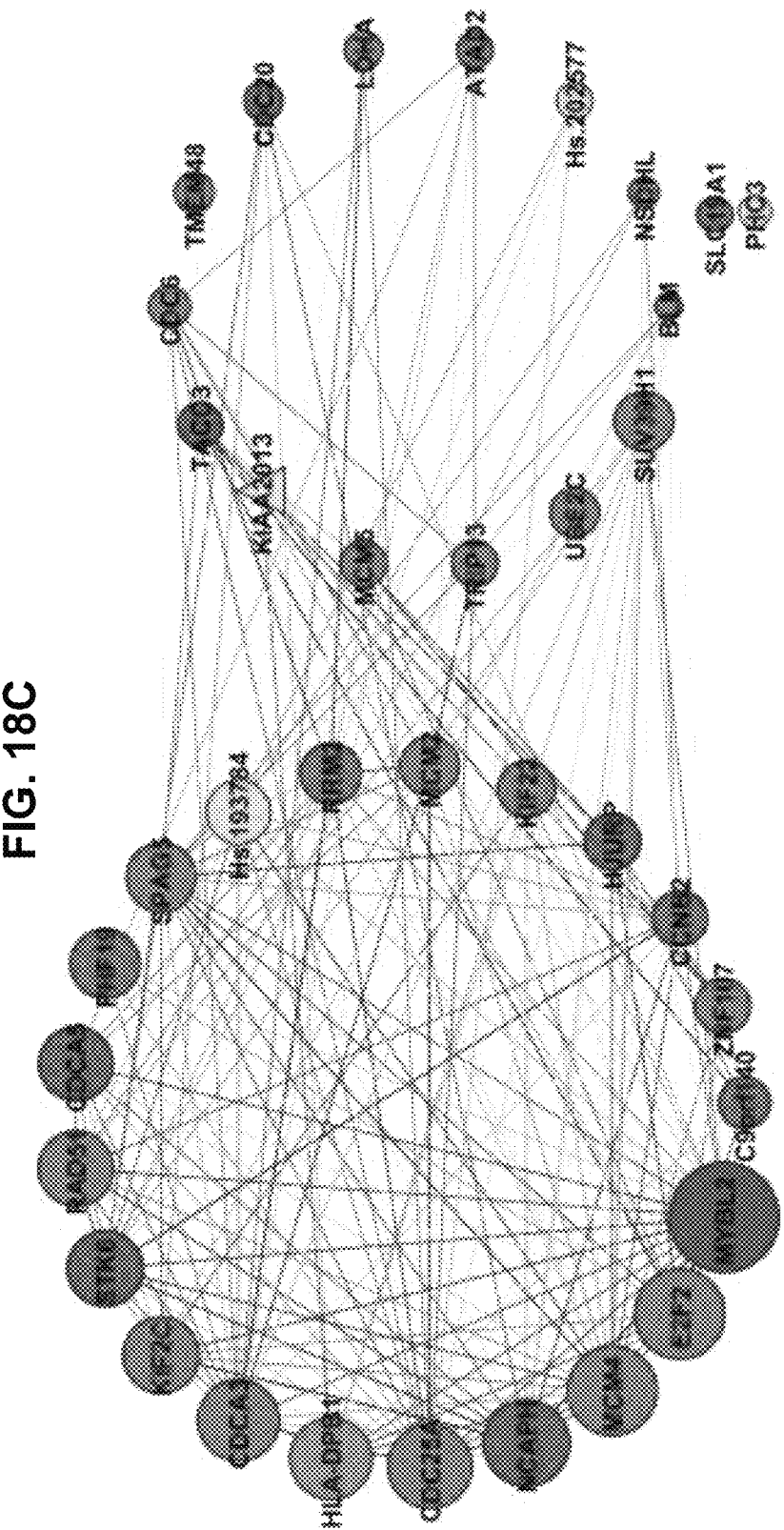
Figure 18D:
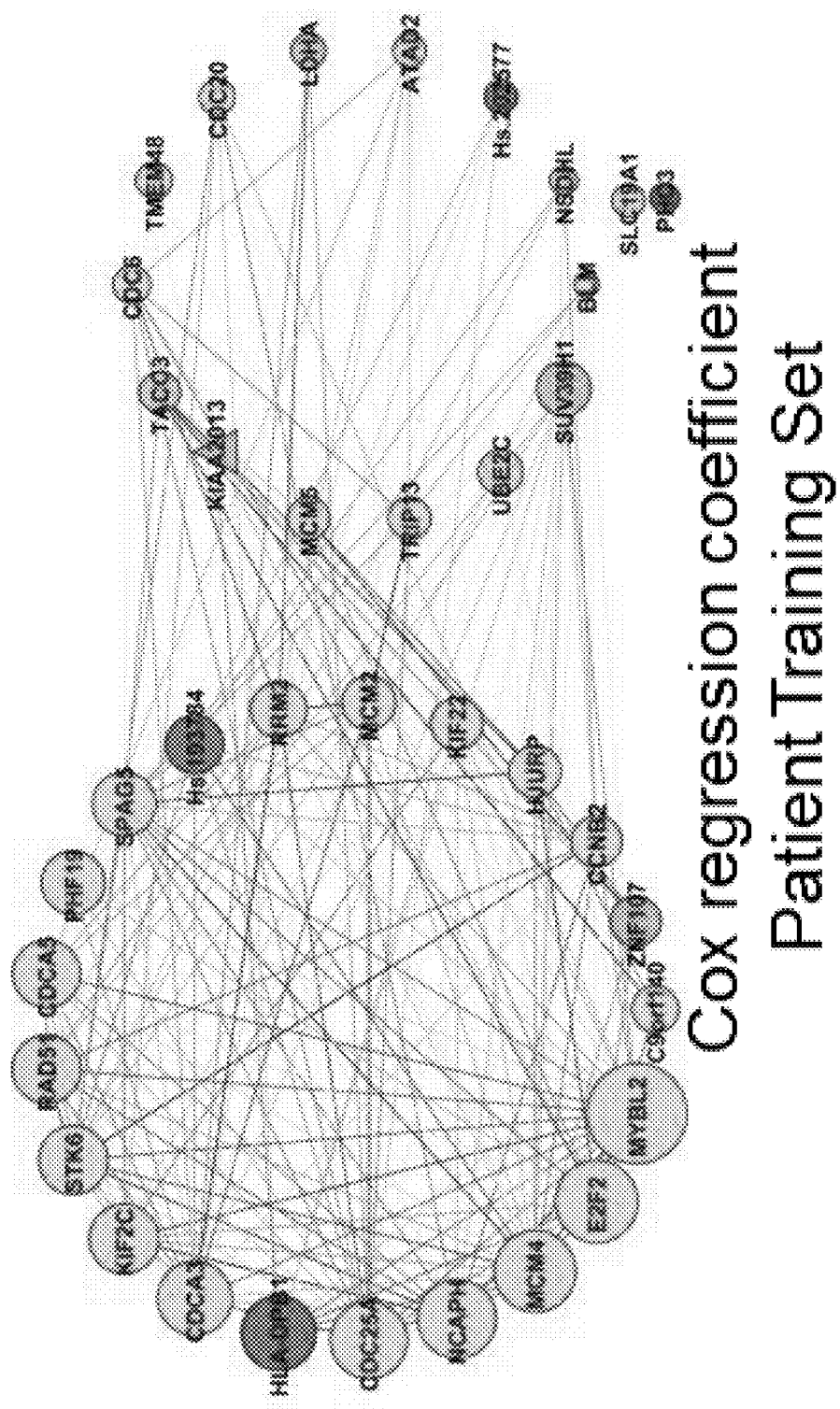

GEPs of the 37 genes in 207 patients from the test set (FIG. 18B) shows overexpression of many of these genes in patients with worse prognosis; predicted risk classifications for each patient are shown in Table 10. The drug-induced expression pattern of the survival genes is the opposite of the gene expression pattern seen in high-risk patients, with one exception (FIGS. 18C-18D). All genes, except KIAA2013 (function unknown), were affected by the drug combination in the direction expected for increased patient survival. Thus, the 37 genes of this classifier may identify a subset of patients likely to benefit from combined mTORi/HDACi (FIGS. 18C-18D). For stratification of patients likely versus unlikely to benefit from combined mTORi/HDACi, the expression of the 37 genes of this classifier could be evaluated by an algorithm to compute a stratifying prognostic index score. As an example of this, the stratifying prognostic index would be computed by the following formula: $\Sigma_i w_i x_i -$ 4.552161, where $w_i$ and $x_i$ are the weight (as defined in Table 7), and logged gene expression of the $i$th gene as detected in a sample of the neoplasm prior to treatment. In this example, a patient with a neoplasm scoring greater than, or equal to, −0.061194 would be classified as likely to benefit from combination treatment with an mTOR pathway inhibitor and a HDAC inhibitor.

Differences with Other Prognostic Classifiers

Figure 31A:
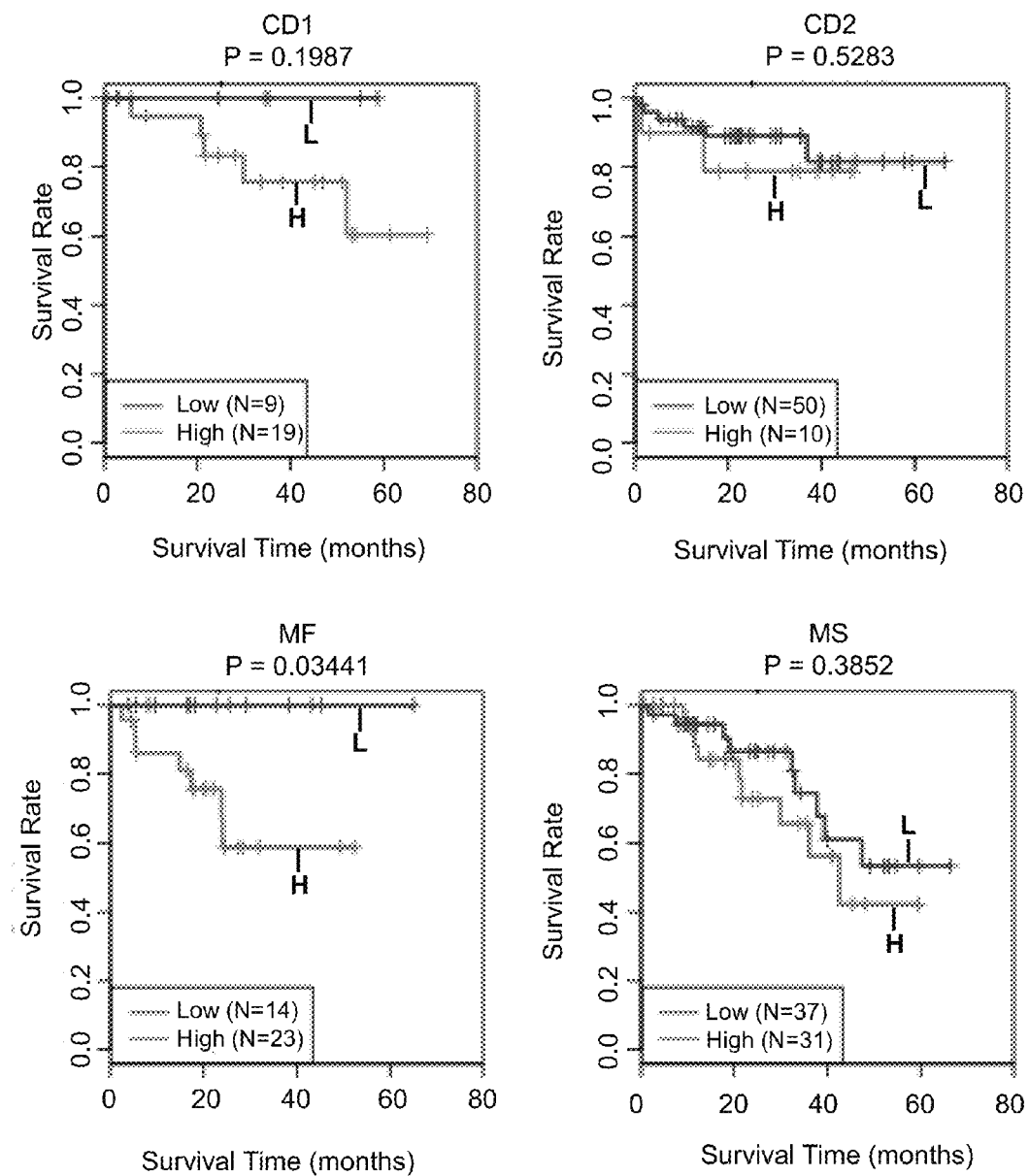
FIGS. 31A-31B show Kaplan-Meier Survival curves for patient groups classified by the 37-gene mTORi/HDACi signature within the seven molecular subtypes of MM (CD-1, CD-2 (CCND1/CCND3 subgroups 1 and 2), HY (hyperdiploid), LB (low bone disease), MF (MAF/MAFB), MS (MMSET), PR (proliferation subgroup)) as defined in GSE4581 (Zhan et al., *Blood,* 108:2020-2028, 2006).
Figure 31B:
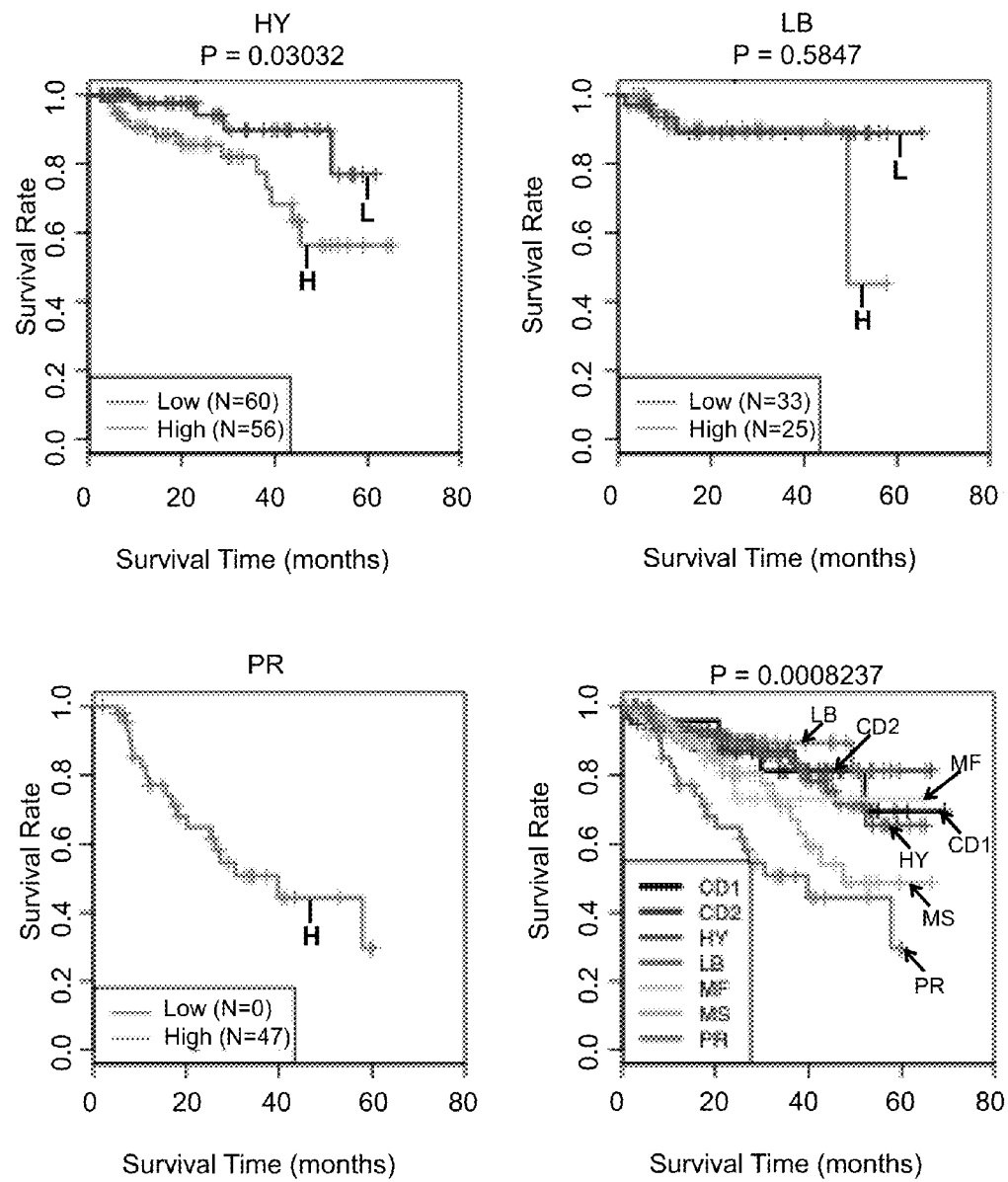

There have been several GEP-based prognostic classifiers reported in MM (Zhan et al., Blood, 108:2020-2028, 2006; Shaughnessy et al., Blood, 109:2276-2284, 2007; Hose et al., Haematologica, 96:87-95, 2011; and Decaux et al., J. Clin. Oncol., 26:4798-4805, 2008), which were evaluated to determine if any could be substituted for stratifying patients' likely sensitive to mTORi/HDACi. In Than et al. (Blood, 108:2020-2028, 2006), a GEP classifier was reported defining seven molecular subtypes in MM, influenced largely by chromosomal translocations and hyperdiploidy. When comparing the subgroup classification of the 414 patients in the Than study with the high/low risk classification using the 37-gene mTORi/HDACi classifier (FIG. 29; Table 10), where it would define patients classified as high-risk by the 37-gene signature as likely to benefit from mTORi/HDACi therapy, it was found that the Than subgroup classifier was unable to sufficiently define which patient segment would likely benefit. While all patients classified in the Than "proliferation" (PR) subtype would be predicted to benefit from mTORi/HDACi, all other subtypes contain both patients predicted to benefit and not benefit from mTORi/HDACi (FIGS. 29, 31; Table 10). Also reported in Than et al. (Blood, 108:2020-2028, 2006), is a proliferation index of 11 genes, of which only two overlap with the 37-gene mTORi/HDACi classifier, suggesting the proliferation index score would be inadequate for predicting sensitivity to mTORi/HDACi. FIG. 30 and Table 10 show the comparison of patients classified by the mTORi/HDACi classifiers and whether the patient has a proliferation index score above or below the median for this 414 patient cohort. These findings demonstrate the proliferation index alone is likely insufficient for predicting mTORi/HDACi benefit. Table 11 summarizes the distribution of the high/low risk classification using the 37-gene mTORi/HDACi classifier among the molecular subgroups from Zhan et al, and between the high/low proliferation index. In five poor prognosis or proliferation classifiers reported in MM (Zhan et al., Blood, 108:2020-2028, 2006; Shaughnessy et al., Blood, 109:2276-2284, 2007; Hose et al., Haematologica, 96:87-95, 2011; and Decaux et al., J. Clin. Oncol., 26:4798-4805, 2008), none contain more than five (13.5%) overlapping genes with the mTORi/HDACi classifier reported here, suggesting this classifier as biologically and functionally distinct from other classifiers (see Tables 13A and 13B; the reference for Tables 13A and 13B are: (1) Shaughnessy et al., Blood. 2007; 109:2276-2284; (2) Decaux et al., J Clin Oncol. 2008; 26:4798-4805; (3) Than et al., Blood. 2006; 108:2020-2028; (4) Hose et al., Haematologica. 2011; 96:87-95; (5) Shaughnessy et al., Blood. 2011; 118:3512-3524; (6) Whitfield et al., Nat Rev Cancer. 2006; 6:99-106; (7) Rosenwald et al., Cancer Cell. 2003; 3:185-197; (8) Dai et al., Cancer Res. 2005; 65:4059-40661; and (9) Paik et al., N Engl J Med. 2004; 351:2817-2826). Of particular note, Shaughnessy et al. (Blood, 109:2276-2284, 2007), specifically built an 80-gene prognostic classifier related to the gene expression change measured in patients treated with the proteasome inhibitor bortezomib, and there are no overlapping genes with the mTORi/HDACi classifier provided herein, which supports a mechanism of action of this combination distinct from proteasome inhibition or generalized drug-induced cell death.

Prognostic-Linked Pharmacodynamic (PD) Biomarker.

Figure 20A:
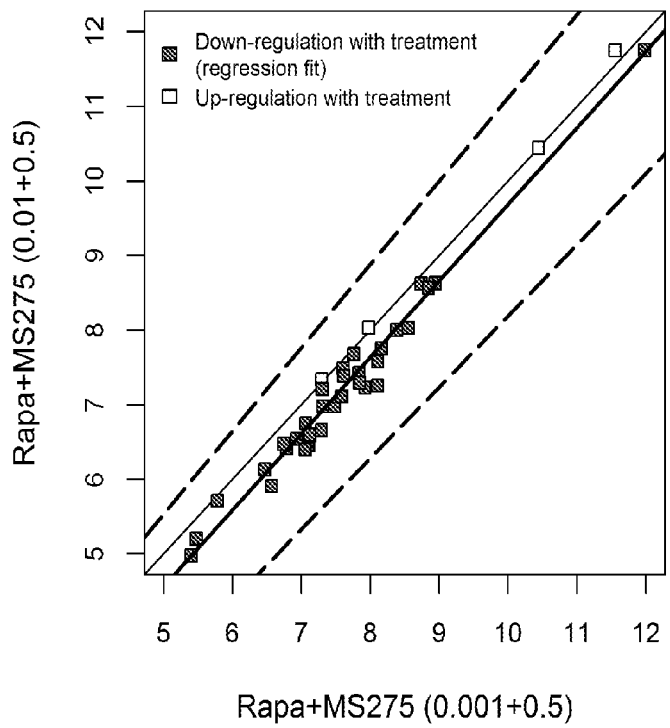
FIGS. 20A-20B are a set of graphs illustrating Passing-Bablok linear regression analysis of the drug dose effect on L363 transcriptional profiles of the 37 genes linked to a survival signature; two different concentrations of sirolimus (1 or 10 nM) were compared when given in combination with 0.5 mM entinostat. (A) Regression of the mean expression values for the 37 genes in the survival signature from GEP experiments between the two different concentrations of Rapamycin (1 or 10 nM). The correlation (Pearson's r=0.9) between the two drug concentrations for expression of the 37 genes was significant ($p<2.2^{e-16}$). (B) The treatment effect of the two different drug combinations is depicted as a log 2 fold change in gene expression of the combination treatment versus untreated L363 cells. Gene order on the x-axis is determined by the degree of difference in gene expression fold change between the two sirolimus doses. These data demonstrate that the 37 gene set acts in a pharmacodynamic manner.
Figure 20B:
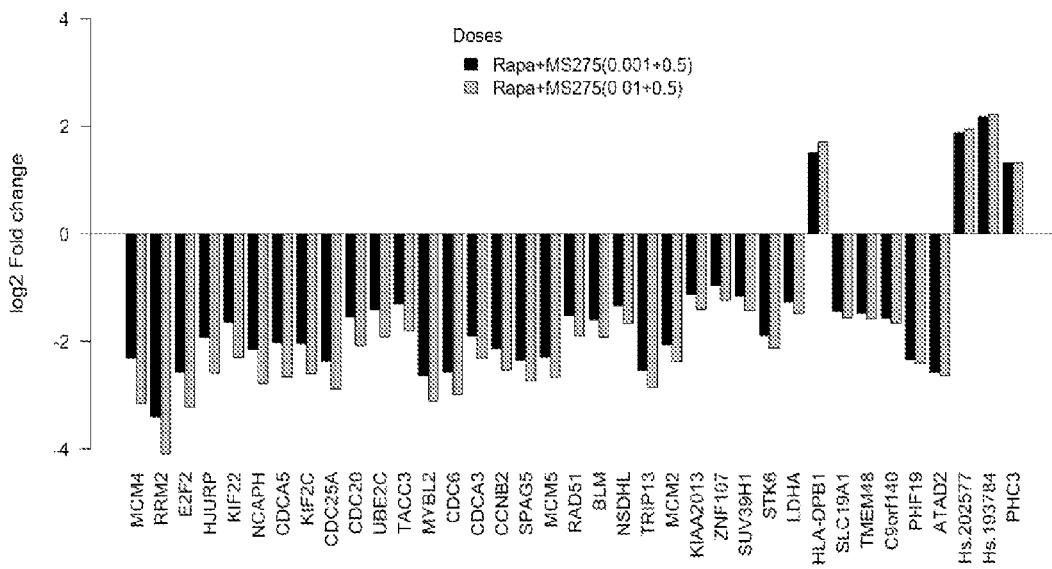

As the development of the classifier reported here began by identifying genes which synergistically respond at the expression level in human MM cells treated with the mTORi/HDACi combination, the expression change of the 37 genes included in this classifier could be used to identify if a patient treated with the drug combination is having a favorable molecular response. Additionally, as this classifier is made up of genes which expression is predictive of overall survival, use of this classifier as a PD biomarker may prove more clinically informative than other PD biomarkers which only indicate target inhibition (i.e., histone acetylation changes in response to HDACi therapy) with no relationship to favorable clinical drug response. Use of this classifier as a prognostically-linked PD biomarker may beneficially inform several clinical decisions. For example, early discontinuation of mTORi/HDACi therapy if insufficient molecular response is measured by analyzing gene expression changes in the neoplasm sample with the classifier, as opposed to continuing mTORi/HDACi therapy until clinical or symptomatic evidence of disease progression. In another example, the 37-gene classifier could be used as a PD biomarker for adjusting to the optimal dose necessary to achieve a prognostically-favorable gene expression change. In GEP of the same MM cell line treated with the same dose of entinostat and a lower dose (1 nM) of sirolimus, a highly linear dose response change in gene expression for the 37-gene classifier was found (Pearson's correlation r=0.98, $p<2.2^{e-16}$, FIG. 20). As might be expected, the lower sirolimus dose resulted in smaller transcriptional effects (FIG. 20). As an example, regression analyses predicted that the gene expression value (y) may determine the sirolimus dose (x) in the following manner: y=−0.563046+1.025323x, so that the optimal dose of sirolimus to achieve expression of gene y could be selected based on this regression equation. It is highly likely a similar regression equation could be derived for optimal HDACi dosing as well. As an example, the genes within the mTORi/HDACi classifier are differentially expressed when comparing healthy CD138+ plasma cells to MM cells in a large patient and healthy volunteer cohort (FIG. 15; Table 4). Thus, it is likely the optimal absolute gene expression level for all genes within the classifier could be defined by an algorithm considering the median expression of each gene within the classifier as measured in a sufficiently-sized cohort of samples from the tissue type of origin for the neoplasm being considered in healthy volunteers. These analyses suggest that adjusting drug dosages for individual patients, as determined by molecular profiling utilizing the mTORi/HDACi classifier, could be beneficial for tailored clinical management.

Figure 21:
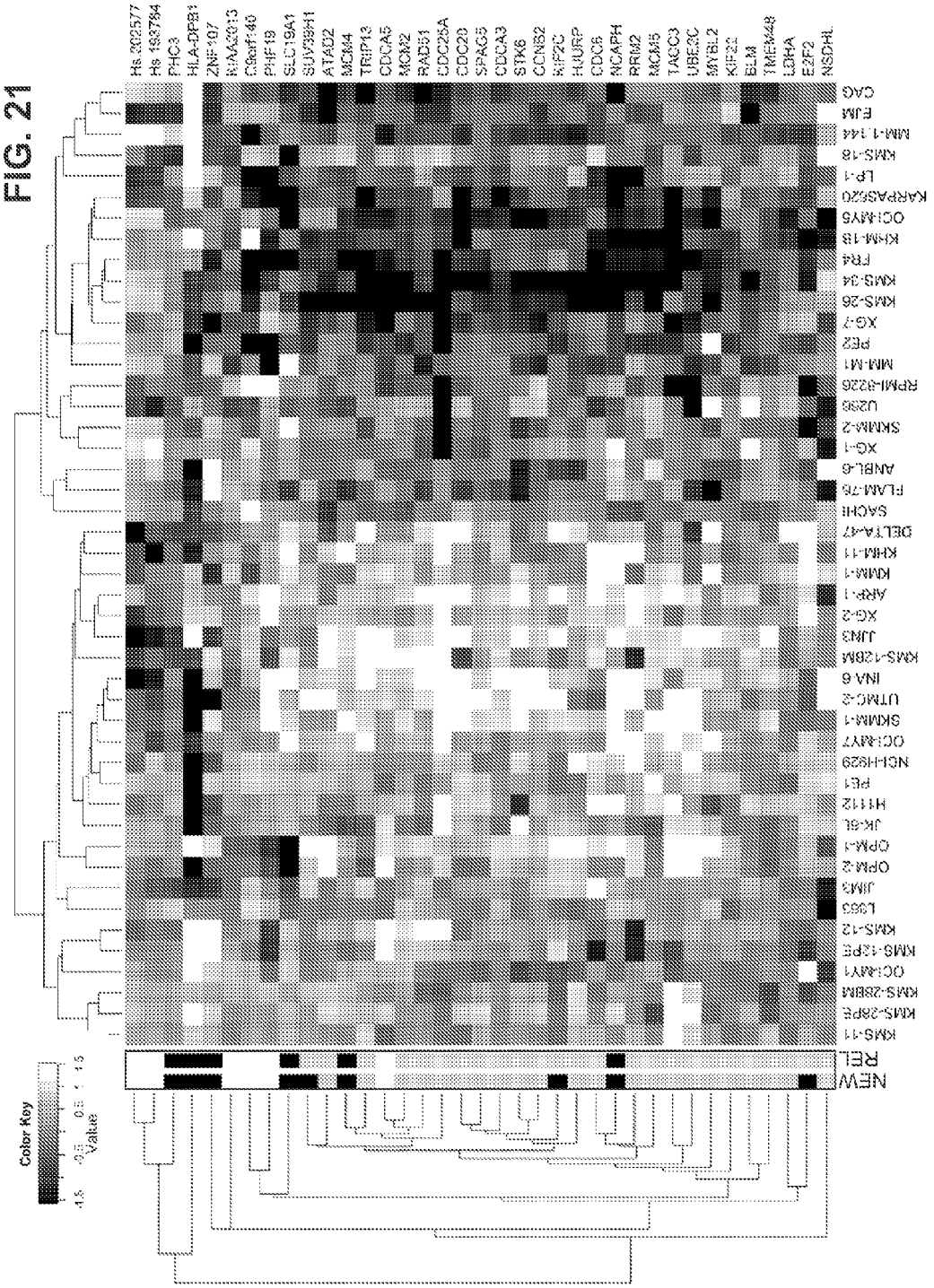
FIG. 21 is a heatmap depicting mean centered expression of the 37 genes (cooperative survival classifier) in a panel of untreated Human MM cell lines. For comparison, the differential expression (log 2 fold change) between normal healthy donor CD138+ cells and cells from newly diagnosed or treatment refractory MM patients (GSE6477; Carrasco et al., *Cancer Cell,* 9:313-325, 2009; Chng et al., *Cancer Res.* 67:2982-2989, 2007). The majority of the 37 genes are overexpressed in MM cell lines with only a few showing underexpression. For newly diagnosed (NEW) and relapsed (REL), black: MM vs ND<0, grey: MM vs ND>0, white: gene not available on the chip (6 genes).
Figure 22:
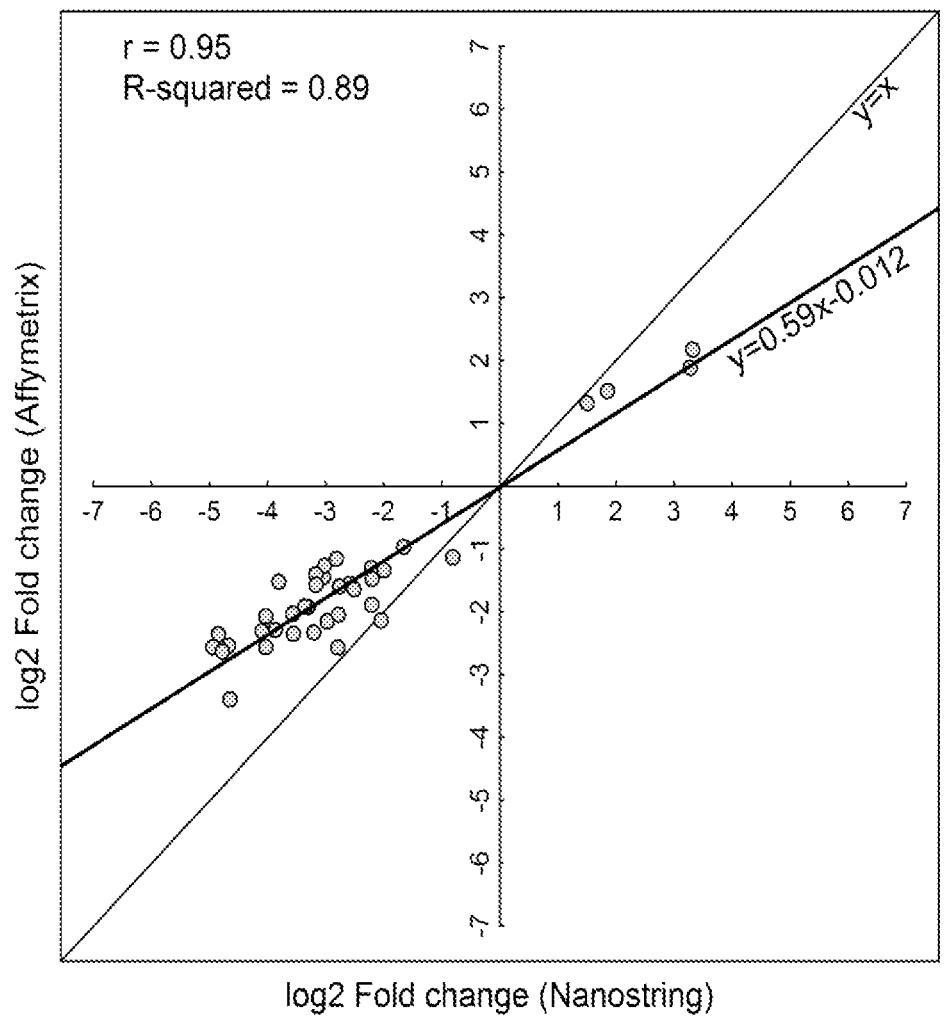
FIG. 22 is a graph depicting the high correlation between expression fold change detection in combination treated L363 cells between the Affymetrix® microarray platform and the Nanostring® probe-based gene expression platform
Figure 25A:
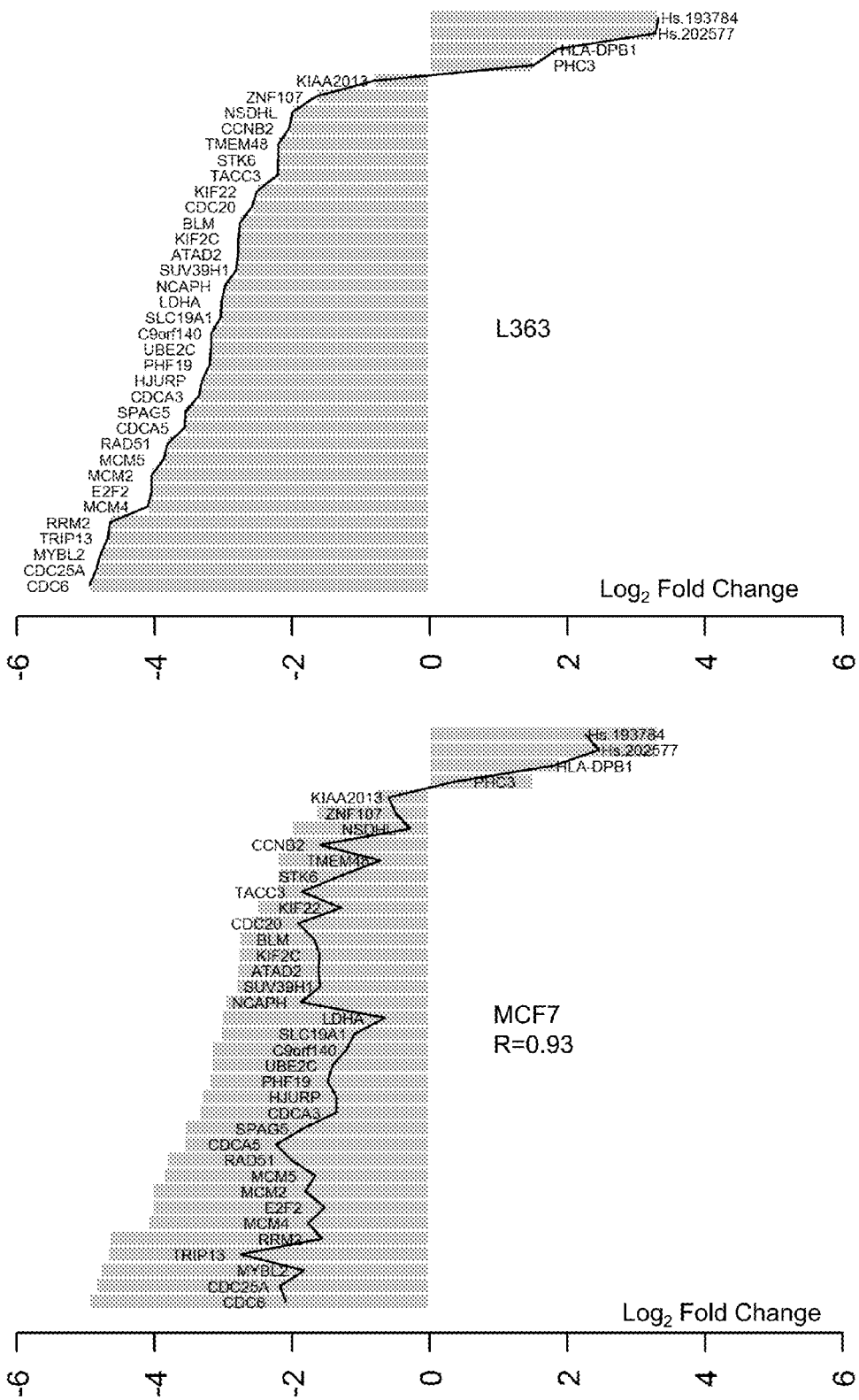
Figure 25B:
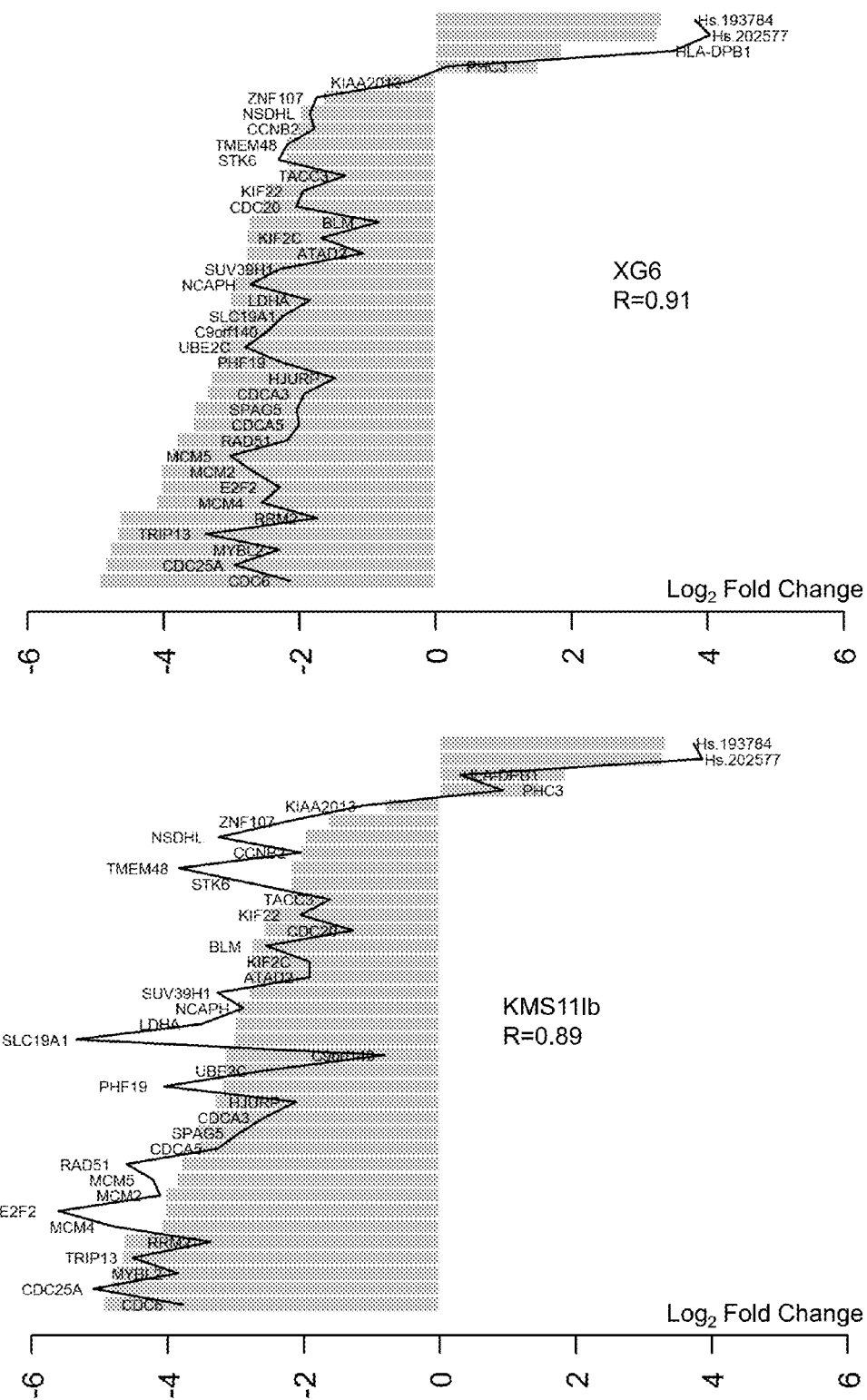
Figure 26:
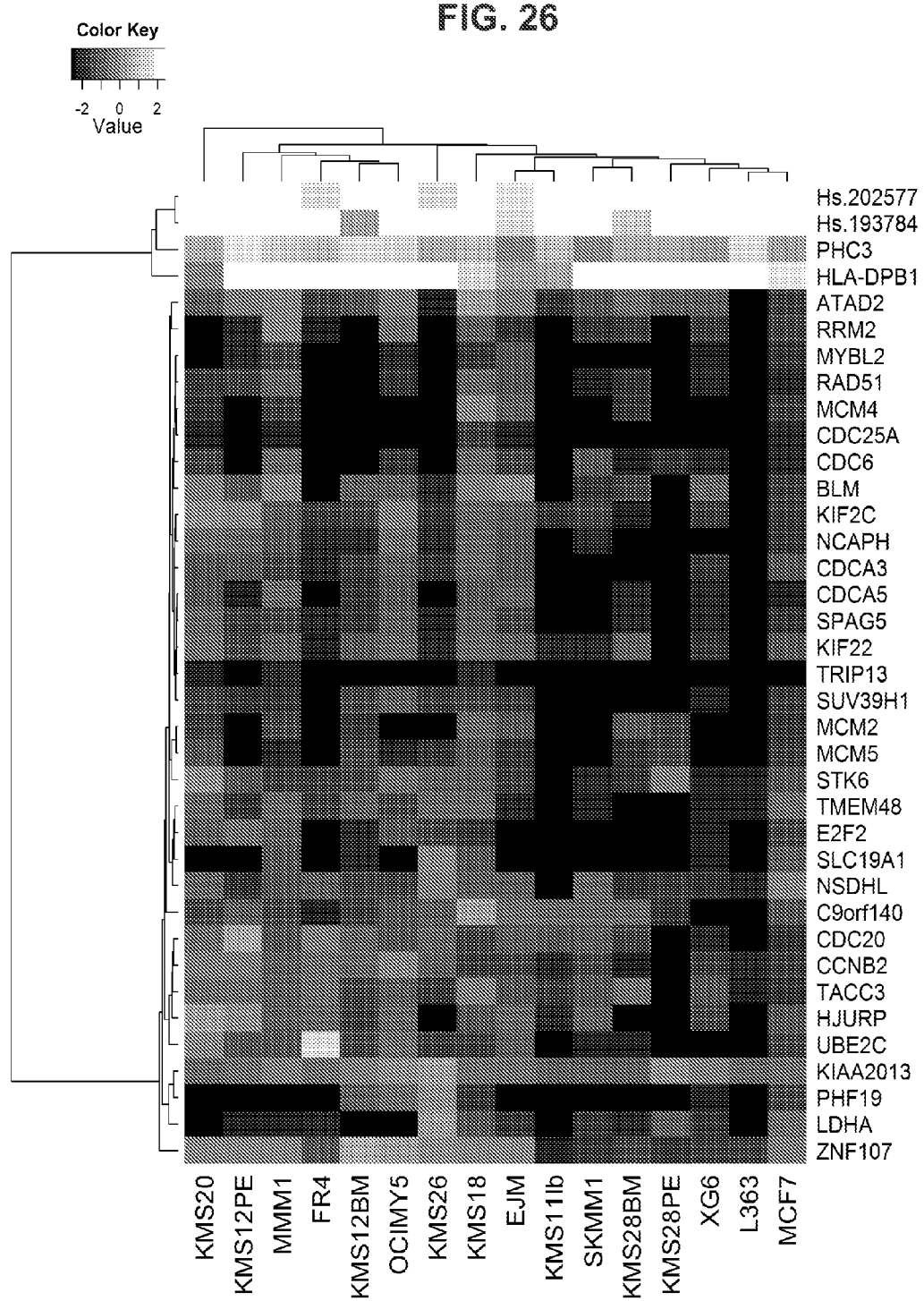
FIG. 26 is a heatmap of log 2 fold change expression (untreated vs. Rapamycin+MS-275) of the survival-associated 37-gene cooperative drug response signature in 15 human MM cell lines and 1 human breast cancer cell line (MCF-7) for comparison. Of particular note, KMS-26, KMS-18, OCI-MY5, KMS-20, and EJM all have <EC50 response to this combination dose (10 nM Rapamycin+500 nM MS-275 for 48 hours).
Figure 27C:
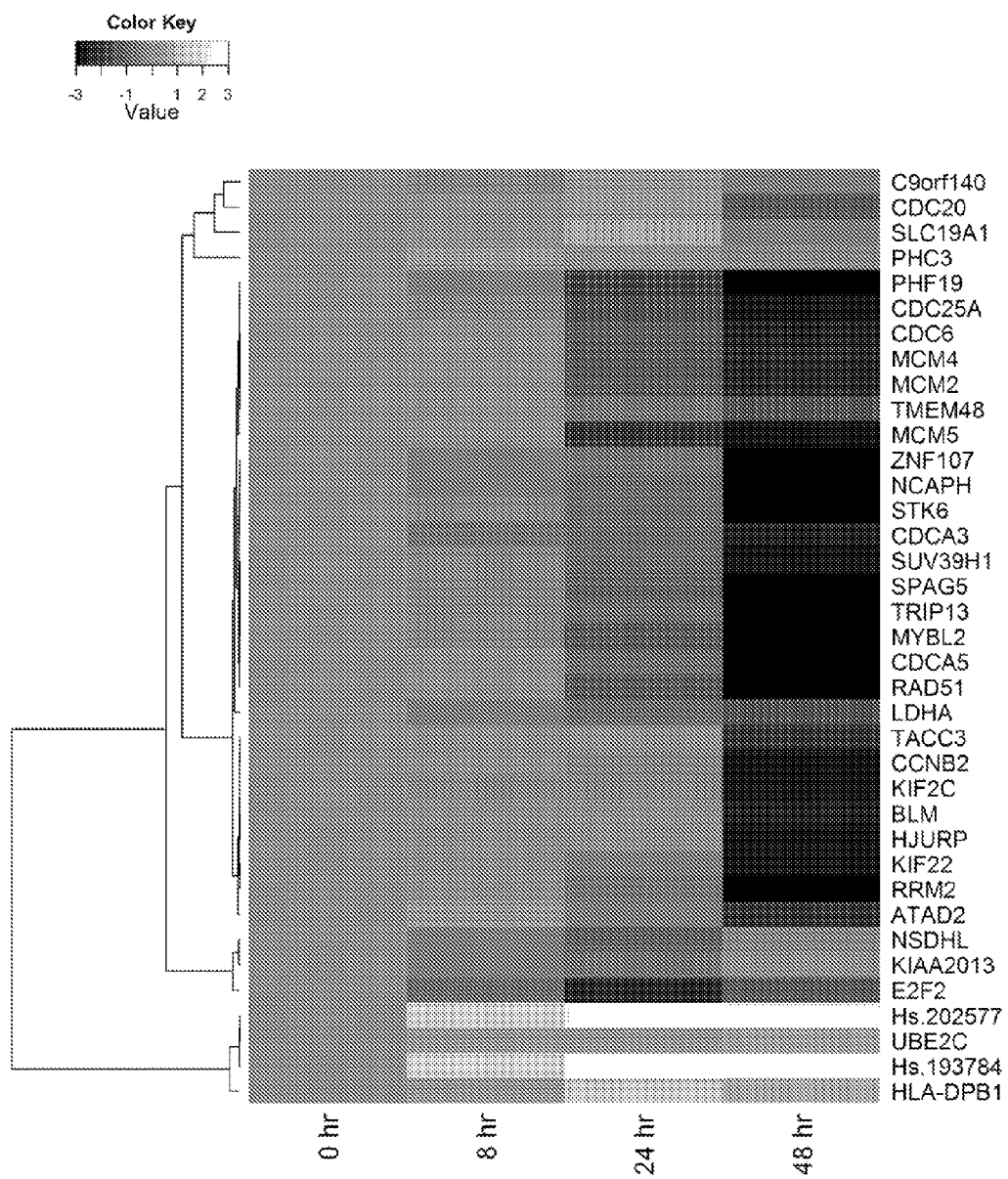

In support of this, additional experimental testing to further validate the pharmacodynamic nature of the mTORi/HDACi classifier was performed. A subset of sixteen cell lines was selected from a large panel of human MM cell lines for further experimental analyses. Hierarchical clustering by median-centered baseline expression of the 37 genes in the entire panel of human MM cell lines is depicted as a heatmap in FIG. 21 indicating the diverse baseline expression of this signature is also represented among in vitro cultured human MM cell lines. Additionally, for comparison, the differential expression (log 2 fold change) between normal healthy donor CD138+ cells and cells from newly diagnosed or treatment refractory MM patients (GSE6477; Carrasco et al., Cancer Cell, 9:313-325, 2009; Chng et al., Cancer Res. 67:2982-2989, 2007) is also shown in FIG. 21. To demonstrate that the classifier is agnostic of the platform of gene expression measurement, FIG. 22 shows the highly linear correlation (r=0.95; R-squared=0.89) between the treatment-induced gene expression fold change in L363 cells as detected by the Affymetrix U133 plus 2.0 chip-based microarray gene expression platform versus the Nanostring® multiplexed, barcode probe-based mRNA detection platform which requires no amplification of mRNA. The heatmap shown in FIG. 23 shows the log 2 fold change in expression of 19 of the 37 classifier genes in the human MM cell line L363 treated with 10 nM Rapamycin, 500 nm MS-275, and the combination as detected by microarray and Nanostring®. Additionally, FIG. 23 indicates substitution of the Class I-specific HDAC inhibitor MS-275 with the pan-HDAC inhibitor panobinostat results in a similar pattern of gene expression change for the classifier genes. These findings are separately confirmed in an additional MM cell line shown in FIG. 24. FIG. 25 shows the log 2 gene expression fold change of each gene in the classifier in response to combination treatment in fifteen human MM cell lines. The shaded bars indicate the expression change as measured in the MM cell line L363, which is highly sensitive to mTORi/HDACi treatment, and the r value is calculated comparing the individual cell line response to the response observed in the L363 line. The compilation of this data (log 2 fold change gene expression) in a single heatmap for all fifteen MM lines is shown in FIG. 26. The intensity of gene expression for each of these lines before and after mTORi/HDACi combination treatment as detected by Nanostring® is shown in FIG. 27A and FIG. 27B, respectively. The pharmocodynamic nature of this gene expression classifier is further illustrated in FIG. 27C, where the log 2 fold change of gene expression is shown as measured at 8, 24, and 48 hour time points after in vitro combination treatment. Eleven of the classifier genes with available antibodies were tested for change in protein expression after 48 hours of combination treatment in a panel of human MM cell lines (FIG. 28).

Figure 37:
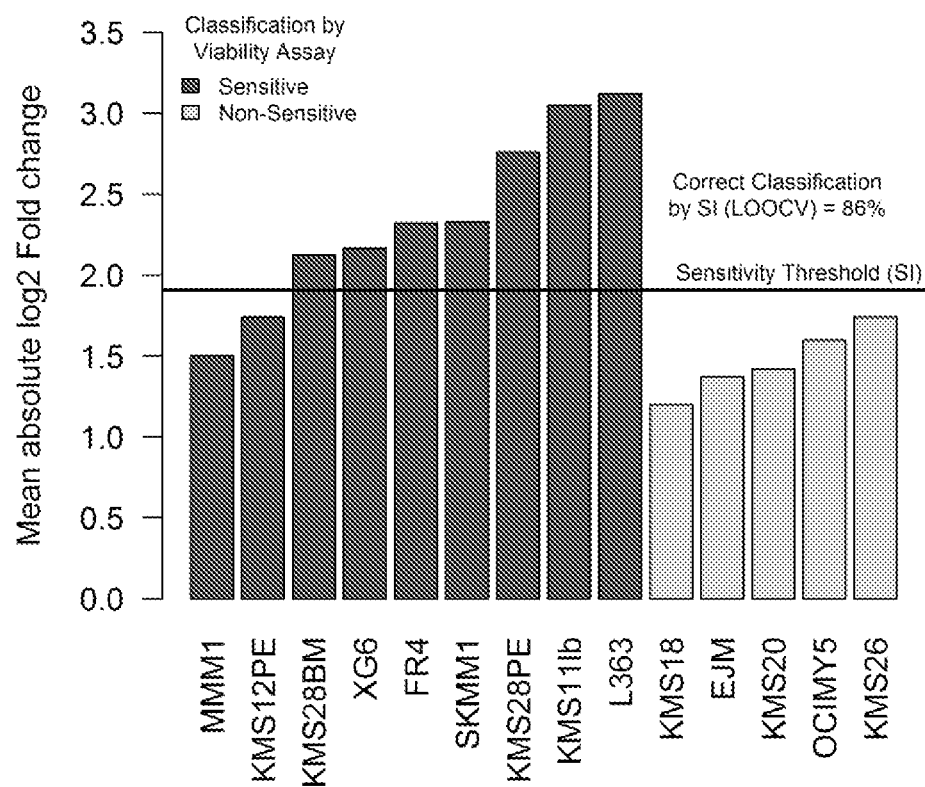
FIG. 37 shows a graph depicting an example application of the Sensitivity Index for the 37-gene signature. Here, this equation is applied to the in vitro data collected on the Nanostring® platform (see FIG. 26), a rule for classifying future sample was developed using 14 multiple myeloma cell lines treated with the combination of 10 nM rapamycin and 500 nM MS-275 for 48 hours. Cell lines were considered sensitive to the combination treatment if at least 50% decrease in viability was observed. The midpoint between the means of the sensitivity index (SI) of the two classes was determined as the threshold value (SI=1.91) for classification of a new sample based on expression changes in the 37 genes due to the combination treatment. To estimate the prediction error leave-one-out cross-validation procedure (Simon et al., J. Nat. Cancer Inst., 95:14-18, 2003) was used and 86% of the cell lines were classified correctly.

As a simple example, a sensitivity index algorithm based on the 37-gene classifier to detect response to combination treatment such as $$SI = \frac{1}{37}\sum_{i=1}^{37} |\log_2 X_{RM_i} - \log_2 X_{UNT_i}|$$

could be used to define whether a patient has a favorable molecular response. The sensitive and insensitive parameters for each individual tumor type would need to be defined within the context of a prospective clinical trial. As an example of applying this equation to the in vitro data collected on the Nanostring platform, a rule for classifying future sample was developed using 14 multiple myeloma cell lines treated with the combination of 10 nM rapamycin and 500 nM MS-275 for 48 hours. Cell lines were considered sensitive to the combination treatment if at least 50% decrease in viability was observed. The midpoint between the means of the sensitivity index (SI) of the two classes was determined as the threshold value (SI=1.91) for classification of a new sample based on expression changes in the 37 genes due to the combination treatment. To estimate the prediction error we used the leave-one-out cross-validation procedure Simon et al., Journal of the National Cancer Institute 95:14-18, 2003) and we found that 86% of the cell lines were classified correctly (FIG. 37).

Numerous models and strategies have been developed for predictive modeling using gene expression data. To present more advanced examples of developing predictors of sensitivity to the combination treatment we also generated models based on the Compound Covariate Predictor (CCP), Diagonal Linear Discriminant Analysis (DLDA), Nearest Neighbor Classifications (NNC), Nearest Centroid Classification (NCC), and Support Vector Machines (SVM) as implemented in the BRB-ArrayTools (linus.nci.nih.gov/BRB-ArrayTools.html by Dr. Richard Simon and BRB-ArrayTools Development Team). The prediction error was estimated by 0.632+ bootstrap method of re-sampling with default parameter of generating 100 random training subsets. Using permutation test (N=1000) we also evaluated the significance of the cross-validated misclassification rate (significance level alpha=0.05). Table 14 shows the percentage of the correct classification level and the permutation p-values for each method. Table 15 and 16 contains the algorithms and weighs or reference expression for the methods with the correct classification rate reaching at least 80% (linear predictors: CCP, DLDA, SVM and NCC classification). For Table 15, the prediction rule is defined by the inner sum of the weights ($w_i$) and expression ($x_i$) of the 37 genes in the classifier. The expression is the log ratios of combination treated vs. untreated samples. A sample is classified to the class Non-Sensitive if the sum is greater than the threshold; that is, $\Sigma_i w_i x_i$>threshold; The threshold for the Compound Covariate Predictor (CCP) is −129.615. The threshold for the Diagonal Linear Discriminant (DLDA) predictor is −86.875; and the threshold for the Support Vector Machine (SVN) predictor is −3.557. For Table 16, the centroid for the Non-sensitive/Sensitive class is a vector containing the means of expression in the 37 genes. The expression is the log ratios of combination treated vs. untreated sample. The distance (d) of the expression profile for the new sample (k) to each of the centroid (C) is measured by Euclidean distance:

$$d(k, C) = \sqrt{\sum_{i=1}^{n} (x_{i_k} - x_{i_C})^2}$$

where $(x_{i_k})$(squared distance) and $(x_{i_c})$ are the log ratios of the 37 genes in a sample and centroid, respectively. The sample is predicted to belong to the class corresponding to the nearest centroid.

Prognostically-Linked PD Biomarker for Detection of Synergistic Activity.

Figure 19A:
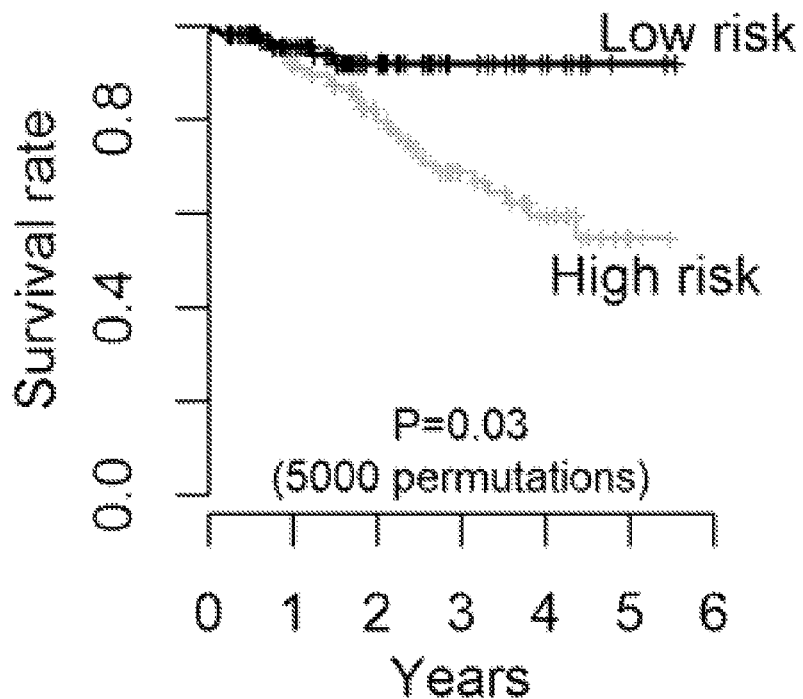
FIGS. 19A-19C are a series of graphs illustrating that expression of drug-response network genes correlates with survival in multiple myeloma patients. The 901 genes of the entire drug response network were input in the multivariate predictor algorithm; 124 genes were selected as the survival classifier. Kaplan-Meier survival curves showing overall survival in patients: (A) Cross-validated "training set" stratified into low risk and high risk groups (principal components classifier). Permutation P-value computed for the log-rank test. (B) Single split test set stratified into low risk and high risk groups. Asymptotic p-values were computed for the log-rank test. (C) Survival predictor gene expression (median centered) heatmap (124 genes) of 207 patients in test set. Samples are ordered by increasing risk score from the survival classifier and plotted above the heatmap. Black bars indicate death. These data indicate that some patients are likely to derive benefit from single agent treatment even though most patients would be likely to benefit from the combination.
Figure 19B:
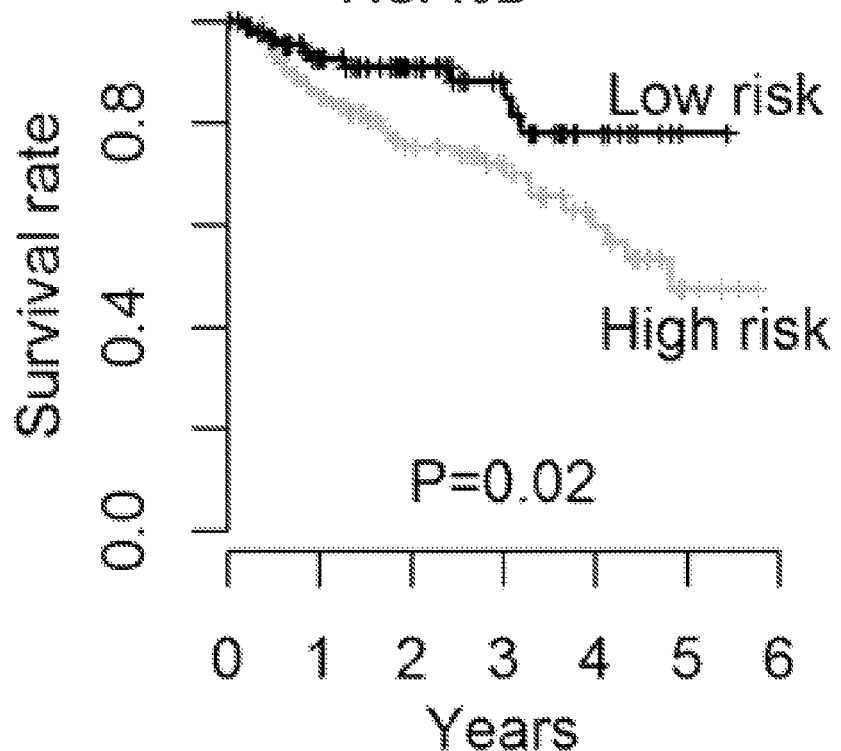
Figure 19C:
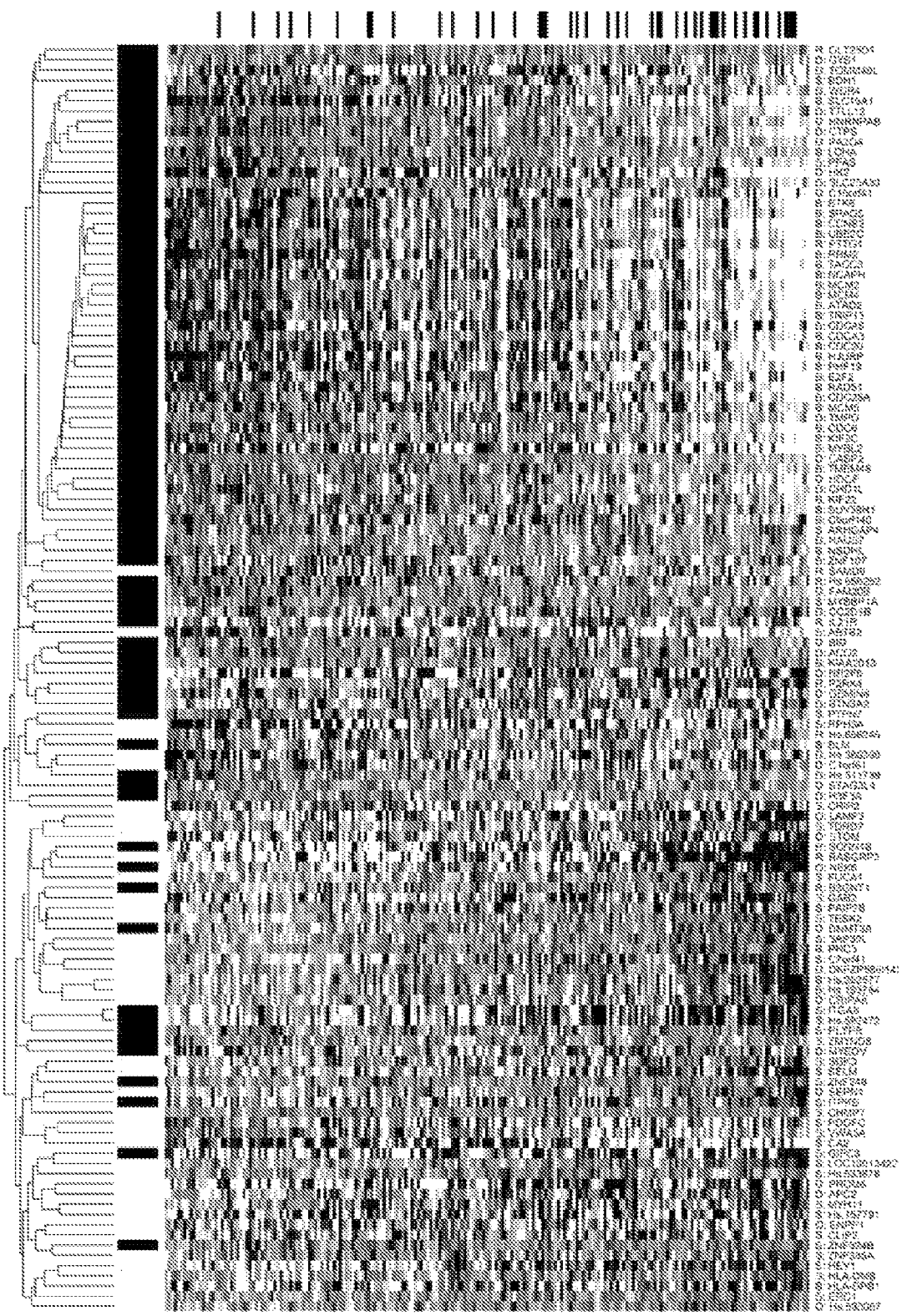

While the 37-gene mTORi/HDACi classifier is comprised of genes which synergistically respond to combined treatment with mTORi/HDACi, as a PD biomarker, it may not differentiate between patients who are having a synergistic favorable molecular response to both drugs in the combination and those patients who are having an exceedingly favorable response to only one drug with little to no benefit from the other. To address the clinical question of whether an individual patient treated simultaneously with the mTORi/HDACi combination is receiving benefit from one or both drugs, the same multivariate predictor modeling used to define the 37-gene signature as a prognostically-linked subset of the genes synergistically affected by both drugs (blue module; 126 genes input) was applied. For this analysis, the 901 genes identified in the transcriptional co-expression network analysis (FIG. 10) as the overall drug response network consisting of genes affected by the both drugs in a cooperative fashion, and those contributed by the affects of one drug alone were used as input for the multivariate predictor modeling. Of the 901 genes, 124 genes were identified to have expression linked to prognosis, and included in these 124 genes are all 37 genes identified as the cooperative classifier (FIG. 19; Table 6). In one example, a neoplasm highly sensitive to the mTOR inhibitor, yet insensitive to the HDAC inhibitor, may be detected as having a favorable molecular response with the 37-gene classifier. Yet by analyzing the expression change after initial combination treatment with the 124 gene classifier, one could detect a lack of favorable change in the seventy-two prognostically-associated genes identified as contributed solely by the HDACi. With the additional information provided by the 124-gene mTORi/HDACi classifier in this example, a clinician may continue treatment only with the mTORi, thus avoiding exposing the patient who is unlikely to receive any benefit from the HDACi to the side-effects and associated risk of continued use of the HDACi therapy.

Example 4

Validation of Gene Signature in Multiple Cancer Types

This example illustrates the utility of determining the gene expression signature including expression of certain genes listed as Blue module genes in Table 6 and Table 7 above for use in the prognosis of a broad range of cancer types. Gene expression datasets were analyzed using the Oncomine platform to ascertain the expression of this gene expression signature in numerous neoplasm types, including squamous cell lung carcinoma, cutaneous melanoma, pleomorphic liposarcoma, colon adenoma, multiple myeloma, papillary renal cell carcinoma, melanoma, glioblastoma, chronic lymphocytic leukemia, invasive breast carcinoma stroma, ovarian serous cystadenocarcinoma, invasive breast carcinoma, glioblastoma, mantle cell lymphoma. Unexpectedly, the results indicate that a gene expression signature composed of genes within the Blue module is dysregulated in nearly all neoplasm types analyzed.

Figure 32A:
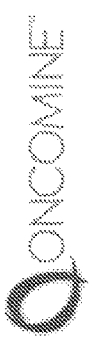
FIGS. 32A-32BB show a series of charts illustrating the use of the identified genes in the Blue module gene expression signature for the prognosis of several different tumor types including squamous cell lung carcinoma (B-C), cutaneous melanoma (D-E), pleomorphic liposarcoma (F-G), colon adenoma (H-I), multiple myeloma (J-K), papillary renal cell carcinoma (L-M), melanoma (N-O), glioblastoma (P-Q), chronic lymphocytic leukemia (R-S), invasive breast carcinoma stroma (T-U), ovarian serous cystadenocarcinoma (V-W), invasive breast carcinoma (X-Y), glioblastoma (Z-AA), mantle cell lymphoma (BB). The genes analyzed are indicated on each chart, and were analyzed using ONCOMINE™ (Compendia Bioscience, Ann Arbor, Mich.). Chart A summarizes the unique expression of the analyzed gene signatures across several tumor types.
Figure 32B:
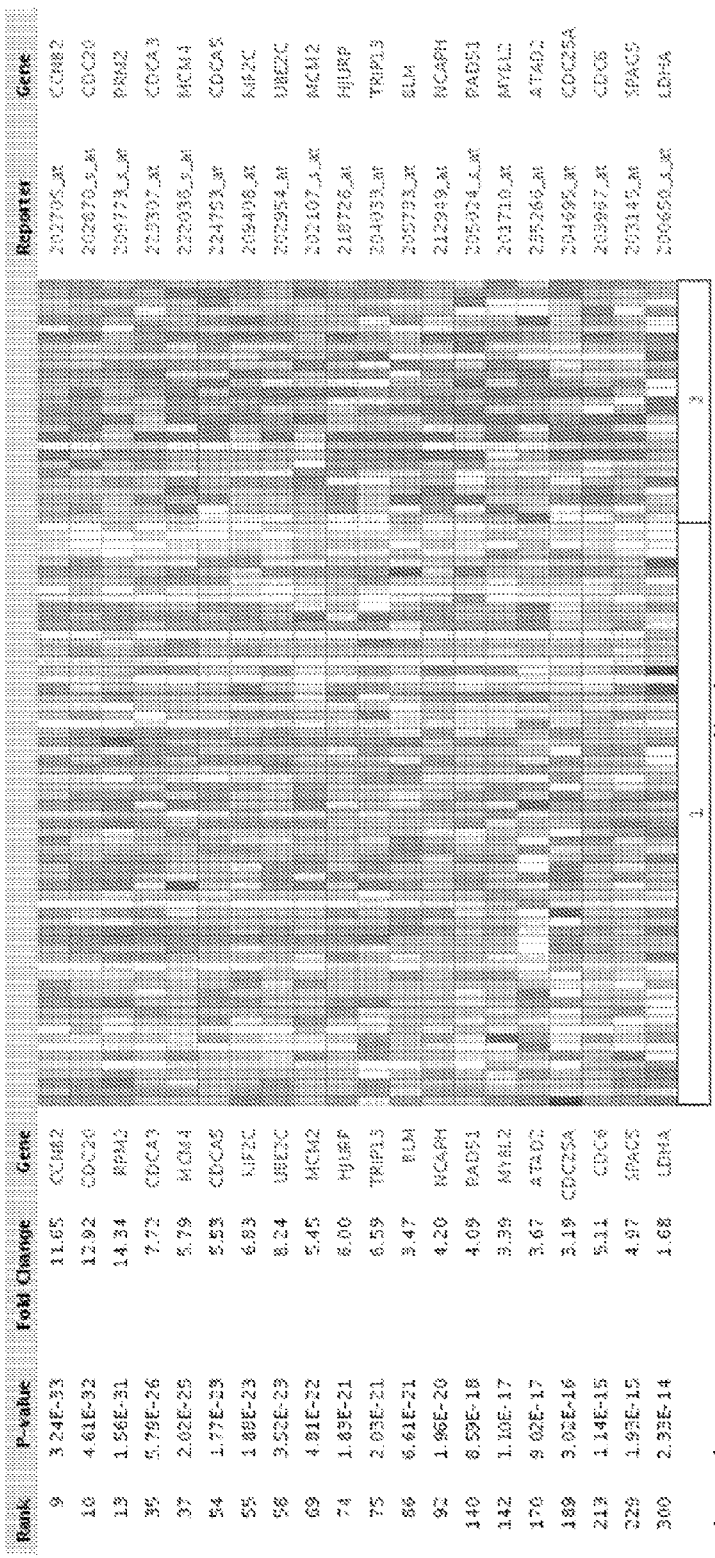
Figure 32C:
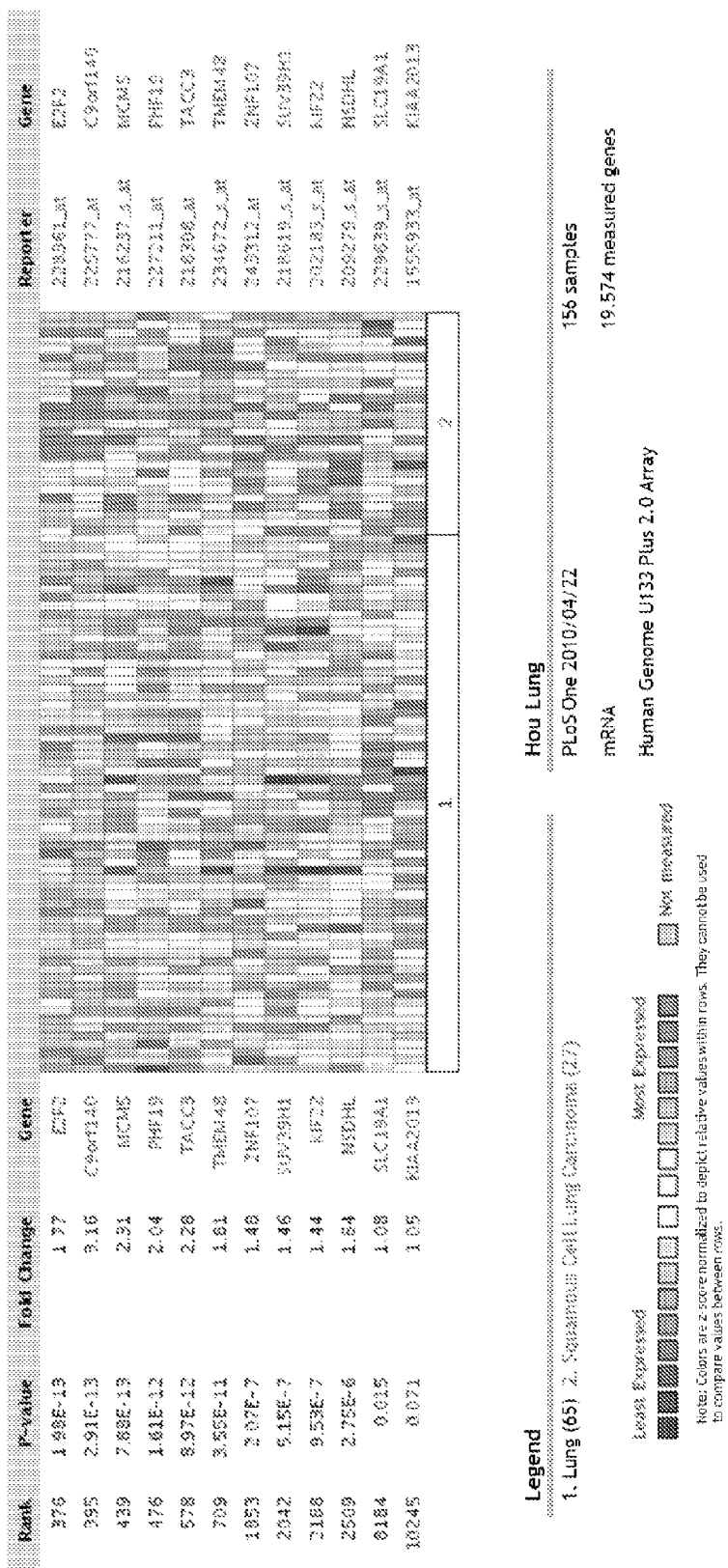
Figure 32D:
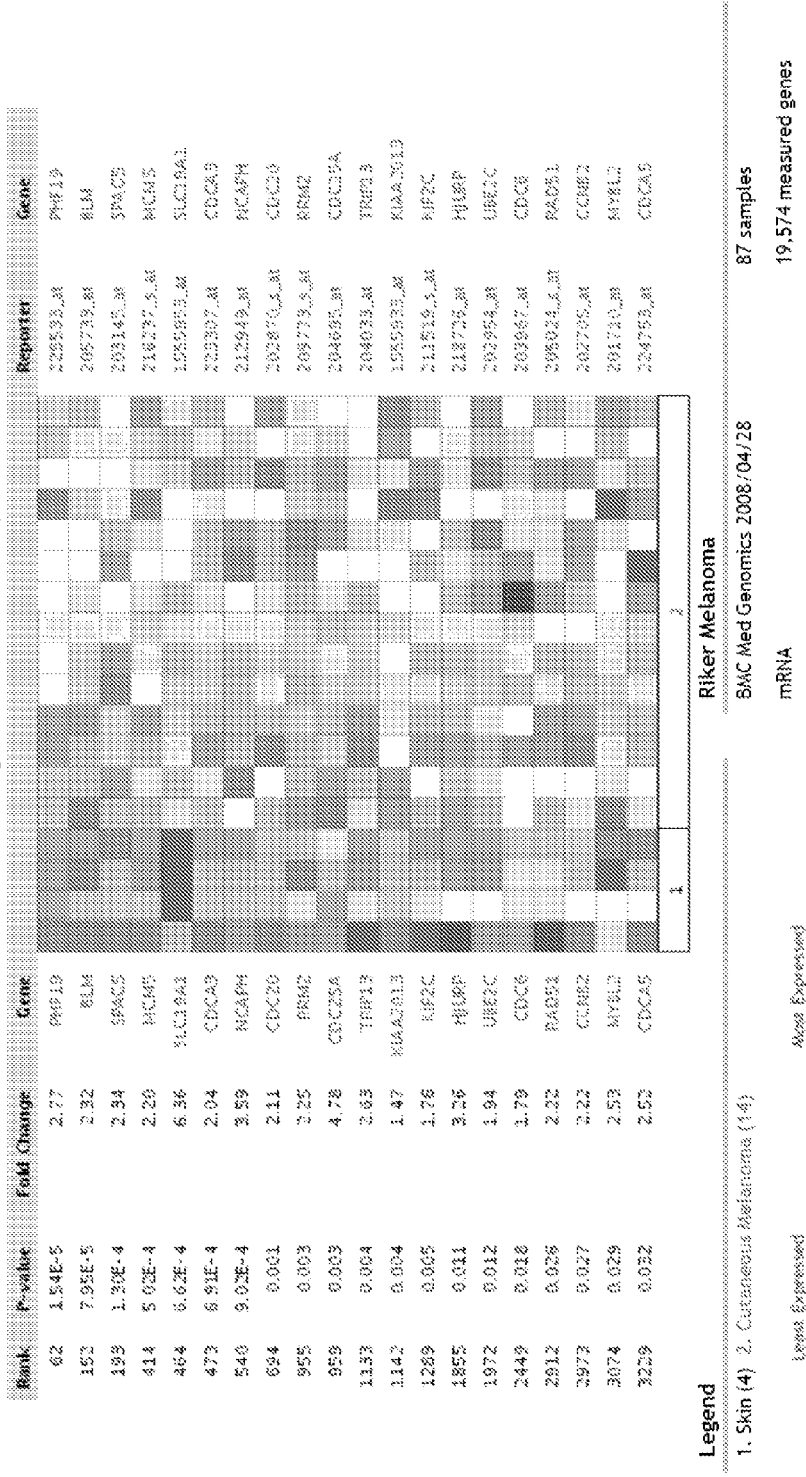
Figure 32E:
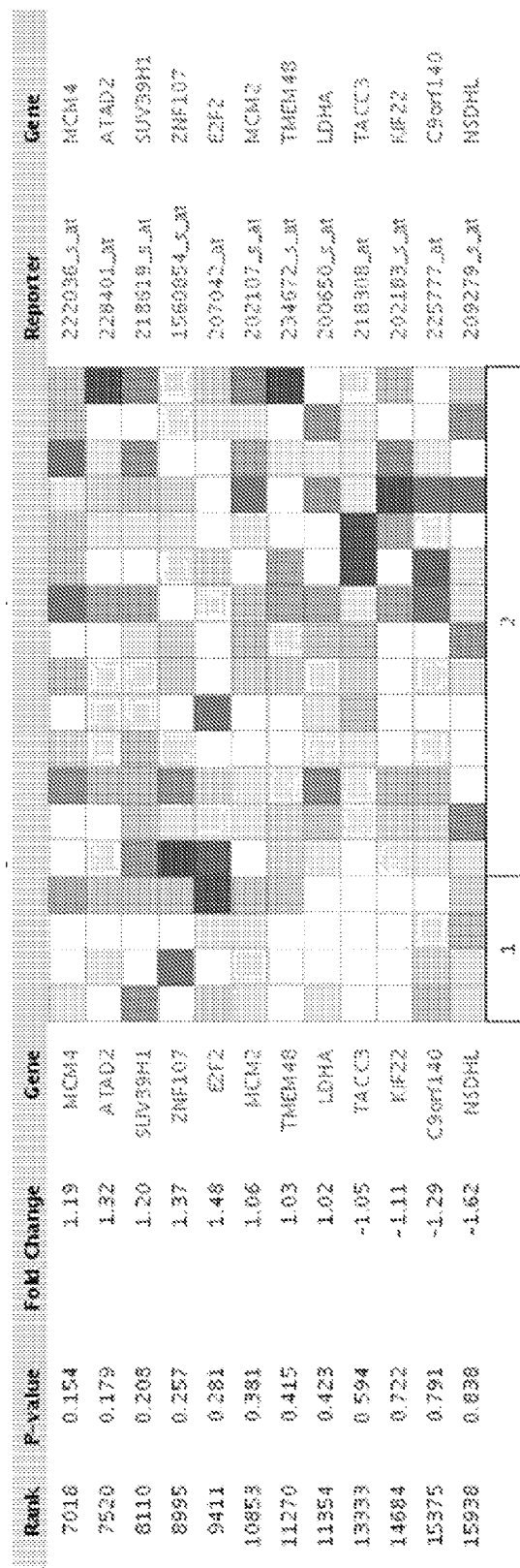
Figure 32F:
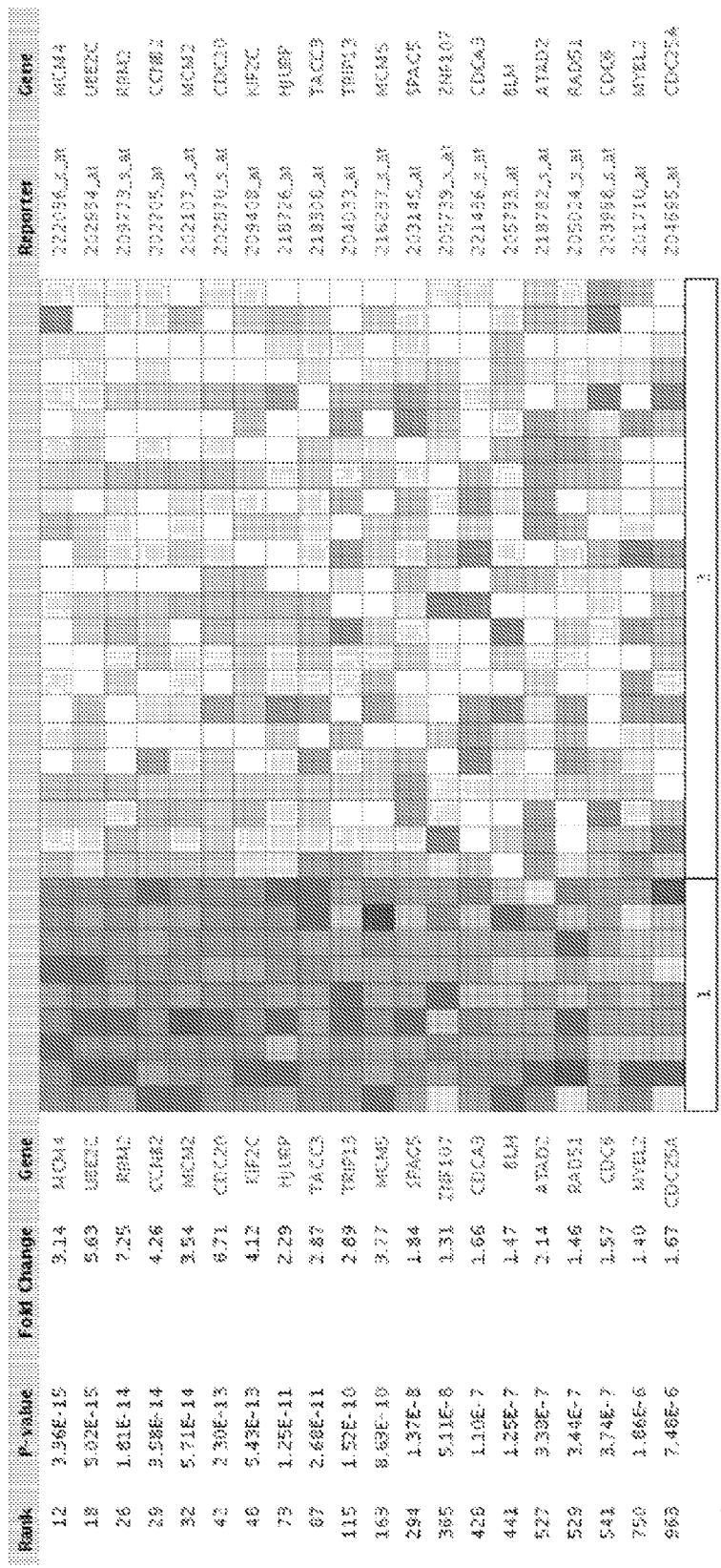
Figure 32G:
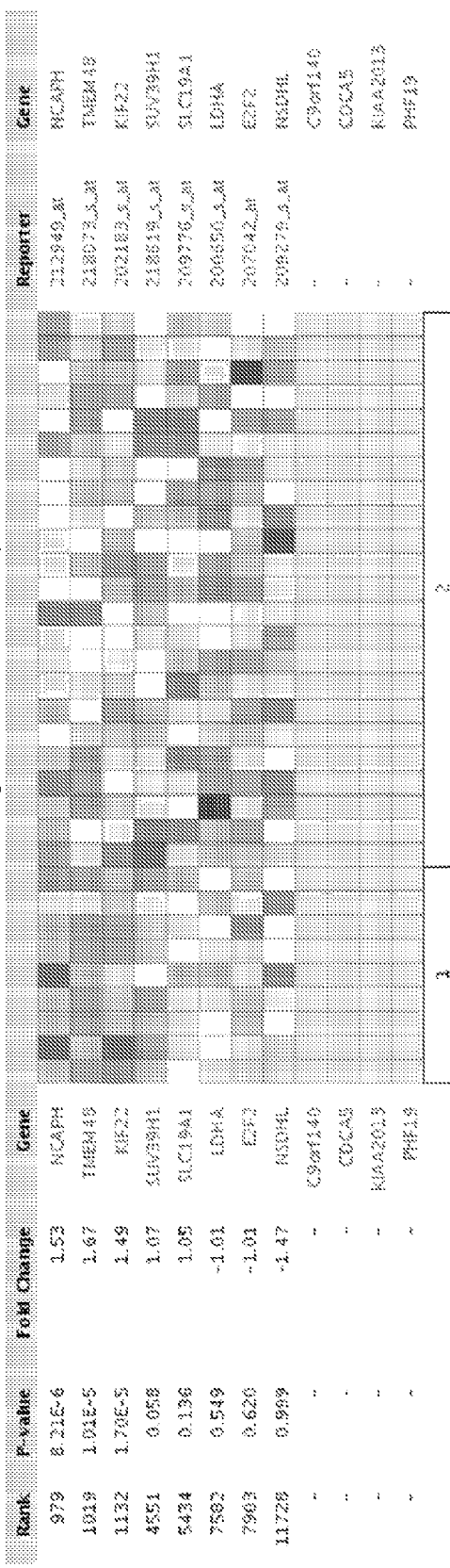
Figure 32H:
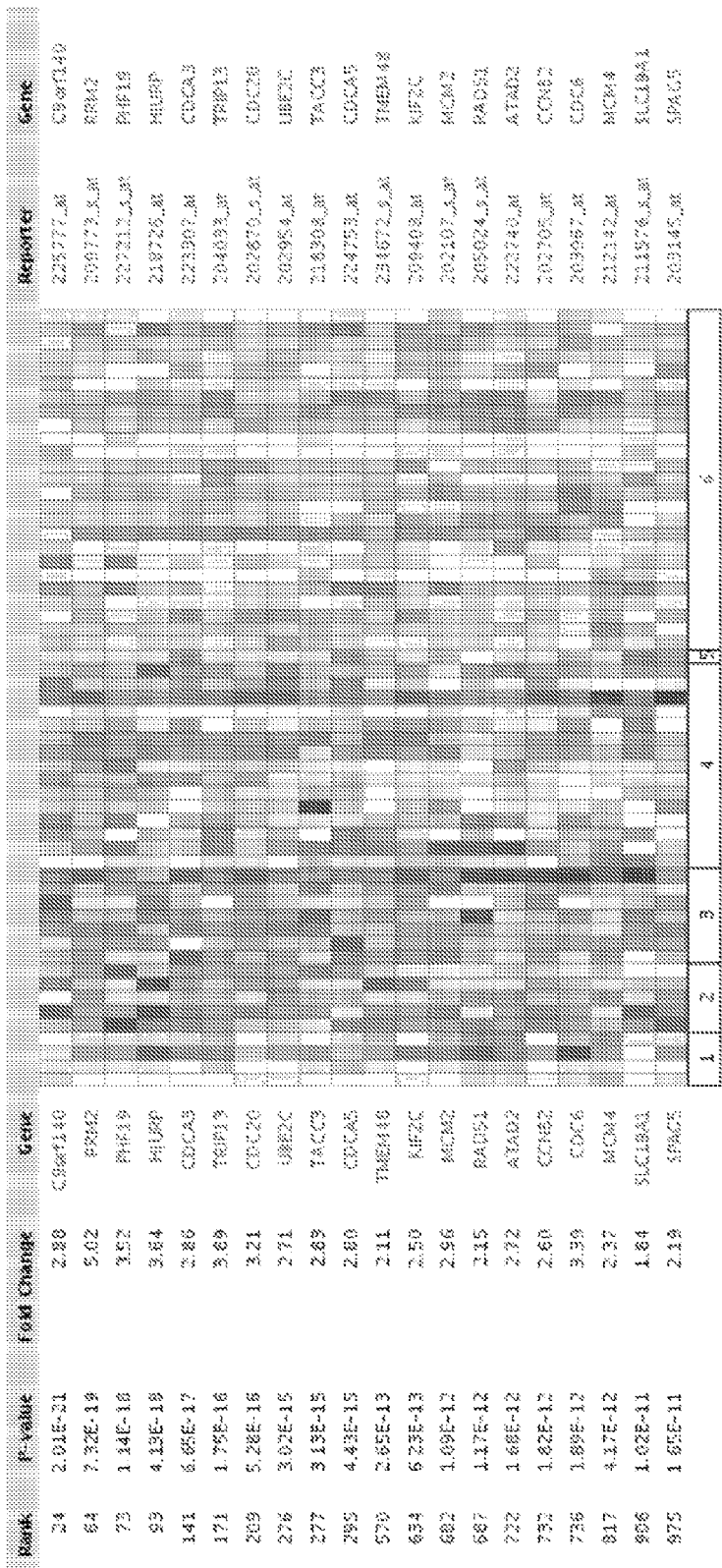
Figure 32I:
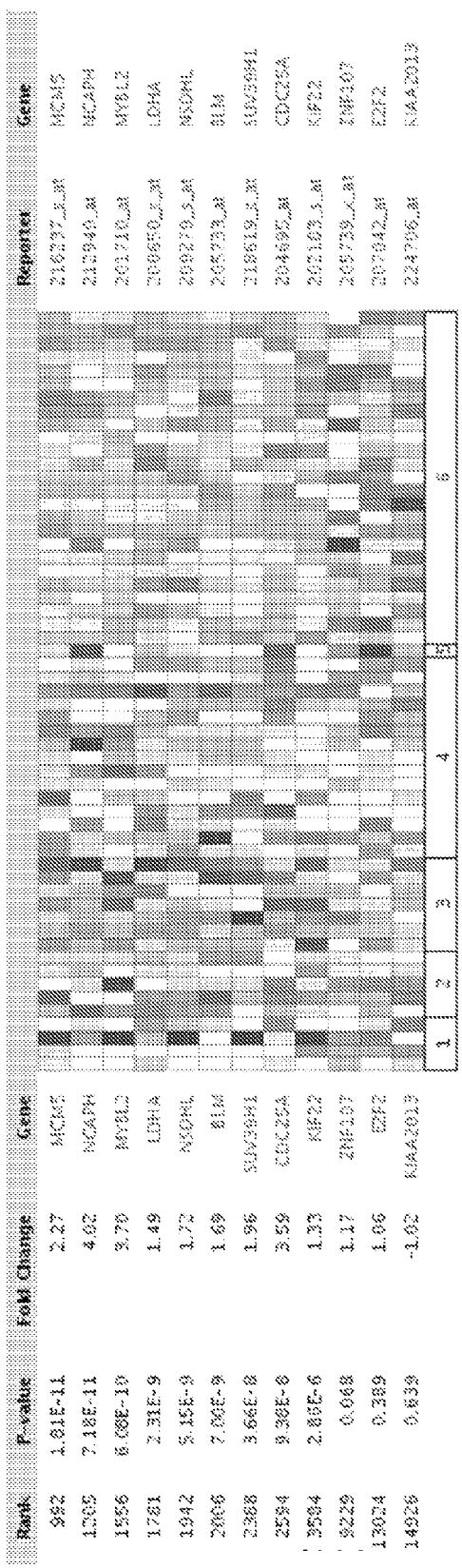
Figure 32J:
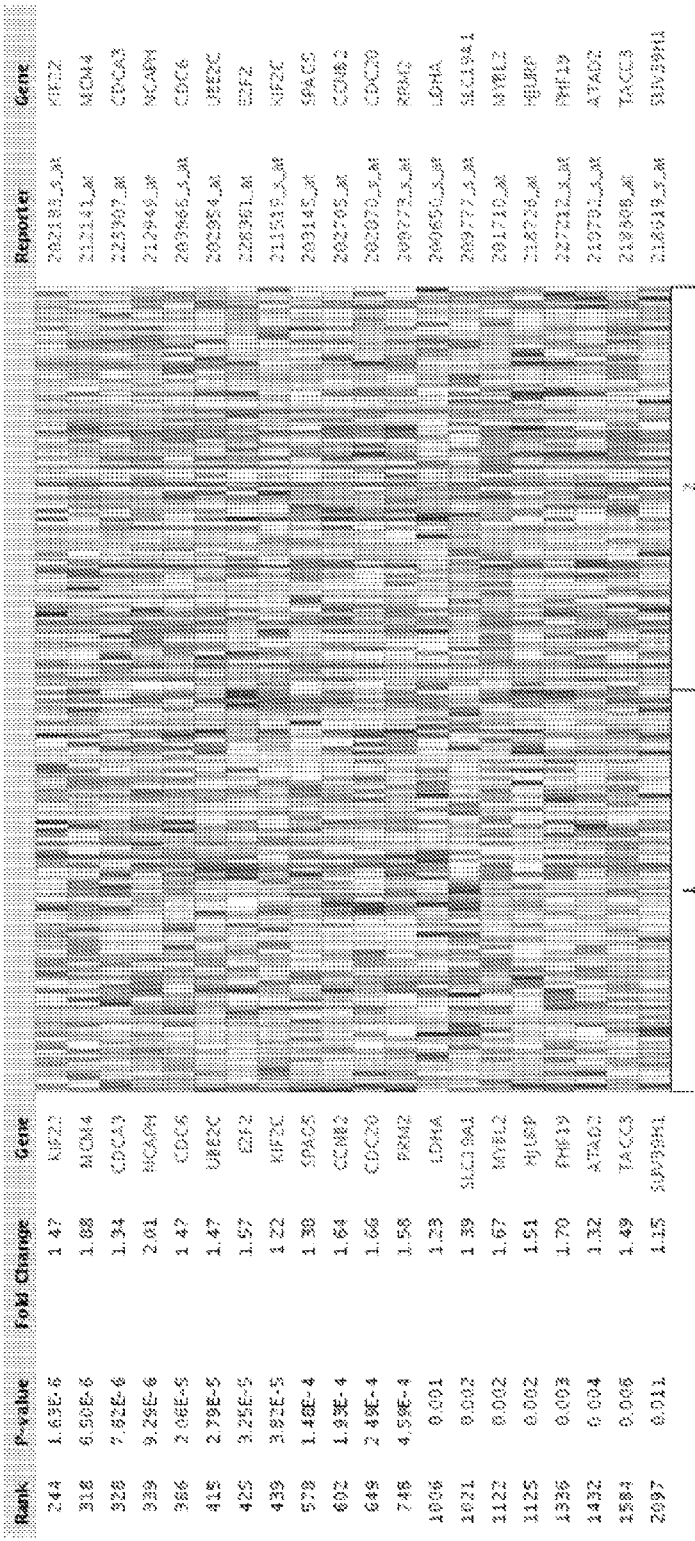
Figure 32K:
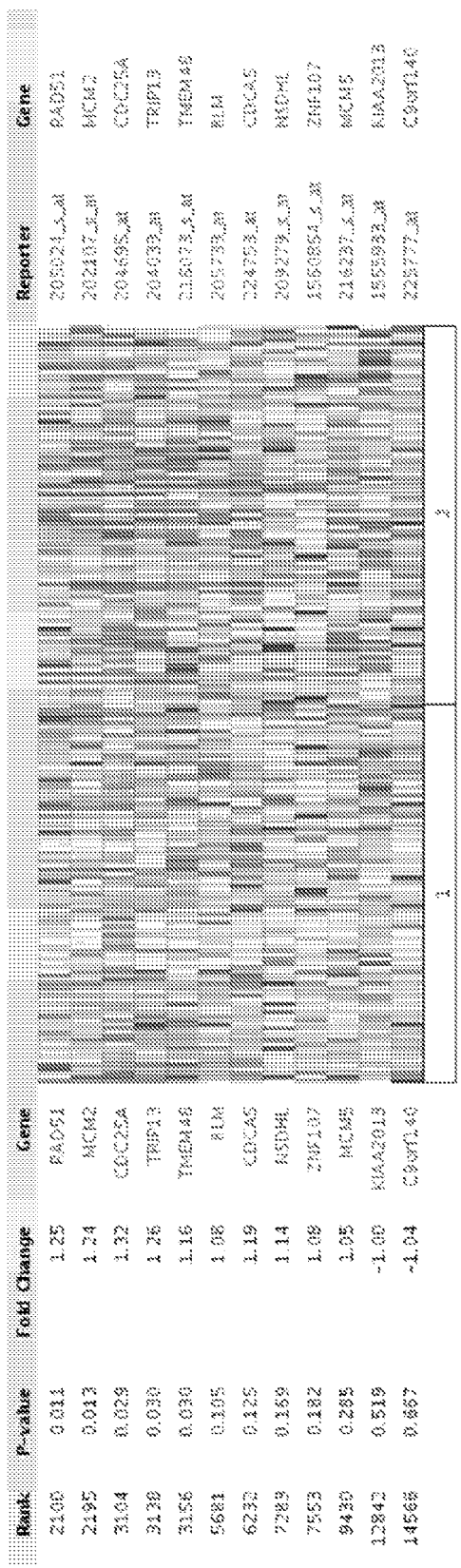
Figure 32L:
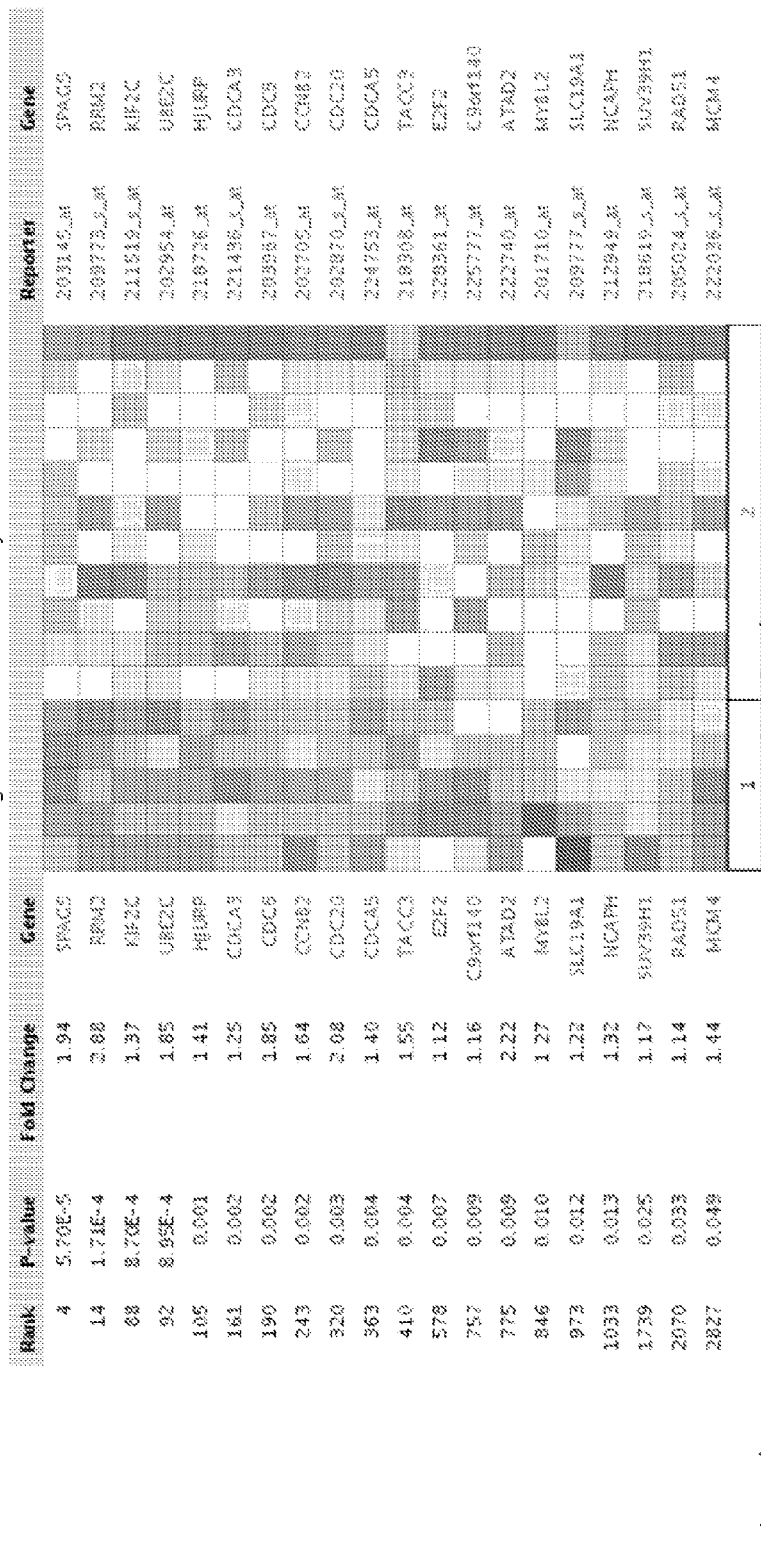
Figure 32M:
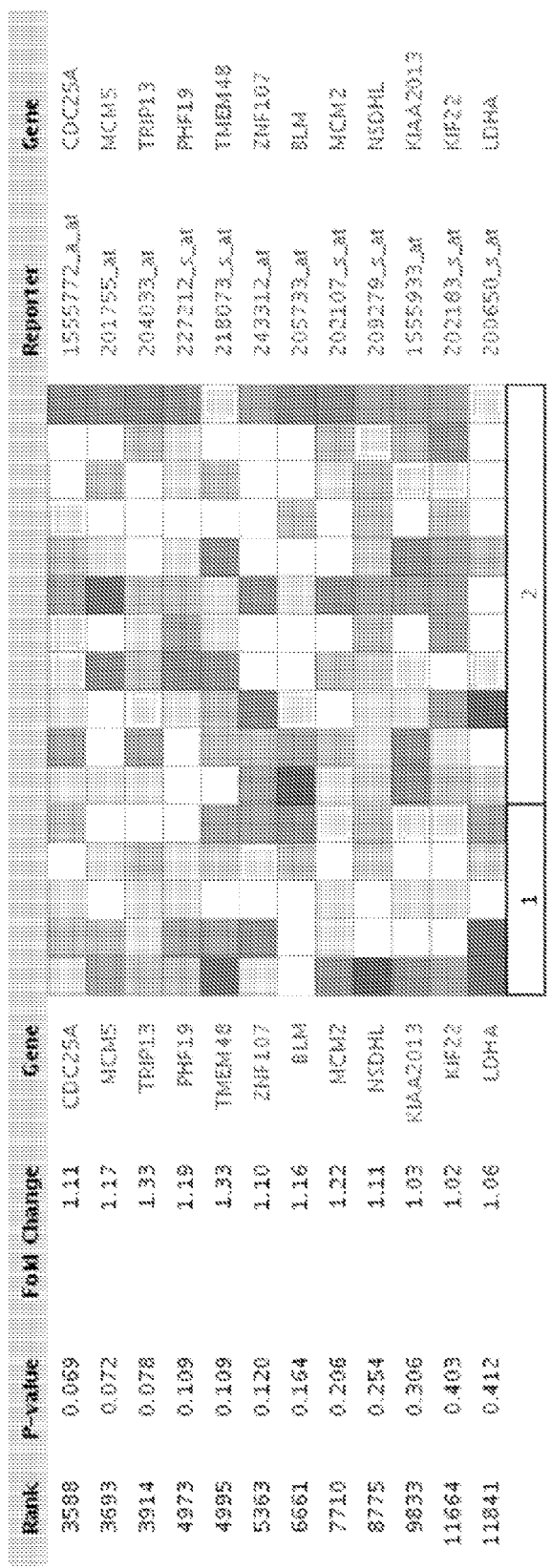
Figure 32N:
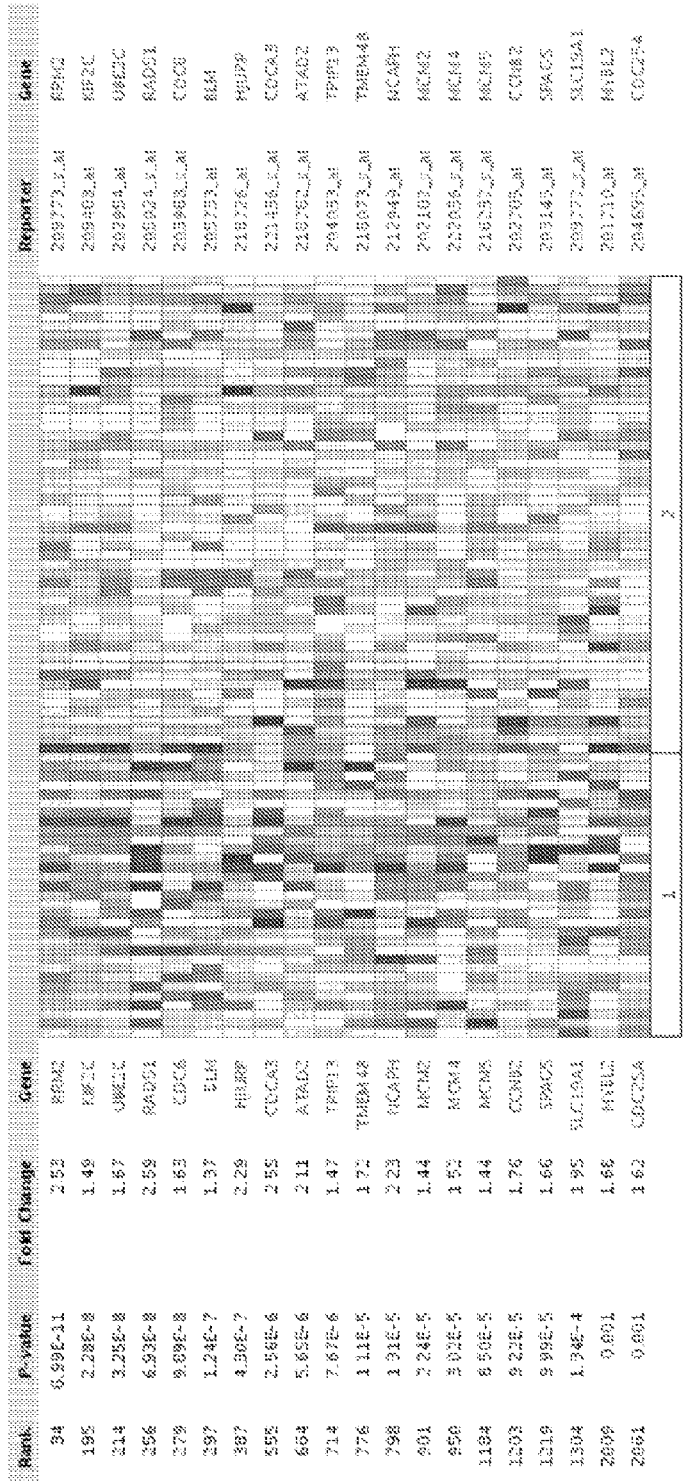
Figure 32O:
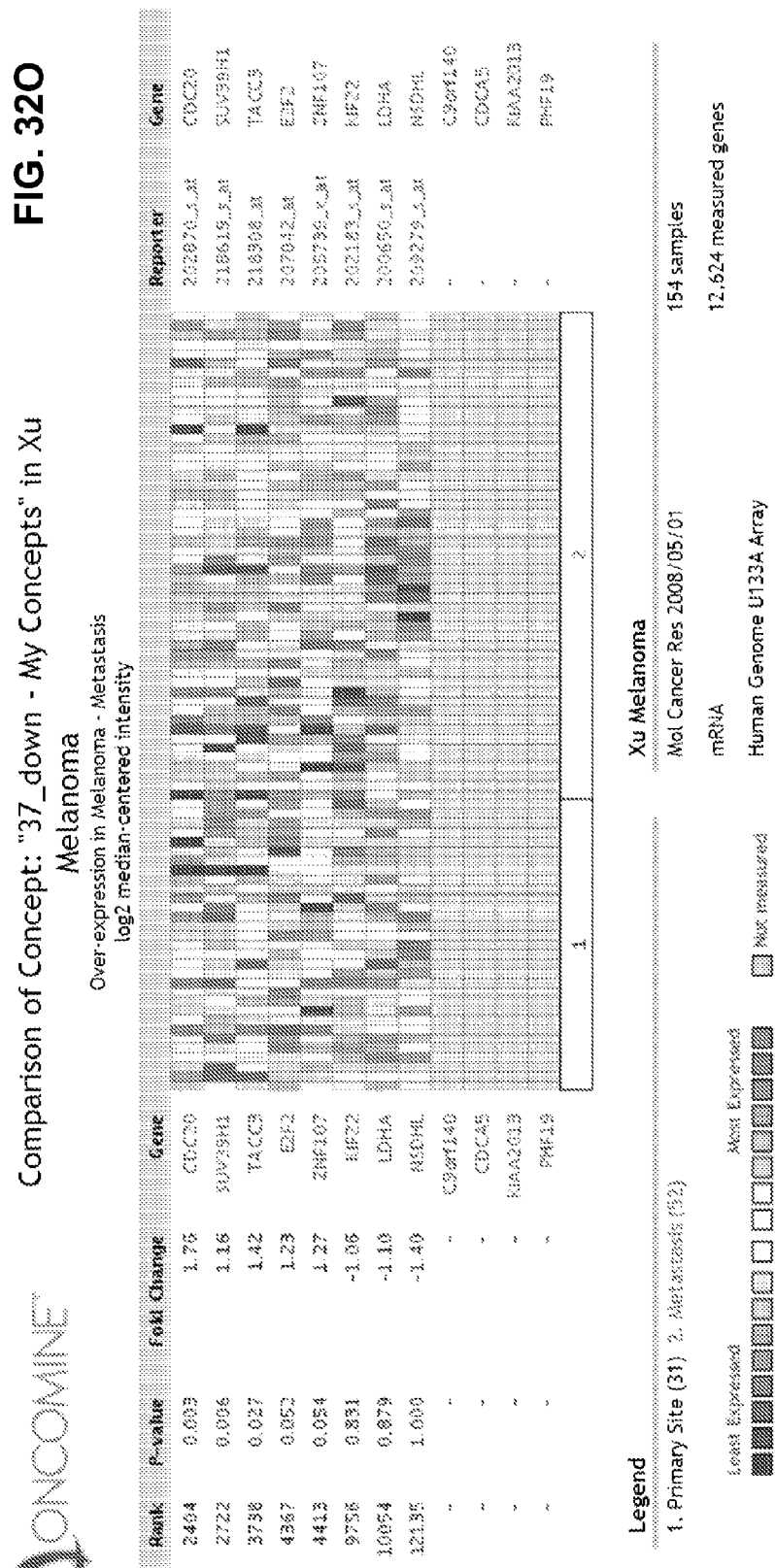
Figure 32P:
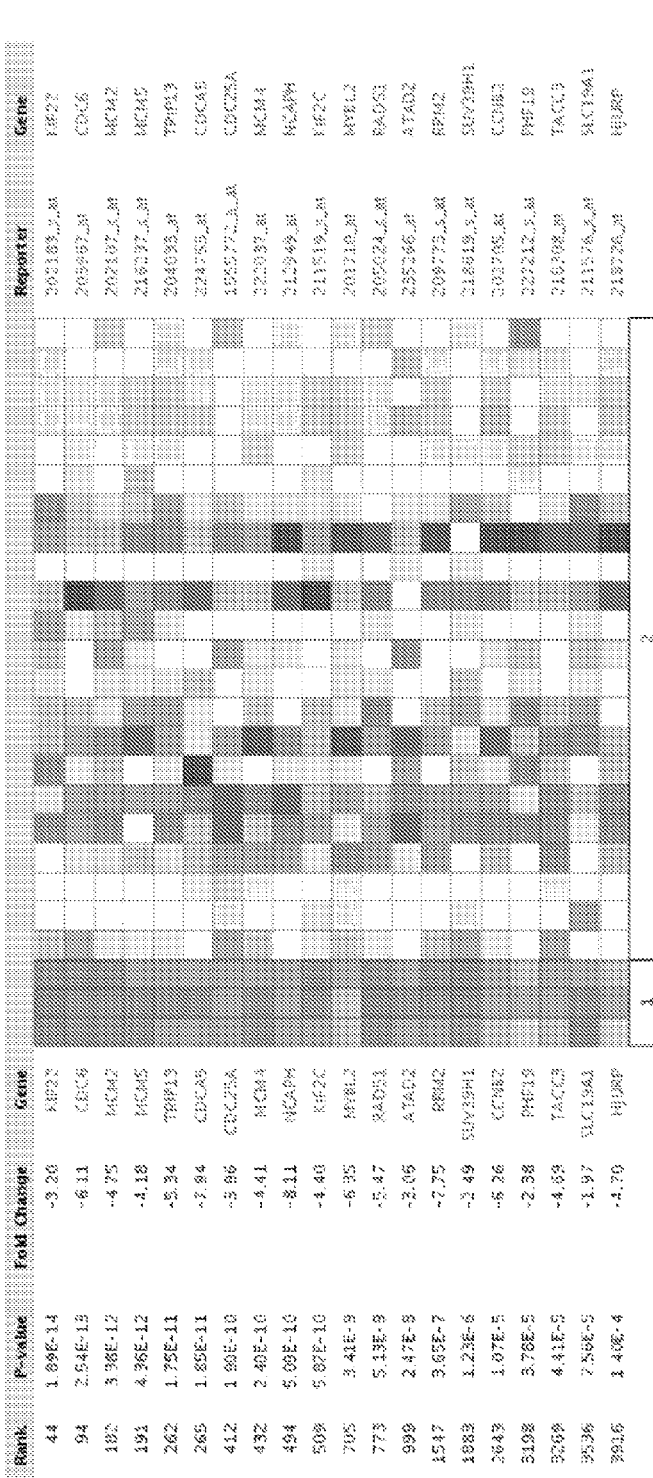
Figure 32Q:
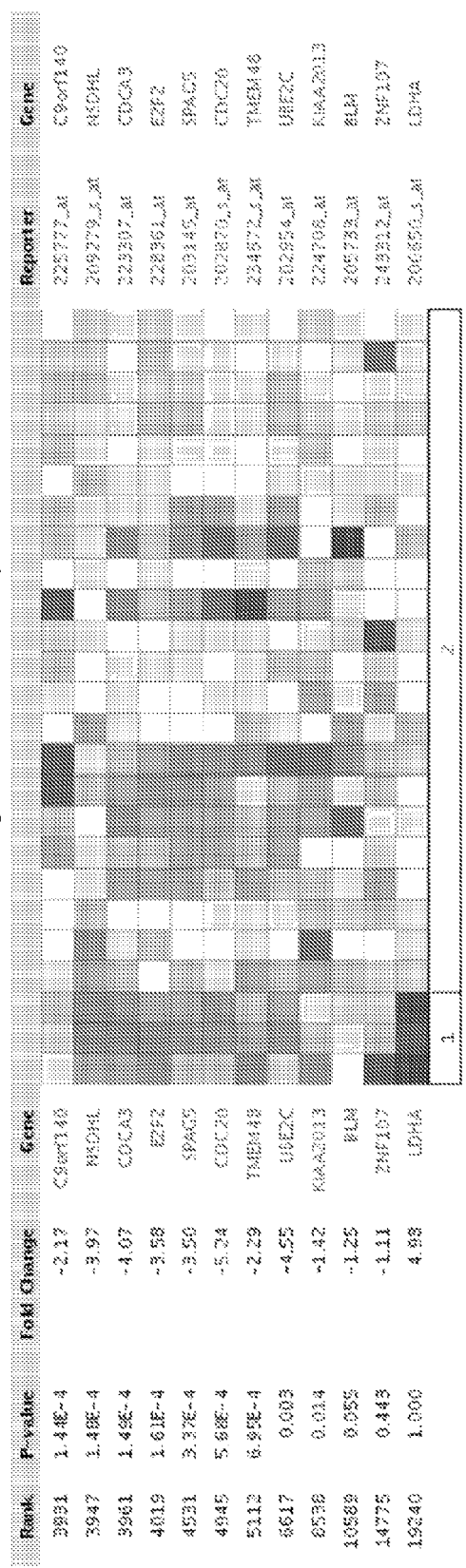
Figure 32R:
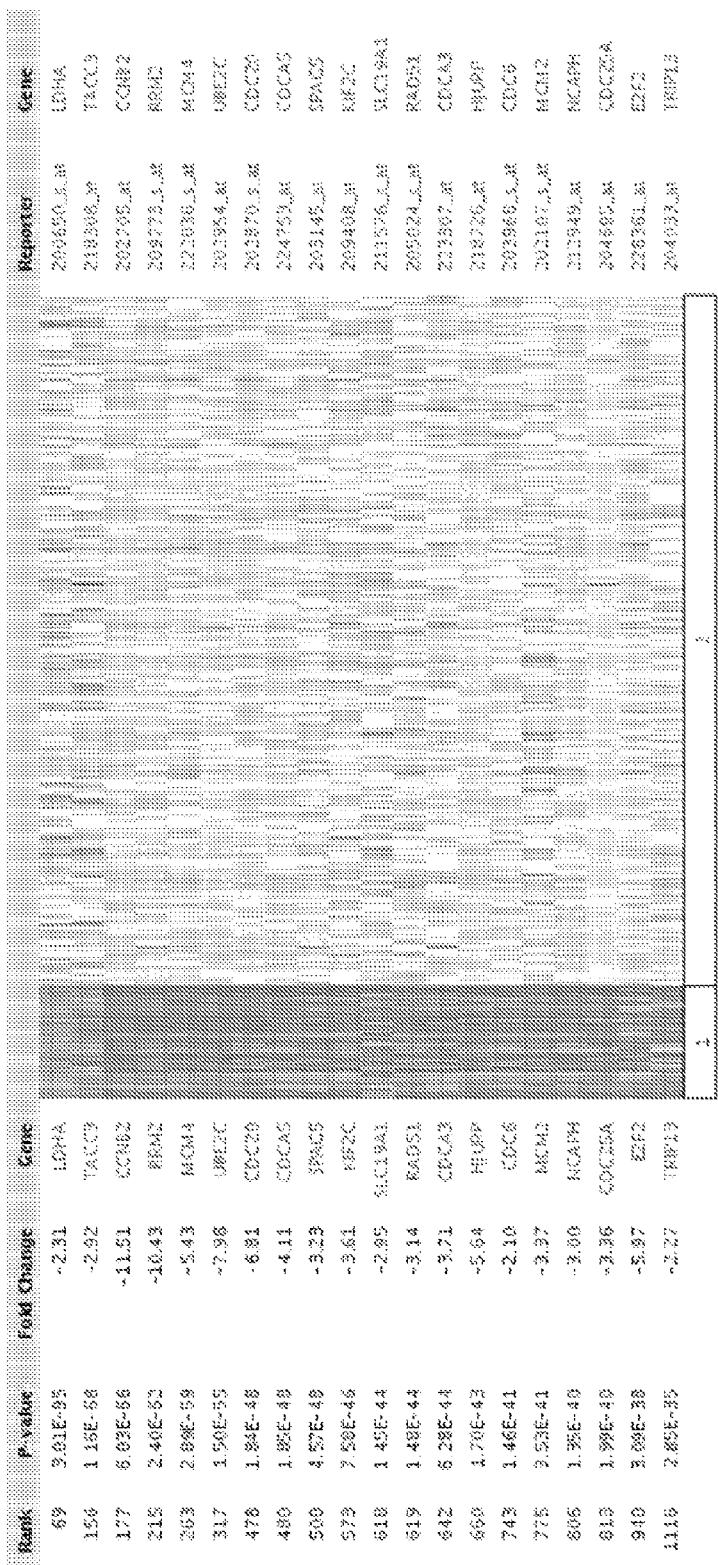
Figure 32T:
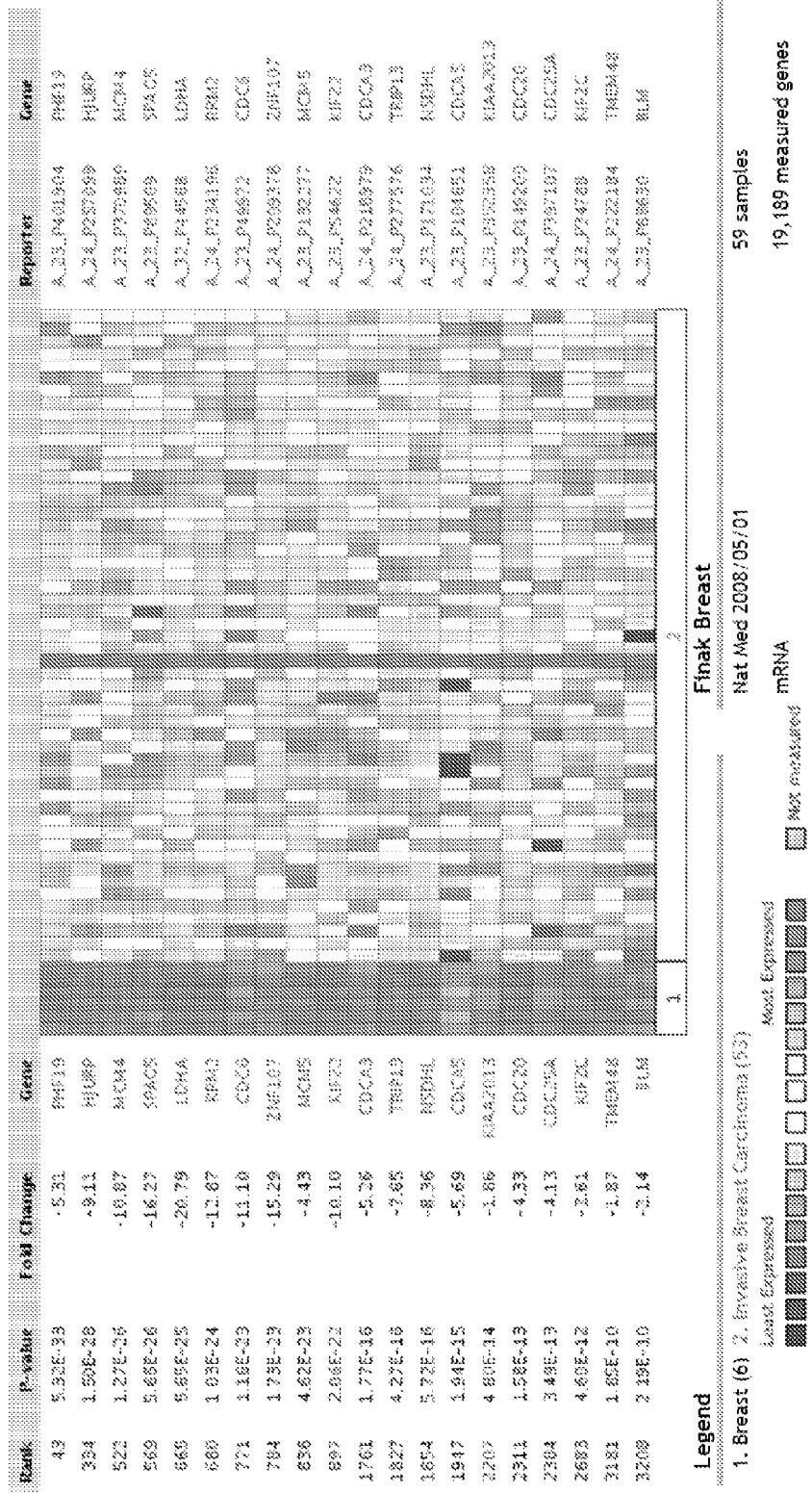
Figure 32U:
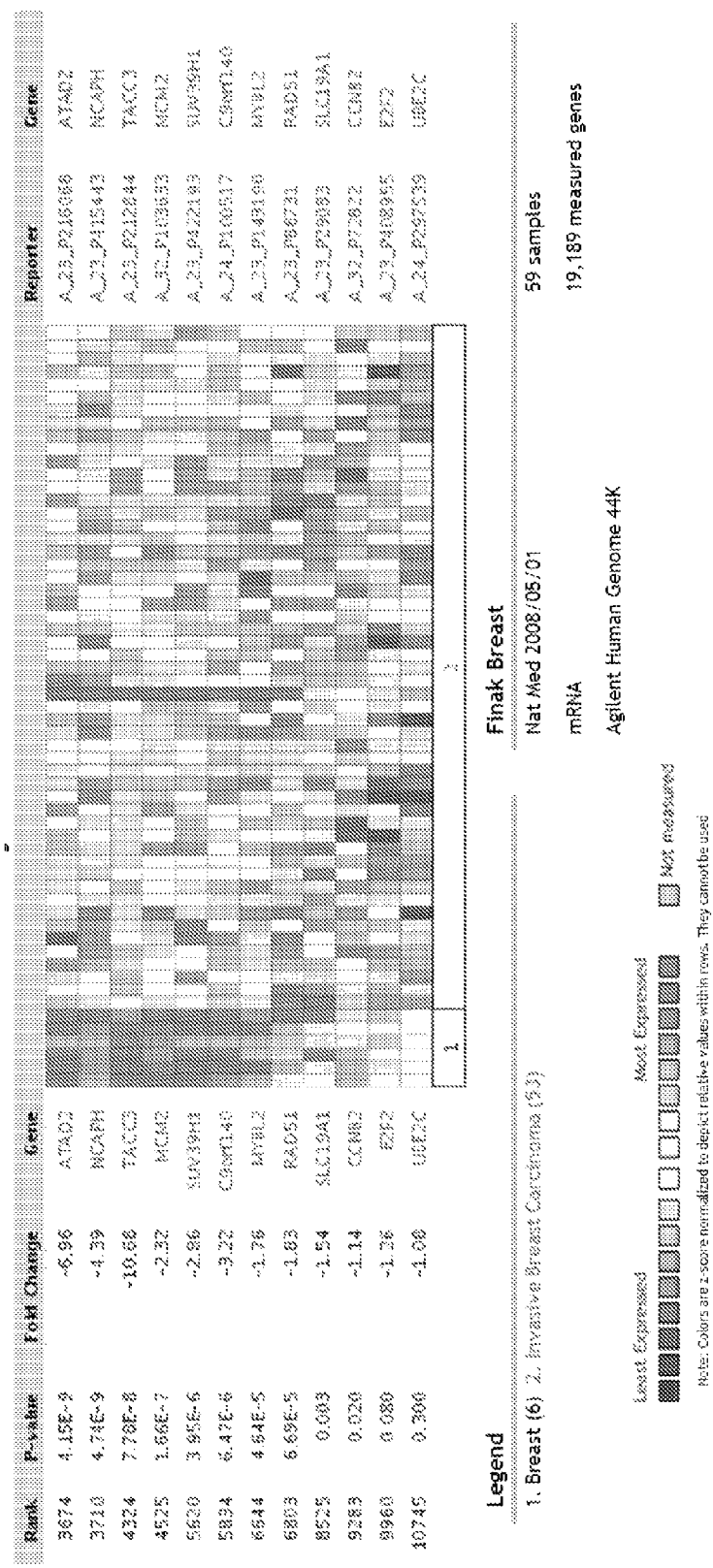
Figure 32V:
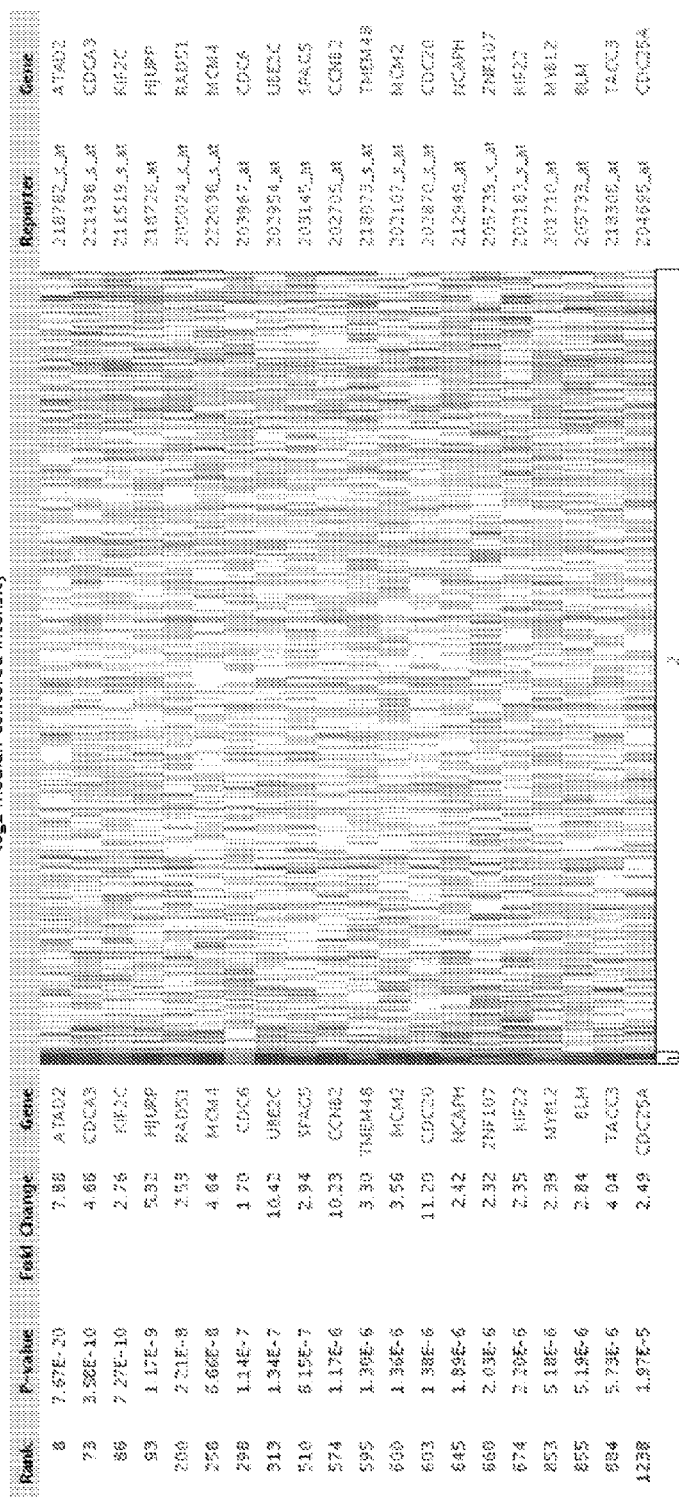
Figure 32W:
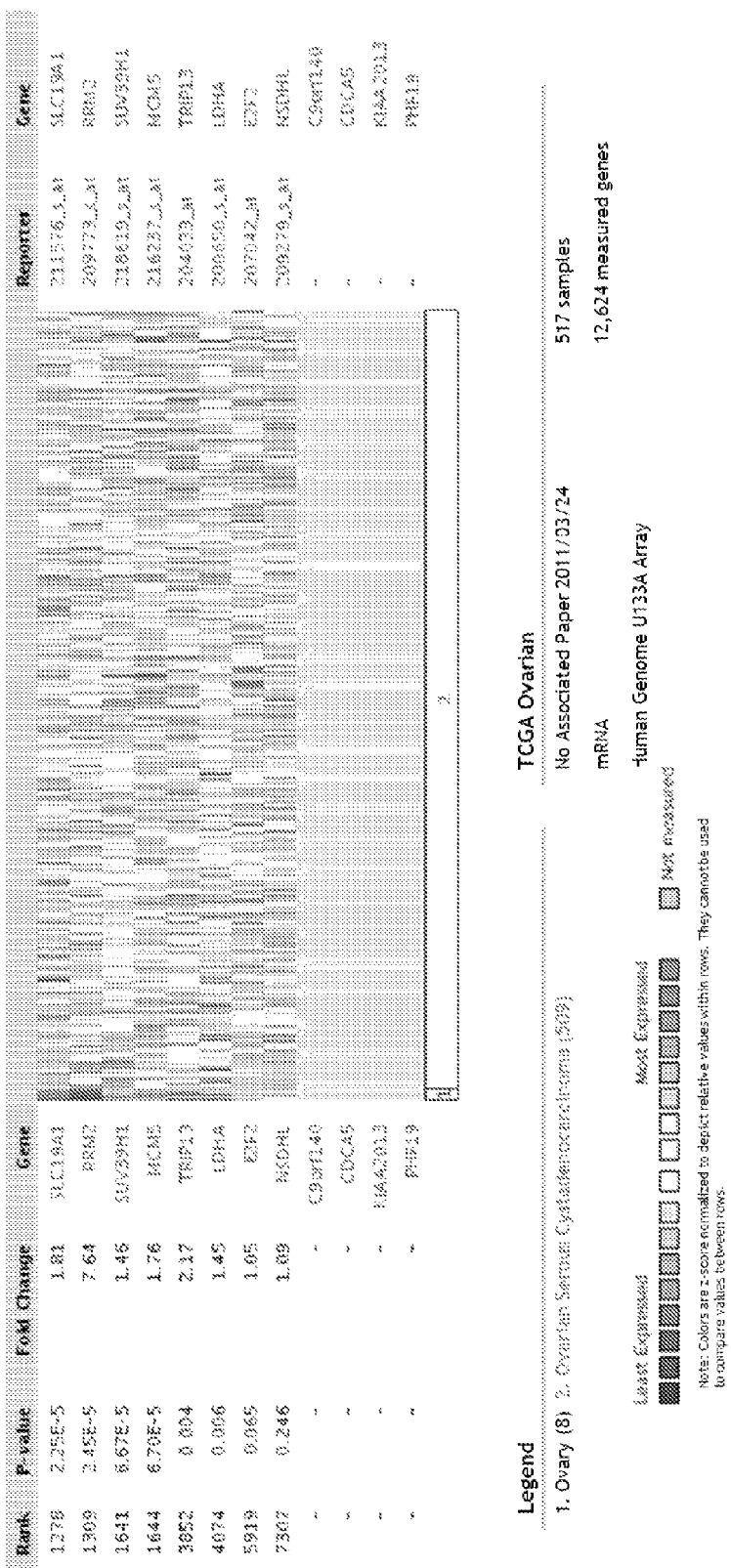
Figure 32X:
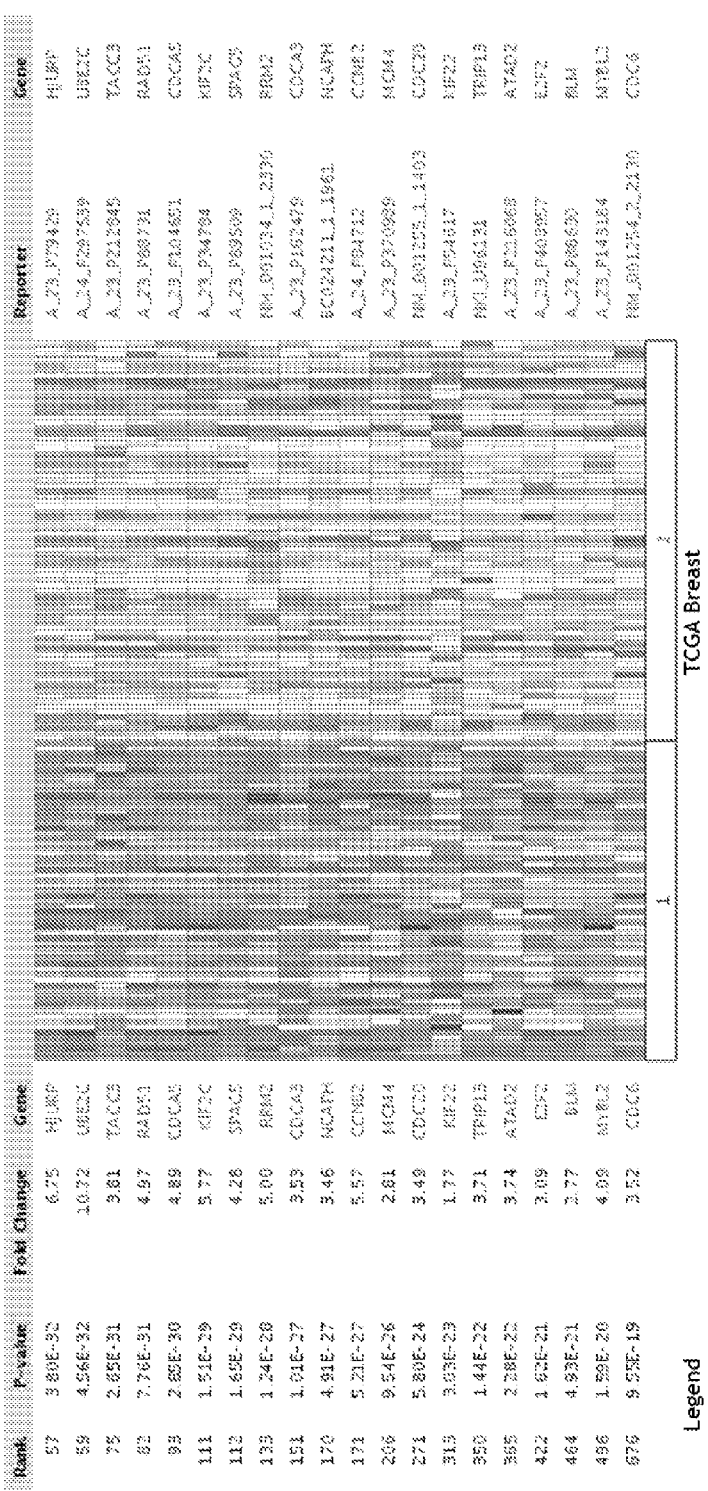
Figure 32Y:
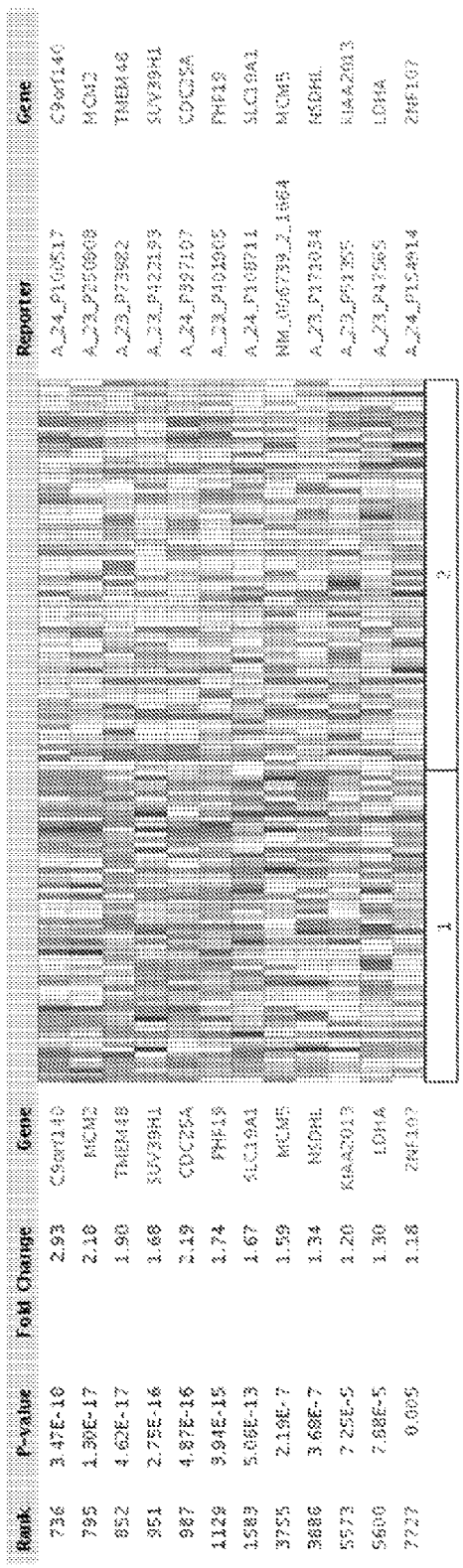
Figure 32Z:
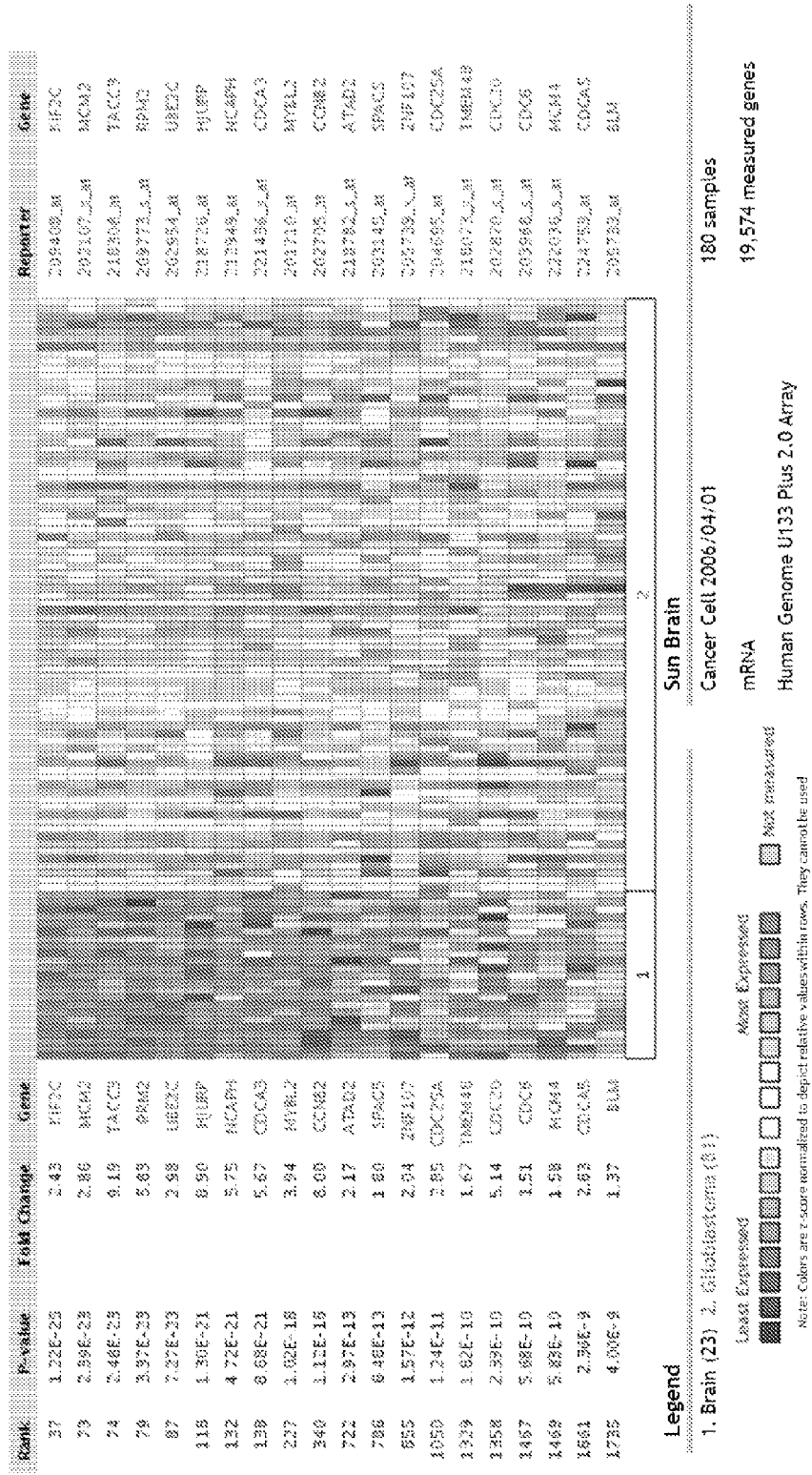
Figure 32A:
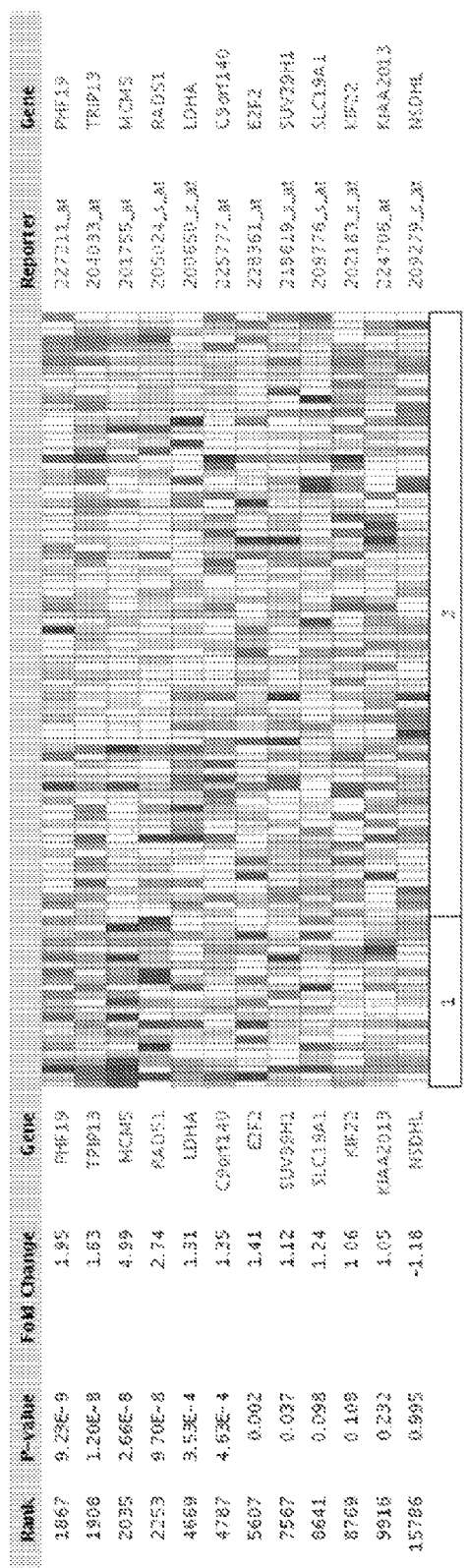
Figure 32B:
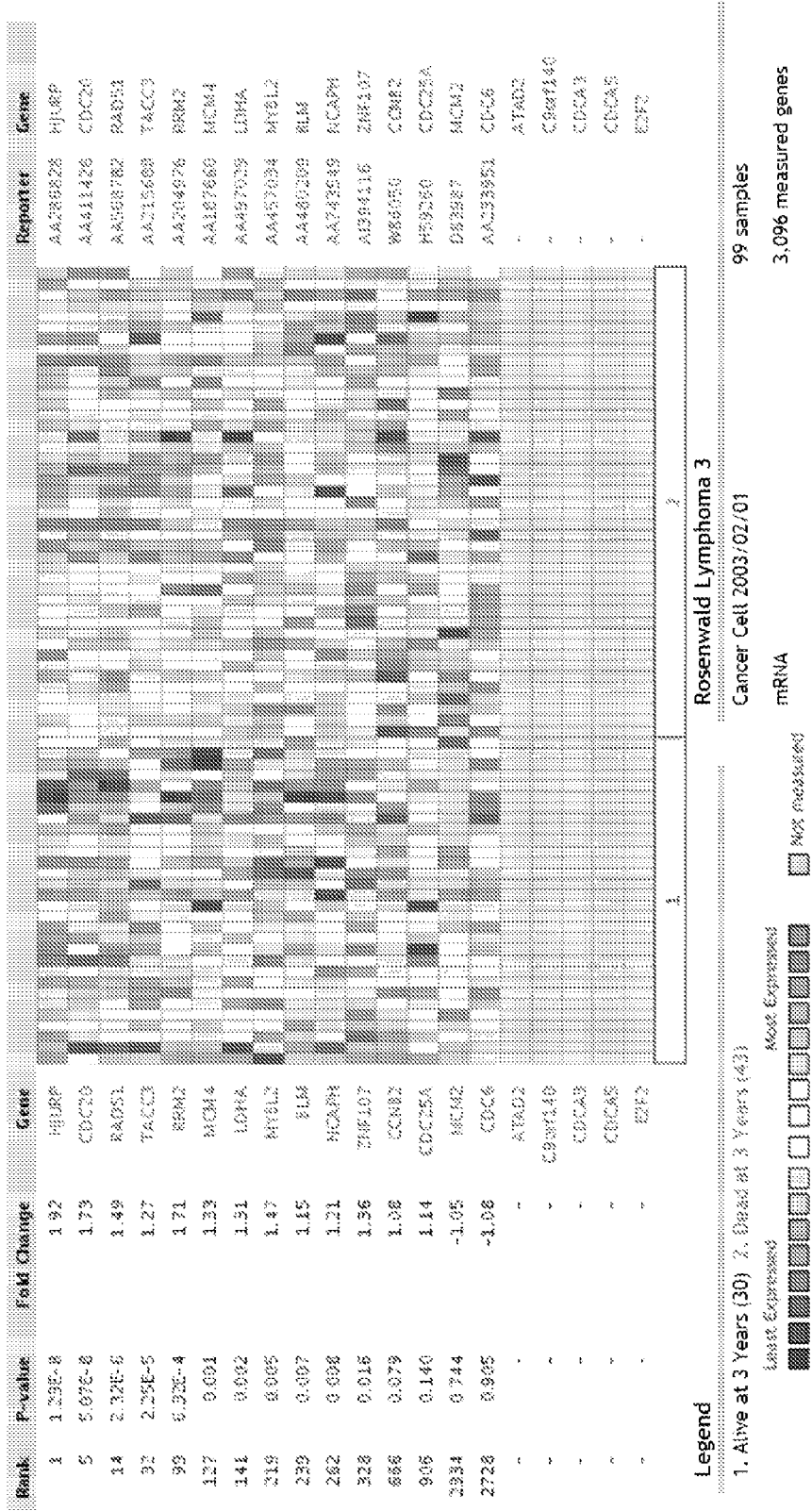

Using the Oncomine gene expression analysis tool, a concept is an aspect of biology represented by a molecular signature. As shown in Table 8, 32 out of 33 genes down-regulated in the 37-Blue module gene expression signature were entered into Oncomine as a concept signature and associated concepts were identified using the default parameters for significant overlap with other signatures (odds ratio>=2, p-value<=1e-4). The particular analysis performed, and gene signature identified is listed on FIGS. 32A-BB. The analyses show that there are many cancer types and specific histological subtypes showing activation of the predictor signature and also involvement in poor outcome (over-expression) when a survival association is observed.

Figure 33:
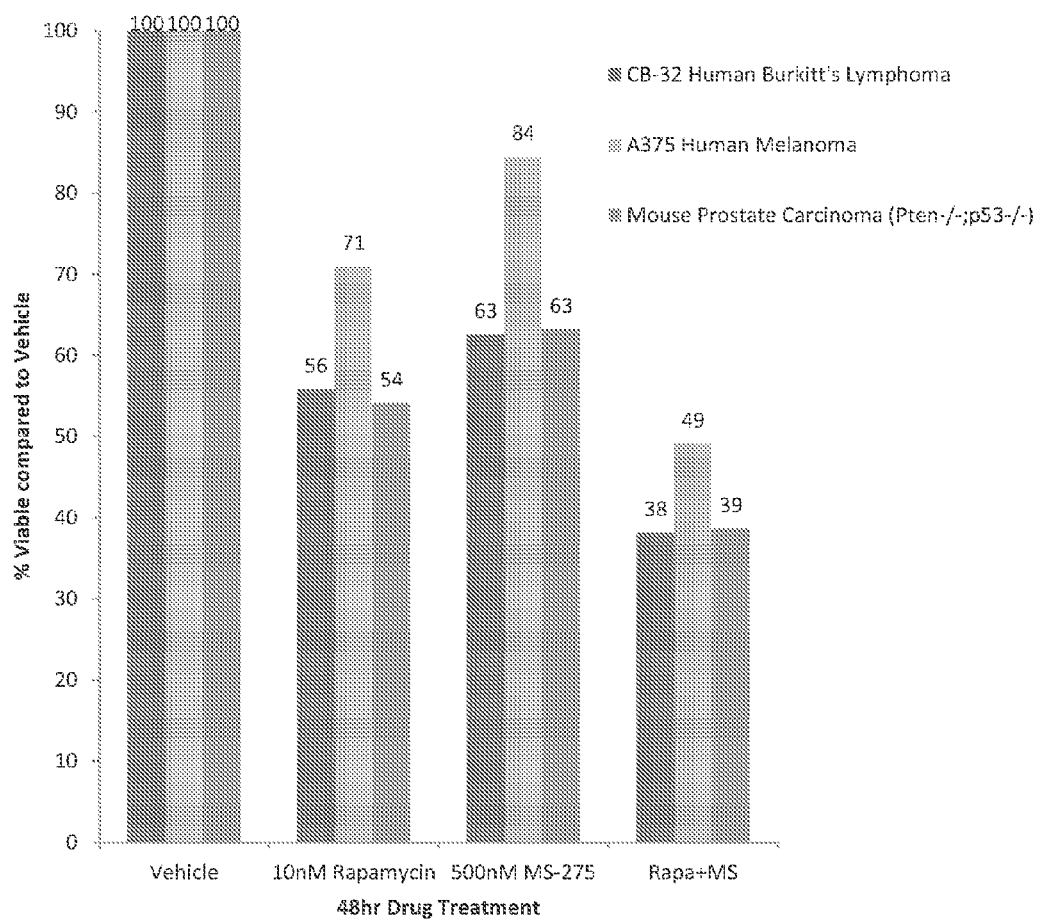
FIG. 33. Human cell lines for Burkitt's lymphoma and melanoma, and a mouse prostate cancer cell line respond to the drug combination in a synergistic fashion with respect to cell proliferation.
Figure 34:
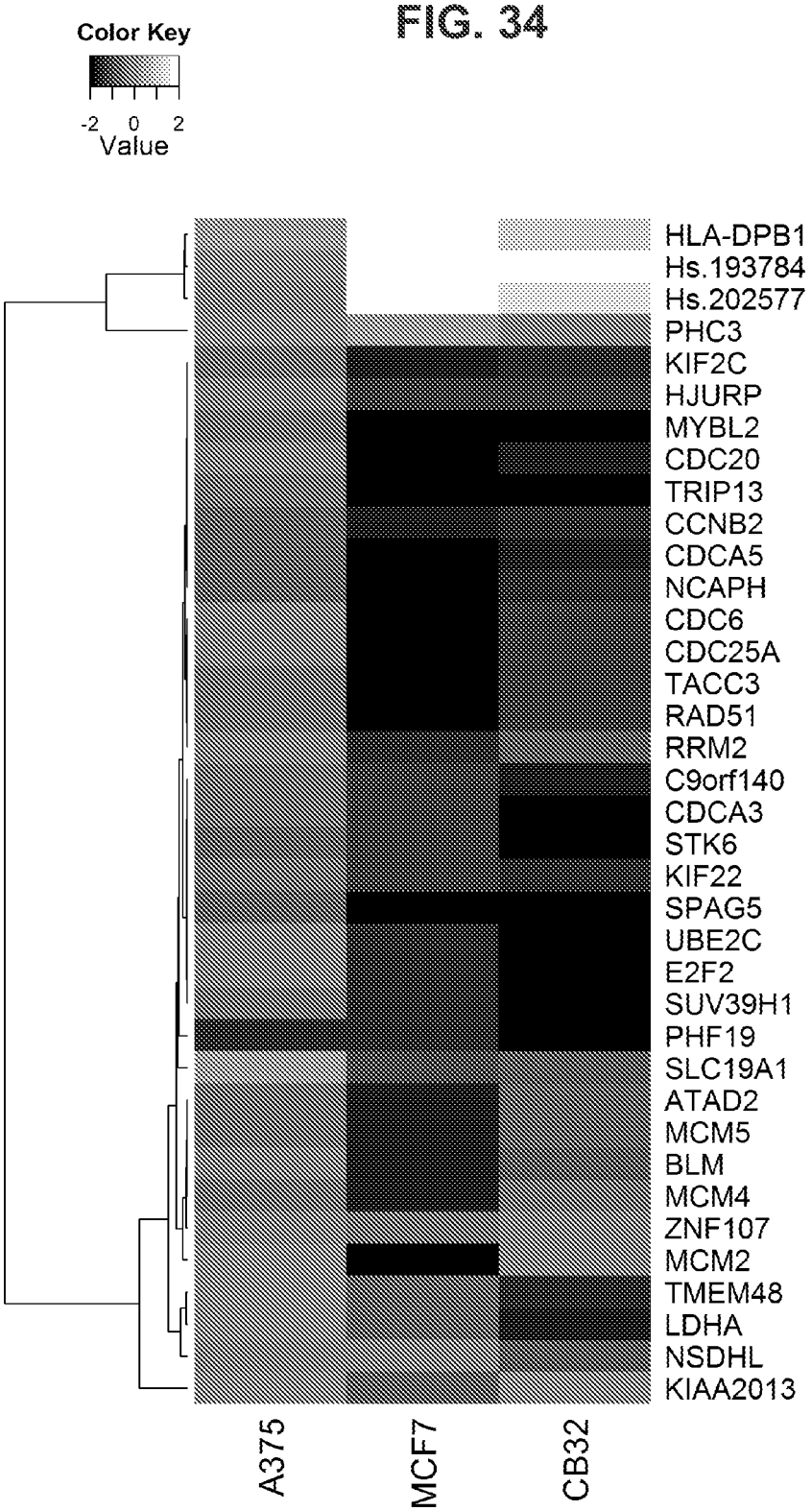
FIG. 34. is a heatmap showing log 2 expression fold change of the 37 survival-associated, cooperatively affected genes in Burkitt's lymphoma, human melanoma and a mouse prostate cancer cell line as detected by the Nanostring platform. Log 2 expression fold change is shown for single agent Rapamycin, MS-275, and panobinostat (a pan-HDAC inhibitor), as well as the combination of Rapamycin/MS-275, and Rapamycin/panobinostat.
Figure 35:
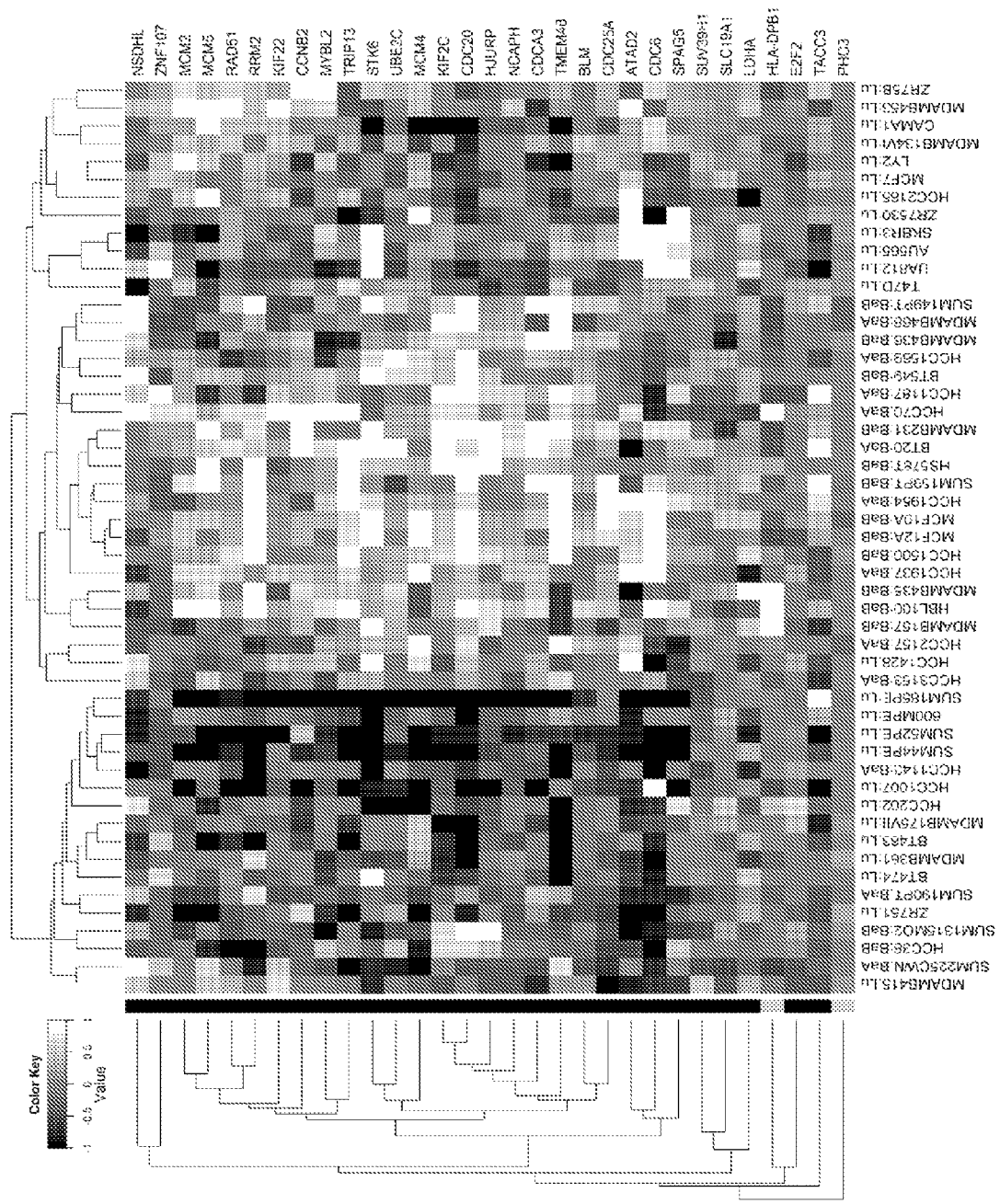
FIG. 35 is a heatmap illustrating the mean centered expression of the 37 genes (cooperative survival classifier) in a panel of untreated Human Breast Cancer cell lines. This heatmap demonstrates that there are a number of human breast cancer cell lines that are likely to respond to the drug combination.
Figure 36A:
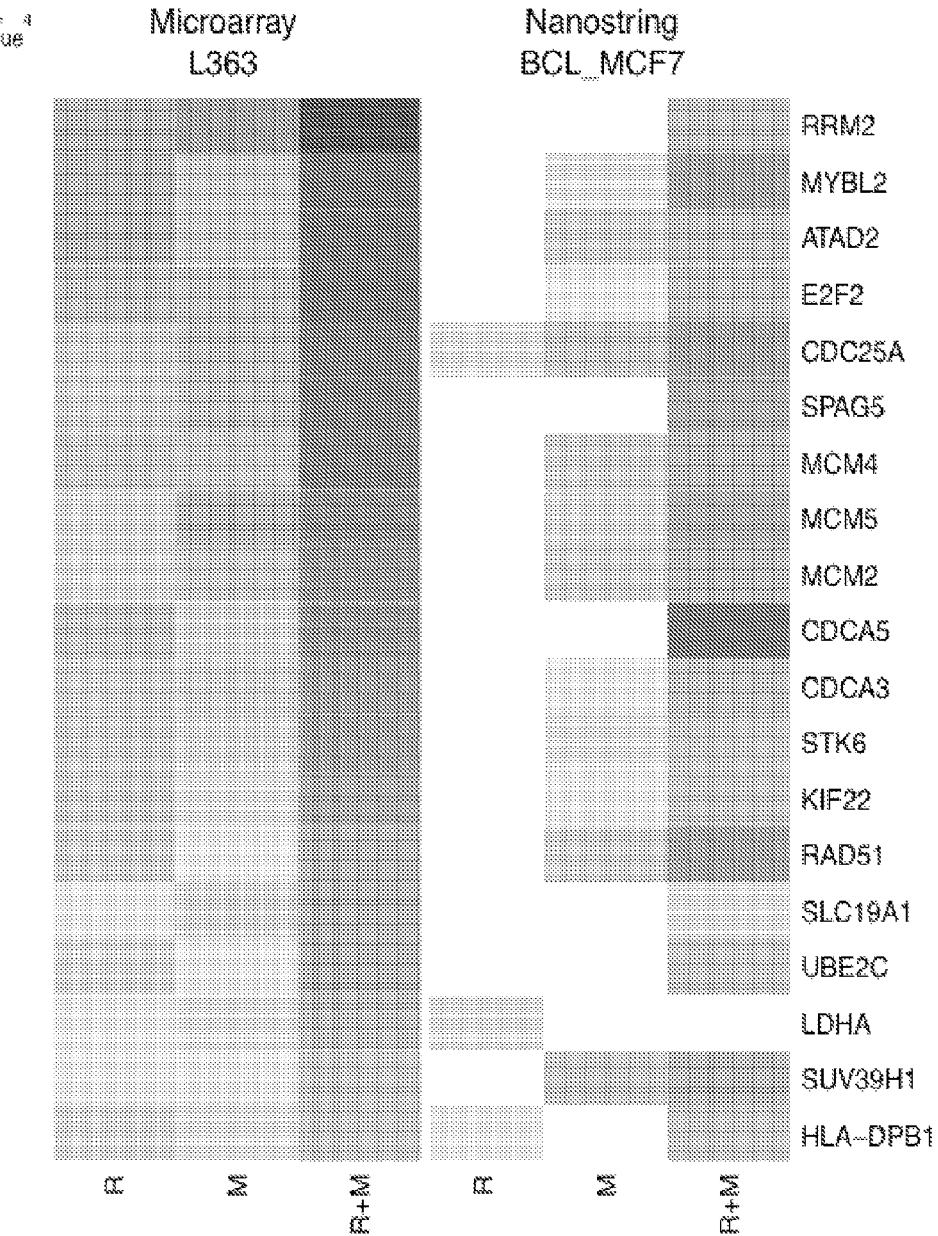
FIGS. 36A-36C are a series of heatmaps showing log 2 expression fold change of the survival-associated, 37-gene mTORi/HDACi signature in the human breast cancer cell lines (A) MCF-7, (B) MD-MBA-231, and (C) MD-MBA-468 as detected by the Nanostring® platform. Log 2 expression fold change is shown for single agent Rapamycin (10 nM), MS-275 (100 nM), as well as the combination of Rapamycin/MS-275 (10 nM/100 nM).
Figure 36B:
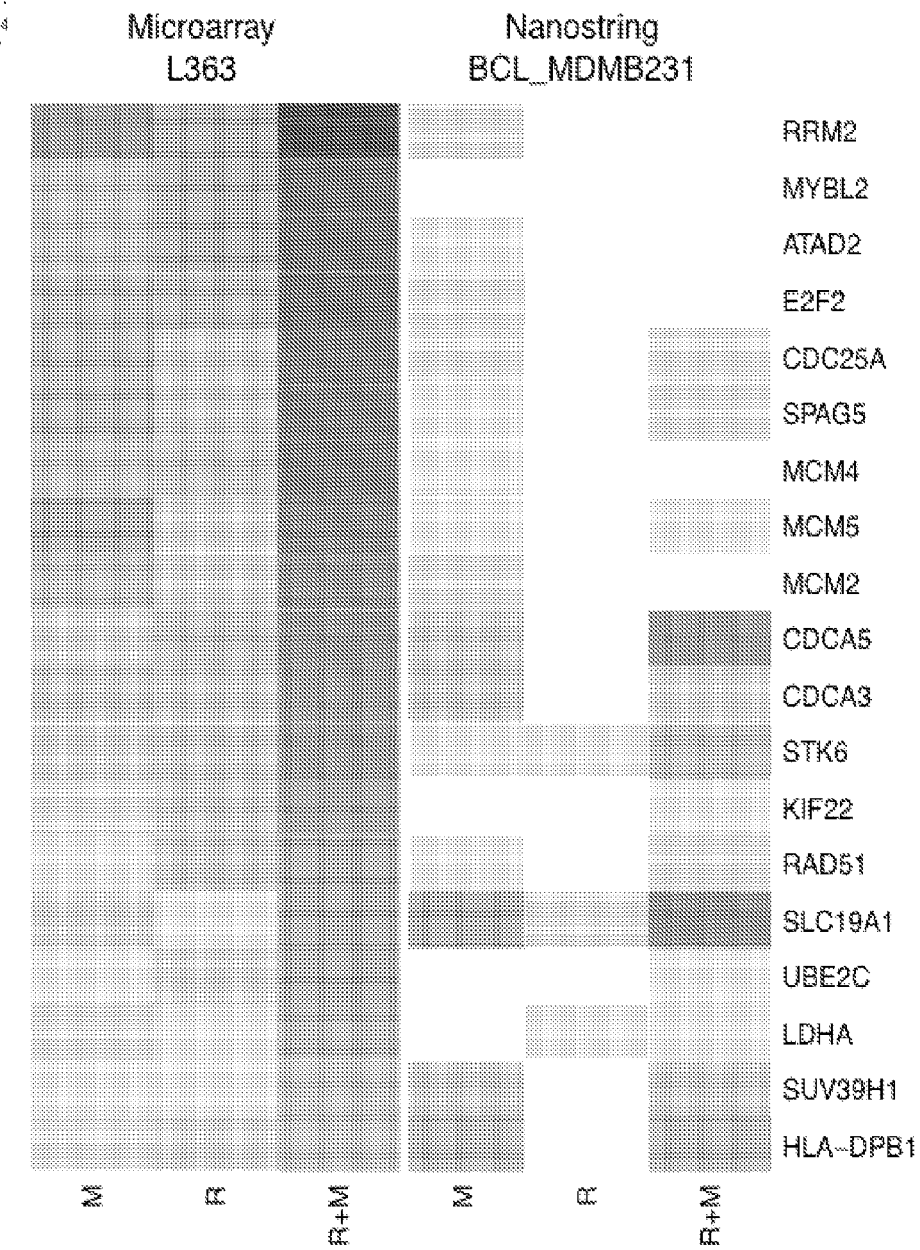
Figure 36C:
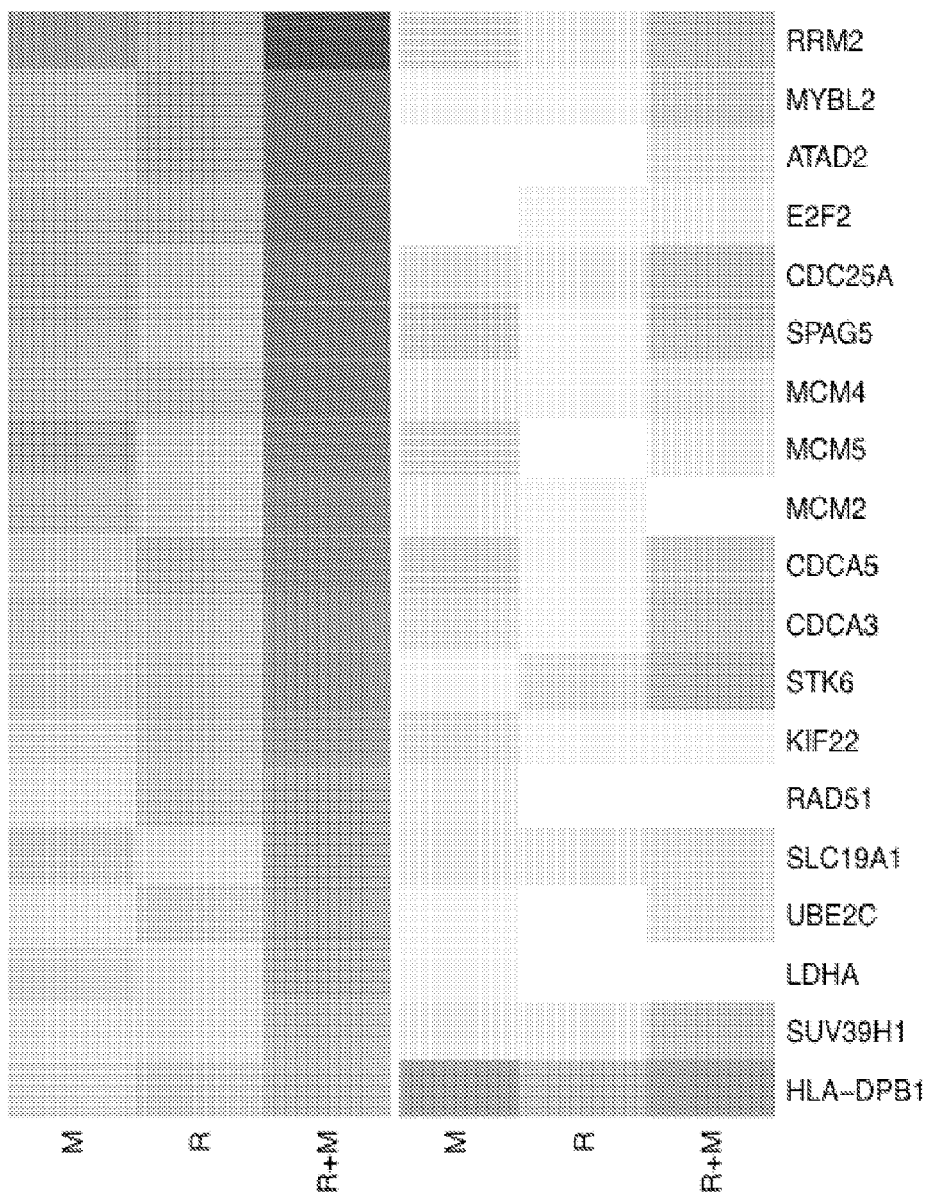

In addition to human MM cell lines, other cell lines from other tumor types were found to be sensitive to combined mTORi/HDACi treatment including human mantle cell lymphoma, human metastatic melanoma, human Burkitt's lymphoma, and a mouse model of prostate cancer representing aggressive, castration-resistant disease (FIGS. 1, 33). The change of the 37-gene classifier was also validated by Nanostring® assay in mTORi/HDACi treated human cell lines from breast cancer (MCF7), Burkitt's lymphoma (CB32), and melanoma (A375) tumor types (FIG. 34). A heatmap showing the mean centered gene expression of the 37-gene classifier in a large panel of human breast cancer cell lines is shown in FIG. 35. Cell lines representing luminal and basal subtypes of breast cancer are shown. Based on the clustering of cell lines related to expression of the mTORi/HDACi classifier genes, it appears unlikely that known molecular subtype classifiers could substitute in predicting likely benefit from treatment with mTORi/HDACi. The synergistic activity of the combination on the classifier genes in three different human breast cancer cell lines is shown in FIGS. 36A-36C.

Example 5

Evaluation of Gene Expression Signature to Predict Sensitivity to mTORi/HDACi Combination Therapy This example describes methods for evaluating a gene expression signature including expression of at least 6 of the 37 genes listed as Blue module genes in Table 6 and Table 7 for predicting sensitivity of a multiple myeloma neoplasm to mTORi/HDACi combination therapy. A panel of biological samples from subjects having a multiple myeloma neoplasm is assembled prior to treatment of the subjects with mTORi/HDACi combination therapy.

The multiple myeloma neoplasm samples, and in some instances adjacent non-neoplasm samples, are obtained from the subjects. Approximately 1-100 μg of tissue is obtained for each sample type, for example, a bone marrow biopsy or aspirate. RNA and/or protein is isolated from the neoplasm and non-neoplasm tissues using routine methods (for example using a commercial kit).

The expression level of at least six (such as all 37) of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 is determined by microarray analysis, Nanostring analysis or real-time quantitative PCR (or another equivalent method). The relative expression level of the at least six (such as all 37) of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 in the neoplasm sample is compared to a control (e.g., RNA isolated from adjacent non-neoplasm tissue from the subject and/or a reference value obtained from gene expression levels in a set of neoplasms of the same type with known outcome). Based on the increase or decrease in expression level of each of the at least six (such as all 37) genes, an aggregate increase or decrease of the gene expression signature (encompassing the at least 6 genes, such as all 37 genes) compared to the control is calculated.

After obtaining the neoplasm sample, the subjects are administered mTORi/HDACi combination therapy. For example the HDACi can be LBH589 or MS-275 and the mTORi can be RAD001 (everolimus) or Rapamycin. For example, the subjects can be orally administered 1, 5, 10, 20, 30, 40, 50, 60, 70, 80, 90 or 100 mg/day LBH589 (Panobinostat), or more, in combination with 0.5, 1, 2, 3, 4, 5, 6, 7, 8, 9 or 10 mg/day RAD001 (everolimus). In some example, the subject is administered the HDACi (e.g., LBH589) on days 1, 3, 5, 15, 17 and 19 of a 28 day cycle and the mTORi (e.g., RAD001) every day of the 28 day cycle. The treatment outcome for each subject treated with the mTORi/HDACi combination therapy is scored according to known methods (e.g., survival time or progression-free survival time) and the outcome of each subject is correlated with the expression level of the 37 genes and/or the aggregate increase or decrease of the gene expression signature. A positive correlation between the expression level of the 37 genes or expression of the gene expression signature prior to mTORi/HDACi treatment and improved outcome of the subject (e.g., increased survival or increased progression free survival) indicates that the subject is sensitive to mTORi/HDACi combination therapy.

Example 6

Determining Sensitivity of a Neoplasm to mTORi/HDACi Combination Therapy

This example describes particular methods that can be used to determine whether a neoplasm is or is likely to be sensitive to mTORi/HDACi combination therapy. One skilled in the art will appreciate that methods that deviate from these specific methods can also be used to successfully determine sensitivity of a neoplasm to mTORi/HDACi combination therapy.

A neoplasm sample, and in some instances adjacent non-neoplasm sample, is obtained from the subject. Approximately 1-100 µg of tissue is obtained for each sample type, for example using a fine needle aspirate. RNA and/or protein is isolated from the neoplasm and non-neoplasm tissues using routine methods (for example using a commercial kit).

The sensitivity of a neoplasm (for example, a multiple myeloma neoplasm) to mTORi/HDACi combination therapy is determined by detecting in a neoplasm sample obtained from a subject expression levels of at least six (such as all 37) of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 by microarray analysis, Nanostring analysis or real-time quantitative PCR (or equivalent method). The relative expression level of the at least six (such as all 37) of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107 in the neoplasm sample is compared to a control (e.g., RNA isolated from adjacent non-neoplasm tissue from the subject and/or a reference value obtained from gene expression levels in a set of neoplasms of the same type with known outcome). An increase in the expression level of one or more of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in the expression level of one or more of Hs.193784, Hs.202577, HLA-DPB1, and PHC3 in the neoplasm sample relative to the control (such as an increase or decrease of at least about 1-fold, for example, at least about 1.5-fold, about 2-fold, about 2.5-fold, about 3-fold, about 4-fold, about 5-fold, about 7-fold or about 10-fold) or an increase of the overall gene expression signature as compared to the reference value indicates that the neoplasm is sensitive to mTORi/HDACi combination therapy. The subject is selected for mTORi/HDACi combination therapy and can be administered one or more appropriate mTORi/HDACi combination therapy. Methods and therapeutic dosages of such therapies are known to those skilled in the art, and can be determined by a skilled clinician.

In another example, the relative expression of proteins of the gene signature is determined at the protein level by methods known to those of ordinary skill in the art, such as protein microarray, Western blot, immunohistochemistry or immunoassay techniques. Total protein is isolated from the neoplasm sample and control (non-neoplasm) sample and compared using any suitable technique. An increase in protein expression level of one or more of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in protein expression level of one or more of Hs.193784, Hs.202577, HLA-DPB1, and PHC3 in the neoplasm sample relative to the control (such as an increase or decrease of at least about 1-fold, for example, at least about 1.5-fold, about 2-fold, about 2.5-fold, about 3-fold, about 4-fold, about 5-fold, about 7-fold or about 10-fold) or an increase of the overall protein expression signature as compared to the reference value indicates that the neoplasm is sensitive to mTORi/HDACi combination therapy. The subject is selected for mTORi/HDACi combination therapy and can be administered one or more appropriate mTORi/HDACi combination therapy. Methods and therapeutic dosages of such therapies are known to those skilled in the art, and can be determined by a skilled clinician.

Example 7

Determination of Clinically-Beneficial Response to Treatment with mTORi/HDACi

This example describes particular methods that can be used to determine if a neoplasm in a subject is likely to respond to HDACi/mTORi therapy after therapy has been initiated, but before a physical indication of response (for example, reduction of tumor burden) could be detected. One skilled in the art will appreciate that methods that deviate from these specific methods can also be used to successfully determine the responsiveness of the neoplasm to the HDACi/mTORi therapy.

A neoplasm sample, and in some instances adjacent non-neoplasm sample, is obtained from the subject before and after initiation of HDACi/mTORi therapy treatment (for example, 8 hours, 12 hours, 1 day, 2 days, 3 days, 4 days, 5 days, six days, 1 week, 2 weeks, 3 weeks or 4 weeks following initiation of treatment). Approximately 1-100 μg of tissue is obtained for each sample type, for example using a fine needle aspirate. RNA and/or protein is isolated from the neoplasm and non-neoplasm tissues using routine methods (for example using a commercial kit).

The sensitivity of the neoplasm to HDACi/mTORi therapy (for example, a multiple myeloma neoplasm) is determined by detecting expression levels of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, ZNF107, Hs.193784, Hs.202577, HLA-DPB1, and PHC3 in the both the sample obtained from the subject before and after initiation of HDACi/mTORi therapy by microarray analysis. The normalized expression level of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, ZNF107, Hs.193784, Hs.202577, HLA-DPB1, and PHC3 in the neoplasm sample taken after initiation of HDACi/mTORi therapy is compared to a control (e.g., the normalized expression level of these genes in the neoplasm sample taken prior to HDACi/mTORi therapy).

An increase in expression of one or more of (such as all of) ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in protein expression level of one or more of (such as all of) Hs.193784, Hs.202577, KIAA2013, HLA-DPB1, and PHC3 in the neoplasm sample relative to the control (such as an increase or decrease of at least about 1-fold, for example, at least about 1.5-fold, about 2-fold, about 2.5-fold, about 3-fold, about 4-fold, about 5-fold, about 7-fold or about 10-fold) or an increase of the overall gene expression signature as compared to the control indicates that the neoplasm is responsive to the HDACi/mTORi therapy.

In another example, the relative expression of proteins of the gene signature is determined at the protein level by methods known to those of ordinary skill in the art, such as protein microarray, Western blot, or immunoassay techniques. Total protein is isolated from the neoplasm sample and control (non-neoplasm) sample and compared using any suitable technique. An increase in protein expression of one or more of ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in protein expression level of one or more of Hs.193784, Hs.202577, KIAA2013, HLA-DPB1, and PHC3 in the neoplasm sample relative to the control (such as an increase or decrease of at least about 1-fold, for example, at least about 1.5-fold, about 2-fold, about 2.5-fold, about 3-fold, about 4-fold, about 5-fold, about 7-fold or about 10-fold) or an increase of the overall protein expression signature as compared to the reference value indicates a poor prognosis, such as a decrease in the likelihood of survival, progression free survival and/or metastasis-free survival, for the subject.

Example 8

Determination of Synergistic Response to Treatment with mTORi/HDACi

Since patients will be treated with the combination simultaneously, the 124-gene signature including gene expression upregulation and downregulation as listed in column (2) of Table 6 will allow for detection of synergy of mTORi/HDACi therapy. This will allow sparing patients who are only responding to one arm of the therapy from unbeneficial treatment with the other drug (thus avoiding side effects of that drug). In one example, a neoplasm highly sensitive to the mTOR inhibitor, yet insensitive to the HDAC inhibitor may be detected as having a favorable molecular response with the 37-gene classifier. Yet by analyzing the expression change after initial combination treatment with the 124 gene classifier, one could detect a lack of favorable change in the seventy-two prognostically-associated genes identified as contributed solely by the HDACi. With the additional information provided by the 124-gene mTORi/HDACi classifier in this example, a clinician may continue treatment only with the mTORi, thus avoiding exposing the patient who is unlikely to receive any benefit from the HDACi to the side-effects and associated risk of continued use of the HDACi therapy.

Example 9

Determining Prognosis of a Subject with a Neoplasm

This example describes particular methods that can be used to determine a prognosis for a subject diagnosed with a neoplasm. One skilled in the art will appreciate that methods that deviate from these specific methods can also be used to successfully determine the prognosis of a subject with a neoplasm.

A neoplasm sample, and in some instances adjacent non-neoplasm sample, is obtained from the subject. Approximately 1-100 μg of tissue is obtained for each sample type, for example using a fine needle aspirate. RNA and/or protein is isolated from the neoplasm and non-neoplasm tissues using routine methods (for example using a commercial kit).

The prognosis of a neoplasm (for example, a multiple myeloma neoplasm) is determined by detecting expression levels of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, ZNF107, Hs.193784, Hs.202577, HLA-DPB1, and PHC3 in a neoplasm sample obtained from a subject by microarray analysis, Nanostring or real-time quantitative PCR. The relative expression level of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, ZNF107, Hs.193784, Hs.202577, HLA-DPB1, and PHC3 in the neoplasm sample is compared to a control (e.g., RNA isolated from adjacent non-neoplasm tissue from the subject and/or a reference value obtained from gene expression levels in a set of neoplasms of the same type with known outcome).

An increase in expression of one or more of ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in protein expression level of one or more of Hs.193784, Hs.202577, KIAA2013, HLA-DPB1, and PHC3 in the neoplasm sample relative to the control (such as an increase or decrease of at least about 1-fold, for example, at least about 1.5-fold, about 2-fold, about 2.5-fold, about 3-fold, about 4-fold, about 5-fold, about 7-fold or about 10-fold) or an increase of the overall gene expression signature as compared to the reference value indicates a poor prognosis, such as a decrease in the likelihood of survival, progression free survival and/or metastasis-free survival, for the subject.

In another example, the relative expression of proteins of the gene signature is determined at the protein level by methods known to those of ordinary skill in the art, such as protein microarray, Western blot, or immunoassay techniques. Total protein is isolated from the neoplasm sample and control (non-neoplasm) sample and compared using any suitable technique. An increase in protein expression of one or more of ATAD2, BLM, C9orf140, CCNB2, CDC20, CDC25A, CDC6, CDCA3, CDCA5, E2F2, HJURP, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107 and/or a decrease in protein expression level of one or more of Hs.193784, Hs.202577, KIAA2013, HLA-DPB1, and PHC3 in the neoplasm sample relative to the control (such as an increase or decrease of at least about 1-fold, for example, at least about 1.5-fold, about 2-fold, about 2.5-fold, about 3-fold, about 4-fold, about 5-fold, about 7-fold or about 10-fold) or an increase of the overall protein expression signature as compared to the reference value indicates a poor prognosis, such as a decrease in the likelihood of survival, progression free survival and/or metastasis-free survival, for the subject.

In view of the many possible embodiments to which the principles of the disclosed embodiments may be applied, it should be recognized that the illustrated embodiments are only preferred examples of the embodiments and should not be taken as limiting. Rather, the scope of the embodiments is defined by the following claims. We therefore claim all that comes within the scope and spirit of these claims.

TABLE 1

The Combination Index (CI) values indicate rapamycin and MS-275 drug synergy in 88% of MM cell lines tested.

| Cell line | Rapamycin (nM) | MS-275 (μM) | Dose Effect* | CI** |
|---|---|---|---|---|
| 1 KMS-12BM | 1 | 0.5 | 0.406 | 0.299 |
|  | 10 | 0.5 | 0.447 | 0.248 |
| 2 KMS18 | 1 | 0.5 | 0.219 | 0.083 |
|  | 10 | 0.5 | 0.273 | 0.155 |
| 3 L363 | 1 | 0.5 | 0.936 | 0.271 |
|  | 10 | 0.5 | 0.949 | 0.280 |
| 4 8226 | 1 | 0.5 | 0.146 | 0.710 |
|  | 10 | 0.5 | 0.293 | 0.5 |
| 5 FR-4 | 1 | 0.5 | 0.505 | 1.646 |
|  | 10 | 0.5 | 0.579 | 1.598 |
| 6 JK-6L | 1 | 0.5 | 0.776 | 0.495 |
|  | 10 | 0.5 | 0.836 | 0.479 |
| 7 ANBL-6 | 1 | 0.5 | 0.868 | 1.025 |
|  | 10 | 0.5 | 0.922 | 0.260 |
| 8 FLAM-76 | 1 | 0.5 | 0.831 | 0.660 |
|  | 10 | 0.5 | 0.864 | 0.570 |
| 9 XG-6 | 1 | 0.5 | 0.929 | 0.208 |
|  | 10 | 0.5 | 0.954 | 0.154 |
| 10 U266 | 1 | 0.5 | 0.618 | 0.139 |
|  | 10 | 0.5 | 0.661 | 0.240 |
| 11 OCI-MY5 | 1 | 0.5 | 0.694 | 1.4 |
|  | 10 | 0.5 | 0.719 | 5.09 |
| 12 LP-1 | 1 | 0.5 | 0.695 | 0.411 |
|  | 10 | 0.5 | 0.751 | 0.344 |
| 13 MM-M1 | 1 | 0.5 | 0.743 | 0.928 |
|  | 10 | 0.5 | 0.766 | 0.846 |
| 14 OCI-MY1 | 1 | 0.5 | 0.664 | 0.632 |
|  | 10 | 0.5 | 0.681 | 0.605 |
| 15 SKMM-1 | 1 | 0.5 | 0.358 | 0.628 |
|  | 10 | 0.5 | 0.473 | 0.543 |
| 16 SACHI | 1 | 0.5 | 0.609 | 0.548 |
|  | 10 | 0.5 | 0.635 | 0.557 |
| 17 EJM | 1 | 0.5 | 0.415 | 0.352 |
|  | 10 | 0.5 | 0.461 | 0.387 |
| 107403 (PCT) | 1.0 | 0.5 | 0.78 | 0.095 |
|  | 10.0 | 0.5 | 0.80 | 0.077 |
|  | 100.0 | 0.5 | 0.82 | 0.101 |
| MOPC265 (PCT) | 1.0 | 0.5 | 0.683 | 0.579 |
|  | 10.0 | 0.5 | 0.755 | 0.563 |
|  | 100.0 | 0.5 | 0.805 | 0.799 |
| MOPC460 (PCT) | 1.0 | 0.5 | 0.596 | 0.865 |
|  | 10.0 | 0.5 | 0.634 | 0.812 |
|  | 100.0 | 0.5 | 0.742 | 0.699 |

*The dose effect is the proportion of viable cells.
**CI <0.1 (very strong synergism);
CI = 0.1-0.3 (strong synergism);
CI = 0.3-0.85 (synergism);
CI = 0.85-0.9 (slightly synergism);
CI = 1 (additive).

TABLE 2

Functionally-related genes determined using gene ontology (GO) terms.

| GO | Rep. GO Term | # of Terms | P-Value | FDR (%) | Mean.kIN$_{sc}$ | Mean Fold Change | Hub Genes DOWN-regulated | Hub Genes UP-regulated | # of Hubs |
|---|---|---|---|---|---|---|---|---|---|
| | | | | | | Blue Module | | | |
| BP | DNA replication | 10 | 3.7e-10-0.0016 | 2.8e-06-3.8 | 0.58-0.66 | (-4.5)-(-2.93) | CDC25A, CDC25C, KIF22, MCM2, MCM4, RAD51, RBM14, RFC2, RRM2, TIMELESS | | 10\|21 |
| BP | cell cycle | 1 | 1.70E-18 | 6.60E-14 | 0.67 | (-3.66) | CCNB2, CDC25A, CDC25C, CDCA3, CDCA5, CIT, DBF4B, E2F2, ESPL1, FOXM1, HJURP, KIF22, KIF2C, MCM2, MKI67, NCAPH, PLK1, RAD51, SPAG5, SPC24, TIMELESS | | 21\|34 |
| BP | chromosome segregation | 1 | 0.00023 | 0.89 | 0.68 | (-3.55) | CDCA5, ESPL1, HJURP, NCAPH | | 4\|6 |
| BP | microtubule-based process | 1 | 0.00031 | 1.0 | 0.68 | (-3.25) | ESPL1, KIF22, KIF2C, SPAG5, TUBA1B, TUBA1C | | 6\|9 |
| BP | cell division | 1 | 1.30E-11 | 1.10E-07 | 0.69 | (-3.77) | CCNB2, CDC25A, CDC25C, CDCA3, CDCA5, CIT, ESPL1, NCAPH, PLK1, SPAG5, SPC24, TIMELESS | | 12\|18 |
| BP | antigen processing and presentation of peptide or polysaccharide antigen via MHC class II | 1 | 0.00017 | 0.69 | 0.71 | (+3.89) | | HLA-DMA, HLA-DPB1, HLA-DQB1, (HLA-DRB1, HLA-DRB4) | 4\|4 |
| BP | sister chromatid segregation | 25 | 1.4e-18-0.0025 | 1.1e-13-5 | 0.56-0.71 | (-3.72)-(-2.74) | CCNB2, CDC25A, CDC25C, CDCA3, CDCA5, CIT, E2F2, ESPL1, HJURP, KIF22, KIF2C, MCM2, MKI67, NCAPH, PLK1, RAD51, RBM14, RRM2, SCARB1, SPAG5, SPC24, TIMELESS, TUBA1B, TUBA1C | HLA-DMA | 25\|41 |
| CC | nuclear lumen | 3 | 1.5e-05-0.0015 | 0.034-1.6 | 0.58-0.64 | (-3.92)-(-2.28) | CDC25A, CDC25C, E2F2, HJURP, LMNB1, MCM2, MCM4, MKI67, PLK1, RAD51, RBM14, RFC2, TIMELESS | | 13\|25 |
| CC | non-membrane-bounded organelle | 1 | 0.00012 | 0.19 | 0.66 | (-3.12) | CCNB2, CDCA5, CENPM, ESPL1, HJURP, KIF22, KIF2C, LMNB1, MCM2, MCM4, MKI67, NCAPH, PLK1, RAD51, RBM14, RFC2, SPAG5, SPC24, TIMELESS, TUBA1B, TUBA1C | | 21\|33 |
| CC | microtubule cytoskeleton | 4 | 1.7e-12-0.0035 | 1.5e-08-3.5 | 0.62-0.67 | (-3.92)-(-3.11) | CCNB2, CDCA5, CENPM, ESPL1, HJURP, KIF22, KIF2C, LMNB1, MCM2, MCM4, MKI67, NCAPH, PLK1, RAD51, RBM14, RFC2, SPAG5, SPC24, TIMELESS, TUBA1B, TUBA1C | | 21\|33 |

TABLE 2-continued

Functionally-related genes determined using gene ontology (GO) terms.

| GO | Rep. GO Term | # of Terms | P-Value | FDR (%) | Mean.kIN$_{sc}$ | Mean Fold Change | DOWN-regulated | UP-regulated | # of Hubs |
|---|---|---|---|---|---|---|---|---|---|
| CC | kinetochore | 10 | 5.8e-13-0.0045 | 1.1e-08-4.2 | 0.53-0.7 | (−3.97)-(−2.21) | CDCA5, CENPM, HJURP, KIF22, KIF2C, MCM2, MKI67, NCAPH, RAD51, RFC2, SPAG5, SPC24, TIMELESS | | 13\|22 |
| CC | MHC protein complex | 2 | 5.1e-05-0.0015 | 0.1-1.6 | 0.71-0.71 | (+3.89)-(+3.89) | | HLA-DMA, HLA-DPB1, HLA-DQB1, (HLA-DRB1, HLA-DRB4) | 4\|4 |
| MF | MHC class II receptor activity | 1 | 4.60E-05 | 1.0 | 0.71 | (+3.89) | | HLA-DMA, HLA-DPB1, HLA-DQB1, (HLA-DRB1, HLA-DRB4) | 4\|4 |

Orange Module

| CC | integral to membrane | 2 | 0.00055-0.0097 | 4.1-4.7 | 0.8-0.8 | (+0.467)-(+0.467) | ADAM23 | C3AR1, ELOVL3, ENPP1, ESAM, GALNT10, LAMP3, SEMA4F, STOM | 9\|20 |

Darkgreen Module

| BP | DNA metabolic process | 1 | 1.80E-05 | 1.3 | 0.56 | (−1.67) | DNMT3A, LIG3, PARP1, SSRP1 | NFIA | 5\|19 |
| BP | macro-molecular complex assembly | 4 | 1e-05-0.00018 | 1.4-5 | 0.56-0.6 | (−1.9)-(−1.62) | C20orf7, CENPV, DNMT3A, FKBP4, GEMIN4, HMGN2, IPO11, PARP1, TSR1, TUBB | APC2 | 11\|33 |
| CC | cytosol | 1 | 0.0005 | 1.7 | 0.56 | (−1.66) | ADA, AHSA1, BID, CIDEB, CTPS, GEMIN4, NTRK2, ODC1, PSMD8, TUBB | | 10\|33 |
| CC | membrane-enclosed lumen | 1 | 3.30E-06 | 0.03 | 0.59 | (−1.75) | ACO2, DDX54, DNMT3A, FKBP4, GEMIN4, KEAP1, LAS1L, LIG3, MIPEP, NOL12, NVL, PARP1, POLR3H, PSMD8, SSRP1, THOC4, TSR1, WDR4 | PDIA5, TBX19 | 20\|48 |
| CC | non-membrane-bounded organelle | 1 | 0.00021 | 0.84 | 0.59 | (−1.54) | ALDOA, CENPV, DDX54, DNMT3A, FKBP4, GEMIN4, HMGN2, KEAP1, LAS1L, NOL12, NTRK2, NVL, PARP1, PSMD8, RCC1, SSRP1, STAG3L4, STOML2, TRIB2, TSR1, TUBB | APC2, TBX19 | 23\|53 |
| CC | intracellular non-membrane-bounded organelle | 1 | 0.00021 | 0.84 | 0.59 | (−1.54) | ALDOA, CENPV, DDX54, DNMT3A, FKBP4, GEMIN4, HMGN2, KEAP1, LAS1L, NOL12, NTRK2, NVL, PARP1, PSMD8, RCC1, SSRP1, STAG3L4, STOML2, TRIB2, TSR1, TUBB | APC2, TBX19 | 23\|53 |

TABLE 2-continued

Functionally-related genes determined using gene ontology (GO) terms.

| GO | Rep. GO Term | # of Terms | P-Value | FDR (%) | Mean.kIN$_{sc}$ | Mean Fold Change | Hub Genes DOWN-regulated | UP-regulated | # of Hubs |
|---|---|---|---|---|---|---|---|---|---|
| CC | envelope | 1 | 0.0012 | 2.9 | 0.60 | (−1.72) | BID, C20orf7, IPO11, PARP1, SLC25A33, STOML2, TOMM40L | | 7\|19 |
| CC | mitochondrion | 5 | 8.5e−05−0.0017 | 0.47−3.8 | 0.57−0.6 | (−1.72)−(−1.38) | ACO2, ACP6, BID, C20orf7, IPO11, MIPEP, PARP1, SLC25A33, STOML2, TOMM40L | | 10\|31 |
| CC | nuclear lumen | 4 | 9.9e−07−1e−04 | 0.027−0.47 | 0.59−0.61 | (−1.8)−(−1.75) | ACO2, DDX54, DNMT3A, FKBP4, GEMIN4, KEAP1, LAS1L, LIG3, MIPEP, NOL12, NVL, PARP1, POLR3H, PSMD8, SSRP1, THOC4, TSR1, WDR4 | PDIA5, TBX19 | 20\|48 |

Springgreen Module

| GO | Rep. GO Term | # of Terms | P-Value | FDR (%) | Mean.kIN$_{sc}$ | Mean Fold Change | Hub Genes DOWN-regulated | UP-regulated | # of Hubs |
|---|---|---|---|---|---|---|---|---|---|
| MF | GTPase regulator activity | 3 | 6e−08−2.8e−07 | 0.0028−0.0044 | 0.55−0.56 | (+0.948)−(+1.14) | TIAM2 | ASAP3, CHN1, FLJ10357, RABGAP1L, RASA2, RASAL2, SYTL3, TIAM1 | 9\|26 |
| MF | cytoskeletal protein binding | 1 | 0.00025 | 2.9 | 0.56 | (+1.48) | | EPB41L5, GSN, JUP, MAPT, MYH11, OBSL1, TNNT1 | 7\|23 |

Red Module

| GO | Rep. GO Term | # of Terms | P-Value | FDR (%) | Mean.kIN$_{sc}$ | Mean Fold Change | Hub Genes DOWN-regulated | UP-regulated | # of Hubs |
|---|---|---|---|---|---|---|---|---|---|
| CC | integral to membrane | 2 | 1.1e−05−2.9e−05 | 0.16−0.21 | 0.71−0.71 | (−1.9)−(−1.9) | ABHD12, C19orf63, CD320, CD79B, CLN6, DHCR7, IL21R, PIGU, SCAMP3, SCNN1B, SLC37A4, SLC7A11, SSR2, TMEM109 | RASGRP3 | 15\|35 |
| CC | endomembrane system | 1 | 0.00021 | 1.0 | 0.72 | (−1.96) | DHCR7, PIGU, SCAMP3, SLC37A4, SSR2, TMEM109 | | 6\|12 |

TABLE 3

Detailed functional enrichment findings for the five drug-related gene expression modules.

| | | | REVIGO results | | | | DAVID results | | | | GE in Combination vs. Control | |
|---|---|---|---|---|---|---|---|---|---|---|---|---|
| GO | GO TermID | GO Name | Dispensability | Mean kIN$_{sc}$ | GO select | filter | P-value EASE score | FDR Benjamini | Fold Enrichment | n | Mean Fold Change | Genes DOWN-regulated | Genes UP-regulated |

Blue Module

| BP | GO: 0000819 | sister chromatid segrt'n | 0 | 0.7127 | 819 | 0 | 2.1E-03 | 4.4E-02 | 15.36 | 4 | -3.72 | CDCA5, ESPL1, NCAPD3, NCAPH | |
| BP | GO: 0000279 | M phase | 0.777 | 0.6804 | 819 | 1 | 1.4E-18 | 1.1E-15 | 10.96 | 25 | -3.63 | CCNB2, CDC20, CDC25A, CDC25C, CDC6, CDCA3, CDCA5, CIT, ESPL1, H2AFX, KIF22, KIF2C, MKI67, NCAPD3, NCAPH, PLK1, RAD51, RAD54L, SKA3, SPAG5, SPC24, TACC3, TIMELESS, TRIP13, UBE2C | |
| BP | GO: 0000280 | nuclear division | 0.99 | 0.7015 | 819 | 1 | 7.5E-15 | 1.1E-12 | 12.38 | 19 | -3.69 | CNB2, CDC20, CDC25A, CDC25C, CDC6, CDCA3, CDCA5, CIT, ESPL1, KIF22, KIF2C, NCAPD3, NCAPH, PLK1, SKA3, SPAG5, SPC24, TIMELESS, UBE2C | |
| BP | GO: 0000070 | mitotic sister chromatid segregation | 0.818 | 0.7127 | 819 | 1 | 2.0E-03 | 4.3E-02 | 15.79 | 4 | -3.72 | CDCA5, ESPL1, NCAPD3, NCAPH | |
| BP | GO: 0051327 | M phase of meiotic cell cycle | 0.997 | 0.6393 | 819 | 1 | 5.1E-05 | 2.4E-03 | 10.47 | 7 | -3.67 | ESPL1, H2AFX, MKI67, PLK1, RAD51, RAD54L, TRIP13 | |
| BP | GO: 0007067 | mitosis | 0.942 | 0.7015 | 819 | 1 | 7.5E-15 | 1.1E-12 | 12.38 | 19 | -3.69 | CCNB2, CDC20, CDC25A, CDC25C, CDC6, CDCA3, CDCA5, CIT, ESPL1, KIF22, KIF2C, NCAPD3, NCAPH, PLK1, SKA3, SPAG5, SPC24, TIMELESS, UBE2C | |
| BP | GO: 0007126 | meiosis | 0.899 | 0.6393 | 819 | 1 | 5.1E-05 | 2.4E-03 | 10.47 | 7 | -3.67 | ESPL1, H2AFX, MKI67, PLK1, RAD51, RAD54L, TRIP13 | |
| BP | GO: 0022403 | cell cycle phase | 0.935 | 0.6713 | 819 | 1 | 2.3E-17 | 5.9E-15 | 9.03 | 26 | -3.61 | BLM, CCNB2, CDC20, CDC25A, CDC25C, CDC6, CDCA3, CDCA5, CIT, ESPL1, H2AFX, KIF22, KIF2C, MKI67, NCAPD3, NCAPH, PLK1, RAD51, RAD54L, SKA3, SPAG5, SPC24, TACC3, TIMELESS, TRIP13, UBE2C | |
| BP | GO: 0000087 | M phase of mitotic cell cycle | 0.948 | 0.7015 | 819 | 1 | 1.0E-14 | 1.3E-12 | 12.16 | 19 | -3.69 | CCNB2, CDC20, CDC25A, CDC25C, CDC6, CDCA3, CDCA5, CIT, ESPL1, KIF22, KIF2C, NCAPD3, NCAPH, PLK1, SKA3, SPAG5, SPC24, TIMELESS, UBE2C | |
| BP | GO: 0002504 | antigen processing and presentation | 0 | 0.7123 | 2504 | 0 | 1.7E-04 | 6.9E-03 | 35.52 | 4 | 3.89 | | HLA-DMA, HLA-DPB1, |

TABLE 3-continued

Detailed functional enrichment findings for the five drug-related gene expression modules.

| GO | GO TermID | GO Name | REVIGO results | | | | DAVID results | | | GE in Combination vs. Control | | |
|---|---|---|---|---|---|---|---|---|---|---|---|---|
| | | | Dispensability | Mean $kIN_{sc}$ | GO select | filter | P-value EASE score | FDR Benjamini | Fold Enrichment | n | Mean Fold Change | Genes DOWN-regulated | Genes UP-regulated |

| GO | GO TermID | GO Name | Dispensability | Mean $kIN_{sc}$ | GO select | filter | EASE score | FDR Benjamini | Fold Enrichment | n | Mean Fold Change | Genes DOWN-regulated | Genes UP-regulated |
|---|---|---|---|---|---|---|---|---|---|---|---|---|---|
| | | of peptide or polysaccharide antigen via MHC class II | | | | | | | | | | | HLA-DQB1, (HLA-DRB1, HLA-DRB4) |
| BP | GO: 0051301 | cell division | 0.018 | 0.6936 | 51301 | 0 | 1.3E-11 | 1.1E-09 | 8.79 | 18 | -3.77 | CCNB2, CDC20, CDC25A, CDC25C, CDC6, CDCA3, CDCA5, CIT, ESPL1, MCM5, NCAPD3, NCAPH, PLK1, SKA3, SPAG5, SPC24, TIMELESS, UBE2C | |
| BP | GO: 0007059 | chromosome segregation | 0.023 | 0.6808 | 7059 | 0 | 2.3E-04 | 8.9E-03 | 10.66 | 6 | -3.55 | CDCA5, ESPL1, HJURP, NCAPD3, NCAPH, SKA3 | |
| BP | GO: 0007017 | micro-tubule-based process | 0.024 | 0.682 | 7017 | 0 | 3.1E-04 | 1.0E-02 | 5.20 | 9 | -3.25 | CENPA, ESPL1, KIF22, KIF2C, SPAG5, TACC3, TUBA1B, TUBA1C, UBE2C | |
| BP | GO: 0007049 | cell cycle | 0.027 | 0.6677 | 7049 | 0 | 1.7E-18 | 6.6E-16 | 6.35 | 34 | -3.66 | BLM, CCNB2, CDC20, CDC25A, CDC25C, CDC6, CDCA3, CDCA5, CENPA, CHAF1B, CIT, DBF4B, E2F2, ESPL1, FOXM1, H2AFX, HJURP, KIF22, KIF2C, MCM2, MKI67, NCAPD3, NCAPH, PLK1, RAD51, RAD54L, SKA3, SPAG5, SPC24, SUV39H1, TACC3, TIMELESS, TRIP13, UBE2C | |
| BP | GO: 0006260 | DNA replication | 0.031 | 0.636 | 6260 | 0 | 3.7E-10 | 2.8E-08 | 10.87 | 14 | -4.50 | BLM, CDC25A, CDC25C, CDC6, CHAF1B, MCM10, MCM2, MCM4, MCM5, POLA2, RAD51, RBM14, RFC2, RRM2 | |
| BP | GO: 0000724 | double-strand break repair via homologous recombination | 0.409 | 0.577 | 724 | 0 | 2.9E-04 | 1.0E-02 | 29.91 | 4 | -2.93 | BLM, H2AFX, RAD51, RAD54L | |
| BP | GO: 0006259 | DNA metabolic process | 0.422 | 0.6165 | 6259 | 0 | 9.1E-10 | 6.3E-08 | 5.75 | 20 | -4.10 | BLM, CDC25A, CDC25C, CDC6, CHAF1B, FANCG, H2AFX, KIF22, MCM10, MCM2, MCM4, MCM5, POLA2, RAD18, RAD51, RAD54L, RBM14, RFC2, RRM2, TRIP13 | |
| BP | GO: 0065003 | macromolecular complex assembly | 0.457 | 0.6483 | 65003 | 0 | 1.6E-03 | 3.9E-02 | 2.87 | 13 | -3.37 | BLM, CENPA, CHAF1B, E2F2, H2AFX, HJURP, MCM2, RAD51, RRM2, TMEM48, TUBA1B, TUBA1C | HLA-DMA |
| BP | GO: 0034621 | cellular macro-molecular complex subunit organization | 0.944 | 0.6397 | 65003 | 1 | 2.5E-03 | 5.0E-02 | 3.77 | 9 | -3.16 | CENPA, CHAF1B, H2AFX, HJURP, KIF2C, MCM2, TMEM48, TUBA1B, TUBA1C | |

TABLE 3-continued

Detailed functional enrichment findings for the five drug-related gene expression modules.

| | | | REVIGO results | | | | DAVID results | | | GE in Combination vs. Control | | |
|---|---|---|---|---|---|---|---|---|---|---|---|---|
| GO | GO TermID | GO Name | Dispensability | Mean kIN$_{sc}$ | GO select | filter | P-value EASE score | FDR Benjamini | Fold Enrichment | n | Mean Fold Change | Genes DOWN-regulated | Genes UP-regulated |
| BP | GO: 0000725 | recombinational repair | 0.467 | 0.577 | 725 | 0 | 2.9E-04 | 1.0E-02 | 29.91 | 4 | -2.93 | BLM, H2AFX, RAD51, RAD54L | |
| BP | GO: 0006261 | DNA-dependent DNA replication | 0.538 | 0.6607 | 6261 | 0 | 7.0E-04 | 2.0E-02 | 12.25 | 5 | -3.99 | BLM, MCM2, MCM4, MCM5, RAD51 | |
| BP | GO: 0000278 | mitotic cell cycle | 0.551 | 0.6792 | 278 | 0 | 5.2E-13 | 5.0E-11 | 8.15 | 21 | -3.66 | BLM, CCNB2, CDC20, CDC25A, CDC25C, CDC6, CDCA3, CDCA5, CENPA, CIT, ESPL1, KIF22, KIF2C, NCAPD3, NCAPH, PLK1, SKA3, SPAG5, SPC24, TIMELESS, UBE2C | |
| BP | GO: 0048285 | organelle fission | 0.573 | 0.7015 | 48285 | 0 | 1.5E-14 | 1.7E-12 | 11.89 | 19 | -3.69 | CCNB2, CDC20, CDC25A, CDC25C, CDC6, CDCA3, CDCA5, CIT, ESPL1, KIF22, KIF2C, NCAPD3, NCAPH, PLK1, SKA3, SPAG5, SPC24, TIMELESS, UBE2C | |
| BP | GO: 0051276 | chromosome organization | 0.755 | 0.6027 | 48285 | 1 | 1.9E-05 | 1.1E-03 | 4.27 | 14 | -2.74 | BLM, CDCA5, CENPA, CHAF1B, ESPL1, H2AFX, HJURP, MCM2, NCAPD3, NCAPH, RAD54L, RBM14, SUV39H1 | SATB1 |
| BP | GO: 0034728 | nucleosome organization | 0.926 | 0.5585 | 48285 | 1 | 2.1E-03 | 4.5E-02 | 9.11 | 5 | -3.39 | CENPA, CHAF1B, H2AFX, HJURP, MCM2 | |
| BP | GO: 0006333 | chromatin assembly or disassembly | 0.925 | 0.5751 | 48285 | 1 | 1.1E-03 | 2.9E-02 | 7.61 | 6 | -3.20 | CENPA, CHAF1B, H2AFX, HJURP, MCM2, SUV39H1 | |
| BP | GO: 0006334 | nucleosome assembly | 0.82 | 0.5585 | 48285 | 1 | 1.3E-03 | 3.5E-02 | 10.29 | 5 | -3.39 | CENPA, CHAF1B, H2AFX, HJURP, MCM2 | |
| BP | GO: 0031497 | chromatin assembly | 0.96 | 0.5585 | 48285 | 1 | 1.6E-03 | 3.9E-02 | 9.87 | 5 | -3.39 | CENPA, CHAF1B, H2AFX, HJURP, MCM2 | |
| BP | GO: 0065004 | protein-DNA complex assembly | 0.997 | 0.5585 | 48285 | 1 | 1.9E-03 | 4.4E-02 | 9.35 | 5 | -3.39 | CENPA, CHAF1B, H2AFX, HJURP, MCM2 | |
| BP | GO: 0051321 | meiotic cell cycle | 0.605 | 0.6393 | 51321 | 0 | 5.7E-05 | 2.6E-03 | 10.25 | 7 | -3.67 | ESPL1, H2AFX, MKI67, PLK1, RAD51, RAD54L, TRIP13 | |
| BP | GO: 0006323 | DNA packaging | 0.61 | 0.6197 | 6323 | 0 | 6.3E-06 | 4.0E-04 | 11.25 | 8 | -3.53 | CDCA5, CENPA, CHAF1B, H2AFX, HJURP, MCM2, NCAPD3, NCAPH | |
| BP | GO: 0000226 | micro-tubule cytoskeleton organization | 0.649 | 0.6747 | 226 | 0 | 4.8E-04 | 1.5E-02 | 6.95 | 7 | -3.42 | CENPA, ESPL1, KIF2C, SPAG5, TACC3, TUBA1B, UBE2C | |
| BP | GO: 0051726 | regulation of cell cycle | 0.652 | 0.6467 | 51726 | 0 | 8.6E-05 | 3.6E-03 | 4.79 | 11 | -3.58 | BLM, CDC25A, CDC25C, CDC6, E2F2, ESPL1, FANCG, H2AFX, TACC3, TIMELESS, UBE2C | |
| BP | GO: 0006310 | DNA recombination | 0.653 | 0.593 | 6310 | 0 | 6.5E-04 | 2.0E-02 | 8.52 | 6 | -3.45 | BLM, H2AFX, RAD51, RAD54L, RBM14, TRIP13 | |

TABLE 3-continued

Detailed functional enrichment findings for the five drug-related gene expression modules.

| | | | REVIGO results | | | | DAVID results | | | GE in Combination vs. Control | | |
|---|---|---|---|---|---|---|---|---|---|---|---|---|
| | | | | | | | P-value | | | | Mean | | |
| GO | GO TermID | GO Name | Dispensability | Mean kIN$_{sc}$ | GO select | filter | EASE score | FDR Benjamini | Fold Enrichment | n | Fold Change | Genes DOWN-regulated | Genes UP-regulated |
| BP | GO: 0006281 | DNA repair | 0.663 | 0.5778 | 6281 | 0 | 2.2E-05 | 1.2E-03 | 5.62 | 11 | -3.03 | BLM, CHAF1B, FANCG, H2AFX, KIF22, RAD18, RAD51, RAD54L, RBM14, RFC2, TRIP13 | |
| BP | GO: 0033554 | cellular response to stress | 0.764 | 0.581 | 6281 | 1 | 1.6E-03 | 3.8E-02 | 3.06 | 12 | -2.96 | BLM, CHAF1B, FANCG, H2AFX, KIF22, RAD18, RAD51, RAD54L, RBM14, RFC2, TIMELESS, TRIP13 | |
| BP | GO: 0006974 | response to DNA damage stimulus | 0.957 | 0.581 | 6281 | 1 | 4.6E-05 | 2.3E-03 | 4.65 | 12 | -2.96 | BLM, CHAF1B, FANCG, H2AFX, KIF22, RAD18, RAD51, RAD54L, RBM14, RFC2, TIMELESS, TRIP13 | |
| BP | GO: 0006302 | double-strand break repair | 0.669 | 0.5762 | 6302 | 0 | 9.0E-04 | 2.5E-02 | 11.46 | 5 | -3.51 | BLM, H2AFX, RAD51, RAD54L, TRIP13 | |
| BP | GO: 0022402 | cell cycle process | 0.68 | 0.6646 | 22402 | 0 | 3.6E-15 | 7.0E-13 | 6.87 | 27 | -3.61 | BLM, CCNB2, CDC20, CDC25A, CDC25C, CDC6, CDCA3, CDCA5, CENPA, CIT, ESPL1, H2AFX, KIF22, KIF2C, MKI67, NCAPD3, NCAPH, PLK1, RAD51, RAD54L, SKA3, SPAG5, SPC24, TACC3, TIMELESS, TRIP13, UBE2C | |
| BP | GO: 0043933 | macromolecular complex subunit organization | 0.695 | 0.6599 | 43933 | 0 | 2.7E-04 | 9.8E-03 | 3.09 | 15 | -3.55 | BLM, CENPA, CHAF1B, E2F2, H2AFX, HJURP, KIF2C, MCM2, RAD51, RRM2, SCARB1, TMEM48, TUBA1B, TUBA1C | HLA-DMA |
| CC | GO: 0042611 | MHC protein complex | 0.000 | 0.712 | 42611 | 0 | 1.5E-03 | 1.6E-02 | 17.24 | 4 | 3.89 | | HLA-DMA, HLA-DPB1, HLA-DQB1, (HLA-DRB1, HLA-DRB4) |
| CC | GO: 0042613 | MHC class II protein complex | 0.773 | 0.712 | 42611 | 1 | 5.1E-05 | 1.0E-03 | 51.72 | 4 | 3.89 | | HLA-DMA, HLA-DPB1, HLA-DQB1, (HLA-DRB1, HLA-DRB4) |
| CC | GO: 0015630 | micro-tubule cytoskeleton | 0.002 | 0.670 | 15630 | 0 | 1.2E-03 | 1.4E-02 | 3.17 | 12 | -3.20 | CCNB2, CDC20, CDC6, ESPL1, KIF22, KIF2C, PLK1, SKA3, SPAG5, TUBA1B, TUBA1C | CAMSAP1L1 |
| CC | GO: 0005819 | spindle | 0.727 | 0.616 | 15630 | 1 | 3.5E-03 | 3.5E-02 | 5.80 | 6 | -3.92 | CDC20, CDC6, KIF22, PLK1, SKA3, SPAG5 | |
| CC | GO: 0031981 | nuclear lumen | 0.173 | 0.641 | 31981 | 0 | 1.5E-03 | 1.6E-02 | 2.09 | 21 | -3.86 | BLM, CDC20, CDC25A, CDC25C, CDC6, CHAF1B, E2F2, H2AFX, HJURP, LMNB1, MCM10, MCM2, MCM4, MCM5, MKI67, PLK1, POLA2, RAD51, RBM14, RFC2, UBE2C | |

TABLE 3-continued

Detailed functional enrichment findings for the five drug-related gene expression modules.

| | | | REVIGO results | | | | DAVID results | | | | GE in Combination vs. Control | |
|---|---|---|---|---|---|---|---|---|---|---|---|---|
| | | | | | | | P-value | | | | Mean | |
| GO | GO TermID | GO Name | Dispensability | Mean kIN$_{sc}$ | GO select | filter | EASE score | FDR Benjamini | Fold Enrichment | n | Fold Change | Genes DOWN-regulated | Genes UP-regulated |
| CC | GO: 0000228 | nuclear chromosome | 0.841 | 0.581 | 31981 | 1 | 1.5E-05 | 3.4E-04 | 7.95 | 9 | -2.28 | BLM, H2AFX, MCM2, NCAPD3, POLA2, RAD51, SUV39H1, TIMELESS | CALCOCO1 |
| CC | GO: 0005654 | nucleo-plasm | 0.902 | 0.636 | 31981 | 1 | 8.3E-05 | 1.4E-03 | 2.94 | 18 | -3.92 | BLM, CDC20, CDC25A, CDC25C, CDC6, CHAF1B, E2F2, H2AFX, MCM10, MCM2, MCM4, MCM5, PLK1, POLA2, RAD51, RBM14, RFC2, UBE2C | |
| CC | GO: 0043228 | non-membrane-bounded organelle | 0.235 | 0.658 | 43228 | 0 | 1.2E-04 | 1.9E-03 | 1.91 | 33 | -3.12 | BLM, CCNB2, CDC20, CDC6, CDCA5, CENPA, CENPM, ESPL1, H2AFX, HJURP, KIF22, KIF2C, LMNB1, MCM2, MCM4, MKI67, NCAPD3, NCAPH, PLK1, POLA2, RAD18, RAD51, RBM14, RFC2, SKA3, SPAG5, SPC24, SUV39H1, TIMELESS, TUBA1B, TUBA1C | CALCOCO1, CAMSAP1L1 |
| CC | GO: 0000776 | kineto-chore | 0.350 | 0.690 | 776 | 0 | 9.8E-07 | 3.5E-05 | 14.78 | 8 | -3.86 | CENPA, CENPM, HJURP, KIF22, KIF2C, SKA3, SPAG5, SPC24 | |
| CC | GO: 0000794 | condensed nuclear chromosome | 0.912 | 0.608 | 776 | 1 | 4.5E-03 | 4.2E-02 | 11.85 | 4 | -2.71 | BLM, NCAPD3, RAD51, SUV39H1 | |
| CC | GO: 0000777 | condensed chromosome kineto-chore | 0.880 | 0.697 | 776 | 1 | 2.8E-06 | 8.5E-05 | 17.16 | 7 | -3.97 | CENPA, CENPM, HJURP, KIF2C, SKA3, SPAG5, SPC24 | |
| CC | GO: 0000779 | condensed chromosome, centro-meric region | 0.918 | 0.697 | 776 | 1 | 6.1E-06 | 1.6E-04 | 15.08 | 7 | -3.97 | CENPA, CENPM, HJURP, KIF2C, SKA3, SPAG5, SPC24 | |
| CC | GO: 0005694 | chromosome | 0.481 | 0.645 | 5694 | 0 | 1.7E-12 | 1.5E-10 | 7.05 | 22 | -3.11 | BLM, CDCA5, CENPA, CENPM, H2AFX, HJURP, KIF22, KIF2C, MCM2, MKI67, NCAPD3, NCAPH, POLA2, RAD18, RAD51, RFC2, SKA3, SPAG5, SPC24, SUV39H1, TIMELESS | CALCOCO1 |
| CC | GO: 0000793 | condensed chromosome | 0.505 | 0.680 | 793 | 0 | 6.8E-11 | 4.1E-09 | 14.44 | 13 | -3.60 | BLM, CENPA, CENPM, HJURP, KIF2C, MKI67, NCAPD3, NCAPH, RAD51, SKA3, SPAG5, SPC24, SUV39H1 | |
| CC | GO: 0044427 | chromosomal part | 0.634 | 0.640 | 44427 | 0 | 5.8E-13 | 1.1E-10 | 8.03 | 21 | -3.12 | BLM, CDCA5, CENPA, CENPM, H2AFX, HJURP, KIF22, KIF2C, MCM2, MKI67, NCAPD3, NCAPH, POLA2, RAD18, RFC2, SKA3, SPAG5, SPC24, SUV39H1, TIMELESS | CALCOCO1 |
| CC | GO: 0044454 | nuclear chromosome part | 0.831 | 0.544 | 44427 | 1 | 1.9E-04 | 2.6E-03 | 8.23 | 7 | -2.21 | BLM, H2AFX, MCM2, NCAPD3, POLA2, TIMELESS | CALCOCO1 |

TABLE 3-continued

Detailed functional enrichment findings for the five drug-related gene expression modules.

| | | | REVIGO results | | | | DAVID results | | | | GE in Combination vs. Control | |
|---|---|---|---|---|---|---|---|---|---|---|---|---|
| | | | | | | | P-value | | | | Mean | |
| GO | GO TermID | GO Name | Dispensability | Mean kIN$_{sc}$ | GO select | filter | EASE score | FDR Benjamini | Fold Enrichment | n | Fold Change | Genes DOWN-regulated | Genes UP-regulated |
| CC | GO:0000785 | chromatin | 0.790 | 0.580 | 44427 | 1 | 3.2E-04 | 4.2E-03 | 6.05 | 8 | -2.21 | CENPA, H2AFX, KIF22, MCM2, RAD18, SUV39H1, TIMELESS | CALCOCO1 |
| CC | GO:0005657 | replication fork | 0.815 | 0.534 | 44427 | 1 | 6.7E-05 | 1.2E-03 | 22.22 | 5 | -2.74 | BLM, H2AFX, POLA2, RAD18, RFC2 | |
| CC | GO:0000775 | chromosome, centro-meric region | 0.657 | 0.686 | 775 | 0 | 1.7E-07 | 7.5E-06 | 11.56 | 10 | -3.68 | CENPA, CENPM, HJURP, KIF22, KIF2C, MKI67, SKA3, SPAG5, SPC24, SUV39H1 | |
| CC | GO:0043232 | intra-cellular non-membrane-bounded organelle | 0.676 | 0.658 | 43232 | 0 | 1.2E-04 | 1.9E-03 | 1.91 | 33 | -3.12 | BLM, CCNB2, CDC20, CDC6, CDCA5, CENPA, CENPM, ESPL1, H2AFX, HJURP, KIF22, KIF2C, LMNB1, MCM2, MCM4, MKI67, NCAPD3, NCAPH, PLK1, POLA2, RAD18, RAD51, RBM14, RFC2, SKA3, SPAG5, SPC24, SUV39H1, TIMELESS, TUBA1B, TUBA1C | CALCOCO1, CAMSAP1L1 |
| MF | GO:0032395 | MHC class II receptor activity | 0.000 | 0.712 | 32395 | 0 | 4.6E-05 | 1.0E-02 | 53.65 | 4 | 3.89 | | HLA-DMA, HLA-DPB1, HLA-DQB1, (HLA-DRB1, HLA-DRB4) |
| | | | | | | | | Orange Module | | | | | |
| CC | GO:0016021 | integral to membrane | 0.000 | 0.804 | 16021 | 0 | 5.5E-04 | 4.7E-02 | 1.87 | 20 | 0.47 | ADAM23, FGFR4, HVCN1, IL13RA1, SLC30A3, SORT1, TMEM107 | C3AR1, CNNM4, ELOVL3, ENPP1, ESAM, GALNT10, IL2RB, KIAA1467, KREMEN1, LAMP3, SEMA4F, STOM, TMEM180 |
| CC | GO:0031224 | intrinsic to membrane | 0.607 | 0.804 | 31224 | 0 | 9.7E-04 | 4.1E-02 | 1.80 | 20 | 0.47 | ADAM23, FGFR4, HVCN1, IL13RA1, SLC30A3, SORT1, TMEM107 | C3AR1, CNNM4, ELOVL3, ENPP1, ESAM, GALNT10, IL2RB, KIAA1467, KREMEN1, LAMP3, SEMA4F, STOM, TMEM180 |
| | | | | | | | | Darkgreen Module | | | | | |
| BP | GO:0006259 | DNA metabolic process | 0.000 | 0.563 | 6259 | 0 | 1.8E-05 | 1.3E-02 | 3.26 | 19 | -1.67 | ABL1, AIFM1, CHD1L, DFFB, DNASE1L1, DNMT3A, GTF2H3, HAUS7, HMGA1, HSPD1, LIG3, NASP, OBFC2B, PARP1, SET, SMARCB1, SSRP1, SUPT16H | NFIA |

TABLE 3-continued

Detailed functional enrichment findings for the five drug-related gene expression modules.

| | | | REVIGO results | | | DAVID results | | | | GE in Combination vs. Control | |
|---|---|---|---|---|---|---|---|---|---|---|---|
| | | | | | | P-value | | | | Mean | |
| GO | GO TermID | GO Name | Dispensability | Mean kIN$_{sc}$ | GO select | filter | EASE score | FDR Benjamini | Fold Enrichment | n | Fold Change | Genes DOWN-regulated | Genes UP-regulated |
| BP | GO: 0065003 | macro-molecular complex assembly | 0.000 | 0.603 | 65003 | 0 | 1.8E-04 | 5.0E-02 | 2.64 | 20 | -1.65 | C20orf7, CENPV, FKBP4, GEMIN4, GTF2H3, H2AFY, H3F3A, HMGA1, HSPD1, IPO11, MED12, PAK2, SET, SF3B3, SHMT1, TSR1, TUBB, TUBGCP4, WDR77 | APC2 |
| BP | GO: 0034621 | cellular macro-molecular complex subunit organization | 0.944 | 0.586 | 65003 | 1 | 1.0E-05 | 1.4E-02 | 4.01 | 16 | -1.90 | C20orf7, CENPV, FKBP4, GEMIN4, H2AFY, H3F3A, HMGA1, HSPD1, IPO11, NASP, PAK2, SET, SUPT16H, TSR1, TUBB, WDR77 | |
| BP | GO: 0051276 | chromosome organization | 0.638 | 0.558 | 51276 | 0 | 3.2E-05 | 1.4E-02 | 3.28 | 18 | -1.62 | AIFM1, AIFM2, CENPV, CHD1L, DFFB, DNMT3A, H2AFY, H3F3A, HMGA1, HMGN2, INO80, NASP, PARP1, SET, SMARCA4, SMARCB1, SUPT16H | PRDM6 |
| BP | GO: 0043933 | macro-molecular complex subunit organization | 0.695 | 0.587 | 43933 | 0 | 5.1E-05 | 1.8E-02 | 2.71 | 22 | -1.67 | C20orf7, CENPV, FKBP4, GEMIN4, GTF2H3, H2AFY, H3F3A, HMGA1, HSPD1, IPO11, MED12, NASP, PAK2, SET, SF3B3, SHMT1, SUPT16H, TSR1, TUBB, TUBGCP4, WDR77 | APC2 |
| CC | GO: 0031974 | membrane-enclosed lumen | 0.000 | 0.590 | 31974 | 0 | 3.3E-06 | 3.1E-04 | 1.96 | 48 | -1.75 | ABL1, ACO2, AIFM1, COIL, DDX54, DFFB, DNMT3A, DUSP7, EXOSC2, FKBP4, GEMIN4, GTF2H3, HCFC1, HMGA1, HNRNPL, HSPD1, IVD, KEAP1, LARS2, LAS1L, LIG3, LMNB2, MED12, MIPEP, MPHOSPH6, MRPS15, NF2, NOL12, NOLC1, NVL, OXCT1, PA2G4, PARP1, POLR3H, PSMD8, SET, SMARCB1, SSRP1, SUPT16H, TH1L, THOC4, TOE1, TRIM25, TSR1, UTP20, WDR4 | PDIA5, TBX19 |
| CC | GO: 0031981 | nuclear lumen | 0.000 | 0.601 | 31981 | 0 | 1.7E-05 | 1.2E-03 | 2.04 | 39 | -1.80 | ABL1, COIL, DDX54, DFFB, DNMT3A, DUSP7, EXOSC2, FKBP4, GEMIN4, GTF2H3, HCFC1, HMGA1, HNRNPL, KEAP1, LAS1L, LIG3, LMNB2, MED12, MPHOSPH6, NF2, NOL12, NOLC1, NVL, PA2G4, PARP1, POLR3H, PSMD8, SET, SMARCB1, SSRP1, SUPT16H, TH1L, THOC4, TOE1, TRIM25, TSR1, UTP20, WDR4 | TBX19 |

TABLE 3-continued

Detailed functional enrichment findings for the five drug-related gene expression modules.

| GO | GO TermID | GO Name | REVIGO results | | | DAVID results | | | | | GE in Combination vs. Control | | |
|---|---|---|---|---|---|---|---|---|---|---|---|---|---|
| | | | Dispensability | Mean kIN$_{sc}$ | GO select | filter | P-value EASE score | FDR Benjamini | Fold Enrichment | n | Mean Fold Change | Genes DOWN-regulated | Genes UP-regulated |
| CC | GO: 0043233 | organelle lumen | 0.983 | 0.590 | 31981 | 1 | 1.9E-06 | 2.7E-04 | 2.00 | 48 | -1.75 | ABL1, ACO2, AIFM1, COIL, DDX54, DFFB, DNMT3A, DUSP7, EXOSC2, FKBP4, GEMIN4, GTF2H3, HCFC1, HMGA1, HNRNPL, HSPD1, IVD, KEAP1, LARS2, LAS1L, LIG3, LMNB2, MED12, MIPEP, MPHOSPH6, MRPS15, NF2, NOL12, NOLC1, NVL, OXCT1, PA2G4, PARP1, POLR3H, PSMD8, SET, SMARCB1, SSRP1, SUPT16H, TH1L, THOC4, TOE1, TRIM25, TSR1, UTP20, WDR4 | PDIA5, TBX19 |
| CC | GO: 0005730 | nucleolus | 0.858 | 0.612 | 31981 | 1 | 1.0E-04 | 4.7E-03 | 2.51 | 23 | -1.76 | ABL1, COIL, DDX54, EXOSC2, FKBP4, GEMIN4, KEAP1, LAS1L, MED12, MPHOSPH6, NF2, NOL12, NOLC1, NVL, PA2G4, PARP1, PSMD8, SMARCB1, TOE1, TRIM25, TSR1, UTP20 | TBX19 |
| CC | GO: 0070013 | intra-cellular organelle lumen | 0.975 | 0.590 | 31981 | 1 | 9.9E-07 | 2.8E-04 | 2.04 | 48 | -1.75 | ABL1, ACO2, AIFM1, COIL, DDX54, DFFB, DNMT3A, DUSP7, EXOSC2, FKBP4, GEMIN4, GTF2H3, HCFC1, HMGA1, HNRNPL, HSPD1, IVD, KEAP1, LARS2, LAS1L, LIG3, LMNB2, MED12, MIPEP, MPHOSPH6, MRPS15, NF2, NOL12, NOLC1, NVL, OXCT1, PA2G4, PARP1, POLR3H, PSMD8, SET, SMARCB1, SSRP1, SUPT16H, TH1L, THOC4, TOE1, TRIM25, TSR1, UTP20, WDR4 | PDIA5, TBX19 |
| CC | GO: 0031975 | envelope | 0.002 | 0.597 | 31975 | 0 | 1.2E-03 | 2.9E-02 | 2.34 | 19 | -1.72 | AIFM1, AIFM2, ALDH18A1, BID, C20orf7, DHODH, EXOG, GCAT, HK2, HSPD1, IPO11, LMNB2, NDUFS3, PARP1, SLC25A33, STOML2, TMPO, TOMM40L | BCL2L11 |
| CC | GO: 0005829 | cytosol | 0.080 | 0.563 | 5829 | 0 | 5.0E-04 | 1.7E-02 | 1.87 | 33 | -1.66 | ABL1, ADA, AHSA1, AIFM2, BID, CABLES1, CASP2, CEP192, CIDEB, CTPS, DFFB, DOCK2, DUSP7, FARSA, GEMIN4, GYS1, HK2, HMGA1, HSPD1, IARS, LDLRAP1, NTRK2, ODC1, PAK2, PSMD8, SET, SHMT1, SPHK2, | BCL2L11, RABGAP1 |

TABLE 3-continued

Detailed functional enrichment findings for the five drug-related gene expression modules.

| | | | REVIGO results | | | DAVID results | | | | GE in Combination vs. Control | |
|---|---|---|---|---|---|---|---|---|---|---|---|
| | | | | | | P-value | | | | Mean | |
| GO | GO TermID | GO Name | Dispensability | Mean kIN$_{sc}$ | GO select | filter | EASE score | FDR Benjamini | Fold Enrichment | n | Fold Change Genes DOWN-regulated | Genes UP-regulated |
| CC | GO: 0043232 | intra-cellular non-membrane-bounded organelle | 0.235 | 0.591 | 43232 | 0 | 2.1E-04 | 8.4E-03 | 1.61 | 53 | -1.54 TUBB, TUBGCP4, UROD ABL1, ALDOA, CENPV, CEP192, COIL, CORO1B, DDX54, DNMT3A, DOCK2, EXOSC2, FKBP4, GEMIN4, H2AFY, H3F3A, HAUS7, HMGA1, HMGN2, KEAP1, LAS1L, LMNB2, MED12, MPHOSPH6, MRPS15, NF2, NOL12, NOLC1, NTRK2, NVL, PA2G4, PAK2, PARP1, PSMD8, RCC1, SMARCA4, SMARCB1, SSRP1, STAG3L4, STOML2, SUPT16H, TMPO, TOE1, TRIB2, TRIM25, TSR1, TUBB, TUBGCP4, UTP20 | APC2, KIF5A, MYO5C, PRDM6, RABGAP1, TBX19 |
| CC | GO: 0043228 | non-membrane-bounded organelle | 0.362 | 0.591 | 43228 | 0 | 2.1E-04 | 8.4E-03 | 1.61 | 53 | -1.54 ABL1, ALDOA, CENPV, CEP192, COIL, CORO1B, DDX54, DNMT3A, DOCK2, EXOSC2, FKBP4, GEMIN4, H2AFY, H3F3A, HAUS7, HMGA1, HMGN2, KEAP1, LAS1L, LMNB2, MED12, MPHOSPH6, MRPS15, NF2, NOL12, NOLC1, NTRK2, NVL, PA2G4, PAK2, PARP1, PSMD8, RCC1, SMARCA4, SMARCB1, SSRP1, STAG3L4, STOML2, SUPT16H, TMPO, TOE1, TRIB2, TRIM25, TSR1, TUBB, TUBGCP4, UTP20 | APC2, KIF5A, MYO5C, PRDM6, RABGAP1, TBX19 |
| CC | GO: 0005739 | mitochondrion | 0.385 | 0.575 | 5739 | 0 | 1.6E-03 | 3.8E-02 | 1.90 | 27 | -1.38 ACO2, ACP6, AIFM1, AIFM2, ALDH18A1, BID, C20orf7, DHODH, ECH1, EXOG, GCAT, HK2, HSPD1, IVD, LARS2, MIPEP, MRPS15, NDUFS3, OXCT1, SHMT1, SLC25A33, STOML2, TOMM40L, TXNRD2 | BCL2L11, IF16, MAPK10 |
| CC | GO: 0031966 | mitochondrial membrane | 0.511 | 0.599 | 31966 | 0 | 1.7E-03 | 3.6E-02 | 2.75 | 14 | -1.61 AIFM2, ALDH18A1, BID, C20orf7, DHODH, EXOG, GCAT, HK2, HSPD1, NDUFS3, SLC25A33, STOML2, TOMM40L | BCL2L11 |
| CC | GO: 0044429 | mitochondrial part | 0.727 | 0.570 | 31966 | 1 | 8.5E-05 | 4.7E-03 | 2.70 | 21 | -1.72 ACO2, AIFM1, AIFM2, ALDH18A1, BID, C20orf7, DHODH, EXOG, GCAT, HK2, HSPD1, IVD, LARS2, MIPEP, | BCL2L11 |

TABLE 3-continued

Detailed functional enrichment findings for the five drug-related gene expression modules.

| GO | GO TermID | GO Name | REVIGO results | | | | DAVID results | | | | | GE in Combination vs. Control | |
|---|---|---|---|---|---|---|---|---|---|---|---|---|---|
| | | | Dispensability | Mean kIN$_{sc}$ | GO select | filter | P-value EASE score | FDR Benjamini | Fold Enrichment | n | Mean Fold Change | Genes DOWN-regulated | Genes UP-regulated |
| CC | GO: 0031967 | organelle envelope | 0.785 | 0.597 | 31966 | 1 | 1.1E-03 | 3.1E-02 | 2.35 | 19 | -1.72 | MRPS15, NDUFS3, OXCT1, SLC25A33, STOML2, TOMM40L AIFM1, AIFM2, ALDH18A1, BID, C20orf7, DHODH, EXOG, GCAT, HK2, HSPD1, IPO11, LMNB2, NDUFS3, PARP1, SLC25A33, STOML2, TMPO, TOMM40L | BCL2L11 |
| CC | GO: 0005740 | mitochondrial envelope | 0.923 | 0.600 | 31966 | 1 | 1.0E-03 | 3.1E-02 | 2.76 | 15 | -1.65 | AIFM1, AIFM2, ALDH18A1, BID, C20orf7, DHODH, EXOG, GCAT, HK2, HSPD1, NDUFS3, SLC25A33, STOML2, TOMM40L | BCL2L11 |
| | | | | | | | | Springgreen Module | | | | | |
| MF | GO: 0008092 | cyto-skeletal protein binding | 0.000 | 0.561 | 8092 | 0 | 2.5E-04 | 2.9E-02 | 2.39 | 23 | 1.48 | CCR5, KLHL3, PARVB, RANBP10 | CAPG, CLIP2, EPB41L5, FMNL2, GSN, HIP1, JUP, KIF1B, KPTN, LIMA1, MAPT, MYH11, MYH15, MYO15A, OBSL1, SPIRE1, SYNE2, TNNT1, VCL |
| MF | GO: 0030695 | GTPase regulator activity | 0.000 | 0.553 | 30695 | 0 | 1.8E-07 | 4.3E-05 | 3.39 | 26 | 1.14 | ARHGAP4, DOCK10, MAP4K1, RANBP10, TBC1D9B, TIAM2 | ARHGEF17 ARHGAP26, ARHGEF9, ASAP1, ASAP3, CHN1, CYTH1, CYTH3, DNMBP, ERC1, FLJ10357, JUN, RABGAP1L, RALGPS1, RASA2, SRGAP2, SYTL3, TIAM1 |
| MF | GO: 0005083 | small GTPase regulator activity | 0.947 | 0.557 | 30695 | 1 | 6.0E-08 | 2.8E-05 | 4.19 | 22 | 0.95 | ARHGAP4, DOCK10, MAP4K1, RANBP10, TBC1D9B, TIAM2 | ARHGAP26, ARHGEF9, ASAP1, ASAP3, CYTH1, CYTH3, DNMBP, ERC1, FLJ10357, JUN, RABGAP1L, RASA2, RASAL2, RPH3A, SYTL3, TIAM1 |
| MF | GO: 0060589 | nucleoside-triphosphatase regulator activity | 0.841 | 0.553 | 30695 | 1 | 2.8E-07 | 4.4E-05 | 3.31 | 26 | 1.14 | ARHGAP4, DOCK10, MAP4K1, RANBP10, TBC1D9B, TIAM2 | ARHGAP17, ARHGAP26, ARHGEF9, ASAP1, ASAP3, CHN1, CYTH1, CYTH3, DNMBP, ERC1, FLJ10357, JUN, RABGAP1L, RALGPS1, RASA2, |

TABLE 3-continued

Detailed functional enrichment findings for the five drug-related gene expression modules.

| | | | REVIGO results | | | | DAVID results | | | GE in Combination vs. Control | | |
|---|---|---|---|---|---|---|---|---|---|---|---|---|
| | | | | | | | P-value | | | | Mean | |
| GO | GO TermID | GO Name | Dispensability | Mean kIN$_{sc}$ | GO select | filter | EASE score | FDR Benjamini | Fold Enrichment | n | Fold Change | Genes DOWN-regulated | Genes UP-regulated |

Red Module

| | | | | | | | | | | | | | RASAL2, RPH3A, SRGAP2, SYTL3, TIAM1 |
|---|---|---|---|---|---|---|---|---|---|---|---|---|---|
| CC | GO: 0012505 | endo-membrane system | 0.000 | 0.718 | 12505 | 0 | 2.1E-04 | 1.0E-02 | 3.74 | 12 | -1.96 | B3GAT3, B3GNT1, CORO1A, DHCR7, NRM, PIGU, SCAMP2, SCAMP3, SLC37A4, SREBF1, SSR2, TMEM109 | |
| CC | GO: 0016021 | integral to membrane | 0.003 | 0.713 | 16021 | 0 | 1.1E-05 | 1.6E-03 | 1.80 | 35 | -1.90 | ABHD12, ATP6V0B, ATP6V0C, B3GAT3, B3GNT1, C19orf63, C20orf3, CD276, CD320, CD79B, CLN6, DHCR7, DHRS7B, IL21R, INSIG1, NINJ1, NRM, P2RX4, PAQR4, PIGU, SCAMP2, SCAMP3, SCNN1B, SLC25A25, SLC37A4, SLC39A3, SLC7A11, SREBF1, SSR2, TMED1, TMED3, TMEM109, TNFRSF13B, ZDHHC12 | RASGRP3 |
| CC | GO: 0031224 | intrinsic to membrane | 0.607 | 0.713 | 31224 | 0 | 2.9E-05 | 2.1E-03 | 1.74 | 35 | -1.90 | ABHD12, ATP6V0B, ATP6V0C, B3GAT3, B3GNT1, C19orf63, C20orf3, CD276, CD320, CD79B, CLN6, DHCR7, DHRS7B, IL21R, INSIG1, NINJ1, NRM, P2RX4, PAQR4, PIGU, SCAMP2, SCAMP3, SCNN1B, SLC25A25, SLC37A4, SLC39A3, SLC7A11, SREBF1, SSR2, TMED1, TMED3, TMEM109, TNFRSF13B, ZDHHC12 | RASGRP3 |

TABLE 4

The GSEA scores for each drug-related gene expression module in newly diagnosed MM, treatment-refractory MM, MGUS, and SMM patients compared to healthy volunteers.

| GSE6477 | NAME | SIZE | ES | NES | NOM.p.val | FDR.q.val | RANK.AT.MAX |
|---|---|---|---|---|---|---|---|
| Negative Enrichment Score (ES) | | | | | | | |
| NEW | Blue_UP | 13 | −0.848 | −2.29 | <1e−4 | <1e−4 | 871 |
| RELAPSED | Blue_UP | 13 | −0.817 | −2.22 | <1e−4 | <1e−4 | 1015 |
| SMM | Blue_UP | 13 | −0.817 | −2.28 | <1e−4 | <1e−4 | 1529 |
| MGUS | Blue_UP | 13 | −0.699 | −1.94 | 0.0017 | 0.0037 | 3003 |
| RELAPSED | Springgreen_UP | 198 | −0.377 | −1.80 | <1e−4 | 0.0043 | 2932 |
| NEW | Springgreen_UP | 198 | −0.361 | −1.71 | <1e−4 | 0.0088 | 2205 |
| SMM | Springgreen_UP | 198 | −0.268 | −1.33 | 0.0243 | 0.1648 | 2472 |
| NEW | Darkggreen_UP | 24 | −0.357 | −1.14 | 0.2727 | 0.2318 | 2755 |
| RELAPSED | Darkggreen_UP | 24 | −0.335 | −1.08 | 0.3304 | 0.3042 | 1852 |
| SMM | Darkggreen_UP | 24 | −0.332 | −1.10 | 0.3124 | 0.3756 | 2142 |
| SMM | Blue_DOWN | 81 | −0.196 | −0.84 | 0.7850 | 0.7598 | 1610 |
| MGUS | Springgreen_DOWN | 70 | −0.147 | −0.61 | 0.9954 | 0.9796 | 3621 |
| MGUS | Darkggreen_DOWN | 144 | −0.140 | −0.66 | 0.9972 | 1 | 2913 |
| MGUS | Darkggreen_UP | 24 | −0.273 | −0.90 | 0.6005 | 1 | 3908 |
| MGUS | Red_DOWN | 40 | −0.192 | −0.71 | 0.9192 | 1 | 1854 |
| MGUS | Blue_DOWN | 81 | −0.217 | −0.93 | 0.6136 | 1 | 1312 |
| MGUS | Springgreen_UP | 198 | −0.197 | −0.97 | 0.5363 | 1 | 2335 |
| Positive Enrichment Score (ES) | | | | | | | |
| RELAPSED | Darkggreen_DOWN | 144 | 0.497 | 2.20 | <1e−4 | <1e−4 | 2683 |
| NEW | Darkggreen_DOWN | 144 | 0.456 | 2.07 | <1e−4 | 0.0007 | 1947 |
| RELAPSED | Blue_DOWN | 81 | 0.483 | 1.94 | <1e−4 | 0.0009 | 2234 |
| NEW | Red_DOWN | 40 | 0.485 | 1.72 | 0.0060 | 0.0101 | 2485 |
| RELAPSED | Red_DOWN | 40 | 0.444 | 1.55 | 0.0196 | 0.0293 | 2288 |
| NEW | Blue_DOWN | 81 | 0.349 | 1.43 | 0.0272 | 0.0682 | 3892 |
| MGUS | Orange_UP$_{MS275}$ | 21 | 0.400 | 1.23 | 0.1807 | 0.1437 | 4769 |
| SMM | Orange_UP$_{MS275}$ | 21 | 0.433 | 1.36 | 0.1025 | 0.2624 | 2906 |
| SMM | Red_DOWN | 40 | 0.298 | 1.09 | 0.3104 | 0.4002 | 3821 |
| SMM | Darkggreen_DOWN | 144 | 0.236 | 1.11 | 0.2340 | 0.5449 | 2633 |
| NEW | Orange_UP$_{MS275}$ | 21 | 0.270 | 0.82 | 0.7255 | 0.7931 | 4074 |
| RELAPSED | Springgreen_DOWN | 70 | 0.166 | 0.65 | 0.9847 | 0.9661 | 3820 |
| SMM | Springgreen_DOWN | 70 | 0.137 | 0.57 | 0.9981 | 0.9896 | 4632 |
| NEW | Springgreen_DOWN | 70 | 0.207 | 0.83 | 0.7988 | 0.9905 | 3646 |
| RELAPSED | Orange_UP$_{MS275}$ | 21 | 0.272 | 0.82 | 0.7378 | 1 | 3118 |

TABLE 5

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| REL | Blue_D | DDRGK1 | 218159_at | 129 | 5.5952 | 0.0185 | Yes | 218159_at | −1.0618 |
| REL | Blue_D | TRIP13 | 204033_at | 133 | 5.5645 | 0.0465 | Yes | 204033_at | −2.5425 |
| REL | Blue_D | HJURP | 218726_at | 195 | 5.1933 | 0.0682 | Yes | 218726_at | −1.9264 |
| REL | Blue_D | MCM10 | 220651_s_at | 242 | 4.9576 | 0.0899 | Yes | 220651_s_at | −2.7011 |
| REL | Blue_D | RRM2 | 209773_s_at | 253 | 4.9231 | 0.1141 | Yes | 209773_s_at | −3.3973 |
| REL | Blue_D | CCNB2 | 202705_at | 332 | 4.6500 | 0.1317 | Yes | 202705_at | −2.1340 |
| REL | Blue_D | RAD51 | 205024_s_at | 373 | 4.5478 | 0.1518 | Yes | 205024_s_at | −1.5192 |
| REL | Blue_D | GPI | 208308_s_at | 395 | 4.4659 | 0.1728 | Yes | 208308_s_at | −1.7204 |
| REL | Blue_D | FDPS | 201275_at | 522 | 4.1431 | 0.1842 | Yes | 201275_at | −1.4558 |
| REL | Blue_D | NCAPD3 | 212789_at | 578 | 4.0306 | 0.2004 | Yes | 212789_at | −1.4511 |
| REL | Blue_D | LDHA | 200650_s_at | 600 | 3.9878 | 0.2191 | Yes | 200650_s_at | −1.2640 |
| REL | Blue_D | MCM2 | 202107_s_at | 656 | 3.9024 | 0.2347 | Yes | 202107_s_at | −2.0679 |
| REL | Blue_D | CENPA | 210821_x_at | 660 | 3.8906 | 0.2542 | Yes | 204962_s_at | −1.8881 |
| REL | Blue_D | UBE2C | 202954_at | 908 | 3.5272 | 0.2530 | Yes | 202954_at | −1.4051 |
| REL | Blue_D | TMEM48 | 218073_s_at | 916 | 3.5125 | 0.2704 | Yes | 234672_s_at | −1.4764 |
| REL | Blue_D | MKI67 | 212021_s_at | 940 | 3.4802 | 0.2863 | Yes | 212021_s_at | −1.8786 |
| REL | Blue_D | CDC20 | 202870_s_at | 960 | 3.4429 | 0.3023 | Yes | 202870_s_at | −1.5564 |
| REL | Blue_D | CIT | 212801_at | 1005 | 3.3970 | 0.3162 | Yes | 212801_at | −1.0713 |
| REL | Blue_D | KIF22 | 202183_s_at | 1014 | 3.3808 | 0.3327 | Yes | 202183_s_at | −1.6422 |
| REL | Blue_D | TIMELESS | 203046_s_at | 1133 | 3.2501 | 0.3402 | Yes | 203046_s_at | −1.1575 |
| REL | Blue_D | NSDHL | 209279_s_at | 1158 | 3.2300 | 0.3547 | Yes | 209279_s_at | −1.3381 |
| REL | Blue_D | C1orf112 | 220840_s_at | 1171 | 3.2161 | 0.3701 | Yes | 220840_s_at | −1.6023 |
| REL | Blue_D | WDR76 | 205519_at | 1174 | 3.2140 | 0.3863 | Yes | 205519_at | −1.4439 |
| REL | Blue_D | SPAG5 | 203145_at | 1346 | 3.0210 | 0.3885 | Yes | 203145_at | −2.3469 |
| REL | Blue_D | RAD54L | 204558_at | 1435 | 2.9363 | 0.3966 | Yes | 204558_at | −1.6082 |
| REL | Blue_D | NDUFA9 | 208969_at | 1443 | 2.9265 | 0.4109 | Yes | 208969_at | −1.0903 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| REL | Blue_D | B4GALNT1 | 206435_at | 1445 | 2.9244 | 0.4257 | Yes | 206435_at | −1.0926 |
| REL | Blue_D | STK6 | 208080_at | 1506 | 2.8620 | 0.4356 | Yes | 208079_s_at | −1.8883 |
| REL | Blue_D | RFC2 | 203696_s_at | 1611 | 2.7822 | 0.4418 | Yes | 203696_s_at | −1.5179 |
| REL | Blue_D | C16orf59 | 219556_at | 1616 | 2.7796 | 0.4556 | Yes | 219556_at | −1.0807 |
| REL | Blue_D | SLC2A1 | 201250_s_at | 1763 | 2.6513 | 0.4578 | Yes | 201250_s_at | −1.9684 |
| REL | Blue_D | CDCA3 | 221436_s_at | 1916 | 2.5188 | 0.4588 | Yes | 223307_at | −1.9094 |
| REL | Blue_D | TACC3 | 218308_at | 1980 | 2.4728 | 0.4665 | Yes | 218308_at | −1.3035 |
| REL | Blue_D | TUBA1C | 209251_x_at | 2026 | 2.4482 | 0.4755 | Yes | 209251_x_at | −1.1616 |
| REL | Blue_D | PGAM1 | 200886_s_at | 2202 | 2.3157 | 0.4738 | Yes | 200886_s_at | −1.2903 |
| REL | Blue_D | ESPL1 | 38158_at | 2234 | 2.2999 | 0.4831 | Yes | 38158_at | −1.8588 |
| REL | Blue_D | CDC45L | 204126_s_at | 2416 | 2.1831 | 0.4802 | No | 204126_s_at | −2.4023 |
| REL | Blue_D | ATAD2 | 218782_s_at | 2746 | 1.9874 | 0.4649 | No | 218782_s_at | −2.5687 |
| REL | Blue_D | H2AFX | 205436_s_at | 2927 | 1.8902 | 0.4606 | No | 205436_s_at | −1.4748 |
| REL | Blue_D | TUBA1B | 211058_x_at | 3081 | 1.8086 | 0.4580 | No | 211058_x_at | −1.1876 |
| REL | Blue_D | SLCO4A1 | 219911_s_at | 3134 | 1.7744 | 0.4630 | No | 219911_s_at | −2.0069 |
| REL | Blue_D | CDC6 | 203968_s_at | 3282 | 1.6954 | 0.4602 | No | 203968_s_at | −2.5641 |
| REL | Blue_D | CHAF1B | 204775_at | 3285 | 1.6946 | 0.4687 | No | 204775_at | −1.3219 |
| REL | Blue_D | SLC7A5 | 201195_s_at | 3837 | 1.4381 | 0.4335 | No | 201195_s_at | −2.6903 |
| REL | Blue_D | EBP | 213787_s_at | 4064 | 1.3233 | 0.4227 | No | 213787_s_at | −1.7595 |
| REL | Blue_D | POLA2 | 204441_s_at | 4299 | 1.2071 | 0.4108 | No | 204441_s_at | −1.5960 |
| REL | Blue_D | SLC7A1 | 212295_s_at | 4336 | 1.1920 | 0.4141 | No | 212295_s_at | −1.0932 |
| REL | Blue_D | FANCG | 203564_at | 4391 | 1.1733 | 0.4159 | No | 203564_at | −1.1180 |
| REL | Blue_D | KIF2C | 209408_at | 4579 | 1.0956 | 0.4070 | No | 209408_at | −2.0440 |
| REL | Blue_D | TOR3A | 218459_at | 5039 | 0.9018 | 0.3761 | No | 218459_at | −1.3546 |
| REL | Blue_D | MYBL2 | 201710_at | 5195 | 0.8274 | 0.3684 | No | 201710_at | −2.6352 |
| REL | Blue_D | MCM5 | 201755_at | 5591 | 0.6541 | 0.3412 | No | 216237_s_at | −2.2926 |
| REL | Blue_D | CDC25A | 204696_s_at | 6005 | 0.4943 | 0.3118 | No | 204695_at | −2.3587 |
| REL | Blue_D | SUV39H1 | 218619_s_at | 6132 | 0.4496 | 0.3044 | No | 218619_s_at | −1.1582 |
| REL | Blue_D | SLC35B1 | 202433_at | 6536 | 0.2903 | 0.2747 | No | 202433_at | −0.8310 |
| REL | Blue_D | LDLR | 217173_s_at | 6549 | 0.2867 | 0.2752 | No | 202068_s_at | −3.1745 |
| REL | Blue_D | BLM | 205733_at | 6657 | 0.2431 | 0.2682 | No | 205733_at | −1.5970 |
| REL | Blue_D | DBF4B | 206661_at | 6833 | 0.1672 | 0.2556 | No | 238508_at | −1.7101 |
| REL | Blue_D | TFRC | 207332_s_at | 6934 | 0.1228 | 0.2485 | No | 207332_s_at | −1.6352 |
| REL | Blue_D | PLK1 | 202240_at | 7122 | 0.0585 | 0.2343 | No | 202240_at | −1.9567 |
| REL | Blue_D | E2F2 | 207042_at | 7247 | 0.0096 | 0.2248 | No | 228361_at | −2.5642 |
| REL | Blue_D | RBM14 | 204178_s_at | 7573 | −0.1153 | 0.2003 | No | 204178_s_at | −1.6436 |
| REL | Blue_D | MPDU1 | 209208_at | 7633 | −0.1409 | 0.1964 | No | 209208_at | −1.7427 |
| REL | Blue_D | MCM4 | 214349_at | 8312 | −0.4196 | 0.1462 | No | 212141_at | −2.3064 |
| REL | Blue_D | LMAN2L | 221274_s_at | 8361 | −0.4396 | 0.1447 | No | 221274_s_at | −0.9061 |
| REL | Blue_D | CDC25C | 216914_at | 8559 | −0.5303 | 0.1322 | No | 205167_s_at | −1.7970 |
| REL | Blue_D | NCAPH | 212949_at | 8816 | −0.6418 | 0.1157 | No | 212949_at | −2.1530 |
| REL | Blue_D | SLC19A1 | 209777_s_at | 9943 | −1.2122 | 0.0349 | No | 209777_s_at | −1.4453 |
| REL | Blue_D | TXNDC15 | 220495_s_at | 10021 | −1.2624 | 0.0354 | No | 220495_s_at | −1.5473 |
| REL | Blue_D | ELOVL1 | 218028_at | 10515 | −1.6001 | 0.0054 | No | 57163_at | −1.0254 |
| REL | Blue_D | LMNB1 | 203276_at | 10790 | −1.7920 | −0.0066 | No | 203276_at | −1.5790 |
| REL | Blue_D | TEX261 | 212083_at | 10963 | −1.9292 | −0.0101 | No | 212083_at | −0.9444 |
| REL | Blue_D | SCARB1 | 201819_at | 11512 | −2.4089 | −0.0402 | No | 1552256_a_at | −2.4284 |
| REL | Blue_D | ZNF107 | 205739_x_at | 11943 | −2.9488 | −0.0584 | No | 243312_at | −0.9633 |
| REL | Blue_D | AMDHD2 | 219082_at | 11980 | −2.9996 | −0.0459 | No | 219082_at | −0.8216 |
| REL | Blue_D | GALE | 202528_at | 12266 | −3.4652 | −0.0503 | No | 202528_at | −1.0641 |
| REL | Blue_D | FOXM1 | 214148_at | 12373 | −3.7001 | −0.0397 | No | 202580_x_at | −2.2845 |
| REL | Blue_D | TPST2 | 204079_at | 12415 | −3.8061 | −0.0235 | No | 204079_at | −0.5365 |
| REL | Blue_D | SCD | 200831_s_at | 12468 | −3.9750 | −0.0073 | No | 200832_s_at | −2.0573 |
| REL | Blue_D | DBNDD2 | 218094_s_at | 12648 | −4.7521 | 0.0030 | No | 238470_at | −0.4043 |
| REL | Blue_D | CENPM | 218741_at | 12732 | −5.1782 | 0.0229 | No | 218741_at | −2.1860 |
| REL | Blue_U | CAMSAP1L1 | 212763_at | 3086 | 1.8072 | −0.2019 | No | 212765_at | 0.8007 |
| REL | Blue_U | SATB1 | 203408_s_at | 4956 | 0.9356 | −0.3273 | No | 203408_s_at | 2.2924 |
| REL | Blue_U | PHC3 | 215521_at | 8656 | −0.5726 | −0.6004 | No | 226508_at | 1.3199 |
| REL | Blue_U | CALCOCO1 | 209002_s_at | 11181 | −2.1165 | −0.7531 | No | 209002_s_at | 1.3443 |
| REL | Blue_U | HLA-DRB4 | 209728_at | 12016 | −3.0505 | −0.7579 | Yes | 209728_at | 3.1361 |
| REL | Blue_U | HLA-DRB6 | 217362_x_at | 12337 | −3.6077 | −0.7124 | Yes | 217362_x_at | 1.3574 |
| REL | Blue_U | LOC731682 | 212671_s_at | 12698 | −5.0029 | −0.6428 | Yes | 212671_s_at | 2.2805 |
| REL | Blue_U | HLA-DMA | 217478_s_at | 12750 | −5.2774 | −0.5441 | Yes | 217478_s_at | 1.4991 |
| REL | Blue_U | HLA-DRB1 | 204670_x_at | 12760 | −5.3403 | −0.4410 | Yes | 208306_x_at | 1.2895 |
| REL | Blue_U | SPARCL1 | 200795_at | 12773 | −5.3886 | −0.3372 | Yes | 200795_at | 1.1056 |
| REL | Blue_U | HLA-DQB1 | 211654_x_at | 12782 | −5.4329 | −0.2322 | Yes | 211654_x_at | 1.3513 |
| REL | Blue_U | HLA-DPB1 | 201137_s_at | 12883 | −6.3478 | −0.1164 | Yes | 201137_s_at | 1.5092 |
| REL | Blue_U | LOC100294276 | 209312_x_at | 12901 | −6.5635 | 0.0098 | Yes | 209312_x_at | 1.3887 |
| REL | DG_D | SET | 200630_x_at | 62 | 6.3658 | 0.0154 | Yes | 200630_x_at | −0.6487 |
| REL | DG_D | PA2G4 | 208676_s_at | 131 | 5.5736 | 0.0278 | Yes | 208676_s_at | −0.8555 |
| REL | DG_D | STOML2 | 215416_s_at | 179 | 5.3046 | 0.0409 | Yes | 215416_s_at | −1.2177 |
| REL | DG_D | CTPS | 202613_at | 200 | 5.1687 | 0.0558 | Yes | 202613_at | −1.3500 |
| REL | DG_D | TUBB | 211714_x_at | 218 | 5.0694 | 0.0705 | Yes | 211714_x_at | −1.5976 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| REL | DG_D | PPP2R4 | 208874_x_at | 219 | 5.0638 | 0.0866 | Yes | 206452_x_at | −1.1045 |
| REL | DG_D | FAM20B | 202915_s_at | 251 | 4.9331 | 0.0998 | Yes | 202916_s_at | −0.8598 |
| REL | DG_D | ANP32B | 201306_s_at | 274 | 4.8179 | 0.1134 | Yes | 201306_s_at | −1.2696 |
| REL | DG_D | UTP20 | 209725_at | 283 | 4.7962 | 0.1280 | Yes | 209725_at | −1.0034 |
| REL | DG_D | HNRNPL | 35201_at | 299 | 4.7494 | 0.1419 | Yes | 35201_at | −0.6733 |
| REL | DG_D | EXOSC2 | 214507_s_at | 380 | 4.5042 | 0.1499 | Yes | 209527_s_at | −0.8969 |
| REL | DG_D | ZNF696 | 220967_s_at | 424 | 4.3760 | 0.1605 | Yes | 220967_s_at | −0.5543 |
| REL | DG_D | OBFC2B | 218903_s_at | 463 | 4.2773 | 0.1711 | Yes | 218903_s_at | −1.0793 |
| REL | DG_D | TTLL12 | 216251_s_at | 495 | 4.2001 | 0.1820 | Yes | 1552257_a_at | −0.8222 |
| REL | DG_D | AVEN | 219366_at | 498 | 4.1955 | 0.1951 | Yes | 219366_at | −1.1898 |
| REL | DG_D | UBL4A | 221746_at | 548 | 4.0907 | 0.2043 | Yes | 221746_at | −0.8816 |
| REL | DG_D | H3F3A | 213828_x_at | 593 | 4.0070 | 0.2136 | Yes | 213828_x_at | −0.5502 |
| REL | DG_D | HCFC1 | 202474_s_at | 606 | 3.9773 | 0.2253 | Yes | 202474_s_at | −0.8665 |
| REL | DG_D | CASP2 | 209812_x_at | 748 | 3.7654 | 0.2263 | Yes | 226032_at | −0.3234 |
| REL | DG_D | SLC10A3 | 204928_s_at | 828 | 3.6249 | 0.2316 | Yes | 204928_s_at | −0.8831 |
| REL | DG_D | HNRNPAB | 201277_s_at | 829 | 3.6242 | 0.2431 | Yes | 201277_s_at | −0.9573 |
| REL | DG_D | TXNRD2 | 211177_s_at | 858 | 3.5880 | 0.2523 | Yes | 211177_s_at | −0.9959 |
| REL | DG_D | HAUS7 | 213334_x_at | 862 | 3.5795 | 0.2634 | Yes | 213334_x_at | −1.1222 |
| REL | DG_D | NTRK2 | 207152_at | 893 | 3.5452 | 0.2723 | Yes | 221795_at | −1.3961 |
| REL | DG_D | HSPD1 | 200807_s_at | 895 | 3.5440 | 0.2835 | Yes | 200807_s_at | −0.7713 |
| REL | DG_D | MRPS15 | 221437_s_at | 918 | 3.5115 | 0.2929 | Yes | 226296_s_at | −1.1799 |
| REL | DG_D | SMARCA4 | 212520_s_at | 948 | 3.4679 | 0.3017 | Yes | 213720_s_at | −0.8869 |
| REL | DG_D | ACP6 | 218795_at | 1006 | 3.3965 | 0.3080 | Yes | 218795_at | −0.7372 |
| REL | DG_D | TMEM231 | 219182_at | 1008 | 3.3912 | 0.3187 | Yes | 219182_at | −0.8038 |
| REL | DG_D | ALDOA | 214687_x_at | 1096 | 3.2870 | 0.3224 | Yes | 200966_x_at | −1.5531 |
| REL | DG_D | FARSA | 216602_s_at | 1100 | 3.2844 | 0.3325 | Yes | 202159_at | −0.5879 |
| REL | DG_D | TH1L | 220607_x_at | 1104 | 3.2803 | 0.3427 | Yes | 225006_x_at | −0.7325 |
| REL | DG_D | AIFM1 | 205512_s_at | 1130 | 3.2555 | 0.3511 | Yes | 205512_s_at | −1.1566 |
| REL | DG_D | PSMD8 | 200820_at | 1139 | 3.2455 | 0.3608 | Yes | 200820_at | −1.0159 |
| REL | DG_D | WBSCR16 | 221247_s_at | 1180 | 3.2048 | 0.3678 | Yes | 221247_s_at | −1.3786 |
| REL | DG_D | IARS | 204744_s_at | 1195 | 3.1883 | 0.3768 | Yes | 204744_s_at | −0.6682 |
| REL | DG_D | LDLRAP1 | 57082_at | 1200 | 3.1828 | 0.3866 | Yes | 57082_at | −0.9713 |
| REL | DG_D | SSRP1 | 200957_s_at | 1220 | 3.1613 | 0.3952 | Yes | 200957_s_at | −1.0802 |
| REL | DG_D | HDGF | 200896_x_at | 1253 | 3.1247 | 0.4026 | Yes | 200896_x_at | −1.6718 |
| REL | DG_D | NOLC1 | 211951_at | 1257 | 3.1190 | 0.4122 | Yes | 211951_at | −0.6006 |
| REL | DG_D | DHODH | 213632_at | 1273 | 3.1067 | 0.4209 | Yes | 213632_at | −1.0196 |
| REL | DG_D | LAS1L | 208117_s_at | 1400 | 2.9714 | 0.4206 | Yes | 208117_s_at | −0.6863 |
| REL | DG_D | NDUFS3 | 201740_at | 1513 | 2.8581 | 0.4209 | Yes | 201740_at | −0.7718 |
| REL | DG_D | HMGA1 | 206074_s_at | 1609 | 2.7830 | 0.4224 | Yes | 206074_s_at | −0.8315 |
| REL | DG_D | MEPCE | 219798_s_at | 1721 | 2.6916 | 0.4223 | Yes | 219798_s_at | −0.5653 |
| REL | DG_D | KEAP1 | 202417_at | 1776 | 2.6446 | 0.4265 | Yes | 202417_at | −1.0833 |
| REL | DG_D | SNRPA | 201770_at | 1833 | 2.5985 | 0.4304 | Yes | 201770_at | −1.0990 |
| REL | DG_D | ECH1 | 200789_at | 1834 | 2.5970 | 0.4386 | Yes | 200789_at | −0.9580 |
| REL | DG_D | CWF19L1 | 218787_x_at | 1870 | 2.5652 | 0.4440 | Yes | 233568_x_at | −0.5411 |
| REL | DG_D | LMNB2 | 216952_s_at | 1956 | 2.4871 | 0.4453 | Yes | 216952_s_at | −0.5609 |
| REL | DG_D | NR2F6 | 209262_s_at | 1981 | 2.4718 | 0.4513 | Yes | 209262_s_at | −0.6575 |
| REL | DG_D | GYS1 | 201673_s_at | 2017 | 2.4539 | 0.4564 | Yes | 201673_s_at | −1.0184 |
| REL | DG_D | OXCT1 | 202780_at | 2059 | 2.4173 | 0.4609 | Yes | 202780_at | −1.1391 |
| REL | DG_D | C2orf18 | 219783_at | 2139 | 2.3666 | 0.4622 | Yes | 225695_at | −0.9088 |
| REL | DG_D | LASS2 | 222212_s_at | 2171 | 2.3438 | 0.4672 | Yes | 222212_s_at | −0.8812 |
| REL | DG_D | WDR4 | 221632_s_at | 2193 | 2.3244 | 0.4730 | Yes | 241937_s_at | −0.9790 |
| REL | DG_D | FASTKD2 | 216996_s_at | 2248 | 2.2891 | 0.4761 | Yes | 216996_s_at | −0.7328 |
| REL | DG_D | PARP1 | 208644_at | 2284 | 2.2666 | 0.4805 | Yes | 208644_at | −0.7776 |
| REL | DG_D | STAG3L4 | 218994_s_at | 2348 | 2.2203 | 0.4827 | Yes | 222801_s_at | −0.8323 |
| REL | DG_D | GCAT | 36475_at | 2433 | 2.1706 | 0.4830 | Yes | 205164_at | −0.8760 |
| REL | DG_D | MBTPS2 | 206473_s_at | 2447 | 2.1620 | 0.4889 | Yes | 226760_at | −1.0883 |
| REL | DG_D | SNRNP25 | 218493_at | 2535 | 2.1041 | 0.4888 | Yes | 218493_at | −1.6572 |
| REL | DG_D | ODC1 | 200790_at | 2616 | 2.0576 | 0.4891 | Yes | 200790_at | −1.2573 |
| REL | DG_D | NASP | 201970_s_at | 2678 | 2.0217 | 0.4908 | Yes | 201970_s_at | −1.1638 |
| REL | DG_D | HK2 | 202934_at | 2683 | 2.0188 | 0.4969 | Yes | 202934_at | −1.3557 |
| REL | DG_D | TUBGCP4 | 211337_s_at | 2900 | 1.8994 | 0.4861 | No | 211337_s_at | −0.7043 |
| REL | DG_D | ADAM22 | 208227_x_at | 2916 | 1.8947 | 0.4910 | No | 208227_x_at | −0.9814 |
| REL | DG_D | DUSP7 | 213848_at | 3106 | 1.7915 | 0.4820 | No | 213848_at | −0.6568 |
| REL | DG_D | RCC1 | 215747_s_at | 3140 | 1.7679 | 0.4850 | No | 206499_s_at | −1.2427 |
| REL | DG_D | TMPO | 203432_at | 3267 | 1.7037 | 0.4807 | No | 209753_s_at | −1.5300 |
| REL | DG_D | TRMT2B | 205238_at | 3339 | 1.6687 | 0.4804 | No | 205238_at | −1.5340 |
| REL | DG_D | MFNG | 204153_s_at | 3454 | 1.6129 | 0.4767 | No | 204153_s_at | −1.2757 |
| REL | DG_D | TRIM25 | 206911_at | 3477 | 1.6021 | 0.4801 | No | 224806_at | −0.6249 |
| REL | DG_D | ADA | 204639_at | 3665 | 1.5152 | 0.4704 | No | 204639_at | −1.2155 |
| REL | DG_D | DDX54 | 219111_s_at | 3776 | 1.4633 | 0.4665 | No | 219111_s_at | −1.0228 |
| REL | DG_D | SPHK2 | 209857_s_at | 3833 | 1.4391 | 0.4667 | No | 40273_at | −0.8702 |
| REL | DG_D | SUPT16H | 217815_at | 3835 | 1.4387 | 0.4712 | No | 217815_at | −0.5370 |
| REL | DG_D | TSHR | 215443_at | 3924 | 1.3918 | 0.4688 | No | 215443_at | −1.4748 |

TABLE 5-continued

The numerical values from the GSEA for each gene contributing to the significant
enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| REL | DG_D | PRR3 | 204795_at | 4040 | 1.3336 | 0.4641 | No | 204795_at | −0.7039 |
| REL | DG_D | IVD | 203682_s_at | 4126 | 1.2920 | 0.4616 | No | 225311_at | −0.5473 |
| REL | DG_D | FKBP4 | 200895_s_at | 4181 | 1.2618 | 0.4614 | No | 200895_s_at | −1.1436 |
| REL | DG_D | EXOG | 205521_at | 4435 | 1.1541 | 0.4454 | No | 205521_at | −1.0107 |
| REL | DG_D | C20orf7 | 219524_s_at | 4555 | 1.1033 | 0.4397 | No | 227160_s_at | −0.7371 |
| REL | DG_D | GTF2H3 | 222104_x_at | 4573 | 1.0975 | 0.4418 | No | 1554599_x_at | −0.6423 |
| REL | DG_D | AHSA1 | 201491_at | 4612 | 1.0833 | 0.4423 | No | 201491_at | −0.9841 |
| REL | DG_D | TRIB2 | 202479_s_at | 4816 | 0.9907 | 0.4297 | No | 202478_s_at | −0.7855 |
| REL | DG_D | TSR1 | 218155_x_at | 4893 | 0.9621 | 0.4268 | No | 218156_s_at | −1.4890 |
| REL | DG_D | WDR77 | 201420_s_at | 5094 | 0.8752 | 0.4141 | No | 201421_s_at | −0.5241 |
| REL | DG_D | UROD | 208971_at | 5159 | 0.8491 | 0.4118 | No | 208970_s_at | −0.6909 |
| REL | DG_D | ALDH18A1 | 217791_s_at | 5322 | 0.7769 | 0.4017 | No | 217791_s_at | −0.8960 |
| REL | DG_D | LOC389906 | 59433_at | 5648 | 0.6302 | 0.3785 | No | 1556102_x_at | −0.4763 |
| REL | DG_D | TOE1 | 204080_at | 5739 | 0.5931 | 0.3734 | No | 204080_at | −1.0473 |
| REL | DG_D | ACACA | 212186_at | 6088 | 0.4629 | 0.3479 | No | 212186_at | −0.8638 |
| REL | DG_D | NVL | 207877_s_at | 6282 | 0.3882 | 0.3341 | No | 207877_s_at | −0.6853 |
| REL | DG_D | FAM57A | 218898_at | 6447 | 0.3281 | 0.3224 | No | 218898_at | −1.7645 |
| REL | DG_D | DNASE1L1 | 203912_s_at | 6579 | 0.2749 | 0.3131 | No | 203912_s_at | −1.0443 |
| REL | DG_D | GEMIN4 | 217099_s_at | 6586 | 0.2711 | 0.3135 | No | 217099_s_at | −1.0276 |
| REL | DG_D | SF3B3 | 200687_s_at | 6633 | 0.2539 | 0.3108 | No | 200687_s_at | −0.7666 |
| REL | DG_D | ACO2 | 200793_s_at | 6640 | 0.2519 | 0.3111 | No | 200793_s_at | −0.9497 |
| REL | DG_D | GPATCH1 | 219818_s_at | 6673 | 0.2377 | 0.3094 | No | 219818_s_at | −0.6849 |
| REL | DG_D | MIPEP | 204305_at | 6750 | 0.2026 | 0.3041 | No | 204305_at | −0.8696 |
| REL | DG_D | PAK2 | 208877_at | 6756 | 0.2014 | 0.3044 | No | 208877_at | −0.6734 |
| REL | DG_D | CHD1L | 212539_at | 6920 | 0.1281 | 0.2921 | No | 212539_at | −0.8681 |
| REL | DG_D | COIL | 203654_s_at | 7197 | 0.0289 | 0.2708 | No | 203654_s_at | −0.6094 |
| REL | DG_D | PPPDE2 | 212527_at | 7229 | 0.0144 | 0.2684 | No | 212527_at | −0.8438 |
| REL | DG_D | JMJD4 | 218560_s_at | 7357 | −0.0285 | 0.2587 | No | 218560_s_at | −0.9034 |
| REL | DG_D | HMGN2 | 208668_x_at | 7464 | −0.0749 | 0.2507 | No | 208668_x_at | −1.0775 |
| REL | DG_D | THOC5 | 209418_s_at | 7505 | −0.0887 | 0.2478 | No | 209418_s_at | −0.7584 |
| REL | DG_D | BID | 211725_s_at | 7733 | −0.1828 | 0.2308 | No | 211725_s_at | −1.3437 |
| REL | DG_D | HNRNPA3P1 | 206809_s_at | 7871 | −0.2393 | 0.2209 | No | 206809_s_at | −1.2047 |
| REL | DG_D | GMIP | 218913_s_at | 7905 | −0.2534 | 0.2192 | No | 218913_s_at | −0.6103 |
| REL | DG_D | SFMBT1 | 213370_s_at | 8017 | −0.2951 | 0.2115 | No | 213370_s_at | −0.6881 |
| REL | DG_D | LARS2 | 204016_at | 8168 | −0.3576 | 0.2010 | No | 204016_at | −0.7286 |
| REL | DG_D | USP13 | 205356_at | 8298 | −0.4157 | 0.1923 | No | 205356_at | −0.8452 |
| REL | DG_D | MED25 | 208110_x_at | 8469 | −0.4948 | 0.1807 | No | 1553993_s_at | −0.6889 |
| REL | DG_D | CCDC22 | 214037_s_at | 8712 | −0.6004 | 0.1638 | No | 206016_at | −0.8115 |
| REL | DG_D | NT5DC2 | 218051_s_at | 8716 | −0.6008 | 0.1655 | No | 218051_s_at | −1.2878 |
| REL | DG_D | MPHOSPH6 | 203740_at | 8749 | −0.6126 | 0.1649 | No | 203740_at | −1.0146 |
| REL | DG_D | DCPS | 218774_at | 9158 | −0.8174 | 0.1359 | No | 218774_at | −1.3790 |
| REL | DG_D | AGAP1 | 204066_s_at | 9351 | −0.9111 | 0.1238 | No | 204066_s_at | −1.1009 |
| REL | DG_D | H2AFY | 207168_s_at | 9384 | −0.9287 | 0.1243 | No | 207168_s_at | −0.6011 |
| REL | DG_D | MAPKAPK5 | 212871_at | 9663 | −1.0671 | 0.1061 | No | 212871_at | −1.1799 |
| REL | DG_D | NOL12 | 219324_at | 9839 | −1.1574 | 0.0962 | No | 219324_at | −1.3931 |
| REL | DG_D | FAM118A | 219629_at | 9860 | −1.1660 | 0.0984 | No | 226475_at | −0.4186 |
| REL | DG_D | MGC72080 | 217499_x_at | 9951 | −1.2165 | 0.0952 | No | 217499_x_at | −1.7349 |
| REL | DG_D | MED12 | 211342_x_at | 10043 | −1.2734 | 0.0922 | No | 216071_x_at | −0.6591 |
| REL | DG_D | NF2 | 218915_at | 10086 | −1.3030 | 0.0931 | No | 218915_at | −0.8814 |
| REL | DG_D | MGLL | 211026_s_at | 10305 | −1.4409 | 0.0807 | No | 211026_s_at | −1.2329 |
| REL | DG_D | DFFB | 206752_s_at | 10395 | −1.5088 | 0.0786 | No | 206752_s_at | −0.6100 |
| REL | DG_D | CEP192 | 218827_s_at | 10498 | −1.5855 | 0.0757 | No | 218827_s_at | −0.5851 |
| REL | DG_D | SMARCB1 | 212167_s_at | 10649 | −1.6943 | 0.0694 | No | 212167_s_at | −1.0464 |
| REL | DG_D | LIG3 | 207348_s_at | 10651 | −1.6966 | 0.0747 | No | 204123_at | −1.5025 |
| REL | DG_D | IKBKE | 204549_at | 10759 | −1.7702 | 0.0721 | No | 204549_at | −0.7580 |
| REL | DG_D | MGC5566 | 220449_at | 11049 | −2.0001 | 0.0560 | No | 220449_at | −0.8044 |
| REL | DG_D | SCMH1 | 221216_s_at | 11108 | −2.0542 | 0.0580 | No | 221216_s_at | −0.6497 |
| REL | DG_D | INPP5A | 203006_at | 11147 | −2.0950 | 0.0617 | No | 203006_at | −0.7522 |
| REL | DG_D | BTN3A2 | 209846_s_at | 11207 | −2.1383 | 0.0639 | No | 209846_s_at | −0.4424 |
| REL | DG_D | ABL1 | 202123_s_at | 11570 | −2.4771 | 0.0436 | No | 202123_s_at | −0.6077 |
| REL | DG_D | DNMT3A | 218457_s_at | 11608 | −2.5326 | 0.0488 | No | 222640_at | −0.8989 |
| REL | DG_D | P2RX5 | 210448_s_at | 11648 | −2.5855 | 0.0540 | No | 210448_s_at | −1.2148 |
| REL | DG_D | CORO1B | 64486_at | 11825 | −2.7980 | 0.0492 | No | 64486_at | −0.5557 |
| REL | DG_D | DOCK2 | 213160_at | 12406 | −3.7855 | 0.0162 | No | 213160_at | −0.9284 |
| REL | DG_D | SHMT1 | 209980_s_at | 12630 | −4.6396 | 0.0136 | No | 224954_at | −0.7602 |
| REL | DG_D | CIDEB | 221188_s_at | 12784 | −5.4631 | 0.0190 | No | 221188_s_at | −0.7572 |
| REL | Red_D | B3GAT3 | 203452_at | 222 | 5.0576 | 0.0417 | Yes | 203452_at | −0.6670 |
| REL | Red_D | SSR2 | 200652_at | 228 | 5.0055 | 0.0995 | Yes | 200652_at | −0.4014 |
| REL | Red_D | CD320 | 218529_at | 269 | 4.8401 | 0.1527 | Yes | 218529_at | −1.4256 |
| REL | Red_D | SCAMP3 | 201771_at | 392 | 4.4735 | 0.1953 | Yes | 201771_at | −0.8416 |
| REL | Red_D | HIST1H2AJ | 208583_x_at | 546 | 4.0930 | 0.2311 | Yes | 208583_x_at | −0.7033 |
| REL | Red_D | TMED1 | 203679_at | 810 | 3.6501 | 0.2532 | Yes | 203679_at | −1.1221 |
| REL | Red_D | HMBS | 203040_s_at | 830 | 3.6231 | 0.2939 | Yes | 203040_s_at | −0.5190 |

TABLE 5-continued

The numerical values from the GSEA for each gene contributing to the significant
enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | $\text{Log}^2$ Fold Change Combination |
|---|---|---|---|---|---|---|---|---|---|
| REL | Red_D | TMED3 | 208837_at | 1037 | 3.3568 | 0.3170 | Yes | 208837_at | −0.8660 |
| REL | Red_D | PTTG1 | 203554_x_at | 1248 | 3.1302 | 0.3373 | Yes | 203554_x_at | −0.8401 |
| REL | Red_D | SCAMP2 | 218143_s_at | 1416 | 2.9547 | 0.3587 | Yes | 218143_s_at | −0.9440 |
| REL | Red_D | DHCR7 | 201790_s_at | 1463 | 2.9060 | 0.3890 | Yes | 201791_s_at | −1.5161 |
| REL | Red_D | SMPD1 | 209420_s_at | 1597 | 2.7967 | 0.4112 | Yes | 209420_s_at | −0.7122 |
| REL | Red_D | CLN6 | 218161_s_at | 1656 | 2.7440 | 0.4387 | Yes | 1567080_s_at | −1.0284 |
| REL | Red_D | CORO1A | 209083_at | 2191 | 2.3267 | 0.4246 | Yes | 209083_at | −1.5068 |
| REL | Red_D | INHBE | 210587_at | 2288 | 2.2638 | 0.4435 | Yes | 210587_at | −3.5505 |
| REL | Red_D | SLC37A4 | 202830_s_at | 2772 | 1.9665 | 0.4292 | No | 202830_s_at | −0.7995 |
| REL | Red_D | SLC7A11 | 207528_s_at | 3605 | 1.5387 | 0.3830 | No | 209921_at | −2.0492 |
| REL | Red_D | TROAP | 204649_at | 3944 | 1.3797 | 0.3731 | No | 1568596_a_at | −1.0917 |
| REL | Red_D | ATP6V0B | 200078_s_at | 4290 | 1.2127 | 0.3606 | No | 200078_s_at | −0.8093 |
| REL | Red_D | TMEM109 | 201361_at | 5650 | 0.6302 | 0.2633 | No | 201361_at | −0.6692 |
| REL | Red_D | KIFC1 | 209680_s_at | 5701 | 0.6070 | 0.2665 | No | 209680_s_at | −1.0635 |
| REL | Red_D | ABHD11 | 221927_s_at | 6076 | 0.4685 | 0.2432 | No | 221927_s_at | −0.5400 |
| REL | Red_D | VAV1 | 206219_s_at | 6286 | 0.3869 | 0.2316 | No | 206219_s_at | −0.8382 |
| REL | Red_D | SREBF1 | 202308_at | 7719 | −0.1743 | 0.1234 | No | 202308_at | −1.5501 |
| REL | Red_D | UPP1 | 203234_at | 7758 | −0.1941 | 0.1227 | No | 203234_at | −0.7584 |
| REL | Red_D | CD79B | 205297_s_at | 8311 | −0.4196 | 0.0851 | No | 205297_s_at | −1.1874 |
| REL | Red_D | DHRS7B | 220690_s_at | 8600 | −0.5498 | 0.0693 | No | 220690_s_at | −1.1801 |
| REL | Red_D | C20orf3 | 206656_s_at | 8672 | −0.5816 | 0.0706 | No | 206656_s_at | −0.4617 |
| REL | Red_D | PAQR4 | 212858_at | 8936 | −0.7100 | 0.0586 | No | 212858_at | −0.5606 |
| REL | Red_D | TNFRSF13B | 207641_at | 9372 | −0.9222 | 0.0358 | No | 207641_at | −0.9554 |
| REL | Red_D | GLT25D1 | 218473_s_at | 9550 | −1.0132 | 0.0340 | No | 218473_s_at | −0.8308 |
| REL | Red_D | ATP6V0C | 36994_at | 9607 | −1.0407 | 0.0418 | No | 36994_at | −0.7413 |
| REL | Red_D | B3GNT1 | 203188_at | 9795 | −1.1335 | 0.0405 | No | 203188_at | −0.4636 |
| REL | Red_D | INSIG1 | 201627_s_at | 9826 | −1.1512 | 0.0516 | No | 201625_s_at | −2.5371 |
| REL | Red_D | P2RX4 | 204088_at | 10907 | −1.8877 | −0.0096 | No | 204088_at | −1.0043 |
| REL | Red_D | DIAPH1 | 215541_s_at | 11154 | −2.1002 | −0.0041 | No | 209190_s_at | −0.6448 |
| REL | Red_D | IL21R | 221658_s_at | 11635 | −2.5666 | −0.0112 | No | 221658_s_at | −0.9819 |
| REL | Red_D | NEU1 | 208926_at | 11686 | −2.6250 | 0.0154 | No | 208926_at | −1.4294 |
| REL | Red_D | NINJ1 | 203045_at | 12396 | −3.7631 | 0.0046 | No | 203045_at | −0.5586 |
| REL | Red_D | SCNN1B | 205464_at | 12407 | −3.7926 | 0.0479 | No | 205464_at | −1.6399 |
| REL | SG_U | PEX16 | 49878_at | 77 | 6.1415 | 0.0097 | No | 49878_at | 0.3663 |
| REL | SG_U | NCAM1 | 212843_at | 371 | 4.5538 | −0.0014 | No | 227394_at | 2.6276 |
| REL | SG_U | BCAS4 | 220588_at | 481 | 4.2354 | 0.0009 | No | 228787_s_at | 0.6012 |
| REL | SG_U | SND1 | 201622_at | 507 | 4.1796 | 0.0097 | No | 201622_at | 0.3683 |
| REL | SG_U | HRASLS2 | 216760_at | 558 | 4.0683 | 0.0162 | No | 221122_at | 2.3804 |
| REL | SG_U | EEF1A2 | 204540_at | 609 | 3.9678 | 0.0225 | No | 204540_at | 1.2188 |
| REL | SG_U | ARHGEF9 | 203263_s_at | 650 | 3.9132 | 0.0294 | No | 203264_s_at | 1.1637 |
| REL | SG_U | IL12A | 207160_at | 713 | 3.8174 | 0.0343 | No | 207160_at | 0.7546 |
| REL | SG_U | FBXL2 | 214436_at | 823 | 3.6326 | 0.0352 | No | 214436_at | 0.9636 |
| REL | SG_U | CBLN1 | 205747_at | 966 | 3.4399 | 0.0329 | No | 205747_at | 0.4504 |
| REL | SG_U | GPRC5D | 221297_at | 1007 | 3.3955 | 0.0385 | No | 221297_at | 1.4466 |
| REL | SG_U | PTPRD | 205712_at | 1140 | 3.2449 | 0.0365 | No | 214043_at | 1.3101 |
| REL | SG_U | CYP26B1 | 219825_at | 1239 | 3.1458 | 0.0369 | No | 219825_at | 1.8184 |
| REL | SG_U | C7orf58 | 220032_at | 1264 | 3.1128 | 0.0430 | No | 228728_at | 1.2195 |
| REL | SG_U | SERPINI1 | 205352_at | 1429 | 2.9449 | 0.0378 | No | 205352_at | 1.2988 |
| REL | SG_U | PPAP2A | 209147_s_at | 1590 | 2.8000 | 0.0325 | No | 209147_s_at | 0.9661 |
| REL | SG_U | SATB2 | 213435_at | 1591 | 2.8000 | 0.0397 | No | 213435_at | 1.0194 |
| REL | SG_U | SERPINE1 | 202627_s_at | 1822 | 2.6065 | 0.0284 | No | 202627_s_at | 0.7062 |
| REL | SG_U | NBEA | 221207_s_at | 1907 | 2.5253 | 0.0284 | No | 226439_at | 0.7562 |
| REL | SG_U | MYH15 | 215331_at | 2016 | 2.4546 | 0.0262 | No | 215331_at | 0.7231 |
| REL | SG_U | TDRD7 | 213361_at | 2046 | 2.4254 | 0.0302 | No | 213361_at | 1.7645 |
| REL | SG_U | CYP2R1 | 207786_at | 2108 | 2.3826 | 0.0315 | No | 227109_at | 0.5272 |
| REL | SG_U | EXOC6B | 215417_at | 2346 | 2.2205 | 0.0188 | No | 225900_at | 1.4931 |
| REL | SG_U | RPH3A | 205230_at | 2376 | 2.2035 | 0.0222 | No | 205230_at | 0.2624 |
| REL | SG_U | CHST11 | 219634_at | 2413 | 2.1850 | 0.0249 | No | 226372_at | 0.7049 |
| REL | SG_U | UPK1A | 214624_at | 2571 | 2.0789 | 0.0180 | No | 214624_at | 1.1307 |
| REL | SG_U | ASPHD1 | 214993_at | 2638 | 2.0421 | 0.0181 | No | 1553997_a_at | 0.5512 |
| REL | SG_U | LOC730227 | 215756_at | 2994 | 1.8536 | −0.0048 | No | 215756_at | 0.6852 |
| REL | SG_U | PLA2G12A | 221027_s_at | 3136 | 1.7700 | −0.0112 | No | 242323_at | 0.9317 |
| REL | SG_U | NR4A3 | 209959_at | 3362 | 1.6572 | −0.0245 | No | 209959_at | 0.3849 |
| REL | SG_U | RASAL2 | 219026_s_at | 3406 | 1.6385 | −0.0237 | No | 222810_s_at | 1.6667 |
| REL | SG_U | FSD1 | 219170_at | 3419 | 1.6306 | −0.0204 | No | 219170_at | 0.4872 |
| REL | SG_U | BTG1 | 200920_s_at | 3684 | 1.5094 | −0.0371 | No | 200920_s_at | 1.3862 |
| REL | SG_U | RIMS3 | 210991_s_at | 3731 | 1.4850 | −0.0369 | No | 204730_at | 0.4244 |
| REL | SG_U | HBG2 | 204419_x_at | 3734 | 1.4833 | −0.0333 | No | 213515_x_at | 1.0411 |
| REL | SG_U | HBE1 | 205919_at | 3827 | 1.4406 | −0.0368 | No | 205919_at | 2.2651 |
| REL | SG_U | H1FX | 204805_s_at | 3933 | 1.3852 | −0.0414 | No | 204805_s_at | 1.6177 |
| REL | SG_U | ERC1 | 215606_s_at | 3959 | 1.3718 | −0.0398 | No | 226049_at | 0.9883 |
| REL | SG_U | AP3M2 | 203410_at | 4034 | 1.3344 | −0.0422 | No | 203410_at | 0.8868 |
| REL | SG_U | DNM1 | 217341_at | 4233 | 1.2381 | −0.0544 | No | 215116_s_at | 0.9290 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| REL | SG_U | SILV | 209848_s_at | 4266 | 1.2242 | −0.0538 | No | 209848_s_at | 1.4400 |
| REL | SG_U | PRAME | 204086_at | 4522 | 1.1152 | −0.0708 | No | 204086_at | 1.2914 |
| REL | SG_U | SQRDL | 217995_at | 4604 | 1.0863 | −0.0743 | No | 217995_at | 0.3155 |
| REL | SG_U | ARHGAP26 | 205068_s_at | 4668 | 1.0593 | −0.0765 | No | 205068_s_at | 0.3358 |
| REL | SG_U | MYH11 | 201497_x_at | 4711 | 1.0419 | −0.0771 | No | 201497_x_at | 1.2708 |
| REL | SG_U | HHLA3 | 220387_at | 4752 | 1.0211 | −0.0776 | No | 234665_x_at | 0.8157 |
| REL | SG_U | LHPP | 215061_at | 4774 | 1.0118 | −0.0767 | No | 218523_at | 0.8186 |
| REL | SG_U | CAV1 | 203065_s_at | 4880 | 0.9665 | −0.0824 | No | 203065_s_at | 1.6979 |
| REL | SG_U | OBSL1 | 214928_at | 4934 | 0.9440 | −0.0841 | No | 213946_s_at | 1.2912 |
| REL | SG_U | TMCC2 | 213096_at | 4945 | 0.9419 | −0.0825 | No | 213096_at | 0.8882 |
| REL | SG_U | MICAL2 | 212472_at | 5025 | 0.9086 | −0.0863 | No | 212473_at | 0.6345 |
| REL | SG_U | CHST7 | 206756_at | 5037 | 0.9027 | −0.0848 | No | 206756_at | 0.7672 |
| REL | SG_U | IL15 | 205992_s_at | 5149 | 0.8531 | −0.0913 | No | 205992_s_at | 2.3102 |
| REL | SG_U | PIK3CD | 211230_s_at | 5177 | 0.8428 | −0.0912 | No | 203879_at | 1.0301 |
| REL | SG_U | KLHL25 | 210307_s_at | 5341 | 0.7694 | −0.1020 | No | 210307_s_at | 0.3425 |
| REL | SG_U | SYT11 | 209197_at | 5411 | 0.7368 | −0.1055 | No | 209197_at | 1.3400 |
| REL | SG_U | SRGN | 201858_s_at | 5455 | 0.7205 | −0.1070 | No | 201858_s_at | 0.4139 |
| REL | SG_U | PBX1 | 212151_at | 5484 | 0.7046 | −0.1073 | No | 212151_at | 1.2989 |
| REL | SG_U | KIAA0319 | 206017_at | 5509 | 0.6921 | −0.1074 | No | 206017_at | 0.6121 |
| REL | SG_U | MARCH2 | 210075_at | 5513 | 0.6904 | −0.1059 | No | 210075_at | 0.7438 |
| REL | SG_U | RASA2 | 206636_at | 5606 | 0.6496 | −0.1114 | No | 230669_at | 0.9736 |
| REL | SG_U | SH3BGR | 204979_s_at | 5663 | 0.6242 | −0.1142 | No | 204979_s_at | 1.0822 |
| REL | SG_U | ABTB2 | 213497_at | 5688 | 0.6153 | −0.1145 | No | 213497_at | 0.6583 |
| REL | SG_U | CRIP2 | 208978_at | 5757 | 0.5835 | −0.1183 | No | 208978_at | 0.9262 |
| REL | SG_U | ZHX3 | 212545_s_at | 5788 | 0.5710 | −0.1191 | No | 217367_s_at | 0.7944 |
| REL | SG_U | TMEM187 | 204340_at | 5791 | 0.5705 | −0.1178 | No | 204340_at | 0.6830 |
| REL | SG_U | DLEU1 | 205677_s_at | 6210 | 0.4165 | −0.1493 | No | 205677_s_at | 1.0707 |
| REL | SG_U | JUP | 201015_s_at | 6257 | 0.3968 | −0.1519 | No | 201015_s_at | 0.7828 |
| REL | SG_U | MYO15A | 220288_at | 6351 | 0.3621 | −0.1582 | No | 220288_at | 0.7058 |
| REL | SG_U | ASAP3 | 222236_s_at | 6387 | 0.3492 | −0.1601 | No | 222236_s_at | 0.7455 |
| REL | SG_U | IFIT3 | 204747_at | 6629 | 0.2575 | −0.1782 | No | 204747_at | 0.6673 |
| REL | SG_U | HEY1 | 44783_s_at | 6734 | 0.2119 | −0.1857 | No | 44783_s_at | 3.2756 |
| REL | SG_U | FXYD1 | 205384_at | 6772 | 0.1943 | −0.1881 | No | 205384_at | 0.4831 |
| REL | SG_U | SRGAP2 | 213329_at | 6845 | 0.1625 | −0.1933 | No | 213329_at | 0.4920 |
| REL | SG_U | HSPB1 | 201841_s_at | 6907 | 0.1334 | −0.1977 | No | 201841_s_at | 0.5158 |
| REL | SG_U | SGK269 | 220008_at | 7008 | 0.1015 | −0.2053 | No | 225913_at | 1.0102 |
| REL | SG_U | WNT11 | 206737_at | 7106 | 0.0641 | −0.2127 | No | 206737_at | 1.1543 |
| REL | SG_U | ASMTL | 209394_at | 7116 | 0.0612 | −0.2132 | No | 36553_at | 1.1999 |
| REL | SG_U | SLC12A6 | 220740_s_at | 7249 | 0.0092 | −0.2235 | No | 226741_at | 0.6098 |
| REL | SG_U | TESK2 | 205486_at | 7390 | −0.0412 | −0.2343 | No | 205486_at | 0.9948 |
| REL | SG_U | CCL5 | 204655_at | 7469 | −0.0758 | −0.2402 | No | 1555759_a_at | 2.7666 |
| REL | SG_U | CHMP7 | 212313_at | 7519 | −0.0909 | −0.2438 | No | 212313_at | 0.4507 |
| REL | SG_U | TLE2 | 40837_at | 7589 | −0.1223 | −0.2488 | No | 40837_at | 1.4735 |
| REL | SG_U | KPTN | 220160_s_at | 7596 | −0.1270 | −0.2490 | No | 220160_s_at | 0.4342 |
| REL | SG_U | CYTH3 | 206523_at | 7634 | −0.1413 | −0.2515 | No | 225147_at | 0.6052 |
| REL | SG_U | TUFT1 | 205807_s_at | 7640 | −0.1423 | −0.2515 | No | 205807_s_at | 0.7280 |
| REL | SG_U | S100A10 | 200872_at | 7761 | −0.1959 | −0.2604 | No | 200872_at | 0.7729 |
| REL | SG_U | ENTPD2 | 207372_s_at | 7766 | −0.1969 | −0.2602 | No | 230430_at | 0.5358 |
| REL | SG_U | SLC4A8 | 207056_s_at | 7823 | −0.2212 | −0.2640 | No | 1554113_a_at | 0.4990 |
| REL | SG_U | SAP30L | 219129_s_at | 7947 | −0.2680 | −0.2729 | No | 225509_at | 1.4699 |
| REL | SG_U | EPB41L5 | 220977_x_at | 8148 | −0.3494 | −0.2875 | No | 225855_at | 1.1081 |
| REL | SG_U | CLIP2 | 211031_s_at | 8172 | −0.3585 | −0.2884 | No | 211031_s_at | 1.4226 |
| REL | SG_U | BTG2 | 201236_s_at | 8203 | −0.3758 | −0.2898 | No | 201236_s_at | 1.0197 |
| REL | SG_U | ARHGAP17 | 218076_s_at | 8227 | −0.3866 | −0.2906 | No | 218076_s_at | 0.9554 |
| REL | SG_U | RALGPS1 | 204199_at | 8282 | −0.4087 | −0.2938 | No | 204199_at | 1.8935 |
| REL | SG_U | MLL | 212078_s_at | 8461 | −0.4903 | −0.3064 | No | 226981_at | 0.6683 |
| REL | SG_U | VWA5A | 205011_at | 8463 | −0.4909 | −0.3052 | No | 205011_at | 0.6620 |
| REL | SG_U | GNAZ | 204993_at | 8585 | −0.5440 | −0.3132 | No | 204993_at | 0.7498 |
| REL | SG_U | MAPT | 203928_x_at | 8610 | −0.5529 | −0.3137 | No | 203929_s_at | 1.2389 |
| REL | SG_U | LPXN | 216250_at | 8691 | −0.5925 | −0.3184 | No | 216250_s_at | 0.8789 |
| REL | SG_U | HEXIM1 | 202814_s_at | 8731 | −0.6055 | −0.3199 | No | 202814_s_at | 1.5943 |
| REL | SG_U | PAIP2B | 221868_at | 8917 | −0.7006 | −0.3325 | No | 221868_at | 1.2146 |
| REL | SG_U | MT2A | 212185_x_at | 8928 | −0.7051 | −0.3315 | No | 212185_x_at | 1.1216 |
| REL | SG_U | FLJ22184 | 220584_at | 8965 | −0.7268 | −0.3324 | No | 220584_at | 0.7091 |
| REL | SG_U | TTLL7 | 219882_at | 8991 | −0.7390 | −0.3325 | No | 219882_at | 1.3565 |
| REL | SG_U | KHDRBS3 | 209781_s_at | 9050 | −0.7675 | −0.3350 | No | 209781_s_at | 0.5985 |
| REL | SG_U | TEAD3 | 209454_s_at | 9135 | −0.8118 | −0.3395 | No | 209454_s_at | 0.9877 |
| REL | SG_U | CAPG | 201850_at | 9246 | −0.8583 | −0.3459 | No | 201850_at | 0.4065 |
| REL | SG_U | TLE1 | 203221_at | 9275 | −0.8734 | −0.3458 | No | 203221_at | 0.6591 |
| REL | SG_U | PLAC8 | 219014_at | 9376 | −0.9252 | −0.3512 | No | 219014_at | 1.1130 |
| REL | SG_U | PHC1 | 218338_at | 9435 | −0.9527 | −0.3533 | No | 218338_at | 0.6767 |
| REL | SG_U | ANXA5 | 200782_at | 9440 | −0.9539 | −0.3512 | No | 200782_at | 0.8349 |
| REL | SG_U | FZD4 | 218665_at | 9455 | −0.9608 | −0.3498 | No | 218665_at | 0.5746 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| REL | SG_U | SLC35A2 | 209326_at | 9481 | −0.9785 | −0.3493 | No | 209326_at | 0.4515 |
| REL | SG_U | GPS2 | 209350_s_at | 9496 | −0.9860 | −0.3478 | No | 209350_s_at | 0.8650 |
| REL | SG_U | GPC1 | 202756_s_at | 9617 | −1.0443 | −0.3545 | No | 202756_s_at | 0.2626 |
| REL | SG_U | RABGAP1L | 203020_at | 9681 | −1.0785 | −0.3566 | No | 213982_s_at | 1.9919 |
| REL | SG_U | UBTD1 | 219172_at | 9758 | −1.1155 | −0.3597 | No | 219172_at | 0.5312 |
| REL | SG_U | ROGDI | 218394_at | 9791 | −1.1321 | −0.3593 | No | 218394_at | 0.7896 |
| REL | SG_U | AP1G1 | 203350_at | 9982 | −1.2364 | −0.3709 | No | 225771_at | 0.8554 |
| REL | SG_U | FKBP1B | 209931_s_at | 10044 | −1.2746 | −0.3724 | No | 206857_s_at | 1.7204 |
| REL | SG_U | OPTN | 202074_s_at | 10099 | −1.3131 | −0.3733 | Yes | 202074_s_at | 0.8466 |
| REL | SG_U | TNNT1 | 213201_s_at | 10103 | −1.3161 | −0.3701 | Yes | 213201_s_at | 1.9121 |
| REL | SG_U | HIP1 | 205426_s_at | 10104 | −1.3171 | −0.3668 | Yes | 226364_at | 0.9342 |
| REL | SG_U | ANKRD11 | 219437_s_at | 10177 | −1.3626 | −0.3689 | Yes | 226012_at | 0.4516 |
| REL | SG_U | NEAT1 | 214657_s_at | 10186 | −1.3765 | −0.3660 | Yes | 224566_at | 0.7719 |
| REL | SG_U | CAPN5 | 205166_at | 10231 | −1.3980 | −0.3658 | Yes | 226292_at | 0.7814 |
| REL | SG_U | FNDC3B | 218618_s_at | 10256 | −1.4135 | −0.3641 | Yes | 218618_s_at | 0.9300 |
| REL | SG_U | EFR3B | 215328_at | 10263 | −1.4177 | −0.3609 | Yes | 227283_at | 1.1424 |
| REL | SG_U | PGCP | 208454_s_at | 10285 | −1.4311 | −0.3589 | Yes | 208454_s_at | 0.8846 |
| REL | SG_U | NCOA3 | 209062_x_at | 10349 | −1.4707 | −0.3600 | Yes | 209061_at | 0.7598 |
| REL | SG_U | DOK4 | 209690_s_at | 10354 | −1.4735 | −0.3566 | Yes | 209691_s_at | 0.4003 |
| REL | SG_U | SRR | 219205_at | 10428 | −1.5340 | −0.3583 | Yes | 219205_at | 0.6989 |
| REL | SG_U | SNN | 218032_at | 10433 | −1.5390 | −0.3547 | Yes | 218032_at | 1.1523 |
| REL | SG_U | FADS3 | 204257_at | 10481 | −1.5741 | −0.3543 | Yes | 204257_at | 0.6793 |
| REL | SG_U | CA2 | 209301_at | 10491 | −1.5810 | −0.3510 | Yes | 209301_at | 2.3006 |
| REL | SG_U | TGFBR2 | 208944_at | 10556 | −1.6278 | −0.3518 | Yes | 208944_at | 1.7261 |
| REL | SG_U | STAT4 | 206118_at | 10597 | −1.6561 | −0.3506 | Yes | 206118_at | 0.7244 |
| REL | SG_U | GSTA4 | 202967_at | 10615 | −1.6714 | −0.3477 | Yes | 202967_at | 1.1781 |
| REL | SG_U | TBXAS1 | 208130_s_at | 10641 | −1.6905 | −0.3453 | Yes | 208130_s_at | 0.9837 |
| REL | SG_U | GSN | 214040_s_at | 10665 | −1.7092 | −0.3427 | Yes | 200696_s_at | 1.5769 |
| REL | SG_U | GAB2 | 203853_s_at | 10666 | −1.7095 | −0.3383 | Yes | 203853_s_at | 0.6217 |
| REL | SG_U | AHNAK | 211986_at | 10979 | −1.9396 | −0.3577 | Yes | 211986_at | 3.0382 |
| REL | SG_U | CTSK | 202450_s_at | 10987 | −1.9430 | −0.3533 | Yes | 202450_s_at | 0.7887 |
| REL | SG_U | TIAM1 | 213135_at | 11036 | −1.9838 | −0.3519 | Yes | 213135_at | 1.2715 |
| REL | SG_U | CST3 | 201360_at | 11088 | −2.0383 | −0.3507 | Yes | 201360_at | 1.7967 |
| REL | SG_U | SMARCD3 | 204099_at | 11100 | −2.0485 | −0.3463 | Yes | 204099_at | 1.7452 |
| REL | SG_U | ELF4 | 203490_at | 11236 | −2.1635 | −0.3512 | Yes | 203490_at | 0.1915 |
| REL | SG_U | LRCH4 | 221956_at | 11267 | −2.1919 | −0.3480 | Yes | 90610_at | 0.6937 |
| REL | SG_U | ASAP1 | 221039_s_at | 11277 | −2.1982 | −0.3430 | Yes | 224796_at | 0.6173 |
| REL | SG_U | ENTPD1 | 209473_at | 11303 | −2.2221 | −0.3393 | Yes | 209473_at | 0.2403 |
| REL | SG_U | KIF13B | 202962_at | 11305 | −2.2258 | −0.3337 | Yes | 202962_at | 0.1920 |
| REL | SG_U | ADAM28 | 208269_s_at | 11380 | −2.2913 | −0.3336 | Yes | 205997_at | 1.6045 |
| REL | SG_U | CHN1 | 212624_s_at | 11450 | −2.3482 | −0.3329 | Yes | 212624_s_at | 0.7418 |
| REL | SG_U | UBR5 | 208884_s_at | 11466 | −2.3591 | −0.3280 | Yes | 208884_s_at | 1.5132 |
| REL | SG_U | FAM164A | 205308_at | 11472 | −2.3603 | −0.3224 | Yes | 205308_at | 0.8831 |
| REL | SG_U | LIMA1 | 217892_s_at | 11542 | −2.4479 | −0.3215 | Yes | 217892_s_at | 0.8689 |
| REL | SG_U | SYNE2 | 202761_s_at | 11546 | −2.4495 | −0.3155 | Yes | 202761_s_at | 0.8638 |
| REL | SG_U | HIF1AN | 218525_s_at | 11671 | −2.6105 | −0.3184 | Yes | 226648_at | 0.6976 |
| REL | SG_U | LPGAT1 | 202651_s_at | 11696 | −2.6357 | −0.3135 | Yes | 227476_at | 0.4155 |
| REL | SG_U | KIF1B | 209234_at | 11834 | −2.8046 | −0.3170 | Yes | 209234_at | 0.4223 |
| REL | SG_U | KCNH2 | 210036_s_at | 11911 | −2.9102 | −0.3155 | Yes | 210036_s_at | 0.4936 |
| REL | SG_U | PDE4DIP | 212390_at | 11972 | −2.9934 | −0.3125 | Yes | 214129_at | 0.1865 |
| REL | SG_U | CYTH1 | 202879_s_at | 12059 | −3.1078 | −0.3112 | Yes | 202880_s_at | 0.4208 |
| REL | SG_U | ProSAPiP1 | 204447_at | 12090 | −3.1518 | −0.3055 | Yes | 204447_at | 0.7388 |
| REL | SG_U | PIM1 | 209193_at | 12207 | −3.3449 | −0.3060 | Yes | 209193_at | 0.4581 |
| REL | SG_U | SLC37A1 | 218928_s_at | 12295 | −3.5334 | −0.3037 | Yes | 218928_s_at | 1.5958 |
| REL | SG_U | ZFP36 | 201531_at | 12354 | −3.6517 | −0.2989 | Yes | 201531_at | 1.1739 |
| REL | SG_U | LGALS3 | 208949_s_at | 12364 | −3.6742 | −0.2902 | Yes | 208949_s_at | 0.9798 |
| REL | SG_U | VCL | 200931_s_at | 12372 | −3.6975 | −0.2812 | Yes | 200931_s_at | 1.5632 |
| REL | SG_U | DNMBP | 212838_at | 12399 | −3.7695 | −0.2736 | Yes | 212838_at | 0.3275 |
| REL | SG_U | TGFBR3 | 204731_at | 12428 | −3.8434 | −0.2659 | Yes | 226625_at | 1.2976 |
| REL | SG_U | MPP1 | 202974_at | 12433 | −3.8620 | −0.2563 | Yes | 202974_at | 0.6470 |
| REL | SG_U | GLS | 203159_at | 12447 | −3.9122 | −0.2473 | Yes | 203159_at | 0.7744 |
| REL | SG_U | CCDC92 | 218175_at | 12448 | −3.9211 | −0.2373 | Yes | 218175_at | 1.1364 |
| REL | SG_U | TANK | 207616_s_at | 12452 | −3.9379 | −0.2274 | Yes | 207616_s_at | 1.2193 |
| REL | SG_U | PHLPP2 | 213407_at | 12462 | −3.9574 | −0.2180 | Yes | 213407_at | 0.6092 |
| REL | SG_U | ALDH2 | 201425_at | 12499 | −4.0734 | −0.2104 | Yes | 201425_at | 0.6952 |
| REL | SG_U | Hs.533878 | 218363_at | 12507 | −4.0850 | −0.2004 | Yes | 229131_at | 0.4206 |
| REL | SG_U | ZCCHC24 | 212419_at | 12520 | −4.1481 | −0.1907 | Yes | 212419_at | 1.1963 |
| REL | SG_U | JUN | 201464_x_at | 12543 | −4.2133 | −0.1817 | Yes | 201464_x_at | 0.9285 |
| REL | SG_U | C17orf91 | 214696_at | 12553 | −4.2619 | −0.1714 | Yes | 214696_at | 0.9025 |
| REL | SG_U | PILRA | 222218_s_at | 12589 | −4.4255 | −0.1628 | Yes | 222218_s_at | 1.2450 |
| REL | SG_U | KIAA0513 | 204546_at | 12594 | −4.4434 | −0.1518 | Yes | 204546_at | 0.9209 |
| REL | SG_U | PDGFC | 218718_at | 12613 | −4.5492 | −0.1415 | Yes | 218718_at | 1.7530 |
| REL | SG_U | C11orf80 | 204922_at | 12627 | −4.6254 | −0.1307 | Yes | 204922_at | 0.3391 |

TABLE 5-continued

The numerical values from the GSEA for each gene contributing to the significant
enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | $\text{Log}^2$ Fold Change Combination |
|---|---|---|---|---|---|---|---|---|---|
| REL | SG_U | FLJ10357 | 220326_s_at | 12638 | −4.6824 | −0.1194 | Yes | 220326_s_at | 0.8886 |
| REL | SG_U | FOXO1 | 202723_s_at | 12641 | −4.7069 | −0.1075 | Yes | 202723_s_at | 1.5149 |
| REL | SG_U | CYP26A1 | 206424_at | 12651 | −4.7627 | −0.0960 | Yes | 206424_at | 0.6489 |
| REL | SG_U | RRAS | 212647_at | 12662 | −4.8203 | −0.0845 | Yes | 212647_at | 1.0321 |
| REL | SG_U | TUBA1A | 209118_s_at | 12683 | −4.9175 | −0.0734 | Yes | 209118_s_at | 1.5498 |
| REL | SG_U | FUCA1 | 202838_at | 12688 | −4.9333 | −0.0611 | Yes | 202838_at | 0.4742 |
| REL | SG_U | HLA-DMB | 203932_at | 12710 | −5.0756 | −0.0497 | Yes | 203932_at | 1.1066 |
| REL | SG_U | BLVRA | 211729_x_at | 12714 | −5.1240 | −0.0368 | Yes | 211729_x_at | 0.5834 |
| REL | SG_U | SGK3 | 220038_at | 12733 | −5.1788 | −0.0250 | Yes | 227627_at | 1.5170 |
| REL | SG_U | IGFBP6 | 203851_at | 12791 | −5.4977 | −0.0153 | Yes | 203851_at | 0.5314 |
| REL | SG_U | SGPP1 | 221268_s_at | 12793 | −5.5009 | −0.0013 | Yes | 223391_at | 1.1439 |
| REL | SG_U | NAGK | 218231_at | 12960 | −7.6576 | 0.0054 | Yes | 218231_at | 0.4800 |
| NEW | Blue_D | DDRGK1 | 218159_at | 60 | 7.0617 | 0.0329 | Yes | 218159_at | −1.0618 |
| NEW | Blue_D | TRIP13 | 204033_at | 418 | 4.6569 | 0.0301 | Yes | 204033_at | −2.5425 |
| NEW | Blue_D | LDHA | 200650_s_at | 444 | 4.6189 | 0.0528 | Yes | 200650_s_at | −1.2640 |
| NEW | Blue_D | FDPS | 201275_at | 474 | 4.5521 | 0.0747 | Yes | 201275_at | −1.4558 |
| NEW | Blue_D | GPI | 208308_s_at | 561 | 4.3179 | 0.0911 | Yes | 208308_s_at | −1.7204 |
| NEW | Blue_D | RRM2 | 209773_s_at | 778 | 3.8907 | 0.0951 | Yes | 209773_s_at | −3.3973 |
| NEW | Blue_D | NDUFA9 | 208969_at | 800 | 3.8600 | 0.1140 | Yes | 208969_at | −1.0903 |
| NEW | Blue_D | WDR76 | 205519_at | 840 | 3.8031 | 0.1312 | Yes | 205519_at | −1.4439 |
| NEW | Blue_D | RAD51 | 205024_s_at | 846 | 3.7872 | 0.1510 | Yes | 205024_s_at | −1.5192 |
| NEW | Blue_D | KIF22 | 202183_s_at | 870 | 3.7649 | 0.1692 | Yes | 202183_s_at | −1.6422 |
| NEW | Blue_D | NSDHL | 209279_s_at | 881 | 3.7487 | 0.1884 | Yes | 209279_s_at | −1.3381 |
| NEW | Blue_D | MCM10 | 220651_s_at | 1097 | 3.4730 | 0.1903 | Yes | 220651_s_at | −2.7011 |
| NEW | Blue_D | CCNB2 | 202705_at | 1175 | 3.3574 | 0.2022 | Yes | 202705_at | −2.1340 |
| NEW | Blue_D | TMEM48 | 218073_s_at | 1367 | 3.1147 | 0.2040 | Yes | 234672_s_at | −1.4764 |
| NEW | Blue_D | PGAM1 | 200886_s_at | 1438 | 3.0369 | 0.2147 | Yes | 200886_s_at | −1.2903 |
| NEW | Blue_D | MKI67 | 212021_s_at | 1607 | 2.8679 | 0.2170 | Yes | 212021_s_at | −1.8786 |
| NEW | Blue_D | CIT | 212801_at | 1747 | 2.7377 | 0.2208 | Yes | 212801_at | −1.0713 |
| NEW | Blue_D | NCAPD3 | 212789_at | 1818 | 2.6711 | 0.2297 | Yes | 212789_at | −1.4511 |
| NEW | Blue_D | C1orf112 | 220840_s_at | 1863 | 2.6300 | 0.2402 | Yes | 220840_s_at | −1.6023 |
| NEW | Blue_D | CDC20 | 202870_s_at | 1888 | 2.6106 | 0.2523 | Yes | 202870_s_at | −1.5564 |
| NEW | Blue_D | RFC2 | 203696_s_at | 1895 | 2.6071 | 0.2657 | Yes | 203696_s_at | −1.5179 |
| NEW | Blue_D | CENPA | 210821_x_at | 1907 | 2.5995 | 0.2787 | Yes | 204962_s_at | −1.8881 |
| NEW | Blue_D | HJURP | 218726_at | 2008 | 2.5256 | 0.2844 | Yes | 218726_at | −1.9264 |
| NEW | Blue_D | C16orf59 | 219556_at | 2147 | 2.4217 | 0.2866 | Yes | 219556_at | −1.0807 |
| NEW | Blue_D | TUBA1C | 209251_x_at | 2173 | 2.4023 | 0.2974 | Yes | 209251_x_at | −1.1616 |
| NEW | Blue_D | STK6 | 208080_at | 2291 | 2.3201 | 0.3007 | Yes | 208079_s_at | −1.8883 |
| NEW | Blue_D | UBE2C | 202954_at | 2316 | 2.3049 | 0.3112 | Yes | 202954_at | −1.4051 |
| NEW | Blue_D | MYBL2 | 201710_at | 2464 | 2.2024 | 0.3115 | Yes | 201710_at | −2.6352 |
| NEW | Blue_D | MCM2 | 202107_s_at | 2512 | 2.1665 | 0.3194 | Yes | 202107_s_at | −2.0679 |
| NEW | Blue_D | TIMELESS | 203046_s_at | 2581 | 2.1203 | 0.3254 | Yes | 203046_s_at | −1.1575 |
| NEW | Blue_D | TACC3 | 218308_at | 2755 | 2.0095 | 0.3228 | Yes | 218308_at | −1.3035 |
| NEW | Blue_D | SLC7A5 | 201195_s_at | 2920 | 1.9163 | 0.3203 | Yes | 201195_s_at | −2.6903 |
| NEW | Blue_D | EBP | 213787_s_at | 2923 | 1.9143 | 0.3303 | Yes | 213787_s_at | −1.7595 |
| NEW | Blue_D | TOR3A | 218459_at | 3091 | 1.8197 | 0.3271 | Yes | 218459_at | −1.3546 |
| NEW | Blue_D | TUBA1B | 211058_x_at | 3214 | 1.7570 | 0.3270 | Yes | 211058_x_at | −1.1876 |
| NEW | Blue_D | ESPL1 | 38158_at | 3242 | 1.7425 | 0.3342 | Yes | 38158_at | −1.8588 |
| NEW | Blue_D | H2AFX | 205436_s_at | 3319 | 1.6928 | 0.3374 | Yes | 205436_s_at | −1.4748 |
| NEW | Blue_D | CDC25A | 204696_s_at | 3380 | 1.6638 | 0.3416 | Yes | 204695_at | −2.3587 |
| NEW | Blue_D | RAD54L | 204558_at | 3645 | 1.5240 | 0.3293 | Yes | 204558_at | −1.6082 |
| NEW | Blue_D | FANCG | 203564_at | 3764 | 1.4669 | 0.3280 | Yes | 203564_at | −1.1180 |
| NEW | Blue_D | LDLR | 217173_s_at | 3802 | 1.4474 | 0.3328 | Yes | 202068_s_at | −3.1745 |
| NEW | Blue_D | B4GALNT1 | 206435_at | 3804 | 1.4467 | 0.3404 | Yes | 206435_at | −1.0926 |
| NEW | Blue_D | SLC35B1 | 202433_at | 3850 | 1.4218 | 0.3445 | Yes | 202433_at | −0.8310 |
| NEW | Blue_D | SLC2A1 | 201250_s_at | 3892 | 1.3987 | 0.3488 | Yes | 201250_s_at | −1.9684 |
| NEW | Blue_D | CDCA3 | 221436_s_at | 4037 | 1.3413 | 0.3448 | No | 223307_at | −1.9094 |
| NEW | Blue_D | CHAF1B | 204775_at | 4233 | 1.2399 | 0.3363 | No | 204775_at | −1.3219 |
| NEW | Blue_D | SLCO4A1 | 219911_s_at | 4362 | 1.1772 | 0.3327 | No | 219911_s_at | −2.0069 |
| NEW | Blue_D | SLC7A1 | 212295_s_at | 4461 | 1.1379 | 0.3312 | No | 212295_s_at | −1.0932 |
| NEW | Blue_D | SPAG5 | 203145_at | 4479 | 1.1295 | 0.3359 | No | 203145_at | −2.3469 |
| NEW | Blue_D | MCM5 | 201755_at | 4987 | 0.8968 | 0.3015 | No | 216237_s_at | −2.2926 |
| NEW | Blue_D | BLM | 205733_at | 5081 | 0.8498 | 0.2989 | No | 205733_at | −1.5970 |
| NEW | Blue_D | CDC6 | 203968_s_at | 5118 | 0.8371 | 0.3005 | No | 203968_s_at | −2.5641 |
| NEW | Blue_D | CDC45L | 204126_s_at | 5777 | 0.5589 | 0.2527 | No | 204126_s_at | −2.4023 |
| NEW | Blue_D | MPDU1 | 209208_at | 5956 | 0.4745 | 0.2415 | No | 209208_at | −1.7427 |
| NEW | Blue_D | ATAD2 | 218782_s_at | 5986 | 0.4630 | 0.2417 | No | 218782_s_at | −2.5687 |
| NEW | Blue_D | RBM14 | 204178_s_at | 6427 | 0.2696 | 0.2091 | No | 204178_s_at | −1.6436 |
| NEW | Blue_D | KIF2C | 209408_at | 7380 | −0.1523 | 0.1364 | No | 209408_at | −2.0440 |
| NEW | Blue_D | SUV39H1 | 218619_s_at | 7666 | −0.2815 | 0.1159 | No | 218619_s_at | −1.1582 |
| NEW | Blue_D | TXNDC15 | 220495_s_at | 7799 | −0.3388 | 0.1075 | No | 220495_s_at | −1.5473 |
| NEW | Blue_D | POLA2 | 204441_s_at | 7825 | −0.3523 | 0.1075 | No | 204441_s_at | −1.5960 |
| NEW | Blue_D | TFRC | 207332_s_at | 8579 | −0.7016 | 0.0531 | No | 207332_s_at | −1.6352 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| NEW | Blue_D | ELOVL1 | 218028_at | 8851 | −0.8448 | 0.0366 | No | 57163_at | −1.0254 |
| NEW | Blue_D | E2F2 | 207042_at | 8890 | −0.8603 | 0.0383 | No | 228361_at | −2.5642 |
| NEW | Blue_D | MCM4 | 214349_at | 8983 | −0.9263 | 0.0361 | No | 212141_at | −2.3064 |
| NEW | Blue_D | PLK1 | 202240_at | 8991 | −0.9312 | 0.0405 | No | 202240_at | −1.9567 |
| NEW | Blue_D | DBF4B | 206661_at | 9091 | −0.9935 | 0.0381 | No | 238508_at | −1.7101 |
| NEW | Blue_D | TEX261 | 212083_at | 10137 | −1.5860 | −0.0341 | No | 212083_at | −0.9444 |
| NEW | Blue_D | NCAPH | 212949_at | 10285 | −1.6792 | −0.0365 | No | 212949_at | −2.1530 |
| NEW | Blue_D | LMAN2L | 221274_s_at | 10838 | −2.1060 | −0.0680 | No | 221274_s_at | −0.9061 |
| NEW | Blue_D | LMNB1 | 203276_at | 10846 | −2.1124 | −0.0573 | No | 203276_at | −1.5790 |
| NEW | Blue_D | SLC19A1 | 209777_s_at | 11362 | −2.5716 | −0.0834 | No | 209777_s_at | −1.4453 |
| NEW | Blue_D | CDC25C | 216914_at | 11583 | −2.7933 | −0.0855 | No | 205167_s_at | −1.7970 |
| NEW | Blue_D | TPST2 | 204079_at | 11601 | −2.8097 | −0.0719 | No | 204079_at | −0.5365 |
| NEW | Blue_D | GALE | 202528_at | 11654 | −2.8780 | −0.0606 | No | 202528_at | −1.0641 |
| NEW | Blue_D | AMDHD2 | 219082_at | 11694 | −2.9167 | −0.0481 | No | 219082_at | −0.8216 |
| NEW | Blue_D | SCARB1 | 201819_at | 12109 | −3.5427 | −0.0612 | No | 1552256_a_at | −2.4284 |
| NEW | Blue_D | FOXM1 | 214148_at | 12120 | −3.5585 | −0.0430 | No | 202580_x_at | −2.2845 |
| NEW | Blue_D | ZNF107 | 205739_x_at | 12343 | −4.0355 | −0.0387 | No | 243312_at | −0.9633 |
| NEW | Blue_D | CENPM | 218741_at | 12654 | −5.1977 | −0.0350 | No | 218741_at | −2.1860 |
| NEW | Blue_D | SCD | 200831_s_at | 12762 | −5.8302 | −0.0123 | No | 200832_s_at | −2.0573 |
| NEW | Blue_D | DBNDD2 | 218094_s_at | 12808 | −6.1672 | 0.0171 | No | 238470_at | −0.4043 |
| NEW | Blue_U | SATB1 | 203408_s_at | 6308 | 0.3203 | −0.4790 | No | 203408_s_at | 2.2924 |
| NEW | Blue_U | CAMSAP1L1 | 212763_at | 7625 | −0.2600 | −0.5756 | No | 212765_at | 0.8007 |
| NEW | Blue_U | PHC3 | 215521_at | 10808 | −2.0786 | −0.7837 | No | 226508_at | 1.3199 |
| NEW | Blue_U | CALCOCO1 | 209002_s_at | 11016 | −2.2524 | −0.7602 | No | 209002_s_at | 1.3443 |
| NEW | Blue_U | HLA-DRB4 | 209728_at | 12160 | −3.6379 | −0.7844 | Yes | 209728_at | 3.1361 |
| NEW | Blue_U | HLA-DRB6 | 217362_x_at | 12595 | −4.9319 | −0.7315 | Yes | 217362_x_at | 1.3574 |
| NEW | Blue_U | LOC731682 | 212671_s_at | 12681 | −5.3108 | −0.6452 | Yes | 212671_s_at | 2.2805 |
| NEW | Blue_U | HLA-DQB1 | 211654_x_at | 12742 | −5.7261 | −0.5497 | Yes | 211654_x_at | 1.3513 |
| NEW | Blue_U | HLA-DMA | 217478_s_at | 12780 | −5.9251 | −0.4490 | Yes | 217478_s_at | 1.4991 |
| NEW | Blue_U | SPARCL1 | 200795_at | 12806 | −6.1241 | −0.3438 | Yes | 200795_at | 1.1056 |
| NEW | Blue_U | HLA-DRB1 | 204670_x_at | 12841 | −6.4598 | −0.2335 | Yes | 208306_x_at | 1.2895 |
| NEW | Blue_U | HLA-DPB1 | 201137_s_at | 12876 | −6.9175 | −0.1152 | Yes | 201137_s_at | 1.5092 |
| NEW | Blue_U | LOC100294276 | 209312_x_at | 12907 | −7.2584 | 0.0094 | Yes | 209312_x_at | 1.3887 |
| NEW | DG_D | SET | 200630_x_at | 73 | 6.8048 | 0.0156 | Yes | 200630_x_at | −0.6487 |
| NEW | DG_D | PA2G4 | 208676_s_at | 168 | 5.7800 | 0.0263 | Yes | 208676_s_at | −0.8555 |
| NEW | DG_D | STOML2 | 215416_s_at | 193 | 5.5504 | 0.0417 | Yes | 215416_s_at | −1.2177 |
| NEW | DG_D | PPP2R4 | 208874_x_at | 225 | 5.3549 | 0.0560 | Yes | 206452_x_at | −1.1045 |
| NEW | DG_D | ANP32B | 201306_s_at | 253 | 5.2044 | 0.0702 | Yes | 201306_s_at | −1.2696 |
| NEW | DG_D | ZNF696 | 220967_s_at | 272 | 5.1345 | 0.0848 | Yes | 220967_s_at | −0.5543 |
| NEW | DG_D | TXNRD2 | 211177_s_at | 358 | 4.8363 | 0.0933 | Yes | 211177_s_at | −0.9959 |
| NEW | DG_D | SMARCA4 | 212520_s_at | 462 | 4.5723 | 0.0996 | Yes | 213720_s_at | −0.8869 |
| NEW | DG_D | HNRNPL | 35201_at | 488 | 4.5057 | 0.1117 | Yes | 35201_at | −0.6733 |
| NEW | DG_D | H3F3A | 213828_x_at | 508 | 4.4565 | 0.1241 | Yes | 213828_x_at | −0.5502 |
| NEW | DG_D | TUBB | 211714_x_at | 523 | 4.4324 | 0.1368 | Yes | 211714_x_at | −1.5976 |
| NEW | DG_D | ECH1 | 200789_at | 536 | 4.3905 | 0.1496 | Yes | 200789_at | −0.9580 |
| NEW | DG_D | PSMD8 | 200820_at | 587 | 4.2646 | 0.1590 | Yes | 200820_at | −1.0159 |
| NEW | DG_D | AVEN | 219366_at | 598 | 4.2430 | 0.1715 | Yes | 219366_at | −1.1898 |
| NEW | DG_D | FARSA | 216602_s_at | 623 | 4.2006 | 0.1827 | Yes | 202159_at | −0.5879 |
| NEW | DG_D | HAUS7 | 213334_x_at | 654 | 4.1386 | 0.1933 | Yes | 213334_x_at | −1.1222 |
| NEW | DG_D | OBFC2B | 218903_s_at | 688 | 4.0740 | 0.2034 | Yes | 218903_s_at | −1.0793 |
| NEW | DG_D | FAM20B | 202915_s_at | 720 | 4.0070 | 0.2135 | Yes | 202916_s_at | −0.8598 |
| NEW | DG_D | ALDOA | 214687_x_at | 777 | 3.8924 | 0.2213 | Yes | 200966_x_at | −1.5531 |
| NEW | DG_D | SLC10A3 | 204928_s_at | 849 | 3.7826 | 0.2276 | Yes | 204928_s_at | −0.8831 |
| NEW | DG_D | WBSCR16 | 221247_s_at | 855 | 3.7780 | 0.2390 | Yes | 221247_s_at | −1.3786 |
| NEW | DG_D | HNRNPAB | 201277_s_at | 895 | 3.7280 | 0.2476 | Yes | 201277_s_at | −0.9573 |
| NEW | DG_D | UBL4A | 221746_at | 906 | 3.7120 | 0.2584 | Yes | 221746_at | −0.8816 |
| NEW | DG_D | IARS | 204744_s_at | 924 | 3.6858 | 0.2686 | Yes | 204744_s_at | −0.6682 |
| NEW | DG_D | CTPS | 202613_at | 928 | 3.6745 | 0.2798 | Yes | 202613_at | −1.3500 |
| NEW | DG_D | EXOSC2 | 214507_s_at | 965 | 3.6259 | 0.2883 | Yes | 209527_at | −0.8969 |
| NEW | DG_D | UTP20 | 209725_at | 967 | 3.6217 | 0.2996 | Yes | 209725_at | −1.0034 |
| NEW | DG_D | SNRPA | 201770_at | 1020 | 3.5511 | 0.3066 | Yes | 201770_at | −1.0990 |
| NEW | DG_D | MEPCE | 219798_s_at | 1022 | 3.5491 | 0.3176 | Yes | 219798_s_at | −0.5653 |
| NEW | DG_D | TTLL12 | 216251_s_at | 1093 | 3.4744 | 0.3230 | Yes | 1552257_a_at | −0.8222 |
| NEW | DG_D | RCC1 | 215747_s_at | 1130 | 3.4198 | 0.3309 | Yes | 206499_s_at | −1.2427 |
| NEW | DG_D | TMEM231 | 219182_at | 1142 | 3.4037 | 0.3406 | Yes | 219182_at | −0.8038 |
| NEW | DG_D | HCFC1 | 202474_s_at | 1174 | 3.3588 | 0.3487 | Yes | 202474_s_at | −0.8665 |
| NEW | DG_D | KEAP1 | 202417_at | 1192 | 3.3498 | 0.3578 | Yes | 202417_at | −1.0833 |
| NEW | DG_D | SSRP1 | 200957_s_at | 1211 | 3.3133 | 0.3668 | Yes | 200957_s_at | −1.0802 |
| NEW | DG_D | NR2F6 | 209262_s_at | 1255 | 3.2620 | 0.3736 | Yes | 209262_s_at | −0.6575 |
| NEW | DG_D | NDUFS3 | 201740_at | 1309 | 3.1981 | 0.3795 | Yes | 201740_at | −0.7718 |
| NEW | DG_D | LASS2 | 222212_s_at | 1324 | 3.1681 | 0.3883 | Yes | 222212_s_at | −0.8812 |
| NEW | DG_D | NOLC1 | 211951_at | 1338 | 3.1457 | 0.3971 | Yes | 211951_at | −0.6006 |
| NEW | DG_D | LAS1L | 208117_s_at | 1408 | 3.0672 | 0.4013 | Yes | 208117_s_at | −0.6863 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| NEW | DG_D | HDGF | 200896_x_at | 1412 | 3.0663 | 0.4106 | Yes | 200896_x_at | −1.6718 |
| NEW | DG_D | PARP1 | 208644_at | 1562 | 2.9092 | 0.4081 | Yes | 208644_at | −0.7776 |
| NEW | DG_D | CASP2 | 209812_x_at | 1571 | 2.9033 | 0.4166 | Yes | 226032_at | −0.3234 |
| NEW | DG_D | ACP6 | 218795_at | 1605 | 2.8691 | 0.4230 | Yes | 218795_at | −0.7372 |
| NEW | DG_D | DDX54 | 219111_s_at | 1665 | 2.8149 | 0.4272 | Yes | 219111_s_at | −1.0228 |
| NEW | DG_D | WDR4 | 221632_s_at | 1686 | 2.7894 | 0.4343 | Yes | 241937_s_at | −0.9790 |
| NEW | DG_D | GYS1 | 201673_s_at | 1736 | 2.7498 | 0.4391 | Yes | 201673_s_at | −1.0184 |
| NEW | DG_D | MRPS15 | 221437_s_at | 1767 | 2.7189 | 0.4452 | Yes | 226296_s_at | −1.1799 |
| NEW | DG_D | HSPD1 | 200807_s_at | 1908 | 2.5987 | 0.4425 | Yes | 200807_s_at | −0.7713 |
| NEW | DG_D | AIFM1 | 205512_s_at | 1942 | 2.5722 | 0.4479 | Yes | 205512_s_at | −1.1566 |
| NEW | DG_D | LMNB2 | 216952_s_at | 1947 | 2.5667 | 0.4556 | Yes | 216952_s_at | −0.5609 |
| NEW | DG_D | ODC1 | 200790_at | 2189 | 2.3893 | 0.4444 | No | 200790_at | −1.2573 |
| NEW | DG_D | HMGA1 | 206074_s_at | 2272 | 2.3369 | 0.4453 | No | 206074_s_at | −0.8315 |
| NEW | DG_D | GCAT | 36475_at | 2476 | 2.1927 | 0.4364 | No | 205164_at | −0.8760 |
| NEW | DG_D | LDLRAP1 | 57082_at | 2484 | 2.1859 | 0.4427 | No | 57082_at | −0.9713 |
| NEW | DG_D | DHODH | 213632_at | 2681 | 2.0640 | 0.4339 | No | 213632_at | −1.0196 |
| NEW | DG_D | ACO2 | 200793_s_at | 2861 | 1.9503 | 0.4261 | No | 200793_s_at | −0.9497 |
| NEW | DG_D | SPHK2 | 209857_s_at | 2929 | 1.9104 | 0.4268 | No | 40273_at | −0.8702 |
| NEW | DG_D | MFNG | 204153_s_at | 3077 | 1.8250 | 0.4211 | No | 204153_s_at | −1.2757 |
| NEW | DG_D | C2orf18 | 219783_at | 3192 | 1.7637 | 0.4178 | No | 225695_at | −0.9088 |
| NEW | DG_D | TSR1 | 218155_x_at | 3256 | 1.7303 | 0.4183 | No | 218156_s_at | −1.4890 |
| NEW | DG_D | NASP | 201970_s_at | 3356 | 1.6767 | 0.4158 | No | 201970_s_at | −1.1638 |
| NEW | DG_D | TUBGCP4 | 211337_s_at | 3593 | 1.5511 | 0.4024 | No | 211337_s_at | −0.7043 |
| NEW | DG_D | TMPO | 203432_at | 3678 | 1.5030 | 0.4005 | No | 209753_s_at | −1.5300 |
| NEW | DG_D | GTF2H3 | 222104_x_at | 3681 | 1.5009 | 0.4051 | No | 1554599_x_at | −0.6423 |
| NEW | DG_D | CWF19L1 | 218787_x_at | 3687 | 1.4969 | 0.4093 | No | 233568_x_at | −0.5411 |
| NEW | DG_D | ADA | 204639_at | 3791 | 1.4536 | 0.4059 | No | 204639_at | −1.2155 |
| NEW | DG_D | MBTPS2 | 206473_at | 3867 | 1.4141 | 0.4045 | No | 226760_at | −1.0883 |
| NEW | DG_D | PAK2 | 208877_at | 3879 | 1.4079 | 0.4080 | No | 208877_at | −0.6734 |
| NEW | DG_D | NTRK2 | 207152_at | 3884 | 1.4047 | 0.4121 | No | 221795_at | −1.3961 |
| NEW | DG_D | DNASE1L1 | 203912_s_at | 4012 | 1.3533 | 0.4064 | No | 203912_s_at | −1.0443 |
| NEW | DG_D | TH1L | 220607_x_at | 4089 | 1.3141 | 0.4046 | No | 225006_x_at | −0.7325 |
| NEW | DG_D | TOE1 | 204080_at | 4187 | 1.2643 | 0.4011 | No | 204080_at | −1.0473 |
| NEW | DG_D | SNRNP25 | 218493_at | 4262 | 1.2197 | 0.3991 | No | 218493_at | −1.6572 |
| NEW | DG_D | DUSP7 | 213848_at | 4366 | 1.1759 | 0.3948 | No | 213848_at | −0.6568 |
| NEW | DG_D | TRMT2B | 205238_at | 4402 | 1.1623 | 0.3957 | No | 205238_at | −1.5340 |
| NEW | DG_D | FASTKD2 | 216996_s_at | 4441 | 1.1493 | 0.3963 | No | 216996_s_at | −0.7328 |
| NEW | DG_D | ALDH18A1 | 217791_s_at | 4448 | 1.1436 | 0.3994 | No | 217791_s_at | −0.8960 |
| NEW | DG_D | TRIM25 | 206911_at | 4695 | 1.0293 | 0.3836 | No | 224806_at | −0.6249 |
| NEW | DG_D | NVL | 207877_s_at | 4940 | 0.9183 | 0.3675 | No | 207877_s_at | −0.6853 |
| NEW | DG_D | C20orf7 | 219524_s_at | 5268 | 0.7731 | 0.3445 | No | 227160_s_at | −0.7371 |
| NEW | DG_D | AHSA1 | 201491_at | 5595 | 0.6273 | 0.3212 | No | 201491_at | −0.9841 |
| NEW | DG_D | TRIB2 | 202479_s_at | 5670 | 0.5971 | 0.3173 | No | 202478_s_at | −0.7855 |
| NEW | DG_D | OXCT1 | 202780_at | 5713 | 0.5808 | 0.3159 | No | 202780_at | −1.1391 |
| NEW | DG_D | FKBP4 | 200895_s_at | 5759 | 0.5627 | 0.3141 | No | 200895_s_at | −1.1436 |
| NEW | DG_D | GPATCH1 | 219818_s_at | 5805 | 0.5475 | 0.3123 | No | 219818_s_at | −0.6849 |
| NEW | DG_D | HK2 | 202934_at | 5868 | 0.5166 | 0.3091 | No | 202934_at | −1.3557 |
| NEW | DG_D | TSHR | 215443_at | 5907 | 0.4979 | 0.3077 | No | 215443_at | −1.4748 |
| NEW | DG_D | UROD | 208971_at | 5977 | 0.4661 | 0.3038 | No | 208970_s_at | −0.6909 |
| NEW | DG_D | STAG3L4 | 218994_s_at | 6038 | 0.4383 | 0.3005 | No | 222801_s_at | −0.8323 |
| NEW | DG_D | GMIP | 218913_s_at | 6039 | 0.4379 | 0.3019 | No | 218913_s_at | −0.6103 |
| NEW | DG_D | HMGN2 | 208668_x_at | 6695 | 0.1603 | 0.2516 | No | 208668_x_at | −1.0775 |
| NEW | DG_D | PPPDE2 | 212527_at | 6747 | 0.1359 | 0.2481 | No | 212527_at | −0.8438 |
| NEW | DG_D | ADAM22 | 208227_x_at | 6839 | 0.0974 | 0.2413 | No | 208227_x_at | −0.9814 |
| NEW | DG_D | FAM57A | 218898_at | 6883 | 0.0760 | 0.2382 | No | 218898_at | −1.7645 |
| NEW | DG_D | SUPT16H | 217815_at | 6941 | 0.0604 | 0.2340 | No | 217815_at | −0.5370 |
| NEW | DG_D | ACACA | 212186_at | 6964 | 0.0508 | 0.2324 | No | 212186_at | −0.8638 |
| NEW | DG_D | CCDC22 | 214037_s_at | 7026 | 0.0155 | 0.2277 | No | 206016_at | −0.8115 |
| NEW | DG_D | MED12 | 211342_x_at | 7047 | 0.0073 | 0.2262 | No | 216071_x_at | −0.6591 |
| NEW | DG_D | MIPEP | 204305_at | 7083 | −0.0113 | 0.2235 | No | 204305_at | −0.8696 |
| NEW | DG_D | THOC5 | 209418_s_at | 7314 | −0.1261 | 0.2061 | No | 209418_s_at | −0.7584 |
| NEW | DG_D | SMARCB1 | 212167_s_at | 7325 | −0.1313 | 0.2057 | No | 212167_s_at | −1.0464 |
| NEW | DG_D | SFMBT1 | 213370_s_at | 7422 | −0.1712 | 0.1988 | No | 213370_s_at | −0.6881 |
| NEW | DG_D | COIL | 203654_s_at | 7448 | −0.1820 | 0.1974 | No | 203654_s_at | −0.6094 |
| NEW | DG_D | MED25 | 208110_x_at | 7700 | −0.2969 | 0.1789 | No | 1553993_s_at | −0.6889 |
| NEW | DG_D | SF3B3 | 200687_s_at | 7702 | −0.2973 | 0.1797 | No | 200687_s_at | −0.7666 |
| NEW | DG_D | PRR3 | 204795_at | 7983 | −0.4157 | 0.1593 | No | 204795_at | −0.7039 |
| NEW | DG_D | BID | 211725_s_at | 8137 | −0.4888 | 0.1489 | No | 211725_s_at | −1.3437 |
| NEW | DG_D | WDR77 | 201420_s_at | 8143 | −0.4920 | 0.1501 | No | 201421_s_at | −0.5241 |
| NEW | DG_D | EXOG | 205521_at | 8196 | −0.5172 | 0.1476 | No | 205521_at | −1.0107 |
| NEW | DG_D | NF2 | 218915_at | 8239 | −0.5373 | 0.1461 | No | 218915_at | −0.8814 |
| NEW | DG_D | IVD | 203682_s_at | 8241 | −0.5374 | 0.1477 | No | 225311_at | −0.5473 |
| NEW | DG_D | MAPKAPK5 | 212871_at | 8557 | −0.6918 | 0.1254 | No | 212871_at | −1.1799 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| NEW | DG_D | P2RX5 | 210448_s_at | 8573 | −0.6984 | 0.1264 | No | 210448_s_at | −1.2148 |
| NEW | DG_D | DFFB | 206752_s_at | 8577 | −0.6999 | 0.1283 | No | 206752_s_at | −0.6100 |
| NEW | DG_D | AGAP1 | 204066_s_at | 8726 | −0.7734 | 0.1193 | No | 204066_s_at | −1.1009 |
| NEW | DG_D | LOC389906 | 59433_at | 9327 | −1.1240 | 0.0762 | No | 1556102_x_at | −0.4763 |
| NEW | DG_D | GEMIN4 | 217099_s_at | 9507 | −1.2214 | 0.0661 | No | 217099_s_at | −1.0276 |
| NEW | DG_D | NOL12 | 219324_at | 9527 | −1.2307 | 0.0685 | No | 219324_at | −1.3931 |
| NEW | DG_D | INPP5A | 203006_at | 9533 | −1.2322 | 0.0719 | No | 203006_at | −0.7522 |
| NEW | DG_D | CHD1L | 212539_at | 9603 | −1.2772 | 0.0706 | No | 212539_at | −0.8681 |
| NEW | DG_D | JMJD4 | 218560_s_at | 9621 | −1.2852 | 0.0733 | No | 218560_s_at | −0.9034 |
| NEW | DG_D | LARS2 | 204016_at | 9853 | −1.4071 | 0.0597 | No | 204016_at | −0.7286 |
| NEW | DG_D | H2AFY | 207168_s_at | 10230 | −1.6424 | 0.0357 | No | 207168_s_at | −0.6011 |
| NEW | DG_D | NT5DC2 | 218051_s_at | 10419 | −1.7702 | 0.0266 | No | 218051_s_at | −1.2878 |
| NEW | DG_D | HNRNPA3P1 | 206809_s_at | 10436 | −1.7842 | 0.0309 | No | 206809_s_at | −1.2047 |
| NEW | DG_D | MGLL | 211026_s_at | 10467 | −1.8153 | 0.0343 | No | 211026_s_at | −1.2329 |
| NEW | DG_D | FAM118A | 219629_at | 10527 | −1.8526 | 0.0355 | No | 226475_at | −0.4186 |
| NEW | DG_D | DCPS | 218774_at | 10681 | −1.9749 | 0.0297 | No | 218774_at | −1.3790 |
| NEW | DG_D | LIG3 | 207348_s_at | 10804 | −2.0709 | 0.0267 | No | 204123_at | −1.5025 |
| NEW | DG_D | IKBKE | 204549_at | 10990 | −2.2250 | 0.0193 | No | 204549_at | −0.7580 |
| NEW | DG_D | USP13 | 205356_at | 11036 | −2.2676 | 0.0229 | No | 205356_at | −0.8452 |
| NEW | DG_D | SCMH1 | 221216_s_at | 11060 | −2.2920 | 0.0283 | No | 221216_s_at | −0.6497 |
| NEW | DG_D | MPHOSPH6 | 203740_at | 11174 | −2.3921 | 0.0270 | No | 203740_at | −1.0146 |
| NEW | DG_D | CEP192 | 218827_s_at | 11200 | −2.4153 | 0.0326 | No | 218827_s_at | −0.5851 |
| NEW | DG_D | DNMT3A | 218457_s_at | 11348 | −2.5552 | 0.0291 | No | 222640_at | −0.8989 |
| NEW | DG_D | MGC72080 | 217499_x_at | 11594 | −2.8050 | 0.0189 | No | 217499_x_at | −1.7349 |
| NEW | DG_D | BTN3A2 | 209846_s_at | 11628 | −2.8399 | 0.0251 | No | 209846_s_at | −0.4424 |
| NEW | DG_D | MGC5566 | 220449_at | 11829 | −3.1093 | 0.0193 | No | 220449_at | −0.8044 |
| NEW | DG_D | DOCK2 | 213160_at | 11933 | −3.2697 | 0.0215 | No | 213160_at | −0.9284 |
| NEW | DG_D | ABL1 | 202123_s_at | 12170 | −3.6675 | 0.0147 | No | 202123_s_at | −0.6077 |
| NEW | DG_D | CORO1B | 64486_at | 12416 | −4.2553 | 0.0089 | No | 64486_at | −0.5557 |
| NEW | DG_D | SHMT1 | 209980_s_at | 12669 | −5.2600 | 0.0058 | No | 224954_at | −0.7602 |
| NEW | DG_D | CIDEB | 221188_s_at | 12895 | −7.0827 | 0.0104 | No | 221188_s_at | −0.7572 |
| NEW | Red_D | B3GAT3 | 203452_at | 89 | 6.4989 | 0.0594 | Yes | 203452_at | −0.6670 |
| NEW | Red_D | SSR2 | 200652_at | 142 | 6.0288 | 0.1168 | Yes | 200652_at | −0.4014 |
| NEW | Red_D | CD320 | 218529_at | 160 | 5.8218 | 0.1748 | Yes | 218529_at | −1.4256 |
| NEW | Red_D | SCAMP3 | 201771_at | 203 | 5.4776 | 0.2274 | Yes | 201771_at | −0.8416 |
| NEW | Red_D | HIST1H2AJ | 208583_x_at | 244 | 5.2394 | 0.2777 | Yes | 208583_x_at | −0.7033 |
| NEW | Red_D | TMED1 | 203679_at | 494 | 4.4784 | 0.3042 | Yes | 203679_at | −1.1221 |
| NEW | Red_D | SMPD1 | 209420_s_at | 666 | 4.1113 | 0.3329 | Yes | 209420_s_at | −0.7122 |
| NEW | Red_D | CLN6 | 218161_s_at | 787 | 3.8809 | 0.3633 | Yes | 1567080_s_at | −1.0284 |
| NEW | Red_D | SCAMP2 | 218143_s_at | 845 | 3.7938 | 0.3975 | Yes | 218143_s_at | −0.9440 |
| NEW | Red_D | DHCR7 | 201790_s_at | 1224 | 3.3025 | 0.4021 | Yes | 201791_s_at | −1.5161 |
| NEW | Red_D | PTTG1 | 203554_x_at | 1399 | 3.0719 | 0.4200 | Yes | 203554_x_at | −0.8401 |
| NEW | Red_D | TMED3 | 208837_at | 1508 | 2.9593 | 0.4418 | Yes | 208837_at | −0.8660 |
| NEW | Red_D | CORO1A | 209083_at | 2121 | 2.4432 | 0.4196 | Yes | 209083_at | −1.5068 |
| NEW | Red_D | HMBS | 203040_s_at | 2150 | 2.4205 | 0.4421 | Yes | 203040_s_at | −0.5190 |
| NEW | Red_D | INHBE | 210587_at | 2312 | 2.3070 | 0.4533 | Yes | 210587_at | −3.5505 |
| NEW | Red_D | TMEM109 | 201361_at | 2409 | 2.2408 | 0.4687 | Yes | 201361_at | −0.6692 |
| NEW | Red_D | ATP6V0B | 200078_s_at | 2485 | 2.1849 | 0.4852 | Yes | 200078_s_at | −0.8093 |
| NEW | Red_D | VAV1 | 206219_s_at | 3313 | 1.6979 | 0.4388 | No | 206219_s_at | −0.8382 |
| NEW | Red_D | SLC37A4 | 202830_s_at | 3427 | 1.6406 | 0.4468 | No | 202830_s_at | −0.7995 |
| NEW | Red_D | TROAP | 204649_at | 3800 | 1.4479 | 0.4330 | No | 1568596_a_at | −1.0917 |
| NEW | Red_D | TNFRSF13B | 207641_at | 4627 | 1.0607 | 0.3802 | No | 207641_at | −0.9554 |
| NEW | Red_D | CD79B | 205297_s_at | 4787 | 0.9873 | 0.3780 | No | 205297_s_at | −1.1874 |
| NEW | Red_D | ABHD11 | 221927_s_at | 4998 | 0.8890 | 0.3709 | No | 221927_s_at | −0.5400 |
| NEW | Red_D | KIFC1 | 209680_s_at | 6230 | 0.3508 | 0.2797 | No | 209680_s_at | −1.0635 |
| NEW | Red_D | SLC7A11 | 207528_s_at | 6285 | 0.3277 | 0.2789 | No | 209921_at | −2.0492 |
| NEW | Red_D | UPP1 | 203234_at | 6353 | 0.3003 | 0.2768 | No | 203234_at | −0.7584 |
| NEW | Red_D | ATP6V0C | 36994_at | 6694 | 0.1610 | 0.2523 | No | 36994_at | −0.7413 |
| NEW | Red_D | SREBF1 | 202308_at | 6783 | 0.1242 | 0.2468 | No | 202308_at | −1.5501 |
| NEW | Red_D | C20orf3 | 206656_s_at | 6994 | 0.0316 | 0.2309 | No | 206656_s_at | −0.4617 |
| NEW | Red_D | DHRS7B | 220690_s_at | 7731 | −0.3097 | 0.1774 | No | 220690_s_at | −1.1801 |
| NEW | Red_D | PAQR4 | 212858_at | 8879 | −0.8566 | 0.0978 | No | 212858_at | −0.5606 |
| NEW | Red_D | P2RX4 | 204088_at | 9199 | −1.0585 | 0.0841 | No | 204088_at | −1.0043 |
| NEW | Red_D | INSIG1 | 201627_s_at | 9230 | −1.0771 | 0.0927 | No | 201625_s_at | −2.5371 |
| NEW | Red_D | B3GNT1 | 203188_at | 9734 | −1.3487 | 0.0678 | No | 203188_at | −0.4636 |
| NEW | Red_D | NEU1 | 208926_at | 10605 | −1.9098 | 0.0202 | No | 208926_at | −1.4294 |
| NEW | Red_D | GLT25D1 | 218473_s_at | 10949 | −2.1997 | 0.0163 | No | 218473_s_at | −0.8308 |
| NEW | Red_D | IL21R | 221658_s_at | 11496 | −2.7075 | 0.0018 | No | 221658_s_at | −0.9819 |
| NEW | Red_D | SCNN1B | 205464_at | 11557 | −2.7714 | 0.0254 | No | 205464_at | −1.6399 |
| NEW | Red_D | DIAPH1 | 215541_s_at | 12313 | −3.9735 | 0.0078 | No | 209190_s_at | −0.6448 |
| NEW | Red_D | NINJ1 | 203045_at | 12524 | −4.6341 | 0.0389 | No | 203045_at | −0.5586 |
| NEW | SG_U | SND1 | 201622_at | 204 | 5.4676 | −0.0026 | No | 201622_at | 0.3683 |
| NEW | SG_U | PEX16 | 49878_at | 268 | 5.1434 | 0.0050 | No | 49878_at | 0.3663 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| NEW | SG_U | BCAS4 | 220588_at | 273 | 5.1320 | 0.0171 | No | 228787_s_at | 0.6012 |
| NEW | SG_U | NCAM1 | 212843_at | 357 | 4.8373 | 0.0224 | No | 227394_at | 2.6276 |
| NEW | SG_U | GPRC5D | 221297_at | 419 | 4.6568 | 0.0290 | No | 221297_at | 1.4466 |
| NEW | SG_U | EEF1A2 | 204540_at | 468 | 4.5652 | 0.0363 | No | 204540_at | 1.2188 |
| NEW | SG_U | NBEA | 221207_s_at | 731 | 3.9950 | 0.0256 | No | 226439_s_at | 0.7562 |
| NEW | SG_U | HRASLS2 | 216760_at | 738 | 3.9793 | 0.0348 | No | 221122_at | 2.3804 |
| NEW | SG_U | FBXL2 | 214436_at | 999 | 3.5805 | 0.0233 | No | 214436_at | 0.9636 |
| NEW | SG_U | ARHGEF9 | 203263_s_at | 1068 | 3.4972 | 0.0265 | No | 203264_s_at | 1.1637 |
| NEW | SG_U | CYP26B1 | 219825_at | 1133 | 3.4148 | 0.0298 | No | 219825_at | 1.8184 |
| NEW | SG_U | TDRD7 | 213361_at | 1144 | 3.4024 | 0.0373 | No | 213361_at | 1.7645 |
| NEW | SG_U | PTPRD | 205712_at | 1155 | 3.3901 | 0.0447 | No | 214043_at | 1.3101 |
| NEW | SG_U | H1FX | 204805_s_at | 1353 | 3.1281 | 0.0370 | No | 204805_s_at | 1.6177 |
| NEW | SG_U | SERPINE1 | 202627_s_at | 1541 | 2.9299 | 0.0295 | No | 202627_s_at | 0.7062 |
| NEW | SG_U | EXOC6B | 215417_at | 1746 | 2.7386 | 0.0203 | No | 225900_at | 1.4931 |
| NEW | SG_U | SERPINI1 | 205352_at | 1763 | 2.7229 | 0.0256 | No | 205352_at | 1.2988 |
| NEW | SG_U | SATB2 | 213435_at | 1802 | 2.6849 | 0.0292 | No | 213435_at | 1.0194 |
| NEW | SG_U | IL12A | 207160_at | 1915 | 2.5959 | 0.0268 | No | 207160_at | 0.7546 |
| NEW | SG_U | ARHGAP26 | 205068_s_at | 1945 | 2.5693 | 0.0308 | No | 205068_s_at | 0.3358 |
| NEW | SG_U | RPH3A | 205230_at | 1968 | 2.5534 | 0.0353 | No | 205230_at | 0.2624 |
| NEW | SG_U | CHST11 | 219634_at | 2087 | 2.4667 | 0.0321 | No | 226372_at | 0.7049 |
| NEW | SG_U | DNM1 | 217341_at | 2099 | 2.4581 | 0.0372 | No | 215116_s_at | 0.9290 |
| NEW | SG_U | SQRDL | 217995_at | 2148 | 2.4210 | 0.0393 | No | 217995_at | 0.3155 |
| NEW | SG_U | LHPP | 215061_at | 2317 | 2.3045 | 0.0318 | No | 218523_at | 0.8186 |
| NEW | SG_U | CYP2R1 | 207786_at | 2344 | 2.2846 | 0.0353 | No | 227109_at | 0.5272 |
| NEW | SG_U | PPAP2A | 209147_s_at | 2590 | 2.1178 | 0.0214 | No | 209147_s_at | 0.9661 |
| NEW | SG_U | SILV | 209848_s_at | 2663 | 2.0728 | 0.0208 | No | 209848_s_at | 1.4400 |
| NEW | SG_U | C7orf58 | 220032_at | 3122 | 1.8071 | -0.0105 | No | 228728_at | 1.2195 |
| NEW | SG_U | PIK3CD | 211230_s_at | 3148 | 1.7914 | -0.0081 | No | 203879_at | 1.0301 |
| NEW | SG_U | ASPHD1 | 214993_at | 3203 | 1.7594 | -0.0080 | No | 1553997_a_at | 0.5512 |
| NEW | SG_U | MARCH2 | 210075_at | 3323 | 1.6915 | -0.0132 | No | 210075_at | 0.7438 |
| NEW | SG_U | TMCC2 | 213096_at | 3350 | 1.6798 | -0.0111 | No | 213096_at | 0.8882 |
| NEW | SG_U | HHLA3 | 220387_s_at | 3442 | 1.6280 | -0.0143 | No | 234665_x_at | 0.8157 |
| NEW | SG_U | MYH11 | 201497_x_at | 3479 | 1.6081 | -0.0132 | No | 201497_x_at | 1.2708 |
| NEW | SG_U | PRAME | 204086_at | 3518 | 1.5913 | -0.0122 | No | 204086_at | 1.2914 |
| NEW | SG_U | MYH15 | 215331_at | 3547 | 1.5742 | -0.0106 | No | 215331_at | 0.7231 |
| NEW | SG_U | SAP30L | 219129_s_at | 3821 | 1.4404 | -0.0284 | No | 225509_at | 1.4699 |
| NEW | SG_U | RASAL2 | 219026_s_at | 3988 | 1.3621 | -0.0380 | No | 222810_s_at | 1.6667 |
| NEW | SG_U | RIMS3 | 210991_s_at | 4067 | 1.3261 | -0.0409 | No | 204730_at | 0.4244 |
| NEW | SG_U | CBLN1 | 205747_at | 4086 | 1.3162 | -0.0391 | No | 205747_at | 0.4504 |
| NEW | SG_U | TUFT1 | 205807_s_at | 4318 | 1.1935 | -0.0542 | No | 205807_s_at | 0.7280 |
| NEW | SG_U | RASA2 | 206636_at | 4324 | 1.1910 | -0.0517 | No | 230669_at | 0.9736 |
| NEW | SG_U | CHMP7 | 212313_at | 4340 | 1.1864 | -0.0500 | No | 212313_at | 0.4507 |
| NEW | SG_U | LOC730227 | 215756_at | 4463 | 1.1377 | -0.0567 | No | 215756_at | 0.6852 |
| NEW | SG_U | ASMTL | 209394_at | 4522 | 1.1118 | -0.0585 | No | 36553_at | 1.1999 |
| NEW | SG_U | TMEM187 | 204340_at | 4568 | 1.0942 | -0.0594 | No | 204340_at | 0.6830 |
| NEW | SG_U | HEY1 | 44783_s_at | 4570 | 1.0933 | -0.0568 | No | 44783_s_at | 3.2756 |
| NEW | SG_U | KIAA0319 | 206017_at | 4678 | 1.0369 | -0.0626 | No | 206017_at | 0.6121 |
| NEW | SG_U | BTG1 | 200920_s_at | 4753 | 1.0018 | -0.0659 | No | 200920_s_at | 1.3862 |
| NEW | SG_U | JUP | 201015_s_at | 4770 | 0.9961 | -0.0648 | No | 201015_s_at | 0.7828 |
| NEW | SG_U | KLHL25 | 210307_s_at | 4811 | 0.9777 | -0.0655 | No | 210307_s_at | 0.3425 |
| NEW | SG_U | ERC1 | 215606_s_at | 4832 | 0.9700 | -0.0647 | No | 226049_at | 0.9883 |
| NEW | SG_U | ENTPD2 | 207372_at | 4883 | 0.9407 | -0.0663 | No | 230430_at | 0.5358 |
| NEW | SG_U | UPK1A | 214624_at | 4915 | 0.9266 | -0.0665 | No | 214624_at | 1.1307 |
| NEW | SG_U | FXYD1 | 205384_at | 4983 | 0.9005 | -0.0695 | No | 205384_at | 0.4831 |
| NEW | SG_U | SH3BGR | 204979_s_at | 4993 | 0.8922 | -0.0680 | No | 204979_s_at | 1.0822 |
| NEW | SG_U | IL15 | 205992_s_at | 5005 | 0.8857 | -0.0668 | No | 205992_s_at | 2.3102 |
| NEW | SG_U | DLEU1 | 205677_s_at | 5090 | 0.8458 | -0.0712 | No | 205677_s_at | 1.0707 |
| NEW | SG_U | IFIT3 | 204747_at | 5265 | 0.7749 | -0.0829 | No | 204747_at | 0.6673 |
| NEW | SG_U | S100A10 | 200872_at | 5274 | 0.7694 | -0.0817 | No | 200872_at | 0.7729 |
| NEW | SG_U | CAV1 | 203065_s_at | 5347 | 0.7354 | -0.0855 | No | 203065_s_at | 1.6979 |
| NEW | SG_U | HSPB1 | 201841_s_at | 5394 | 0.7127 | -0.0873 | No | 201841_s_at | 0.5158 |
| NEW | SG_U | RALGPS1 | 204199_at | 5456 | 0.6856 | -0.0904 | No | 204199_at | 1.8935 |
| NEW | SG_U | ABTB2 | 213497_at | 5752 | 0.5642 | -0.1121 | No | 213497_at | 0.6583 |
| NEW | SG_U | CYTH3 | 206523_at | 5980 | 0.4645 | -0.1286 | No | 225147_at | 0.6052 |
| NEW | SG_U | NR4A3 | 209959_at | 6288 | 0.3273 | -0.1517 | No | 209959_at | 0.3849 |
| NEW | SG_U | AP3M2 | 203410_at | 6429 | 0.2673 | -0.1620 | No | 203410_at | 0.8868 |
| NEW | SG_U | PLA2G12A | 221027_s_at | 6506 | 0.2373 | -0.1674 | No | 242323_at | 0.9317 |
| NEW | SG_U | ANXA5 | 200782_at | 6544 | 0.2225 | -0.1697 | No | 200782_at | 0.8349 |
| NEW | SG_U | ASAP3 | 222236_s_at | 6548 | 0.2197 | -0.1694 | No | 222236_s_at | 0.7455 |
| NEW | SG_U | OBSL1 | 214928_at | 6584 | 0.2079 | -0.1716 | No | 213946_s_at | 1.2912 |
| NEW | SG_U | ZHX3 | 212545_s_at | 6658 | 0.1794 | -0.1769 | No | 217367_s_at | 0.7944 |
| NEW | SG_U | TESK2 | 205486_at | 6752 | 0.1336 | -0.1838 | No | 205486_at | 0.9948 |
| NEW | SG_U | TTLL7 | 219882_at | 6764 | 0.1320 | -0.1843 | No | 219882_at | 1.3565 |

TABLE 5-continued

The numerical values from the GSEA for each gene contributing to the significant
enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log$^2$ Fold Change Combination |
|---|---|---|---|---|---|---|---|---|---|
| NEW | SG_U | MLL | 212078_s_at | 6838 | 0.0976 | −0.1898 | No | 226981_at | 0.6683 |
| NEW | SG_U | SRGAP2 | 213329_at | 6842 | 0.0952 | −0.1898 | No | 213329_at | 0.4920 |
| NEW | SG_U | GPS2 | 209350_s_at | 6914 | 0.0667 | −0.1952 | No | 209350_s_at | 0.8650 |
| NEW | SG_U | CHST7 | 206756_at | 6988 | 0.0355 | −0.2008 | No | 206756_at | 0.7672 |
| NEW | SG_U | FSD1 | 219170_at | 7009 | 0.0229 | −0.2023 | No | 219170_at | 0.4872 |
| NEW | SG_U | SYT11 | 209197_at | 7035 | 0.0123 | −0.2042 | No | 209197_at | 1.3400 |
| NEW | SG_U | SLC35A2 | 209326_at | 7165 | −0.0448 | −0.2141 | No | 209326_at | 0.4515 |
| NEW | SG_U | SRGN | 201858_s_at | 7220 | −0.0710 | −0.2182 | No | 201858_s_at | 0.4139 |
| NEW | SG_U | PBX1 | 212151_at | 7326 | −0.1321 | −0.2260 | No | 212151_at | 1.2989 |
| NEW | SG_U | KPTN | 220160_s_at | 7342 | −0.1402 | −0.2269 | No | 220160_s_at | 0.4342 |
| NEW | SG_U | RABGAP1L | 203020_at | 7403 | −0.1616 | −0.2311 | No | 213982_s_at | 1.9919 |
| NEW | SG_U | CRIP2 | 208978_at | 7467 | −0.1909 | −0.2356 | No | 208978_at | 0.9262 |
| NEW | SG_U | WNT11 | 206737_at | 7489 | −0.2040 | −0.2367 | No | 206737_at | 1.1543 |
| NEW | SG_U | TLE1 | 203221_at | 7544 | −0.2264 | −0.2404 | No | 203221_at | 0.6591 |
| NEW | SG_U | MYO15A | 220288_at | 7632 | −0.2687 | −0.2465 | No | 220288_at | 0.7058 |
| NEW | SG_U | TBXAS1 | 208130_s_at | 7817 | −0.3500 | −0.2600 | No | 208130_s_at | 0.9837 |
| NEW | SG_U | PAIP2B | 221868_at | 7854 | −0.3628 | −0.2619 | No | 221868_at | 1.2146 |
| NEW | SG_U | HBE1 | 205919_at | 7871 | −0.3712 | −0.2623 | No | 205919_at | 2.2651 |
| NEW | SG_U | MICAL2 | 212472_at | 7907 | −0.3875 | −0.2640 | No | 212473_s_at | 0.6345 |
| NEW | SG_U | BTG2 | 201236_s_at | 8081 | −0.4620 | −0.2764 | No | 201236_s_at | 1.0197 |
| NEW | SG_U | VWA5A | 205011_at | 8159 | −0.4991 | −0.2812 | No | 205011_at | 0.6620 |
| NEW | SG_U | CCL5 | 204655_at | 8180 | −0.5083 | −0.2815 | No | 1555759_a_at | 2.7666 |
| NEW | SG_U | GNAZ | 204993_at | 8279 | −0.5560 | −0.2878 | No | 204993_at | 0.7498 |
| NEW | SG_U | OPTN | 202074_s_at | 8423 | −0.6288 | −0.2974 | No | 202074_s_at | 0.8466 |
| NEW | SG_U | SLC4A8 | 207056_s_at | 8428 | −0.6320 | −0.2962 | No | 1554113_a_at | 0.4990 |
| NEW | SG_U | PGCP | 208454_s_at | 8509 | −0.6685 | −0.3008 | No | 208454_s_at | 0.8846 |
| NEW | SG_U | CLIP2 | 211031_s_at | 8576 | −0.6993 | −0.3043 | No | 211031_s_at | 1.4226 |
| NEW | SG_U | TLE2 | 40837_at | 8695 | −0.7611 | −0.3116 | No | 40837_at | 1.4735 |
| NEW | SG_U | GAB2 | 203853_s_at | 8758 | −0.7957 | −0.3145 | No | 203853_s_at | 0.6217 |
| NEW | SG_U | SNN | 218032_at | 8770 | −0.8018 | −0.3134 | No | 218032_at | 1.1523 |
| NEW | SG_U | HBG2 | 204419_x_at | 8900 | −0.8671 | −0.3214 | No | 213515_x_at | 1.0411 |
| NEW | SG_U | CAPG | 201850_at | 8919 | −0.8768 | −0.3206 | No | 201850_at | 0.4065 |
| NEW | SG_U | FLJ22184 | 220584_at | 8930 | −0.8843 | −0.3193 | No | 220584_at | 0.7091 |
| NEW | SG_U | GPC1 | 202756_s_at | 9012 | −0.9423 | −0.3233 | No | 202756_s_at | 0.2626 |
| NEW | SG_U | LPXN | 216250_s_at | 9027 | −0.9509 | −0.3221 | No | 216250_s_at | 0.8789 |
| NEW | SG_U | FAM164A | 205308_at | 9072 | −0.9793 | −0.3231 | No | 205308_at | 0.8831 |
| NEW | SG_U | HEXIM1 | 202814_s_at | 9075 | −0.9800 | −0.3209 | No | 202814_s_at | 1.5943 |
| NEW | SG_U | TEAD3 | 209454_s_at | 9120 | −1.0100 | −0.3219 | No | 209454_s_at | 0.9877 |
| NEW | SG_U | LRCH4 | 221956_at | 9196 | −1.0557 | −0.3251 | No | 90610_at | 0.6937 |
| NEW | SG_U | UBTD1 | 219172_at | 9261 | −1.0914 | −0.3275 | No | 219172_at | 0.5312 |
| NEW | SG_U | SLC12A6 | 220740_s_at | 9289 | −1.1077 | −0.3269 | No | 226741_at | 0.6098 |
| NEW | SG_U | FZD4 | 218665_at | 9402 | −1.1668 | −0.3328 | No | 218665_at | 0.5746 |
| NEW | SG_U | ANKRD11 | 219437_s_at | 9425 | −1.1794 | −0.3316 | No | 226012_at | 0.4516 |
| NEW | SG_U | DOK4 | 209690_s_at | 9448 | −1.1915 | −0.3304 | No | 209691_s_at | 0.4003 |
| NEW | SG_U | AHNAK | 211986_at | 9480 | −1.2084 | −0.3299 | No | 211986_at | 3.0382 |
| NEW | SG_U | NCOA3 | 209062_x_at | 9520 | −1.2275 | −0.3300 | No | 209061_at | 0.7598 |
| NEW | SG_U | ARHGAP17 | 218076_s_at | 9538 | −1.2339 | −0.3283 | No | 218076_s_at | 0.9554 |
| NEW | SG_U | FADS3 | 204257_at | 9561 | −1.2511 | −0.3270 | No | 204257_at | 0.6793 |
| NEW | SG_U | MT2A | 212185_x_at | 9612 | −1.2809 | −0.3278 | No | 212185_x_at | 1.1216 |
| NEW | SG_U | EFR3B | 215328_at | 9655 | −1.3089 | −0.3279 | No | 227283_at | 1.1424 |
| NEW | SG_U | FNDC3B | 218618_s_at | 9665 | −1.3134 | −0.3254 | No | 218618_s_at | 0.9300 |
| NEW | SG_U | ENTPD1 | 209473_at | 9704 | −1.3315 | −0.3251 | No | 209473_at | 0.2403 |
| NEW | SG_U | FKBP1B | 209931_s_at | 9709 | −1.3331 | −0.3222 | No | 206857_s_at | 1.7204 |
| NEW | SG_U | CAPN5 | 205166_at | 9855 | −1.4082 | −0.3300 | No | 226292_at | 0.7814 |
| NEW | SG_U | NEAT1 | 214657_s_at | 9896 | −1.4346 | −0.3297 | No | 224566_at | 0.7719 |
| NEW | SG_U | ADAM28 | 208269_at | 9903 | −1.4383 | −0.3267 | No | 205997_at | 1.6045 |
| NEW | SG_U | GSN | 214040_s_at | 10054 | −1.5340 | −0.3346 | No | 200696_s_at | 1.5769 |
| NEW | SG_U | EPB41L5 | 220977_x_at | 10058 | −1.5361 | −0.3311 | No | 225855_at | 1.1081 |
| NEW | SG_U | PLAC8 | 219014_at | 10185 | −1.6136 | −0.3370 | No | 219014_at | 1.1130 |
| NEW | SG_U | ROGDI | 218394_at | 10199 | −1.6221 | −0.3341 | No | 218394_at | 0.7896 |
| NEW | SG_U | MAPT | 203928_x_at | 10220 | −1.6328 | −0.3317 | No | 203929_s_at | 1.2389 |
| NEW | SG_U | TIAM1 | 213135_at | 10324 | −1.7061 | −0.3356 | No | 213135_at | 1.2715 |
| NEW | SG_U | SRR | 219205_at | 10365 | −1.7278 | −0.3345 | No | 219205_at | 0.6989 |
| NEW | SG_U | SYNE2 | 202761_s_at | 10488 | −1.8265 | −0.3395 | No | 202761_s_at | 0.8638 |
| NEW | SG_U | GSTA4 | 202967_at | 10552 | −1.8698 | −0.3399 | No | 202967_at | 1.1781 |
| NEW | SG_U | STAT4 | 206118_at | 10826 | −2.0939 | −0.3561 | Yes | 206118_at | 0.7244 |
| NEW | SG_U | PIM1 | 209193_at | 10861 | −2.1270 | −0.3536 | Yes | 209193_at | 0.4581 |
| NEW | SG_U | CHN1 | 212624_s_at | 10869 | −2.1344 | −0.3489 | Yes | 212624_s_at | 0.7418 |
| NEW | SG_U | SMARCD3 | 204099_at | 10870 | −2.1349 | −0.3438 | Yes | 204099_at | 1.7452 |
| NEW | SG_U | TNNT1 | 213201_s_at | 11022 | −2.2565 | −0.3500 | Yes | 213201_s_at | 1.9121 |
| NEW | SG_U | PHC1 | 218338_at | 11044 | −2.2759 | −0.3461 | Yes | 218338_at | 0.6767 |
| NEW | SG_U | TGFBR2 | 208944_at | 11062 | −2.2937 | −0.3419 | Yes | 208944_at | 1.7261 |
| NEW | SG_U | AP1G1 | 203350_at | 11187 | −2.4041 | −0.3457 | Yes | 225771_at | 0.8554 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | $\text{Log}^2$ Fold Change Combination |
|---|---|---|---|---|---|---|---|---|---|
| NEW | SG_U | KIF13B | 202962_at | 11227 | −2.4435 | −0.3428 | Yes | 202962_at | 0.1920 |
| NEW | SG_U | ASAP1 | 221039_s_at | 11239 | −2.4477 | −0.3377 | Yes | 224796_at | 0.6173 |
| NEW | SG_U | SGK269 | 220008_at | 11278 | −2.4878 | −0.3346 | Yes | 225913_at | 1.0102 |
| NEW | SG_U | KHDRBS3 | 209781_s_at | 11386 | −2.6000 | −0.3367 | Yes | 209781_s_at | 0.5985 |
| NEW | SG_U | PDE4DIP | 212390_at | 11396 | −2.6100 | −0.3310 | Yes | 214129_at | 0.1865 |
| NEW | SG_U | LPGAT1 | 202651_at | 11472 | −2.6866 | −0.3303 | Yes | 227476_at | 0.4155 |
| NEW | SG_U | HIF1AN | 218525_s_at | 11511 | −2.7267 | −0.3267 | Yes | 226648_at | 0.6976 |
| NEW | SG_U | CST3 | 201360_at | 11528 | −2.7407 | −0.3213 | Yes | 201360_at | 1.7967 |
| NEW | SG_U | ZFP36 | 201531_at | 11578 | −2.7873 | −0.3183 | Yes | 201531_at | 1.1739 |
| NEW | SG_U | CCDC92 | 218175_at | 11603 | −2.8117 | −0.3133 | Yes | 218175_at | 1.1364 |
| NEW | SG_U | TANK | 207616_s_at | 11612 | −2.8202 | −0.3071 | Yes | 207616_s_at | 1.2193 |
| NEW | SG_U | ELF4 | 203490_at | 11673 | −2.8995 | −0.3047 | Yes | 203490_at | 0.1915 |
| NEW | SG_U | CA2 | 209301_at | 11763 | −3.0227 | −0.3043 | Yes | 209301_at | 2.3006 |
| NEW | SG_U | CYTH1 | 202879_s_at | 11795 | −3.0664 | −0.2993 | Yes | 202880_s_at | 0.4208 |
| NEW | SG_U | SLC37A1 | 218928_s_at | 11811 | −3.0853 | −0.2930 | Yes | 218928_s_at | 1.5958 |
| NEW | SG_U | ALDH2 | 201425_at | 11827 | −3.1072 | −0.2866 | Yes | 201425_at | 0.6952 |
| NEW | SG_U | UBR5 | 208884_s_at | 11849 | −3.1303 | −0.2806 | Yes | 208884_s_at | 1.5132 |
| NEW | SG_U | KCNH2 | 210036_s_at | 11869 | −3.1636 | −0.2744 | Yes | 210036_s_at | 0.4936 |
| NEW | SG_U | CTSK | 202450_s_at | 11899 | −3.2104 | −0.2689 | Yes | 202450_s_at | 0.7887 |
| NEW | SG_U | KIF1B | 209234_at | 11931 | −3.2684 | −0.2634 | Yes | 209234_at | 0.4223 |
| NEW | SG_U | GLS | 203159_at | 11995 | −3.3740 | −0.2601 | Yes | 203159_at | 0.7744 |
| NEW | SG_U | LIMA1 | 217892_s_at | 12042 | −3.4391 | −0.2553 | Yes | 217892_s_at | 0.8689 |
| NEW | SG_U | ProSAPiP1 | 204447_at | 12050 | −3.4449 | −0.2475 | Yes | 204447_at | 0.7388 |
| NEW | SG_U | FOXO1 | 202723_s_at | 12052 | −3.4461 | −0.2392 | Yes | 202723_s_at | 1.5149 |
| NEW | SG_U | LGALS3 | 208949_s_at | 12162 | −3.6437 | −0.2388 | Yes | 208949_s_at | 0.9798 |
| NEW | SG_U | JUN | 201464_x_at | 12180 | −3.6830 | −0.2312 | Yes | 201464_x_at | 0.9285 |
| NEW | SG_U | C11orf80 | 204922_at | 12231 | −3.7747 | −0.2259 | Yes | 204922_at | 0.3391 |
| NEW | SG_U | KIAA0513 | 204546_at | 12289 | −3.9079 | −0.2209 | Yes | 204546_at | 0.9209 |
| NEW | SG_U | RRAS | 212647_at | 12300 | −3.9350 | −0.2121 | Yes | 212647_at | 1.0321 |
| NEW | SG_U | BLVRA | 211729_x_at | 12342 | −4.0352 | −0.2055 | Yes | 211729_x_at | 0.5834 |
| NEW | SG_U | HIP1 | 205426_s_at | 12361 | −4.0838 | −0.1969 | Yes | 226364_at | 0.9342 |
| NEW | SG_U | DNMBP | 212838_at | 12377 | −4.1303 | −0.1881 | Yes | 212838_at | 0.3275 |
| NEW | SG_U | VCL | 200931_s_at | 12404 | −4.2174 | −0.1799 | Yes | 200931_s_at | 1.5632 |
| NEW | SG_U | FUCA1 | 202838_at | 12506 | −4.5862 | −0.1766 | Yes | 202838_at | 0.4742 |
| NEW | SG_U | TGFBR3 | 204731_at | 12533 | −4.6900 | −0.1672 | Yes | 226625_at | 1.2976 |
| NEW | SG_U | C17orf91 | 214696_at | 12534 | −4.6908 | −0.1558 | Yes | 214696_at | 0.9025 |
| NEW | SG_U | HLA-DMB | 203932_at | 12536 | −4.6958 | −0.1445 | Yes | 203932_at | 1.1066 |
| NEW | SG_U | PHLPP2 | 213407_at | 12573 | −4.8635 | −0.1355 | Yes | 213407_at | 0.6092 |
| NEW | SG_U | Hs.533878 | 218363_at | 12588 | −4.9065 | −0.1246 | Yes | 229131_at | 0.4206 |
| NEW | SG_U | TUBA1A | 209118_s_at | 12607 | −4.9831 | −0.1139 | Yes | 209118_s_at | 1.5498 |
| NEW | SG_U | SGK3 | 220038_at | 12636 | −5.1187 | −0.1037 | Yes | 227627_at | 1.5170 |
| NEW | SG_U | MPP1 | 202974_at | 12713 | −5.5067 | −0.0962 | Yes | 202974_at | 0.6470 |
| NEW | SG_U | SGPP1 | 221268_s_at | 12733 | −5.6854 | −0.0839 | Yes | 223391_at | 1.1439 |
| NEW | SG_U | CYP26A1 | 206424_at | 12740 | −5.7182 | −0.0705 | Yes | 206424_at | 0.6489 |
| NEW | SG_U | ZCCHC24 | 212419_at | 12768 | −5.8700 | −0.0583 | Yes | 212419_at | 1.1963 |
| NEW | SG_U | PDGFC | 218718_at | 12769 | −5.8731 | −0.0440 | Yes | 218718_at | 1.7530 |
| NEW | SG_U | FLJ10357 | 220326_s_at | 12776 | −5.9162 | −0.0301 | Yes | 220326_s_at | 0.8886 |
| NEW | SG_U | PILRA | 222218_s_at | 12837 | −6.4399 | −0.0192 | Yes | 222218_s_at | 1.2450 |
| NEW | SG_U | IGFBP6 | 203851_at | 12838 | −6.4408 | −0.0035 | Yes | 203851_at | 0.5314 |
| NEW | SG_U | NAGK | 218231_at | 12918 | −7.5351 | 0.0087 | Yes | 218231_at | 0.4800 |
| SMM | Blue_U | SATB1 | 203408_s_at | 3624 | 1.4106 | −0.2436 | No | 203408_s_at | 2.2924 |
| SMM | Blue_U | CAMSAP1L1 | 212763_at | 7931 | −0.3792 | −0.5650 | No | 212765_at | 0.8007 |
| SMM | Blue_U | PHC3 | 215521_at | 9176 | −0.9064 | −0.6382 | No | 226508_at | 1.3199 |
| SMM | Blue_U | HLA-DRB4 | 209728_at | 11502 | −2.3419 | −0.7590 | Yes | 209728_at | 3.1361 |
| SMM | Blue_U | CALCOCO1 | 209002_s_at | 11526 | −2.3632 | −0.7024 | Yes | 209002_s_at | 1.3443 |
| SMM | Blue_U | HLA-DRB6 | 217362_x_at | 11680 | −2.4852 | −0.6528 | Yes | 217362_x_at | 1.3574 |
| SMM | Blue_U | HLA-DQB1 | 211654_x_at | 12005 | −2.8292 | −0.6079 | Yes | 211654_x_at | 1.3513 |
| SMM | Blue_U | LOC731682 | 212671_s_at | 12557 | −3.8494 | −0.5552 | Yes | 212671_s_at | 2.2805 |
| SMM | Blue_U | HLA-DRB1 | 204670_x_at | 12672 | −4.1997 | −0.4602 | Yes | 208306_x_at | 1.2895 |
| SMM | Blue_U | HLA-DMA | 217478_s_at | 12745 | −4.5116 | −0.3544 | Yes | 217478_s_at | 1.4991 |
| SMM | Blue_U | HLA-DPB1 | 201137_s_at | 12752 | −4.5780 | −0.2418 | Yes | 201137_s_at | 1.5092 |
| SMM | Blue_U | LOC100294276 | 209312_x_at | 12828 | −4.9259 | −0.1260 | Yes | 209312_x_at | 1.3887 |
| SMM | Blue_U | SPARCL1 | 200795_at | 12921 | −5.7240 | 0.0083 | Yes | 200795_at | 1.1056 |
| MGUS | Blue_U | SATB1 | 203408_s_at | 3704 | 1.1197 | −0.2458 | No | 203408_s_at | 2.2924 |
| MGUS | Blue_U | CALCOCO1 | 209002_s_at | 9412 | −0.9381 | −0.6518 | No | 209002_s_at | 1.3443 |
| MGUS | Blue_U | HLA-DRB6 | 217362_x_at | 10028 | −1.1922 | −0.6578 | Yes | 217362_x_at | 1.3574 |
| MGUS | Blue_U | HLA-DRB4 | 209728_at | 10324 | −1.3338 | −0.6343 | Yes | 209728_at | 3.1361 |
| MGUS | Blue_U | CAMSAP1L1 | 212763_at | 10424 | −1.3740 | −0.5944 | Yes | 212765_at | 0.8007 |
| MGUS | Blue_U | PHC3 | 215521_at | 10897 | −1.6480 | −0.5736 | Yes | 226508_at | 1.3199 |
| MGUS | Blue_U | HLA-DQB1 | 211654_x_at | 11531 | −2.0553 | −0.5511 | Yes | 211654_x_at | 1.3513 |
| MGUS | Blue_U | LOC731682 | 212671_s_at | 12068 | −2.5487 | −0.5041 | Yes | 212671_s_at | 2.2805 |
| MGUS | Blue_U | HLA-DMA | 217478_s_at | 12176 | −2.6813 | −0.4196 | Yes | 217478_s_at | 1.4991 |
| MGUS | Blue_U | HLA-DPB1 | 201137_s_at | 12362 | −2.9258 | −0.3326 | Yes | 201137_s_at | 1.5092 |

TABLE 5-continued

The numerical values from the GSEA for each gene contributing to the significant enrichment of drug-affected genes in the patient groups compared to healthy volunteers.

| MM Group | Gene Set | Gene Symbol | Probe | Rank in Gene List | Rank Metric Score | Running Es | Core Enrichment | AffyID Combination | Log² Fold Change Combination |
|---|---|---|---|---|---|---|---|---|---|
| MGUS | Blue_U | HLA-DRB1 | 204670_x_at | 12429 | −3.0428 | −0.2324 | Yes | 208306_x_at | 1.2895 |
| MGUS | Blue_U | LOC100294276 | 209312_x_at | 12659 | −3.6620 | −0.1233 | Yes | 209312_x_at | 1.3887 |
| MGUS | Blue_U | SPARCL1 | 200795_at | 12855 | −4.3821 | 0.0134 | Yes | 200795_at | 1.1056 |

TABLE 6

Summary of gene expression in MM patients with poor prognosis and regulation of gene expression in MM cells treated with HDACi/mTORi combination.*

| Mod. | Gene Identifier | Gene Description | Exemplary Accession No. | (1) | (2) | (3) | (4) |
|---|---|---|---|---|---|---|---|
| B | E2F2 | E2F transcKIAAription factor 2 (E2F2), mRNA. | NM_004091 | Up | Down | Up | Down |
| B | SLC19A1 | solute carrier family 19 (folate transporter), member 1 (SLC19A1), mRNA. | NM_001205207 | Up | Down | Up | Down |
| B | LDHA | lactate dehydrogenase A (LDHA), transcript variant 4, mRNA. | NM_001165416 | Up | Down | Up | Down |
| B | UBE2C | ubiquitin-conjugating enzyme E2C (UBE2C), transcript variant 1, mRNA. | NM_181800 | Up | Down | Up | Down |
| B | TRIP13 | thyroid hormone receptor interactor 13 (TRIP13), transcript variant 1, mRNA. | NM_004237 | Up | Down | Up | Down |
| B | RRM2 | ribonucleotide reductase M2 (RRM2), transcript variant 2, mRNA. | NM_001165931 | Up | Down | Up | Down |
| B | NCAPH | non-SMC condensin I complex, subunit H (NCAPH), mRNA. | NM_015341 | Up | Down | Up | Down |
| B | CDC25A | cell division cycle 25 homolog A (S. pombe) (CDC25A), transcript variant 2, mRNA. | NM_001789 | Up | Down | Up | Down |
| B | MCM5 | minichromosome maintenance complex component 5 (MCM5), mRNA. | NM_006739 | Up | Down | Up | Down |
| B | CCNB2 | cyclin B2 (CCNB2), mRNA. | NM_004701 | Up | Down | Up | Down |
| B | RAD51 | RAD51 homolog (RecA homolog, E. coli) (S. cerevisiae) (RAD51), transcript variant 4, mRNA. | NM_002875 | Up | Down | Up | Down |
| B | MCM4 | Minichromosome maintenance complex component 4 | NM_005914 | Up | Down | Up | Down |
| B | PHC3 | polyhomeotic homolog 3 (Drosophila) (PHC3), mRNA. | NM_024947 | Down | Up | Down | Up |
| B | SPAG5 | sperm associated antigen 5 (SPAG5), mRNA. | NM_006461 | Up | Down | Up | Down |
| B | PHF19 | PHD finger protein 19 (PHF19), transcript variant 2, mRNA. | NM_015675 | Up | Down | Up | Down |
| B | MCM2 | minichromosome maintenance complex component 2 (MCM2), mRNA. | NM_004526 | Up | Down | Up | Down |
| B | STK6 | serine/threonine kinase 6 | NM_198436 | Up | Down | Up | Down |
| B | CDCA5 | cell division cycle associated 5 (CDCA5), mRNA. | NM_080668 | Up | Down | Up | Down |
| B | HJURP | Holliday junction recognition protein (HJURP), mRNA. | NM_018410 | Up | Down | Up | Down |
| B | Hs.193784 | MRNA; cDNA DKFZp586K1922 (from clone DKFZp586K1922) | BF476076 | Down | Up | Down | Up |
| B | TACC3 | transforming, acidic coiled-coil containing protein 3 (TACC3), mRNA. | NM_006342 | Up | Down | Up | Down |
| B | CDC20 | cell division cycle 20 homolog (S. cerevisiae) (CDC20), mRNA. | NM_001255 | Up | Down | Up | Down |
| B | ATAD2 | ATPase family, AAA domain containing 2 (ATAD2), mRNA. | NM_014109 | Up | Down | Up | Down |
| B | Hs.202577 | CDNA FLJ34585 fis, clone KIDNE2008758 | AU_144961 | Down | Up | Down | Up |

TABLE 6-continued

Summary of gene expression in MM patients with poor prognosis and regulation of gene expression in MM cells treated with HDACi/mTORi combination.*

| Mod. | Gene Identifier | Gene Description | Exemplary Accession No. | (1) | (2) | (3) | (4) |
|---|---|---|---|---|---|---|---|
| B | TMEM48 | transmembrane protein 48 (TMEM48), transcript variant 2, mRNA. | NM_018087 | Up | Down | Up | Down |
| B | CDCA3 | cell division cycle associated 3 (CDCA3), mRNA. | NM_031299 | Up | Down | Up | Down |
| B | CDC6 | cell division cycle 6 homolog (*S. cerevisiae*) (CDC6), mRNA. | NM_001254 | Up | Down | Up | Down |
| B | SUV39H1 | suppressor of variegation 3-9 homolog 1 (*Drosophila*) (SUV39H1), mRNA. | NM_003173 | Up | Down | Up | Down |
| B | BLM | Bloom syndrome, RecQ helicase-like (BLM), mRNA. | NM_014109 | Up | Down | Up | Down |
| B | KIF2C | kinesin family member 2C (KIF2C), mRNA. | NM_006845 | Up | Down | Up | Down |
| B | ZNF107 | zinc finger protein 107 (ZNF107), transcript variant 2, mRNA. | NM_016220 | Up | Down | Up | Down |
| B | C9orf140 | chromosome 9 open reading frame 140 (C9orf140), mRNA. | NM_178448 | Up | Down | Up | Down |
| B | KIF22 | kinesin family member 22 (KIF22), mRNA. | NM_007317 | Up | Down | Up | Down |
| B | MYBL2 | v-myb myeloblastosis viral oncogene homolog (avian)-like 2 (MYBL2), mRNA. | NM_002466 | Up | Down | Up | Down |
| B | KIAA2013 | KIAA2013 (KIAA2013), mRNA. | NM_138346 | Down | Down | UP | Down |
| B | HLA-DPB1 | Major histocompatibility complex, class II, DP beta 1 | NM_002121 | Down | Up | Down | Up |
| B | NSDHL | NAD(P) dependent steroid dehydrogenase-like | NM_015922 | Up | Down | Up | Down |
| DG | CTPS | CTP synthase (CTPS), mRNA. | NM_001905 | Up | Down | Up | |
| DG | C15orf41 | chromosome 15 open reading frame 41 (C15orf41), transcript variant 1, mRNA. | NM_001130010 | Up | Down | Up | |
| DG | FAM20B | family with sequence similarity 20, member B (FAM20B), mRNA. | NM_014864 | Up | Down | Up | |
| DG | HK2 | hexokinase 2 (HK2), mRNA. | NM_000189 | Up | Down | Up | |
| DG | CHD1L | chromodomain helicase DNA binding protein 1-like (CHD1L), mRNA. | NM_004284 | Up | Down | Up | |
| DG | SLC25A33 | solute carrier family 25, member 33 (SLC25A33), mRNA. | NM_032315 | Up | Down | Up | |
| DG | CRIPAK | cysteine rich PAK1 inhibitor (CRIPAK), mRNA. | NM_175918 | Down | Up | Down | |
| DG | HNRNPAB | heterogeneous nuclear ribonucleoprotein A/B (HNRNPAB), transcript variant 2, mRNA. | NM_004499 | Up | Down | Up | |
| DG | PA2G4 | proliferation-associated 2G4, 38 kDa (PA2G4), mRNA. | NM_006191 | Up | Down | Up | |
| DG | CASP2 | caspase 2, apoptosis-related cysteine peptidase (CASP2), transcript variant 3, mRNA. | NM_032983 | Up | Down | Up | |
| DG | GYS1 | glycogen synthase 1 (muscle) (GYS1), transcript variant 2, mRNA. | NM_001161587 | Up | Down | Up | |
| DG | DNMT3A | DNA (cytosine-5-)-methyltransferase 3 alpha (DNMT3A), transcript variant 4, mRNA. | NM_153759 | Down | Down | Up | |
| DG | HAUS7 | HAUS augmin-like complex, subunit 7 (HAUS7), mRNA. | NM_017518 | Up | Down | Up | |
| DG | DKFZP586I1420 | hypothetical protein DKFZp586I1420 (DKFZP586I1420), non-coding RNA. | NR_002186 | Down | Up | Down | |
| DG | SEPN1 | selenoprotein N, 1 (SEPN1), transcript variant 2, mRNA. | NM_206926 | Down | Up | Down | |
| DG | C1orf61 | chromosome 1 open reading frame 61 (C1orf61), mRNA. | NM_006365 | Up | Up | Down | |
| DG | WDR4 | WD repeat domain 4 (WDR4), transcript variant 2, mRNA. | NM_033661 | Up | Down | Up | |

TABLE 6-continued

Summary of gene expression in MM patients with poor prognosis and regulation of gene expression in MM cells treated with HDACi/mTORi combination.*

| Mod. | Gene Identifier | Gene Description | Exemplary Accession No. | (1) | (2) | (3) | (4) |
|---|---|---|---|---|---|---|---|
| DG | NR2F6 | nuclear receptor subfamily 2, group F, member 6 (NR2F6), mRNA. | NM_005234 | Down | Down | Up | |
| DG | BTN3A2 | butyrophilin, subfamily 3, member A2 (BTN3A2), mRNA. | NM_007047 | Down | Down | Up | |
| DG | GEMIN4 | gem (nuclear organelle) associated protein 4 (GEMIN4), mRNA. | NM_015721 | Up | Down | Up | |
| DG | MYEOV | Myeloma overexpressed (in a subset of t(11; 14) positive multiple myelomas) | AA621983 | Down | Down | Up | |
| DG | TOMM40L | translocase of outer mitochondrial membrane 40 homolog (yeast)-like (TOMM40L), nuclear gene encoding mitochondrial protein, mRNA. | NM_032174 | Up | Down | Up | |
| DG | CC2D1B | coiled-coil and C2 domain containing 1B (CC2D1B), mRNA. | NM_032449 | Down | Down | Up | |
| DG | ACO2 | aconitase 2, mitochondrial (ACO2), nuclear gene encoding mitochondrial protein, mRNA. | NM_001098 | Up | Down | Up | |
| DG | H3F3A | H3 histone, family 3A (H3F3A), mRNA. | NM_002107 | Up | Down | Up | |
| DG | HDGF | hepatoma-derived growth factor (high-mobility group protein 1-like) (HDGF), transcript variant 3, mRNA. | NM_001126051 | Up | Down | Up | |
| DG | TTLL12 | tubulin tyrosine ligase-like family, member 12 (TTLL12), mRNA. | NM_015140 | Up | Down | Up | |
| DG | BID | BH3 interacting domain death agonist (BID), transcript variant 3, mRNA. | NM_197967 | Up | Down | Up | |
| DG | APC2 | adenomatosis polyposis coli 2 (APC2), mRNA. | NM_005883 | Down | Up | Down | |
| DG | PRDM6 | PR domain containing 6 | NM_001136239 | Down | Up | Down | |
| DG | STAG3L4 | stromal antigen 3-like 4 (STAG3L4), mRNA. | NM_022906 | Down | Down | Up | |
| DG | Hs.380390 | CDNA FLJ12204 fis, clone MAMMA1000921 | AK022266 | Up | Up | Down | |
| DG | TMPO | thymopoietin (TMPO), transcript variant 3, mRNA. | NM_001032284 | Up | Down | Up | |
| DG | Hs.511739 | Transcribed locus | AA974493 | Up | Down | Up | |
| O | NEK6 | NIMA (never in mitosis gene a)-related kinase 6 (NEK6), transcript variant 5, mRNA. | NM_001166168 | Down | Down | Up | |
| O | ENPP1 | ectonucleotide pyrophosphatase/phosphodiesterase 1 (ENPP1), mRNA. | NM_006208 | Up | Up | Down | |
| O | LAMP3 | lysosomal-associated membrane protein 3 (LAMP3), mRNA. | NM_014398 | Down | Up | Down | |
| O | STOM | Stomatin | M81635 | Down | Up | Down | |
| O | Hs.593067 | Clone CDABP0105 mRNA sequence | AW296194 | Down | Up | Down | |
| red | PTTG1 | pituitary tumor transforming 1 (PTTG1), mRNA. | NM_004219 | Up | Down | Up | |
| red | SAMD9 | sterile alpha motif domain containing 9 (SAMD9), mRNA. | NM_017654 | Up | Up | Down | |
| red | RASGRP3 | RAS guanyl releasing protein 3 (calcium and DAG-regulated) (RASGRP3), transcript variant 3, mRNA. | NM_015376 | Down | Up | Down | |
| red | P2RX4 | purinergic receptor P2X, ligand-gated ion channel, 4 (P2RX4), mRNA. | NM_002560 | Down | Down | Up | |
| red | B3GNT1 | UDP-GlcNAc:betaGal beta-1,3-N-acetylglucosaminyltransferase 1 (B3GNT1), mRNA. | NM_006876 | Down | Down | Up | |
| red | Hs.656245 | CDNA FLJ42308 fis, clone TRACH2005796 | AI743092 | Up | Up | Down | |
| red | Hs.656252 | CDNA FLJ31688 fis, clone NT2RI2005520 | AI693193 | Up | Down | Up | |

TABLE 6-continued

Summary of gene expression in MM patients with poor prognosis and regulation of gene expression in MM cells treated with HDACi/mTORi combination.*

| Mod. | Gene Identifier | Gene Description | Exemplary Accession No. | (1) | (2) | (3) | (4) |
|---|---|---|---|---|---|---|---|
| red | GLT25D1 | glycosyltransferase 25 domain containing 1 (GLT25D1), mRNA. | NM_024656 | Up | Down | Up | |
| red | SCNN1B | sodium channel, nonvoltage-gated 1, beta (SCNN1B), mRNA. | NM_000336 | Down | Down | Up | |
| red | IL21R | interleukin 21 receptor (IL21R), transcript variant 1, mRNA. | NM_021798 | Up | Down | Up | |
| SG | Hs.592472 | Transcribed locus | AA903473 | Down | Down | Up | |
| SG | Hs.157791 | Transcribed locus | BE857611 | Down | Up | Down | |
| SG | BDH1 | 3-hydroxybutyrate dehydrogenase, type 1 (BDH1), nuclear gene encoding mitochondrial protein, transcript variant 2, mRNA. | NM_203315 | Up | Down | Up | |
| SG | CHMP7 | CHMP family, member 7 (CHMP7), mRNA. | NM_152272 | Down | Up | Down | |
| SG | FUCA1 | fucosidase, alpha-L- 1, tissue (FUCA1), mRNA. | NM_000147 | Down | Up | Down | |
| SG | ZNF248 | zinc finger protein 248 (ZNF248), mRNA. | NM_021045 | Down | Down | Up | |
| SG | TESK2 | testis-specific kinase 2 (TESK2), mRNA. | NM_007170 | Down | Up | Down | |
| SG | PFAS | phosphoribosylformylglycinamidine synthase (PFAS), mRNA. | NM_012393 | Up | Down | Up | |
| SG | HLA-DMB | major histocompatibility complex, class II, DM beta (HLA-DMB), mRNA. | NM_002118 | Down | Up | Down | |
| SG | CLIP2 | CAP-GLY domain containing linker protein 2 (CLIP2), transcript variant 2, mRNA. | NM_032421 | Down | Up | Down | |
| SG | RLTPR | RGD motif, leucine rich repeats, tropomodulin domain and proline-rich containing (RLTPR), mRNA. | NM_001013838 | Down | Down | Up | |
| SG | ITPKB | inositol 1,4,5-trisphosphate 3-kinase B (ITPKB), mRNA. | NM_002221 | Down | Down | Up | |
| SG | HEY1 | hairy/enhancer-of-split related with YRPW motif 1 (HEY1), transcript variant 1, mRNA. | NM_012258 | Down | Up | Down | |
| SG | PTPN7 | Protein tyrosine phosphatase, non-receptor type 7 | NM_002832 | Up | Down | Up | |
| SG | LOC100134229 | hypothetical protein LOC100134229 (LOC100134229), non-coding RNA. | NR_024451 | Down | Up | Down | |
| SG | SAP30L | SAP30-like (SAP30L), transcript variant 3, mRNA. | NM_001131063 | Down | Up | Down | |
| SG | PAIP2B | Poly(A) binding protein interacting protein 2B | AB032981 | Down | Up | Down | |
| SG | RPH3A | rabphilin 3A homolog (mouse) (RPH3A), transcript variant 2, mRNA. | NM_014954 | Up | Up | Down | |
| SG | ARHGAP4 | Rho GTPase activating protein 4 (ARHGAP4), transcript variant 2, mRNA. | NM_001666 | Up | Down | Up | |
| SG | CA2 | carbonic anhydrase II (CA2), mRNA. | NM_000067 | Up | Up | Down | |
| SG | CRIP2 | cysteine-rich protein 2 (CRIP2), mRNA. | NM_001312 | Up | Up | Down | |
| SG | SELM | selenoprotein M (SELM), mRNA. | NM_080430 | Down | Up | Down | |
| SG | VWA5A | von Willebrand factor A domain containing 5A (VWA5A), transcript variant 1, mRNA. | NM_014622 | Up | Up | Down | |
| SG | TDRD7 | tudor domain containing 7 (TDRD7), mRNA. | NM_014290 | Down | Up | Down | |
| SG | GAB2 | GRB2-associated binding protein 2 (GAB2), transcript variant 2, mRNA. | NM_012296 | Down | Up | Down | |
| SG | ZNF324B | zinc finger protein 324B (ZNF324B), mRNA. | NM_207395 | Down | Down | Up | |

TABLE 6-continued

Summary of gene expression in MM patients with poor prognosis and regulation of gene expression in MM cells treated with HDACi/mTORi combination.*

| Mod. | Gene Identifier | Gene Description | Exemplary Accession No. | (1) | (2) | (3) | (4) |
|---|---|---|---|---|---|---|---|
| SG | ZNF385A | zinc finger protein 385A (ZNF385A), transcript variant 2, mRNA. | NM_001130968 | Down | Up | Down | |
| SG | MYBBP1A | MYB binding protein (P160) 1a (MYBBP1A), transcript variant 2, mRNA. | NM_014520 | Up | Down | Up | |
| SG | ABTB2 | ankyrin repeat and BTB (POZ) domain containing 2 (ABTB2), mRNA. | NM_145804 | Up | Up | Down | |
| SG | Hs.533878 | Transcribed locus | AI702450 | Down | Up | Down | |
| SG | C7orf41 | chromosome 7 open reading frame 41 (C7orf41), mRNA. | NM_152793 | Down | Up | Down | |
| SG | ITGA8 | integrin, alpha 8 (ITGA8), mRNA. | NM_003638 | Down | Down | Up | |
| SG | ZMYND8 | zinc finger, MYND-type containing 8 (ZMYND8), transcript variant 3, mRNA. | NM_183048 | Up | Down | Up | |
| SG | PDGFC | platelet derived growth factor C (PDGFC), mRNA. | NM_016205 | Up | Up | Down | |
| SG | GIPC3 | GIPC PDZ domain containing family, member 3 (GIPC3), mRNA. | NM_133261 | Down | Down | Up | |
| SG | MYH11 | myosin, heavy chain 11, smooth muscle (MYH11), transcript variant SM1A, mRNA. | NM_002474 | Down | Up | Down | |
| SG | ERC1 | ELKS/RAB6-interacting/CAST family member 1 (ERC1), transcript variant delta, mRNA. | NM_178039 | Down | Up | Down | |
| SG | SGK3 | serum/glucocorticoid regulated kinase family, member 3 (SGK3), transcript variant 2, mRNA. | NM_170709 | Down | Up | Down | |

*Module (Mod.) is indicated by B (blue module), SG (springgreen module), DG (darkgreen module), O (orange module) and R (red module).
(1) Gene expression signature in MM patients with poor prognosis;
(2) Regulation of gene expression by mTORi/HDACi combination treatment;
(3) Gene expression signature in neoplasms sensitive to mTORi/HDACi combination treatment before mTORi/HDACi combination treatment;
(4) Gene expression signature in a neoplasm sensitive to mTORi/HDACi combination treatment, where treatment has been initiated, and the neoplasm is responding to treatment following initiation of mTORi/HDACi combination treatment.
"Up" refers to upregulation of gene extression;
"Down" refers to down regulation of gene exression.

TABLE 7

Hazards ratios and Cox regression coefficients for the 37 genes comprising the survival risk predictor gene set.*

| No | AffyID GSE4581 | GeneID | % CV Support | Weight ($w_i$) | Cox regression coefficient | Hazards Ratio | univariate Cox p-value | AffyID Combination | Log2 Fold Change Combination |
|---|---|---|---|---|---|---|---|---|---|
| 1 | 228361_at | E2F2 | 100 | −0.017203 | 0.706 | 2.026 | 0.000161 | 228361_at | −2.5642 |
| 2 | 211576_s_at | SLC19A1 | 100 | 0.203801 | 0.415 | 1.515 | 0.000313 | 209777_s_at | −1.4453 |
| 3 | 200650_s_at | LDHA | 100 | 0.040212 | 1.267 | 3.551 | 0.000749 | 200650_s_at | −1.2640 |
| 4 | 202954_at | UBE2C | 100 | 0.017179 | 0.597 | 1.817 | 0.000767 | 202954_at | −1.4051 |
| 5 | 204033_at | TRIP13 | 100 | 0.046076 | 0.534 | 1.705 | 0.000809 | 204033_at | −2.5425 |
| 6 | 201890_at | RRM2 | 100 | 0.069265 | 0.421 | 1.524 | 0.000853 | 209773_s_at | −3.3973 |
| 7 | 212949_at | NCAPH | 100 | 0.011961 | 0.338 | 1.403 | 0.000902 | 212949_at | −2.1530 |
| 8 | 1555772_a_at | CDC25A | 100 | 0.031373 | 0.629 | 1.875 | 0.001141 | 204695_at | −2.3587 |
| 9 | 216237_s_at | MCM5 | 100 | −0.003184 | 0.764 | 2.147 | 0.001254 | 216237_s_at | −2.2926 |
| 10 | 202705_at | CCNB2 | 100 | 0.054831 | 0.403 | 1.496 | 0.001369 | 202705_at | −2.1340 |
| 11 | 205024_s_at | RAD51 | 100 | 0.028679 | 0.606 | 1.832 | 0.001635 | 205024_s_at | −1.5192 |
| 12 | 222036_s_at | MCM4 | 100 | 0.020637 | 0.701 | 2.015 | 0.003035 | 212141_at | −2.3064 |
| 13 | 226508_at | PHC3 | 100 | −0.01545 | −0.979 | 0.376 | 0.003840 | 226508_at | 1.3199 |
| 14 | 203145_at | SPAG5 | 100 | 0.015318 | 0.679 | 1.972 | 0.003990 | 203145_at | −2.3469 |
| 15 | 227211_at | PHF19 | 100 | −0.015882 | 0.408 | 1.504 | 0.005021 | 227212_s_at | −2.3316 |
| 16 | 202107_s_at | MCM2 | 100 | 0.028639 | 0.571 | 1.769 | 0.005803 | 202107_s_at | −2.0679 |
| 17 | 208079_s_at | STK6 | 100 | 0.033502 | 0.329 | 1.390 | 0.007843 | 208079_s_at | −1.8883 |
| 18 | 224753_at | CDCA5 | 100 | 0.05834 | 0.326 | 1.385 | 0.008636 | 224753_at | −2.0297 |
| 19 | 218726_at | HJURP | 100 | 0.098946 | 0.332 | 1.394 | 0.008934 | 218726_at | −1.9264 |

TABLE 7-continued

Hazards ratios and Cox regression coefficients for the 37 genes comprising the survival risk predictor gene set.*

| No | AffyID GSE4581 | GeneID | % CV Support | Weight ($w_i$) | Cox regression coefficient | Hazards Ratio | univariate Cox p-value | AffyID Combination | Log2 Fold Change Combination |
|---|---|---|---|---|---|---|---|---|---|
| 20 | 223307_at | CDCA3 | 80 | 0.011455 | 0.634 | 1.886 | 0.009810 | 223307_at | −1.9094 |
| 21 | 227121_at | Hs.193784 | 100 | −0.014023 | −0.570 | 0.566 | 0.011597 | 227121_at | 2.1723 |
| 22 | 202870_s_at | CDC20 | 90 | −0.013444 | 0.340 | 1.404 | 0.011909 | 202870_s_at | −1.5564 |
| 23 | 218308_at | TACC3 | 100 | 0.034436 | 0.280 | 1.324 | 0.012977 | 218308_at | −1.3035 |
| 24 | 203968_s_at | CDC6 | 80 | 0.002627 | 0.511 | 1.667 | 0.015071 | 203968_s_at | −2.5641 |
| 25 | 218782_s_at | ATAD2 | 90 | 0.002874 | 0.454 | 1.575 | 0.01598 | 2218782_s_at | −2.5687 |
| 26 | 226252_at | Hs.202577 | 90 | −0.024384 | −0.606 | 0.546 | 0.016669 | 226250_at | 1.8818 |
| 27 | 218619_s_at | SUV39H1 | 70 | −0.007072 | 0.723 | 2.060 | 0.0183 | 22218619_s_at | −1.1582 |
| 28 | 234672_s_at | TMEM48 | 90 | 0.016871 | 0.704 | 2.021 | 0.023457 | 234672_s_at | −1.4764 |
| 29 | 201710_at | MYBL2 | 50 | −0.056413 | 0.214 | 1.239 | 0.029821 | 201710_at | −2.6352 |
| 30 | 205733_at | BLM | 70 | 0.009443 | 0.565 | 1.760 | 0.031636 | 205733_at | −1.5970 |
| 31 | 209408_at | KIF2C | 60 | 0.010982 | 0.616 | 1.852 | 0.033569 | 209408_at | −2.0440 |
| 32 | 224706_at | KIAA2013 | 50 | −0.021992 | −0.576 | 0.562 | 0.035131 | 224706_at | −1.1300 |
| 33 | 205739_x_at | ZNF107 | 60 | 0.009985 | 0.501 | 1.651 | 0.035876 | 243312_at | −0.9633 |
| 34 | 225777_at | C9orf140 | 60 | 0.068912 | 0.396 | 1.485 | 0.037516 | 225777_at | −1.5692 |
| 35 | 202183_s_at | KIF22 | 60 | −0.015944 | 0.481 | 1.618 | 0.045240 | 202183_s_at | −1.6422 |
| 36 | 201137_s_at | HLA-DPB1 | 50 | −0.190465 | −0.254 | 0.776 | 0.04619 | 2201137_s_at | 1.5092 |
| 37 | 215093_at | NSDHL | 30 | 0.016074 | 0.700 | 2.013 | 0.047773 | 209279_s_at | −1.3381 |

*The prognostic index is computed by the formula: $\Sigma_i w_i x_i - 4.552161$, where $w_i$ and $x_i$ are the weight and logged gene expression for the i-th gene. A new sample is predicted as high (low) risk if its prognostic index is larger than (smaller than or equal to) −0.061194.

TABLE 8

Gene expression analyzed for GOBO and Oncomine analysis.

| | GeneID | Oncomine Analysis | GOBO Analysis |
|---|---|---|---|
| Down-regulated with HDACi/mTORi combination therapy | | | |
| 1 | ATAD2 | YES | YES |
| 2 | BLM | YES | YES |
| 3 | C9orf140 | YES | not mapped |
| 4 | CCNB2 | YES | YES |
| 5 | CDC20 | YES | YES |
| 6 | CDC25A | YES | YES |
| 7 | CDC6 | YES | YES |
| 8 | CDCA3 | YES | YES |
| 9 | CDCA5 | YES | not mapped |
| 10 | E2F2 | YES | YES |
| 11 | HJURP | YES | YES |
| 12 | KIAA2013 | YES | not mapped |
| 13 | KIF22 | YES | YES |
| 14 | KIF2C | YES | YES |
| 15 | LDHA | YES | YES |
| 16 | MCM2 | YES | YES |
| 17 | MCM4 | YES | YES |
| 18 | MCM5 | YES | YES |
| 19 | MYBL2 | YES | YES |
| 20 | NCAPH | YES | YES |
| 21 | NSDHL | YES | YES |
| 22 | PHF19 | YES | not mapped |
| 23 | RAD51 | YES | YES |
| 24 | RRM2 | YES | YES |
| 25 | SLC19A1 | YES | YES |
| 26 | SPAG5 | YES | YES |
| 27 | STK6 | not mapped | not mapped |
| 28 | SUV39H1 | YES | YES |
| 29 | TACC3 | YES | YES |
| 30 | TMEM48 | YES | YES |
| 31 | TRIP13 | YES | YES |
| 32 | UBE2C | YES | YES |
| 33 | ZNF107 | YES | not mapped |
| Up-regulated with HDACi/mTORi combination therapy | | | |
| 34 | HLA-DPB1 | | not entered |
| 35 | Hs.193784 | | |
| 36 | Hs.202577 | | |
| 37 | PHC3 | | |

TABLE 9

Hazards ratios, Cox regression coefficients Log2 fold change in expression in response to HDACi/mTORi treatment for the 124 genes predictive of survival and affected by the drug combination comprising the survival risk predictor gene set.*

| Mod | GeneID | % CV Support | Is. hub | Cox regression coefficient | Hazard Ratio | univariate Cox p-value | Log2 Fold Change Combination |
|---|---|---|---|---|---|---|---|
| B | E2F2 | 100 | TRUE | 0.7060 | 2.0258 | 0.0002 | −5.90 |
| B | SLC19A1 | 100 | FALSE | 0.4154 | 1.5150 | 0.0003 | −2.73 |
| B | LDHA | 100 | FALSE | 1.2672 | 3.5509 | 0.0007 | −2.39 |
| B | UBE2C | 100 | FALSE | 0.5971 | 1.8168 | 0.0008 | −2.66 |
| B | TRIP13 | 100 | FALSE | 0.5337 | 1.7052 | 0.0008 | −5.82 |
| B | RRM2 | 100 | TRUE | 0.4214 | 1.5241 | 0.0009 | −10.56 |
| B | NCAPH | 100 | TRUE | 0.3384 | 1.4028 | 0.0009 | −4.44 |
| B | CDC25A | 100 | TRUE | 0.6286 | 1.8751 | 0.0011 | −5.13 |
| B | MCM5 | 100 | FALSE | 0.7639 | 2.1467 | 0.0013 | −4.89 |

TABLE 9-continued

Hazards ratios, Cox regression coefficients Log2 fold change in expression in response to HDACi/mTORi treatment for the 124 genes predictive of survival and affected by the drug combination comprising the survival risk predictor gene set.*

| Mod | GeneID | % CV Support | Is. hub | Cox regression coefficient | Hazard Ratio | univariate Cox p-value | Log2 Fold Change Combination |
|---|---|---|---|---|---|---|---|
| B | CCNB2 | 100 | TRUE | 0.4031 | 1.4965 | 0.0014 | −4.38 |
| B | RAD51 | 100 | TRUE | 0.6056 | 1.8324 | 0.0016 | −2.87 |
| B | MCM4 | 100 | TRUE | 0.7007 | 2.0152 | 0.0030 | −4.96 |
| B | PHC3 | 100 | FALSE | −0.9787 | 0.3758 | 0.0038 | 2.50 |
| B | SPAG5 | 100 | TRUE | 0.6788 | 1.9716 | 0.0040 | −5.10 |
| B | PHF19 | 100 | TRUE | 0.4081 | 1.5039 | 0.0050 | −5.03 |
| B | MCM2 | 100 | TRUE | 0.5706 | 1.7693 | 0.0058 | −4.20 |
| B | STK6 | 100 | TRUE | 0.3292 | 1.3899 | 0.0078 | −3.71 |
| B | CDCA5 | 100 | TRUE | 0.3257 | 1.3850 | 0.0086 | −4.08 |
| B | HJURP | 100 | TRUE | 0.3321 | 1.3939 | 0.0089 | −3.81 |
| B | Hs.193784 | 100 | TRUE | −0.5696 | 0.5658 | 0.0116 | 4.50 |
| B | TACC3 | 100 | FALSE | 0.2805 | 1.3237 | 0.0130 | −2.46 |
| B | CDC20 | 90 | FALSE | 0.3395 | 1.4043 | 0.0119 | −2.95 |
| B | ATAD2 | 90 | FALSE | 0.4540 | 1.5745 | 0.0160 | −5.94 |
| B | Hs.202577 | 90 | FALSE | −0.6056 | 0.5458 | 0.0167 | 3.68 |
| B | TMEM48 | 90 | FALSE | 0.7038 | 2.0214 | 0.0235 | −2.79 |
| B | CDCA3 | 80 | TRUE | 0.6344 | 1.8860 | 0.0098 | −3.76 |
| B | CDC6 | 80 | FALSE | 0.5111 | 1.6672 | 0.0151 | −5.90 |
| B | SUV39H1 | 70 | FALSE | 0.7227 | 2.0600 | 0.0183 | −2.23 |
| B | BLM | 70 | FALSE | 0.5653 | 1.7599 | 0.0316 | −3.03 |
| B | KIF2C | 60 | TRUE | 0.6160 | 1.8516 | 0.0336 | −4.11 |
| B | ZNF107 | 60 | TRUE | 0.5012 | 1.6507 | 0.0359 | −1.95 |
| B | C9orf140 | 60 | TRUE | 0.3956 | 1.4852 | 0.0375 | −2.97 |
| B | KIF22 | 60 | TRUE | 0.4813 | 1.6182 | 0.0452 | −3.12 |
| B | MYBL2 | 50 | TRUE | 0.2144 | 1.2391 | 0.0298 | −6.23 |
| B | KIAA2013 | 50 | FALSE | −0.5762 | 0.5620 | 0.0351 | −2.19 |
| B | HLA-DPB1 | 50 | TRUE | −0.2538 | 0.7758 | 0.0462 | 2.85 |
| B | NSDHL | 30 | FALSE | 0.6998 | 2.0134 | 0.0478 | −2.53 |
| DG | CTPS | 100 | TRUE | 0.8910 | 2.4376 | 0.0007 | −2.55 |
| DG | C15orf41 | 100 | FALSE | 0.6388 | 1.8942 | 0.0007 | −1.57 |
| DG | FAM20B | 100 | FALSE | 1.0114 | 2.7494 | 0.0010 | −1.82 |
| DG | HK2 | 100 | FALSE | 0.3191 | 1.3758 | 0.0011 | −2.57 |
| DG | CHD1L | 100 | FALSE | 0.8316 | 2.2970 | 0.0018 | −1.83 |
| DG | SLC25A33 | 100 | TRUE | 1.0619 | 2.8918 | 0.0018 | −1.92 |
| DG | CRIPAK | 100 | FALSE | −0.8472 | 0.4286 | 0.0023 | 2.00 |
| DG | HNRNPAB | 100 | FALSE | 0.8949 | 2.4471 | 0.0048 | −1.95 |
| DG | PA2G4 | 100 | FALSE | 0.9535 | 2.5948 | 0.0058 | −1.82 |
| DG | CASP2 | 100 | FALSE | 1.1726 | 3.2304 | 0.0097 | −1.25 |
| DG | GYS1 | 90 | FALSE | 0.8504 | 2.3406 | 0.0073 | −2.03 |
| DG | DNMT3A | 90 | TRUE | −0.5714 | 0.5647 | 0.0084 | −1.87 |
| DG | HAUS7 | 90 | FALSE | 0.9227 | 2.5161 | 0.0087 | −2.17 |
| DG | DKFZP586I1420 | 90 | FALSE | −0.8374 | 0.4328 | 0.0112 | 2.64 |
| DG | SEPN1 | 90 | FALSE | −0.3558 | 0.7006 | 0.0130 | 1.88 |
| DG | C1orf61 | 90 | FALSE | 0.5109 | 1.6669 | 0.0136 | 1.37 |
| DG | WDR4 | 90 | TRUE | 0.5190 | 1.6803 | 0.0157 | −1.97 |
| DG | NR2F6 | 90 | FALSE | −0.2589 | 0.7719 | 0.0158 | −1.58 |
| DG | BTN3A2 | 90 | FALSE | −0.4043 | 0.6675 | 0.0174 | −1.36 |
| DG | GEMIN4 | 80 | TRUE | 0.4985 | 1.6462 | 0.0190 | −2.04 |
| DG | MYEOV | 80 | FALSE | −0.3691 | 0.6914 | 0.0233 | −3.68 |
| DG | TOMM40L | 70 | TRUE | 0.3643 | 1.4395 | 0.0206 | −1.85 |
| DG | CC2D1B | 70 | FALSE | −0.4042 | 0.6675 | 0.0214 | −1.92 |
| DG | ACO2 | 70 | TRUE | 0.5765 | 1.7798 | 0.0302 | −1.93 |
| DG | H3F3A | 60 | FALSE | 0.9332 | 2.5426 | 0.0296 | −1.46 |
| DG | HDGF | 60 | TRUE | 0.6002 | 1.8224 | 0.0319 | −3.18 |
| DG | TTLL12 | 60 | TRUE | 0.6135 | 1.8469 | 0.0329 | −1.77 |
| DG | BID | 60 | TRUE | 0.7283 | 2.0715 | 0.0332 | −2.53 |
| DG | APC2 | 60 | TRUE | −0.3685 | 0.6918 | 0.0364 | 1.88 |
| DG | PRDM6 | 50 | FALSE | −0.2554 | 0.7746 | 0.0394 | 1.39 |
| DG | STAG3L4 | 50 | TRUE | −0.6818 | 0.5057 | 0.0449 | −1.78 |
| DG | Hs.380390 | 40 | TRUE | 0.3128 | 1.3672 | 0.0385 | 1.99 |
| DG | TMPO | 40 | FALSE | 0.5988 | 1.8198 | 0.0439 | −2.89 |
| DG | Hs.511739 | 40 | FALSE | 0.5763 | 1.7794 | 0.0483 | −1.75 |
| O | NEK6 | 100 | FALSE | −0.3593 | 0.6982 | 0.0059 | −1.14 |
| O | ENPP1 | 90 | TRUE | 0.5066 | 1.6597 | 0.0202 | 1.01 |
| O | LAMP3 | 70 | TRUE | −0.3429 | 0.7097 | 0.0259 | 2.64 |
| O | STOM | 70 | TRUE | −0.3578 | 0.6992 | 0.0327 | 1.22 |
| O | Hs.593067 | 40 | FALSE | −0.3690 | 0.6914 | 0.0401 | 1.05 |
| R | PTTG1 | 100 | FALSE | 0.5712 | 1.7705 | 0.0028 | −1.79 |
| R | SAMD9 | 100 | TRUE | 0.5727 | 1.7731 | 0.0037 | 2.10 |
| R | RASGRP3 | 80 | TRUE | −0.2361 | 0.7897 | 0.0115 | 3.53 |
| R | P2RX4 | 80 | FALSE | −0.4011 | 0.6696 | 0.0272 | −2.00 |
| R | B3GNT1 | 70 | FALSE | −0.5994 | 0.5492 | 0.0237 | −1.38 |

TABLE 9-continued

Hazards ratios, Cox regression coefficients Log2 fold change in expression in response to HDACi/mTORi treatment for the 124 genes predictive of survival and affected by the drug combination comprising the survival risk predictor gene set.*

| Mod | GeneID | % CV Support | Is. hub | Cox regression coefficient | Hazard Ratio | univariate Cox p-value | Log2 Fold Change Combination |
|---|---|---|---|---|---|---|---|
| R | Hs.656245 | 60 | FALSE | 0.4102 | 1.5072 | 0.0347 | 1.47 |
| R | Hs.656252 | 60 | FALSE | 0.4595 | 1.5833 | 0.0377 | −1.35 |
| R | GLT25D1 | 50 | TRUE | 0.9534 | 2.5945 | 0.0398 | −1.78 |
| R | SCNN1B | 50 | TRUE | −0.1832 | 0.8326 | 0.0496 | −3.12 |
| R | IL21R | 40 | TRUE | 0.2293 | 1.2577 | 0.0442 | −1.97 |
| SG | Hs.592472 | 100 | TRUE | −0.4231 | 0.6550 | 0.0002 | −2.58 |
| SG | Hs.157791 | 100 | TRUE | −0.4701 | 0.6250 | 0.0006 | 1.79 |
| SG | BDH1 | 100 | TRUE | 0.7036 | 2.0210 | 0.0007 | −3.27 |
| SG | CHMP7 | 100 | FALSE | −1.6010 | 0.2017 | 0.0017 | 1.37 |
| SG | FUCA1 | 100 | FALSE | −0.8137 | 0.4432 | 0.0018 | 1.39 |
| SG | ZNF248 | 100 | FALSE | −1.0365 | 0.3547 | 0.0024 | −1.56 |
| SG | TESK2 | 100 | FALSE | −0.6572 | 0.5183 | 0.0049 | 1.99 |
| SG | PFAS | 100 | TRUE | 0.6640 | 1.9425 | 0.0051 | −1.92 |
| SG | HLA-DMB | 100 | FALSE | −0.9324 | 0.3936 | 0.0056 | 2.16 |
| SG | CLIP2 | 100 | FALSE | −0.4037 | 0.6679 | 0.0072 | 2.68 |
| SG | RLTPR | 100 | FALSE | −0.5643 | 0.5687 | 0.0073 | −1.84 |
| SG | ITPKB | 100 | FALSE | −0.3761 | 0.6865 | 0.0086 | −1.74 |
| SG | HEY1 | 100 | TRUE | −0.4962 | 0.6089 | 0.0093 | 9.71 |
| SG | PTPN7 | 100 | FALSE | 0.6646 | 1.9436 | 0.0178 | −2.64 |
| SG | LOC100134229 | 90 | TRUE | −0.7586 | 0.4683 | 0.0075 | 1.52 |
| SG | SAP30L | 90 | FALSE | −0.8343 | 0.4342 | 0.0094 | 2.77 |
| SG | PAIP2B | 90 | TRUE | −0.5109 | 0.5999 | 0.0107 | 2.31 |
| SG | RPH3A | 90 | FALSE | 0.3124 | 1.3667 | 0.0154 | 1.20 |
| SG | ARHGAP4 | 90 | FALSE | 0.6316 | 1.8807 | 0.0160 | −1.80 |
| SG | CA2 | 90 | TRUE | 0.2410 | 1.2725 | 0.0161 | 4.92 |
| SG | CRIP2 | 90 | TRUE | 0.2908 | 1.3375 | 0.0209 | 1.91 |
| SG | SELM | 90 | FALSE | −0.3342 | 0.7159 | 0.0216 | 1.60 |
| SG | VWA5A | 90 | TRUE | 0.6243 | 1.8669 | 0.0237 | 1.58 |
| SG | TDRD7 | 90 | TRUE | −0.6616 | 0.5160 | 0.0240 | 3.39 |
| SG | GAB2 | 80 | TRUE | −0.3037 | 0.7381 | 0.0078 | 1.54 |
| SG | ZNF324B | 80 | FALSE | −0.6600 | 0.5169 | 0.0249 | −1.30 |
| SG | ZNF385A | 70 | TRUE | −0.5437 | 0.5806 | 0.0193 | 1.49 |
| SG | MYBBP1A | 70 | TRUE | 0.8429 | 2.3232 | 0.0238 | −1.58 |
| SG | ABTB2 | 70 | TRUE | 0.3177 | 1.3739 | 0.0264 | 1.58 |
| SG | Hs.533878 | 70 | FALSE | −0.6679 | 0.5128 | 0.0305 | 1.34 |
| SG | C7orf41 | 70 | FALSE | −0.2872 | 0.7503 | 0.0309 | 4.08 |
| SG | ITGA8 | 70 | FALSE | −0.2411 | 0.7858 | 0.0319 | −4.26 |
| SG | ZMYND8 | 60 | TRUE | 0.6600 | 1.9348 | 0.0244 | −2.33 |
| SG | PDGFC | 60 | TRUE | 0.2241 | 1.2512 | 0.0397 | 3.36 |
| SG | GIPC3 | 50 | FALSE | −0.3154 | 0.7295 | 0.0434 | −2.35 |
| SG | MYH11 | 50 | TRUE | −0.3636 | 0.6951 | 0.0466 | 2.41 |
| SG | ERC1 | 40 | FALSE | −0.8090 | 0.4453 | 0.0414 | 1.99 |
| SG | SGK3 | 40 | TRUE | −0.4591 | 0.6319 | 0.0443 | 2.87 |

*Module (Mod.) is indicated by B (blue module), SG (springgreen module), DG (darkgreen module), O (orange module) and R (red module).

TABLE 10 predicted risk classifications

| No | Sample_ID | RiskGroup_SRP37 | MM_Subgroup | PI | RiskGroup_SRP124 |
|---|---|---|---|---|---|
| 1 | GSM50988 | low | CD2 | Low PI | low |
| 2 | GSM50990 | high | MS | Low PI | high |
| 3 | GSM50991 | low | MF | Low PI | low |
| 4 | GSM50997 | high | PR | High PI | high |
| 5 | GSM51000 | high | HY | Low PI | low |
| 6 | GSM51003 | low | HY | Low PI | high |
| 7 | GSM51006 | high | HY | High PI | high |
| 8 | GSM51008 | high | PR | High PI | high |
| 9 | GSM51011 | high | PR | Low PI | high |
| 10 | GSM51013 | low | LB | High PI | low |
| 11 | GSM51015 | high | CD1 | Low PI | high |
| 12 | GSM51020 | low | CD2 | High PI | high |
| 13 | GSM51023 | high | PR | High PI | high |
| 14 | GSM51029 | low | LB | Low PI | high |
| 15 | GSM51032 | low | HY | Low PI | low |
| 16 | GSM51035 | high | MS | High PI | high |
| 17 | GSM51037 | low | HY | Low PI | high |
| 18 | GSM51038 | low | MS | High PI | high |

TABLE 10-continued predicted risk classifications

| No | Sample_ID | RiskGroup_SRP37 | MM_Subgroup | PI | RiskGroup_SRP124 |
|---|---|---|---|---|---|
| 19 | GSM51043 | high | MS | High PI | high |
| 20 | GSM51045 | high | MF | High PI | high |
| 21 | GSM51049 | high | HY | High PI | high |
| 22 | GSM51053 | low | MS | Low PI | high |
| 23 | GSM51054 | low | CD2 | High PI | low |
| 24 | GSM51056 | high | MF | Low PI | high |
| 25 | GSM51057 | high | PR | High PI | high |
| 26 | GSM51058 | low | LB | Low PI | high |
| 27 | GSM51061 | low | MS | High PI | low |
| 28 | GSM51063 | low | LB | High PI | low |
| 29 | GSM51064 | low | HY | High PI | low |
| 30 | GSM51065 | high | CD1 | Low PI | high |
| 31 | GSM51066 | low | LB | Low PI | high |
| 32 | GSM51071 | low | MS | Low PI | high |
| 33 | GSM51074 | high | CD1 | High PI | high |
| 34 | GSM51076 | high | MS | High PI | high |
| 35 | GSM51081 | low | MS | Low PI | high |
| 36 | GSM51082 | high | HY | High PI | high |
| 37 | GSM51086 | low | MS | Low PI | high |
| 38 | GSM51088 | low | MS | High PI | low |
| 39 | GSM51089 | low | MS | Low PI | high |
| 40 | GSM51091 | high | PR | High PI | high |
| 41 | GSM51092 | low | HY | Low PI | low |
| 42 | GSM51093 | low | HY | Low PI | high |
| 43 | GSM51096 | high | CD1 | High PI | high |
| 44 | GSM51097 | high | HY | Low PI | high |
| 45 | GSM51098 | low | LB | Low PI | low |
| 46 | GSM51101 | low | MS | High PI | high |
| 47 | GSM51104 | high | MF | High PI | high |
| 48 | GSM51105 | low | LB | Low PI | low |
| 49 | GSM51108 | high | MS | High PI | high |
| 50 | GSM51110 | low | CD2 | Low PI | low |
| 51 | GSM51112 | high | CD1 | High PI | high |
| 52 | GSM51124 | high | MS | High PI | high |
| 53 | GSM51128 | low | MF | Low PI | high |
| 54 | GSM51129 | high | CD1 | Low PI | high |
| 55 | GSM51131 | high | HY | Low PI | high |
| 56 | GSM51132 | high | HY | Low PI | high |
| 57 | GSM51133 | high | LB | Low PI | low |
| 58 | GSM51134 | high | LB | High PI | high |
| 59 | GSM51137 | high | HY | Low PI | low |
| 60 | GSM51144 | low | CD2 | Low PI | low |
| 61 | GSM51145 | high | HY | High PI | high |
| 62 | GSM51146 | high | PR | High PI | high |
| 63 | GSM51150 | low | HY | Low PI | high |
| 64 | GSM51151 | high | MS | High PI | high |
| 65 | GSM51155 | low | HY | Low PI | low |
| 66 | GSM51157 | low | CD2 | Low PI | high |
| 67 | GSM51163 | high | MF | Low PI | high |
| 68 | GSM51167 | low | HY | Low PI | low |
| 69 | GSM51174 | low | CD2 | Low PI | low |
| 70 | GSM51179 | low | MF | Low PI | low |
| 71 | GSM51180 | high | CD2 | High PI | high |
| 72 | GSM51182 | low | LB | Low PI | low |
| 73 | GSM51185 | low | MS | Low PI | high |
| 74 | GSM51186 | high | CD1 | Low PI | high |
| 75 | GSM51190 | high | MS | High PI | high |
| 76 | GSM51201 | high | PR | High PI | high |
| 77 | GSM51202 | high | MS | High PI | high |
| 78 | GSM51204 | low | HY | Low PI | low |
| 79 | GSM51209 | low | CD2 | Low PI | high |
| 80 | GSM51211 | low | MS | High PI | high |
| 81 | GSM51213 | low | HY | Low PI | low |
| 82 | GSM51219 | high | PR | High PI | high |
| 83 | GSM51221 | high | HY | Low PI | high |
| 84 | GSM51222 | low | LB | Low PI | low |
| 85 | GSM51223 | high | PR | High PI | high |
| 86 | GSM51229 | low | LB | Low PI | high |
| 87 | GSM51234 | high | MF | Low PI | low |
| 88 | GSM51236 | low | CD2 | Low PI | low |
| 89 | GSM51238 | low | CD2 | High PI | low |
| 90 | GSM51239 | low | CD2 | High PI | low |
| 91 | GSM51243 | low | HY | Low PI | low |
| 92 | GSM51248 | high | LB | High PI | high |
| 93 | GSM51252 | low | HY | Low PI | high |
| 94 | GSM51254 | high | HY | High PI | high |

TABLE 10-continued

| | | predicted risk classifications | | | |
|---|---|---|---|---|---|
| No | Sample_ID | RiskGroup_SRP37 | MM_Subgroup | PI | RiskGroup_SRP124 |
| 95 | GSM51258 | high | CD1 | High PI | high |
| 96 | GSM51259 | high | CD2 | High PI | low |
| 97 | GSM51268 | high | PR | High PI | high |
| 98 | GSM51269 | low | MS | High PI | high |
| 99 | GSM51270 | high | PR | High PI | high |
| 100 | GSM51274 | high | HY | High PI | high |
| 101 | GSM51279 | high | PR | High PI | high |
| 102 | GSM51282 | high | HY | High PI | low |
| 103 | GSM51283 | high | HY | Low PI | low |
| 104 | GSM51285 | low | CD1 | Low PI | low |
| 105 | GSM51286 | high | MS | Low PI | high |
| 106 | GSM51287 | low | CD2 | Low PI | low |
| 107 | GSM51288 | low | CD2 | High PI | low |
| 108 | GSM51289 | low | LB | Low PI | low |
| 109 | GSM51292 | low | CD2 | High PI | low |
| 110 | GSM51293 | high | PR | High PI | high |
| 111 | GSM51295 | low | CD2 | High PI | low |
| 112 | GSM51297 | high | CD2 | High PI | low |
| 113 | GSM51298 | low | MS | Low PI | low |
| 114 | GSM51302 | low | HY | Low PI | low |
| 115 | GSM51308 | high | LB | High PI | low |
| 116 | GSM51315 | high | LB | Low PI | high |
| 117 | GSM51316 | high | CD1 | High PI | low |
| 118 | GSM51319 | low | HY | Low PI | high |
| 119 | GSM51326 | low | CD2 | Low PI | low |
| 120 | GSM51328 | low | CD2 | Low PI | low |
| 121 | GSM51329 | low | HY | Low PI | high |
| 122 | GSM51334 | high | HY | High PI | high |
| 123 | GSM51335 | high | MS | High PI | high |
| 124 | GSM95646 | low | CD2 | Low PI | low |
| 125 | GSM95647 | high | MF | High PI | high |
| 126 | GSM95648 | high | HY | Low PI | low |
| 127 | GSM95654 | high | HY | High PI | low |
| 128 | GSM95655 | high | MS | High PI | high |
| 129 | GSM95658 | high | CD1 | High PI | high |
| 130 | GSM95659 | low | CD2 | High PI | low |
| 131 | GSM95660 | high | CD2 | High PI | high |
| 132 | GSM95661 | low | CD2 | Low PI | low |
| 133 | GSM95663 | high | MF | High PI | high |
| 134 | GSM95669 | high | LB | High PI | low |
| 135 | GSM95672 | high | MF | High PI | high |
| 136 | GSM95676 | high | MF | High PI | high |
| 137 | GSM95678 | high | LB | Low PI | low |
| 138 | GSM95682 | high | LB | Low PI | high |
| 139 | GSM95684 | low | CD2 | Low PI | low |
| 140 | GSM95687 | low | MF | High PI | low |
| 141 | GSM95689 | high | HY | High PI | low |
| 142 | GSM95692 | low | HY | Low PI | low |
| 143 | GSM95693 | low | HY | Low PI | low |
| 144 | GSM95694 | high | PR | High PI | high |
| 145 | GSM95695 | low | LB | High PI | low |
| 146 | GSM95696 | high | LB | Low PI | high |
| 147 | GSM95697 | low | HY | Low PI | low |
| 148 | GSM95708 | low | LB | Low PI | low |
| 149 | GSM95716 | low | HY | Low PI | low |
| 150 | GSM95719 | high | HY | High PI | low |
| 151 | GSM95720 | high | PR | High PI | high |
| 152 | GSM95721 | low | MS | High PI | low |
| 153 | GSM95724 | low | CD2 | Low PI | low |
| 154 | GSM95727 | high | MS | Low PI | high |
| 155 | GSM95728 | low | HY | Low PI | low |
| 156 | GSM95729 | low | CD2 | Low PI | low |
| 157 | GSM95730 | low | CD2 | High PI | low |
| 158 | GSM95733 | low | HY | Low PI | low |
| 159 | GSM95738 | high | HY | Low PI | high |
| 160 | GSM95739 | low | MS | High PI | high |
| 161 | GSM95740 | high | PR | High PI | high |
| 162 | GSM95741 | high | PR | High PI | high |
| 163 | GSM95747 | high | HY | High PI | low |
| 164 | GSM95748 | low | HY | Low PI | low |
| 165 | GSM95752 | low | HY | Low PI | low |
| 166 | GSM95754 | low | MS | High PI | high |
| 167 | GSM95755 | low | HY | Low PI | high |
| 168 | GSM95757 | high | MS | High PI | high |
| 169 | GSM95759 | high | LB | Low PI | low |
| 170 | GSM95764 | low | LB | Low PI | low |

TABLE 10-continued predicted risk classifications

| No | Sample_ID | RiskGroup_SRP37 | MM_Subgroup | PI | RiskGroup_SRP124 |
|---|---|---|---|---|---|
| 171 | GSM95766 | low | CD2 | Low PI | low |
| 172 | GSM95768 | low | LB | Low PI | low |
| 173 | GSM95773 | low | MS | Low PI | low |
| 174 | GSM95775 | low | HY | Low PI | low |
| 175 | GSM95776 | high | LB | High PI | high |
| 176 | GSM95777 | low | MF | Low PI | low |
| 177 | GSM95782 | low | MS | Low PI | high |
| 178 | GSM95784 | low | CD2 | Low PI | low |
| 179 | GSM95785 | low | CD1 | Low PI | low |
| 180 | GSM95787 | low | HY | Low PI | low |
| 181 | GSM95788 | low | HY | Low PI | low |
| 182 | GSM95789 | high | PR | High PI | low |
| 183 | GSM95792 | low | HY | Low PI | low |
| 184 | GSM95795 | high | HY | Low PI | low |
| 185 | GSM95799 | high | HY | High PI | low |
| 186 | GSM95800 | high | PR | High PI | high |
| 187 | GSM95803 | high | PR | High PI | high |
| 188 | GSM95805 | low | HY | Low PI | low |
| 189 | GSM95806 | low | HY | Low PI | low |
| 190 | GSM95808 | high | MF | High PI | high |
| 191 | GSM95810 | high | LB | Low PI | low |
| 192 | GSM95815 | low | CD1 | Low PI | low |
| 193 | GSM95816 | low | HY | Low PI | low |
| 194 | GSM95823 | low | LB | Low PI | low |
| 195 | GSM102609 | high | MS | High PI | high |
| 196 | GSM102611 | high | HY | Low PI | low |
| 197 | GSM102612 | low | HY | Low PI | low |
| 198 | GSM102613 | high | HY | High PI | high |
| 199 | GSM102615 | high | PR | High PI | high |
| 200 | GSM102616 | low | HY | Low PI | low |
| 201 | GSM102617 | high | MF | High PI | low |
| 202 | GSM102620 | high | LB | High PI | low |
| 203 | GSM102624 | high | MS | High PI | high |
| 204 | GSM102625 | low | HY | Low PI | low |
| 205 | GSM102627 | low | LB | Low PI | low |
| 206 | GSM102628 | low | MS | High PI | high |
| 207 | GSM102630 | low | HY | Low PI | low |
| 208 | GSM50986 | high | CD1 | High PI | high |
| 209 | GSM50989 | low | MS | Low PI | high |
| 210 | GSM50992 | high | HY | High PI | low |
| 211 | GSM50993 | high | HY | Low PI | low |
| 212 | GSM50995 | high | HY | Low PI | high |
| 213 | GSM51001 | high | MS | High PI | high |
| 214 | GSM51002 | high | PR | High PI | high |
| 215 | GSM51004 | low | HY | Low PI | low |
| 216 | GSM51005 | high | PR | High PI | high |
| 217 | GSM51007 | high | CD1 | High PI | high |
| 218 | GSM51010 | high | CD1 | High PI | high |
| 219 | GSM51012 | high | HY | Low PI | high |
| 220 | GSM51014 | low | CD2 | High PI | high |
| 221 | GSM51018 | high | LB | Low PI | low |
| 222 | GSM51019 | high | MS | High PI | high |
| 223 | GSM51021 | low | LB | Low PI | low |
| 224 | GSM51022 | low | CD1 | Low PI | high |
| 225 | GSM51025 | high | LB | High PI | high |
| 226 | GSM51026 | high | HY | Low PI | high |
| 227 | GSM51039 | high | PR | High PI | high |
| 228 | GSM51040 | low | HY | Low PI | low |
| 229 | GSM51042 | low | HY | Low PI | low |
| 230 | GSM51044 | low | MS | Low PI | high |
| 231 | GSM51046 | low | HY | High PI | low |
| 232 | GSM51047 | low | LB | Low PI | high |
| 233 | GSM51048 | high | HY | High PI | high |
| 234 | GSM51051 | low | CD1 | High PI | high |
| 235 | GSM51052 | high | MS | High PI | high |
| 236 | GSM51060 | low | MS | High PI | high |
| 237 | GSM51067 | high | HY | High PI | high |
| 238 | GSM51070 | low | CD2 | Low PI | low |
| 239 | GSM51072 | low | LB | Low PI | high |
| 240 | GSM51073 | low | CD2 | High PI | low |
| 241 | GSM51075 | high | PR | High PI | high |
| 242 | GSM51077 | low | MS | High PI | high |
| 243 | GSM51078 | high | HY | Low PI | low |
| 244 | GSM51080 | high | MF | Low PI | low |
| 245 | GSM51090 | high | HY | High PI | low |
| 246 | GSM51099 | high | MF | High PI | high |

TABLE 10-continued

| | | predicted risk classifications | | | |
|---|---|---|---|---|---|
| No | Sample_ID | RiskGroup_SRP37 | MM_Subgroup | PI | RiskGroup_SRP124 |
| 247 | GSM51100 | high | HY | Low PI | high |
| 248 | GSM51102 | low | HY | Low PI | low |
| 249 | GSM51103 | low | LB | Low PI | low |
| 250 | GSM51107 | low | HY | Low PI | low |
| 251 | GSM51113 | low | CD2 | Low PI | low |
| 252 | GSM51114 | low | HY | Low PI | high |
| 253 | GSM51116 | low | MS | Low PI | high |
| 254 | GSM51117 | high | PR | High PI | high |
| 255 | GSM51120 | low | MS | Low PI | low |
| 256 | GSM51123 | high | MS | High PI | high |
| 257 | GSM51125 | high | HY | Low PI | low |
| 258 | GSM51126 | high | LB | High PI | low |
| 259 | GSM51127 | high | HY | High PI | low |
| 260 | GSM51130 | high | CD1 | High PI | high |
| 261 | GSM51135 | high | HY | Low PI | high |
| 262 | GSM51136 | high | CD2 | High PI | high |
| 263 | GSM51140 | low | CD2 | Low PI | low |
| 264 | GSM51141 | high | HY | High PI | high |
| 265 | GSM51142 | high | PR | High PI | high |
| 266 | GSM51143 | low | HY | Low PI | low |
| 267 | GSM51148 | low | MF | Low PI | low |
| 268 | GSM51154 | high | CD2 | High PI | low |
| 269 | GSM51160 | high | PR | High PI | high |
| 270 | GSM51162 | high | MS | High PI | high |
| 271 | GSM51165 | high | MS | Low PI | high |
| 272 | GSM51166 | high | PR | High PI | high |
| 273 | GSM51170 | low | MS | High PI | low |
| 274 | GSM51171 | low | CD2 | Low PI | low |
| 275 | GSM51172 | low | CD2 | Low PI | low |
| 276 | GSM51175 | low | HY | Low PI | low |
| 277 | GSM51178 | low | CD2 | High PI | low |
| 278 | GSM51181 | low | LB | Low PI | low |
| 279 | GSM51184 | low | CD2 | Low PI | low |
| 280 | GSM51188 | high | CD1 | High PI | high |
| 281 | GSM51189 | low | HY | Low PI | low |
| 282 | GSM51191 | high | PR | High PI | high |
| 283 | GSM51194 | low | LB | Low PI | high |
| 284 | GSM51198 | low | CD1 | Low PI | high |
| 285 | GSM51199 | high | MF | High PI | high |
| 286 | GSM51200 | low | CD1 | Low PI | low |
| 287 | GSM51205 | high | CD2 | High PI | high |
| 288 | GSM51208 | low | CD2 | Low PI | low |
| 289 | GSM51210 | high | CD2 | High PI | high |
| 290 | GSM51214 | high | PR | High PI | high |
| 291 | GSM51215 | high | CD1 | High PI | high |
| 292 | GSM51216 | high | CD1 | Low PI | high |
| 293 | GSM51217 | high | MS | Low PI | High |
| 294 | GSM51224 | low | MS | Low PI | High |
| 295 | GSM51225 | high | LB | High PI | Low |
| 296 | GSM51228 | high | PR | High PI | High |
| 297 | GSM51231 | high | HY | Low PI | High |
| 298 | GSM51233 | high | MF | High PI | High |
| 299 | GSM51235 | high | LB | Low PI | Low |
| 300 | GSM51237 | high | HY | High PI | Low |
| 301 | GSM51240 | low | MS | High PI | High |
| 302 | GSM51242 | high | HY | High PI | High |
| 303 | GSM51244 | high | LB | High PI | High |
| 304 | GSM51246 | high | PR | High PI | High |
| 305 | GSM51250 | low | CD2 | High PI | Low |
| 306 | GSM51251 | high | MF | High PI | Low |
| 307 | GSM51256 | low | CD2 | Low PI | Low |
| 308 | GSM51257 | high | HY | Low PI | High |
| 309 | GSM51260 | low | LB | Low PI | Low |
| 310 | GSM51263 | low | MF | High PI | Low |
| 311 | GSM51264 | low | HY | Low PI | Low |
| 312 | GSM51272 | high | MF | High PI | High |
| 313 | GSM51273 | high | PR | High PI | High |
| 314 | GSM51277 | low | MF | Low PI | Low |
| 315 | GSM51278 | low | HY | Low PI | High |
| 316 | GSM51284 | low | MS | Low PI | Low |
| 317 | GSM51290 | low | CD2 | Low PI | Low |
| 318 | GSM51291 | high | MF | High PI | High |
| 319 | GSM51294 | low | MS | Low PI | Low |
| 320 | GSM51296 | low | HY | Low PI | Low |
| 321 | GSM51299 | low | HY | Low PI | Low |
| 322 | GSM51300 | low | CD2 | Low PI | High |

TABLE 10-continued predicted risk classifications

| No | Sample_ID | RiskGroup_SRP37 | MM_Subgroup | PI | RiskGroup_SRP124 |
|---|---|---|---|---|---|
| 323 | GSM51301 | high | PR | High PI | High |
| 324 | GSM51303 | high | CD1 | High PI | Low |
| 325 | GSM51306 | low | CD2 | High PI | Low |
| 326 | GSM51307 | high | HY | High PI | High |
| 327 | GSM51310 | low | HY | Low PI | Low |
| 328 | GSM51311 | low | CD2 | High PI | Low |
| 329 | GSM51312 | low | MF | High PI | Low |
| 330 | GSM51313 | low | CD2 | High PI | Low |
| 331 | GSM51317 | low | MS | High PI | High |
| 332 | GSM51318 | high | MS | High PI | High |
| 333 | GSM51321 | low | HY | Low PI | Low |
| 334 | GSM51322 | low | LB | Low PI | Low |
| 335 | GSM51324 | high | MF | High PI | High |
| 336 | GSM51327 | high | MF | Low PI | High |
| 337 | GSM51330 | low | CD2 | Low PI | Low |
| 338 | GSM51331 | high | PR | High PI | High |
| 339 | GSM51333 | low | CD2 | Low PI | Low |
| 340 | GSM51336 | low | LB | Low PI | High |
| 341 | GSM95649 | low | HY | High PI | Low |
| 342 | GSM95650 | low | HY | Low PI | Low |
| 343 | GSM95653 | low | MS | High PI | High |
| 344 | GSM95664 | low | MF | High PI | Low |
| 345 | GSM95667 | high | PR | High PI | High |
| 346 | GSM95668 | high | MS | High PI | High |
| 347 | GSM95670 | high | PR | High PI | High |
| 348 | GSM95671 | high | HY | High PI | High |
| 349 | GSM95673 | low | HY | Low PI | Low |
| 350 | GSM95674 | high | MF | High PI | Low |
| 351 | GSM95675 | low | MF | Low PI | Low |
| 352 | GSM95677 | high | CD2 | High PI | Low |
| 353 | GSM95680 | high | LB | High PI | Low |
| 354 | GSM95681 | high | HY | High PI | High |
| 355 | GSM95690 | high | LB | Low PI | High |
| 356 | GSM95691 | high | MS | High PI | High |
| 357 | GSM95699 | high | HY | High PI | High |
| 358 | GSM95702 | high | HY | Low PI | High |
| 359 | GSM95703 | high | HY | High PI | High |
| 360 | GSM95706 | high | MS | High PI | High |
| 361 | GSM95709 | low | MS | Low PI | High |
| 362 | GSM95714 | high | PR | High PI | High |
| 363 | GSM95715 | high | HY | High PI | Low |
| 364 | GSM95718 | high | LB | High PI | High |
| 365 | GSM95725 | low | LB | Low PI | Low |
| 366 | GSM95726 | high | PR | High PI | High |
| 367 | GSM95734 | high | MF | High PI | High |
| 368 | GSM95737 | low | CD2 | High PI | Low |
| 369 | GSM95742 | high | PR | High PI | High |
| 370 | GSM95743 | low | MS | Low PI | High |
| 371 | GSM95744 | high | LB | Low PI | Low |
| 372 | GSM95746 | low | LB | Low PI | Low |
| 373 | GSM95749 | high | HY | High PI | Low |
| 374 | GSM95751 | high | HY | Low PI | High |
| 375 | GSM95753 | low | MF | Low PI | Low |
| 376 | GSM95760 | low | MS | Low PI | Low |
| 377 | GSM95763 | high | HY | High PI | High |
| 378 | GSM95767 | low | MS | Low PI | Low |
| 379 | GSM95771 | high | PR | High PI | High |
| 380 | GSM95778 | high | HY | High PI | Low |
| 381 | GSM95779 | low | HY | High PI | Low |
| 382 | GSM95780 | low | CD2 | Low PI | Low |
| 383 | GSM95781 | low | HY | Low PI | Low |
| 384 | GSM95783 | high | PR | High PI | High |
| 385 | GSM95786 | high | HY | High PI | High |
| 386 | GSM95790 | low | CD2 | Low PI | Low |
| 387 | GSM95791 | high | LB | High PI | Low |
| 388 | GSM95793 | low | CD1 | Low PI | Low |
| 389 | GSM95794 | low | HY | Low PI | High |
| 390 | GSM95796 | low | LB | Low PI | Low |
| 391 | GSM95802 | low | MF | Low PI | Low |
| 392 | GSM95804 | high | PR | High PI | High |
| 393 | GSM95807 | high | MS | Low PI | High |
| 394 | GSM95809 | low | MF | Low PI | Low |
| 395 | GSM95811 | high | PR | High PI | High |
| 396 | GSM95812 | low | MS | Low PI | High |
| 397 | GSM95817 | low | CD1 | High PI | High |
| 398 | GSM95818 | high | LB | High PI | Low |

TABLE 10-continued predicted risk classifications

| No | Sample_ID | RiskGroup_SRP37 | MM_Subgroup | PI | RiskGroup_SRP124 |
|---|---|---|---|---|---|
| 399 | GSM95819 | low | CD2 | Low PI | Low |
| 400 | GSM95825 | high | MS | High PI | High |
| 401 | GSM102606 | low | CD2 | Low PI | Low |
| 402 | GSM102607 | high | CD1 | High PI | High |
| 403 | GSM102610 | low | LB | Low PI | Low |
| 404 | GSM102614 | high | PR | High PI | High |
| 405 | GSM102618 | low | LB | High PI | Low |
| 406 | GSM102621 | low | LB | Low PI | High |
| 407 | GSM102622 | high | MF | High PI | High |
| 408 | GSM102623 | high | HY | High PI | High |
| 409 | GSM102626 | high | MS | High PI | High |
| 410 | GSM102629 | low | HY | Low PI | Low |
| 411 | GSM102631 | high | CD2 | High PI | High |
| 412 | GSM102632 | high | MS | High PI | Low |
| 413 | GSM102633 | low | LB | Low PI | Low |
| 414 | GSM102634 | low | HY | Low PI | Low |

TABLE 11

| SRP37/Subgroup | CD1 | CD2 | HY | LB | MF | MS | PR |
|---|---|---|---|---|---|---|---|
| high | 19 | 10 | 56 | 25 | 23 | 31 | 47 |
| low | 9 | 50 | 60 | 33 | 14 | 37 | 0 |

| SRP37/PI | High PI | Low PI |
|---|---|---|
| high | 160 | 51 |
| low | 47 | 156 |

| SRP37/SRP124 | high | low |
|---|---|---|
| high | 160 | 51 |
| low | 59 | 144 |

| SRP124/Subgroup | CD1 | CD2 | HY | LB | MF | MS | PR |
|---|---|---|---|---|---|---|---|
| high | 21 | 10 | 46 | 20 | 19 | 57 | 46 |
| low | 7 | 50 | 70 | 38 | 18 | 11 | 1 |

| SRP124/PI | High PI | Low PI |
|---|---|---|
| high | 143 | 76 |
| low | 64 | 131 |

TABLE 12

| | Gene | | Module |
|---|---|---|---|
| | | AffyID | |
| 1 | STK6 | 208079_s_at | blue |
| 2 | TRIP13 | 204033_at | blue |
| | | Clone | |
| 1 | ALDOA | 200966_x_at | darkgreen |
| 2 | TMPO | 209753_s_at | darkgreen |
| 3 | LARS2 | 204016_at | darkgreen |
| 4 | LAS1L | 208117_s_at | darkgreen |
| 5 | TRIP13 | 204033_at | royalblue |
| 6 | RAD18 | 238670_at | blue |
| 7 | STK6 | 208079_s_at | blue |
| 8 | FUCA1 | 202838_at | springgreen |
| 1 | ALDOA | 200966_x_at | darkgreen |
| 2 | LAS1L | 208117_s_at | darkgreen |
| 3 | STK6 | 208079_s_at | blue |

TABLE 13A

| Reference † | Indication of Signature | Tumor type | # genes | Genes overlapping with published signature | | PMID | Report Summary |
|---|---|---|---|---|---|---|---|
| 1 | Prognosis | MM | 70 | 3 of 70* | STK6, SLC19A1, TRIP13 | 17105813 | 532 patients; identifies patients with very high risk disease |
| 1 | Prognosis | MM | 17 | 1 of 17 | SLC19A1 | 17105813 | |
| 2 | Prognosis | MM | 15 | 0 of 15 | None | 18591550250 | independent patients (from other datasets); identifies high risk disease |
| 3 | Proliferation | MM | 11 | 2 of 11 | CCNB2, STK6 | 16728730 | Genes defined as having expression correlated with survival 414 patients 22 healthy donors and 45 cell lines |
| 4 | Proliferation | MM | 50 | 5 of 50 | CCNB2, STK6, KIF2C, TRIP13; CDC6 | 208847122 | independent cohorts totaling 643 patients; proliferation validated by secondary measures in training set; also prognostic |

TABLE 13A-continued

| Reference† | Indication of Signature | Tumor type | # genes | Genes overlapping with published signature | | PMID | Report Summary |
|---|---|---|---|---|---|---|---|
| 5 | Drug Response | MM | 80 | 0 of 80 | None | 21628408 | Signature identified by comparing pre- & 48 hr post-bortezomib treatment inpatients prognostic value defined with PFS annotated GEP of 480 patients |
| 6 | Proliferation | Breast | 45 | 5 of 45 | MCM5 CDC20 CDC6; RRM2 MCM4; | 16491069 | Comparison of breast cancer cell lines primary tumors and normal breast tissue |
| 7 | Proliferation | MCL | 20 | 2 of 20 | MCM2 CDC20 | 12620412 | Defined from 92 patient GEP also prognostic |
| 8 | Proliferation/ prognosis | ER + Breast | 50 | 5 of 50 | CCNB2 STK6 KIF2 CCDC6 BLM | 15899795 | GEP of 311 annotated breast carcinoma samples |
| 9 | Recurrence | ER + Breast | 16 | 1 of 16 | MYBL2 | 15591335 | RT-PCR of pre-identified genes in 668 recurrence annotated node negative ER + breast cancer |

†1 Shaughnessy 2007;
2 Decaux;
3 Than;
4 Hose;
5 Shaughnessy 2011;
6 Whitfield
7 Rosenwald;
8 Dai;
9 Paik;
see text of specification for complete citations.
*number of genes from the 37 gene signature that are overlapping with a published signature out of the total number of genes in the published signature

TABLE 13B

| Indicator Type | HI[1] | HI[1] | HI[2] | PI[3] | PI[4] | DR[5] | PI[6] | PI[7] | PI/Prognosis[8] | Recurrence[9] |
|---|---|---|---|---|---|---|---|---|---|---|
| # Genes | 70 | 17 | 15 | 11 | 50 | 80 | 45 | 20 | 50 | 16 |
| Disease | MM | MM | MM | MM | MM | MM | Breast | MCL | ER + Breast | Breast |
| E2F2 | | | | | | | | | | |
| RRM2 | | | | | | | Yes | | | |
| NCAPH | | | | | | | | | | |
| CDC25A | | | | | | | | | | |
| CCNB2 | | | | Yes | Yes | | | | Yes | |
| RAD51 | | | | | | | | | | |
| MCM4 | | | | | | | Yes | | | |
| SPAG5 | | | | | | | | | | |
| PHF19 | | | | | | | | | | |
| MCM2 | | | | | | | | Yes | Yes | |
| STK6 | Yes | | | Yes | Yes | | | | | |
| CDCA5 | | | | | | | | | | |
| HJURP | | | | | | | | | | |
| CDCA3 | | | | | | | | | | |
| Hs.193784 | | | | | | | | | | |
| MYBL2 | | | | | | | | | | Yes |
| KIF2C | | | | | Yes | | | | Yes | |
| ZNF107 | | | | | | | | | | |
| C9orf140 | | | | | | | | | | |
| KIF22 | | | | | | | | | | |
| HLA-DPB1 | | | | | | | | | | |
| SLC19A1 | Yes | Yes | | | | | | | | |
| LDHA | | | | | | | | | | |
| UBE2C | | | | | | | | | | |
| TRIP13 | Yes | | | | Yes | | | | | |
| MCM5 | | | | | | | Yes | | | |
| PHC3 | | | | | | | | | | |

TABLE 13B-continued

| Indicator Type | HI[1] | HI[1] | HI[2] | PI[3] | PI[4] | DR[5] | PI[6] | PI[7] | PI/Prognosis[8] | Recurrence[9] |
|---|---|---|---|---|---|---|---|---|---|---|
| CDC20 | | | | | | | Yes | Yes | | |
| TACC3 | | | | | | | | | | |
| CDC6 | | | | | Yes | | Yes | | Yes | |
| ATAD2 | | | | | | | | | | |
| Hs.202577 | | | | | | | | | | |
| SUV39H1 | | | | | | | | | | |
| TMEM48 | | | | | | | | | | |
| BLM | | | | | | | | | Yes | |
| KIAA2013 | | | | | | | | | | |
| E2F2 | | | | | | | | | | |
| NSDHL | | | | | | | | | | |
| Overlap | 3 of 70 | 1 of 17 | 0 of 15 | 2 of 11 | 5 of 50 | 0 of 80 | 5 of 45 | 2 of 20 | 5 of 50 | 1 of 16 |

[1]Shaughnessy 2007;
[2]Decaux;
[3]Zhan;
[4]Hose;
[5]Shaughnessy 2011;
[6]Whitfield;
[7]Rosenwald;
[8]Dai;
[9]Paik;
see text of specification for complete citations.

TABLE 14

| Index | Cell Line | Class Label | Number of genes in classifier | CCP | DLDA | NN1 | NN3 | NC | SVM |
|---|---|---|---|---|---|---|---|---|---|
| 1 | EJM | Non-Sensitive | 37 | 95 | 95 | 100 | 86 | 100 | 95 |
| 2 | KMS20 | Non-Sensitive | 37 | 96 | 96 | 100 | 88 | 100 | 88 |
| 3 | KMS18 | Non-Sensitive | 37 | 100 | 100 | 93 | 72 | 100 | 97 |
| 4 | OCIMY5 | Non-Sensitive | 37 | 77 | 97 | 0 | 0 | 43 | 3 |
| 5 | KMS26 | Non-Sensitive | 37 | 43 | 43 | 11 | 32 | 54 | 57 |
| 6 | L363 | Sensitive | 37 | 100 | 100 | 100 | 100 | 100 | 100 |
| 7 | SKMM1 | Sensitive | 37 | 100 | 100 | 100 | 100 | 100 | 100 |
| 8 | MMM1 | Sensitive | 37 | 0 | 0 | 14 | 43 | 6 | 37 |
| 9 | KMS28BM | Sensitive | 37 | 100 | 100 | 100 | 100 | 100 | 96 |
| 10 | KMS28PE | Sensitive | 37 | 100 | 100 | 100 | 100 | 100 | 100 |
| 11 | KMS11lb | Sensitive | 37 | 100 | 100 | 100 | 100 | 100 | 98 |
| 12 | XG6 | Sensitive | 37 | 100 | 100 | 100 | 97 | 100 | 100 |
| 13 | FR4 | Sensitive | 37 | 97 | 95 | 76 | 84 | 100 | 89 |
| 14 | KMS12PE | Sensitive | 37 | 3 | 3 | 26 | 47 | 6 | 24 |
| | | | Mean % of correct classification | 81 | 82 | 78 | 76 | 81 | 82 |
| | | | Permutation p-value (N = 1000) | 0.03 | 0.03 | 0.04 | 0.11 | 0.03 | 0.02 |

TABLE 15

| Index | Genes | CCP | DLDA | SVM |
|---|---|---|---|---|
| 1 | E2F2 | 1.8484 | 0.7744 | −0.136 |
| 2 | SLC19A1 | 2.0049 | 1.0255 | −0.087 |
| 3 | LDHA | 0.7742 | 0.4517 | 0.009 |
| 4 | UBE2C | 1.3134 | 0.5584 | 0.1551 |
| 5 | TRIP13 | 2.5648 | 1.8351 | −0.026 |
| 6 | RRM2 | 0.4182 | 0.1875 | −0.016 |
| 7 | NCAPH | 2.9523 | 2.4646 | 0.1158 |
| 8 | CDC25A | 1.679 | 0.9236 | −0.092 |
| 9 | MCM5 | 2.911 | 1.7937 | 0.2401 |
| 10 | CCNB2 | 1.5637 | 1.1436 | 0.0575 |
| 11 | RAD51 | 1.5852 | 0.8196 | −0.125 |
| 12 | MCM4 | 1.7276 | 0.8487 | 0.1049 |
| 13 | PHC3 | −0.558 | −0.509 | −0.092 |
| 14 | SPAG5 | 2.7768 | 2.226 | 0.1532 |
| 15 | PHF19 | 2.8593 | 1.6495 | 0.4208 |
| 16 | MCM2 | 1.7324 | 0.928 | 0.0428 |
| 17 | STK6 | 2.3073 | 1.9972 | 0.1914 |
| 18 | CDCA5 | 2.3345 | 1.6137 | 0.0547 |
| 19 | HJURP | 1.2206 | 0.6179 | −0.032 |
| 20 | CDCA3 | 2.8014 | 1.8374 | 0.1807 |
| 21 | Hs.193784 | −0.613 | −0.383 | −0.084 |
| 22 | CDC20 | 0.7571 | 0.4442 | −0.191 |
| 23 | TACC3 | 0.8627 | 0.6053 | 0.0085 |
| 24 | CDC6 | 1.368 | 0.6811 | 0.0039 |
| 25 | ATAD2 | 0.8924 | 0.6141 | 0.0079 |
| 26 | Hs.202577 | −0.796 | −0.5 | −0.091 |
| 27 | SUV39H1 | 4.1805 | 4.2695 | 0.2384 |
| 28 | TMEM48 | 2.5335 | 1.8282 | 0.0131 |
| 29 | MYBL2 | 1.3405 | 0.801 | −0.07 |
| 30 | BLM | 1.8186 | 1.1832 | −0.049 |

TABLE 15-continued

| Index | Genes | CCP | DLDA | SVM |
|---|---|---|---|---|
| 31 | KIF2C | 1.9541 | 1.4251 | 0.0346 |
| 32 | KIAA2013 | 1.1628 | 1.6662 | 0.0594 |
| 33 | ZNF107 | 3.6738 | 3.3095 | 0.0922 |
| 34 | C9orf140 | 1.8192 | 1.2875 | 0.147 |
| 35 | KIF22 | 2.5068 | 2.4752 | 0.1182 |
| 36 | HLA-DPB1 | −1.583 | −0.388 | −0.127 |
| 37 | NSDHL | 2.2211 | 2.0594 | 0.1065 |

TABLE 16

| Index | Genes | Non-Sensitive | Sensitive |
|---|---|---|---|
| 1 | E2F2 | −1.7519 | −3.1246 |
| 2 | SLC19A1 | −1.9524 | −3.1719 |
| 3 | LDHA | −1.8238 | −2.2366 |
| 4 | UBE2C | −1.082 | −2.0431 |
| 5 | TRIP13 | −2.5585 | −3.6737 |
| 6 | RRM2 | −2.028 | −2.3183 |
| 7 | NCAPH | −1.1227 | −2.2229 |
| 8 | CDC25A | −2.7243 | −3.6739 |
| 9 | MCM5 | −1.6539 | −3.1236 |
| 10 | CCNB2 | −1.0284 | −1.6936 |
| 11 | RAD51 | −1.6895 | −2.6433 |
| 12 | MCM4 | −1.8748 | −2.9689 |
| 13 | PHC3 | 0.6017 | 0.7921 |
| 14 | SPAG5 | −1.3687 | −2.4464 |
| 15 | PHF19 | −1.5353 | −3.0774 |
| 16 | MCM2 | −1.8126 | −2.8187 |
| 17 | STK6 | −0.9744 | −1.8037 |
| 18 | CDCA5 | −1.4866 | −2.5373 |
| 19 | HJURP | −1.0543 | −1.8044 |
| 20 | CDCA3 | −1.2476 | −2.5764 |
| 21 | Hs.193784 | 2.4856 | 2.7906 |
| 22 | CDC20 | −1.0935 | −1.4949 |
| 23 | TACC3 | −1.0676 | −1.4502 |
| 24 | CDC6 | −1.7431 | −2.598 |
| 25 | ATAD2 | −0.8479 | −1.2513 |
| 26 | Hs.202577 | 2.6322 | 3.0261 |
| 27 | SUV39H1 | −1.4743 | −2.7478 |
| 28 | TMEM48 | −1.215 | −2.3073 |
| 29 | MYBL2 | −2.2767 | −2.9747 |
| 30 | BLM | −0.9315 | −1.8011 |
| 31 | KIF2C | −0.9213 | −1.7549 |
| 32 | KIAA2013 | −0.4459 | −0.6983 |
| 33 | ZNF107 | −0.1494 | −1.4182 |
| 34 | C9orf140 | −0.8778 | −1.6775 |
| 35 | KIF22 | −1.1461 | −1.9359 |
| 36 | HLA-DPB1 | 1.8945 | 3.9065 |
| 37 | NSDHL | −1.0091 | −1.7544 |

We claim:

1. A method of determining if a hematological neoplasm is sensitive to treatment with histone deacetylase inhibitor (HDACi) and mechanistic Target of Rapamycin (mTOR) inhibitor (mTORi) combination therapy and treating the neoplasm, comprising:
  obtaining a blood sample from a subject with a hematological neoplasm;
  detecting the level of expression of six or more genes in the blood sample, wherein the six or more genes are selected from the group consisting of ATPase family, AAA domain containing 2 (ATAD2); Bloom syndrome, RecQ helicase-like (BLM); chromosome 9 open reading frame 140 (C9orf140); cyclin B2 (CCNB2); cell division cycle 20 homolog (S. cerevisiae) (CDC20); cell division cycle 25 homolog A (S. pombe) (CDC25A); cell division cycle 6 homolog (S. cerevisiae) (CDC6); cell division cycle associated 3 (CDCA3); cell division cycle associated 5 (CDCA5); E2F transcription factor 2 (E2F2); Holliday junction recognition protein (HJURP); major histocompatibility complex, class II, DP beta 1 (HLA-DPB1); Hs.193784; Hs.202577; KIAA2013; kinesin family member 22 (KIF22); kinesin family member 2C (KIF2C); lactate dehydrogenase A (LDHA); minichromosome maintenance complex component 2 (MCM2); minichromosome maintenance complex component 4 (MCM4); minichromosome maintenance complex component 5 (MCM5); v-myb myeloblastosis viral oncogene homolog (avian)-like 2 (MYBL2); non-SMC condensin I complex, subunit H (NCAPH); NAD(P) dependent steroid dehydrogenase-like (NSDHL); polyhomeotic homolog 3 (Drosophila) (PHC3); PHD finger protein 19 (PHF19); RAD51 homolog (RecA homolog, E. coli) (S. cerevisiae) (RAD51); ribonucleotide reductase M2 (RRM2); solute carrier family 19 (folate transporter), member 1 (SLC19A1); sperm associated antigen 5 (SPAG5); aurora kinase A (STK6); suppressor of variegation 3-9 homolog 1 (Drosophila) (SUV39H1); transforming, acidic coiled-coil containing protein 3 (TACC3); transmembrane protein 48 (TMEM48); thyroid hormone receptor interactor 13 (TRIP13); ubiquitin-conjugating enzyme E2C (UBE2C); and Zinc finger protein 107 (ZNF107);
  wherein the six or more genes comprise at least CDC25A, E2F2, RRM2, RAD51, MCM4, BLM, CDC6, CDCA5, HJURP, MCM2, MCM5, MYBL2, PHF19, SLC19A1, UBE2C, Hs.193784, Hs.202577, and HLA-DPB1;
  identifying the neoplasm as sensitive to treatment with HDACi and mTORi combination therapy if there is a difference in the level of expression of the six or more genes in the neoplasm sample as compared to a control; and
  administering a therapeutically effective amount of a HDACi and mTORi combination therapy to the subject if the neoplasm is identified as sensitive to treatment with HDACi and mTORi combination therapy.

2. The method of claim 1, wherein the six or more genes comprise each of ATAD2, BLM, C9orf140, CCNB2, CDC20, CDC25A, CDC6, CDCA3, CDCA5, E2F2, HJURP, HLA-DPB1, Hs.193784, Hs.202577, KIAA2013, KIF22, KIF2C, LDHA, MCM2, MCM4, MCM5, MYBL2, NCAPH, NSDHL, PHC3, PHF19, RAD51, RRM2, SLC19A1, SPAG5, STK6, SUV39H1, TACC3, TMEM48, TRIP13, UBE2C, and ZNF107.

3. The method of claim 2, wherein identifying the neoplasm as sensitive to treatment with HDACi and mTORi combination therapy occurs prior to HDACi and mTORi combination therapy, and wherein the difference in the level of expression comprises:
  (a) an increase in the level of expression of one or more of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107; and
  (b) a decrease in the level of expression of one or more of Hs.193784, Hs.202577, HLA-DPB1, and PHC3.

4. The method of claim 3, wherein the difference in the level of expression comprises:
  (c) an increase in an aggregate gene expression value calculated from the level of expression of two or more of ATAD2, BLM, C9orf140, CCNB2, CDC20, CDC25A, CDC6, CDCA3, CDCA5, E2F2, HJURP, KIAA2013, KIF22, KIF2C, LDHA, MCM2, MCM4, MCM5, MYBL2, NCAPH, NSDHL, PHF19, RAD51, RRM2, SLC19A1, SPAG5, STK6, SUV39H1, TACC3, TMEM48, TRIP13, UBE2C, and ZNF107; and
(d) a decrease in an aggregate gene expression value calculated from the level of expression of two or more of Hs.193784, Hs.202577, HLA-DPB1, and PHC3.

5. The method of claim 1, wherein detecting the level of expression of the six or more genes comprises microarray analysis.

6. The method of claim 1, wherein the control comprises the level of expression of the six or more genes in a control sample.

7. The method of claim 1, wherein identifying the neoplasm as sensitive to treatment with HDACi and mTORi combination therapy occurs prior to HDACi and mTORi combination therapy, and wherein the difference in the level of expression comprises:
   (a) an increase in the level of expression of BLM, CDC25A, CDC6, CDCA5, E2F2, HJURP, MCM2, MCM4, MCM5, MYBL2, PHF19, RAD51, RRM2, SLC19A1, and UBE2C; and
   (b) a decrease in the level of expression of Hs.193784, Hs.202577, and HLA-DPB1.

8. The method of claim 7, wherein the difference in the level of expression comprises:
   (c) an increase in an aggregate gene expression value calculated from the level of expression of BLM, CDC25A, CDC6, CDCA5, E2F2, HJURP, MCM2, MCM4, MCM5, MYBL2, PHF19, RAD51, RRM2, SLC19A1, and UBE2C; and
   (d) a decrease in an aggregate gene expression value calculated from the level of expression of Hs.193784, Hs.202577, and HLA-DPB1.

9. The method of claim 1, wherein the HDACi is MS-275 and the mTORi is Rapamycin.

10. The method of claim 1, wherein detecting the level of expression of the six or more genes comprises:
    contacting RNA or cDNA prepared from the blood sample with probes for each of the six or more genes, wherein the probes are spatially arranged in addressable locations on a substrate; and
    performing an array analysis to detect the level of expression of the six or more genes.

* * * * *